United States Patent
Aktoudianakis et al.

(10) Patent No.: US 9,458,145 B2
(45) Date of Patent: Oct. 4, 2016

(54) BENZIMIDAZOLE DERIVATIVES AS BROMODOMAIN INHIBITORS

(71) Applicant: Gilead Sciences, Inc., Foster City, CA (US)

(72) Inventors: Evangelos Aktoudianakis, San Mateo, CA (US); Gregory Chin, San Francisco, CA (US); Britton Kenneth Corkey, Redwood City, CA (US); Jinfa Du, Redwood City, CA (US); Kristyna Elbel, South San Francisco, CA (US); Robert H. Jiang, Cupertino, CA (US); Tetsuya Kobayashi, Pleasanton, CA (US); Rick Lee, Livermore, CA (US); Ruben Martinez, San Diego, CA (US); Samuel E. Metobo, Newark, CA (US); Michael Mish, Foster City, CA (US); Manuel Munoz, San Mateo, CA (US); Sophie Shevick, San Francisco, CA (US); David Sperandio, Palo Alto, CA (US); Hai Yang, San Mateo, CA (US); Jeff Zablocki, Los Altos, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 14/273,147

(22) Filed: May 8, 2014

(65) Prior Publication Data

US 2014/0336190 A1 Nov. 13, 2014

Related U.S. Application Data

(60) Provisional application No. 61/821,612, filed on May 9, 2013, provisional application No. 61/826,912, filed on May 23, 2013, provisional application No. 61/860,229, filed on Jul. 30, 2013, provisional application No. 61/951,347, filed on Mar. 11, 2014.

(51) Int. Cl.
  C07D 471/04 (2006.01)
  C07D 417/14 (2006.01)
  C07D 413/14 (2006.01)
  C07D 413/04 (2006.01)

(52) U.S. Cl.
  CPC ........... *C07D 413/04* (2013.01); *C07D 413/14* (2013.01); *C07D 417/14* (2013.01); *C07D 471/04* (2013.01)

(58) Field of Classification Search
  None
  See application file for complete search history.

(56) References Cited

U.S. PATENT DOCUMENTS 6,162,804 A 12/2000 Bilodeau et al.
2007/0275984 A1 11/2007 Imogai et al.

2009/0176778 A1 7/2009 Schmitz et al.
2010/0204265 A1 8/2010 Baskaran et al.
2012/0121540 A1 5/2012 Schmitz et al.
2012/0232074 A1 9/2012 Bouillot et al.
2014/0187533 A1 7/2014 Pajouhesh et al.

FOREIGN PATENT DOCUMENTS

WO WO-2004/098494 A2 11/2004

OTHER PUBLICATIONS

Hay et al, J. Am. Chem. Soc. 2014, 136, 9308-9319.*
Bamborogh, P. et al. (2012) "Fragment-Based Discovery of Bromodomain Inhibitors Part 2: Optimization of Phenylisoxazole Sulfonamides", J. Med. Chem., 55: 587-596.
Chun-Wa, C. et al. (2012) "Fragment-Based Discovery of Bromodomain Inhibitors Part 1: Inhibitor Binding Modes and Implications for Lead Discovery", J. Med. Chem., 55: 576-586.
Hewings, D.S. et al. (2011) "3,5-Dimethylisoxazoles Act as Acetyl-Lysine-Mimetic Bromodomain Ligands" J. Med. Chem., 54: 6761-6770.
Mirguet, O. et al. (2013) "Discovery of Epigenetic Regulator I-BET762: Lead Optimisation to Afford a Clinical Candidate Inhibitor of the BET Bromodomains", J. Med. Chem., 56: 7501-7515.
Hay et al., "The design and synthesis of 5- and 6-isoxazolylbenzimidazoles as selective inhibitors of the BET bromodomains," Med. Chem. Commun., 2013, 4, 140-144, Royal Society of Chemistry (published online Aug. 13, 2012).†

* cited by examiner
† cited by third party

*Primary Examiner* — Kamal Saeed

(57) ABSTRACT

This application relates to chemical compounds which may act as inhibitors of, or which may otherwise modulate the activity of, a bromodomain-containing protein, including bromodomain-containing protein 4 (BRD4), and to compositions and formulations containing such compounds, and methods of using and making such compounds. Compounds include compounds of Formula (I)

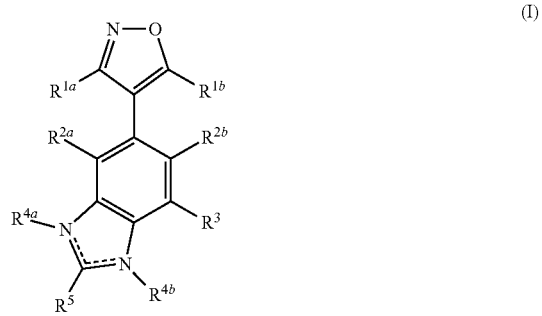

wherein $R^{1a}$, $R^{1b}$, $R^{2a}$, $R^{2b}$, $R^3$, $R^{4a}$, $R^{4b}$, and $R^5$ are described herein.

9 Claims, 4 Drawing Sheets

BENZIMIDAZOLE DERIVATIVES AS BROMODOMAIN INHIBITORS

This application claims the benefits of U.S. Provisional Application 61/821,612, filed on May 9, 2013, U.S. Provisional Application 61/826,912, filed on May 23, 2013, U.S. Provisional Application 61/860,229, filed on Jul. 30, 2013, and U.S. Provisional Application 61/951,347, filed on Mar. 11, 2014, the disclosures of all of which are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 1020-P4C_Sequence_Listing.txt. The text file is 2 KB, was created on Jul. 3, 2014, and is being submitted electronically via EFS-Web.

FIELD

This application relates to chemical compounds which may inhibit, or which may otherwise modulate the activity of, a bromodomain-containing protein, including bromodomain-containing protein 4 (BRD4), and to compositions and formulations containing such compounds, and methods of using and making such compounds.

BACKGROUND

The bromodomain and extraterminal (BET) family of proteins (BET proteins) are readers of the epigenetic code that couple acetylation of lysine residues on histones to changes in chromatin structure and gene expression. The BET family includes BRD2, BRD3, BRD4, and BRDT, all of which are widely expressed across diverse tissues, with the exception of BRDT, whose expression is restricted to the testes. See Wu, S. Y. & Chiang, C. M., *J. Biol. Chem.*, 282: 13141-13145 (2007). Each BET family member contains tandem bromodomains in the N-terminal regions that specifically bind acetylated lysine residues in histones H3 and H4. Id. Once bound to histones, BET proteins recruit protein complexes that modulate gene transcription either directly, such as transcriptional activators or repressors, or indirectly such as chromatin remodeling complexes. BRD4 is the most well studied member of the BET family and is known to preferentially recognize tetra-acetylated histone H4 epigenetic marks. See Filippakopoulos, P., et al., *Cell*, 149: 214-231 (2012). BRD4 recruits the p-TEFb complex to nucleosomes, which in turn phosphorylates the C-terminal tail of RNA polymerase II and increases the transcriptional elongation of neighboring genes. See Yang, Z., et al., *Mol. Cell. Biol.*, 28: 967-976 (2008); Urano, E., et al., *FEBS Lett.*, 582: 4053-4058 (2008).

The epigenetic code, including histone acetylation, is highly perturbed in many pathological disease states, resulting in the aberrant expression of genes that control cell fate, cell differentiation, cell survival, and inflammatory processes. See, e.g., Cohen, I., et al., *Genes Cancer*, 2: 631-647 (2011); Brooks, W. H., et al., *J. Autoimmun.*, 34: 3207-219 (2010); Wierda, R J., et al., *J. Cell Mol. Med.*, 14: 1225-1240 (2010); Shirodkar, A. V. & Marsden, P. A., *Curr. Opin. Cardiol.*, 26: 209-215 (2011); Villeneuve, L. M., et al., *Clin. Exp. Pharmacol. Physiol.*, 38: 401-409 (2011). BET proteins including BRD4 have been identified as important mediators of altered gene expression profiles found in numerous diseases including cancer, diabetes, obesity, atherosclerosis, cardiovascular and renal disorders, and viral infection. See Muller, S., et al., *Expert Rev. Mol. Med.*, 13: e29 (2011); Zhou, M., et al, *J. Virol.*, 83: 1036-1044 (2009); Chung, C. W., et al., *J. Med. Chem.*, 54: 3827-3838 (2011). For example, MYC has been implicated in the majority of human cancers and BET proteins have been identified as regulatory factors of c-Myc; inhibition of BET proteins, including BRD4, has been shown to downregulate MYC transcription. See Delmore, J. E., et al. *Cell*, 146, 904-17 (2011); Lovén, J. et al., *Cell*, 153, 320-34 (2013). Inhibitors and modulators of BET proteins, including BRD4, are therefore needed.

SUMMARY

One aspect provides for a compound of Formula (I)

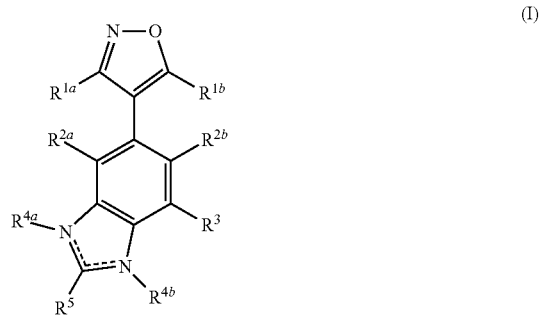

(I)

wherein
R$^{1a}$ and R$^{1b}$ are each independently C$_{1-6}$ alkyl optionally substituted with from 1 to 5 R$^{20}$ groups;
R$^{2a}$ and R$^{2b}$ are each independently H or halo;
R$^{3}$ is
  boronic acid or halo; or
  —C(O)OR$^{a}$, —NHC(O)OR$^{a}$, —NHS(O)$_{2}$R$^{a}$, or —S(O)$_{2}$NR$^{a}$R$^{b}$; or
  selected from the group consisting of C$_{1-10}$ alkyl, C$_{1-10}$ alkoxy, amino, C$_{5-10}$ aryl, C$_{6-20}$ arylalkyl, C$_{1-10}$ heteroalkyl, C$_{5-10}$ heteroaryl, and C$_{6-20}$ heteroarylalkyl, each of which is optionally substituted with from 1 to 5 R$^{20}$ groups;
one of R$^{4a}$ and R$^{4b}$ is selected from the group consisting of H and C$_{1-6}$ alkyl optionally substituted with from 1 to 5 R$^{20}$ groups, and the other is absent;
R$^{5}$ is
  —C(O)OR$^{a}$, —NHC(O)OR$^{a}$, —NHS(O)$_{2}$R$^{a}$, or —S(O)$_{2}$NR$^{a}$R$^{b}$; or
  selected from the group consisting of H, C$_{1-10}$ alkyl, C$_{1-10}$ haloalkyl, C$_{1-10}$ alkoxy, amino, C$_{5-10}$ aryl, C$_{6-20}$ arylalkyl, C$_{1-10}$ heteroalkyl, C$_{5-10}$ heteroaryl, and C$_{6-20}$ heteroarylalkyl, each of which is optionally substituted with from 1 to 5 R$^{20}$ groups;
each R$^{a}$ and R$^{b}$ is independently selected from the group consisting of H, C$_{1-10}$-alkyl, C$_{5-10}$ aryl, C$_{6-20}$ arylalkyl, C$_{1-10}$ heteroalkyl, C$_{5-10}$ heteroaryl, and C$_{6-20}$ heteroarylalkyl, each of which is optionally substituted with from 1 to 5 R$^{20}$ groups; and
each R$^{20}$ is independently selected from the group consisting of acyl, C$_{5-10}$ alkyl, C$_{1-10}$ alkoxy, amino, amido, amidino, C$_{5-10}$ aryl, C$_{6-20}$ arylalkyl, azido, carbamoyl, carboxyl, carboxyl ester, cyano, guanidino, halo, $C_{1-10}$ haloalkyl, $C_{1-10}$ heteroalkyl, $C_{5-10}$ heteroaryl, $C_{6-20}$ heteroarylalkyl, hydroxy, hydrazino, imino, oxo, nitro, sulfinyl, sulfonic acid, sulfonyl, thiocyanate, thiol, and thione;

wherein the $C_{1-10}$ alkyl, $C_{5-10}$ aryl, $C_{6-20}$ arylalkyl, $C_{1-10}$ heteroalkyl, $C_{5-10}$ heteroaryl, and $C_{6-20}$ heteroarylalkyl groups are optionally substituted with from 1 to 3 substituents independently selected from $C_{1-6}$ alkyl, $C_{5-10}$ aryl, halo, $C_{1-6}$ haloalkyl, cyano, hydroxy, and $C_{1-6}$ alkoxy;

or a pharmaceutically acceptable salt thereof.

Another aspect provides for a compound selected from the group consisting of

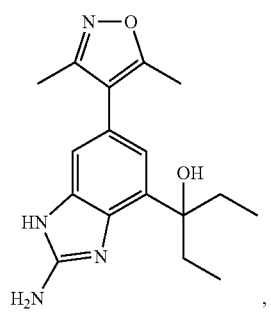

,

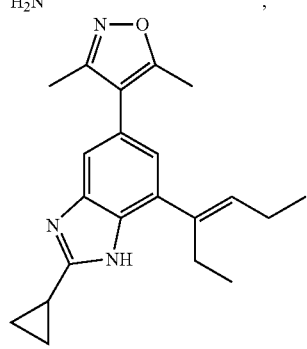

,

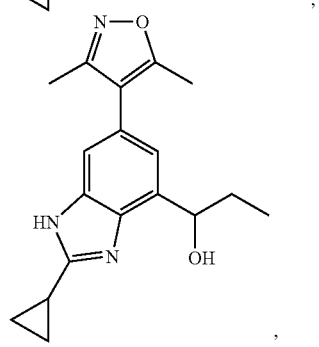

,

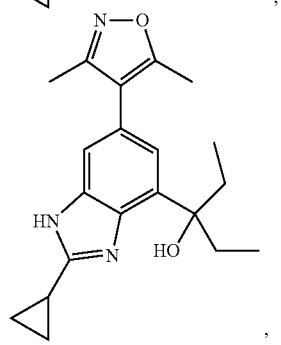

,

-continued

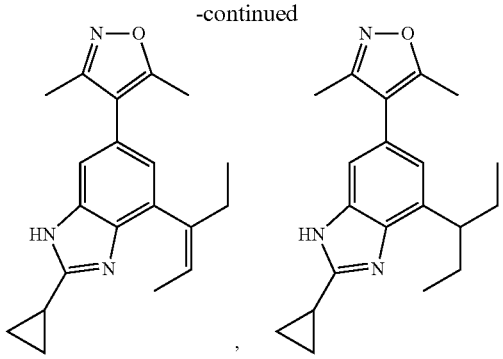

,

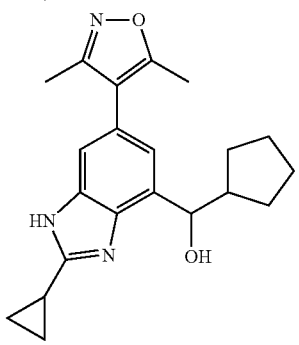

,

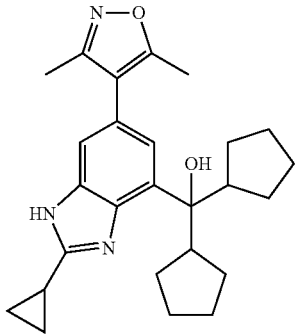

,

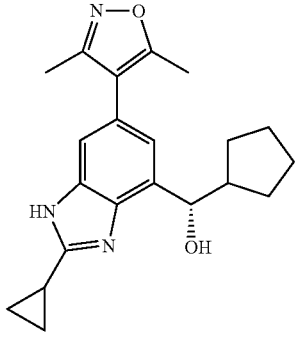

,

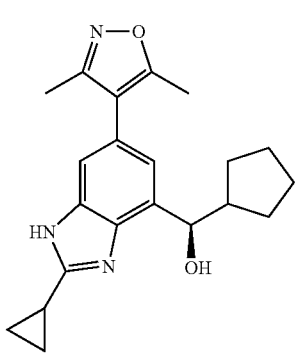

,

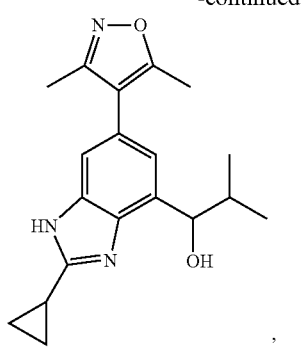
,
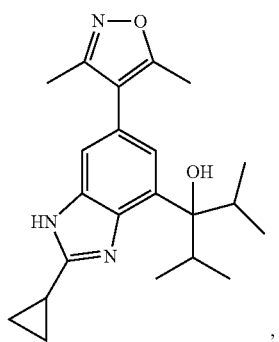
,
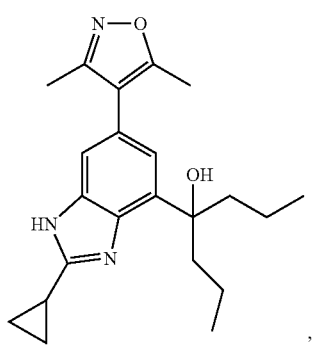
,
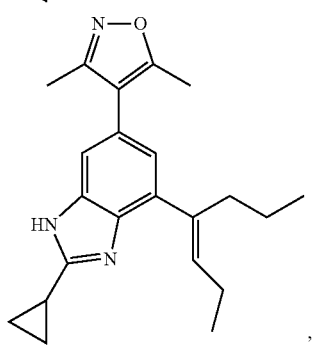
,
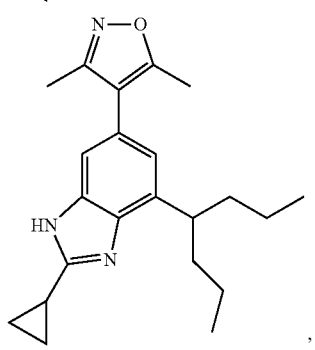
,
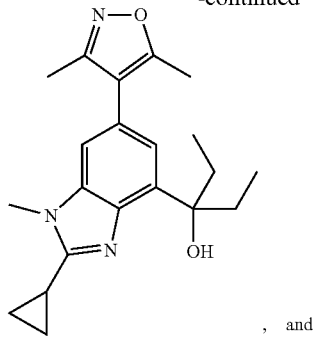
, and
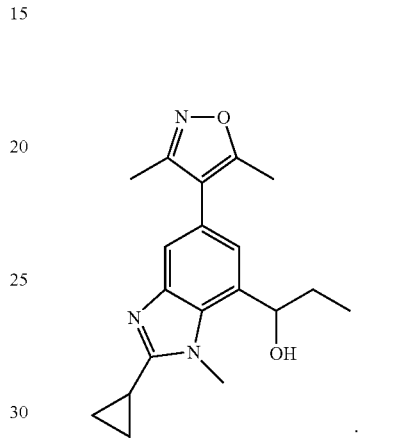
.
Another aspect provides for a compound selected from the group consisting of
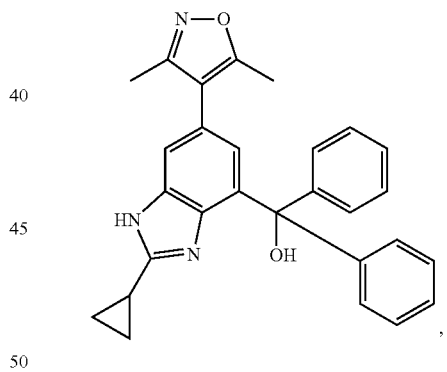
,
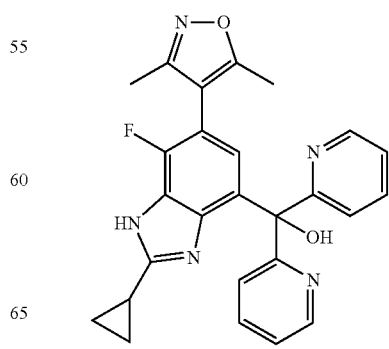
, -continued
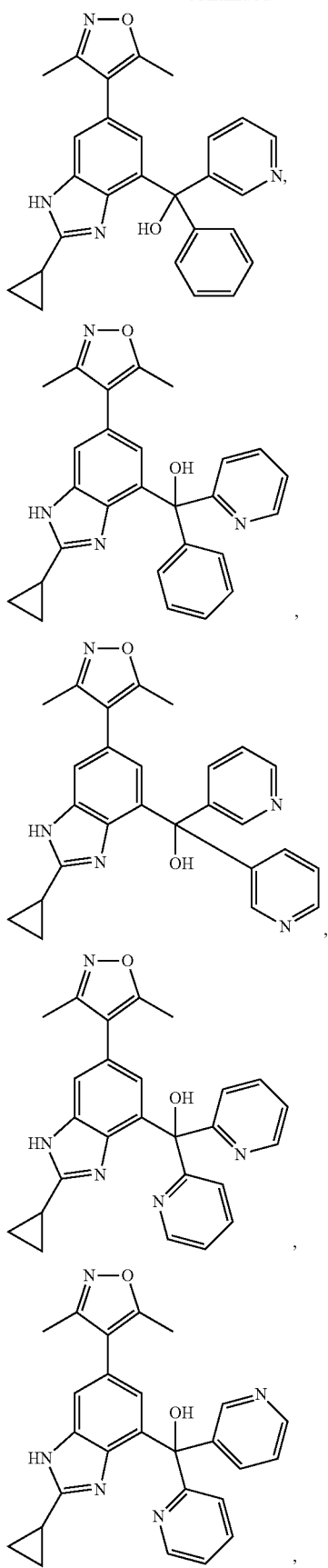
-continued
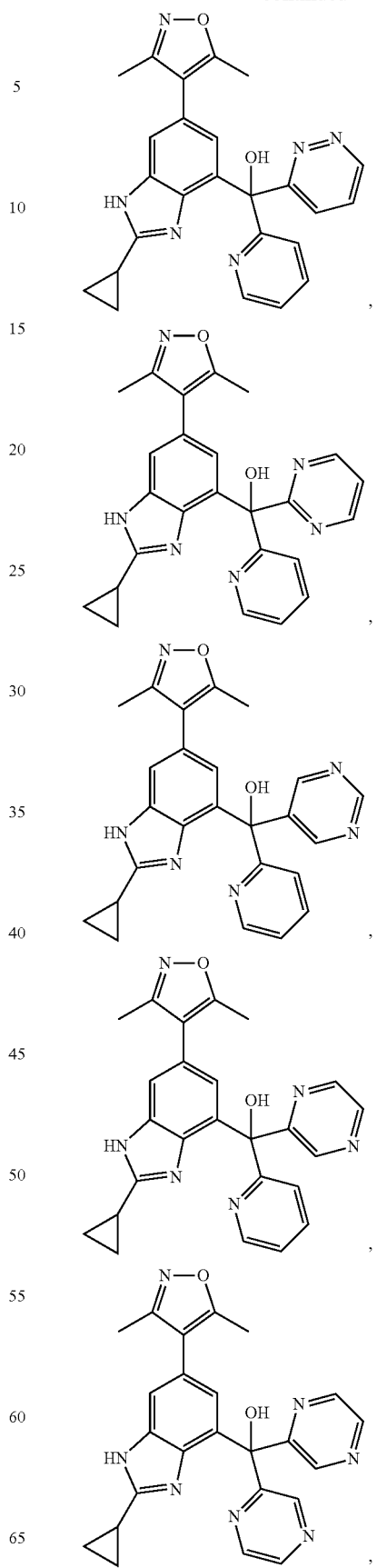

-continued
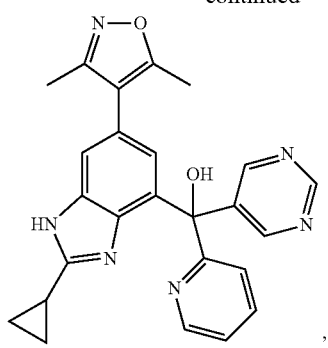
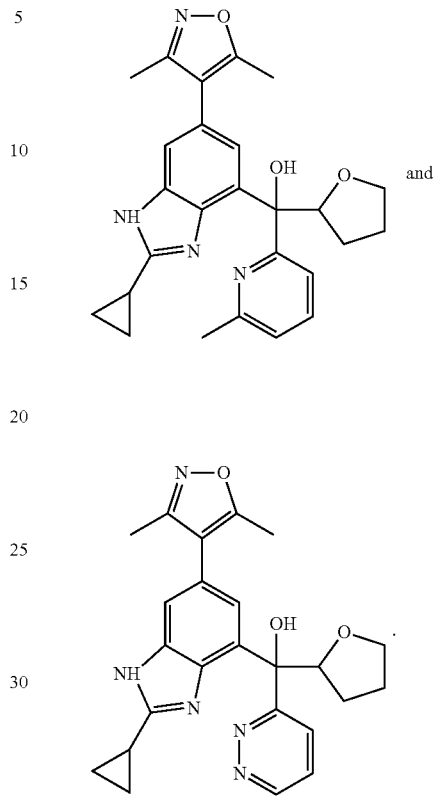
Another aspect provides for a compound selected from the group consisting of
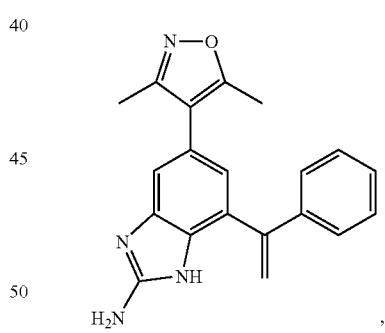
and
Another aspect provides for a compound selected from the group consisting of
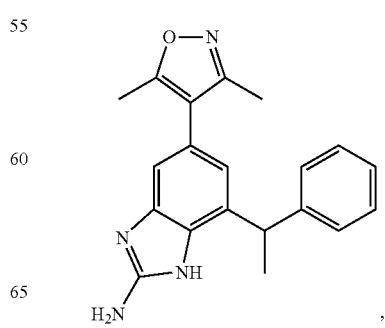

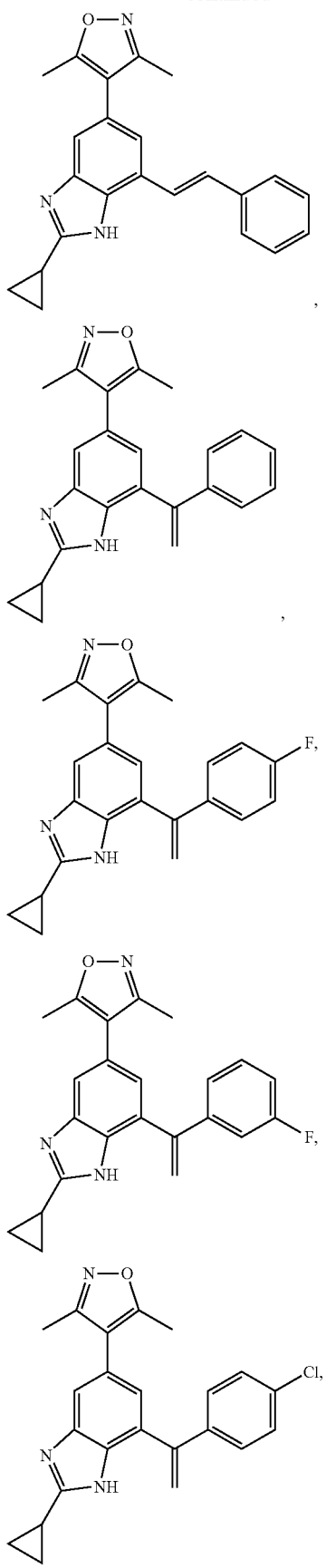
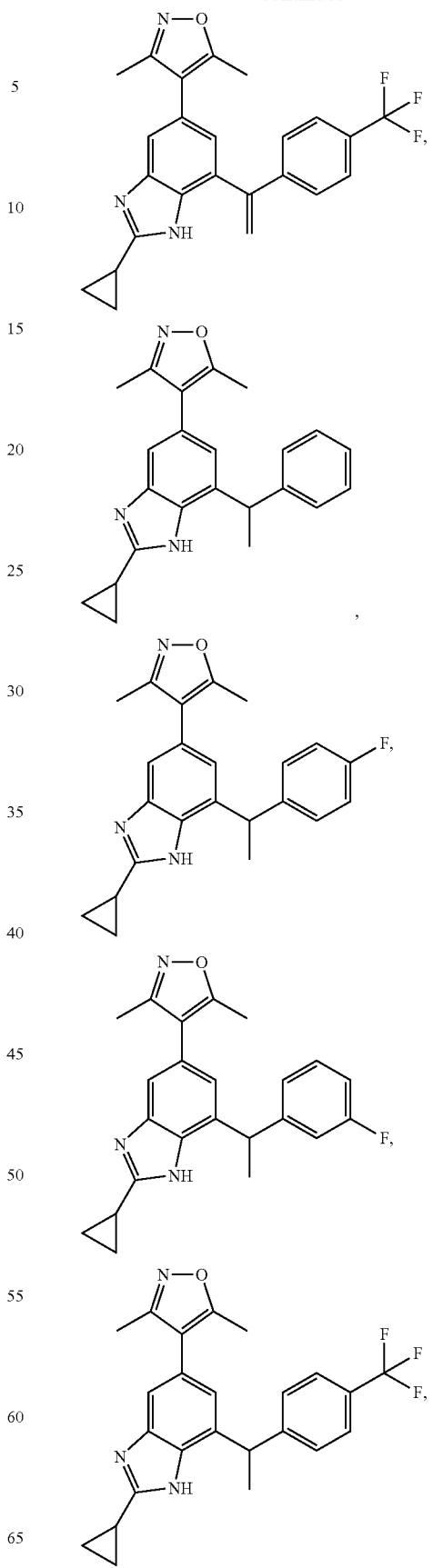

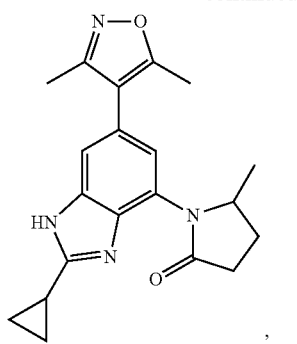
,
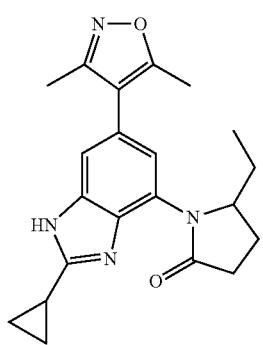
and
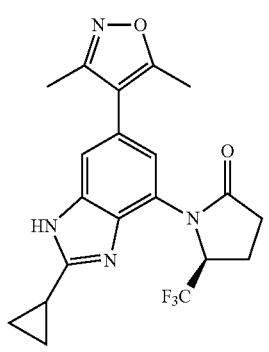
.
Another aspect provides for a compound selected from the group consisting of
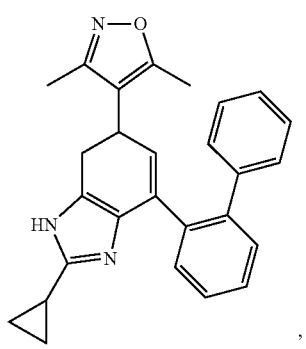
,
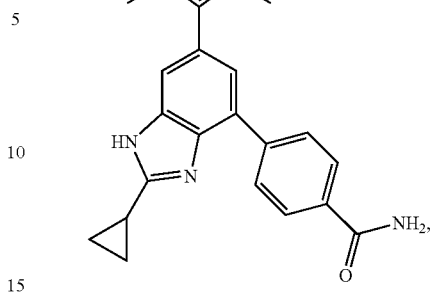
,
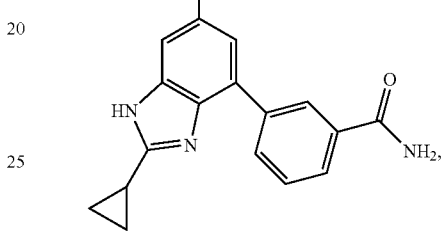
,
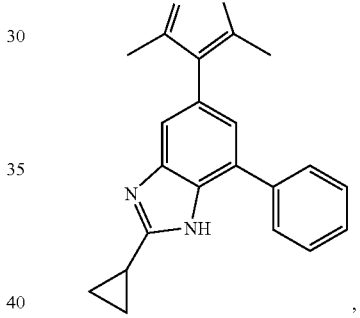
,
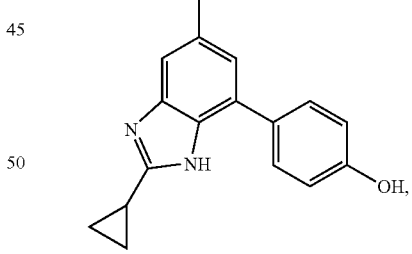
,
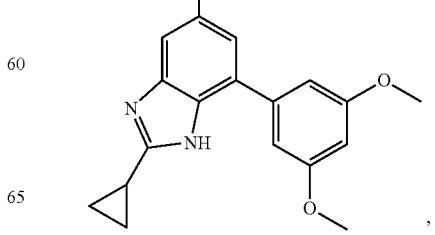
,

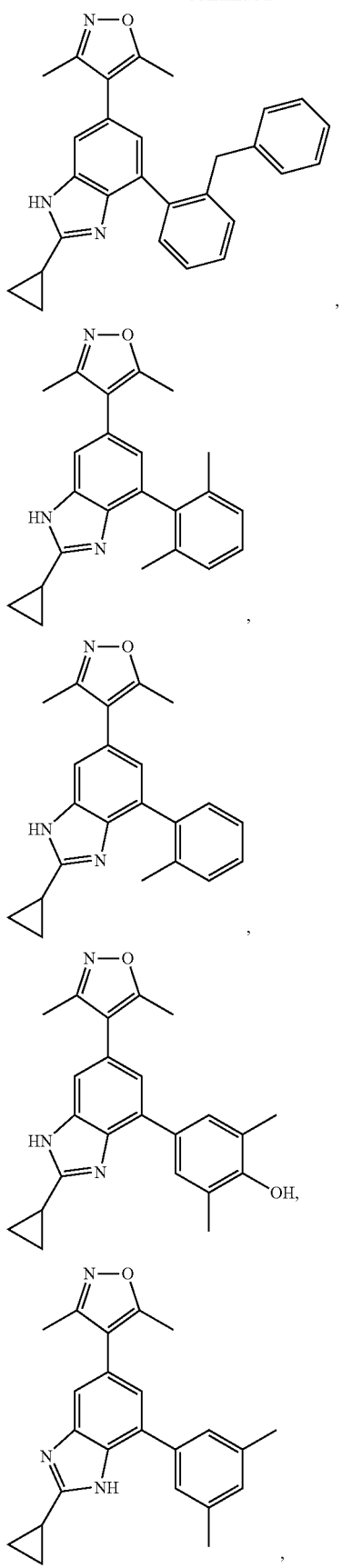
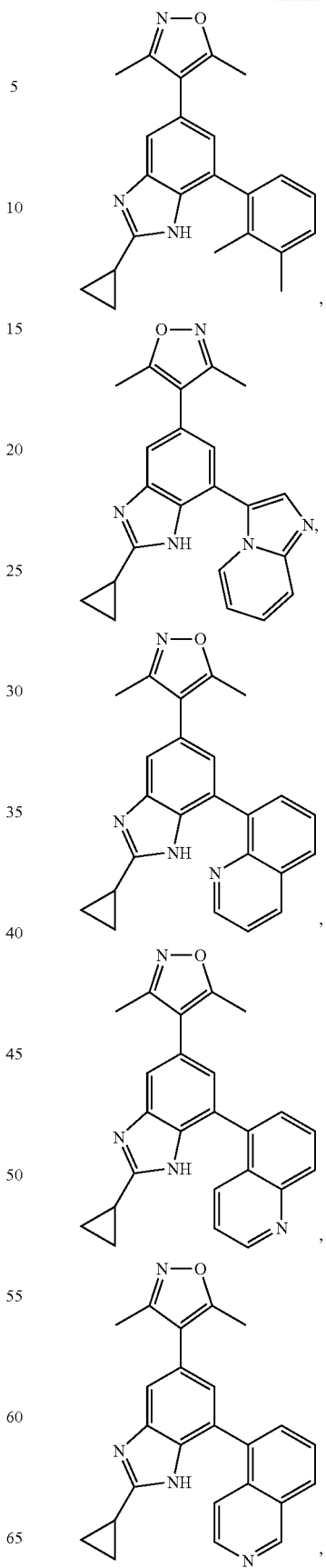

-continued
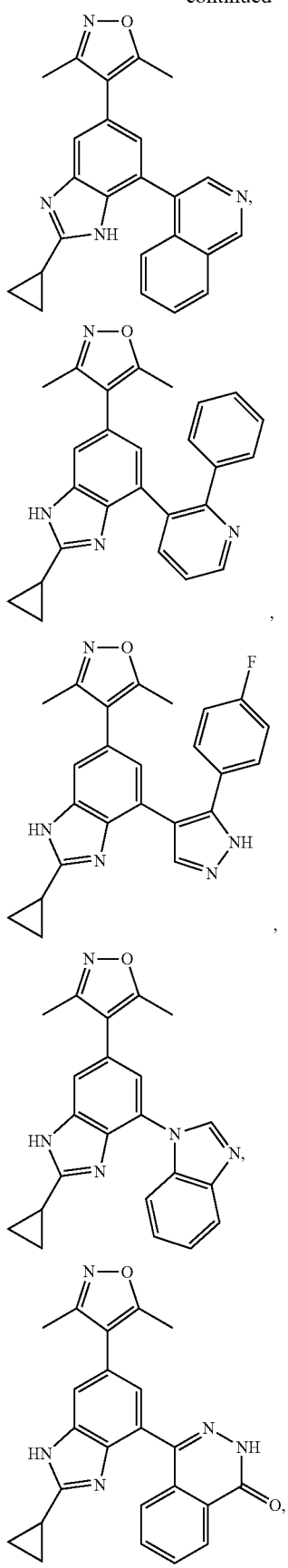
-continued
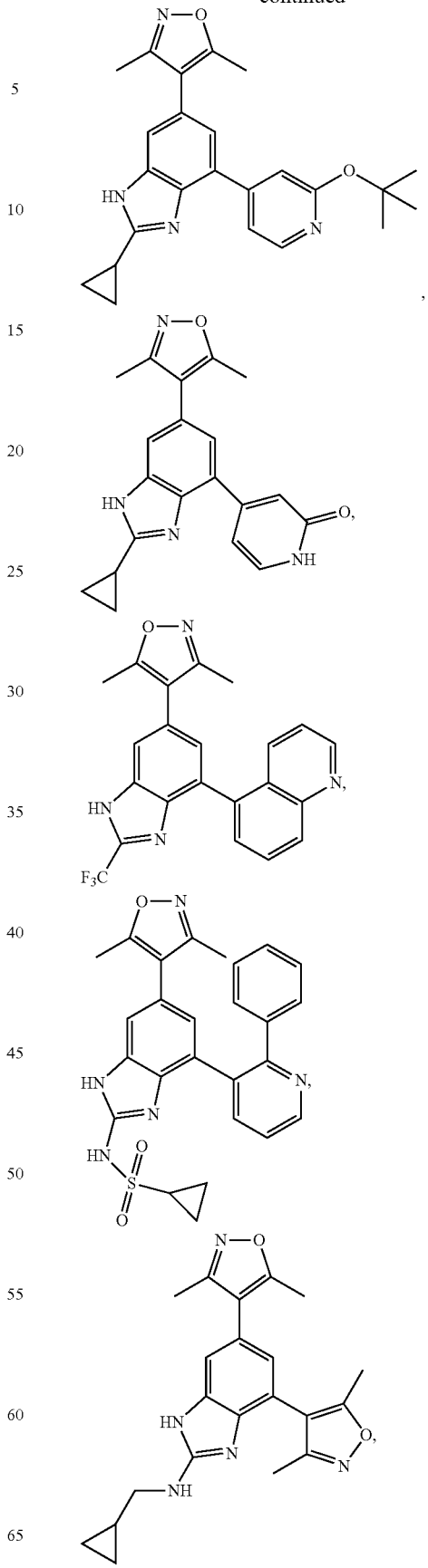

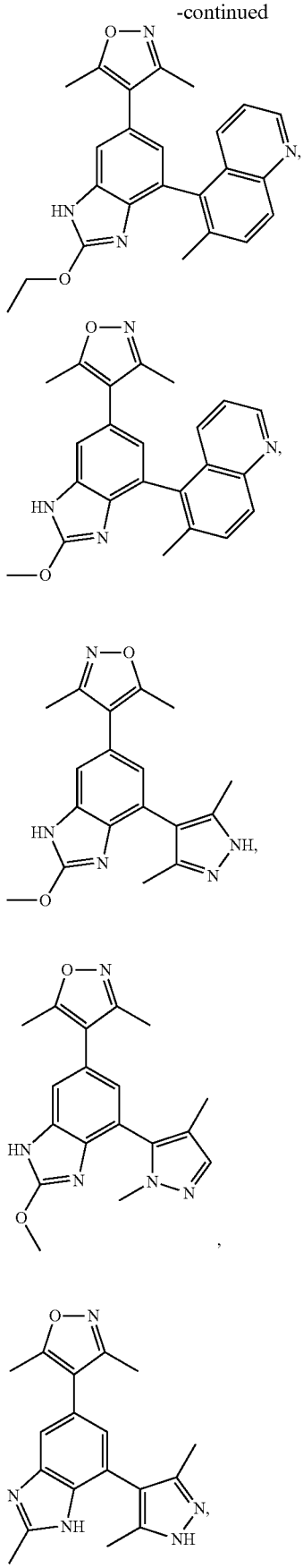
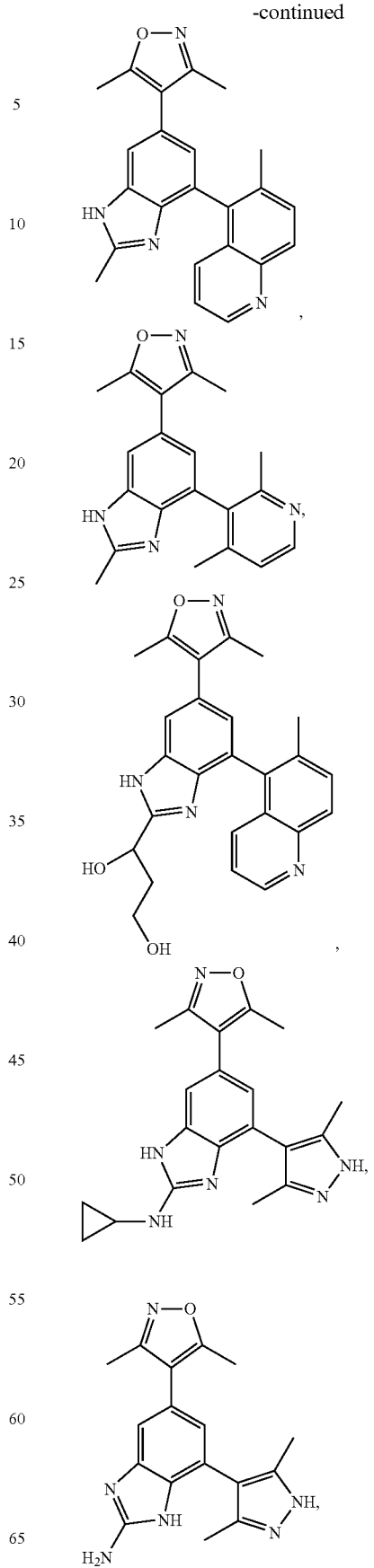

21
-continued
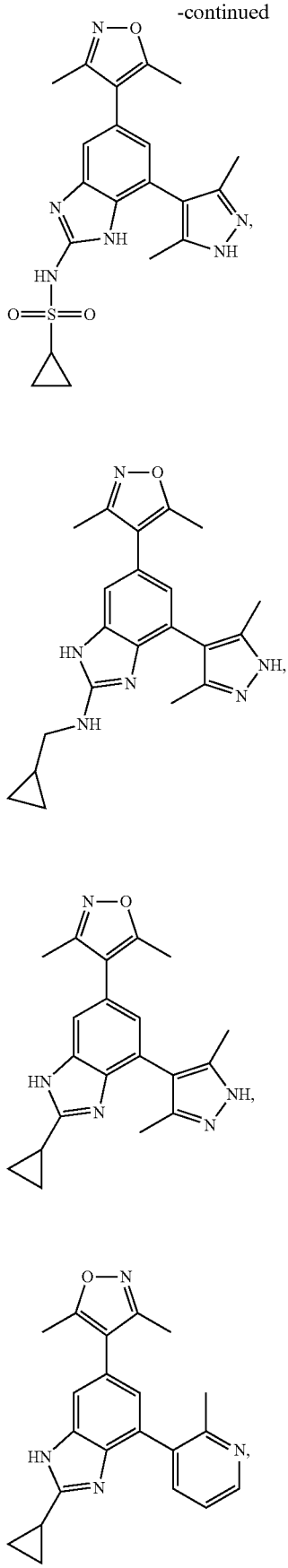
22
-continued
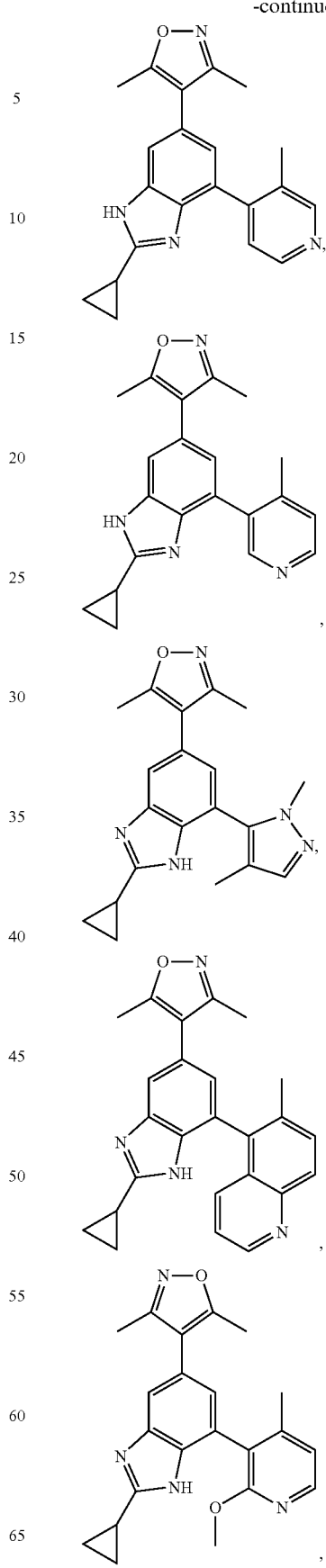

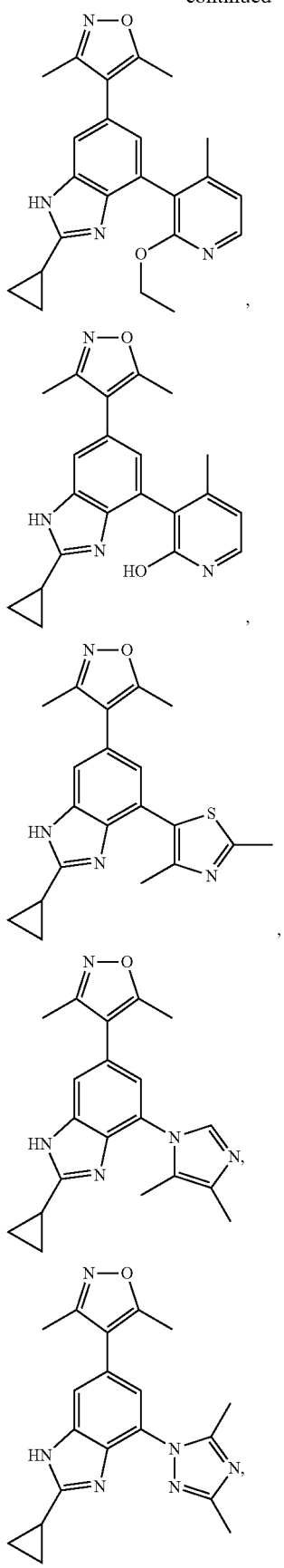
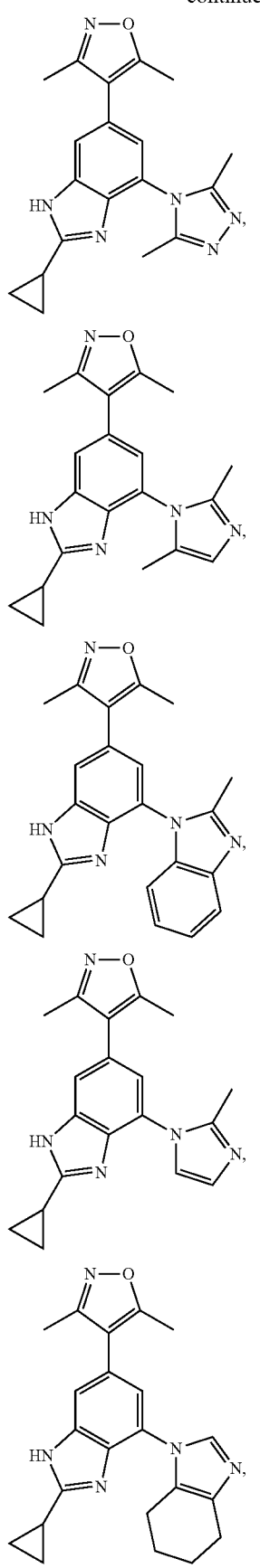

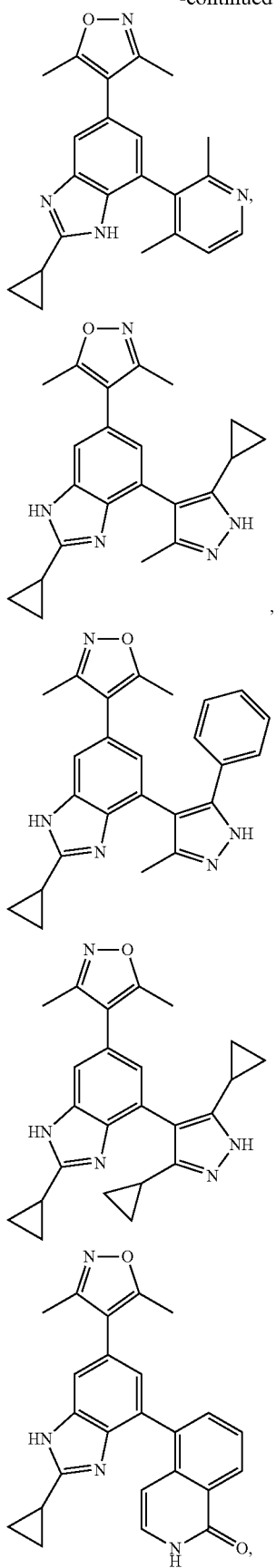
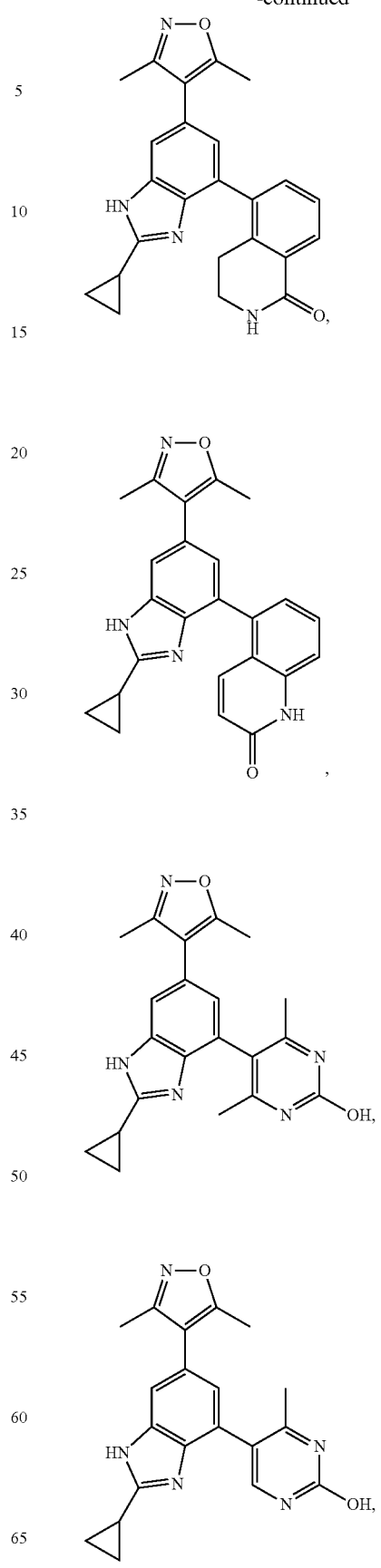

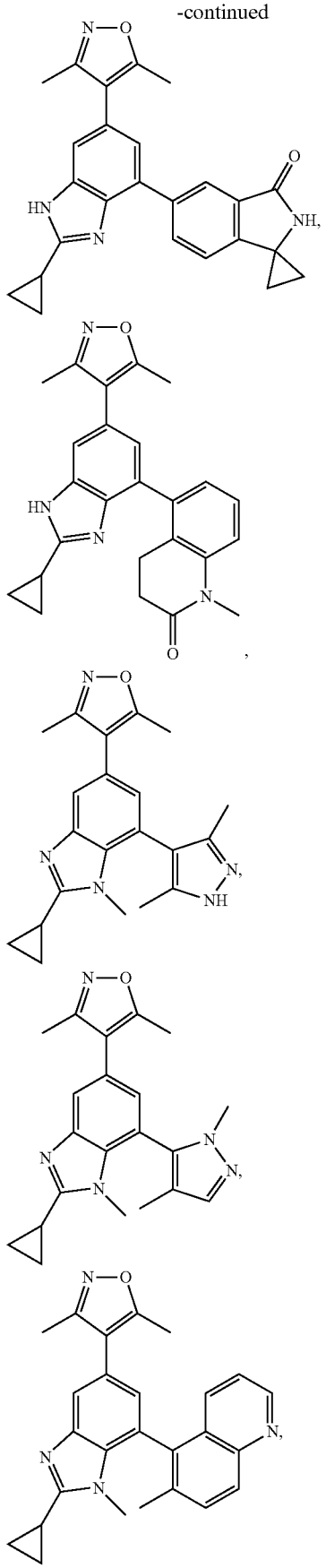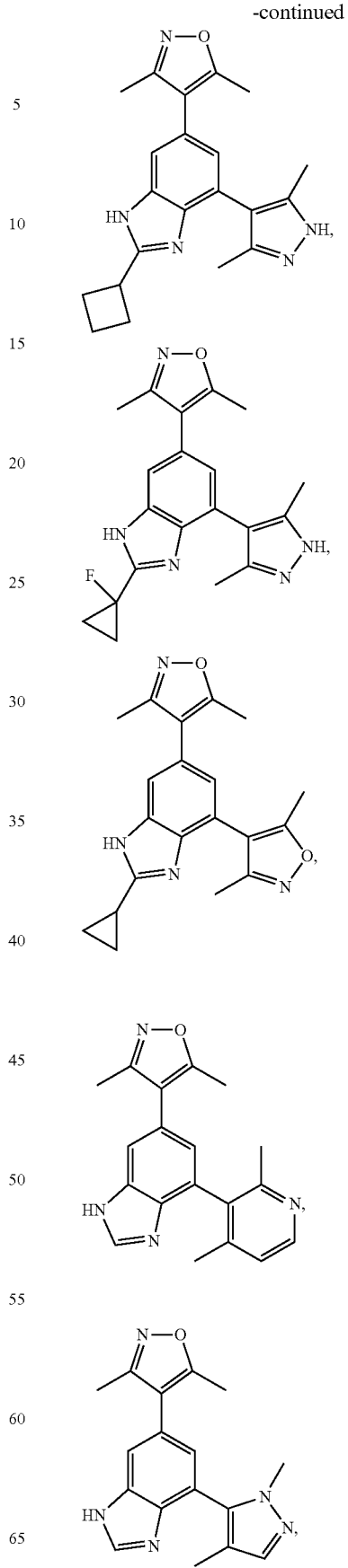

-continued
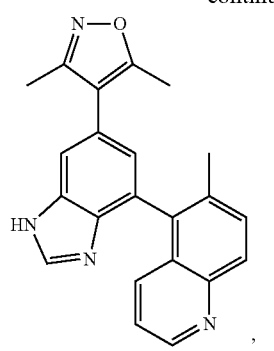
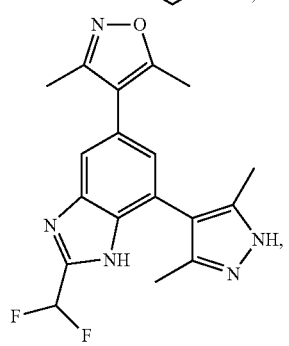
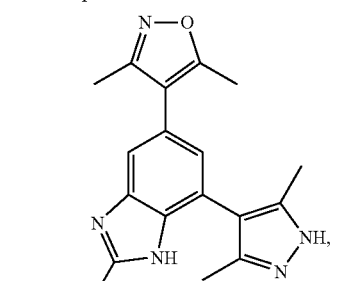
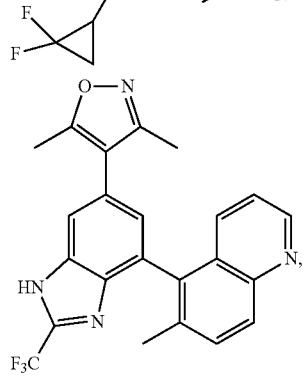
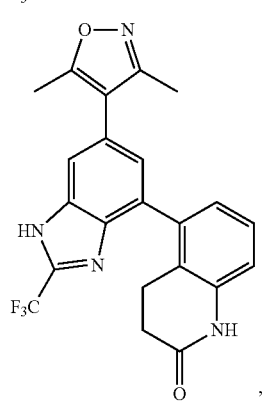
-continued
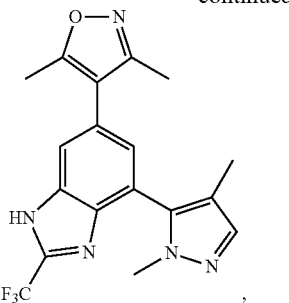
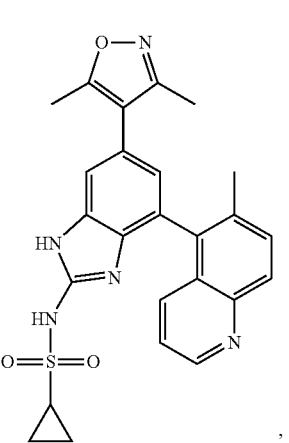
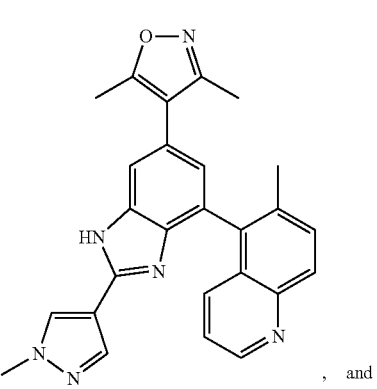
, and
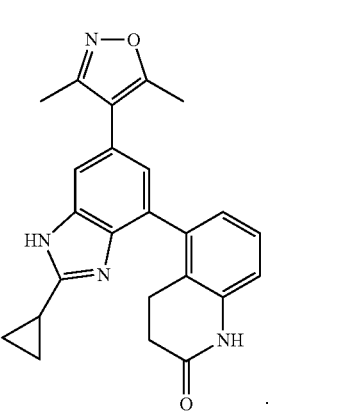

Another aspect provides for a compound selected from the group consisting of
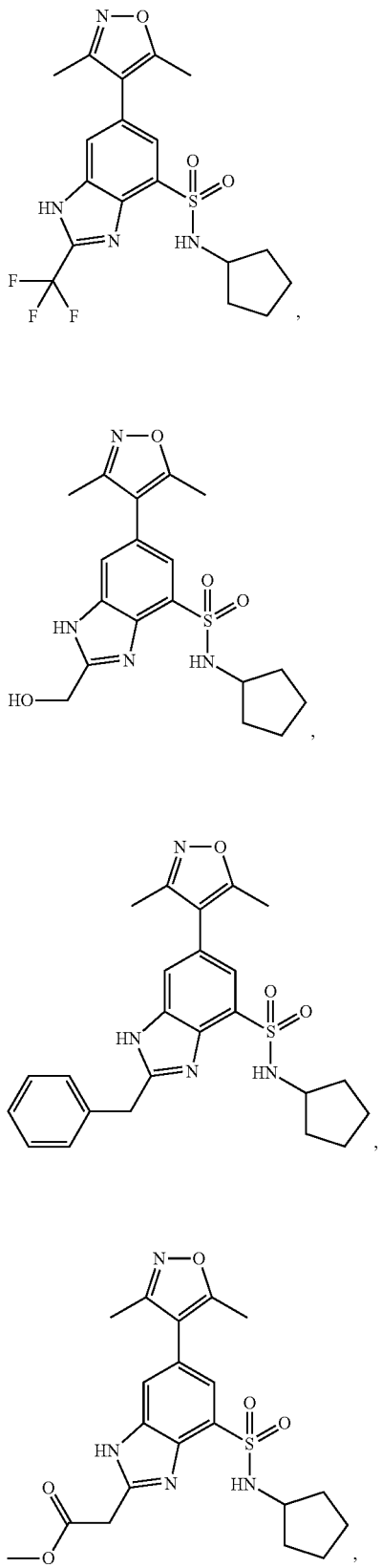
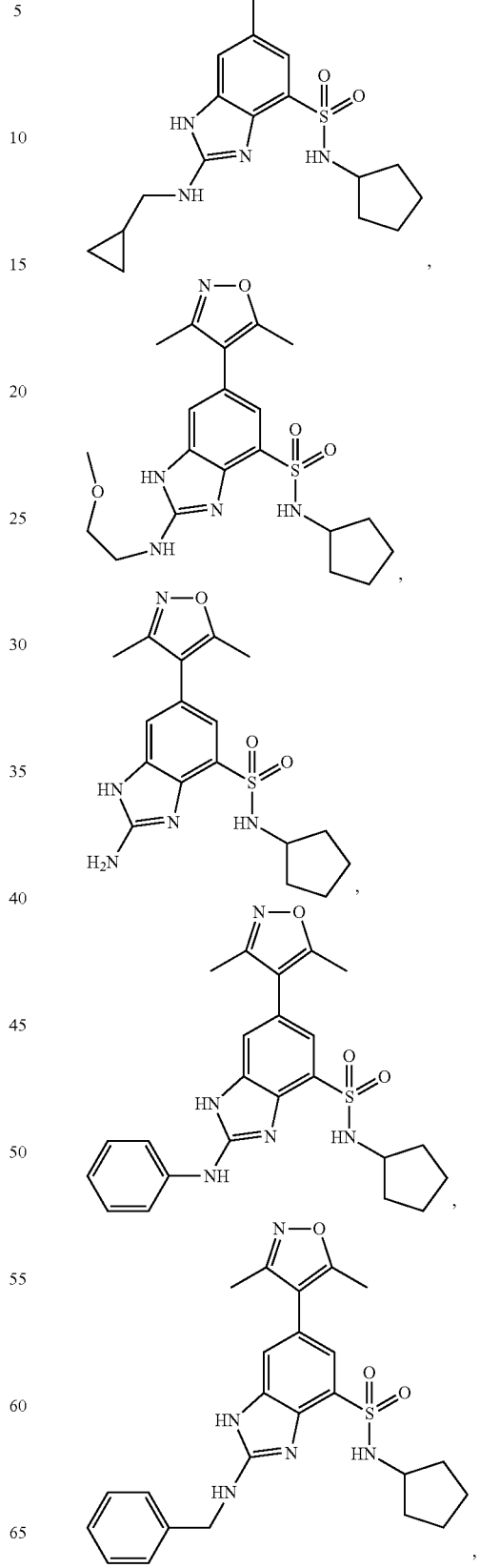

-continued
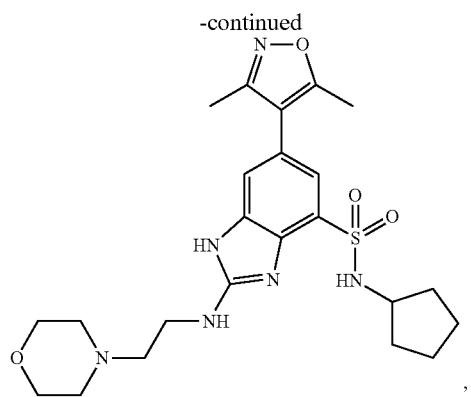
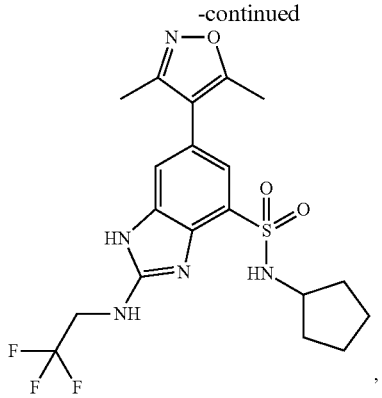
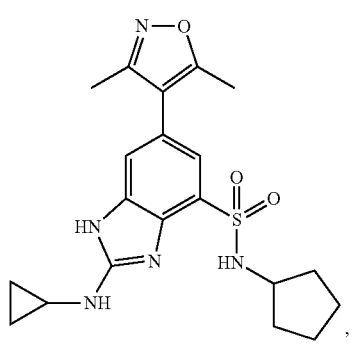
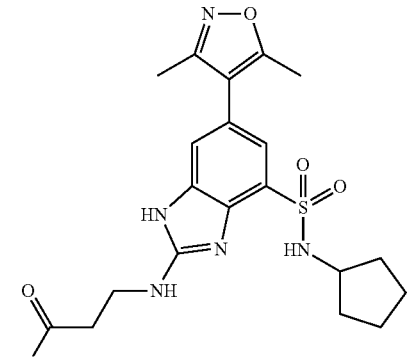
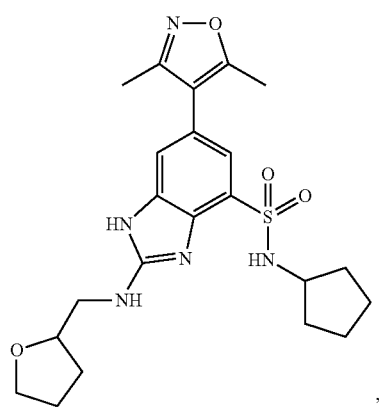
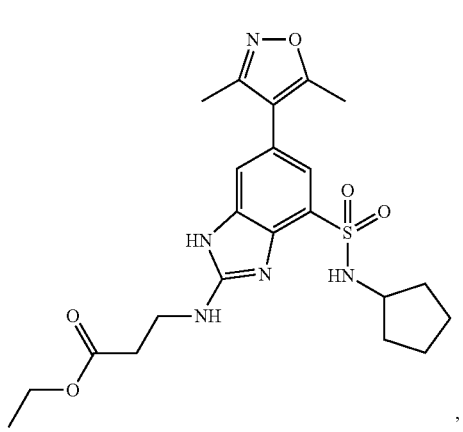
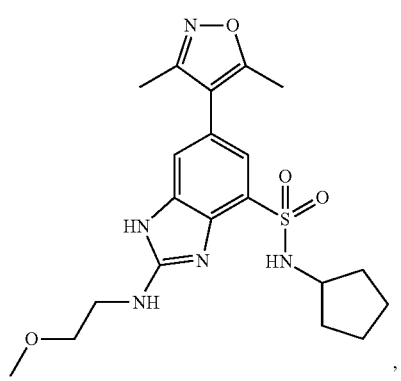
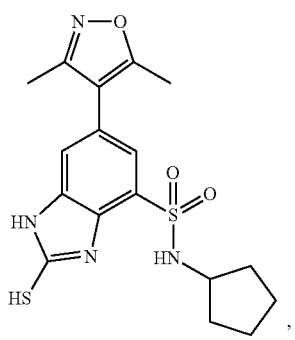

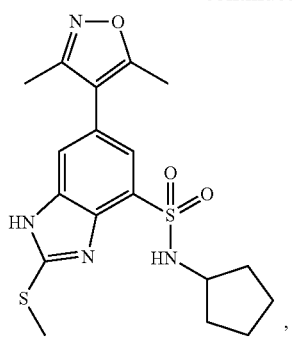
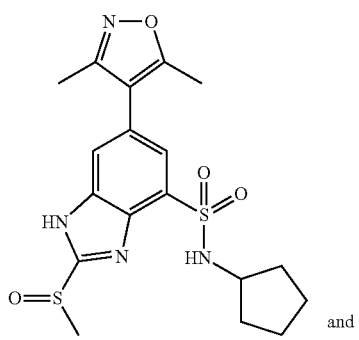
and
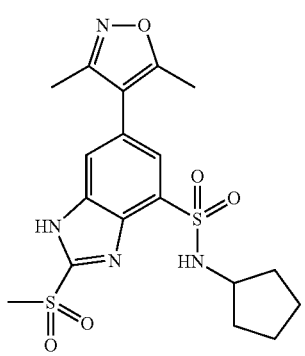
Another aspect provides for a compound selected from the group consisting of
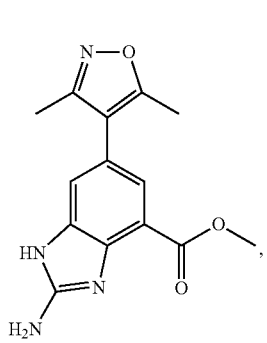
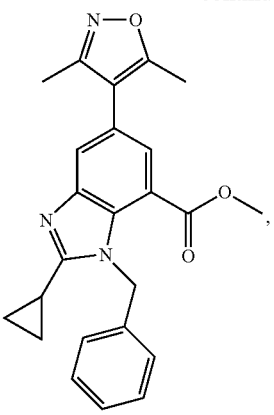
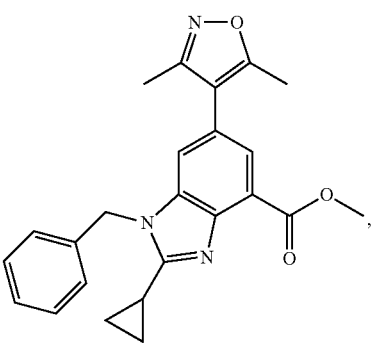
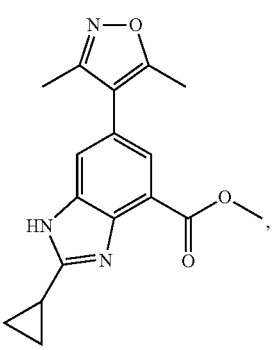 [SMILES: CCC(O)c1cc(-c2c(C)noc2C)cc2nc(C3CC3)n(C)c12]
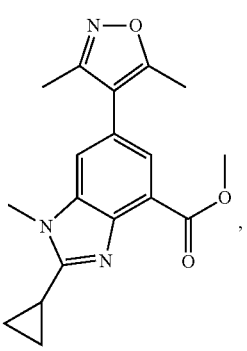

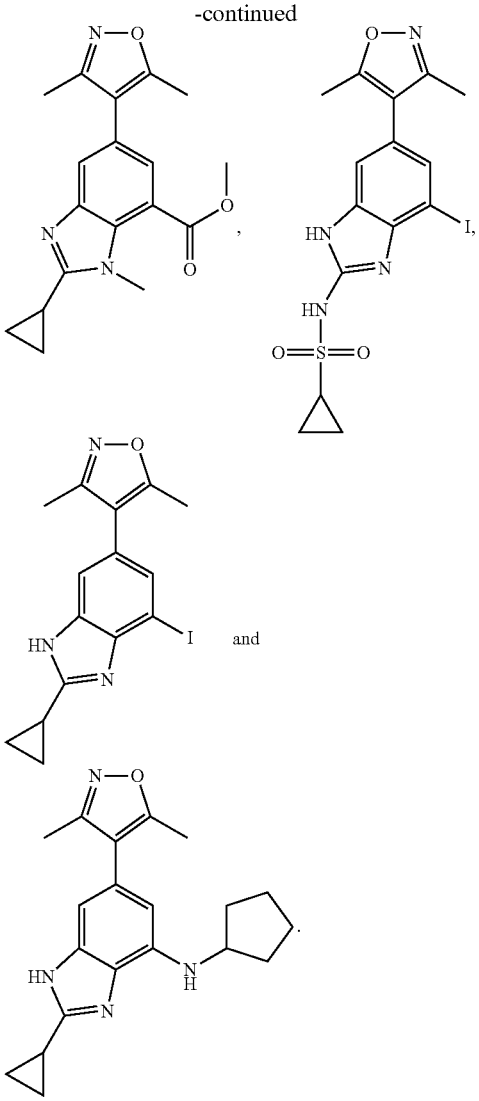

Another aspect provides for a pharmaceutical composition comprising a compound described herein, or a pharmaceutically acceptable salt thereof, and a pharmaceutically acceptable carrier.

Another aspect provides for a use of a compound of Formula (I), or a pharmaceutically acceptable salt thereof, in therapy. Another aspect provides for a method of treating a subject having a disease or condition responsive to the inhibition of a bromodomain-containing protein, comprising administering a therapeutically effective amount of a compound of Formula (I), or a pharmaceutically acceptable salt thereof. In some aspects, the bromodomain-containing protein is BRD4.

In some aspects, the disease or condition is chosen from an autoimmune disease, an inflammatory disease, a neurodegenerative disease, a cardiovascular disorder, a renal disorder, a viral infection, and obesity. In some aspects, the disease or condition is chosen from rheumatoid arthritis, osteoarthritis, atherosclerosis, psoriasis, systemic lupus erythematosus, multiple sclerosis, inflammatory bowel disease, asthma, chronic obstructive airways disease, pneumonitis, dermatitis, alopecia, nephritis, vasculitis, atherosclerosis, Alzheimer's disease, hepatitis, primary biliary cirrhosis, sclerosing cholangitis, diabetes (including type I diabetes), and acute rejection of transplanted organs. In some aspects the disease or condition is cancer, including hematological cancers, lymphoma, multiple myelomas, leukemias, a neoplasm or a tumor (for example a solid tumor). In some aspects the disease or condition is a neoplasm or cancer of the colon, rectum, prostate (for example castrate resistant prostate cancer), lung (for example non-small cell lung cancer, and small-cell lung cancer), pancreas, liver, kidney, cervix, uterus, stomach, ovary, breast (for example basal or basal-like breast cancer, and triple-negative breast cancer), skin (for example melanoma), the nervous system (including the brain, meninges, and central nervous system, including a neuroblastoma, a glioblastoma, a meningioma, and a medulloblastoma). In some aspects the disease or condition is a carcinoma. In some aspects, the disease or condition is hepatocellular carcinoma. In some aspects, the disease or condition is a lymphoma. In some aspects, the disease or condition is a B-cell lymphoma. In some aspects, the disease or condition is Burkitt's lymphoma. In some aspects, the disease or condition is diffuse large B-cell lymphoma. In some aspects, the disease or condition is multiple myeloma. In some aspects, the disease or condition is chronic lymphocytic leukemia. In some aspects the disease or condition is NUT midline cardinoma. In some aspects the subject is a human.

In some aspects, the compound is administered intravenously, intramuscularly, parenterally, nasally, or orally. In one aspect, the compound is administered orally.

Also provided is a method of inhibiting a bromodomain, comprising contacting the bromodomain with a compound of Formula (I), or a pharmaceutically acceptable salt thereof.

Also provided is the use of a compound of Formula (I), or a pharmaceutically acceptable salt thereof, in the manufacture of a medicament for the treatment of a disease or condition responsive to bromodomain inhibition.

Also provided is a compound of Formula (I), or a pharmaceutically acceptable salt thereof, for use in therapy. Further provided is a compound of Formula (I), or a pharmaceutically acceptable salt thereof, for use in treating a subject having a disease or condition responsive to the inhibition of a bromodomain-containing protein. Also provided is a compound of Formula (I), or a pharmaceutically acceptable salt thereof, for use in a method of treatment described above. Also provided is the use of a compound of Formula (I), or a pharmaceutically acceptable salt thereof, in the manufacture of a medicament for the treatment of a subject having a disease or condition responsive to the inhibition of a bromodomain-containing protein. Also provided is the use of a compound of Formula (I), or a pharmaceutically acceptable salt thereof, in the manufacture of a medicament for use in a method of treatment described above.

Also provided are kits that include a compound of Formula (I), or a pharmaceutically acceptable salt thereof. In one aspect, the kit further includes instructions for use. In one aspect, a kit includes a compound of Formula (I), or a pharmaceutically acceptable salt thereof, and instructions for use of the compounds in the treatment of the diseases or conditions described above.

Also provided are articles of manufacture that include a compound of Formula (I), or a pharmaceutically acceptable salt thereof. In one embodiment, the container may be a vial, jar, ampoule, preloaded syringe, or an intravenous bag.

DETAILED DESCRIPTION

Figure 1:
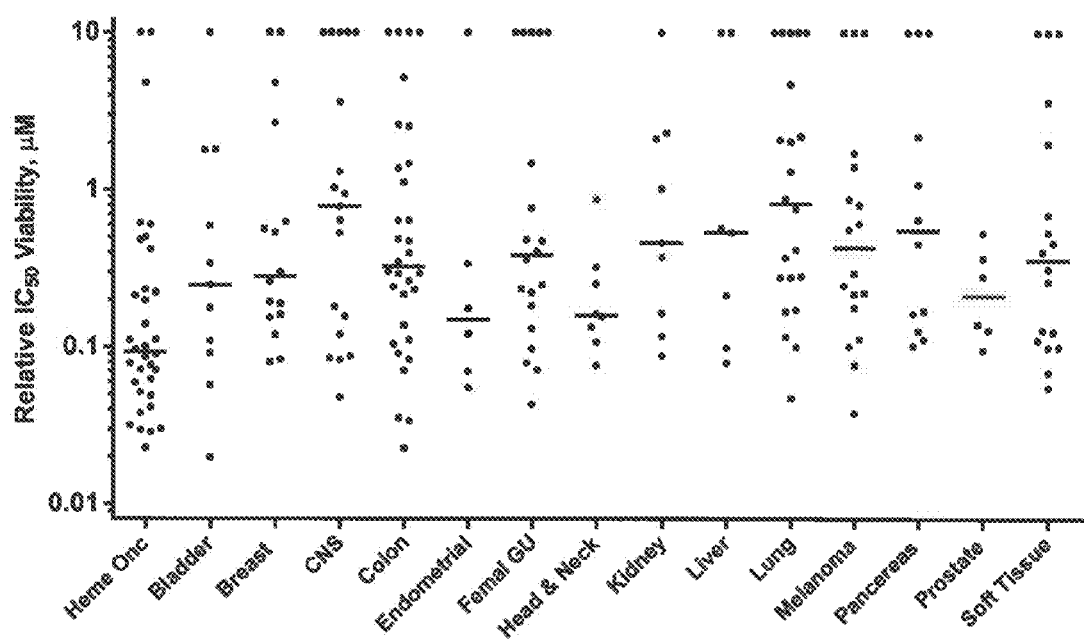
FIG. 1 shows compound 1020-18 inhibited the viability of 240 cancer cell lines. Relative $IC_{50}$ values are reported.

Described herein are compounds of Formula (I), which include compounds of Formulae (Ia), (Ib), (Ic), (Id) and (Ie), compositions and formulations containing such compounds, and methods of using and making such compounds.

One aspect of the current disclosure relates to compounds of Formula (I)

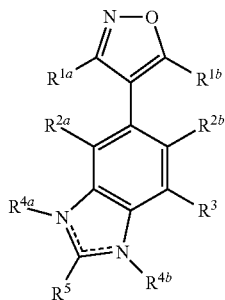

(I)

wherein
$R^{1a}$ and $R^{1b}$ are each independently $C_{1-4}$ alkyl optionally substituted with from 1 to 5 $R^{20}$ groups;
$R^{2a}$ and $R^{2b}$ are each independently H or halo;
$R^3$ is
  boronic acid or halo; or
  —C(O)OR$^a$, —NHC(O)OR$^a$, —NHS(O)$_2$R$^a$, or —S(O)$_2$NR$^a$R$^b$; or
  selected from the group consisting of $C_{1-10}$ alkyl, $C_{1-10}$ alkoxy, amino, $C_{5-10}$ aryl, $C_{6-20}$ arylalkyl, $C_{1-10}$ heteroalkyl, $C_{5-10}$ heteroaryl, and $C_{6-20}$ heteroarylalkyl, each of which is optionally substituted with from 1 to 5 $R^{20}$ groups;
one of $R^{4a}$ and $R^{4b}$ is selected from the group consisting of H and $C_{1-6}$ alkyl optionally substituted with from 1 to 5 $R^{20}$ groups, and the other is absent;
$R^5$ is
  —C(O)OR$^a$, —NHC(O)OR$^a$, —NHS(O)$_2$R$^a$, or —S(O)$_2$NR$^a$R$^b$; or
  selected from the group consisting of H, $C_{1-10}$ alkyl, $C_{1-10}$ haloalkyl, $C_{1-10}$ alkoxy, amino, $C_{5-10}$ aryl, $C_{6-20}$ arylalkyl, $C_{1-10}$ heteroalkyl, $C_{1-10}$ heteroaryl, and $C_{1-20}$ heteroarylalkyl, each of which is optionally substituted with from 1 to 5 $R^{20}$ groups;
each $R^a$ and $R^b$ is independently selected from the group consisting of H, $C_{1-10}$ alkyl, $C_{5-10}$ aryl, $C_{6-20}$ arylalkyl, $C_{1-10}$ heteroalkyl, $C_{5-10}$ heteroaryl, and $C_{6-20}$ heteroarylalkyl, each of which is optionally substituted with from 1 to 5 $R^{20}$ groups; and
each $R^{20}$ is independently selected from the group consisting of acyl, $C_{1-10}$ alkyl, $C_{1-10}$ alkoxy, amino, amido, amidino, $C_{5-10}$ aryl, $C_{6-20}$ arylalkyl, azido, carbamoyl, carboxyl, carboxyl ester, cyano, guanidino, halo, $C_{5-10}$ haloalkyl, $C_{1-10}$ heteroalkyl, $C_{5-10}$ heteroaryl, $C_{6-20}$ heteroarylalkyl, hydroxy, hydrazino, imino, oxo, nitro, sulfinyl, sulfonic acid, sulfonyl, thiocyanate, thiol, and thione;

wherein the $C_{1-10}$ alkyl, $C_{5-10}$ aryl, $C_{6-20}$ arylalkyl, $C_{1-10}$ heteroalkyl, $C_{5-10}$ heteroaryl, and $C_{6-20}$ heteroarylalkyl groups are optionally substituted with from 1 to 3 substituents independently selected from $C_{1-6}$ alkyl, $C_{5-10}$ aryl, halo, $C_{1-6}$ haloalkyl, cyano, hydroxy, and $C_{1-6}$ alkoxy;
or a pharmaceutically acceptable salt thereof.

Compounds of Formula (I) (which include compounds of any of Formulae (Ia), (Ib), (Ic), (Id) and (Ie), described below) can include, independently, one or more of the following features. It will be recognized that features specified in each embodiment may be combined with other specified features to provide further embodiments.

In some compounds, $R^{1a}$ and $R^{1b}$ are each independently $C_{1-6}$ alkyl which, as defined herein, includes alkenyl, alkynyl and cycloalkyl. In some compounds, $R^{1a}$ and $R^{1b}$ are different, and in other compounds $R^{1a}$ and $R^{1b}$ are the same. In some compounds, $R^{1a}$ and $R^{1b}$ are each independently a $C_{1-6}$ alkyl optionally substituted with 1-5 $R^{20}$ groups. In some compounds, $R^{1a}$ and $R^{1b}$ are both methyl. In some compounds, one of $R^{1a}$ or $R^{1b}$ is a methyl and the other is a methyl substituted with a hydroxy. In some compounds, $R^{1a}$ and $R^{1b}$ are both methyl substituted with a hydroxy. In some compounds, one of $R^{1a}$ or $R^{1b}$ is a methyl and the other is a methyl substituted with an amine. In some compounds, $R^{1a}$ and $R^{1b}$ are both methyl substituted with an amine.

In some compounds, $R^{2a}$ and $R^{2b}$ are both H. In some compounds, $R^{2a}$ and $R^{2b}$ are both halo. In some compounds, one of $R^{2a}$ and $R^{2b}$ is H and the other is halo. In some compounds the halo is —F or —Cl.

In some compounds, $R^3$ is boronic acid, a boronic acid ester, or halo. In some compounds, $R^3$ is —C(O)OR$^a$, —NHC(O)OR$^a$, —NHS(O)$_2$R$^a$, or —S(O)$_2$NR$^a$R$^b$ wherein $R^a$ and $R^b$ are described above. In some compounds, $R^3$ is —C(O)OR$^a$, —NHC(O)OR$^a$, —NHS(O)$_2$R$^a$, or —S(O)$_2$NR$^a$R$^b$, wherein each $R^a$ and $R^b$ is independently $C_{1-10}$ alkyl, $C_{5-10}$ aryl, $C_{1-10}$ heteroalkyl or $C_{5-10}$ heteroaryl, each of which may be optionally substituted as described above. For example, in some compounds $R^3$ is —C(O)OR$^a$, —NHC(O)OR$^a$, —NHS(O)$_2$R$^a$, or —S(O)$_2$NR$^a$R$^b$, wherein each $R^a$ and $R^b$ is independently $C_{5-10}$ aryl or $C_{5-10}$ heteroaryl. In some compounds, $R^3$ is selected from the group consisting of $C_{1-10}$ alkyl, $C_{1-10}$ alkoxy, amino, $C_{5-10}$ aryl, $C_{6-20}$ arylalkyl, $C_{1-10}$ heteroalkyl, $C_{5-10}$ heteroaryl, and $C_{6-20}$ heteroarylalkyl, each of which is optionally substituted with from 1 to 5 $R^{20}$ groups, wherein $R^{20}$ is described above. In some compounds, $R^3$ is $C_{1-10}$ alkyl, $C_{1-10}$ alkoxy, or $C_{1-10}$ heteroalkyl, each of which may be optionally substituted as described above. In some compounds, the heteroalkyl is a heterocycloalkyl. In other compounds, $R^3$ is $C_{6-20}$ arylalkyl or $C_{6-20}$ heteroarylalkyl, each of which may be optionally substituted as described above. In other compounds, $R^3$ is $C_{5-10}$ aryl, $C_{6-20}$ arylalkyl, $C_{5-10}$ heteroaryl, or $C_{6-20}$ heteroarylalkyl, each of which may be optionally substituted as described above. In some compounds, $R^3$ is amino optionally substituted as described above. For example, in some compounds $R^3$ is —NH$_2$, and in other compounds $R^3$ is —NR$^y$R$^z$, wherein R$^y$ and R$^z$ together with the nitrogen to which they are bonded form a $C_{1-10}$ heteroalkyl or $C_{5-10}$ heteroaryl, each of which may be optionally substituted as described above.

Other non-limiting examples of $R^3$ include the following:

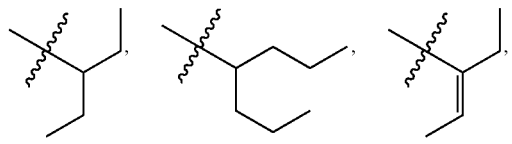

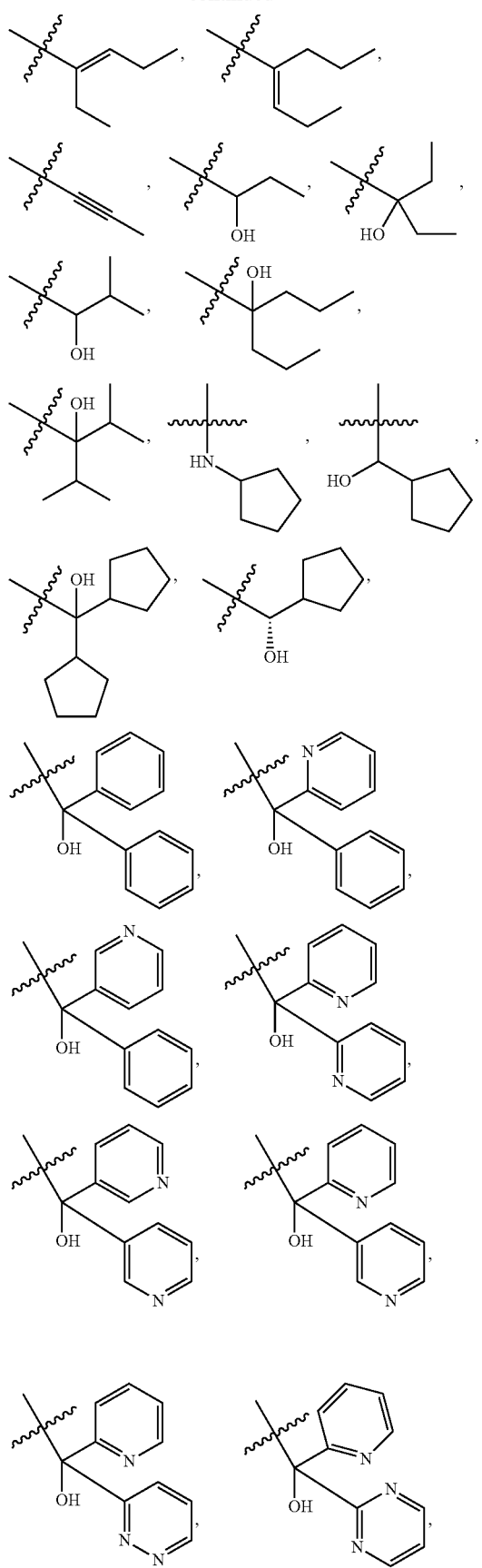
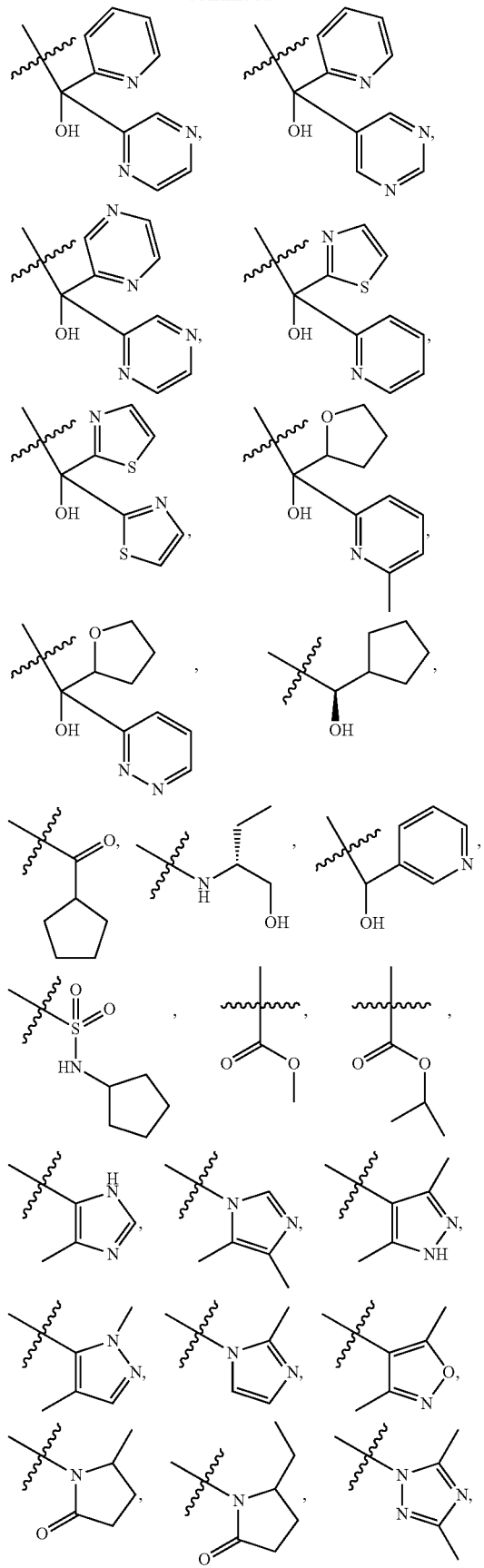

-continued
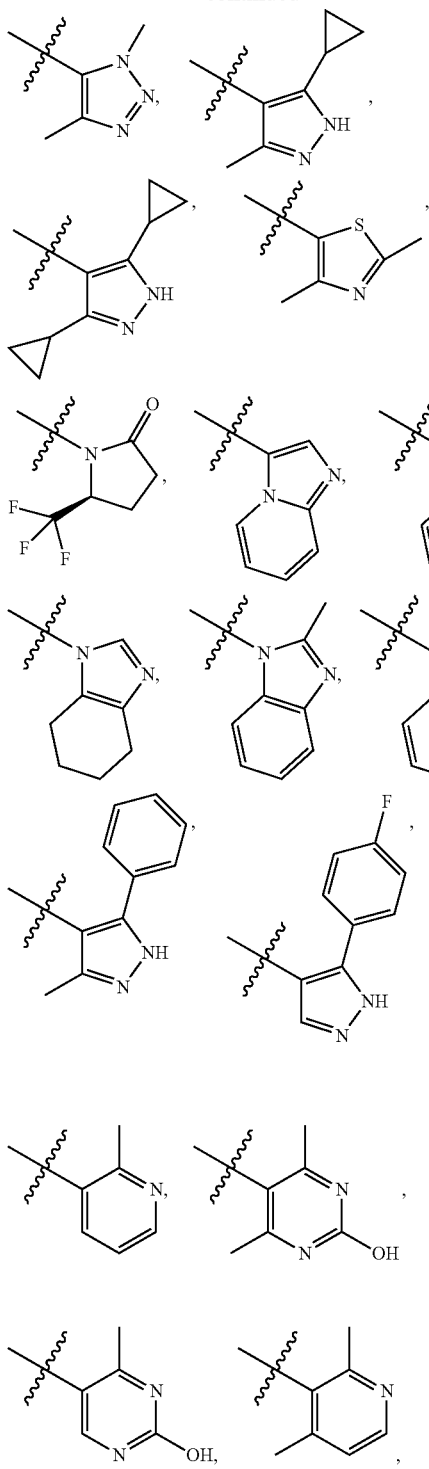
-continued
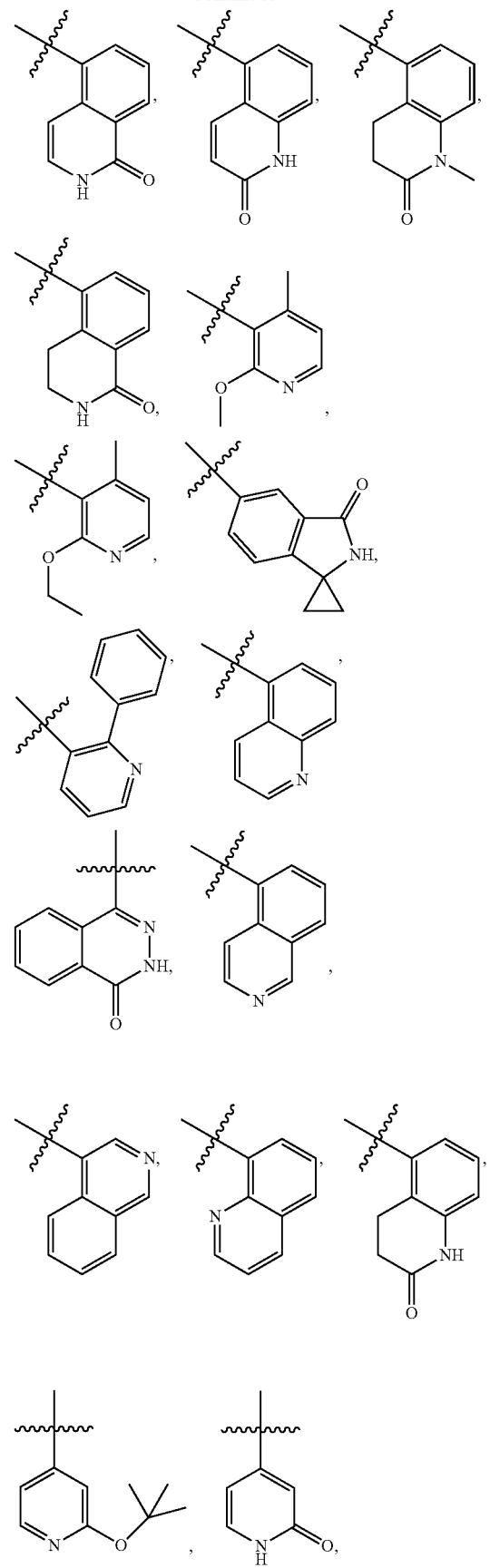

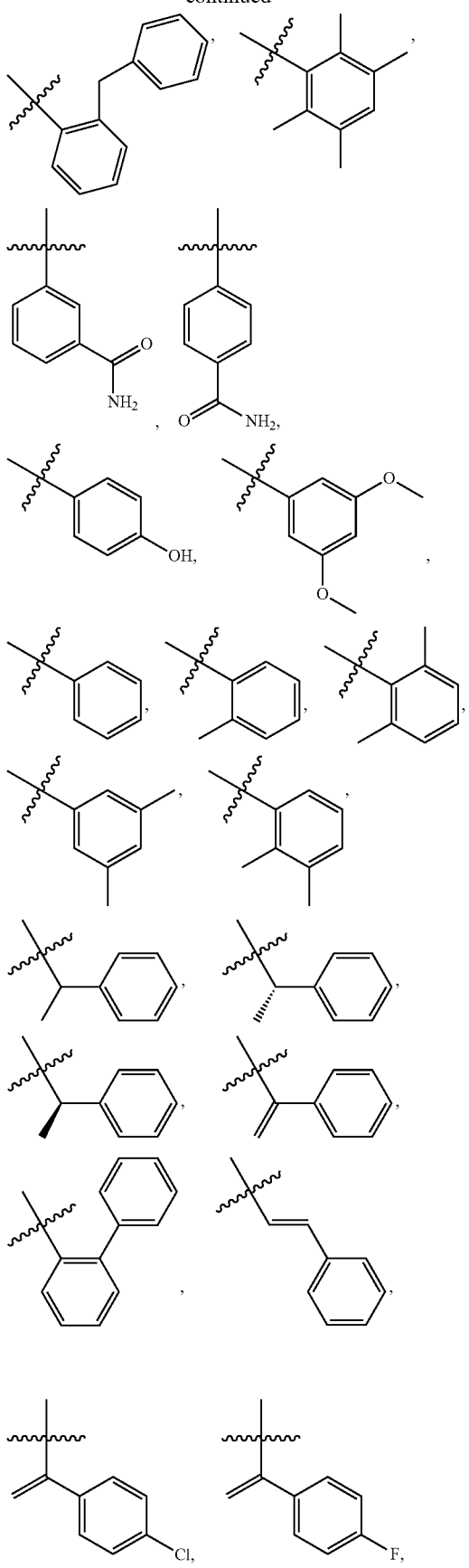

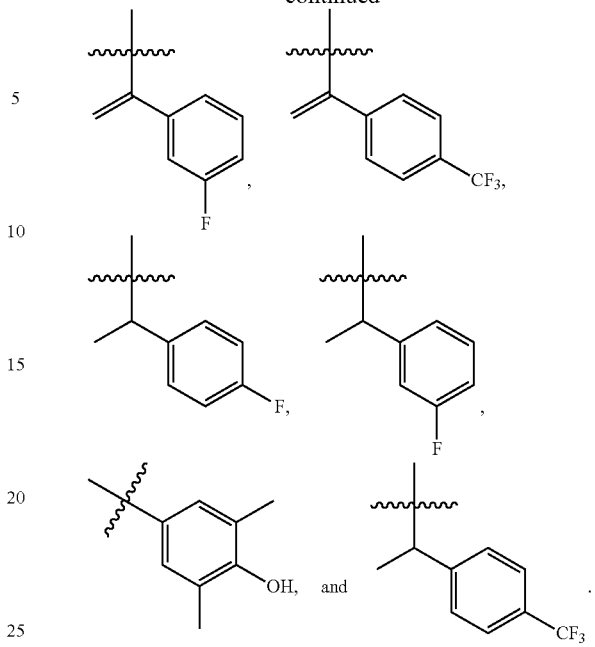

In some compounds, one of $R^{4a}$ or $R^{4b}$ is H and the other is absent, that is, in some compounds $R^{4a}$ is H and $R^{4b}$ is absent, and in other compounds $R^{4a}$ is absent and $R^{4b}$ is H. In other compounds, one of $R^{4a}$ and $R^{4b}$ is alkyl and the other is absent, that is, in some compounds $R^{4a}$ is alkyl and $R^{4b}$ is absent, and in other compounds $R^{4a}$ is absent and $R^{4b}$ is alkyl. In some compounds the alkyl is methyl.

In some compounds, $R^5$ is —C(O)OR$^a$, —NHC(O)OR$^a$, —NHS(O)$_2$R$^a$, or —S(O)$_2$NR$^a$R$^b$, wherein R$^a$ and R$^b$ are described above. In some compounds, $R^5$ is —C(O)OR$^a$, —NHC(O)OR$^a$, —NHS(O)$_2$R$^a$, or —S(O)$_2$NR$^a$R$^b$, wherein each R$^a$ and R$^b$ is independently $C_{1-10}$ alkyl or $C_{5-10}$ aryl, each of which may be optionally substituted as described above. For example, in some compounds $R^5$ is —NHC(O)OR$^a$, wherein R$^a$ is methyl. In some compounds, $R^5$ is —NHS(O)$_2$R$^a$, wherein R$^a$ is $C_{1-10}$ alkyl or $C_{5-10}$ aryl, each of which may be optionally substituted as described above. For example, in some compounds $R^5$ is —NHS(O)$_2$R$^a$, wherein R$^a$ is cyclopropyl. In some compounds, $R^5$ is selected from the group consisting of H, $C_{1-10}$ alkyl, $C_{1-10}$ haloalkyl, $C_{1-10}$ alkoxy, amino, $C_{5-10}$ aryl, $C_{6-20}$ arylalkyl, $C_{1-10}$ heteroalkyl, $C_{5-10}$ heteroaryl, and $C_{6-20}$ heteroarylalkyl, each of which is optionally substituted with from 1 to 5 $R^{20}$ groups, wherein $R^{20}$ is described above. In some compounds, $R^5$ is $C_{1-10}$ alkyl optionally substituted as described above. In some compounds the $C_{1-10}$ alkyl is a $C_{1-10}$ cycloalkyl, e.g. cyclopropyl. In other compounds, $R^5$ is amino optionally substituted as described above. For example, in some compounds $R^5$ is —NH$_2$, and in other compounds $R^5$ is —NR$^y$R$^z$, wherein R$^y$ is H and R$^z$ is alkyl, e.g. cyclopropyl. In other compounds, $R^5$ is alkoxy, e.g. methoxy.

In some compounds, $R^{1a}$, $R^{1b}$, $R^3$, $R^{4a}$, $R^{4b}$ and $R^5$ are optionally substituted with from 1 to 5 (i.e. 1, 2, 3, 4 or 5) $R^{20}$ groups as described above. In some compounds, $R^{1a}$, $R^{1b}$, $R^3$, $R^{4a}$, $R^{4b}$ and $R^5$ are optionally substituted with 1, 2, or 3 $R^{20}$ groups. In some compounds, each $R^{20}$ is independently selected from the group consisting of alkyl, alkoxy, amino, cyano, halo, haloalkyl, heteroalkyl, hydroxy, and sulfonyl. In some compounds, each $R^{20}$ is independently selected from the group consisting of aryl, alkylaryl, heteroaryl, and heteroalkylaryl. In some compounds, $R^{1a}$, $R^{1b}$, $R^3$, $R^{4a}$, $R^{4b}$ and $R^5$ are not substituted. In some compounds, $R^{20}$ is not substituted.

One subset of compounds of Formula (I) relates to compounds of Formula (Ia)

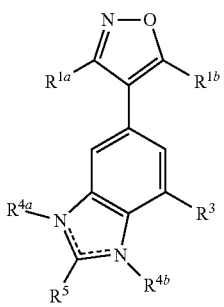

(Ia)

wherein
  $R^{1a}$ and $R^{1b}$ are each independently $C_{1-6}$ alkyl optionally substituted with from 1 to 5 $R^{20}$ groups;
  $R^3$ is
    boronic acid or halo; or
    —C(O)OR$^a$, —NHC(O)OR$^a$, —NHS(O)$_2$R$^a$, or —S(O)$_2$NR$^a$R$^b$; or
    selected from the group consisting of $C_{1-10}$ alkyl, $C_{1-10}$-alkoxy, amino, $C_{5-10}$ aryl, $C_{6-20}$ arylalkyl, $C_{1-10}$ heteroalkyl, $C_{5-10}$ heteroaryl, and $C_{6-20}$ heteroarylalkyl, each of which is optionally substituted with from 1 to 5 $R^{20}$ groups;
  one of $R^{4a}$ and $R^{4b}$ is selected from the group consisting of H and $C_{1-6}$ alkyl optionally substituted with from 1 to 5 $R^{20}$ groups, and the other is absent;
  $R^5$ is
    —C(O)OR$^a$, —NHC(O)OR$^a$, —NHS(O)$_2$R$^a$, or —S(O)$_2$NR$^a$R$^b$; or
    selected from the group consisting of H, $C_{1-10}$ alkyl, $C_{1-10}$ haloalkyl, $C_{1-10}$ alkoxy, amino, $C_{5-10}$ aryl, $C_{6-20}$ arylalkyl, $C_{1-10}$ heteroalkyl, $C_{5-10}$ heteroaryl, and $C_{6-20}$ heteroarylalkyl, each of which is optionally substituted with from 1 to 5 $R^{20}$ groups;
  each R$^a$ and R$^b$ is independently selected from the group consisting of H, $C_{1-10}$ alkyl, $C_{5-10}$ aryl, $C_{6-20}$ arylalkyl, $C_{1-10}$ heteroalkyl, $C_{5-10}$ heteroaryl, and $C_{6-20}$ heteroarylalkyl, each of which is optionally substituted with from 1 to 5 $R^2$ groups; and
  each $R^{20}$ is independently selected from the group consisting of acyl, $C_{1-10}$ alkyl, $C_{1-10}$ alkoxy, amino, amido, amidino, $C_{5-10}$ aryl, $C_{6-20}$ arylalkyl, azido, carbamoyl, carboxyl, carboxyl ester, cyano, guanidino, halo, $C_{1-10}$ haloalkyl, $C_{1-10}$ heteroalkyl, $C_{5-10}$ heteroaryl, $C_{6-20}$ heteroarylalkyl, hydroxy, hydrazino, imino, oxo, nitro, sulfinyl, sulfonic acid, sulfonyl, thiocyanate, thiol, and thione;
    wherein the $C_{1-10}$ alkyl, $C_{5-10}$ aryl, $C_{6-20}$ arylalkyl, $C_{1-10}$ heteroalkyl, $C_{5-10}$ heteroaryl, and $C_{6-20}$ heteroarylalkyl groups are optionally substituted with from 1 to 3 substituents independently selected from $C_{1-6}$ alkyl, $C_{5-10}$ aryl, halo, $C_{1-6}$ haloalkyl, cyano, hydroxy, and $C_{1-6}$ alkoxy;
or a pharmaceutically acceptable salt thereof.

Another subset of compounds of Formula (I) relates to compounds of Formula (Ib)

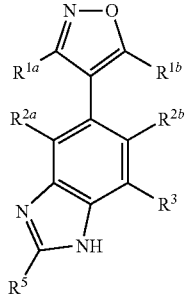

(Ib)

wherein
  $R^{1a}$ and $R^{1b}$ are each independently $C_{1-6}$ alkyl optionally substituted with from 1 to 5 $R^{20}$ groups;
  $R^{2a}$ and $R^{2b}$ are each independently H or halo;
  $R^3$ is
    boronic acid or halo; or
    —C(O)OR$^a$, —NHC(O)OR$^a$, —NHS(O)$_2$R$^a$, or —S(O)$_2$NR$^a$R$^b$; or
    selected from the group consisting of $C_{1-10}$ alkyl, $C_{1-10}$ alkoxy, amino, $C_{5-10}$ aryl, $C_{6-20}$ arylalkyl, $C_{1-10}$ heteroalkyl, $C_{5-10}$ heteroaryl, and $C_{6-20}$ heteroarylalkyl, each of which is optionally substituted with from 1 to 5 $R^{20}$ groups;
  $R^5$ is
    —C(O)OR$^a$, —NHC(O)OR$^a$, —NHS(O)$_2$R$^a$, or —S(O)$_2$NR$^a$R$^b$; or
    selected from the group consisting of H, $C_{1-10}$ alkyl, $C_{1-10}$ haloalkyl, $C_{1-10}$ alkoxy, amino, $C_{5-10}$ aryl, $C_{6-20}$ arylalkyl, $C_{1-10}$ heteroalkyl, $C_{5-10}$ heteroaryl, and $C_{6-20}$ heteroarylalkyl, each of which is optionally substituted with from 1 to 5 $R^{20}$ groups;
  each R$^a$ and R$^b$ is independently selected from the group consisting of H, $C_{1-10}$ alkyl, $C_{5-10}$ aryl, $C_{6-20}$ arylalkyl, $C_{1-10}$ heteroalkyl, $C_{5-10}$ heteroaryl, and $C_{6-20}$ heteroarylalkyl, each of which is optionally substituted with from 1 to 5 $R^{20}$ groups; and
  each $R^{20}$ is independently selected from the group consisting of acyl, $C_{1-10}$ alkyl, $C_{1-10}$ alkoxy, amino, amido, amidino, $C_{5-10}$ aryl, $C_{6-20}$ arylalkyl, azido, carbamoyl, carboxyl, carboxyl ester, cyano, guanidino, halo, $C_{1-10}$ to haloalkyl, $C_{1-10}$ heteroalkyl, $C_{5-10}$ heteroaryl, $C_{6-20}$ heteroarylalkyl, hydroxy, hydrazino, imino, oxo, nitro, sulfinyl, sulfonic acid, sulfonyl, thiocyanate, thiol, and thione;
    wherein the $C_{1-10}$ alkyl, $C_{5-10}$ aryl, $C_{6-20}$ arylalkyl, $C_{1-10}$ heteroalkyl, $C_{5-10}$ heteroaryl, and $C_{6-20}$ heteroarylalkyl groups are optionally substituted with from 1 to 3 substituents independently selected from $C_{1-6}$ alkyl, $C_{5-10}$ aryl, halo, $C_{1-6}$ haloalkyl, cyano, hydroxy, and $C_{1-6}$ alkoxy;
or a pharmaceutically acceptable salt thereof.

Another subset of compounds of Formula (I) relates to compounds of Formula (Ic)

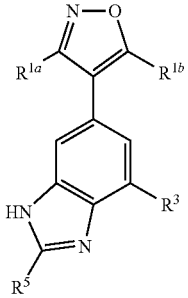

(Ic)

wherein
R$^{1a}$ and R$^{1b}$ are each independently C$_{1-6}$ alkyl optionally substituted with from 1 to 5 R$^{20}$ groups;
R$^{13}$ is
boronic acid or halo; or
—C(O)OR$^a$, —NHC(O)OR$^a$, —NHS(O)$_2$R$^a$, or —S(O)$_2$NR$^a$R$^b$; or
selected from the group consisting of C$_{1-10}$ alkyl, C$_{1-10}$ alkoxy, amino, C$_{5-10}$ aryl, C$_{6-20}$ arylalkyl, C$_{1-10}$ heteroalkyl, C$_{5-10}$ heteroaryl, and C$_{6-20}$ heteroarylalkyl, each of which is optionally substituted with from 1 to 5 R$^{20}$ groups;
R$^5$ is
—C(O)OR$^a$, —NHC(O)OR$^a$, —NHS(O)$_2$R$^a$, or —S(O)$_2$NR$^a$R$^b$; or
selected from the group consisting of H, C$_{1-10}$ alkyl, C$_{1-10}$ haloalkyl, C$_{1-10}$ alkoxy, amino, C$_{5-10}$ aryl, C$_{6-20}$ arylalkyl, C$_{1-10}$ heteroalkyl, C$_{5-10}$ heteroaryl, and C$_{6-20}$ heteroarylalkyl, each of which is optionally substituted with from 1 to 5 R$^{20}$ groups;
each R$^a$ and R$^b$ is independently selected from the group consisting of H, C$_{1-10}$ alkyl, C$_{5-10}$ aryl, C$_{6-20}$ arylalkyl, C$_{1-10}$ heteroalkyl, C$_{5-10}$ heteroaryl, and C$_{6-20}$ heteroarylalkyl, each of which is optionally substituted with from 1 to 5 R$^{20}$ groups; and
each R$^{20}$ is independently selected from the group consisting of acyl, C$_{1-10}$ alkyl, C$_{1-10}$alkoxy, amino, amido, amidino, C$_{5-10}$ aryl, C$_{6-20}$ arylalkyl, azido, carbamoyl, carboxyl, carboxyl ester, cyano, guanidino, halo, C$_{1-10}$ haloalkyl, C$_{1-10}$ heteroalkyl, C$_{5-10}$ heteroaryl, C$_{6-20}$ heteroarylalkyl, hydroxy, hydrazino, imino, oxo, nitro, sulfinyl, sulfonic acid, sulfonyl, thiocyanate, thiol, and thione;
wherein the C$_{1-10}$ alkyl, C$_{5-10}$ aryl, C$_{6-20}$ arylalkyl, C$_{1-10}$ heteroalkyl, C$_{5-10}$ heteroaryl, and C$_{6-20}$ heteroarylalkyl groups are optionally substituted with from 1 to 3 substituents independently selected from C$_{1-6}$ alkyl, C$_{5-10}$ aryl, halo, C$_{1-6}$ haloalkyl, cyano, hydroxy, and C$_{1-6}$ alkoxy;
or a pharmaceutically acceptable salt thereof.

Another subset of compounds of Formula (I) relates to compounds of Formula (Id)

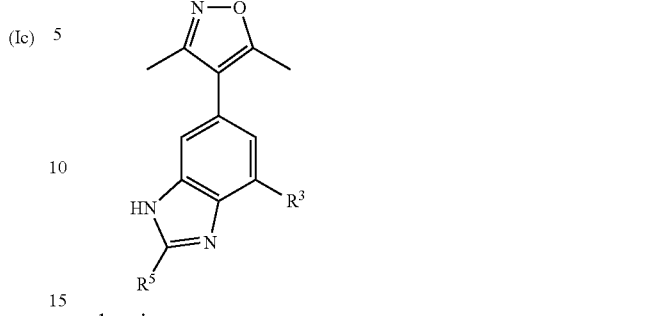

(Id)

wherein
R$^3$ is
boronic acid or halo; or
—C(O)OR$^a$, —NHC(O)OR$^a$, —NHS(O)$_2$R$^a$, or —S(O)$_2$NR$^a$R$^b$; or
selected from the group consisting of C$_{1-10}$ alkyl, C$_{1-10}$ alkoxy, amino, C$_{5-10}$ aryl, C$_{6-20}$ arylalkyl, C$_{1-10}$ heteroalkyl, C$_{5-10}$ heteroaryl, and C$_{1-20}$ heteroarylalkyl, each of which is optionally substituted with from 1 to 5 R$^{20}$ groups;
R$^5$ is
—C(O)OR$^a$, —NHC(O)OR$^a$, —NHS(O)$_2$R$^a$, or —S(O)$_2$NR$^a$R$^b$; or
selected from the group consisting of H, C$_{1-10}$ alkyl, C$_{1-10}$ haloalkyl, C$_{1-10}$ alkoxy, amino, C$_{5-10}$ aryl, C$_{6-20}$ arylalkyl, C$_{1-10}$ heteroalkyl, C$_{5-10}$ heteroaryl, and C$_{6-20}$ heteroarylalkyl, each of which is optionally substituted with from 1 to 5 R$^{20}$ groups;
each R$^a$ and R$^b$ is independently selected from the group consisting of H, C$_{1-10}$ alkyl, C$_{5-10}$ aryl, C$_{6-20}$ arylalkyl, C$_{1-10}$ heteroalkyl, C$_{5-10}$ heteroaryl, and C$_{6-20}$ heteroarylalkyl, each of which is optionally substituted with from 1 to 5 R$^{20}$ groups; and
each R$^{20}$ is independently selected from the group consisting of acyl, C$_{1-10}$ alkyl, C$_{1-10}$ alkoxy, amino, amido, amidino, C$_{5-10}$ aryl, C$_{6-20}$ arylalkyl, azido, carbamoyl, carboxyl, carboxyl ester, cyano, guanidino, halo, C$_{1-10}$ haloalkyl, C$_{1-10}$ heteroalkyl, C$_{5-10}$ heteroaryl, C$_{6-20}$ heteroarylalkyl, hydroxy, hydrazino, imino, oxo, nitro, sulfinyl, sulfonic acid, sulfonyl, thiocyanate, thiol, and thione;
wherein the C$_{1-10}$ alkyl, C$_{5-10}$ aryl, C$_{6-20}$ arylalkyl, C$_{1-10}$ heteroalkyl, C$_{5-10}$ heteroaryl, and C$_{6-20}$ heteroarylalkyl groups are optionally substituted with from 1 to 3 substituents independently selected from C$_{1-6}$ alkyl, C$_{5-10}$ aryl, halo, C$_{1-6}$ haloalkyl, cyano, hydroxy, and C$_{1-6}$ alkoxy;
or a pharmaceutically acceptable salt thereof.

Another subset of compounds of Formula (I) relates to compounds of Formula (Ie)

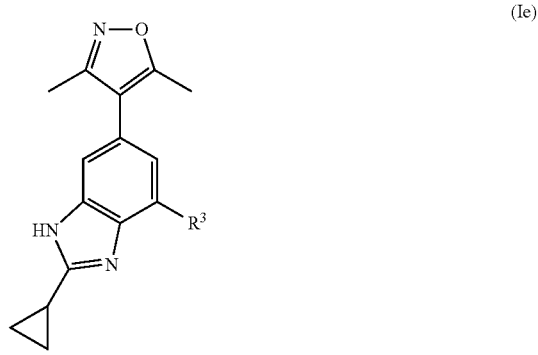

(Ie)

wherein
R³ is
boronic acid or halo; or
—C(O)OR$^a$, —NHC(O)OR$^a$, —NHS(O)$_2$R$^a$, or —S(O)$_2$NR$^a$R$^b$; or
selected from the group consisting of C$_{1-10}$ alkyl, C$_{1-10}$ alkoxy, amino, C$_{5-10}$ aryl, C$_{6-20}$ arylalkyl, C$_{1-10}$ heteroalkyl, C$_{5-10}$ heteroaryl, and C$_{6-20}$ heteroarylalkyl, each of which is optionally substituted with from 1 to 5 R$^{20}$ groups;
each R$^a$ and R$^b$ is independently selected from the group consisting of H, C$_{1-10}$ alkyl, C$_{5-10}$ aryl, C$_{6-20}$ arylalkyl, C$_{1-10}$ heteroalkyl, C$_{5-10}$ heteroaryl, and C$_{6-20}$ heteroarylalkyl, each of which is optionally substituted with from 1 to 5 R$^{20}$ groups; and
each R$^{20}$ is independently selected from the group consisting of acyl, C$_{1-10}$ alkyl, C$_{1-10}$ alkoxy, amino, amido, amidino, C$_{5-10}$ aryl, C$_{6-20}$ arylalkyl, azido, carbamoyl, carboxyl, carboxyl ester, cyano, guanidino, halo, C$_{1-10}$ haloalkyl, C$_{1-10}$ heteroalkyl, C$_{5-10}$ heteroaryl, C$_{6-20}$ heteroarylalkyl, hydroxy, hydrazino, imino, oxo, nitro, sulfinyl, sulfonic acid, sulfonyl, thiocyanate, thiol, and thione;
wherein the C$_{1-10}$ alkyl, C$_{5-10}$ aryl, C$_{6-20}$ arylalkyl, C$_{1-10}$ heteroalkyl, C$_{5-10}$ heteroaryl, and C$_{6-20}$ heteroarylalkyl groups are optionally substituted with from 1 to 3 substituents independently selected from C$_{1-6}$ alkyl, C$_{5-10}$ aryl, halo, C$_{1-6}$ haloalkyl, cyano, hydroxy, and C$_{1-6}$ alkoxy;
or a pharmaceutically acceptable salt thereof.

Unless defined otherwise, all technical and scientific terms used herein have the same meaning as commonly understood by one of ordinary skill in the art. It must be noted that as used herein and in the appended claims, the singular forms "a", "and", and "the" include plural referents unless the context clearly dictates otherwise. Thus, e.g., reference to "the compound" includes a plurality of such compounds and reference to "the assay" includes reference to one or more assays and equivalents thereof known to those skilled in the art, and so forth.

A dash at the front or end of a chemical group is a matter of convenience; chemical groups may be depicted with or without one or more dashes without losing their ordinary meaning. A wavy line drawn through a line in a structure indicates a point of attachment of a group. A dashed line indicates an optional bond. Unless chemically or structurally required, no directionality is indicated or implied by the order in which a chemical group is written. For instance, the group "—SO$_2$CH$_2$—" is equivalent to "—CH$_2$SO$_2$—" and both may be connected in either direction. The prefix "C$_{u-v}$" indicates that the following group has from u to v carbon atoms, one or more of which, in certain groups (e.g. heteroalkyl, heteroaryl, heteroarylalkyl, etc.), may be replaced with one or more heteroatoms or heteroatomic groups. For example, "C$_{1-6}$ alkyl" indicates that the alkyl group has from 1 to 6 carbon atoms.

Also, certain commonly used alternative chemical names may or may not be used. For example, a divalent group such as a divalent "alkyl" group, a divalent "aryl" group, etc., may also be referred to as an "alkylene" group or an "alkylenyl" group, an "arylene" group or an "arylenyl" group, respectively.

"Alkyl" refers to any aliphatic hydrocarbon group, i.e. any linear, branched, cyclic, or spiro nonaromatic hydrocarbon group or an isomer or combination thereof. As used herein, the term "alkyl" includes terms used in the art to describe saturated and unsaturated aliphatic hydrocarbon groups with one or more points of attachment, including alkenyl (an aliphatic group containing at least one carbon-carbon double bond), alkylene (a divalent aliphatic group), alkynyl (an aliphatic group containing at least one carbon-carbon triple bond), cycloalkyl (a cyclic aliphatic group), alkylcycloalkyl (a linear or branched aliphatic group attached to a cyclic aliphatic group), and the like. Alkyl groups include, but are not limited to, methyl; ethyl; propyls such as propan-1-yl, propan-2-yl (iso-propyl), and cyclopropyls such as cyclopropan-1-yl, etc.; butyls such as butan-1-yl, butan-2-yl (sec-butyl), 2-methyl-propan-1-yl (iso-butyl), 2-methyl-propan-2-yl (t-butyl), cyclobutan-1-yl; butenes (e.g. (E)-but-2-ene, (Z)-but-2-ene); pentyls; pentenes; hexyls; hexenes; octyls; decyls; cyclopropyl, cyclobutyl, cyclopentyl, cyclohexyl, methylcyclohexyl, spiro[2,4]heptyl, and the like. An alkyl group comprises from 1 to about 10 carbon atoms, e.g., from 1 to 6 carbon atoms. In some embodiments, alkyl is a monovalent, linear or branched, saturated aliphatic hydrocarbon group comprising from 1 to about 10 carbon atoms, e.g., from 1 to 6 carbon atoms.

"Alkenyl" is a subset of "alkyl" and refers to an aliphatic group containing at least one carbon-carbon double bond and having from 2 to about 10 carbon atoms, e.g., from 2 to 6 carbon atoms or 2 to 4 carbon atoms and having at least one site of vinyl unsaturation (>C=C<). Alkenyl groups include ethenyl, propenyl, 1,3-butadienyl, and the like. Alkynyl may have from 2 to about 10 carbon atoms, e.g. from 2 to 6 carbon atoms or 2 to 4 carbon atoms.

"Alkynyl" is a subset of "alkyl" and refers to an aliphatic group containing at least one carbon-carbon triple bond. The term "alkynyl" is also meant to include those groups having one triple bond and one double bond.

"Alkoxy" refers to the group —O-alkyl, wherein the alkyl group may be optionally substituted. Alkoxy includes, by way of example, methoxy, ethoxy, n-propoxy, isopropoxy, n-butoxy, t-butoxy, sec-butoxy, and n-pentoxy.

"Acyl" refers to a group —C(=O)R$^a$, where R is hydrogen, alkyl, cycloalkyl, cycloheteroalkyl, aryl, arylalkyl, heteroalkyl, heteroaryl or heteroarylalkyl as defined herein, each of which may be optionally substituted, as defined herein. Representative examples include, but are not limited to formyl, acetyl, cyclohexylcarbonyl, cyclohexylmethyl-carbonyl, benzoyl, benzyloxycarbonyl and the like.

"Amido" refers to both a "C-amido" group which refers to the group —C(=O)NR$^y$R$^z$ and an "N-amido" group which refers to the group —NR$^y$C(=O)R$^z$, wherein R$^y$ and R$^z$ are independently selected from the group consisting of hydrogen, alkyl, aryl, heteralkyl, heteroaryl (each of which may be optionally substituted), and where R$^y$ and R$^z$ are optionally joined together with the nitrogen or carbon bound thereto to form an optionally substituted heterocycloalkyl.

"Amino" refers to the group —NR$^y$R$^z$ wherein R$^y$ and R$^z$ are independently selected from the group consisting of hydrogen, alkyl, aryl, heteralkyl, heteroaryl (each of which may be optionally substituted), and where R$^y$ and R$^z$ are optionally joined together with the nitrogen bound thereto to form a heterocycloalkyl or heteroaryl heteroaryl (each of which may be optionally substituted).

"Amidino" refers to the group —C(=NR$^x$)NR$^y$R$^z$ where R$^x$, R$^y$, and R$^z$ are independently selected from the group consisting of hydrogen, alkyl, aryl, heteralkyl, heteroaryl (each of which may be optionally substituted), and where R$^y$ and R$^z$ are optionally joined together with the nitrogen bound thereto to form a heterocycloalkyl or heteroaryl (each of which may be optionally substituted).

"Aryl" refers to a group with one or more aromatic rings. It may be a single aromatic ring or multiple aromatic rings which are fused together, linked covalently, or linked via one or more such as a methylene or ethylene moiety. Aryl groups include, but are not limited to, those groups derived from acenaphthylene, anthracene, azulene, benzene, biphenyl, chrysene, cyclopentadienyl anion, diphenylmethyl, fluoranthene, fluorene, indane, indene, naphthalene, perylene, phenalene, phenanthrene, pyrene, triphenylene, and the like. An aryl group comprises from 5 to about 20 carbon atoms, e.g., from 5 to 20 carbon atoms, e.g. from 5 to 10 carbon atoms. In some embodiments, aryl is a single aromatic ring or multiple aromatic rings which are fused together.

"Arylalkyl" (also "aralkyl") refers to an aryl group attached to an alkyl group. Arylalkyl groups include, but are not limited to, benzyl, tolyl, dimethylphenyl, 2-phenylethan-1-yl, 2-naphthylmethyl, 2-naphthylethan-1-yl, naphthobenzyl, phenylvinyl, diphenylmethyl, and the like. For example, the "arylalkyl" may be attached to the rest of the compound of formula (I) through the aryl group. Alternatively, the "arylalkyl" may be attached to the rest of the compound of formula (I) through the alkyl group. Where specific alkyl moieties are intended, the nomenclature arylalkanyl, arylalkenyl and/or arylalkynyl may be used. An arylalkyl group comprises from 6 to about 30 carbon atoms, e.g. the alkyl portion of the arylalkyl group can comprise from 1 to about 10 carbon atoms and the aryl portion of the arylalkyl group can comprise from 5 to about 20 carbon atoms. In some instances an arylalkyl group comprises from 6 to about 20 carbon atoms, e.g. the alkyl portion of the arylalkyl group can comprise from 1 to about 10 carbon atoms and the aryl portion of the arylalkyl group can comprise from 5 to about 10 carbon atoms.

"Aryloxy" refers to the group —O-aryl, including by way of example, phenoxy and naphthoxy.

"Azido" refers to the group —$N_3$.

"Boronic acid" refers to the group —$B(OH)_2$.

"Boronic acid ester" refers to an ester derivative of a boronic acid compound. Suitable boronic acid ester derivatives include those of the formula —$B(OR)_2$ where R is hydrogen, alkyl, aryl, arylalkyl, heteroalkyl, or heteroaryl, each of which may be optionally substituted. For example, boronic acid ester may be pinacol ester or catechol ester.

"Carbamoyl" refers to the group —C(O)$NR^yR^z$ where $R^y$ and $R^z$ are defined as in "amino" above.

"Carbonyl" refers to the divalent group —C(O)— which is equivalent to —C(=O)—.

"Carboxyl" or "carboxy" refers to —COOH or salts thereof.

"Carboxyl ester" or "carboxy ester" refers to the groups —C(O)OR, wherein R is hydrogen, alkyl, aryl, arylalkyl, heteroalkyl, or heteroaryl, each of which may be optionally substituted. In one embodiment, R is alkyl, aryl, arylalkyl, heteroalkyl, or heteroaryl, each of which may be optionally substituted.

"Cyano" or "carbonitrile" refers to the group —CN.

"Cycloalkyl" is a subset of "alkyl" and refers to a saturated or partially saturated cyclic group of from 3 to about 10 carbon atoms and no ring heteroatoms and having a single ring or multiple rings including fused, bridged, and spiro ring systems. For multiple ring systems having aromatic and non-aromatic rings that have no ring heteroatoms, the term "cycloalkyl" applies when the point of attachment is at a non-aromatic carbon atom (e.g., 5,6,7,8,-tetrahydronaphthalene-5-yl). The term "cycloalkyl" includes cycloalkenyl groups. Examples of cycloalkyl groups include, for instance, adamantyl, cyclopropyl, cyclobutyl, cyclopentyl, cyclooctyl, and cyclohexenyl.

"Guanidino" refers to the group —NHC(=NH)$NH_2$.

"Halo" or "halogen" refers to fluoro, chloro, bromo and iodo.

"Haloalkyl" refers to substitution of alkyl groups with 1 to 5 or, in some embodiments, 1 to 3 halo groups, e.g., —$CH_2Cl$, —$CH_2F$, —$CH_2Br$, —$CFClBr$, —$CH_2CH_2Cl$, —$CH_2CH_2F$, —$CF_3$, —$CH_2CF_3$, —$CH_2CCl_3$, and the like, and further includes those alkyl groups such as perfluoroalkyl in which all hydrogen atoms are replaced by fluorine atoms.

"Haloaryl" refers to aryl groups with one or more halo or halogen substituents. For example, haloaryl groups include phenyl groups in which from 1 to 5 hydrogens are replaced with a halogen. Haloaryl groups include, for example, fluorophenyl, difluorophenyl, trifluorophenyl, chlorophenyl, clorofluorophenyl, and the like.

"Heteroalkyl" refers to an alkyl group in which one or more of the carbon atoms (and any associated hydrogen atoms) are each independently replaced with the same or different heteroatom or heteroatomic group. For example, heteroalkyl may include 1, 2 or 3 heteroatomic groups, e.g. 1 heteroatomic group. Heteroatoms include, but are not limited to, N, P, O, S, etc. Heteroatomic groups include, but are not limited to, —NR—, —O—, —S—, —PH—, —$P(O)_2$—, —S(O)—, —$S(O)_2$—, and the like, where R is H, alkyl, aryl, cycloalkyl, heteroalkyl, heteroaryl or cycloheteroalkyl. The term "heteroalkyl" includes heterocycloalkyl (a cyclic heteroalkyl group), alkyl-heterocycloalkyl (a linear or branched aliphatic group attached to a cyclic heteroalkyl group), and the like. Heteroalkyl groups include, but are not limited to, —$OCH_3$, —$CH_2OCH_3$, —$SCH_3$, —$CH_2SCH_3$, —$NRCH_3$, —$CH_2NRCH_3$, and the like, where R is hydrogen, alkyl, aryl, arylalkyl, heteroalkyl, or heteroaryl, each of which may be optionally substituted. A heteroalkyl group comprises from 1 to about 10 carbon and hetero atoms, e.g., from 1 to 6 carbon and hetero atoms.

"Heteroaryl" refers to an aryl group in which one or more of the carbon atoms (and any associated hydrogen atoms) are each independently replaced with the same or different heteroatoms, as defined above. For example, heteroaryl may include 1, 2 or 3 heteroatomic groups, e.g. 1 heteroatomic group. Heteroaryl groups include, but are not limited to, groups derived from acridine, benzoimidazole, benzothiophene, benzofuran, benzoxazole, benzothiazole, carbazole, carboline, cinnoline, furan, imidazole, imidazopyridine, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. A heteroaryl group comprises from 5 to about 20 carbon and hetero atoms in the ring or rings, e.g., from 5 to 20 carbon and hetero atoms, e.g. from 5 to 10 carbon and hetero atoms.

"Heteroarylalkyl" refers to an arylalkyl group in which one or more carbon atoms (and any associated hydrogen atoms) are independently replaced with the same or different heteroatoms, as defined above. For example, heteroarylalkyl may include 1, 2 or 3 heteroatomic groups. Heteroarylalkyl groups include, but are not limited to, groups derived from heteroaryl groups with alkyl substituents (e.g. methylpyridine, dimethylisoxazole, etc.), hydrogenated heteroaryl groups (dihydroquinolines, e.g. 3,4-dihydroquinoline, dihydroisoquinolines, e.g. 1,2-dihydroisoquinoline, dihydroimidazole, tetrahydroimidazole, etc.), isoindoline, isoindolones (e.g. isoindolin-1-one), dihydrophthalazine, quinolinone, spiro[cyclopropane-1,1'-isoindolin]-3'-one, di(pyridin-2-yl)methyl, di(pyridin-3-yl)methyl, di(pyridin-4-yl)methyl, and the like. A heteroarylalkyl group comprises from 6 to about 30 carbon and hetero atoms, for example from 6 to about 20 carbon and hetero atoms.

"Heterocycloalkyl" is a subset of "heteroalkyl" and refers to a saturated or unsaturated cycloalkyl group in which one or more carbon atoms (and any associated hydrogen atoms) are independently replaced with the same or different heteroatom. Heteroatoms include, but are not limited to, N, P, O, S, etc. A heterocycloalkyl group may also contain a charged heteroatom or group, e.g., a quaternized ammonium group such as —N+(R)2- wherein R is alkyl, e.g., methyl, ethyl, etc. Heterocycloalkyl groups include, but are not limited to, groups derived from epoxide, imidazolidine, morpholine, piperazine, piperidine, pyrazolidine, piperidine, pyrrolidine, pyrrolidinone, tetrahydrofuran, tetrahydrothiophene, dihydropyridine, tetrahydropyridine, quinuclidine, N-bromopyrrolidine, N-bromopiperidine, N-chloropyrrolidine, N-chloropiperidine, an N,N-dialkylpyrrolidinium, such as N,N-dimethylpyrrolidinium, a N,N-dialkylpiperidinium such as N,N-dimethylpiperidinium, and the like. The heterocycloalkyl group comprises from 3 to about 10 carbon and hetero atoms in the ring or rings. In some embodiments, heterocycloalkyl includes 1, 2 or 3 heteroatomic groups.

"Hydrazino" refers to the group —NHNH$_2$.

"Hydroxy" or "hydroxyl" refers to the group —OH.

"Imino" refers to the group —C(=NR)— wherein R is hydrogen, alkyl, aryl, arylalkyl, heteroalkyl, or heteroaryl, each of which may be optionally substituted.

"Nitro" refers to the group —NO$_2$.

The terms "optional" or "optionally" mean that the subsequently described event or circumstance may but need not occur, and that the description includes instances where the event or circumstance occurs and instances in which it does not.

"Oxide" refers to products resulting from the oxidation of one or more heteroatoms. Examples include N-oxides, sulfoxides, and sulfones.

"Oxo" refers to a double-bonded oxygen (=O). In compounds where an oxo group is bound to an sp$^2$ nitrogen atom, an N-oxide is indicated.

"Racemates" refers to a mixture of enantiomers.

"Stereoisomer" or "stereoisomers" refer to compounds that differ in the chirality of one or more stereocenters. Stereoisomers include enantiomers and diastereomers. The compounds may exist in stereoisomeric form if they possess one or more asymmetric centers or a double bond with asymmetric substitution and, therefore, can be produced as individual stereoisomers or as mixtures. Unless otherwise indicated, the description is intended to include individual stereoisomers as well as mixtures. The methods for the determination of stereochemistry and the separation of stereoisomers are well-known in the art (see, e.g., Chapter 4 of Advanced Organic Chemistry, 4th ed., J. March, John Wiley and Sons, New York, 1992).

"Substituted" (as in, e.g., "substituted alkyl") refers to a group wherein one or more hydrogens have been independently replaced with one or more substituents including, but not limited to, alkyl, alkenyl, alkynyl, alkoxy, acyl, amino, amido, amidino, aryl, azido, carbamoyl, carboxyl, carboxyl ester, cyano, guanidino, halo, haloalkyl, heteroalkyl, heteroaryl, heterocycloalkyl, hydroxy, hydrazino, hydroxyl, imino, oxo, nitro, sulfinyl, sulfonic acid, sulfonyl, thiocyanate, thiol, thione, or combinations thereof. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to -substituted aryl-(substituted aryl)-substituted aryl. For example, in some embodiments, when a group described above as being "optionally substituted" is substituted, that substituent is itself unsubstituted. Similarly, it is understood that the above definitions are not intended to include impermissible substitution patterns (e.g., methyl substituted with 5 fluoro groups or heteroaryl groups having two adjacent oxygen ring atoms). Such impermissible substitution patterns are well known to the skilled artisan. When used to modify a chemical group, the term "substituted" may describe other chemical groups defined herein. For example, the term "substituted aryl" includes, but is not limited to, "arylalkyl." Generally, substituted groups will have 1 to 5 substituents, 1 to 3 substituents, 1 or 2 substituents or 1 substituent. Alternatively, the optionally substituted groups of the invention may be unsubstituted.

"Sulfonyl" refers to the divalent group —S(O)$_2$—.

"Tautomer" refers to alternate forms of a compound that differ in the position of a proton, such as enol-keto and imine-enamine tautomers, or the tautomeric forms of heteroaryl groups containing a ring atom attached to both a ring —NH— moiety and a ring =N-moiety such as pyrazoles, imidazoles, benzimidazoles, triazoles, and tetrazoles.

"Thiocyanate" refers to the group —SCN.

"Thiol" refers to the group —SH.

"Thione" refers to a thioketone (=S) group.

"Pharmaceutically acceptable" refers to compounds, salts, compositions, dosage forms and other materials which are useful in preparing a pharmaceutical composition that is suitable for veterinary or human pharmaceutical use.

"Pharmaceutically acceptable salt" refers to a salt of a compound that is pharmaceutically acceptable and that possesses (or can be converted to a form that possesses) the desired pharmacological activity of the parent compound. Such salts include acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic acid, camphorsulfonic acid, citric acid, ethanesulfonic acid, fumaric acid, glucoheptonic acid, gluconic acid, lactic acid, maleic acid, malonic acid, mandelic acid, methanesulfonic acid, 2-napthalenesulfonic acid, oleic acid, palmitic acid, propionic acid, stearic acid, succinic acid, tartaric acid, p-toluenesulfonic acid, trimethylacetic acid, and the like, and salts formed when an acidic proton present in the parent compound is replaced by either a metal ion, e.g., an alkali metal ion, an alkaline earth ion, or an aluminum ion; or coordinates with an organic base such as diethanolamine, triethanolamine, N-methylglucamine and the like. Also included in this definition are ammonium and substituted or quaternized ammonium salts. Representative non-limiting lists of pharmaceutically acceptable salts can be found in S. M. Berge et al., J. Pharma Sci., 66(1), 1-19 (1977), and Remington: The Science and Practice of Pharmacy, R. Hendrickson, ed., 21st edition, Lippincott, Williams & Wilkins, Philadelphia, Pa., (2005), at p. 732, Table 38-5, both of which are hereby incorporated by reference herein.

The following abbreviations may also be used: AcOH: acetic acid; nBuLi: n-butyllithium; CC: column chromatography, $Cs_2CO_3$: cesium carbonate; $CH_2Cl_2$ or DCM: dichloromethane; $CH_3MgI$: methyl magnesium iodide; $CuCl_2$: copper chloride; DAST: (diethylamino)sulfur trifluoride; DEAD: diethyl azodicarboxylate; DIBAL: diisobutylaluminum hydride; DIPEA: diisopropylethylamine; DMF: dimethylformamide; DMSO: dimethyl sulfoxide; $Et_3N$: triethylamine; EtOAc: ethyl acetate; EtOH: ethanol; g: gram(s); h: hour, $H_2$: hydrogen; HBr: hydrogen bromide; HCl: hydrogen chloride; $H_2O$: water; $H_2O_2$: hydrogen peroxide; HPLC: high performance liquid chromatography; KCN: potassium cyanide; LHMDS: lithium hexamethyldisilazide; $LiAlH_4$: lithium aluminum hydride; LiOH: lithium hydroxide; M: molar; McCN: acetonitrile; MeI: methyl iodide; MeOH: methanol; $MgSO_4$: magnesium sulfate; $MgCO_3$: magnesium carbonate; mg: millilgram; MsCl: mesyl chloride; mmol: millimoles mL: milliliter; sodium hydrogen sulfite; mCPBA: meta-chloroperoxybenzoic acid; N: normality; $N_2$: nitrogen; $Na_2CO_3$: sodium carbonate; $NaHCO_3$: sodium bicarbonate; $NaNO_2$: sodium nitrite; NaOH: sodium hydroxide; $Na_2S_2O_3$: sodium bisulfate; $Na_2SO_4$: sodium sulfate; NBS: N-bromosuccinimide; $NH_4Cl$: ammonium chloride; $NH_4OAc$: ammonium acetate; NMR: nuclear magnetic resonance; Pd/C: palladium on carbon; $PPh_3$: triphenyl phosphine; iPrOH: isopropyl alcohol; RT: room temperature; $SOCl_2$: thionyl chloride; THF: tetrahydrofuran; TLC: thin layer chromatography; μL: microliter.

It understood that combinations of chemical groups may be used and will be recognized by persons of ordinary skill in the art. For instance, the group "hydroxyalkyl" would refer to a hydroxyl group attached to an alkyl group. A great number of such combinations may be readily envisaged.

Provided are also compounds in which from 1 to n hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such compounds exhibit may increase resistance to metabolism, and thus may be useful for increasing the half-life of the compounds when administered to a mammal. See, e.g., Foster, "Deuterium Isotope Effects in Studies of Drug Metabolism", Trends Pharmacol. Sci., 5(12):524-527 (1984). Such compounds are synthesized by means well known in the art, for example by employing starting materials in which one or more hydrogen atoms have been replaced by deuterium.

Compounds of a given formula described herein encompasses the compound disclosed and all pharmaceutically acceptable salts, esters, stereoisomers, tautomers, prodrugs, solvates, and deuterated forms thereof unless otherwise specified.

"Effective amount" or "therapeutically effective amount" means the amount of a compound described herein that may be effective to elicit the desired biological or medical response. These terms include the amount of a compound that, when administered to a subject for treating a disease, is sufficient to effect such treatment for the disease. The effective amount will vary depending on the compound, the disease and its severity and the age, weight, etc., of the subject to be treated.

"Subject" and "subjects" refers to humans, domestic animals (e.g., dogs and cats), farm animals (e.g., cattle, horses, sheep, goats and pigs), laboratory animals (e.g., mice, rats, hamsters, guinea pigs, pigs, rabbits, dogs, and monkeys), and the like.

"Treating" and "treatment" of a disease include the following: (1) preventing or reducing the risk of developing the disease, i.e., causing the clinical symptoms of the disease not to develop in a subject that may be exposed to or predisposed to the disease but does not yet experience or display symptoms of the disease, (2) inhibiting the disease, i.e., arresting or reducing the development of the disease or its clinical symptoms, and (3) relieving the disease, i.e., causing regression of the disease or its clinical symptoms.

In some aspects, the disease or condition is chosen from an autoimmune disease, an inflammatory disease, a neurodegenerative disease, a cardiovascular disorder, a renal disorder, a viral infection, and obesity. In some aspects, the disease or condition is chosen from rheumatoid arthritis, osteoarthritis, atherosclerosis, psoriasis, systemic lupus erythematosus, multiple sclerosis, inflammatory bowel disease, asthma, chronic obstructive airways disease, pneumonitis, dermatitis, alopecia, nephritis, vasculitis, atherosclerosis, Alzheimer's disease, hepatitis, primary biliary cirrhosis, sclerosing cholangitis, diabetes (including type I diabetes), and acute rejection of transplanted organs. In some aspects the disease or condition is cancer, including hematological cancers, lymphoma, multiple myelomas, leukemias, a neoplasm, cancer or tumor (for example a solid tumor). In some aspects the disease or condition is a neoplasm, cancer or tumor of the colon, rectum, prostate (for example castrate resistant prostate cancer), lung (for example non-small cell lung cancer, and small-cell lung cancer), pancreas, liver, kidney, cervix, uterus, stomach, ovary, breast (for example basal or basal-like breast cancer, and triple-negative breast cancer), skin (for example melanoma), the nervous system (including the brain, meninges, and central nervous system, including a neuroblastoma, a glioblastoma, a meningioma, and a medulloblastoma). In some aspects the disease or condition is a carcinoma. In some aspects, the disease or condition is hepatocellular carcinoma. In some aspects, the disease or condition is a lymphoma. In some aspects, the disease or condition is a B-cell lymphoma. In some aspects, the disease or condition is Burkitt's lymphoma. In some aspects, the disease or condition is diffuse large B-cell lymphoma. In some aspects, the disease or condition is multiple myeloma. In some aspects, the disease or condition is chronic lymphocytic leukemia. In some aspects the disease or condition is NUT midline cardinoma. In some aspects the subject is a human.

The pharmaceutical compositions may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

In one aspect, the compounds described herein may be administered orally. Oral administration may be via, for example, capsule or enteric coated tablets. In making the pharmaceutical compositions that include at least one compound of Formula (I), or a pharmaceutically acceptable salt thereof, the active ingredient is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The compositions that include at least one compound of Formula (I), or a pharmaceutically acceptable salt thereof, can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions may, in some embodiments, be formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds are generally administered in a pharmaceutically effective amount. In some embodiments, for oral administration, each dosage unit contains from about 10 mg to about 1000 mg of a compound described herein, for example from about 50 mg to about 500 mg, for example about 50 mg, about 75 mg, about 100 mg, about 150 mg, about 200 mg, about 250 mg, or about 300 mg. In other embodiments, for parenteral administration, each dosage unit contains from 0.1 to 700 mg of a compound a compound described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual subject, and the severity of the subject's symptoms.

In certain embodiments, dosage levels may be from 0.1 mg to 100 mg per kilogram of body weight per day, for example from about 1 mg to about 50 mg per kilogram, for example from about 5 mg to about 30 mg per kilogram. Such dosage levels may, in certain instances, be useful in the treatment of the above-indicated conditions. In other embodiments, dosage levels may be from about 10 mg to about 2000 mg per subject per day. The amount of active ingredient that may be combined with the vehicle to produce a single dosage form will vary depending upon the host treated and the particular mode of administration. Dosage unit forms may contain from 1 mg to 500 mg of an active ingredient.

Frequency of dosage may also vary depending on the compound used and the particular disease or condition treated. In some embodiments, for example, for the treatment of an autoimmune and/or inflammatory disease, a dosage regimen of 4 times daily or less is used. In some embodiments, a dosage regimen of 1 or 2 times daily is used. It will be understood, however, that the specific dose level for any particular subject will depend upon a variety of factors including the activity of the specific compound employed, the age, body weight, general health, sex, diet, time of administration, route of administration, and rate of excretion, drug combination and the severity of the particular disease in the subject undergoing therapy.

For preparing solid compositions such as tablets, the principal active ingredient may be mixed with a pharmaceutical excipient to form a solid preformulation composition containing a homogeneous mixture of a compound of Formula (I), or a pharmaceutically acceptable salt thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Kits that include a compound of Formula (I), or a pharmaceutically acceptable salt, thereof, and suitable packaging are provided. In one embodiment, a kit further includes instructions for use. In one aspect, a kit includes a compound of Formula (I), or a pharmaceutically acceptable salt thereof, and instructions for use of the compounds in the treatment of the diseases or conditions described herein.

Articles of manufacture that include a compound of Formula (I), or a pharmaceutically acceptable salt thereof, in a suitable container are provided. The container may be a vial, jar, ampoule, preloaded syringe, and intravenous bag.

Compounds of Formula (I) may be combined or administered with one or more additional anti-cancer or anti-inflammatory agents. For example, compounds of Formula (I) may be administered simultaneously with the one or more additional anti-cancer or anti-inflammatory agents, or may be administered sequentially (before or after) the one or more additional anti-cancer or anti-inflammatory agents.

Sequential administration or administered sequentially means that the inhibitors, compounds, or drugs are administered with a time separation of a few seconds, several minutes, hours, days, or weeks. Compounds may be administered with a time separation of up to 30 seconds, up to 15 minutes, up to 30 minutes, up to 60 minutes, or 1 day, 2 days, 3 days, 4 days, 5 days, 6 days, or 7 days, or 2 weeks, 3 weeks, 4 weeks, 5 weeks, 6 weeks, 7 weeks, or 8 weeks. When administered sequentially, the compounds or drugs may be administered in two or more administrations, and the compounds or drugs may be contained in separate compositions or dosage forms, which may be contained in the same or different package or packages.

Simultaneous administration or administered simultaneously means that the inhibitors, compounds, or drugs are administered with a time separation of no more than a few minutes or seconds. Compounds are administered with a time separate of no more than about 15 minutes, about 10 minutes, about 5 minutes, or 1 minute. When administered simultaneously, the inhibitors, compounds or drugs may be in separate compositions or dosage forms, or the same composition or dosage form.

In some aspects, compounds of Formula (I) may be combined with the additional anti-cancer or anti-inflammatory agents in a unitary dosage form (for example for oral administration). In other aspects, compounds of Formula (I) and the one or more additional anti-cancer or anti-inflammatory agents may be separate dosage forms.

Suitable additional anti-cancer or anti-inflammatory agents include but are not limited to the following. Various kinase inhibitors are being used and are being developed to treat various cancers. For example, the activation of the phosphatidylinositol 3-kinase (PI3K) pathway is observed in human cancer, and agents inhibiting PI3K are being investigated or developed as potential anti-cancer drugs and for the use in anti-cancer therapies. Additional kinase inhibitors include inhibitors of spleen tyrosine kinase (Syk) and Janus kinase (JAK). Other agents inhibiting related pathways are also of interest as anti-cancer or anti-inflammatory agents, including agents inhibiting the Ras/Raf/MEK/ERK pathway and the PI3K/PTEN/Akt/mTOR pathway. As described herein, such inhibitors include agents that inhibit all subclasses of a target (e.g. PI3K alpha, beta, delta and gamma), agents that inhibit primarily one subclass, and agents that inhibit a subset of all subclasses. Compounds of Formula (I) may also be combined or administered with one or more additional anti-cancer or anti-inflammatory agents including inhibitors or antagonists of lysyl oxidase-like 2 (LOXL2), and inhibitors or antagonists of adenosine A2B receptor.

Further examples of kinase inhibitors include PI3K inhibitors, Syk inhibitors and JAK inhibitors. Examples of PI3K inhibitors include Compound A, Compound B, and Compound C:

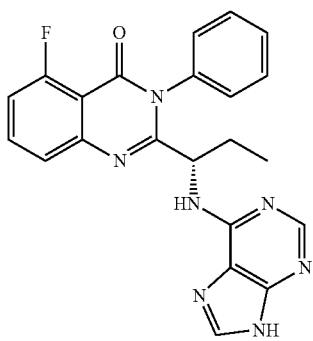
(Compound A)

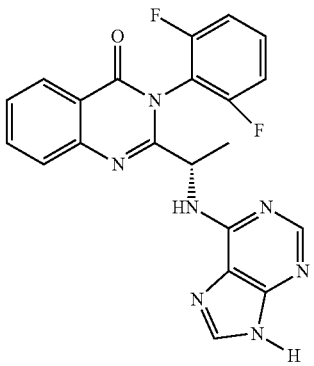
(Compound B)

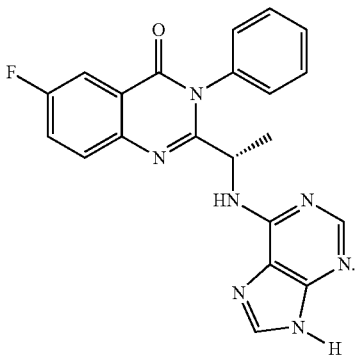
(Compound C)

Additional examples of PI3K inhibitors include XL147, BKM120, GDC-0941, BAY80-6946, PX-866, CH5132799, XL756, BEZ235, and GDC-0980, wortmannin, LY294002, PI3K II, TGR-1202, AMG-319, GSK2269557, X-339, X-414, RP5090, KAR4141, XL499, OXY111A, IPI-145, IPI-443, GSK2636771, BAY 10824391, buparlisib, BYL719, RG7604, MLN1117, WX-037, AEZS-129, PA799, AS252424, TGX221, TGI00115, IC87114, and ZSTK474.

Inhibitors of mTOR include OSI-027, AZD2014, and CC-223.

Inhibitors of AKT include MK-2206, GDC-0068 and GSK795.

Examples of Syk inhibitors include compound D:

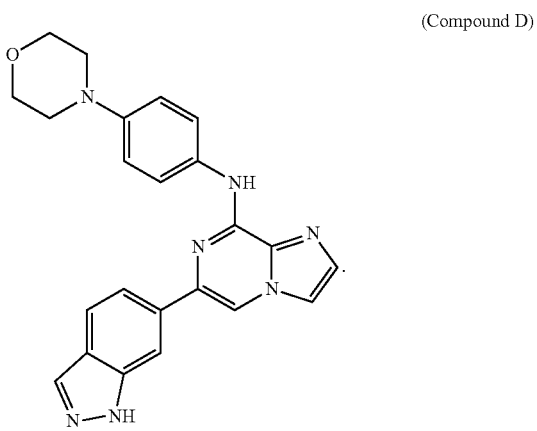 [SMILES: c1cn2cc(-c3ccc4cn[nH]c4c3)nc(Nc3ccc(N4CCOCC4)cc3)c2n1]
(Compound D)

Additional Syk inhibitors include R788 (fostamatinib), R-406 (tamatinib), and PRT062607.

Examples of JAK inhibitors include Compound E:

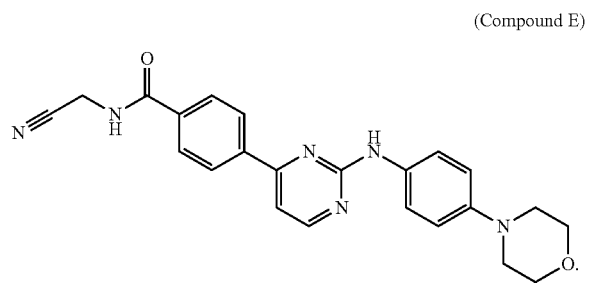 [SMILES: N#CCNC(=O)c1ccc(-c2ccnc(Nc3ccc(N4CCOCC4)cc3)n2)cc1]

(Compound E)

Compound E is described in U.S. Pat. No. 8,486,941.

Additional JAK inhibitors include ruxolitinib (INCB018424), fedratinib (SAR302503, TG101348), tofacitinib, baricitinib, lestaurtinib, pacritinib (SB1518), XL019, AZD1480, INCB039110, LY2784544, BMS911543, and NS018.

In other aspects, compounds of Formula (I) may be combined or administered with one or more inhibitors or modulators (e.g. antagonists) of LOXL2, inhibitors or modulators of adenosine A2B receptor, or inhibitors or modulators of MMP-9.

In other aspects, compounds of Formula (I) may be combined or administered with one or more agents that activate or reactivate latent human immunodeficiency virus (HIV). For example, compounds of Formula (I) may be combined or administered with a histone deacetylase (HDAC) inhibitor or a protein kinase C(PKC) activator. For example, compounds of Formula (I) may be combined or administered with romidepsin or panobinostat.

Compounds of Formula (I) may also be combined or administered with one or more anti-androgenic agents (for example, bicalutamide, flutamide, megestrol, and nilutamide).

Compounds of Formula (I) may also be combined or administered with one or more immunotherapeutic agents such as abagovomab, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, cetuximab, citatuzumab, cixutumumab, clivatuzumab, conatumumab, daratumumab, drozitumab, duligotumab, dusigitumab, detumomab, dacetuzumab, dalotuzumab, ecromeximab, elotuzumab, ensituximab, ertumaxomab, etaracizumab, farietuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab, iratumumab, labetuzumab, lexatumumab, lintuzumab, lorvotumumab, lucatumumab, mapatumumab, matuzumab, milatuzumab, minretumomab, mitumomab, moxetumomab, narnatumab, naptumomab, necitumumab, nimotuzumab, nofetumomabn, ocaratuzumab, ofatumumab, olaratumab, onartuzumab, oportuzumab, oregovomab, panitumumab, parsatuzumab, patritumab, pemtumomab, pertuzumab, pintumomab, pritumumab, racotumomab, radretumab, rilotumumab, rituximab, robatumumab, satumomab, sibrotuzumab, siltuximab, simtuzumab, solitomab, tacatuzumab, taplitumomab, tenatumomab, teprotumumab, tigatuzumab, tositumomab, trastuzumab, tucotuzumab, ublituximab, veltuzumab, vorsetuzumab, votumumab, zalutumumab, CC49 and 3F8. The exemplified therapeutic antibodies may be further labeled or combined with a radioisotope particle, such as indium In 111, yttrium Y 90, iodine I-131.

EXAMPLES

Synthesis of certain compounds of Formula (I), and intermediates used to prepare them, is detailed in the following sections. Any compound numbers are listed for convenience.

All operations involving moisture and/or oxygen sensitive materials were conducted under an atmosphere of dry nitrogen in pre-dried glassware. Unless noted otherwise, materials were obtained from commercially available sources and used without further purification.

Flash chromatography was performed on an Isco Combiflash Companion using RediSep Rf silica gel cartridges by Teledyne Isco. Thin layer chromatography was performed using precoated plates purchased from E. Merck (silica gel 60 PF254, 0.25 mm) and spots were visualized with longwave ultraviolet light followed by an appropriate staining reagent.

Nuclear magnetic resonance ("NMR") spectra were recorded on a Varian 400 MHz resonance spectrometer. $^1$H NMR chemical shifts are given in parts per million ($\delta$) downfield from tetramethylsilane ("TMS") using TMS or the residual solvent signal (CHCl3=$\delta$ 7.24, DMSO=$\delta$ 2.50) as internal standard. $^1$H NMR information is tabulated in the following format: multiplicity (s, singlet; d, doublet; t, triplet; q, quartet; m, multiplet), coupling constant(s) (J) in Hertz, number of protons. The prefix app is occasionally applied in cases where the true signal multiplicity was unresolved and br indicates the signal in question was broadened.

The compounds were named using ChemBioDraw Ultra Version 12.0.

LCMS analysis was performed using a PE SCIEX API 2000 spectrometer with a Phenomenex Luna 5 micron $C_{18}$ column.

Preparatory HPLC was performed on a Gilson HPLC 215 or 271 liquid handler with a Phenomenex column (Luna 5µ, $C_{18}$, 100 A or Gemini 10µ, $C_{18}$, 110 A) and a UV/VIS 156 detector.

When production of starting materials is not particularly described, the compounds are known or may be prepared analogously to methods known in the art or as disclosed in the Examples. One of skill in the art will appreciate that synthetic methodologies described herein are only representative of methods for preparation of the compounds described herein, and that other known methods and variants of methods described herein may be used. The methods or features described in various Examples may be combined or adapted in various ways to provide additional ways of making the compounds described herein.

Methods for obtaining the novel compounds described herein will be apparent to those of ordinary skill in the art, procedures described in, for example, the reaction schemes and examples below, and in the references cited herein.

Scheme 1

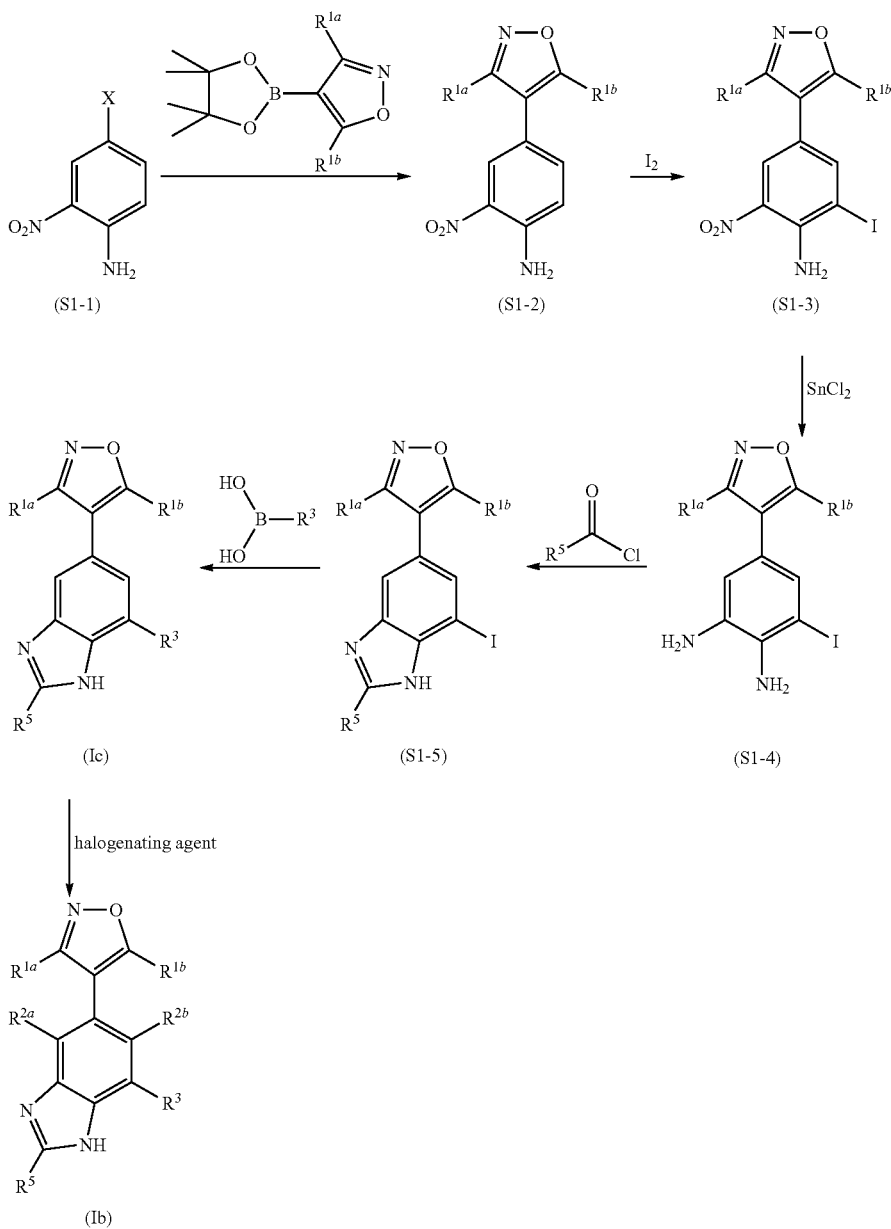

Step 1: Preparation of (S1-2)

A compound of Formula (S1-2), wherein $R^{1a}$ and $R^{1b}$ are as defined for compounds of Formula (I), can be prepared by Suzuki coupling of a nitro aniline (S1-1) to a substituted isoxazole boronate ester in the presence of a base. It is understood that isoxazole boronic acids, other boronate esters, or other appropriate boron complexes (e.g. —BF$_3$K salts, etc.) may also be used in Suzuki coupling reactions. Substituent X on nitro aniline (S1-1) may be any appropriate leaving group (e.g., Cl, Br, I, OTf), and X at each occurrence may be the same or different. Suitable catalysts include palladium catalysts, such as (1,3-bis(2,6-diisopropylphenyl) imidazolidene)(3-chlompyridyl)palladium(II) dichloride (Peppsi-iPr). Suitable bases include, for example, cesium carbonate or 1,8-diazobicycloundec-7-ene. Suitable solvents include a combination of organic solvents and water, including, for example, dimethoxyethane and water. The reaction is carried out in an appropriate solvent under nitrogen, at 70 to 150° C., for 30 minutes to 5 hours. When the reaction is substantially complete, the reaction is allowed to cool to room temperature. The reaction mixture can be partitioned between an aqueous phase and an organic phase. The aqueous phase is discarded, and the organic phase is purified by chromatography on silica gel. Alternatively, the compound of Formula (S1-2) may be used in the next step without purification.

Step 2: Preparation of (S1-3)

A compound of Formula (S1-2) can then be iodinated in the presence of an appropriate iodine source, for example, elemental iodine. The reaction is typically conducted in the presence of a silver salt in an appropriate solvent. Suitable silver salts include, for example, silver nitrate. Suitable solvents include alcoholic solvents, including, for example, ethanol. The starting materials are typically combined at room temperature and allowed to react for 12-18 hours. When the reaction is substantially complete, the compound of Formula (S1-3) is isolated by conventional means, such as by extraction using brine and an organic solvent such as ethyl acetate. The organic layer is dried and concentrated. The crude compound of Formula (S1-3) may be purified using chromatography on silica gel, or be used in the next step without purification.

Step 3: Preparation of (S1-4)

The nitro group of compound (S1-3) can be reduced in the presence of an appropriate reducing agent, for example, stannous chloride, in an appropriate solvent, including alcoholic solvents such as ethanol. The starting materials are combined and brought to an elevated temperature such as 50 to 100° C., and kept at an elevated temperature for 3-10 hours. When the reaction is substantially complete, the compound of Formula (S1-4) is isolated by conventional means, such as by extraction, and purified by chromatography on silica gel.

Step 4: Preparation of (S1-5)

An appropriately substituted acyl chloride with substituent $R^5$, as defined for compounds of Formula (I), is then reacted with the compound of Formula (S1-4) in an appropriate solvent, and allowed to react for a period of time such as 1-5 hours at a temperature near room temperature to form an acylated intermediate. Appropriate solvents include basic organic solvents such as Pyridine. It is understood that in place of an acyl chloride, other appropriate acylating reagents may be used, such as acyl bromides or acid anhydrides. When reaction is sufficiently complete, solvent is removed under reduced pressure, and crude acylated intermediate is taken up into an appropriate acidic solvent, such as glacial acetic acid. Strong acid, such as concentrated hydrochloric acid, may then be added, and the reaction mixture is stirred at a refluxing temperature for 12-18 hours. When the reaction is substantially complete, the compound of Formula (S1-5) is isolated by conventional means, such as by neutralization of acidic solvent followed by extraction, and either used without further purification or purified by chromatography on silica gel.

Alternative Step 4: Preparation of (S1-5)

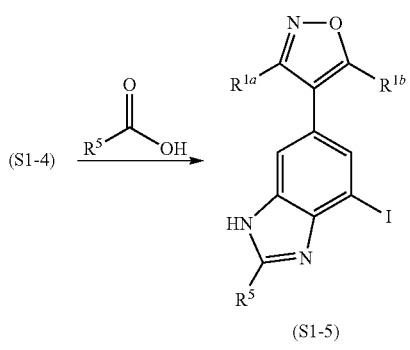

A substituted carboxylic acid with substituent $R^5$, as defined for compounds of Formula (I), or alternatively a mixture of acyl chloride bearing a substituent of $R^5$ in a suitable acidic solvent such as glacial acetic acid, is reacted neat with the compound (S1-4) for 15 minutes to 24 hours at the refluxing temperature of the solvent acid. When the reaction is substantially complete, compound (S1-5) is isolated by conventional means, such as by neutralization of acidic solvent followed by extraction, and either used without further purification or purified by chromatography on silica gel.

Step 5: Preparation of (Ic)

A compound of Formula (Ic) can be prepared by Suzuki coupling of a compound (S1-5) to a boronic acid in the presence of a base. As shown above, boronic acid is substituted with carbon-linked aryl or heteroaryl $R^4$ as defined for compounds of Formula (I). Boronate esters, or other appropriate boron complexes (e.g. —$BF_3K$ salts, etc.) may also be used in place of a boronic acid. Suitable catalysts include palladium catalysts, such as (1,3-bis(2,6-diisopropylphenyl)imidazolidene)(3-chloropyridyl)palladium(II) dichloride (Peppsi-iPr). Suitable bases include, for example, cesium carbonate or 1,8-diazobicycloundec-7-ene. Suitable solvents include a combination of organic solvents and water, including, for example, dimethoxyethane or dimethylformamide and water. The reaction is carried out in an appropriate solvent under nitrogen, at 70 to 150° C., for 30 seconds to 5 hours. When the reaction is substantially complete, the reaction is allowed to cool to room temperature. The reaction mixture can be partitioned between an aqueous phase and an organic phase. The aqueous phase is discarded, and the organic phase concentrated under reduced pressure, and the residue is purified by reverse phase high-performance liquid chromatography, eluting with an appropriate solvent mixture such as acetonitrile and water, to isolate compounds. Alternatively, the compound (Ic) may be purified by other conventional means, such as silica gel chromatography or recrystallization.

Step 6: Preparation of (Ib)

A compound of Formula (Ib) can be prepared by halogenation of a compound (Ic) with a halogenation agent such as NCS, NBS or NIS in an appropriate solvent such as THF, DMF, $CH_2Cl_2$ or $CHCl_3$. The reaction is carried out at 0 to 150° C., for 30 seconds to 5 hours. When the reaction is substantially complete, the reaction is allowed to cool to room temperature. The reaction mixture can be partitioned between an aqueous phase and an organic phase. The aqueous phase is discarded, and the organic phase concentrated under reduced pressure, and the residue is purified by reverse phase high-performance liquid chromatography, eluting with an appropriate solvent mixture such as acetonitrile and water, to isolate compounds. Alternatively, the compound (Ib) may be purified by other conventional means, such as silica gel chromatography or recrystallization.

Scheme 2

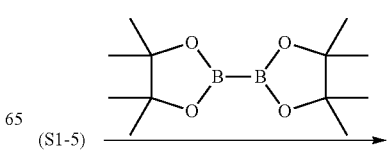

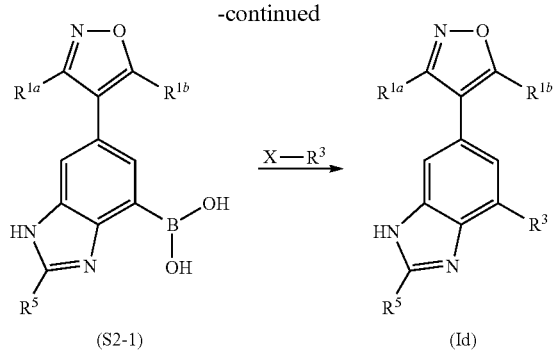

(S2-1) (Id)

Scheme 2 describes an exemplary method of preparing compounds of Formula (Id) wherein $R^{1a}$, $R^{1b}$ and $R^5$ are as described for compounds of Formula (Id), and $R^3$ is aryl or heteraryl, each of which may be optionally substituted as described for compounds of Formual (Id).

Step 1: Preparation of (S2-1)

The compound (52-1) can be prepared by borylation of compound (S1-5), described above, with a borylating reagent such as bis(pinacolato)diboron, shown, in the presence of a base such as potassium acetate, in a suitable solvent. Suitable catalysts include palladium catalysts, such as [1,1'-Bis(diphenylphosphino)ferrocene]dichloropalladium(II). Suitable solvents include polar organic solvents such as dimethylformamide or dimethylsulfoxide. The reaction is carried out in an appropriate solvent under nitrogen, at about 70 to 130° C., for 1-18 hours. When the reaction is substantially complete, the reaction is allowed to cool to room temperature. The reaction mixture can be partitioned between an aqueous phase and an organic phase. The aqueous phase is discarded, the organic phase concentrated under reduced pressure, and the residue is purified by reverse phase high-performance liquid chromatography, eluting with an appropriate solvent mixture such as acetonitrile and water with 0.1% TFA, with spontaneous boronic ester hydrolysis occurring under purification conditions, to isolate compound (S5-1) as a boronic acid. Alternatively, compound (S5-1) may be used in Step 2 in its crude boronate ester form.

Step 2: Preparation of (Id)

The compound (Id) can be prepared by Suzuki coupling of compound (S5-1) in the presence of a base to X—$R^3$, wherein X is a leaving group such as bromide or iodide and $R^3$ is an aryl or heteroaryl, each of which may be optionally substituted as described for compounds of Formula (Id). Suitable catalysts include palladium catalysts, such as (1,3-bis(2,6-diisopropylphenyl)imidazolidene)(3-chloropyridyl) palladium(II) dichloride (Peppsi-iPr). Suitable bases include, for example, cesium carbonate or 1,8-diazobicycloundec-7-ene. Suitable solvents include a combination of organic solvents and water, including, for example, dimethoxyethane or dimethylformamide and water. The reaction is carried out in an appropriate solvent under nitrogen, at about 70 to 150° C., for 30 seconds to 5 hours. When the reaction is substantially complete, the reaction is allowed to cool to room temperature. The reaction mixture can be partitioned between an aqueous phase and an organic phase. The aqueous phase is discarded, and the organic phase concentrated under reduced pressure, and the residue is purified by reverse phase high-performance liquid chromatography, eluting with an appropriate solvent mixture such as acetonitrile and water, to isolate compound (Ie), wherein $R^3$ is aryl or heteroaryl, each of which may be optionally substituted as described for compounds of Formula (I). Alternatively, the compound (Ie) may be purified by other conventional means, as described above.

Scheme 3

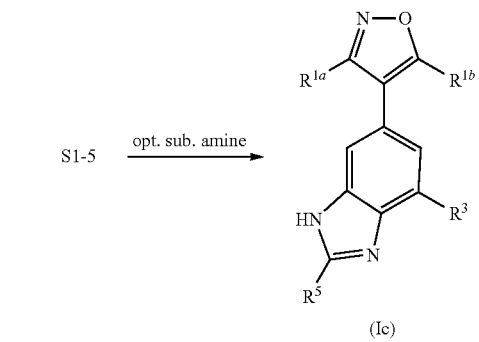

(Ic)

Scheme 3 describes an exemplary method of preparing compounds of Formula (Ic) wherein $R^{1a}$, $R^{1b}$ and $R^5$ are as described for compounds of Formula (I), and $R^3$ is an optionally substituted amino group as described for compounds of Formula (I).

Compound (S1-5) may be reacted with a primary or secondary amine NHR³R² (see definition of "amino" above) or heterocycle bearing NH in the present of palladium or copper catalyst (eg, CuI, CuOAc, CuO, Cu₂O) and an appropriate ligand such as 4,7-dimethoxy-1,10-phenanthroline in the presence of a suitable base, such as cesium carbonate, and PEG-3350 in a suitable solvent (e.g. butyronitrile, THF, DMF, DMA pyridine, toluene or 1,4-dioxane) to produce a compound (Id), wherein $R^3$ is an optionally substituted amino group as described for compounds of Formula (Id). The reaction mixture is carried out at 100 to 150° C. for 24-96 hours. When the reaction is substantially complete, the reaction is allowed to cool to room temperature. The reaction mixture can be concentrated and purified as described above to obtain the compound (Id).

Scheme 4

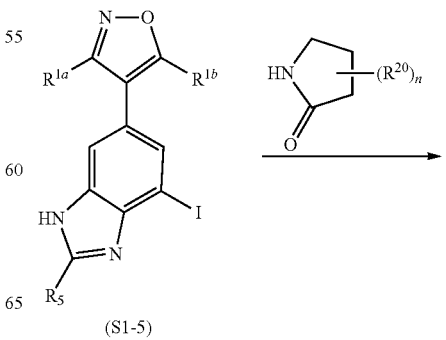

(S1-5)

-continued

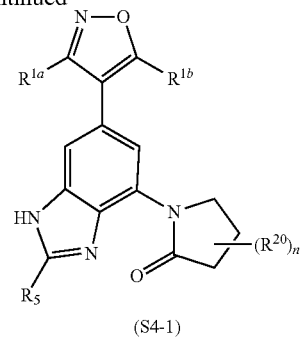

(S4-1)

Scheme 4 describes a particular subset of the reaction described in Scheme 3 in which compound (S1-5) is reacted with a cyclic amine (e.g. an optionally substituted lactam, as shown) to yield compound of Formula (S4-1) wherein $R^{1a}$, $R^{1b}$ and $R^5$ are as described for compounds of Formula (Id), and $R^3$ is an optionally substituted heteroalkyl or heterarylalkyl, in this case an optionally substituted lactam group wherein each $R^{20}$ is as described for compounds of Formula (Id) and n is from 0 to 5, e.g. 0, 1, or 2.

The compound of (S4-1) can be prepared by coupling an optionally substituted lactam to compound (S1-5) in the presence of a copper catalyst, an amino ligand, and a base. As shown above, $R^5$ and $R^{20}$ are defined above for compounds of Formula (I). As described there, each $R^{20}$ may be independently selected from the groups listed, and n is from 0 to 5. An appropriate copper catalyst could be copper halide, such as copper (I) iodide. The amino ligand could be a substituted amine, such as N,N'-dimethylethane-1,2-diamine. The base is an appropriate inorganic base, such as cesium carbonate. The reaction is carried out in an appropriate solvent, such as 1-methylpyrrolidin-2-one (NMP), at 50 to 200° C. for 0.5-24 hours under conventional heating or microwave-assisted heating. When the reaction is substantially complete, the product (S4-1) is isolated by conventional means, such as by filtration, extraction, followed by purification by chromatography of the residue on silica gel.

Scheme 5

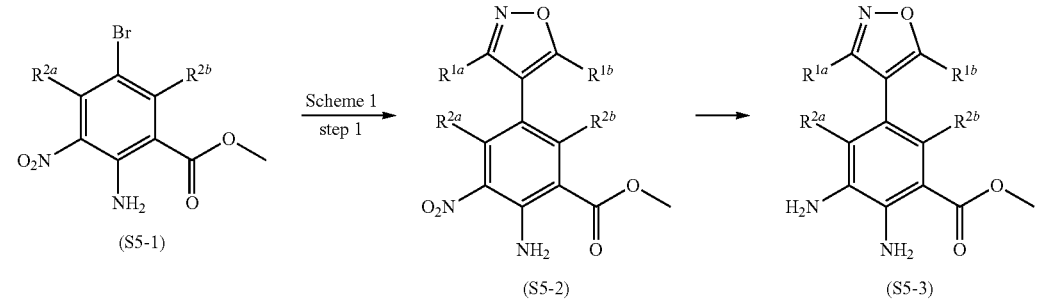

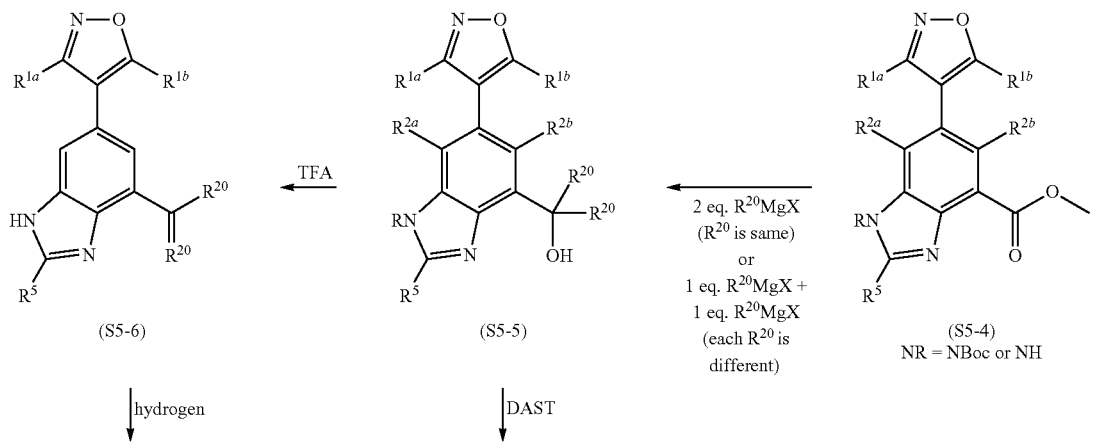

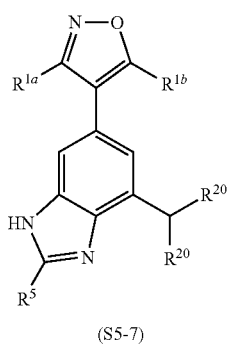 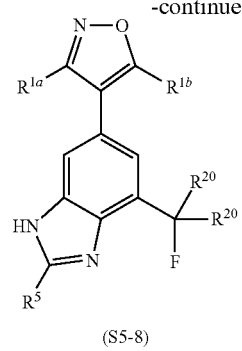 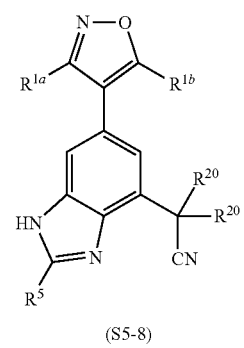

(S5-7)  (S5-8)  (S5-8)

Scheme 5 describes an exemplary method of preparing compounds of Formula (S5-5), (S5-6) and (S5-7), all subgenera of Formula (I), wherein $R^{1a}$, $R^{1b}$, $R^5$, and $R^{20}$ are as described for compounds of Formula (I), and $R^3$ is alkyl optionally substituted with 1 to 5 $R^{20}$ groups, wherein each $R^{20}$ is independently selected from the group described for compounds of Formula (I).

Step 1: Preparation of (S5-2)

Compound (S5-2) may be prepared by reacting (S5-1) with a substituted isoxazole boronate ester as described in Scheme 1, Step 1.

Step 2: Preparation of (S5-3)

Compound (S5-3) may be prepared by reducing the nitro group in the presence of an appropriate reducing agent such as stannous chloride, as described in Scheme 1, Step 3. Other reducing agents such as palladium may also be used.

Step 3: Preparation of (S5-4)

Compound S5-4 may be prepared from (S5-3) in a similar manner as that described in Scheme 1, Step 4. Alternatively, this process can be carried out by treating with ethyl alkylcarbimidate hydrochloride in alcoholic solvent such as MeOH at elevated temperature for a few to several hours.

Step 4: Preparation of (S5-5)

The compound (S5-5) can be prepared by coupling one or more Grignard reagents to (S5-4) in the presence of a base. In this example, each $R^{20}$ may be the same or different, that is, each $R^{20}$ may be independently selected from the group of substituents described for compounds of Formula (I). Where each $R^{20}$ is the same group, two equivalents of $R^{20}MgX$ can be used. Where each $R^{20}$ is a different, one equivalent of $R^{20}MgX$ may be used followed by one equivalent of a different $R^{20}MgX$. The reactions are carried out in an appropriate solvent, such as tetrahydrofuran (THF), at temperatures ranging from −78° C. to ambient temperature from anywhere from an hour to 24 hours. The reaction mixture can be allowed to warm to room temperature. When the reaction is substantially complete, it can be quenched with for example, water or methanol and the product of Formula 2 is isolated by conventional means, such as by extraction, followed by purification by chromatography of the residue on silica gel. Alternatively, the compound (S5-5) can be prepared by reacting with alkyl lithium agent or lithium reagent generated from (hetero)aromatic compound or (hetero)aromatic halide with strong base such as LDA, LiHMP, n-BuLi, sec-BuLi, tert-BuLi in an appropriate solvent such as hexane, THF, diethyl ether, dichloromethane at lower temperature if necessary.

This process can be carried out after protection of N on the benzimidazole with appropriate protecting group such as Boc to improve the chemical yield.

Step 5: Preparation of (S5-6)

The compound (S5-5) can then undergo a dehydroxylation in the presence of an acid to obtain corresponding alkenes such as those of compound (S5-6). It is understood that a large variety of both organic and inorganic acids can facilitate this reaction. Suitable solvents include as toluene or acetonitrile. The reaction may also be performed neat, that is using the reagent acid as the solvent. Examples of strong acid that can be used include sulfuric or phosphoric acid and also trifluoroacetic acid. The reaction is carried out in an appropriate solvent under nitrogen, at an elevated temperature of about 70 to 150° C., for 30 minutes to 5 hours by conventional heating or by use of microwave irradiation. When the reaction is substantially complete, the reaction is allowed to cool to room temperature. The reaction mixture can be partitioned between an aqueous phase and an organic phase. The aqueous phase is discarded, and the organic phase is purified by chromatography on silica gel. Alternatively, compound (S5-6) may be used in the next step without purification.

Step 6: Preparation of (S5-7)

Compound (S5-6) can then be reduced in the presence of an appropriate metal catalyst and hydrogen to furnish compound of (S5-7). The reaction is typically conducted in the presence of a catalyst like 10% palladium on carbon and a solvent such ethanol or ethyl acetate. When the reaction is substantially complete, the solid is filtered off and the filtrate is concentrated under vacuum. The reaction mixture can be partitioned between an aqueous phase and an organic phase. The aqueous phase is discarded, and the organic phase is purified by chromatography on silica gel. It should be noted that the compound (S5-7) can also be made directly from compounds (S5-5) using methodology readily available to those skilled in the art.

Step 7: Preparation of (S5-8)

Compound (S5-8) can then be prepared from (S5-5) by treating with a fluorinating agent such as DAST in inert solvent toward electrophilic fluorination such as dichloromethane at appropriate temperature from 0° C. to rt.

Step 8: Preparation of (5-9)

Compound (S5-9) can then be prepared from (S5-8) by treating with a cyanide such as NaCN, KCN or CuCN in polar solvent such as water, acetonitrile, DMF. THF, dioxane or mixed solvent system if necessary and at appropriate temperature from 0° C. to elevated temperature desirably at rt.

Alternative Method for the Preparation of (S5-5)

Step 9: Preparation of (S5-10)

Compound (S5-4) can be hydrolyzed to give the carboxylic acid (S5-10) by treating with LiOH, NaOH or KOH in water and polar solvent such as MeOH, EtOH, THF, dioxane or mixed solvent system if necessary and at appropriate temperature from rt to elevated temperature.

Step 10: Preparation of (S5-11)

Compound (5-11) can be obtained from the carboxylic acid (S5-10) by treating with N,O dimethyl hydroxylamine hydrochloride, organo tert-amine and appropriate coupling agent such as HATU, DCC or EDC in an appropriate solvent such as DMF, THF, dioxane or dichloromethane and at appropriate temperature from rt to elevated temperature.

Step 11: Preparation of (S5-12)

Compound (S5-12) can be obtained from (S5-11) by protecting NH on the benzimidazole with Boc$_2$O in the presence of organo tert-amine and DMAP if necessary at rt.

Step 12 and 13: Preparation of (S5-5)

Compound (S5-12) was sequentially treated with organi lithium reagent or organo magnesium reagent in an appropriate solvent such as hexane, THF, diethyl ether, dioxane or dichloromethane at lower temperature to rt to install two same or different $R^{20}$ onto the tert alcohol. The protecting group on the N of benzimidazole falls off during the reaction in some cases. But the product has to be treated with TFA to remove Boc if it stays.

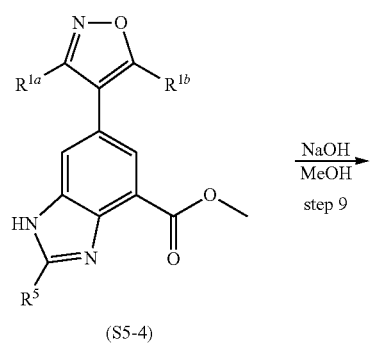

(S5-4)

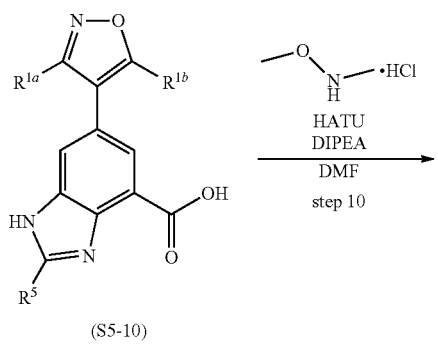

(S5-10)

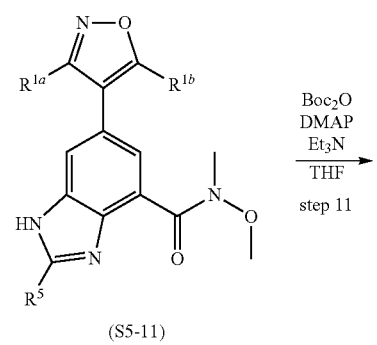

(S5-11)

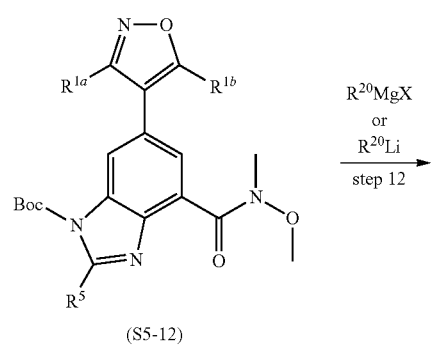

(S5-12)

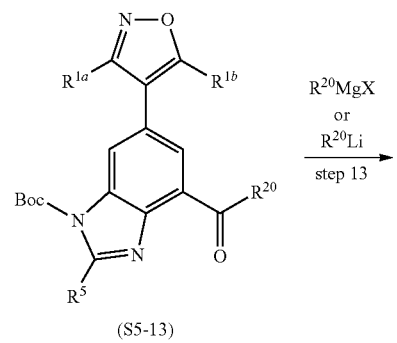

(S5-13)

-continued

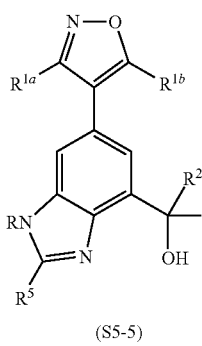

(S5-5)

NR = NH or NBoc

Alternative Method for the Preparation of (S5-2)

When the phenyl ring is mono-fluorinated at $R^{2a}$ or $R^{2b}$ position, compound (S5-15) can be prepared from (S5-14) in a similar manner as that described in Scheme 1, Step 1. And then, the compound (S5-15) can be nitrated under conditions generating $NO^{2+}$ to afford (S5-2, $R^{2a}$ or $R^{2b}$ is F).

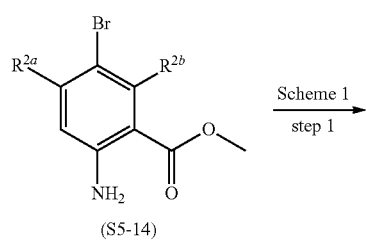

(S5-14)

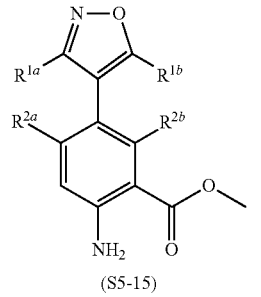

(S5-15)

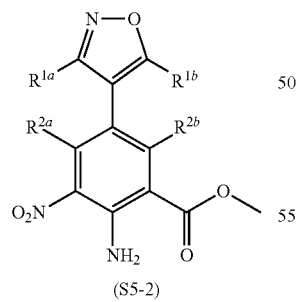

(S5-2)

Alternative Method for the Preparation of (S5-13)

The compound (S5-13) can be prepared from (S5-16) by means of lithiation using appropriate strong base such as BuLi, sec-BuLi or tert-BuLi at lower temperature such as −78° C. in appropriate solvent such as hexane, THF or diethyl ether. Generated lithium intermediate can be trapped with carbonyl derivative such as Wienreb amide to give (S5-13).

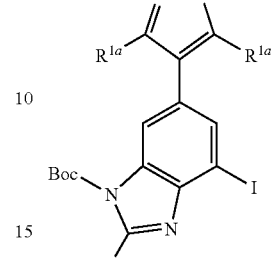

(S5-16)

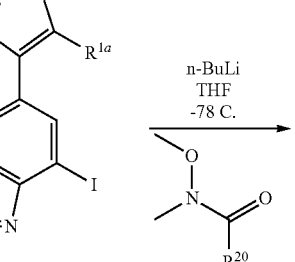

(S5-13)

Alternative Method for the Preparation of (S5-13)

When $R^{20}$ on (S5-13) is a saturated ring system, the present keton can be prepared from the compound (S5-11) in 3 steps sequence.

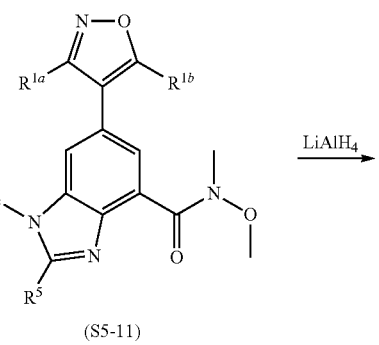

(S5-11)

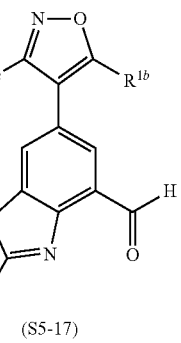

(S5-17)

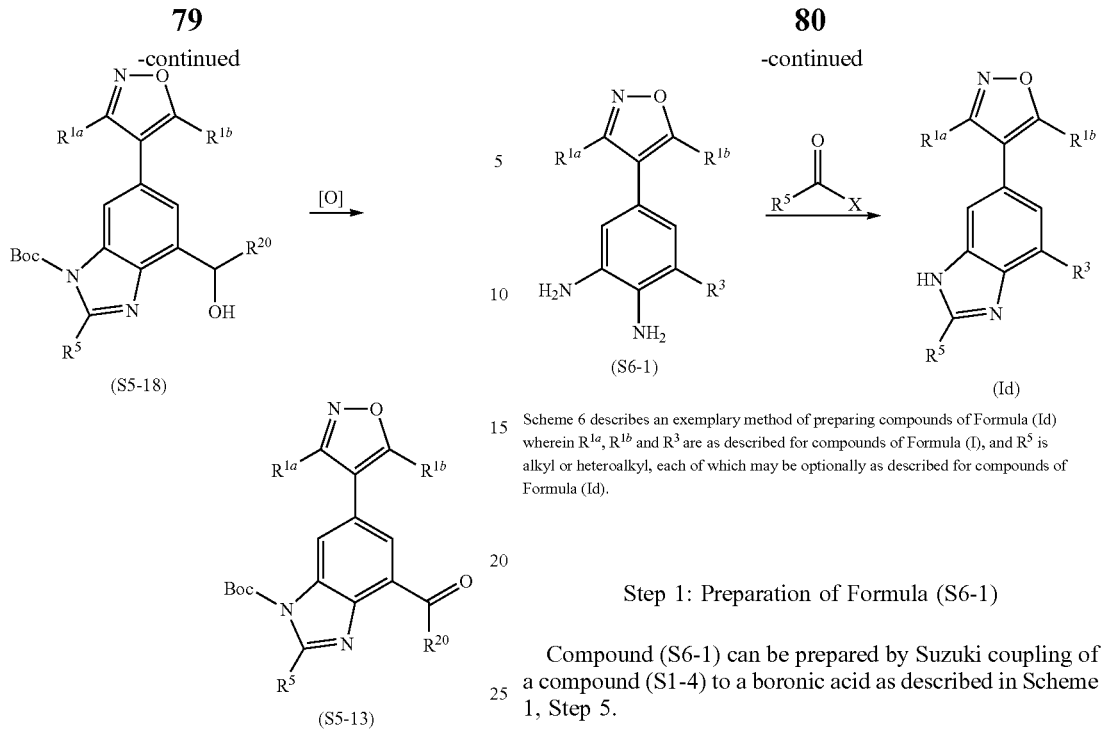

Scheme 6 describes an exemplary method of preparing compounds of Formula (Id) wherein $R^{1a}$, $R^{1b}$ and $R^3$ are as described for compounds of Formula (I), and $R^5$ is alkyl or heteroalkyl, each of which may be optionally as described for compounds of Formula (Id).

Step 1: Preparation of Formula (S6-1)

Compound (S6-1) can be prepared by Suzuki coupling of a compound (S1-4) to a boronic acid as described in Scheme 1, Step 5.

Step 2: Preparation of (Id)

A substituted acyl halide ($R^5C(O)X$ wherein X is a halide, e.g. Cl, and $R^5$ is alkyl or heteroalkyl, each of which may be optionally as described for compounds of Formula (I)) is then reacted with compound (S6-1) in an appropriate solvent for 1-5 hours at room temperature to form an acylated intermediate. Appropriate solvents include basic organic solvents such as pyridine. It is understood that in place of an acyl chloride, other appropriate acylating reagents may be used, such as acyl bromides or acid anhydrides. Other acylation strategies, such as peptide coupling, can also be used to form such an acylated intermediate. When the reaction is sufficiently complete, solvent is removed under reduced pressure and crude acylated intermediate is taken up into an appropriate acidic solvent such as glacial acetic acid. Strong acid, such as trifluoroacetic acid, may then be added and the reaction mixture is stirred at refluxing temperature for 12-18 hours. When the reaction is substantially complete, the reaction mixture is subjected to neutralization of acidic solvent followed by extraction, and purified by reverse phase high-performance liquid chromatography, eluting with an appropriate solvent mixture such as acetonitrile and water, to isolate compound (Id).

Step 1: Preparation of (S5-17)

The compound (S5-11) is reduced by an appropriate reducing agent such as LAH to give compound (S5-17).

Step 2: Preparation of (S5-18)

A saturated ring precursor can be treated with tert-butylhydroperoxide to generate radical intermediate (in case the ring precursor is a cyclic ether) or strong base such as LDA to generate lithium enorate intermediate (in case the ring system is a cyclic ketone) in an appropriate solvent. The intermediate can react with the compound (S5-17) to give the alcohol (S5-18).

Step 3: Preparation of (S5-13)

The alcohol (S5-18) can be oxidized by an appropriate oxidizer such as Dess-Martin reagent in an appropriate solvent such as dichloromethane or chloroform to give (1-13).

Scheme 6

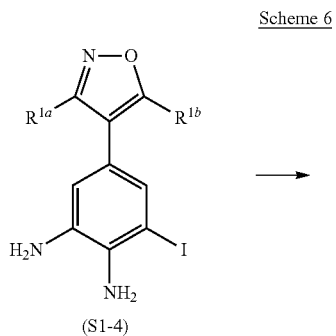

Scheme 7

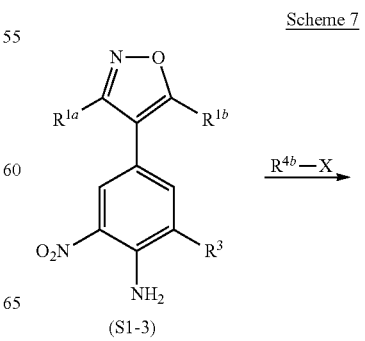

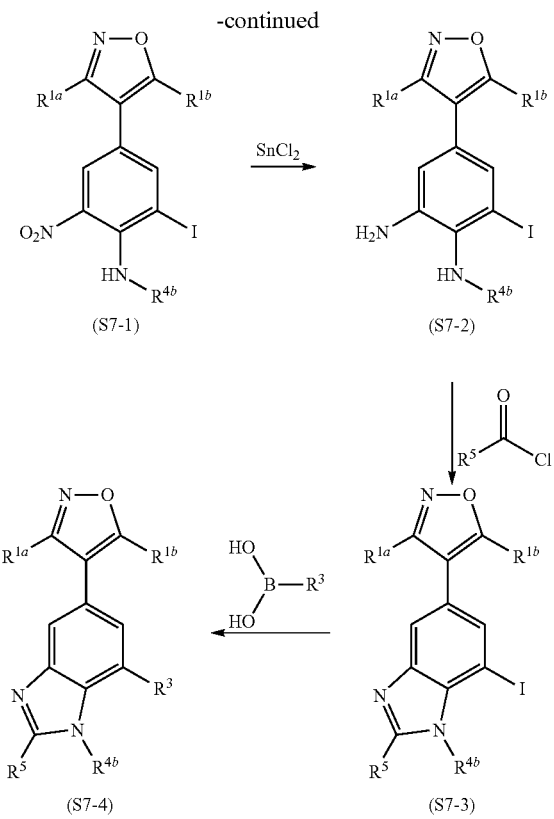

Scheme 7 describes an exemplary method of preparing compounds of Formula (S7-4) wherein $R^{1a}$, $R^{1b}$, are described for compounds of Formula (I) and $R^{4b}$ is an optionally substituted alkyl as described for compounds of Formula (I)

Step 1: Preparation of (S7-1)

Compound (S7-1) wherein may be prepared by alkylating the compound (S1-3) with $R^{4b}$—X, wherein $R^{4b}$ is an optionally substituted alkyl as defined for compounds of Formula (I) and X is an appropriate leaving group, e.g. iodo or triflate, in a suitable organic solvent such as dimethylformamide in presence of a suitable base such as cesium carbonate. The starting materials are combined and allowed to react for 30 minutes to 5 hours. When the reaction is substantially complete, the compound of (S7-1) is isolated by conventional means, such as by extraction, and purified by chromatography on silica gel.

Step 2: Preparation of (S7-2)

The nitro group of compound (S7-1) can then have reduced in the presence of an appropriate reducing agent, for example, stannous chloride, in an appropriate solvent, including alcoholic solvents such as ethanol. The starting materials are combined and brought to an elevated temperature such as 50 to 100° C., and kept at an elevated temperature for 3 to 10 hours. When the reaction is substantially complete, the compound of (S7-2) is isolated by conventional means, such as by extraction, and purified by chromatography on silica gel.

Step 3: Preparation of (S7-3)

An appropriately substituted acyl chloride with substituent $R^5$, as defined in the specification for compounds of Formula (I), is then reacted with the compound (S7-2) in an appropriate solvent, and allowed to react for a period of time such as 1-5 hours at a temperature near room temperature to form an acylated intermediate. Appropriate solvents include basic organic solvents such as Pyridine. It should be understood that in place of an acyl chloride, other appropriate acylating reagents may be used, such as acyl bromides or acid anhydrides. When reaction is sufficiently complete, solvent is removed under reduced pressure, and crude acylated intermediate is taken up into an appropriate acidic solvent, such as glacial acetic acid. Strong acid, such as concentrated hydrochloric acid, may then be added, and the reaction mixture is stirred at refluxing temperature for 12-18 hours. When the reaction is substantially complete, the compound (S7-3) is isolated by conventional means, such as by neutralization of acidic solvent followed by extraction, and either used without further purification or purified by chromatography on silica gel.

Step 4—Preparation of (S7-4)

The compound (S7-4) can be prepared by Suzuki coupling of compound (S7-3) to commercially available boronic acid shown above in the presence of a base. As shown above, boronic acid is substituted with carbon-linked aryl or heteroaryl $R^3$ as defined in the specification for compounds of Formula (I). It should be understood that boronate esters, or other appropriate boron complexes (i.e. —$BF_3K$ salts, etc.) may also be used in place of a boronic acid. Suitable catalysts may include palladium catalysts, such as (1,3-bis(2,6-diisopropylphenyl)imidazolidene)(3-chloropyridyl) palladium(II) dichloride (Peppsi-iPr). Suitable bases may include, for example, cesium carbonate or 1,8-diazobicycloundec-7-ene. Suitable solvents may include a combination of organic solvents and water, including, for example, dimethoxyethane or dimethylformamide and water. The reaction is carried out in an appropriate solvent under nitrogen, at an elevated temperature of about 70° C. to 150° C., for about 30 seconds to 5 hours. When the reaction is substantially complete, the reaction is allowed to cool to room temperature. The reaction mixture can be partitioned between an aqueous phase and an organic phase. The aqueous phase is discarded, and the organic phase concentrated under reduced pressure, and the residue is purified by reverse phase high-performance liquid chromatography, eluting with an appropriate solvent mixture such as acetonitrile and water, to isolate compound (xiii). Alternatively, the compound (xiii) may be purified by other conventional means, such as silica gel chromatography or recrystallization.

Scheme 8

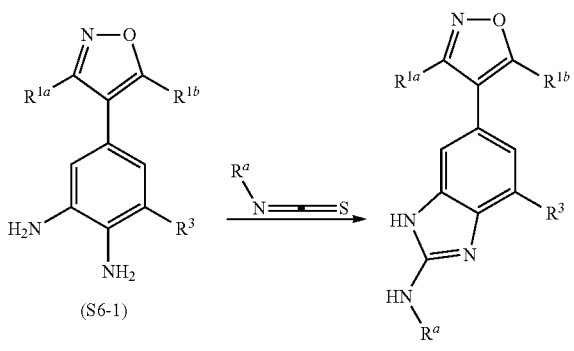

Scheme 8 describes an exemplary method of preparing compounds of Formula (S8-1) wherein $R^{1a}$, $R^{1b}$, $R^3$, and $R^a$ are as described for compounds of Formula (I).

An isothiocyanate substituted with substituent R²⁰, as defined in this Scheme, is reacted with compound (S6-1) in an appropriate solvent, such as tetrahydrofuran, in presence of an appropriate base, such as triethylamine, for 1-5 hours at 50 to 100° C., at which point an activating carbodiimide such as 1-ethyl-3-(3-dimethylaminopropyl)carbodiimide hydrogen chloride is added and the reaction is allowed to continue for an additional 1-5 hours. When the reaction is substantially complete, the solvent is removed under reduced pressure and the crude residue is purified by reverse phase high-performance liquid chromatography, eluting with an appropriate solvent mixture such as acetonitrile and water, to isolate compound (S8-1).

Scheme 9

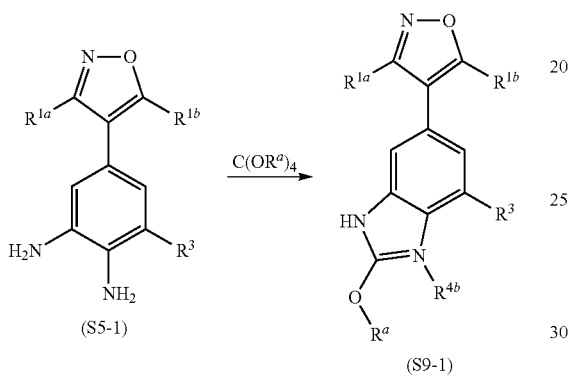

(S5-1) → C(OR$^a$)$_4$ → (S9-1)

Scheme 9 describes an exemplary method of preparing compounds of Formula (S9-1) wherein R$^{1a}$, R$^{1b}$, R$^3$ and R$^a$ are described for compounds of Formula (I).

An orthocarbonate C(OR$^a$)$_4$, (wherein R$^a$ is described above, e.g. alkyl, haloalkyl) is reacted with compound (S5-1) either neat or in the presence of an appropriate acid, such as acetic acid, and allowed to react for 30 minutes to 18 hours 25 to 150° C. When the reaction is substantially complete, the solvent is removed under reduced pressure and the crude residue is purified by reverse phase high-performance liquid chromatography, eluting with an appropriate solvent mixture such as acetonitrile and water, or by conventional means such as silica gel chromatography, to isolate compound (S9-1).

Scheme 10

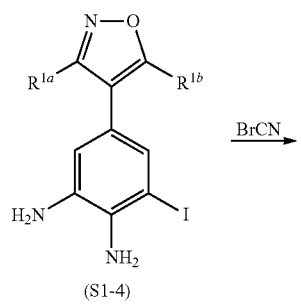

(S1-4) → BrCN →

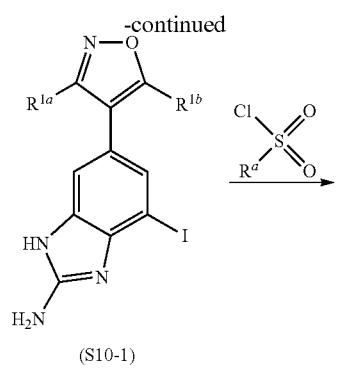

(S10-1)

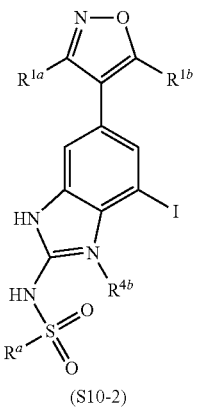

(S10-2)

(S10-3)

Scheme 10 describes an exemplary method of preparing compounds of Formula (S10-3) wherein R$^{1a}$, R$^{1b}$, R$^3$ and R$^a$ are described for compounds of Formula (I).

Step 1: Preparation of (S10-1)

Compound (S1-4) in an appropriate solvent mixture such as ethanol, acetonitrile, and water, with an appropriate base, such as sodium bicarbonate, is cooled to a low temperature such as 0° C. An appropriate cyanogen halide, such as cyanogen bromide, shown, is added to the reaction mixture and the reaction mixture is allowed to warm to room temperature and to react for 12-18 hours. When the reaction is substantially complete, ethanol is added, the reaction mixture is filtered, solvents are removed under vacuum, and the crude residue is purified by conventional means such as silica gel chromatography, to isolate compound of (S10-1).

Step 2: Preparation of (S10-2)

Compound of (S10-1) is combined in an appropriate solvent, such as tetrahydrofuran, with an appropriate base, such as triethylamine. An appropriate sulfonylating reagent, such as cyclopropanesulfonyl chloride, is added to the reaction mixture and the reaction is allowed to react for a time of 12 to 18 hours. When the reaction is substantially complete, the reaction mixture may be isolated by conventional means, such as extraction followed by removal of organic solvents, and the crude residue is purified by conventional means such as silica gel chromatography, to isolate compound of (S10-2).

Step 3: Preparation of (S10-3)

The compound (S10-3) can be prepared by Suzuki coupling of a compound (S10-2) to a substituted boronic acid, as described in Scheme 1 above.

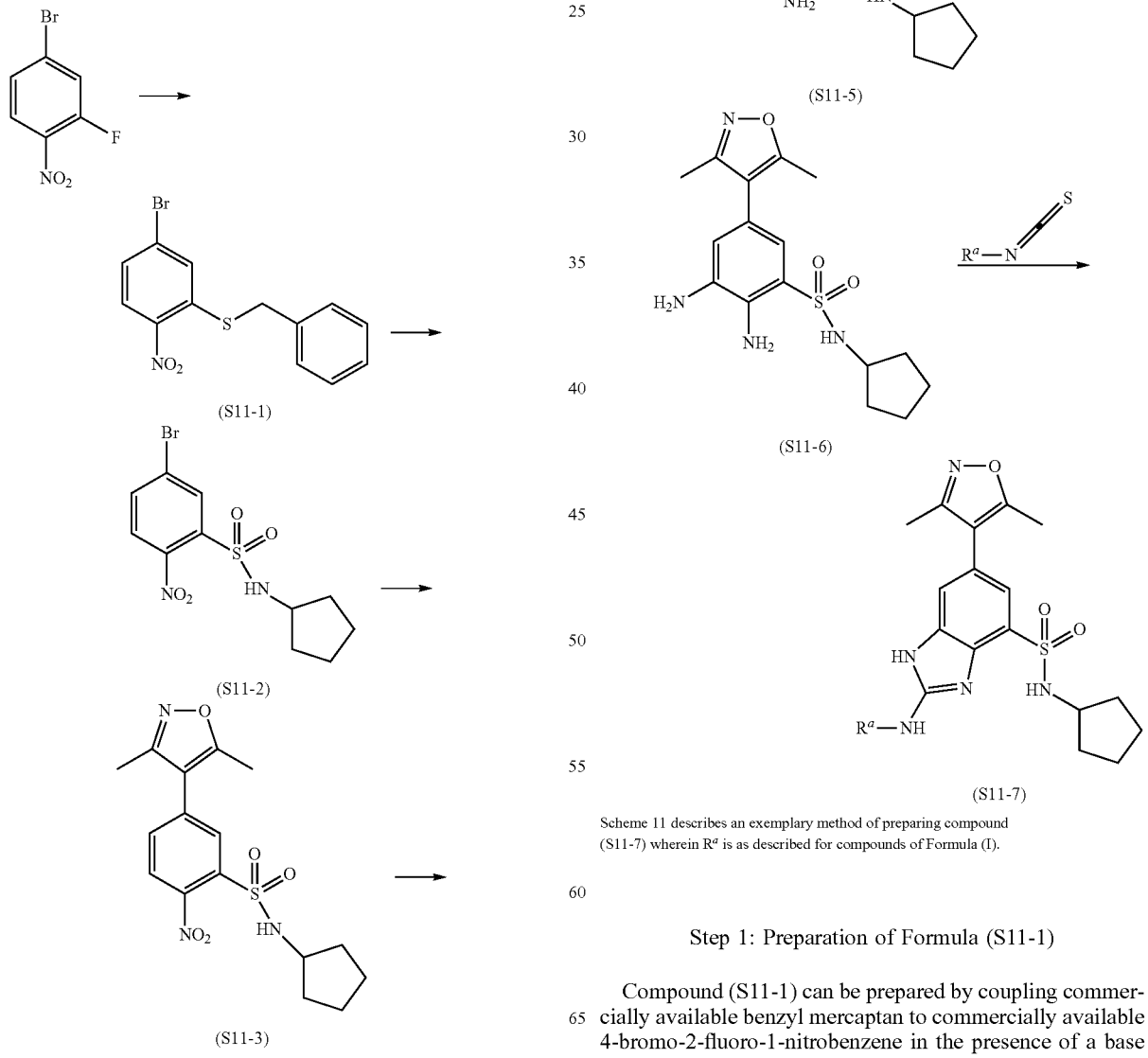

Scheme 11 describes an exemplary method of preparing compound (S11-7) wherein $R^a$ is as described for compounds of Formula (I).

Step 1: Preparation of Formula (S11-1)

Compound (S11-1) can be prepared by coupling commercially available benzyl mercaptan to commercially available 4-bromo-2-fluoro-1-nitrobenzene in the presence of a base such as cesium carbonate. The reaction is carried out in an appropriate solvent, such as dimethylformamide (DMF), at a temperature of from 0° C. to RT for about 2 hours. When the reaction is substantially complete, the product (S11-1) is isolated by conventional means, such as by extraction, followed by purification by chromatography of the residue on silica gel. Alternatively, the compound (S11-1) may be used in the next step without purification.

Step 2: Preparation of Formula (S11-2)

Compound (S11-1) can then be oxidized in the presence of an appropriately substituted haloimidazolidine-2,4-dione compound, for example, 1,3-dichloro-5,5-dimethylimidazolidine-2,4-dione. The reaction is typically conducted in the presence of an acid in an appropriate solvent. Suitable acids may include, for example, acetic acid. Suitable solvents may include a combination of solvents, including, for example, acetonitrile and water. The reaction was conducted at 0° C. and then was allowed to warm to room temperature and stirred for 1 hour before being partitioned between brine and ethyl acetate. The organic layer was dried using sodium sulfate and evaporated. The crude sulfonyl chloride was used without further purification in the next step.

Step 3: Preparation of (S11-3)

The compound (S11-2) can then be used in a Suzuki coupling reaction with a boronate ester, as described in Scheme 1, Step 1.

Step 4: Preparation of (S11-4)

Compound (S11-3) can be dissolved in solvent such as HOAc and reduced with Zn powder at RT. After stirring for about 25 min, the Zn powder is filtered off. Volatiles are removed and the crude aniline in taken up in AcOEt, washed with carbonate solution, and purified by chromatography on silica gel to afford (S11-5).

Step 5: Preparation of (S11-5)

Compound (S11-4) can be nitrated using $NO_2BF_4$ in solvents like DCM/acetonitrile. The reaction is conducted at 0° C. and then the temperature is slowly raised to RT overnight. The solvent is then evaporated, the residue was dissolved in EtOAc, washed with sat. $NaHCO_3$ solution. The organic solvent is then evaporated and purified with chromatography on silica gel to afford (S11-5).

Step 6: Preparation of (S11-6)

Compound (S11-5) can be reduced using catalytic hydrogenation. The reaction can be conducted in solvent such as MeOH and catalyst used was Pd (10% on carbon). The reaction is completed in 2 h at RT. The reaction mixture is filtered and solvent is evaporated. The residue is then purified with chromatography on silica gel to afford (S11-6).

Step 7: Preparation of (S11-7)

Compound (S11-6) can be reacted with an isothiocyanate derivative. The reaction can be conducted in solvent such as THF in the presence of base such as triethylamine. The reaction is heated to about 80° C. for 3-5 h before 1-ethyl-3-(3-dimethylaminopropyl)-carbodiimide hydrogen chloride is added and heated at 80° C. for 30 mins. The solvent is then evaporated. The residue is then purified with prep-HPLC to afford (S11-7).

Scheme 12

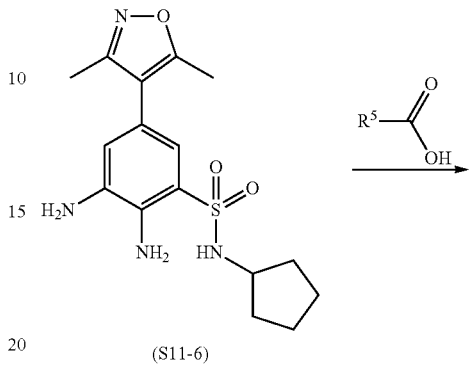

(S11-6)

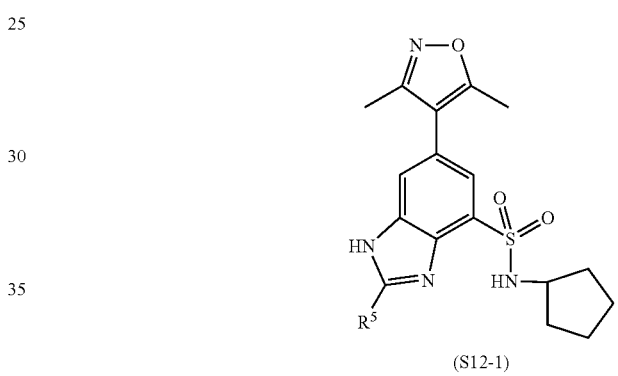

(S12-1)

Scheme 12 describes an exemplary method of preparing compounds of Formula (S12-1) wherein $R^5$ is as described for compounds of Formula (I).

Preparation of (S12-1)

Compound (S11-6) can be reacted with a substituted carboxylic acid as described in Scheme 1, Alternative Step 4, to afford (S12-1).

Scheme 13

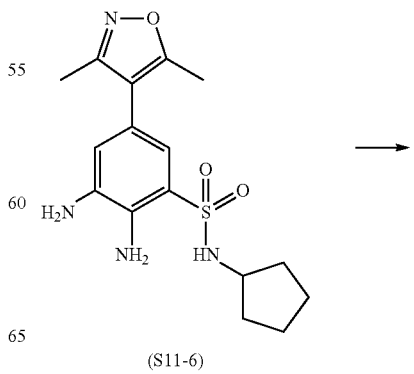

(S11-6)

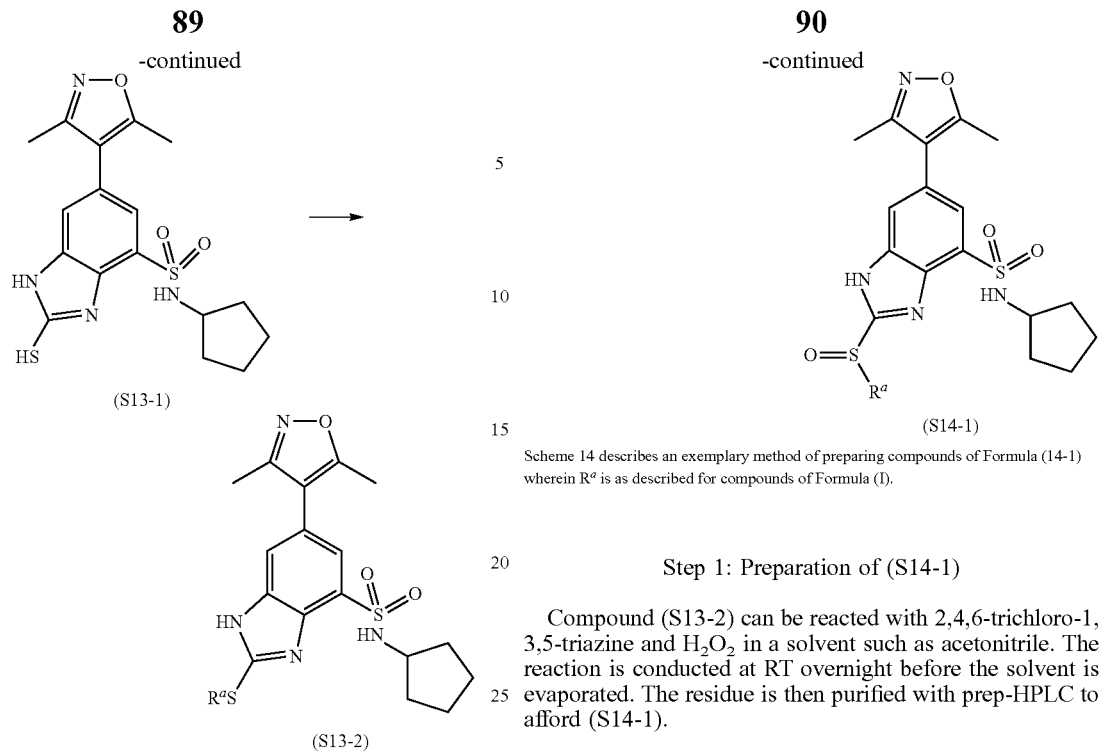

(S13-1)

(S13-2)

Scheme 13 describes an exemplary method of preparing compounds of Formula (13-2) wherein $R^a$ is as described for compounds of Formula (I).

Step 1: Preparation of (S13-1)

Compound (S11-6) can be reacted with 1,1'-thiocarbonyl-diimidazole in a solvent such as DMF. The reaction is conducted at temperature of 90° C. overnight before the solvent is evaporated. The residue is then purified with prep-HPLC to afford (S13-1).

Step 2: Preparation of (S13-2)

Compound (S13-1) can be reacted with an iodide derivative (e.g. an optionally substituted alkyl iodide) in solvent such as EtOH in the presence of base such as KOH. The reaction is conducted at RT overnight before the solvent was evaporated. The residue was then purified with prep-HPLC to afford (S13-2).

Scheme 14

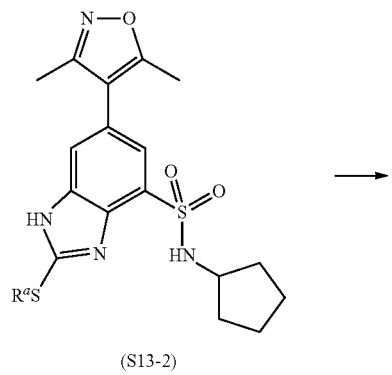

(S13-2)

(S14-1)

Scheme 14 describes an exemplary method of preparing compounds of Formula (14-1) wherein $R^a$ is as described for compounds of Formula (I).

Step 1: Preparation of (S14-1)

Compound (S13-2) can be reacted with 2,4,6-trichloro-1,3,5-triazine and $H_2O_2$ in a solvent such as acetonitrile. The reaction is conducted at RT overnight before the solvent is evaporated. The residue is then purified with prep-HPLC to afford (S14-1).

Scheme 15

(S13-2)

(S15-1)

Scheme 15 describes an exemplary method of preparing compounds of Formula (S15-1) wherein $R^a$ is as described for compounds of Formula (I).

Preparation of (S15-1)

Compound (S13-2) can be reacted with mCPBA or $H_2O_2$ in solvent such as DCM. The reaction is conducted at RT for 30 mins before the solvent is evaporated. The residue is then purified with prep-HPLC to afford (S15-1).

Compounds of Formula (I) also include the following:
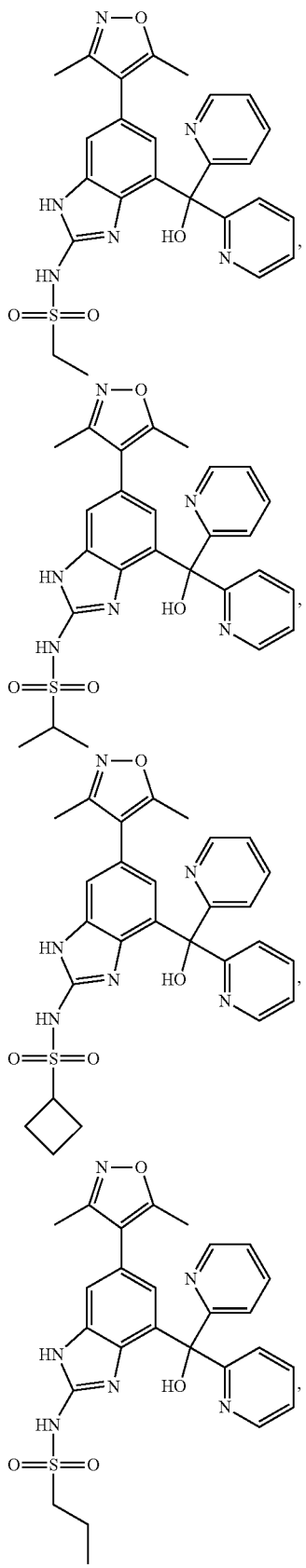
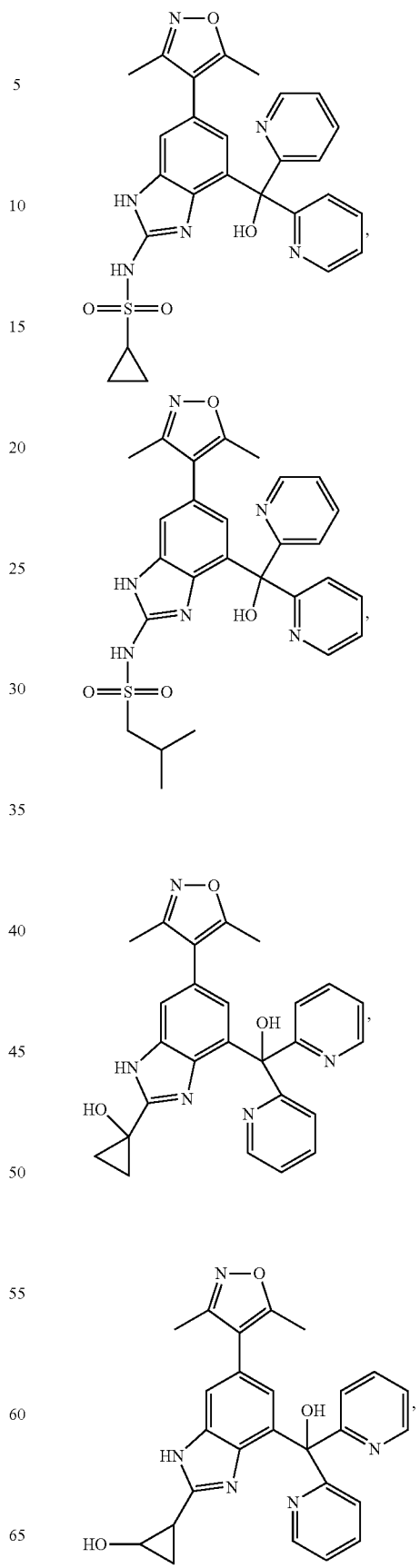

93
-continued
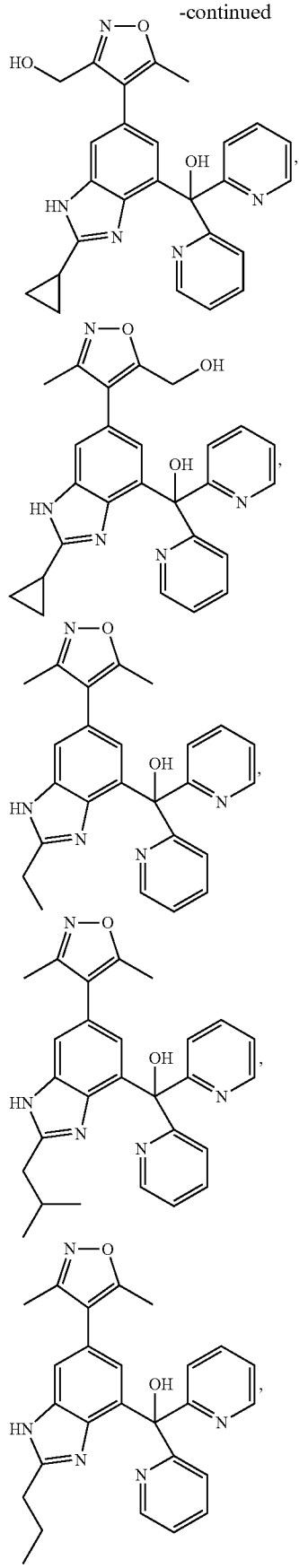
94
-continued
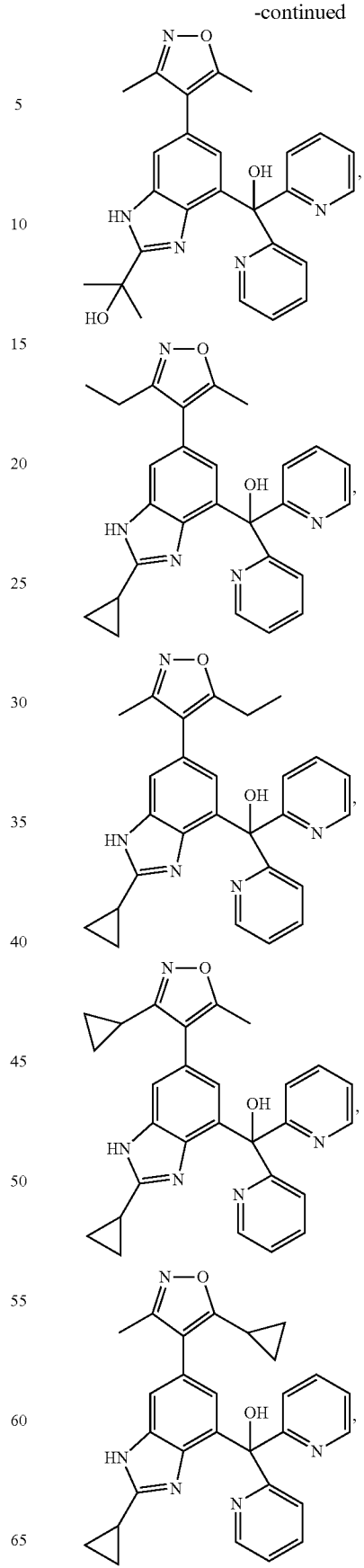

95
-continued
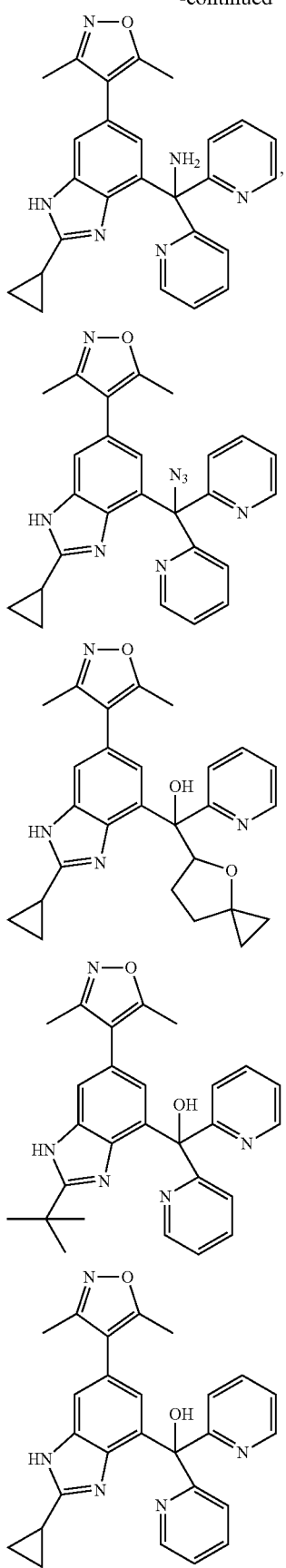
96
-continued
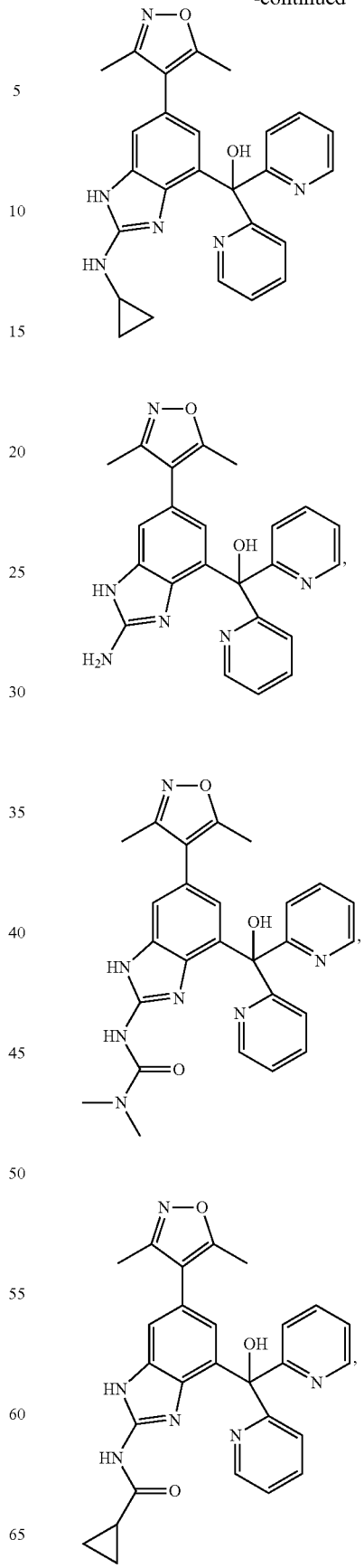

97
-continued
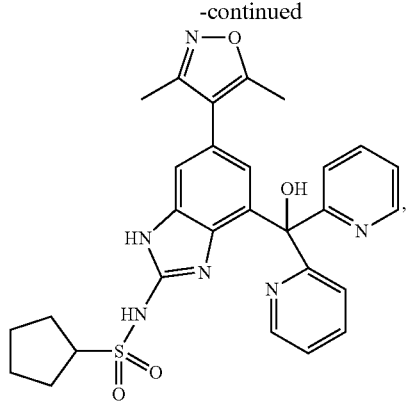
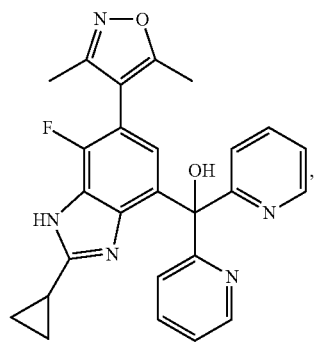
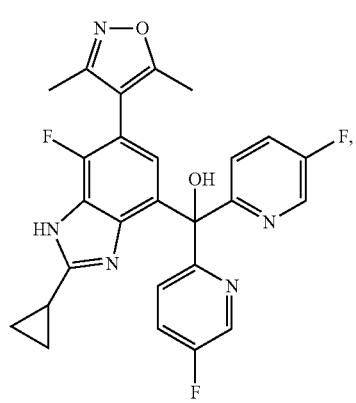
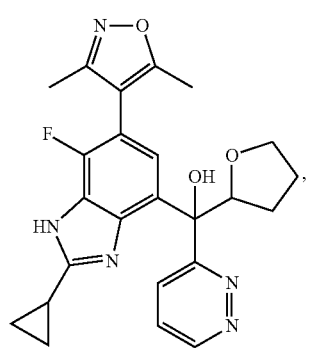
98
-continued
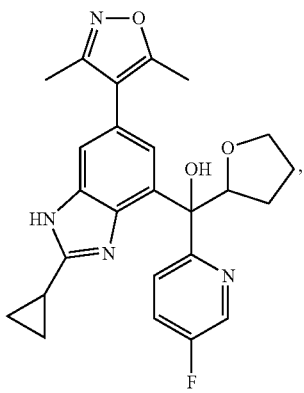
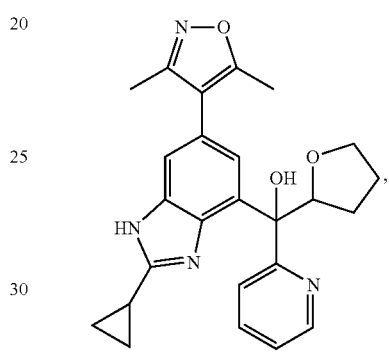
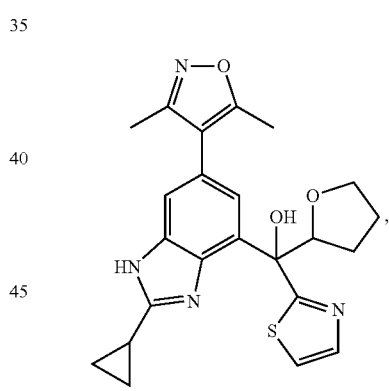
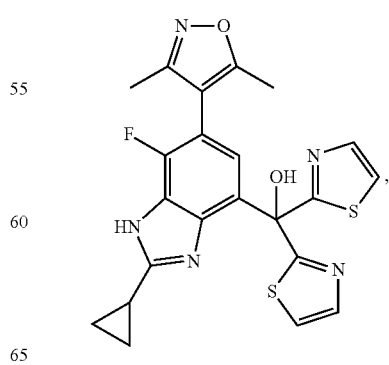

99
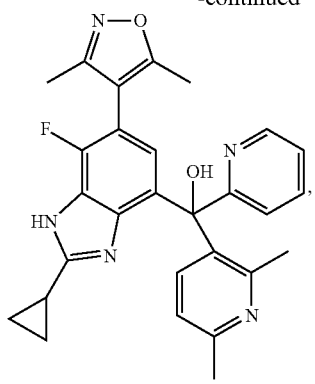
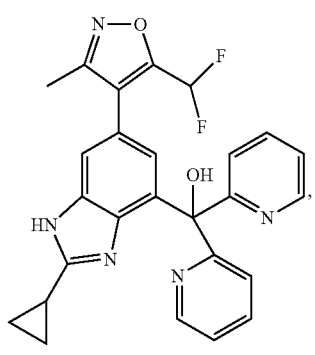
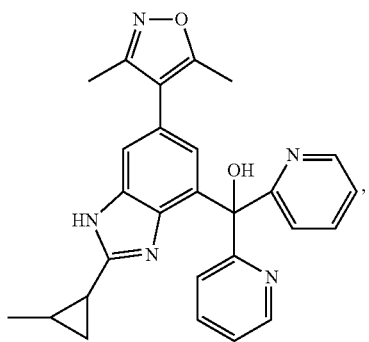
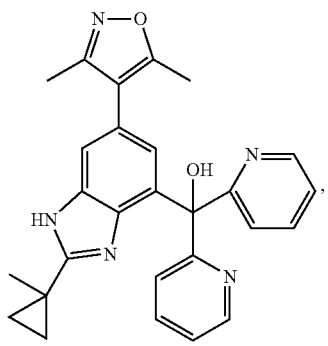
100
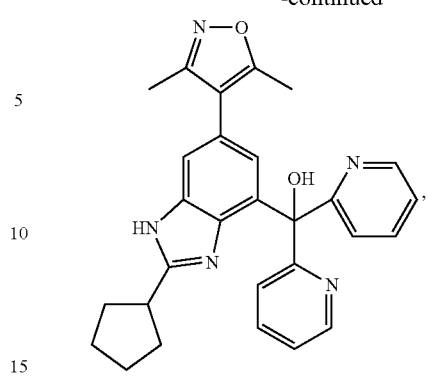
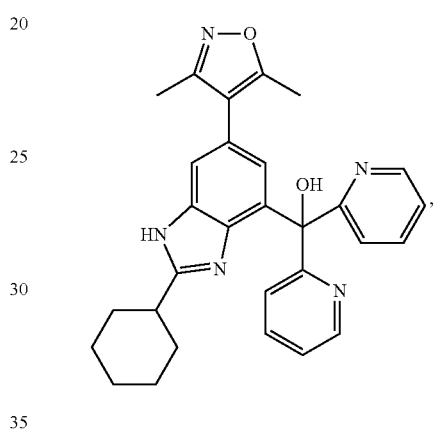
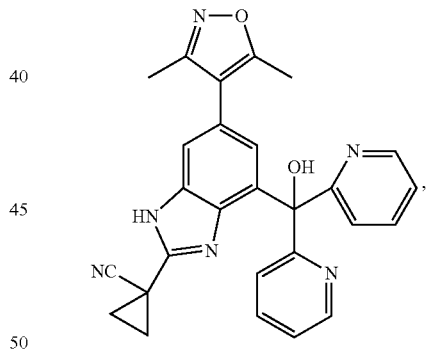
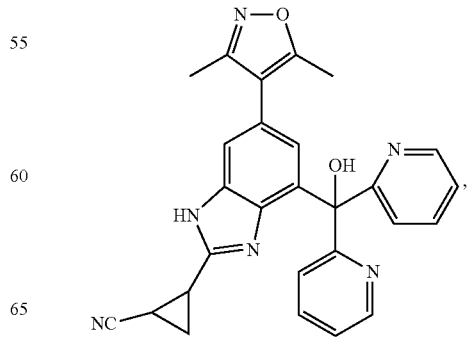

101
-continued
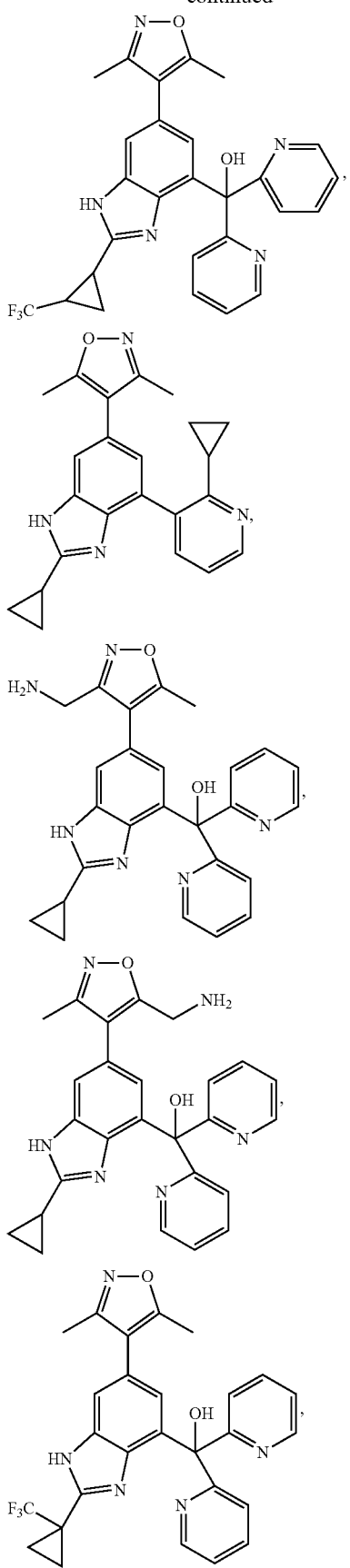
102
-continued
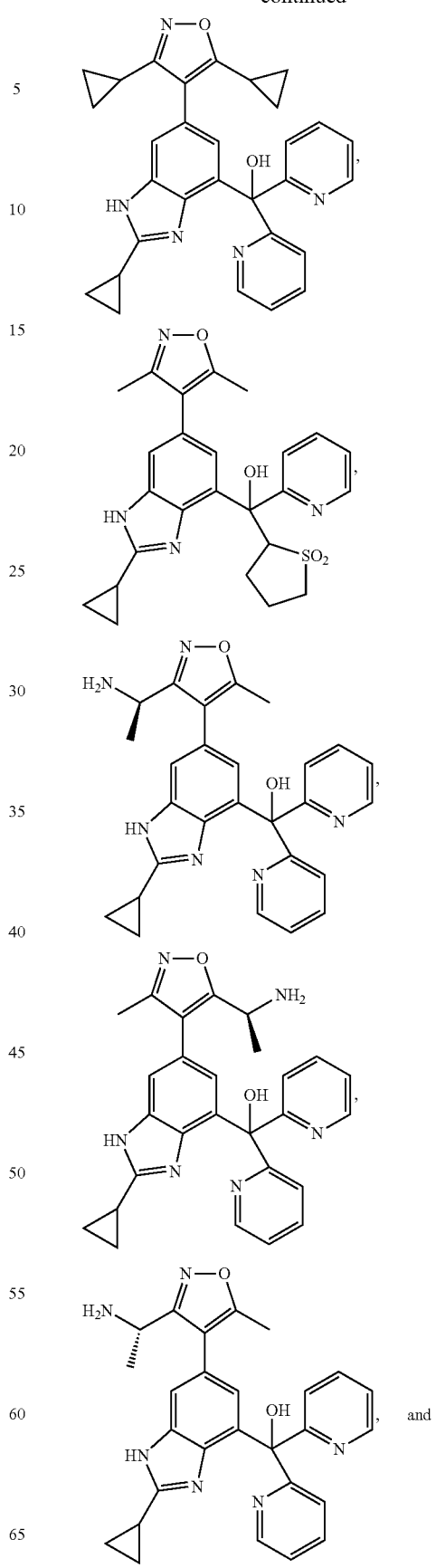

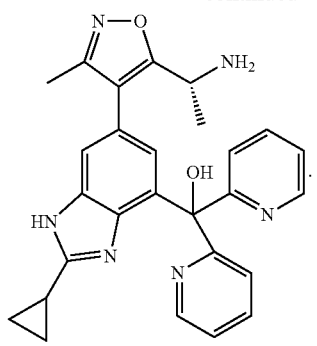
Compounds of Formula (I) also include the following:
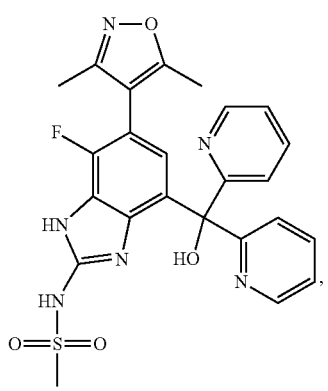
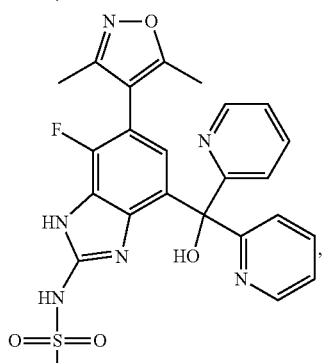
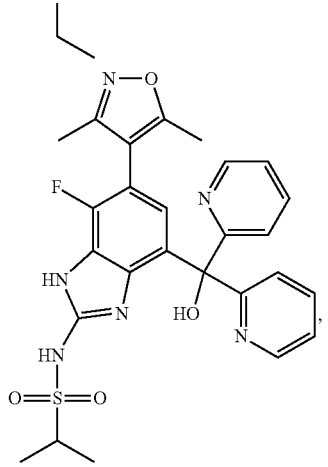
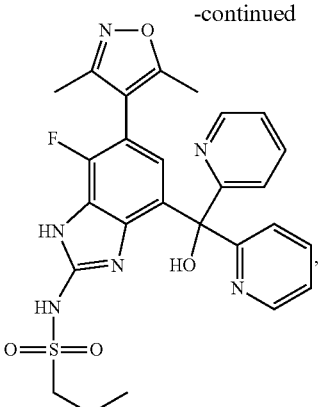
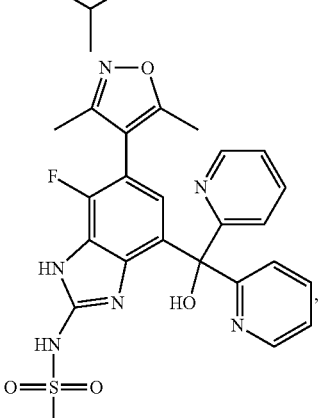
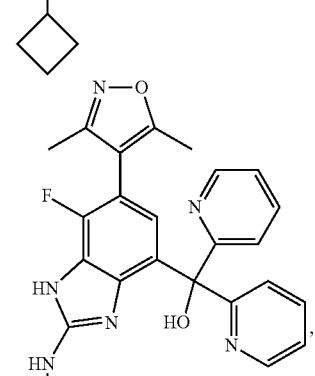
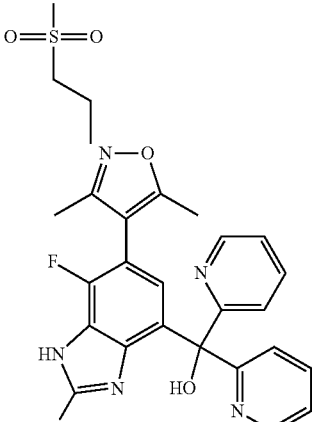
and

-continued

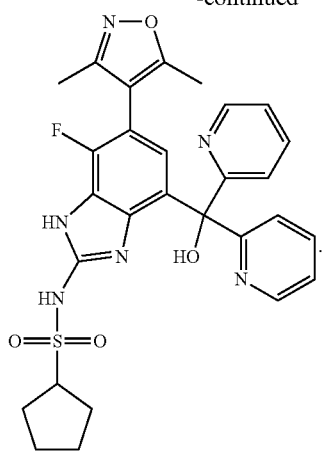

The following examples illustrate further aspects, and provide additional compounds of Formula (I).

Example 1

N-Cyclopentyl-2-(cyclopropylmethylamino)-6-(3,5-dimethylisoxazol-4-yl)-1H-benzo[d]imidazole-4-sulfonamide (1020-1)

Step 1: Preparation of 1-bromo-3-benzylthio-4-nitrobenzene

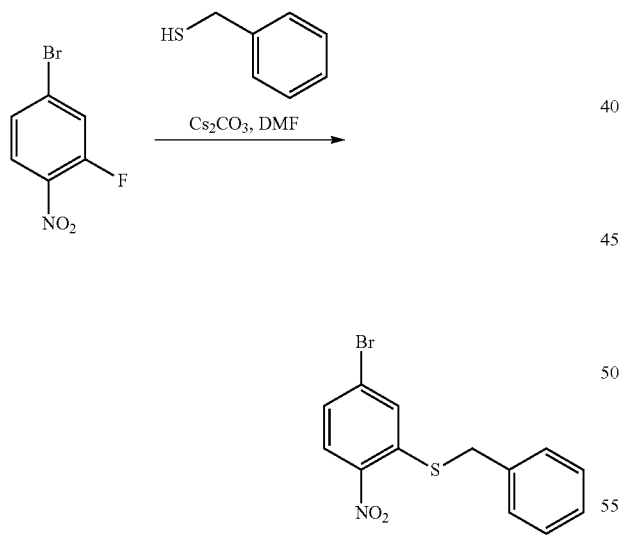

Benzyl mercaptan (2.36 g, 19 mmol) was added dropwise to a mixture of 1-bromo-3-fluoro-4-nitrobenzene (5 g, 19 mmol), cesium carbonate (7.87 g, 57 mmol) at 0° C. in DMF (25 ml) under nitrogen. The reaction mixture was allowed to warm to room temperature, stirred for 2 hours and partitioned between ethyl acetate and water. The organic phase was washed with brine (4x), dried with sodium sulfate and concentrated. Crystallization from hot EtOAc afforded the product 1-bromo Step 2: Preparation of 5-bromo-N-cyclopentyl-2-nitrobenzenesulfonamide

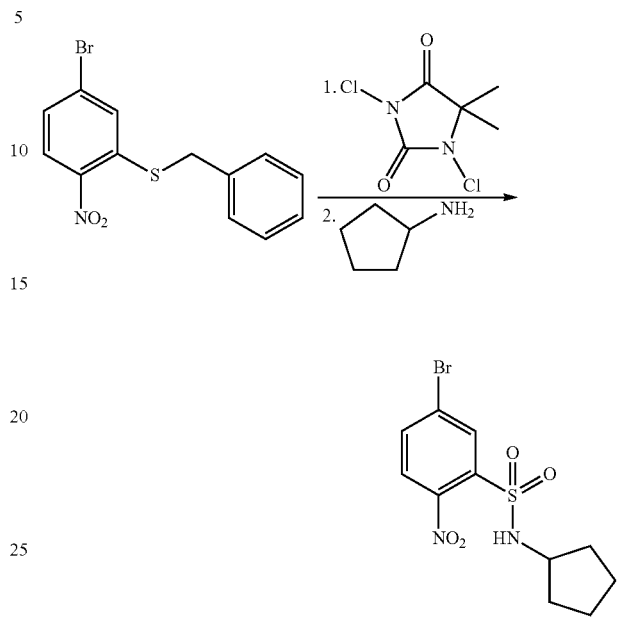

Solid 1,3-dichloro-5,5-dimethylimidazolidine-2,4-dione (1.21 g, 6.19 mmol) was added to an ice-cold suspension of the 1-bromo-3-benzylthio-4-nitrobenzene (1 g, 3.09 mmol) in acetonitrile (25 mL), acetic acid (1 ml) and water (0.62 ml). The clear solution was allowed to warm to room temperature and stirred for 1 hour before being partitioned between brine and ethyl acetate. The organic layer was dried using sodium sulfate and evaporated. The crude sulfonyl chloride (rf=0.23 in 9:1 hexanes/ethyl acetate, starting material rf=0.57) was used without further purification in the next step.

To a solution of cyclopentyl amine (0.52 g, 6.18 mmol) in pyridine (5 ml) was added above sulfonyl chloride in DCM (5 mL) at 0° C. The reaction was stirred at room temperature for 15 minutes before being partitioned between brine and ethyl acetate. The organic layer was washed with brine, dil. HCl and again brine, and dried over sodium sulfate. Purification on silica gel (rf=0.33 in 9:1 hexanes/ethyl acetate) afforded the product 5-bromo-N-cyclopentyl-2-nitrobenzenesulfonamide as an off-white powder.

Step 3: Preparation of N-cyclopentyl-5-(3,5-dimethylisoxazol-4-yl)-2-nitrobenzenesulfonamide

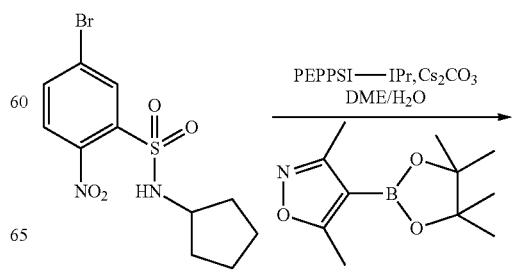

-continued

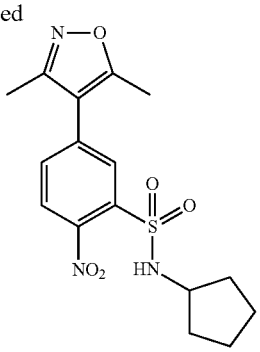

To a mixture of the 5-bromo-N-cyclopentyl-2-nitrobenzenesulfonamide (1.394 g, 4 mmol), 3,5-dimethylisoxazole-4-boronic acid pinacol ester (1.78 g, 8 mmol), PEPPSI™-IPr (Sigma-Aldrich Corporation) (0.271 g, 0.4 mmol) and cesium carbonate (3.90 g, 12 mmol) under nitrogen were added dimethoxyethane (20 mL) and water (10 mL). The reaction mixture was degassed with $N_2$ and then heated to 90° C. for 1 hour. The mixture was partitioned between water and ethyl acetate, the organics concentrated and purified by silica gel chromatography (gradient DCM to DCM/ethyl acetate=1/1) to give the product N-cyclopentyl-5-(3,5-dimethylisoxazol-4-yl)-2-nitrobenzenesulfonamide as a white powder.

Step 4: Preparation of 2-amino-N-cyclopentyl-5-(3,5-dimethylisoxazol-4-yl)benzenesulfonamide

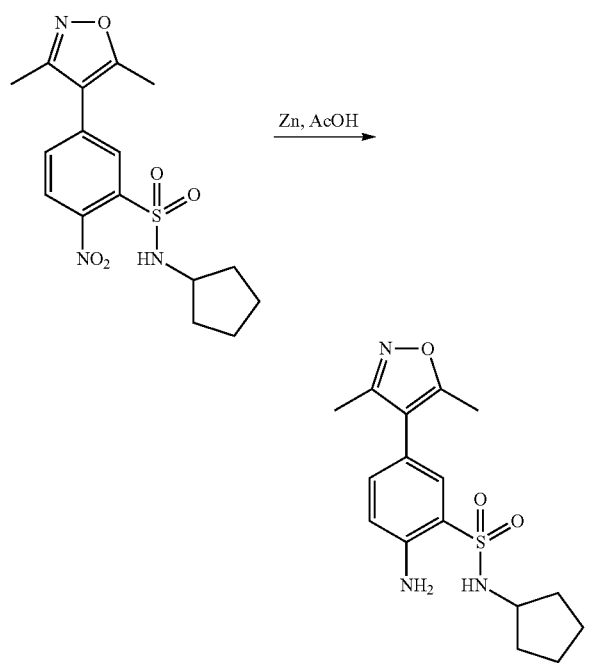

The N-cyclopentyl-5-(3,5-dimethylisoxazol-4-yl)-2-nitrobenzenesulfonamide (1.27 g, 3.5 mmol) was dissolved in AcOH with stirring and Zn powder (20 g) added in portions (5×, in 5 min intervals) at RT. After stirring for 25 min., the Zn powder was filtered off. Volatiles were removed and the crude aniline taken up in EtOAc, washed 4× with aq. carbonate solution, and purified by column chromatography (rf=0.2, hexane/EtOAc: 1/1) to afford 2-amino-N-cyclopentyl-5-(3,5-dimethylisoxazol-4-yl)benzenesulfonamide as a white powder.

Step 5: Preparation of 2-amino-3-bromo-N-cyclopentyl-5-(3,5-dimethylisoxazol-4-yl)benzenesulfonamide

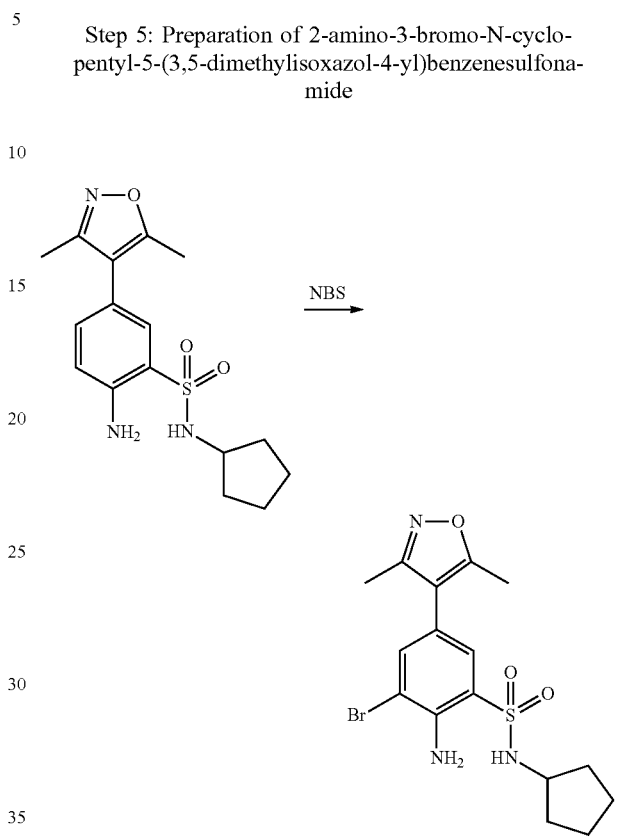

The 2-amino-N-cyclopentyl-5-(3,5-dimethylisoxazol-4-yl)benzenesulfonamide (0.26 g, 0.763 mmol) was taken up in DMF (5 ml) and cooled to 0° C. NBS (0.136 g, 0.763 mmol) was added and stirred for 10 min at 0° C. followed by 20 min at RT. The solution was diluted with EtOAc (20 ml) and washed 5× with brine. The product (rf=0.5, hexane/EtOAc=1/1) was purified by CC (loaded in DCM, gradient hexane to hexane/EtOAc=1/1) to afford 2-amino-3-bromo-N-cyclopentyl-5-(3,5-dimethylisoxazol-4-yl)benzenesulfonamide as a white powder.

Step 6: Preparation of 2-amino-N-cyclopentyl-5-(3,5-dimethylisoxazol-4-yl)benzenesulfonamide

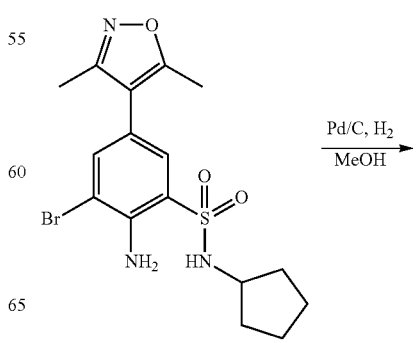

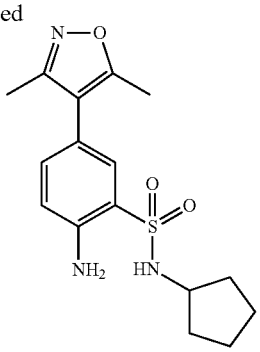

The 2-amino-3-bromo-N-cyclopentyl-5-(3,5-dimethylisoxazol-4-yl)benzenesulfonamide (4 g) was dissolved in MeOH (150 ml) and DCM (10 mL). To the solution was added Pd/C (2 g, 10% on carbon) and the flask was charged with H$_2$. The reaction was completed overnight. The reaction mixture was filtered and the solvent was evaporated. The residue was purified by silica gel column chromatography (0-70% EtOAc/Hexane) to afford 2-amino-N-cyclopentyl-5-(3,5-dimethylisoxazol-4-yl)benzenesulfonamide.

Step 7: Preparation of 2-amino-N-cyclopentyl-5-(3,5-dimethylisoxazol-4-yl)-3-nitrobenzonesulfonamide

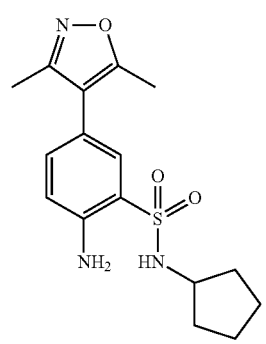

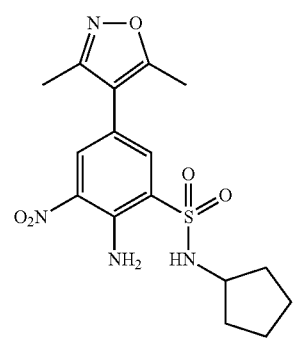

The 2-amino-N-cyclopentyl-5-(3,5-dimethylisoxazol-4-yl)benzenesulfonamide (336 mg, 1 mmol)) was dissolved in DCM/acetonitrile (15/15 ml). To the solution was added NO$_2$BF$_4$ (1.4 mmol, 2.8 mL (0.5M)) at 0° C. The temperature was slowly raised to RT. Reaction completed about 30% after 1 h. To the solution was added 0.1 eq of NO$_2$BF$_4$. The reaction completed about 50% after 3 h. To the solution was added another 0.2 eq of NO$_2$BF$_4$ and stirred at RT overnight. The solvent was then evaporated, the residue was dissolved in EtOAc, washed with sat. NaHCO$_3$ solution. The organic solvent was then evaporated and purified with silica gel column chromatography (0-60% EtOAc/Hexane) to afford 2-amino-N-cyclopentyl-5-(3,5-dimethylisoxazol-4-yl)-3-nitrobenzenesulfonamide.

Step 8: Preparation of 2,3-diamino-N-cyclopentyl-5-(3,5-dimethylisoxazol-4-yl)benzenesulfonamide

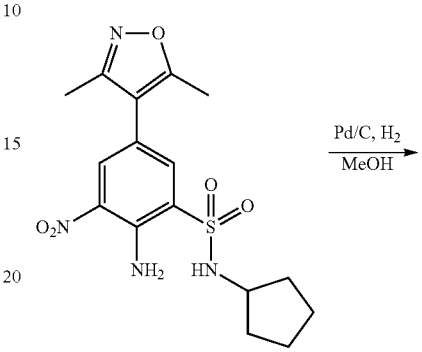

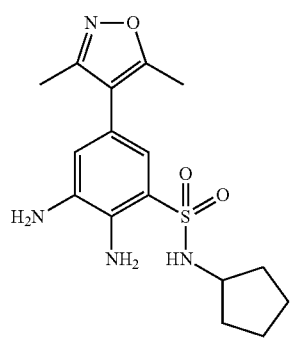

The 2-amino-N-cyclopentyl-5-(3,5-dimethylisoxazol-4-yl)-3-nitrobenzenesulfonamide (400 mg) was dissolved in MeOH (20 ml). To the solution was added Pd/C (200 mg, 10% on carbon) and then placed under a hydrogen atmosphere while stirring. When the reaction was completed the mixture was filtered and the solvent was evaporated. The residue was then purified by silica gel column chromatography (0-20% MeOH/DCM) to afford 2,3-diamino-N-cyclopentyl-5-(3,5-dimethylisoxazol-4-yl)benzenesulfonamide.

Step 9: Preparation of N-cyclopentyl-2-(cyclopropylmethylamino)-6-(3,5-dimethylisoxazol-4-yl)-1H-benzo[d]imidazolo-4-sulfonamide

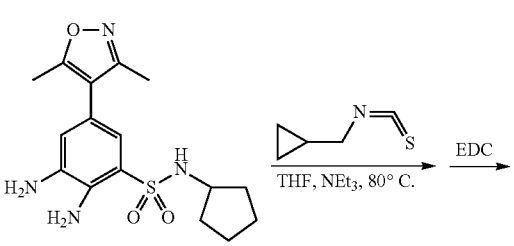

-continued

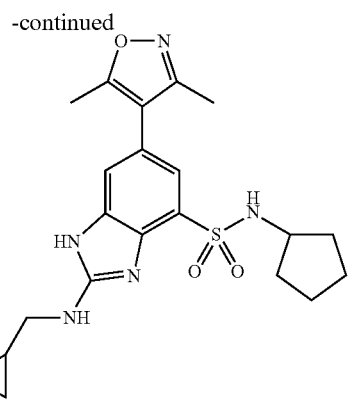

2,3-diamino-N-cyclopentyl-5-(3,5-dimethylisoxazol-4-yl)benzenesulfonamide (20 mg, 0.06 mmol) was dissolved in THF (1 mL) and to this solution was added cyclopropylmethyl isothiocyanate (8 mg, 0.07 mmol) and triethylamine (84 µL). The reaction was heated at 80° C. overnight before 1-ethyl-3-(3-dimethylaminopropyl)-carbodiimide hydrogen chloride (13 mg, 0.07 mmol) was added and heated at 80° C. for 2 h. The solvent was then evaporated under vacuum and the residue was purified by preparative HPLC (0-100% $CH_3CN/H_2O$) to afford N-cyclopentyl-2-(cyclopropylmethylamino)-6-(3,5-dimethylisoxazol-4-yl)-1H-benzo[d]imidazole-4-sulfonamide.

$C_{21}H_{27}N_5O_3S$. 430.2 (M+1). $^1H$ NMR (400 MHz, $CD_3OD$) δ 7.65 (s, 1H), 7.54 (s, 1H), 3.66-3.57 (m, 3H), 2.38 (s, 3H), 2.25 (s, 3H), 2.00-1.51 (m, 4H), 1.49-1.39 (m, 4H), 0.84-0.80 (m, 1H), 0.32-0.27 (m, 2H), 0.08-0.05 (m, 2H).

Example 2

N-Cyclopentyl-6-(3,5-dimethylisoxazol-4-yl)-2-(3-methoxypropylamino)-1H-benzo[d]imidazole-4-sulfonamide (1020-2)

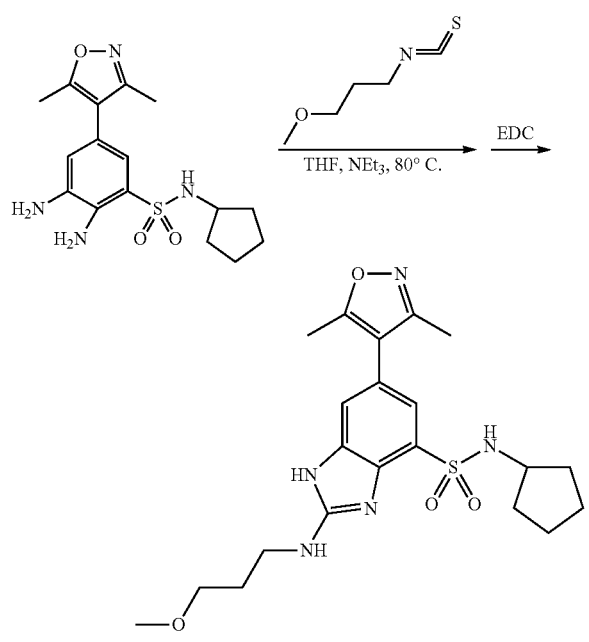

2,3-diamino-N-cyclopentyl-5-(3,5-dimethylisoxazol-4-yl)benzenesulfonamide (25 mg, 0.07 mmol) (see Example 1, Step 8) was dissolved in THF (1 mL). To the solution was added 3-methoxypropyl isothiocyanate (11 mg, 0.09 mmol) and triethylamine (300 µL). The reaction was heated at 80° C. for 4 h before 1-ethyl-3-(3-dimethylaminopropyl)-carbodiimide hydrogen chloride (16 mg, 0.08 mmol) was added and heated at 80° C. for 30 mins. The solvent was then evaporated under vacuum and the residue was purified with preparative HPLC (0-100% $CH_3CN/H_2O$) to afford N-cyclopentyl-6-(3,5-dimethylisoxazol-4-yl)-2-(3-methoxypropylamino)-1H-benzo[d]imidazole-4-sulfonamide.

$C_{21}H_{29}N_5O_4S$. 448.2 (M+1). $^1H$ NMR (400 MHz, $CD_3OD$) δ 7.56 (s, 1H), 7.53 (s, 1H), 3.66-3.57 (m, 5H), 3.38 (s, 3H), 2.44 (s, 3H), 2.27 (s, 3H), 2.26-2.10 (m, 2H), 2.00-1.51 (m, 4H), 1.49-1.39 (m, 4H).

Example 3

N-Cyclopentyl-6-(3,5-dimethylisoxazol-4-yl)-2-mercapto-1H-benzo[d]imidazole-4-sulfonamide (1020-3)

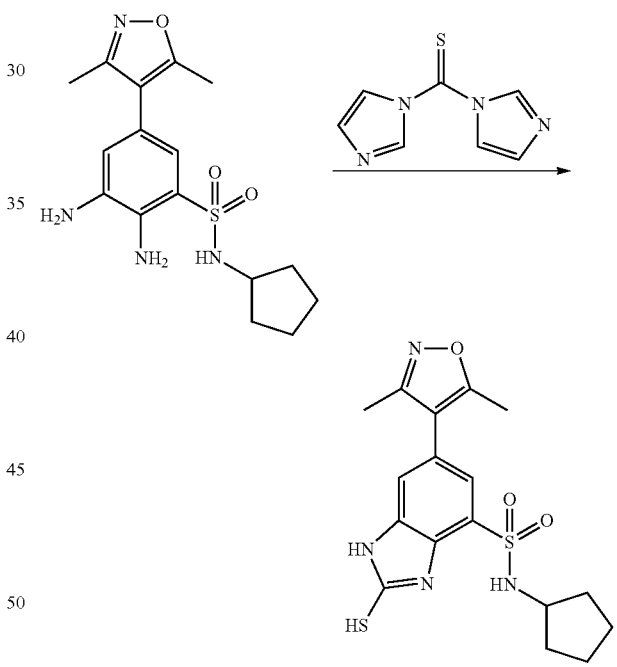

2,3-diamino-N-cyclopentyl-5-(3,5-dimethylisoxazol-4-yl)benzenesulfonamide (40 mg, 0.12 mmol) was dissolved in DMF (2 mL). To the solution was added 1,1'-Thiocarbonyldiimidazole (43 mg, 0.24 mmol). The reaction was heated at 90° C. overnight before being evaporated under vacuum. The residue was purified by preparative HPLC (0-100% CH3CN/H2O) to afford N-cyclopentyl-6-(3,5-dimethylisoxazol-4-yl)-2-mercapto-1H-benzo[d]imidazole-4-sulfonamide.

C17H20N4O3S2. 393.1 (M+1). $^1H$ NMR (400 MHz, $CD_3OD$) δ 7.66 (s, 1H), 7.36 (s, 1H), 3.75-3.55 (m, 1H), 2.32 (s, 3H), 2.28 (s, 3H), 2.09-1.85 (m, 4H), 1.64-1.47 (m, 4H).

Example 4

N-Cyclopentyl-6-(3,5-dimethylisoxazol-4-yl)-2-(methylthio)-1H-benzo[d]imidazole-4-sulfonamide (1020-4)

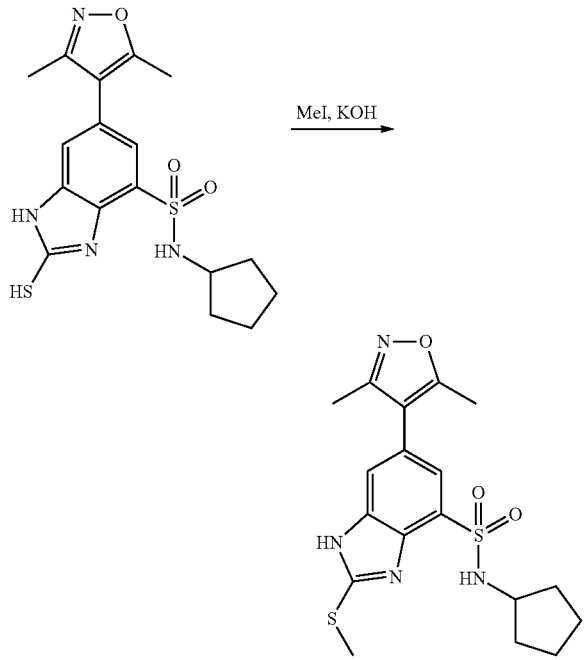

N-cyclopentyl-6-(3,5-dimethylisoxazol-4-yl)-2-mercapto-1H-benzo[d]imidazole-4-sulfonamide (12 mg, 0.03 mmol) was dissolved in EtOH (2 mL). To the solution was added methyliodide (5 mg, 0.037 mmol) and KOH (2.5 mg, 0.045 mmol). The reaction was stirred overnight before being evaporated under vacuum. The residue was purified by preparative HPLC (0-100% CH3CN/H2O) to afford N-cyclopentyl-6-(3,5-dimethylisoxazol-4-yl)-2-(methylthio)-1H-benzo[d]imidazole-4-sulfonamide.

$C_{18}H_{22}N_4O_3S_2$. 407.0 (M+1). $^1$H NMR (400 MHz, CD$_3$OD) δ 7.54 (s, 1H), 7.35 (s, 1H), 3.62-3.48 (m, 1H), 2.58 (s, 3H), 2.33 (s, 3H), 2.27 (s, 3H), 2.07-1.88 (m, 4H), 1.68-1.45 (m, 4H).

Example 5

N-Cyclopentyl-6-(3,5-dimethylisoxazol-4-yl)-2-(methylsulfinyl)-1H-benzo[d]imidazole-4-sulfonamide (1020-5)

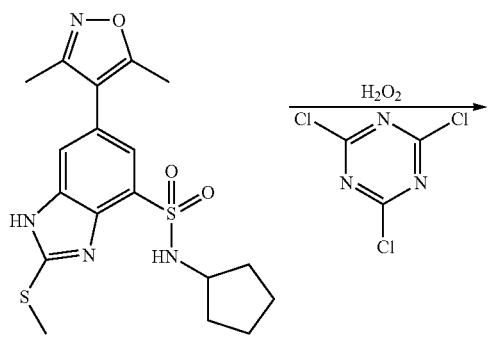

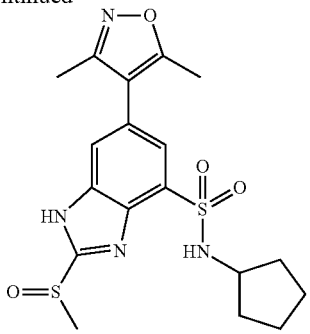

N-cyclopentyl-6-(3,5-dimethylisoxazol-4-yl)-2-(methylthio)-1H-benzo[d]imidazole-4-sulfonamide (3.4 mg, 0.008 mmol) was dissolved in CH$_3$CN (1 mL). To the solution was added 2,4,6-trichloro-1,3,5-triazine (1.5 mg, 0.008 mmol) and H$_2$O$_2$ (0.2 mL, 30% in water). The reaction was stirred overnight before being evaporated under vacuum. The residue was purified by preparative HPLC (0-100% CH3CN/H2O) to afford N-cyclopentyl-6-(3,5-dimethylisoxazol-4-yl)-2-(methylsufinyl)-1H-benzo[d]imidazole-4-sulfonamide.

$C_{18}H_{22}N_4O_4S_2$. 423.0 (M+1). $^1$H NMR (400 MHz, CD$_3$OD) δ 7.68 (s, 1H), 7.42 (s, 1H), 3.71-3.52 (m, 1H), 2.98 (s, 3H), 2.34 (s, 3H), 2.29 (s, 3H), 2.11-1.92 (m, 4H), 1.72-1.44 (m, 4H).

Example 6

N-Cyclopentyl-6-(3,5-dimethylisoxazol-4-yl)-2-(methylsulfonyl)-1H-benzo[d]imidazole-4-sulfonamide (1020-6)

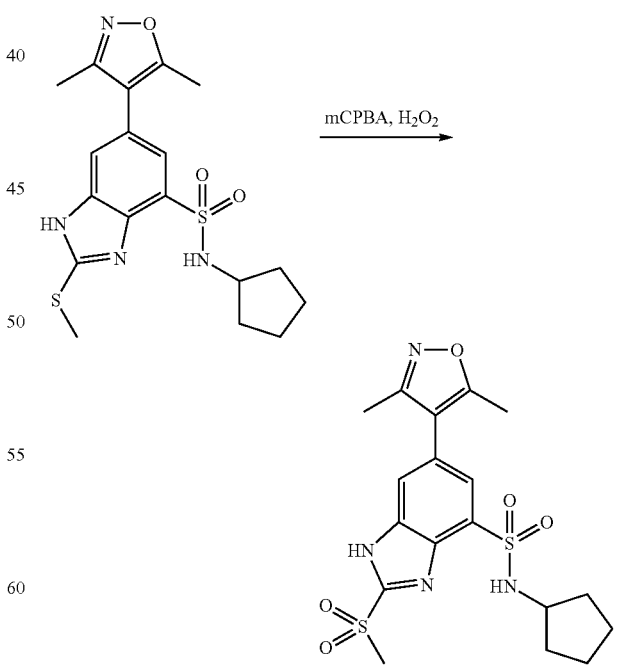

N-cyclopentyl-6-(3,5-dimethylisoxazol-4-yl)-2-(methylsulfinyl)-1H-benzo[d]imidazole-4-sulfonamide (3.4 mg, 0.008 mmol) was dissolved in DCM (1 mL). To the solution was added mCPBA (2.6 mg, 0.015 mmol) and H₂O₂ (1 mL, 30% in water). The reaction was stirred for 30 mins before being evaporated under vacuum. The residue was purified by preparative HPLC (0-100% CH₃CN/H₂O) to afford N-cyclopentyl-6-(3,5-dimethylisoxazol-4-yl)-2-(methylsulfonyl)-1H-benzo[d]imidazole-4-sulfonamide.

C₁₈H₂₂N₄O₅S₂. 439.0 (M+1). ¹H NMR (400 MHz, CD₃OD) δ 7.91 (s, 1H), 7.85 (s, 1H), 3.72-3.64 (m, 1H), 3.49 (s, 3H), 2.46 (s, 3H), 2.30 (s, 3H), 1.64-1.60 (m, 4H), 1.45-1.29 (m, 4H).

Example 7

N-Cyclopentyl-6-(3,5-dimethylisoxazol-4-yl)-2-(trifluoromethyl)-1H-benzo[d]imidazole-4-sulfonamide (1020-7)

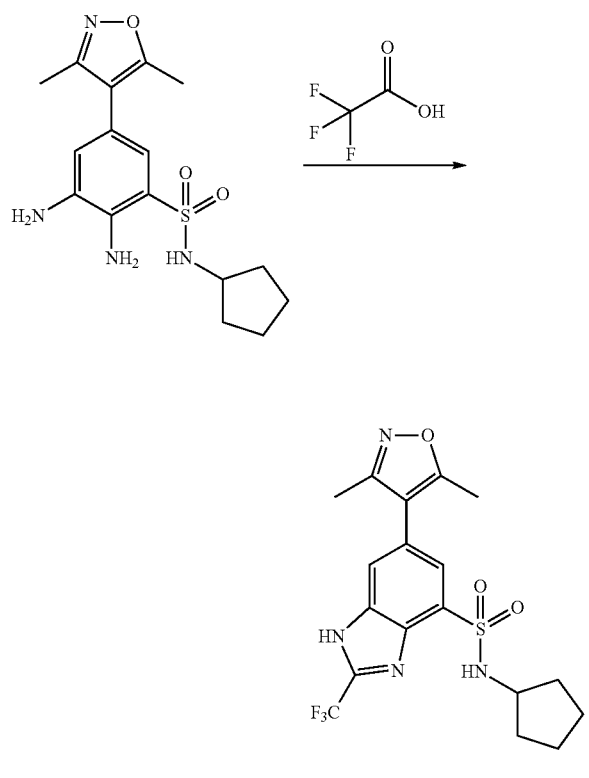

2,3-diamino-N-cyclopentyl-5-(3,5-dimethylisoxazol-4-yl)benzenesulfonamide (20 mg, 0.06 mmol) was dissolved in 4N HCl (2 mL). To the solution was added trifluoroacetic acid (65 mg, 0.6 mmol). The reaction was refluxed overnight before being evaporated under vacuum. The residue was purified by preparative HPLC (0-100% CH3CN/H2O) to afford N-cyclopentyl-6-(3,5-dimethylisoxazol-4-yl)-2-(trifluoromethyl)-1H-benzo[d]imidazole-4-sulfonamide.

C18H19F3N4O3S. 429.0 (M+1). ¹H NMR (400 MHz, CD3OD) δ 7.51 (s, 1H), 7.45 (s, 1H), 3.62-3.52 (m, 1H), 2.44 (s, 3H), 2.31 (s, 3H), 1.68-1.52 (m, 4H), 1.42-1.25 (m, 4H).

Example 8

4-(2-Cyclopropyl-4-(3,5-dimethyl-1H-pyrazol-4-yl)-1H-benzo[d]imidazol-6-yl)-3,5-dimethylisoxazole (1020-8)

Step 1: Preparation of 4-(3,5-dimethylpyrazol-4-yl)-2-nitroaniline

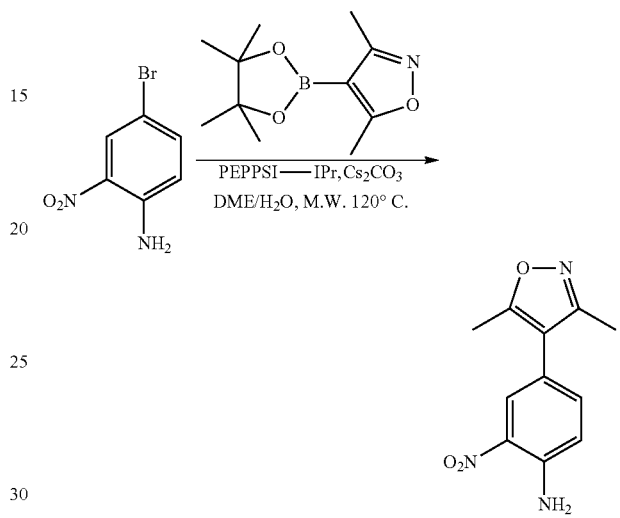

Starting material 4-bromo-2-nitroaniline (1 g, 4.6 mmol) and 3,5-dimethylisoxazole-4-boronic acid pinacol ester (2 g, 9.2 mmol) was added to a solvent mixture of 1,2-dimethoxyethane (12 ml) and water (6 ml). To the above mixture were added PEPPSI-IPr (312 mg, 0.46 mmol) and Cs₂CO₃ (4.5 g, 13.8 mmol). The reaction mixture was heated at 120° C. for 30 mins. The reaction mixture was then diluted with EtOAc (100 ml), washed with bring (50 mL×2). The organic solvent was evaporated and the residue was dissolved in DCM and purified with silica gel chromatography (product came out at 50% EtOAc/Hexane) to afford 4-(3,5-dimethylpyrazol-4-yl)-2-nitroaniline as a yellow solid.

C₁₁H₁₁N₃O₃. 234.3 (M+1).

Step 2: Preparation of 4-(3,5-dimethylisoxazol-4-yl)-2-iodo-6-nitroaniline

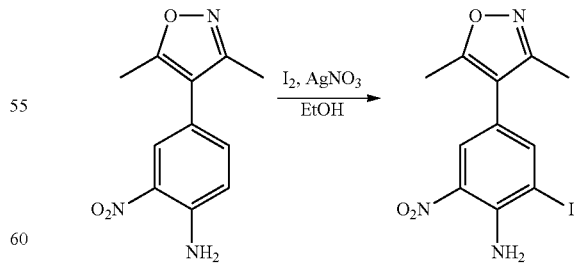

Starting material compound 4-(3,5-dimethylpyrazol-4-yl)-2-nitroaniline (1 g, 4.6 mmol) was added to EtOH (50 ml), to the mixture were added 12 (1.4 g, 5.5 mmol) and AgNO₃ (0.94 g, 5.5 mmol). The reaction mixture was stirred at RT overnight. The solvent was evaporated and then the residue was dissolved in EtOAc (50 ml) and washed with brine (30 mL×2). The organics were evaporated and the residue was dissolved in DCM and purified by silica gel column chromatography (product came out at 35% EtOAc/Hexane) to afford 4-(3,5-dimethylisoxazol-4-yl)-2-iodo-6-nitroaniline as an orange solid.

C₁₁H₁₀N₃O₃. 360.2 (M+1).

Step 3: Preparation of 5-(3,5-dimethylisoxazol-4-yl)-3-iodobenzene-1,2-diamine

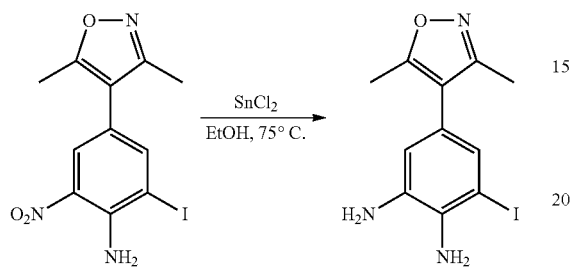

4-(3,5-dimethylisoxazol-4-yl)-2-iodo-6-nitroaniline (0.9 g, 2.5 mmol) was added to EtOH (50 ml), to the mixture were added SnCl₂ (2.4 g, 12.5 mmol). The reaction mixture was stirred at 75° C. for 7 h. The solvent was evaporated and then the residue was dissolved in EtOAc (100 ml) and washed with 1N NaOH (100 mL×3). The organic solvent was evaporated and the residue was dissolved in DCM and purified with silica gel column chromatography (product came out at 60% EtOAc/Hexane) to afford 5-(3,5-dimethylisoxazol-4-yl)-3-iodobenzene-1,2-diamine as a brown solid.

C11H12IN3O 330.1 (M+1). 1H NMR (400 MHz, CD3OD) δ 2.21 (s, 3H), 2.39 (s, 3H), 7.16 (d, 1H), 7.62 (d, 1H).

Step 4: Preparation of 4-(2-cyclopropyl-4-iodo-1H-benzo[d]imidazol-6-yl)-3,5-dimethylisoxazole

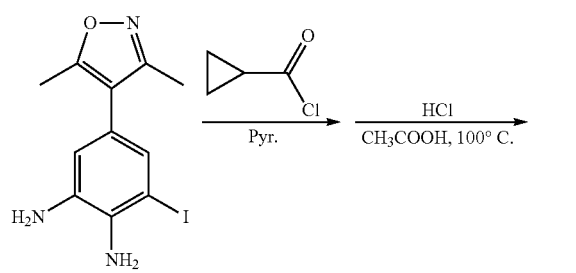

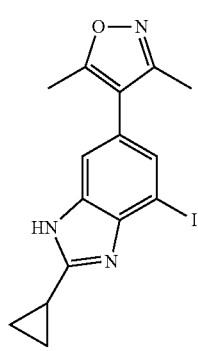

5-(3,5-dimethylisoxazol-4-yl)-3-iodobenzene-1,2-diamine (0.92 g, 2.8 mmol) was dissolved in pyridine (10 ml), to the solution was added cyclopropyl carbonyl chloride (0.29 g, 2.8 mmol). The reaction was stirred at RT for 3 h before solvent was evaporated. The residue was dissolved in acetic acid (5 ml) and to the solution was added hydrogen chloride (1 ml). The reaction mixture was then heated at 100° C. overnight. The acid was then evaporated under reduced pressure and the residue was dissolved in DCM and purified by silica gel column chromatography (product came out at 70% EtOAc/Hexane) to afford product 4-(2-cyclopropyl-4-iodo-1H-benzo[d]imidazol-6-yl)-3,5-dimethylisoxazoleas as a brown solid.

C₁₅H₁₄IN₃O. 380.1 (M+1).

Step 5: Preparation of 4-(2-cyclopropyl-4-(3,5-dimethyl-1H-pyrazol-4-yl)-1H-benzo[d]imidazol-6-yl)-3,5-dimethylisoxazole

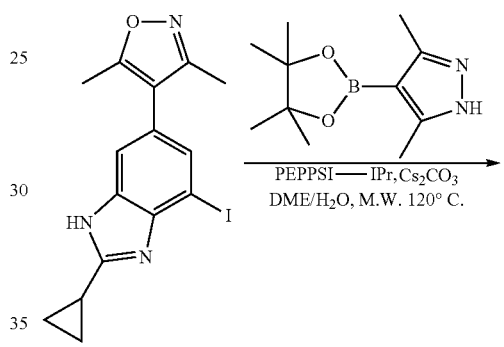

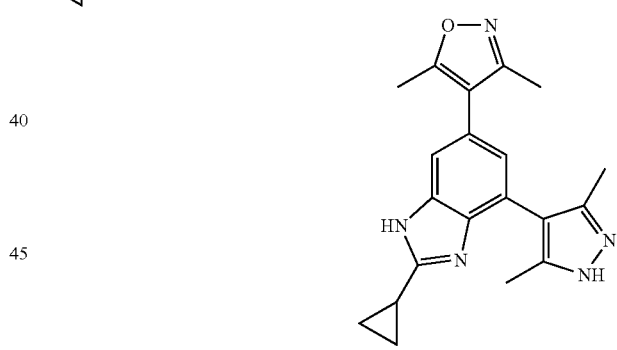

3,5-dimethylpyrazole-4-boronic acid, pinacol ester (29 mg, 0.13 mmol) was added to a solution of 4-(2-cyclopropyl-4-iodo-1H-benzo[d]imidazol-6-yl)-3,5-dimethylisoxazole (25 mg, 0.066 mmol) in 1,2-dimethoxyethane and water (2/1 mL). To the mixture was added cesium carbonate (65 mg, 0.2 mmol) and PEPPSI-IPr (5 mg, 0.0066 mmol). The reaction was put in microwave reactor and heated at 120° C. for 30 minutes before being evaporated under vacuum. The residue was purified by preparative HPLC (0-100% CH₃CN/H₂O) to afford 4-(2-cyclopropyl-4-(3,5-dimethyl-1H-pyrazol-4-yl)-1H-benzo[d]imidazol-6-yl)-3,5-dimethylisoxazole.

C₂₀H₂₁N₅O. 348.2 (M+1). ¹H NMR (400 MHz, CD₃OD) δ 7.56 (s, 1H), 7.32 (s, 1H), 2.46 (s, 3H), 2.45-2.44 (m, 1H), 2.30 (s, 3H), 2.21 (s, 6H), 1.53-1.51 (m, 2H), 1.41-1.39 (m, 2H).

119

Example 9

4-(2-Cyclopropyl-7-(2-methylpyridin-3-yl)-1H-benzo[d]imidazol-5-yl)-3,5-dimethylisoxazole (1020-9)

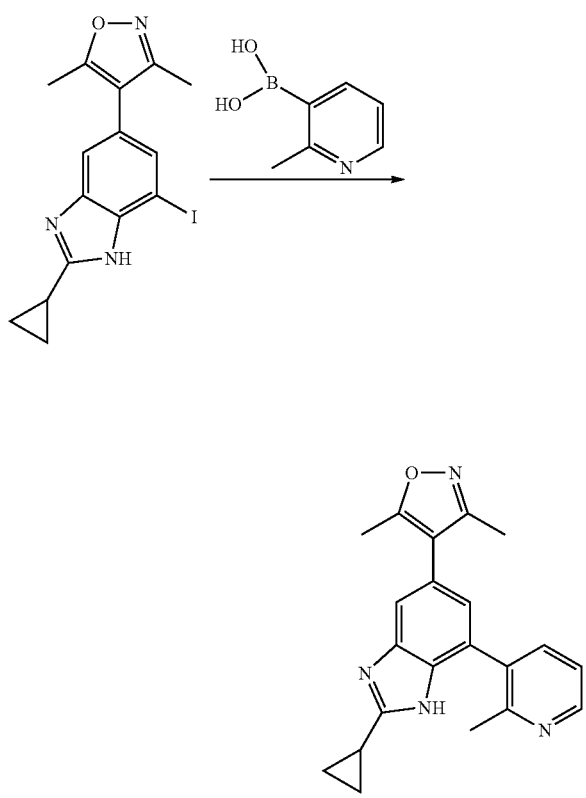

To a 0.5 to 2 mL Smith process vial equipped with a stir bar was added 2-methylpyridin-3-ylboronic acid (0.45 mmol, 62 mg), 4-(2-cyclopropyl-4-iodo-1H-benzo[d]imidazol-6-yl)-3,5-dimethylisoxazole (37.9 mg, 0.1 mmol) (Example 8, Step 4), potassium carbonate (0.90 mmol, 125 mg), and PEPPSI-IPr catalyst (0.01 mmol, 6.8 mg). The reaction vessel was capped with a rubber septum, evacuated and backfilled three times with $N_2$, followed by the addition of 1,4-dioxane (0.4 mL) and water (0.1 mL). The reaction mixture was then heated in a microwave reactor for 30 minutes at 130° C. The organic layer was then removed by syringe, filtered, and directly injected for purification by preparative reverse phase high performance liquid chromatography (Phenomenex Gemini C18 column, 5% to 50% gradient acetonitrile in water with 0.1% TFA) to give 4-(2-cyclopropyl-7-(2-methylpyridin-3-yl)-1H-benzo[d]imidazol-5-yl)-3,5-dimethylisoxazole as a TFA salt.

$C_{21}H_{20}N_4O$. 345.2 (M+1). 1H NMR (400 MHz, CD3OD) δ 8.81 (dd, J=5.7, 1.5 Hz, 1H), 8.43 (dd, J=7.9, 1.5 Hz, 1H), 7.93 (dd, J=7.8, 5.8 Hz, 1H), 7.70 (d, J=1.4 Hz, 1H), 7.42 (d, J=1.5 Hz, 1H), 2.62 (s, 3H), 2.47 (s, 3H), 2.45-2.34 (m, 1H), 2.31 (s, 3H), 1.53-1.42 (m, 2H), 1.39-1.31 (m, 2H).

120

Example 10

4-(2-Cyclopropyl-7-(3-methylpyridin-4-yl)-1H-benzo[d]imidazol-5-yl)-3,5-dimethylisoxazole (1020-10)

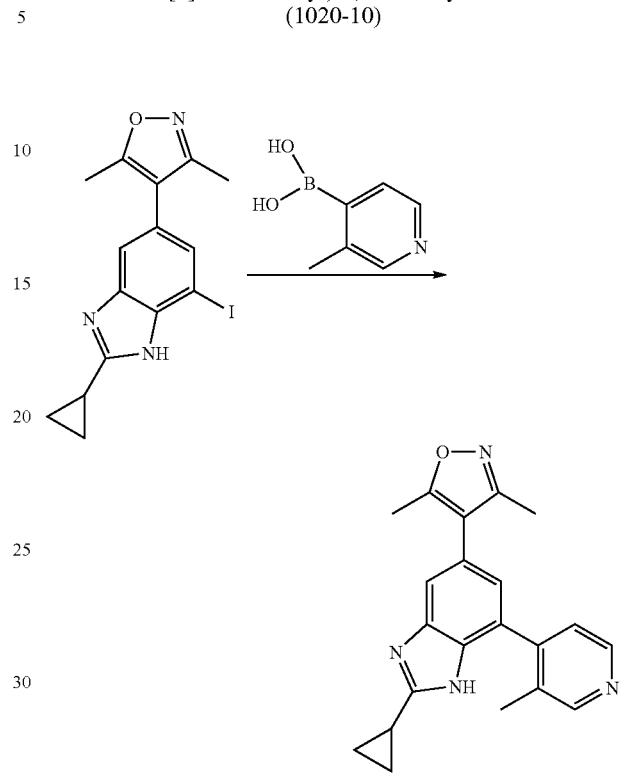

4-(2-cyclopropyl-7-(3-methylpyridin-4-yl)-1H-benzo[d]imidazol-5-yl)-3,5-dimethylisoxazole (5.8 mg, 13%) was prepared as a TFA salt in a manner similar to that of Example 9 substituting 3-methylpyridin-4-ylboronic acid for 2-methylpyridin-3-ylboronic acid.

$C_{21}H_{20}N_4O$. 345.2 (M+1). $^1$H NMR (400 MHz, CD$_3$OD) δ 8.77 (s, 1H), 8.68 (d, J=5.6 Hz, 1H), 7.81 (d, J=5.5 Hz, 1H), 7.63 (d, J=1.5 Hz, 1H), 7.32 (d, J=1.5 Hz, 1H), 2.45 (s, 3H), 2.35 (s, 3H), 2.35-2.29 (m, 1H), 2.29 (s, 3H), 1.44-1.34 (m, 2H), 1.34-1.24 (m, 2H).

Example 11

4-(2-Cyclopropyl-7-(4-methylpyridin-3-yl)-1H-benzo[d]imidazol-5-yl)-3,5-dimethylisoxazole (1020-11)

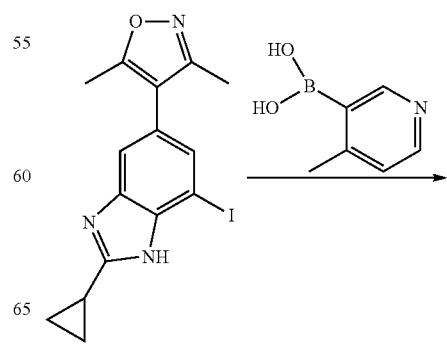

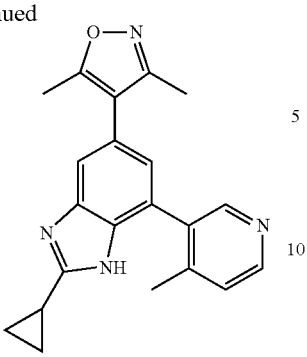

4-(2-cyclopropyl-7-(4-methylpyridin-3-yl)-1H-benzo[d]imidazol-5-yl)-3,5-dimethylisoxazole (4.4 mg, 9.9%) was prepared as a TFA salt in a manner similar to that of Example 9 substituting 4-methylpyridin-3-ylboronic acid for 2-methylpyridin-3-ylboronic acid.

$C_{21}H_{20}N_4O$. 345.2 (M+1). $^1$H NMR (400 MHz, CD$_3$OD) δ 8.68 (d, J=4.4 Hz, 1H), 7.83 (d, J=5.5 Hz, 1H), 7.64 (d, J=1.4 Hz, 1H), 7.35 (d, J=1.4 Hz, 1H), 2.47 (s, 3H), 2.43 (s, 3H), 2.39-2.33 (m, 1H), 2.31 (s, 3H), 1.46-1.36 (m, 2H), 1.36-1.25 (m, 2H).

Example 12

4-(2-Cyclopropyl-7-(1,4-dimethyl-1H-pyrazol-5-yl)-1H-benzo[d]imidazol-5-yl)-3,5-dimethylisoxazole (1020-12)

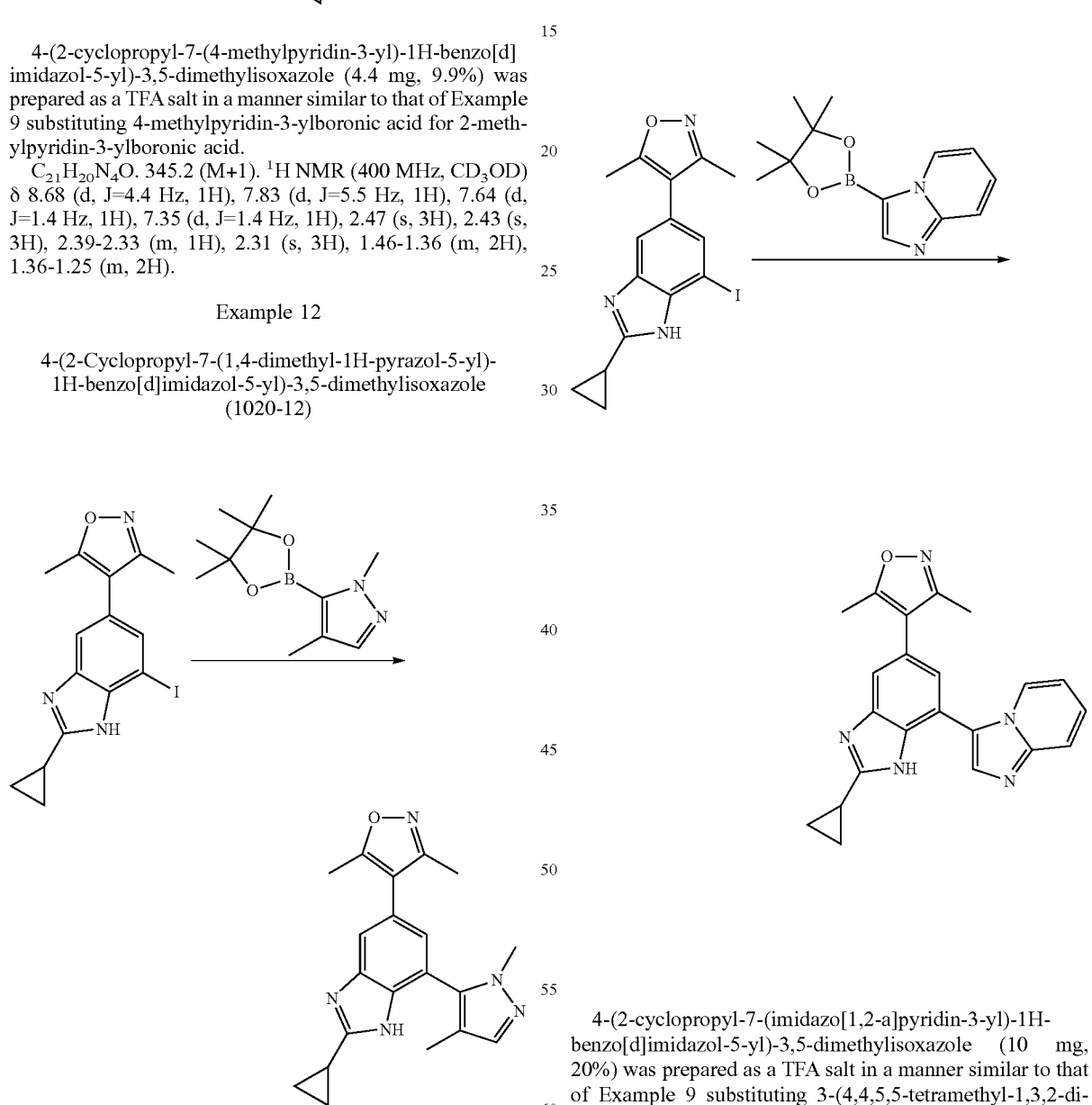

4-(2-cyclopropyl-7-(1,4-dimethyl-1H-pyrazol-5-yl)-1H-benzo[d]imidazol-5-yl)-3,5-dimethylisoxazole (21 mg, 46%) was prepared as a TFA salt in a manner similar to Example 9 substituting 1,4-dimethyl-5-(4,4,5,5-tetramethyl-1,3,2-dioxaborolan-2-yl)-1H-pyrazole for 2-methylpyridin-3-ylboronic acid.

$C_{20}H_{21}N_5O$. 348.1 (M+1). $^1$H NMR (400 MHz, CD$_3$OD) δ 7.75 (d, J=1.4 Hz, 1H), 7.53 (s, 1H), 7.46 (d, J=1.4 Hz, 1H), 3.74 (s, 3H), 2.59-2.40 (m, 4H), 2.31 (s, 3H), 2.00 (s, 3H), 1.65-1.51 (m, 2H), 1.51-1.35 (m, 2H).

Example 13

4-(2-Cyclopropyl-7-(imidazo[1,2-a]pyridin-3-yl)-1H-benzo[d]imidazol-5-yl)-3,5-dimethylisoxazole (1020-13)

4-(2-cyclopropyl-7-(imidazo[1,2-a]pyridin-3-yl)-1H-benzo[d]imidazol-5-yl)-3,5-dimethylisoxazole (10 mg, 20%) was prepared as a TFA salt in a manner similar to that of Example 9 substituting 3-(4,4,5,5-tetramethyl-1,3,2-dioxaborolan-2-yl)imidazo[1,2-a]pyridine for 2-methylpyridin-3-ylboronic acid.

$C_{22}H_{19}N_5O$. 370.1 (M+1). $^1$H NMR (400 MHz, CD$_3$OD) δ 8.42 (dd, J=6.9, 1.0 Hz, 1H), 8.34 (d, J=1.3 Hz, 1H), 8.06-8.01 (m, 2H), 7.83-7.77 (m, 1H), 7.68-7.63 (m, 1H), 7.47 (ddd, J=7.0, 4.9, 3.3 Hz, 1H), 2.46-2.33 (m, 4H), 2.26 (s, 3H), 1.50-1.37 (m, 2H), 1.32 (dd, J=8.2, 3.7 Hz, 2H).

Example 14

4-(2-Cyclopropyl-7-(quinolin-8-yl)-1H-benzo[d]imidazol-5-yl)-3,5-dimethylisoxazole (1020-14)

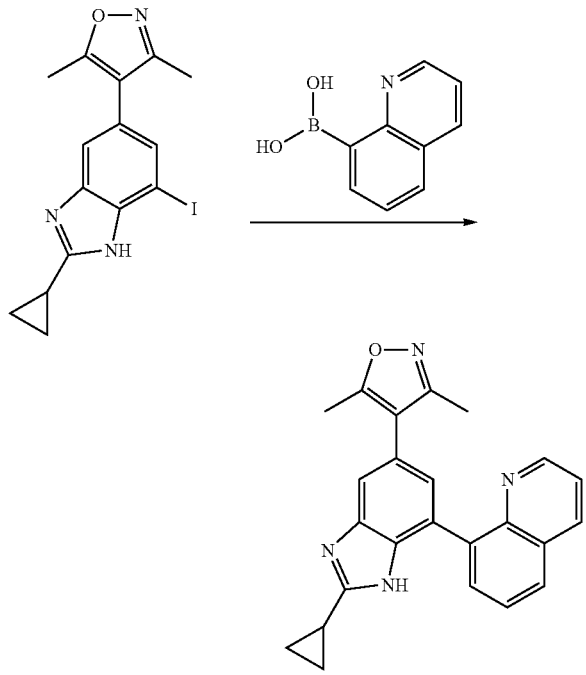

4-(2-cyclopropyl-7-(quinolin-8-yl)-1H-benzo[d]imidazol-5-yl)-3,5-dimethylisoxazole (1.7 mg, 2.8%) was prepared as a TFA salt in a manner similar to that of Example 9 substituting quinolin-8-ylboronic acid for 2-methylpyridin-3-ylboronic acid.

$C_{24}H_{20}N_4O$. 381.1 (M+1). 1H NMR (400 MHz, $CD_3OD$) δ 8.82 (dd, J=4.3, 1.7 Hz, 1H), 8.54 (dd, J=8.3, 1.7 Hz, 1H), 8.18 (dd, J=8.2, 1.3 Hz, 1H), 7.97 (dd, J=7.1, 1.4 Hz, 1H), 7.82 (dd, J=8.0, 7.3 Hz, 2H), 7.69-7.63 (m, 2H), 2.48 (s, 3H), 2.40-2.33 (m, 1H), 2.32 (s, 3H), 1.53-1.42 (m, 2H), 1.39-1.27 (m, 2H).

Example 15

4-(2-Cyclopropyl-7-(quinolin-5-yl)-1H-benzo[d]imidazol-5-yl)-3,5-dimethylisoxazole

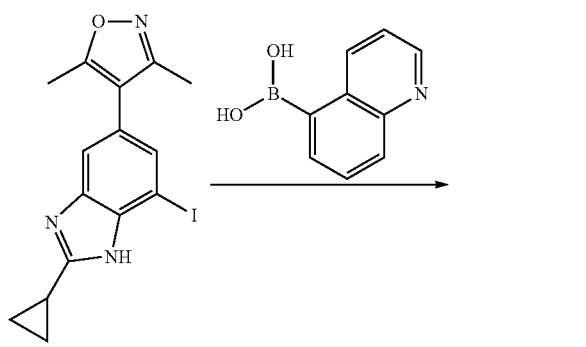

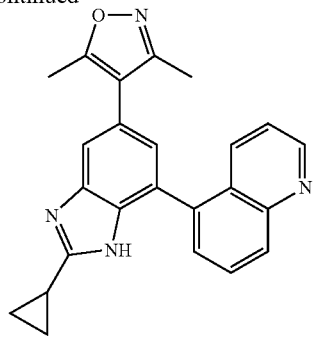

4-(2-cyclopropyl-7-(quinolin-5-yl)-1H-benzo[d]imidazol-5-yl)-3,5-dimethylisoxazole (30 mg, 49%) was prepared as a TFA salt in a manner similar to that of Example 9 substituting quinolin-5-ylboronic acid for 2-methylpyridin-3-ylboronic acid.

$C_{24}H_2N_4O$. 381.1 (M+1). $^1$H NMR (400 MHz, $CD_3OD$) δ 9.08 (dd, J=4.7, 1.5 Hz, 1H), 8.35 (dd, J=18.7, 8.5 Hz, 2H), 8.11 (dd, J=8.6, 7.2 Hz, 1H), 7.93 (dd, J=7.1, 1.0 Hz, 1H), 7.79-7.69 (m, 2H), 7.53 (d, J=1.5 Hz, 1H), 2.48 (s, 3H), 2.36 (tt, J=8.5, 5.1 Hz, 1H), 2.32 (s, 3H), 1.53-1.42 (m, 2H), 1.40-1.29 (m, 2H).

Example 16

4-(2-Cyclopropyl-7-(isoquinolin-5-yl)-1H-benzo[d]imidazol-5-yl)-3,5-dimethylisoxazole

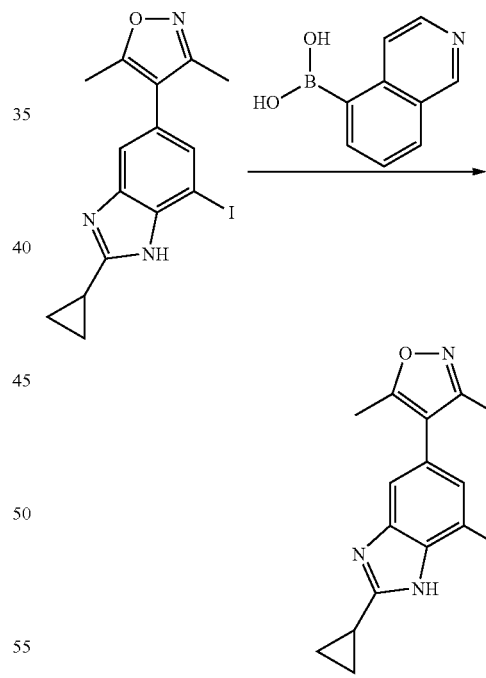

4-(2-cyclopropyl-7-(isoquinolin-5-yl)-1H-benzo[d]imidazol-5-yl)-3,5-dimethylisoxazole (26.7 mg, 44%) was prepared as a TFA salt in a manner similar to that of Example 9 substituting isoquinolin-5-ylboronic acid for 2-methylpyridin-3-ylboronic acid.

$C_{24}H_{20}N_4O$. 381.1 (M+1). $^1$H NMR (400 MHz, $CD_3OD$) δ 9.82 (s, 1H), 8.62 (d, J=8.3 Hz, 1H), 8.53 (d, J=6.6 Hz, 1H), 8.29 (dd, J=7.2, 1.0 Hz, 1H), 8.14 (dd, J=8.2, 7.3 Hz, 1H), 7.98 (d, J=6.6 Hz, 1H), 7.77 (d, J=1.4 Hz, 1H), 7.55 (d, J=1.4 Hz, 1H), 2.48 (s, 3H), 2.37 (tt, J=8.4, 5.0 Hz, 1H), 2.32 (s, 3H), 1.52-1.42 (m, 2H), 1.41-1.29 (m, 2H).

Example 17

4-(2-Cyclopropyl-7-(isoquinolin-4-yl)-1H-benzo[d]imidazol-5-yl)-3,5-dimethylisoxazole (1020-17)

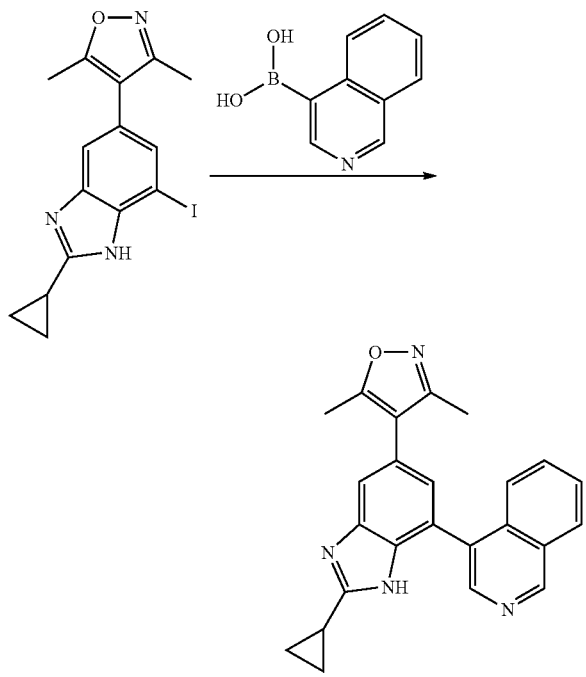

4-(2-cyclopropyl-7-(isoquinolin-4-yl)-1H-benzo[d]imidazol-5-yl)-3,5-dimethylisoxazole (10.2 mg, 17%) was prepared as a TFA salt in a manner similar to that of Example 9 substituting isoquinolin-4-ylboronic acid for 2-methylpyridin-3-ylboronic acid.

$C_{24}H_{22}N_4O$. 381.1 (M+1). $^1$H NMR (400 MHz, CD$_3$OD) δ 9.86 (s, 1H), 8.78 (s, 1H), 8.61 (d, J=8.0 Hz, 1H), 8.14 (ddd, J=8.4, 7.0, 1.3 Hz, 1H), 8.06 (ddd, J=8.2, 7.0, 1.1 Hz, 1H), 7.88 (d, J=8.4 Hz, 1H), 7.84 (d, J=1.5 Hz, 1H), 7.64 (d, J=1.4 Hz, 1H), 2.50 (s, 3H), 2.41 (tt, J=8.4, 5.0 Hz, 1H), 2.34 (s, 3H), 1.56-1.45 (m, 2H), 1.43-1.33 (m, 2H).

Example 18

4-(2-Cyclopropyl-7-(6-methylquinolin-5-yl)-1H-benzo[d]imidazol-5-yl)-3,5-dimethylisoxazole (1020-18)

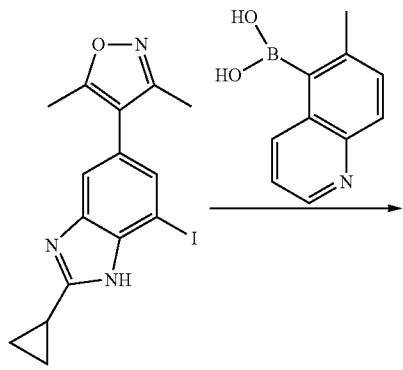

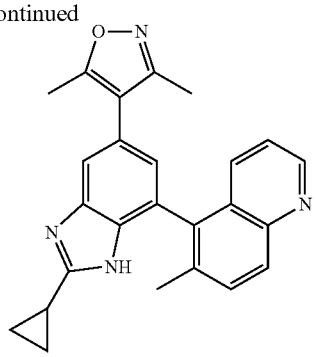

To a 2 to 5 mL Smith process vial equipped with a stir bar was added 6-methylquinolin-5-ylboronic acid (3 mmol, 561 mg), 4-(2-cyclopropyl-7-iodo-1H-benzo[d]imidazol-5-yl)-3,5-dimethylisoxazole (379 mg, 1 mmol), potassium carbonate (10 mmol, 1.38 g), and PEPPSI-IPr catalyst (0.1 mmol, 68 mg). The reaction vessel was capped with a rubber septum, evacuated and backfilled three times with N$_2$, followed by the addition of 1,4-dioxane (4 mL) and water (1 mL). The reaction mixture was then heated in a microwave reactor for 1 hour at 135° C. The organic layer was then removed by syringe, filtered, and directly injected for purification by preparative reverse phase high performance liquid chromatography (Phenomenex Gemini C18 column, 5% to 50% gradient acetonitrile in water with 0.1% TFA). The eluting fraction containing the desired product was then concentrated under reduced pressure and purified again using silica gel chromatography (0% to 20% gradient methanol in ethyl acetate) to give 4-(2-cyclopropyl-7-(6-methylquinolin-5-yl)-1H-benzo[d]imidazol-5-yl)-3,5-dimethylisoxazole.

$C_{25}H_{22}N_4O$. 395.2 (M+1). $^1$H NMR (400 MHz, CD$_3$OD) δ 8.48 (dd, J=6.9, 1.0 Hz, 1H), 8.39 (d, J=1.3 Hz, 1H), 8.12-8.07 (m, 2H), 7.89-7.83 (m, 1H), 7.74-7.68 (m, 1H), 7.52 (ddd, J=7.0, 4.9, 3.3 Hz, 1H), 2.51-2.38 (m, 4H), 2.31 (s, 3H), 1.55-1.43 (m, 2H), 1.42-1.29 (m, 2H).

Example 19

4-(2-Cyclopropyl-4-(2-phenylpyridin-3-yl)-1H-benzo[d]imidazol-6-yl)-3,5-dimethylisoxazole (1020-19)

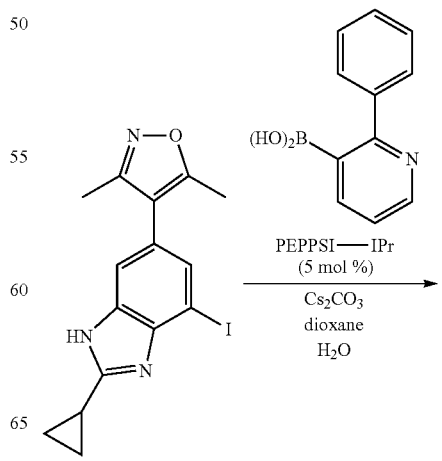

-continued

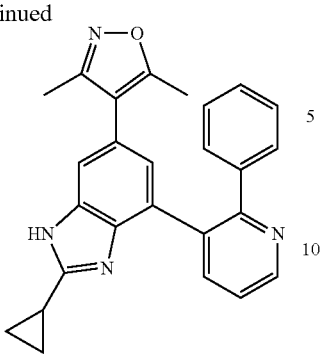

4-(2-cyclopropyl-4-iodo-1H-benzo[d]imidazol-6-yl)-3,5-dimethylisoxazole (50.0 mg, 0.132 mmol) was treated with 2-phenylpyridin-3-ylboronic acid (39.4 mg, 0.198 mmol, 1.5 equiv.), 2M Na$_2$CO$_3$ (aq) (1 mL) in the presence of PEPPSI-IPr (4.5 mg, 0.0066 mmol, 0.05 equiv) in 1,4-dioxane (3 mL) at 15° C. for 10 min in microwave reactor. To the reaction mixture was added water (30 mL) and EtOAc (70 mL), then the mixtures was filtered through Celite (3 g) and then organic layer was separated from the filtrate. The organic layer was washed with brine (30 mL) and dried over Na$_2$SO$_4$. The solvent was removed under a reduced pressure to give the crude product. The crude product was purified by a preparative HPLC (5-95% acetonitrile: water with 0.05% trifluoroacetic acid, on a Phenomenex Luna C18 column) to give 4-(2-cyclopropyl-4-(2-phenylpyridin-3-yl)-1H-benzo[d]imidazol-6-yl)-3,5-dimethylisoxazole.

C$_{26}$H$_{22}$N$_4$O. MS. 407.2 (M+1). $^1$H NMR (MeOH-d$_4$) δ 8.87 (dd, J=5.0, 1.7 Hz, 1H), 8.35 (dd, J=8.3, 1.7 Hz, 1H), 7.83 (dd, J=8.3, 5.0 Hz, 1H), 7.56 (d, J=1.7 Hz, 1H), 7.42-7.28 (m, 5H), 7.22 (d, J=1.7 Hz, 1H), 2.43-2.34 (m, 1H), 2.22 (s, 3H), 2.05 (s, 3H), 1.52-1.46 (m, 2H), 0.36-1.30 (m, 2H).

Example 20

4-(2-Cyclopropyl-4-(5-(4-fluorophenyl)-1H-pyrazol-4-yl)-1H-benzo[d]imidazol-6-yl)-3,5-dimethylisoxazole (1020-20)

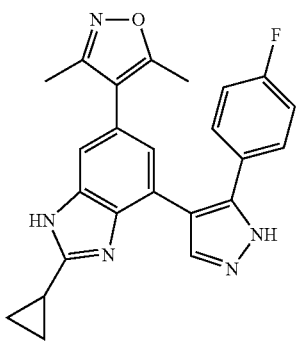 [SMILES: Cc1noc(C)c1-c1cc(-c2cn[nH]c2-c2ccc(F)cc2)c2nc(C3CC3)[nH]c2c1]

4-(2-cyclopropyl-4-(5-(4-fluorophenyl)-1H-pyrazol-4-yl)-1H-benzo[d]imidazol-6-yl)-3,5-dimethylisoxazole was synthesized in a manner similar to that of Example 19 using 5-(4-fluorophenyl)-1H-pyrazol-4-ylboronic acid.

C$_{24}$H$_{20}$FN$_5$O. MS. 414.1 (M+1). $^1$H NMR (MeOH-d$_4$) δ 8.03 (s, 1H), 7.53 (d, J=1.5 Hz, 1H), 7.41 (dd, J=8.8, 5.3 Hz, 2H), 7.20 (d, J=1.5 Hz, 1H), 7.07 (t, J=8.8 Hz, 2H), 2.42 (tt, J=8.5, 5.1 Hz, 1H), 2.29 (s, 3H), 2.12 (s, 3H), 1.56-1.46 (m, 2H), 1.35 (dt, J=7.5, 4.7 Hz, 2H).

Example 21

4-(4-(Biphenyl-2-yl)-2-cyclopropyl-1H-benzo[d]imidazol-6-yl)-3,5-dimethylisoxazole (1020-21)

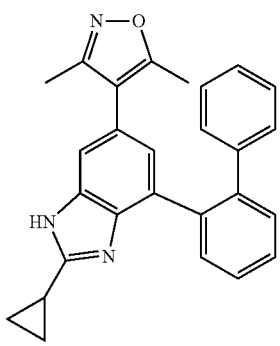 [SMILES: Cc1noc(C)c1-c1cc(-c2ccccc2-c2ccccc2)c2nc(C3CC3)[nH]c2c1]

4-(4-(biphenyl-2-yl)-2-cyclopropyl-1H-benzo[d]imidazol-6-yl)-3,5-dimethylisoxazole was synthesized in a manner similar to that of Example 19 using biphenyl-2-ylboronic acid.

C$_{27}$H$_{23}$N$_3$O. MS. 406.2 (M+1). $^1$H NMR (MeOH-d$_4$) δ 7.66-7.09 (m, 11H), 2.43-2.32 (m, 1H), 2.20 (s, 3H), 2.03 (s, 3H), 1.54-1.44 (m, 2H), 1.38-1.27 (m, 2H).

Example 22

4-(4-(2-Benzylphenyl)-2-cyclopropyl-1H-benzo[d]imidazol-6-yl)-3,5-dimethylisoxazole (1020-22)

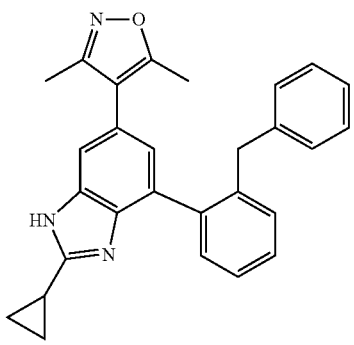 [SMILES: Cc1noc(C)c1-c1cc(-c2ccccc2Cc2ccccc2)c2nc(C3CC3)[nH]c2c1]

4-(4-(2-benzylphenyl)-2-cyclopropyl-1H-benzo[d]imidazol-6-yl)-3,5-dimethylisoxazole was synthesized in a manner similar to that of Example 19 using 2-benzylphenylboronic acid.

C$_{28}$H$_{25}$N$_3$O. MS. 420.2 (M+1). $^1$H NMR (MeOH-d$_4$) δ 7.60-7.50 (m, 3H), 7.45 (td, J=7.2, 2.0 Hz, 1H), 7.38-7.31 (m, 1H), 7.21 (d, J=1.4 Hz, 1H), 7.02-6.93 (m, 3H), 6.67-6.60 (m, 2H), 3.92 (d, J=11.5 Hz, 1H), 3.87 (d, J=11.5 Hz, 1H), 2.40 (s, 1H), 2.25 (s, 1H), 2.30-2.22 (m, 1H), 1.53-1.45 (dt, J=8.1, 3.5 Hz, 1H), 1.35-1.27 (m, 1H).

Example 23

4-(2-Cyclopropyl-6-(3,5-dimethylisoxazol-4-yl)-1H-benzo[d]imidazol-4-yl)benzamide (1020-23)

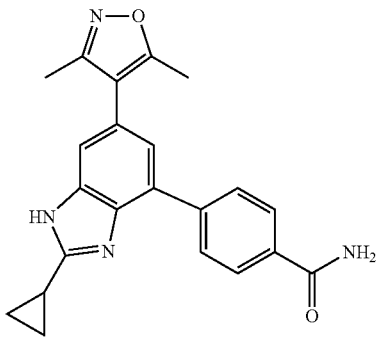 [SMILES: Cc1noc(C)c1-c1cc(-c2ccc(C(N)=O)cc2)c2nc(C3CC3)[nH]c2c1]

4-(2-cyclopropyl-6-(3,5-dimethylisoxazol-4-yl)-1H-benzo[d]imidazol-4-yl)benzamide was synthesized in a manner similar to that of Example 19 using 4-carbamoyl-phenyl-boronic acid.

$C_{22}H_{20}N_4O_2$. MS. 373.1 (M+1). $^1$H NMR (MeOH-d$_4$) δ 8.1 (d, J=8.3 Hz, 2H), 7.80 (d, J=8.3 Hz, 2H), 7.62 (d, J=1.5 Hz, 1H), 7.52 (d, J=1.5 Hz, 1H), 2.56-2.48 (tt, J=8.5, 5.0 Hz, 1H), 2.46 (s, 3H), 2.30 (s, 3H), 1.61-1.50 (m, 2H), 1.50-1.41 (m, 2H).

Example 24

3-(2-Cyclopropyl-6-(3,5-dimethylisoxazol-4-yl)-1H-benzo[d]imidazol-4-yl)benzamide (1020-24)

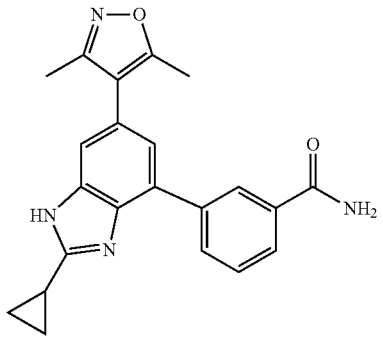 [SMILES: Cc1noc(C)c1-c1cc(-c2cccc(C(N)=O)c2)c2nc(C3CC3)[nH]c2c1]

3-(2-cyclopropyl-6-(3,5-dimethylisoxazol-4-yl)-1H-benzo[d]imidazol-4-yl)benzamide was synthesized in a manner similar to that of Example 19 using 3-carbamoyl-phenyl-boronic acid.

$C_{22}H_{20}N_4O_2$. MS. 373.1 (M+1). $^1$H NMR (MeOH-d$_4$) δ 8.16 (t, J=1.4 Hz, 1H), 8.02 (dt, J=7.7, 1.4 Hz, 1H), 7.88 (dt, J=7.7, 1.4 Hz, 1H), 7.71 (t, J=7.7 Hz, 1H), 7.61 (d, J=1.4 Hz, 1H), 7.54 (d, J=1.4 Hz, 1H), 2.56-2.47 (m, 1H), 2.46 (s, 3H), 2.30 (s, 3H), 1.58-1.50 (m, 2H), 1.49-1.42 (m, 2H).

Example 25

4-(2-Cyclopropyl-4-(2-methoxy-4-methylpyridin-3-yl)-1H-benzo[d]imidazol-6-yl)-3,5-dimethylisoxazole (1020-25)

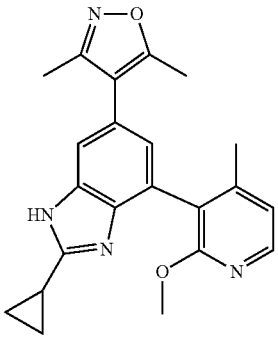 [SMILES: COc1nccc(C)c1-c1cc(-c2c(C)noc2C)cc2[nH]c(C3CC3)nc12]

4-(2-cyclopropyl-4-(2-methoxy-4-methylpyridin-3-yl)-1H-benzo[d]imidazol-6-yl)-3,5-dimethylisoxazole was synthesized in a manner similar to that of Example 19 using 2-methoxy-4-methylpyridin-3-ylboronic acid.

$C_{22}H_{22}N_4O_2$. MS. 374.9 (M+1). $^1$H NMR (MeOH-d$_4$) δ 8.17 (d, J=5.3 Hz, 1H), 7.62 (d, J=1.5 Hz, 1H), 7.34 (d, J=1.5 Hz, 1H), 7.07 (d, J=5.3 Hz, 1H), 3.86 (s, 3H), 2.50-2.38 (m, 2H), 2.46 (s, 3H), 2.29 (s, 3H), 2.19 (s, 3H), 1.56-1.49 (m, 2H), 1.46-1.35 (m, 2H).

Example 26

4-(2-Cyclopropyl-4-(2-ethoxy-4-methylpyridin-3-yl)-1H-benzo[d]imidazol-6-yl)-3,5-dimethylisoxazole (1020-26)

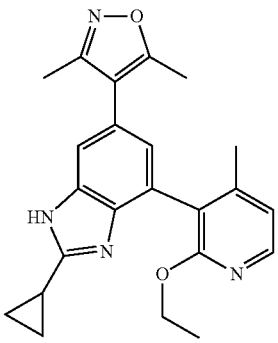 [SMILES: CCOc1nccc(C)c1-c1cc(-c2c(C)noc2C)cc2[nH]c(C3CC3)nc12]

4-(2-cyclopropyl-4-(2-ethoxy-4-methylpyridin-3-yl)-1H-benzo[d]imidazol-6-yl)-3,5-dimethylisoxazole was synthesized in a manner similar to that of Example 19 using 2-ethoxy-4-methylpyridin-3-ylboronic acid.

$C_{23}H_{24}N_4O_2$. MS. 388.9 (M+1). $^1$H NMR (MeOH-d$_4$) δ 8.14 (d, J=5.3 Hz, 1H), 7.62 (d, J=1.4 Hz, 1H), 7.34 (d, J=1.4 Hz, 1H), 7.04 (d, J=5.3 Hz, 1H), 4.40-4.23 (m, 2H), 2.46 (s, 3H), 2.46-2.38 (m, 1H), 2.29 (s, 3H), 2.19 (s, 3H), 1.60-1.47 (m, 2H), 1.45-1.34 (m, 2H), 1.15 (t, J=7.0 Hz, 3H).

Example 27

3-(2-Cyclopropyl-6-(3,5-dimethylisoxazol-4-yl)-1H-benzo[d]imidazol-4-yl)-4-methylpyridin-2-ol (1020-27)

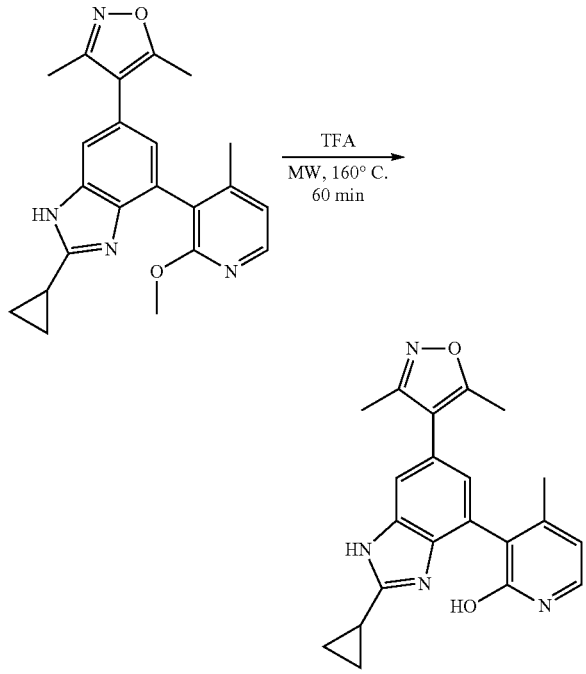

A solution of 4-(2-cyclopropyl-4-(2-methoxy-4-methylpyridin-3-yl)-1H-benzo[d]imidazol-6-yl)-3,5-dimethylisoxazole (40.0 mg, 0.08189 mmol) in TFA (3 mL) was heated at 160° C. for 1 h in microwave reactor. The solvent was removed under a reduced pressure to give the crude material. The crude material was purified by a preparative HPLC (5-95% acetonitrile: water with 0.05% trifluoroacetic acid, on a Phenomenex Luna C18 column) to give 3-(2-cyclopropyl-6-(3,5-dimethylisoxazol-4-yl)-1H-benzo[d]imidazol-4-yl)-4-methylpyridin-2-ol.

$C_{21}H_{20}N_4O_2$. MS. 361.1 (M+1). $^1$H NMR (MeOH-$d_4$) δ 7.59 (d, J=1.4 Hz, 1H), 7.50 (d, J=6.8 Hz, 1H), 7.34 (d, J=1.5 Hz, 1H), 6.50 (d, J=6.8 Hz, 1H), 2.47-2.39 (m, 1H), 2.45 (s, 3H), 2.28 (s, 3H), 2.18 (s, 3H), 1.57-1.47 (m, 2H), 1.44-1.37 (m, 2H).

Example 28

(E)-4-(2-Cyclopropyl-4-(hex-3-en-3-yl)-1H-benzo[d]imidazol-6-yl)-3,5-dimethylisoxazole (1020-28)

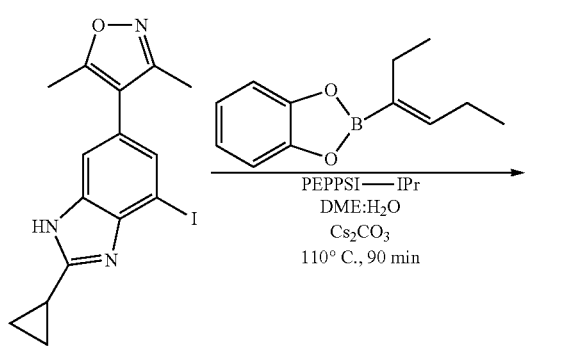

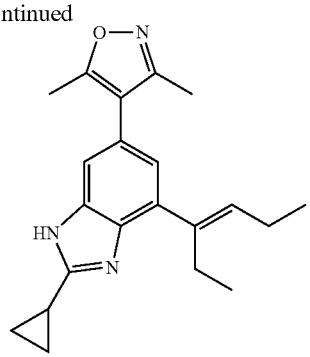

A suspension of 4-(2-cyclopropyl-4-iodo-1H-benzo[d]imidazol-6-yl)-3,5-dimethylisoxazole (100 mg, 0.265 mmol) (Example 8, Step 4), (Z)-3-Hexenyl-3-boronic acid catechol ester (81 mg, 0.400 mmol), caesium carbonate (260 mg, 0.8 mmol) and PEPPSI-IPr™ (18 mg, 0.026 mmol) in 10 mL DME:H$_2$ (2:1) was heated by microwave in a sealed vessel at 10° C. for 90 minute. The reaction was then cooled and partitioned between water and ethyl acetate. The organic layer was washed with brine and dried over sodium sulfate. Purification on silica gel (rf=0.5 in 60% ethyl acetate in hexanes) afforded (E)-4-(2-cyclopropyl-4-(hex-3-en-3-yl)-1H-benzo[d]imidazol-6-yl)-3,5-dimethylisoxazole as an off-white solid.

$C_{21}H_{25}N_3O$. 336.2 (M+1). $^1$H NMR (400 MHz, Methanol-$d_4$) δ 7.28 (d, J=1.5 Hz, 1H), 6.92 (d, J=1.6 Hz, 1H), 5.68 (t, J=7.2 Hz, 1H), 2.66 (q, J=7.5 Hz, 2H), 2.47-2.17 (m, 9H), 1.38-1.24 (m, 1H), 1.20-1.08 (m, 7H), 0.95 (t, J=7.5 Hz, 3H).

Example 29

4-(2-Cyclopropyl-4-(2,6-dimethylphenyl)-1H-benzo[d]imidazol-6-yl)-3,5-dimethylisoxazole (1020-29)

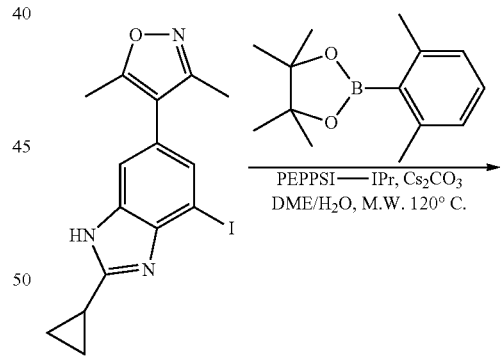

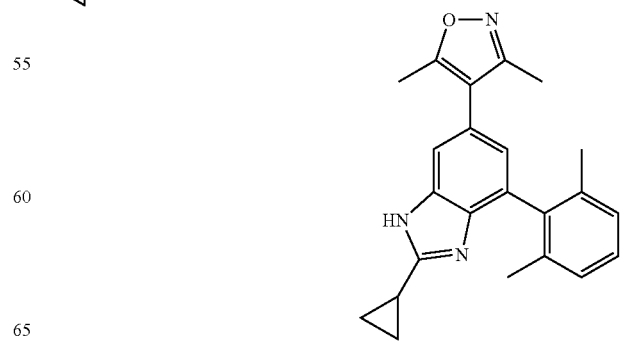

2,6-Dimethylphenylboronic acid, pinacol ester (33 mg, 0.22 mmol) was added to a solution of 4-(2-cyclopropyl-4-iodo-1H-benzo[d]imidazol-6-yl)-3,5-dimethylisoxazole (40 mg, 0.11 mmol) (Example 8, Step 4) in 1,2-dimethoxyethane and water (2/1 mL). To the mixture was added cesium carbonate (107 mg, 0.33 mmol) and PEPPSI-IPr (8 mg, 0.011 mmol). The reaction was put in microwave reactor and heated at 120° C. for 30 minutes before being evaporated under vacuum. The residue was purified by preparative HPLC (0-100% $CH_3CN/H_2O$) to afford 4-(2-cyclopropyl-4-(2,6-dimethylphenyl)-1H-benzo[d]imidazol-6-yl)-3,5-dimethylisoxazole. $C_{23}H_{23}N_3O$. 358.3 (M+1). $^1$H NMR (400 MHz, $CD_3OD$) δ 7.58 (s, 1H), 7.33-7.31 (m, 1H), 7.29-7.21 (m, 2H), 7.06-7.02 (m, 1H), 6.93-6.90 (m, 2H), 2.45 (s, 3H), 2.39-2.33 (m, 1H), 2.29 (s, 3H), 2.28 (s, 3H), 1.50-1.45 (m, 2H), 1.38-1.35 (m, 2H).

Example 30

4-(2-Cyclopropyl-4-o-tolyl-1H-benzo[d]imidazol-6-yl)-3,5-dimethylisoxazole (1020-30)

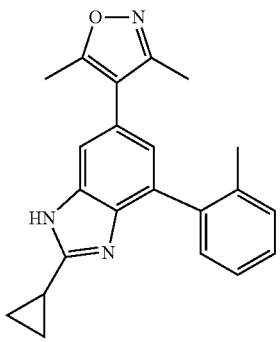 [SMILES: Cc1ccccc1-c1cc(-c2c(C)noc2C)cc2[nH]c(C3CC3)nc12]

4-(2-cyclopropyl-4-o-tolyl-1H-benzo[d]imidazol-6-yl)-3,5-dimethylisoxazole was synthesized by reacting 4-(2-cyclopropyl-4-iodo-1H-benzo[d]imidazol-6-yl)-3,5-dimethylisoxazole (Example 8, Step 4) with 2-methylphenylboronic acid in a manner similar to that of Example 29. $C_{22}H_{21}N_3O$. 344.3 (M+1). $^1$H NMR (400 MHz, $CD_3OD$) δ 8.75 (dd, J=5.0, 1.3 Hz, 1H), 8.33 (d, J=8.5 Hz, 1H), 8.08 (d, J=8.6 Hz, 1H), 7.82-7.74 (m, 1H), 7.65-7.62 (m, 1H), 7.20 (s, 1H), 2.74-2.71 (m, 1H), 2.35 (s, 3H), 2.26 (s, 3H), 2.19 (s, 3H), 1.14-1.10 (m, 2H), 0.97-0.82 (m, 2H).

Example 31

4-(2-Cyclopropyl-4-phenyl-1H-benzo[d]imidazol-6-yl)-3,5-dimethylisoxazole (1020-31)

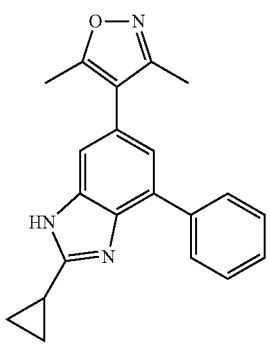 [SMILES: Cc1noc(C)c1-c1cc(-c2ccccc2)c2nc(C3CC3)[nH]c2c1]

4-(2-Cyclopropyl-4-phenyl-1H-benzo[d]imidazol-6-yl)-3,5-dimethylisoxazole (40 mg, 46%) was synthesized by reacting 4-(2-cyclopropyl-4-iodo-1H-benzo[d]imidazol-6-yl)-3,5-dimethylisoxazole (Example 8, Step 4) with phenylboronic acid in a manner similar to that of Example 29. $C_{21}H_{19}N_3O$. 330.2 (M+1). $^1$H NMR (400 MHz, Methanol-$d_4$) δ 7.78 (d, J=53.8 Hz, 2H), 7.54 (t, J=7.0 Hz, 2H), 7.45 (d, J=9.1 Hz, 2H), 7.16 (s, 1H), 2.46 (s, 3H), 2.31 (s, 4H), 1.25-1.07 (m, 4H).

Example 32

4-(2-Cyclopropyl-6-(3,5-dimethylisoxazol-4-yl)-1H-benzo[d]imidazol-4-yl)phenol (1020-32)

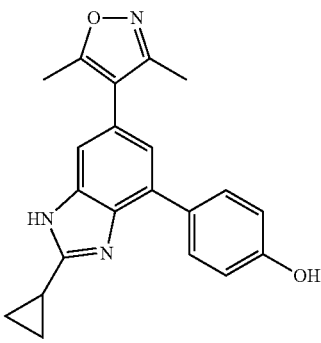 [SMILES: Cc1noc(C)c1-c1cc(-c2ccc(O)cc2)c2nc(C3CC3)[nH]c2c1]

4-(2-cyclopropyl-6-(3,5-dimethylisoxazol-4-yl)-1H-benzo[d]imidazol-4-yl)phenol was synthesized by reacting 4-(2-cyclopropyl-4-iodo-1H-benzo[d]imidazol-6-yl)-3,5-dimethylisoxazole (Example 8, Step 4) with 4-(4,4,5,5-tetramethyl-1,3,2-dioxaborolan-2-yl)phenol in a manner similar to that of Example 29. $C_{21}H_{19}N_3O_2$. 346.2 (M+1). $^1$H NMR (400 MHz, Methanol-$d_4$) δ 7.47 (s, 2H), 7.31 (s, 1H), 7.05 (s, 1H), 6.99-6.87 (m, 2H), 2.41 (s, 3H), 2.26 (s, 3H), 2.19 (d, J=6.2 Hz, 1H), 1.20-1.06 (m, 4H).

Example 33

4-(2-Cyclopropyl-6-(3,5-dimethylisoxazol-4-yl)-1H-benzo[d]imidazol-4-yl)-2,6-dimethylphenol (1020-33)

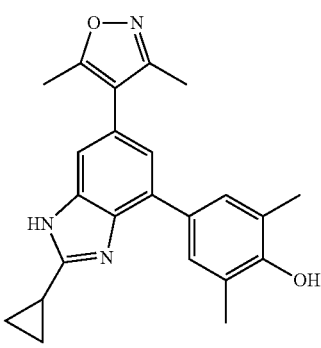 [SMILES: Cc1cc(-c2cc(-c3c(C)noc3C)cc3[nH]c(C4CC4)nc23)cc(C)c1O]

4-(2-cyclopropyl-6-(3,5-dimethylisoxazol-4-yl)-1H-benzo[d]imidazol-4-yl)-2,6-dimethylphenol was synthesized by reacting 4-(2-cyclopropyl-4-iodo-1H-benzo[d]imidazol-6-yl)-3,5-dimethylisoxazole (Example 8, Step 4) with 4-hydroxy-3,5-dimethylphenylboronic acid pinacol ester in a manner similar to that of Example 29.

$C_{23}H_{23}N_{32}$. 374.2 (M+1). $^1$H NMR (400 MHz, Methanol-$d_4$) δ 7.31 (d, J=1.5 Hz, 1H), 7.28 (s, 2H), 7.06 (d, J=1.6 Hz, 1H), 2.44 (s, 3H), 2.33 (s, 6H), 2.29 (s, 3H), 2.27-2.21 (m, 1H), 1.17 (ddd, J=7.6, 4.0, 2.5 Hz, 4H).

Example 34

4-(2-Cyclopropyl-4-(3,5-dimethylphenyl)-1H-benzo[d]imidazol-6-yl)-3,5-dimethylisoxazole (1020-34)

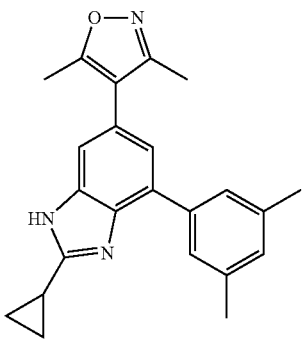 [SMILES: Cc1cc(C)cc(-c2cc(-c3c(C)noc3C)cc3[nH]c(C4CC4)nc23)c1]

4-(2-Cyclopropyl-4-(3,5-dimethylphenyl)-1H-benzo[d]imidazol-6-yl)-3,5-dimethylisoxazole was synthesized by reacting 4-(2-cyclopropyl-4-iodo-1H-benzo[d]imidazol-6-yl)-3,5-dimethylisoxazole (Example 8, Step 4) with 3,5-dimethylphenylboronic acid in a manner similar to that of Example 29.

$C_{23}H_{23}N_3O$. 358.2 (M+1). $^1$H NMR (400 MHz, Methanol-$d_4$) δ 7.34 (d, J=29.8 Hz, 3H), 7.11 (d, J=8.2 Hz, 2H), 2.44 (d, J=13.2 Hz, 9H), 2.31 (s, 3H), 2.24 (p, J=6.8 Hz, 1H), 1.23-1.07 (m, 4H).

Example 35

4-(2-Cyclopropyl-4-(2,3-dimethylphenyl)-1H-benzo[d]imidazol-6-yl)-3,5-dimethylisoxazole (1020-35)

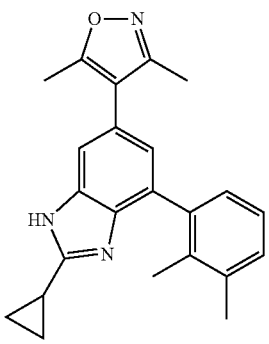 [SMILES: Cc1cccc(-c2cc(-c3c(C)noc3C)cc3[nH]c(C4CC4)nc23)c1C]

4-(2-cyclopropyl-4-(2,3-dimethylphenyl)-1H-benzo[d]imidazol-6-yl)-3,5-dimethylisoxazole was synthesized by reacting 4-(2-cyclopropyl-4-iodo-1H-benzo[d]imidazol-6-yl)-3,5-dimethylisoxazole (Example 8, Step 4) with 2,3-dimethylphenylboronic acid in a manner similar to that of Example 29.

$C_{23}H_{23}N_3O$. 358.2 (M+1). $^1$H NMR (400 MHz, Methanol-$d_4$) δ 7.41 (s, 1H), 7.31-7.08 (m, 3H), 6.94 (d, J=1.6 Hz, 1H), 2.45 (s, 3H), 2.40 (s, 3H), 2.30 (s, 3H), 2.10 (s, 4H), 1.24-1.04 (m, 4H).

Example 36

4-(2-cyclopropyl-4-(3,5-dimethoxyphenyl)-1H-benzo[d]imidazol-6-yl)-3,5-dimethylisoxazole (1020-36)

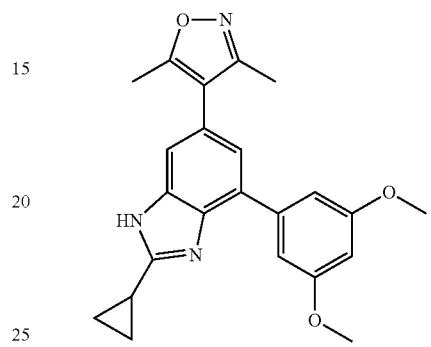

4-(2-cyclopropyl-4-(3,5-dimethoxyphenyl)-1H-benzo[d]imidazol-6-yl)-3,5-dimethylisoxazole was synthesized by reacting 4-(2-cyclopropyl-4-iodo-1H-benzo[d]imidazol-6-yl)-3,5-dimethylisoxazole (Example 8, Step 4) with 2-(3,5-dimethoxy)-phenyl-4,4,5,5-tetramethyl-(1,3,2)-dioxaborolane in a manner similar to that of Example 29.

$C_{23}H_{23}N_3O_3$. 390.3 (M+1). $^1$H NMR (400 MHz, Methanol-$d_4$) δ 7.45-7.30 (m, 1H), 7.15 (d, J=1.7 Hz, 1H), 6.87 (s, 2H), 6.65-6.48 (m, 1H), 3.87 (s, 6H), 2.46 (s, 3H), 2.30 (s, 4H), 1.24-1.05 (m, 4H).

Example 37

(E)-4-(2-cyclopropyl-4-styryl-1H-benzo[d]imidazol-6-yl)-3,5-dimethylisoxazole (1020-37)

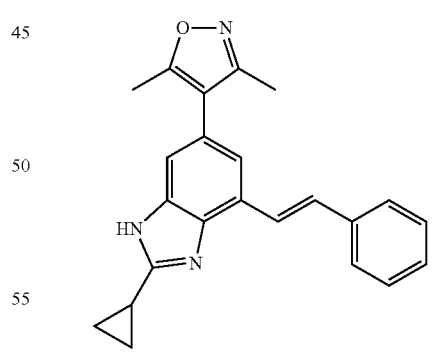

(E)-4-(2-cyclopropyl-4-styryl-1H-benzo[d]imidazol-6-yl)-3,5-dimethylisoxazole was synthesized by reacting 4-(2-cyclopropyl-4-iodo-1H-benzo[d]imidazol-6-yl)-3,5-dimethylisoxazole (Example 8, Step 4) with trans-2-phenylvinylboronic acid in a manner similar to that of Example 29.

$C_{23}H_{21}N_3O$. 356.2 (M+1). $^1$H NMR (400 MHz, Methanol-$d_4$) δ 7.77-7.64 (m, 3H), 7.50-7.35 (m, 4H), 7.33-7.24 (m, 2H), 2.45 (s, 3H), 2.30 (s, 4H), 1.33-1.16 (m, 4H)

Example 38

4-(2-Cyclopropyl-4-(1-phenylvinyl)-1H-benzo[d]imidazol-6-yl)-3,5-dimethylisoxazole

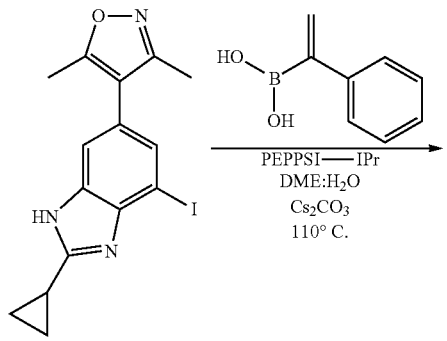

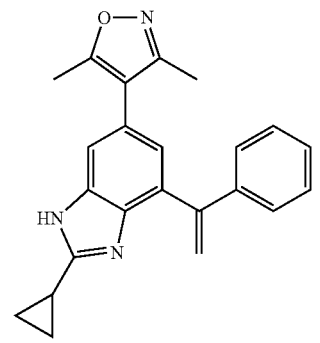

A suspension of 4-(2-cyclopropyl-4-iodo-1H-benzo[d]imidazol-6-yl)-3,5-dimethylisoxazole (100 mg, 0.265 mmol) (Example 8, Step 4), 1-phenylvinylboronic acid (59 mg, 0.400 mmol), caesium carbonate (260 mg, 0.8 mmol) and PEPPSI-IPr™ (18 mg, 0.026 mmol) in 10 mL DME:H$_2$O (2:1) was heated by microwave in a sealed vessel at 110° C. for 90 minutes. The reaction was then cooled and partitioned between water and ethyl acetate. The organic layer was washed with brine and dried over sodium sulfate. Purification on silica gel (rf=0.6 in 60% ethyl acetate in hexanes) afforded 4-(2-cyclopropyl-4-(1-phenylvinyl)-1H-benzo[d]imidazol-6-yl)-3,5-dimethylisoxazole.

C$_{23}$H$_{21}$N3O. 356.2 (M+1). $^1$H NMR (CDCl$_3$) δ 7.48 (s, 1H), 7.39 (m, 5H), 7.04 (s, 1H), 5.73 (s, 1H), 5.59 (br, 1H), 3.69 (s, 1H), 2.39 (s, 3H), 2.26 (s, 3H), 1.87 (br, 1H), 1.14-1.03 (m, 4H).

Example 39

4-(2-Cyclopropyl-4-(1-(4-fluorophenyl)vinyl)-1H-benzo[d]imidazol-6-yl)-3,5-dimethylisoxazole
(1020-39)

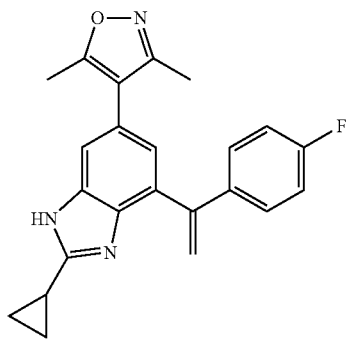 [SMILES: C=C(c1ccc(F)cc1)c1cc(-c2c(C)noc2C)cc2[nH]c(C3CC3)nc12]

4-(2-Cyclopropyl-4-(1-(4-fluorophenyl)vinyl)-1H-benzo[d]imidazol-6-yl)-3,5-dimethylisoxazole was synthesized by reacting 4-(2-cyclopropyl-4-iodo-1H-benzo[d]imidazol-6-yl)-3,5-dimethylisoxazole (Example 8, Step 4) with 1-(4-fluorophenyl)vinylboronic acid, pinacol ester in a manner similar to that of Example 38.

C$_{23}$H$_{20}$FN$_3$O. 374.2 (M+1). $^1$H NMR (400 MHz, Methanol-d$_4$) δ 7.61-7.24 (m, 3H), 7.09 (t, J=8.8 Hz, 2H), 6.93 (d, J=1.5 Hz, 1H), 5.93 (d, J=0.9 Hz, 1H), 5.63 (s, 1H), 2.40 (s, 3H), 2.33-2.10 (m, 4H), 1.27-1.07 (m, 4H). $^{19}$F NMR (376 MHz, Methanol-d$_4$) δ −116.27.

Example 40

4-(2-Cyclopropyl-4-(1-(3-fluorophenyl)vinyl)-1H-benzo[d]imidazol-6-yl)-3,5-dimethylisoxazole
(1020-40)

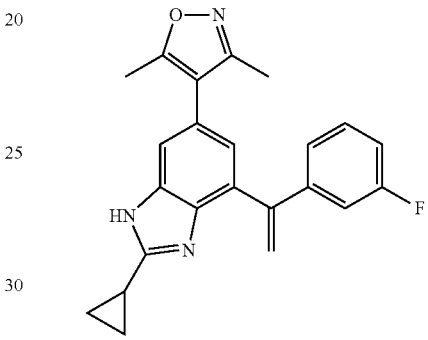

4-(2-Cyclopropyl-4-(1-(3-fluorophenyl)vinyl)-1H-benzo[d]imidazol-6-yl)-3,5-dimethylisoxazole was synthesized by reacting 4-(2-cyclopropyl-4-iodo-1H-benzo[d]imidazol-6-yl)-3,5-dimethylisoxazole (Example 8, Step 4) with 1-(3-fluorophenyl)vinylboronic acid, pinacol ester in a manner similar to that of Example 38.

C$_{23}$H$_{20}$FN$_3$O. 374.2 (M+1). $^1$H NMR (400 MHz, Methanol-d$_4$) δ 7.46-7.30 (m, 2H), 7.23-7.01 (m, 3H), 6.89 (d, J=1.6 Hz, 1H), 5.99 (d, J=1.0 Hz, 1H), 5.70 (s, 1H), 3.67 (s, 1H), 2.39 (s, 3H), 2.26-2.12 (m, 4H), 1.19-1.09 (m, 4H). $^{19}$F NMR (376 MHz, Methanol-d$_4$) δ −116.09.

Example 41

4-(4-(1-(4-Chlorophenyl)vinyl)-2-cyclopropyl-1H-benzo[d]imidazol-6-yl)-3,5-dimethylisoxazole
(1020-41)


4-(4-(1-(4-Chlorophenyl)vinyl)-2-cyclopropyl-1H-benzo[d]imidazol-6-yl)-3,5-dimethylisoxazole was synthesized by reacting 4-(2-cyclopropyl-4-iodo-1H-benzo[d]imidazol-6-yl)-3,5-dimethylisoxazole (Example 8, Step 4) with 1-(4-chlorophenyl)vinylboronic acid, pinacol ester in a manner similar to that of Example 38.

$C_{23}H_{20}ClN_3O$. 390.2 (M+1). $^1$H NMR (400 MHz, Methanol-$d_4$) δ 7.44-7.32 (m, 5H), 6.91 (d, J=1.6 Hz, 1H), 5.97 (d, J=0.9 Hz, 1H), 5.67 (d, J=0.9 Hz, 1H), 2.40 (s, 3H), 2.27-2.13 (m, 4H), 1.42 (s, 1H), 1.17 (d, J=6.7 Hz, 4H).

Example 42

4-(2-Cyclopropyl-4-(1-(4-(trifluoromethyl)phenyl)vinyl)-1H-benzo[d]imidazol-6-yl)-3,5-dimethylisoxazole (1020-42)

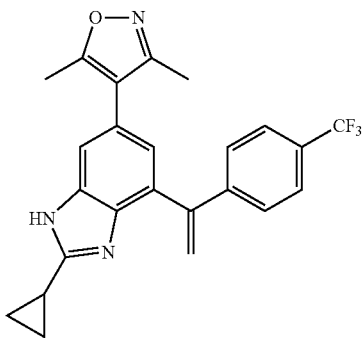 [SMILES: C=C(c1ccc(C(F)(F)F)cc1)c1cc(-c2c(C)noc2C)cc2[nH]c(C3CC3)nc12]

4-(2-Cyclopropyl-4-(1-(4-(trifluoromethyl)phenyl)vinyl)-1H-benzo[d]imidazol-6-yl)-3,5-dimethylisoxazole was synthesized by reacting 4-(2-cyclopropyl-4-iodo-1H-benzo[d]imidazol-6-yl)-3,5-dimethylisoxazole (Example 8, Step 4) with 1-(4-trifluoromethylphenyl)-vinylboronic acid, pinacol ester in a manner similar to that of Example 38.

$C_{24}H_{20}F_3N_3O$. 424.2 (M+1). $^1$H NMR (400 MHz, Methanol-$d_4$) δ 7.63 (d, J=8.4 Hz, 2H), 7.54 (d, J=8.6 Hz, 2H), 7.41 (s, 1H), 6.86 (s, 1H), 6.04 (s, 1H), 5.77 (d, J=48.9 Hz, 1H), 2.36 (s, 3H), 2.20 (s, 4H), 1.18-1.00 (m, 4H). $^{19}$F NMR (376 MHz, Methanol-$d_4$) δ −64.6.

Example 43

4-(2-Cyclopropyl-4-(1-phenylethyl)-1H-benzo[d]imidazol-6-yl)-3,5-dimethylisoxazole (1020-43)

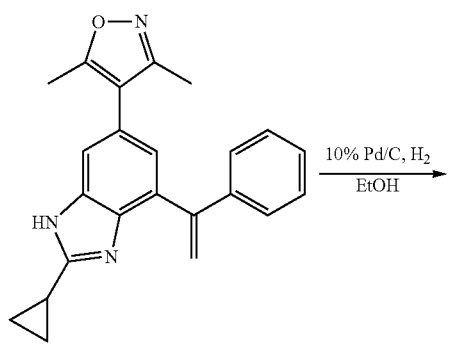

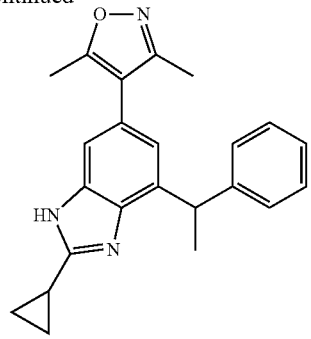

A suspension of 4-(2-cyclopropyl-4-(1-phenylvinyl)-1H-benzo[d]imidazol-6-yl)-3,5-dimethylisoxazole (50 mg, 0.141 mmol) (Example 38) and 10% palladium on carbon (10 mg) in 5 mL ethanol was purged with hydrogen gas and allowed to stir for 2 hours. The reaction was then filtered and the solvents evaporated. Purification on silica gel (rf=0.6 in 60% ethyl acetate in hexanes) afforded 4-(2-cyclopropyl-4-(1-phenylethyl)-1H-benzo[d]imidazol-6-yl)-3,5-dimethylisoxazole.

$C_{23}H_{23}N_3O$. 358.2 (M+1). $^1$H NMR (CDCl$_3$) δ 7.4-7.2 (m, 6H), 6.96 (s, 1H), 4.41 (br, 1H), 2.38 (s, 3H), 2.21 (s, 3H), 1.85 (br, 1H), 1.74 (d, 3H, J=7.2 Hz), 1.24 (br, 1H), 1.05 (m, 4H).

Example 44

4-(2-Cyclopropyl-4-(1-(4-fluorophenyl)ethyl)-1H-benzo[d]imidazol-6-yl)-3,5-dimethylisoxazole (1020-44)

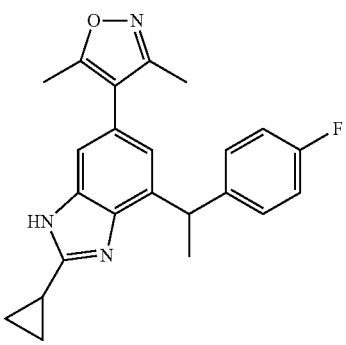 [SMILES: Cc1noc(C)c1-c1cc(C(C)c2ccc(F)cc2)c2nc(C3CC3)[nH]c2c1]

4-(2-Cyclopropyl-4-(1-(4-fluorophenyl)ethyl)-1H-benzo[d]imidazol-6-yl)-3,5-dimethylisoxazole was obtained by reducing 4-(2-cyclopropyl-4-(1-(4-fluorophenyl)vinyl)-1H-benzo[d]imidazol-6-yl)-3,5-dimethylisoxazole (Example 39) in a manner similar to that of Example 43.

$C_{23}H_{22}FN_3O$. 376.2 (M+1). $^1$H NMR (400 MHz, Methanol-$d_4$) δ 7.45-7.25 (m, 2H), 7.20 (s, 1H), 6.99 (t, J=8.8 Hz, 2H), 6.80 (s, 1H), 2.32 (s, 3H), 2.16 (d, J=3.2 Hz, 4H), 1.70 (d, J=7.2 Hz, 3H), 1.38 (s, 1H), 1.20-1.06 (m, 3H). $^{19}$F NMR (376 MHz, Methanol-$d_4$) δ −119.6.

Example 45

4-(2-Cyclopropyl-4-(1-(3-fluorophenyl)ethyl)-1H-benzo[d]imidazol-6-yl)-3,5-dimethylisoxazole (1020-45)

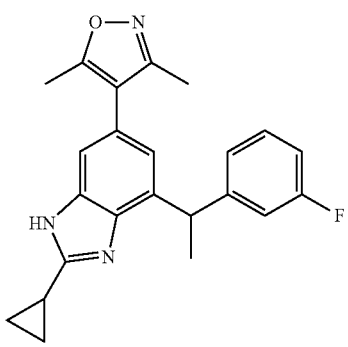 [SMILES: Cc1noc(C)c1-c1cc(C(C)c2cccc(F)c2)c2nc(C3CC3)[nH]c2c1]

4-(2-Cyclopropyl-4-(1-(3-fluorophenyl)ethyl)-1H-benzo[d]imidazol-6-yl)-3,5-dimethylisoxazole was obtained by reducing 4-(2-cyclopropyl-4-(1-(3-fluorophenyl)vinyl)-1H-benzo[d]imidazol-6-yl)-3,5-dimethylisoxazole (Example 40) in a manner similar to that of Example 43.

$C_{23}H_{22}FN_3O$. 376.2 (M+1). $^1$H NMR (400 MHz, Methanol-$d_4$) δ 7.34-7.23 (m, 2H), 7.20-7.13 (m, 1H), 7.13-7.06 (m, 1H), 6.93 (dt, J=8.6, 4.5 Hz, 1H), 6.87 (s, 1H), 2.36 (s, 3H), 2.20 (s, 4H), 1.75 (d, J=7.2 Hz, 3H), 1.41 (s, 1H), 1.22-1.13 (m, 4H). $^{19}$F NMR (376 MHz, Methanol-$d_4$) δ −116.1.

Example 46

4-(2-Cyclopropyl-4-(1-(4-(trifluoromethyl)phenyl)ethyl)-1H-benzo[d]imidazol-6-yl)-3,5-dimethylisoxazole (1020-46)

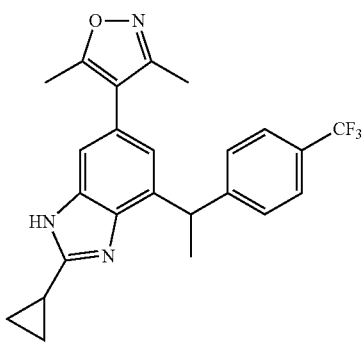 [SMILES: Cc1noc(C)c1-c1cc(C(C)c2ccc(C(F)(F)F)cc2)c2nc(C3CC3)[nH]c2c1]

4-(2-cyclopropyl-4-(1-(4-(trifluoromethyl)phenyl)ethyl)-1H-benzo[d]imidazol-6-yl)-3,5-dimethylisoxazole was obtained by reducing 4-(2-cyclopropyl-4-(1-(4-(trifluoromethyl)phenyl)vinyl)-1H-benzo[d]imidazol-6-yl)-3,5-dimethylisoxazole (Example 42) in a manner similar to that of Example 43.

$C_{24}H_{22}F_3N_3O$. 426.2 (M+1). $^1$H NMR (400 MHz, Methanol-$d_4$) δ 7.60-7.47 (m, 4H), 7.23 (d, J=1.5 Hz, 1H), 6.86 (d, J=1.5 Hz, 1H), 2.32 (s, 3H), 2.24-2.13 (m, 4H), 1.76 (d, J=7.2 Hz, 3H), 1.20-1.11 (m, 4H). $^{19}$F NMR (376 MHz, Methanol-$d_4$) δ −64.6.

Example 47

4-(2-Cyclopropyl-4-(2,4-dimethylthiazol-5-yl)-1H-benzo[d]imidazol-6-yl)-3,5-dimethylisoxazole (1020-47)

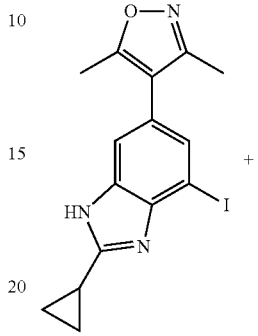

To a mixture of 2-cyclopropyl-4-iodo-6-(3,5-dimethylisoxazol-4-yl)benzimidazole (30 mg, 0.079 mmol) (Example 8, Step 4), 2,4-dimethyl-5-(4,4,5,5-tetramethyl-1,3,2-dioxaborolan-2-yl)-1,3-thiazole (38 mg, 0.158 mmol) and DBU (75 µL, 0.50 mmol) under nitrogen was added DMF (1.6 mL) and water (0.8 mL), followed by PEPPSI-IPr Pd catalyst (6 mg, 0.008 mmol). The reaction mixture was capped, heated to 130° C. for 30 min in a microwave reactor. The mixture partitioned between water and ethyl acetate, the aqueous phase was extracted with ethyl acetate twice, and the combined organic phase was washed with 1M aqueous $K_2CO_3$, brine, dried, filtered through a layer of celite and concentrated. The crude product was purified by reverse phase HPLC eluting with 0.1% TFA-containing acetonitrile/water to give 4-(2-cyclopropyl-4-(2,4-dimethylthiazol-5-yl)-1H-benzo[d]imidazol-6-yl)-3,5-dimethylisoxazole.

$C_{20}H_{20}N_4OS$. 365.1 (M+1). $^1$H NMR (DMSO-$d_6$) δ 7.59 (s, 1H), 7.29 (s, 1H), 2.73 (m, 4H), 2.47 (s, 3H), 2.36 (m, 4H), 2.29 (s, 3H), 1.27 (m, 4H).

Example 48

4-(2-Cyclopropyl-4-(4,5-dimethyl-1H-imidazol-1-yl)-1H-benzo[d]imidazol-6-yl)-3,5-dimethylisoxazole (1020-48)

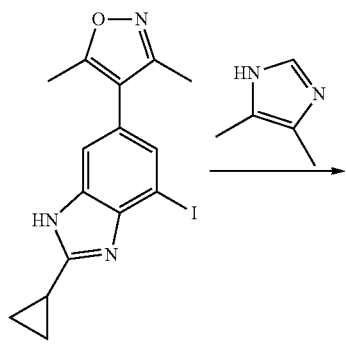

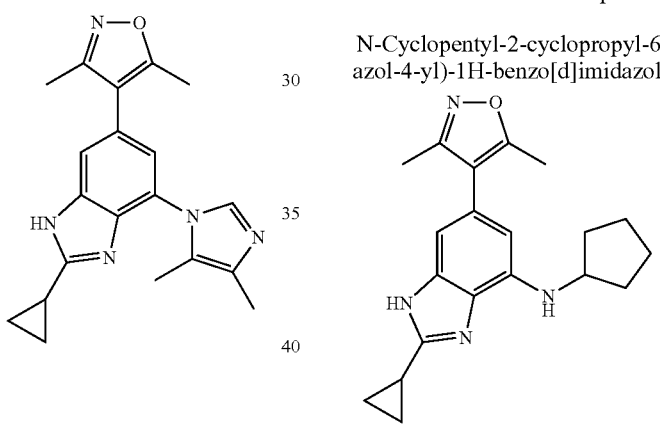

A suspension of 4-(2-cyclopropyl-4-iodo-1H-benzo[d]imidazol-6-yl)-3,5-dimethylisoxazole (35 mg, 0.13 mmol) (Example 8, Step 4), 4,5-dimethylimidazole (50 mg), Cu$_2$O (1 mg, 0.007 mmol), 4,7-dimethoxy-1,10-phenanthroline (3 mg, 0.012 mmol), cesium carbonate (41 mg, 0.126 mmol), and PEG-3350 (20 mg) in butyronitrile (1 mL) was heated at 120° C. for 72 hours. The solvent was removed and the residue was purified by preparative HPLC to give 4-(2-cyclopropyl-4-(4,5-dimethyl-1H-imidazol-1-yl)-1H-benzo[d]imidazol-6-yl)-3,5-dimethylisoxazole.

$C_{20}H_{21}N_5O$. 348.1 (M+1). $^1$H NMR (DMSO) δ 9.34 (s, 1H), 7.64 (s, 1H), 7.39 (s, 1H), 2.45 (s, 3H), 2.36 (s, 3H), 2.27 (s, 3H), 2.18 (m, 1H), 2.13 (s, 3H), 1.12 (m, 2H), 1.04 (m, 2H).

Compounds (1020-49), (1020-50), (1020-51), (1020-52), (1020-53), (1020-54), (1020-55) and (1020-56) were prepared in a similar manner as Example 48 by substituting the appropriate commercially available heterocycle for 4,5-dimethylimidazole:

Example 49

4-(2-Cyclopropyl-4-(3,5-dimethyl-1H-1,2,4-triazol-1-yl)-1H-benzo[d]imidazol-6-yl)-3,5-dimethylisoxazole (1020-49)

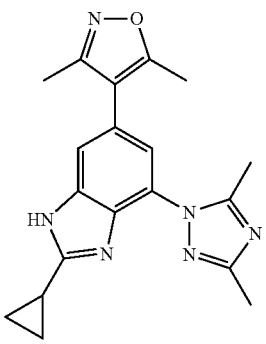 [SMILES: Cc1nc(C)n(-c2cc(-c3c(C)noc3C)cc3[nH]c(C4CC4)nc23)n1]

$C_{19}H_{20}N_6O$. 349.1 (M+1). $^1$H NMR (DMSO) δ 7.62 (s, 1H), 7.38 (s, 1H), 2.42 (s, 3H), 2.37 (s, 3H), 2.32 (s, 3H), 2.30 (m, 1H), 2.23 (s, 3H), 1.21 (m, 4H).

Example 50

N-Cyclopentyl-2-cyclopropyl-6-(3,5-dimethylisoxazol-4-yl)-1H-benzo[d]imidazol-4-amine (1020-50)

$C_{20}H_{24}N_4O$. 337.1 (M+1). $^1$H NMR (DMSO) δ 6.76 (s, 1H), 6.43 (s, 1H), 5.75 (br, 1H), 3.95 (br, 1H), 2.40 (s, 3H), 2.39 (m, 1H), 2.22 (s, 3H), 2.03 (m, 2H), 1.8-1.2 (m, 12H).

Example 51

4-(2-Cyclopropyl-4-(3,5-dimethyl-4H-1,2,4-triazol-4-yl)-1H-benzo[d]imidazol-6-yl)-3,5-dimethylisoxazole (1020-51)

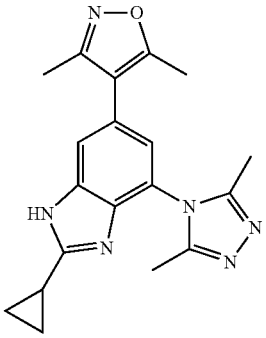 [SMILES: Cc1noc(C)c1-c1cc(-n2c(C)nnc2C)c2nc(C3CC3)[nH]c2c1]

$C_{19}H_{20}N_6O$. 349.1 (M+1). $^1$H NMR (DMSO) δ 10.19 (s, 1H), 7.41 (s, 1H), 7.33 (s, 1H), 2.50 (s, 3H), 2.43 (m, 1H), 2.39 (s, 3H), 2.21 (s, 3H), 2.16 (s, 3H), 1.29 (m, 4H).

Example 52

4-(2-Cyclopropyl-4-(2,5-dimethyl-1H-imidazol-1-yl)-1H-benzo[d]imidazol-6-yl)-3,5-dimethylisoxazole (1020-52)

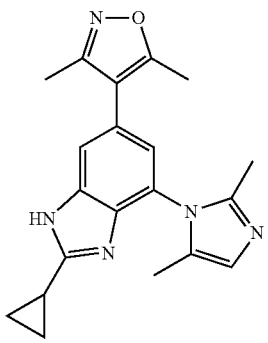 [SMILES: Cc1noc(C)c1-c1cc(-n2c(C)cnc2C)c2nc(C3CC3)[nH]c2c1]

$C_{20}H_{21}N_5O$. 348.1 (M+1). $^1$H NMR (DMSO) δ 7.66 (s, 1H), 7.58 (s, 1H), 7.40 (s, 1H), 2.45 (s, 3H), 2.40 (s, 3H), 2.27 (s, 3H), 2.18 (m, 1H), 2.06 (s, 3H), 1.2-1.0 (m, 4H).

Example 53

4-(2'-Cyclopropyl-2-methyl-1'H-1,4'-bibenzo[d]imidazol-6'-yl)-3,5-dimethylisoxazole (1020-53)

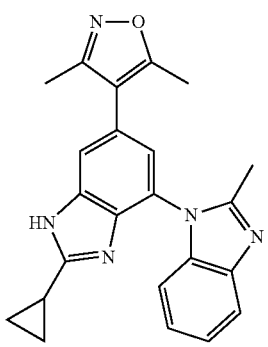 [SMILES: Cc1noc(C)c1-c1cc(-n2c(C)nc3ccccc32)c2nc(C3CC3)[nH]c2c1]

$C_{23}H_{21}N_5O$. 384.1 (M+1). $^1$H NMR (DMSO) δ 7.91 (d, J=8.4 Hz, 1H), 7.75 (s, 1H), 7.6-7.4 (m, 3H), 7.32 (d, J=8.0 Hz, 1H), 2.67 (s, 3H), 2.48 (s, 3H), 2.30 (s, 3H), 2.17 (m, 1H), 1.2-1.0 (m, 4H).

Example 54

4-(2-Cyclopropyl-4-(2-methyl-1H-imidazol-1-yl)-1H-benzo[d]imidazol-6-yl)-3,5-dimethylisoxazole (1020-54)

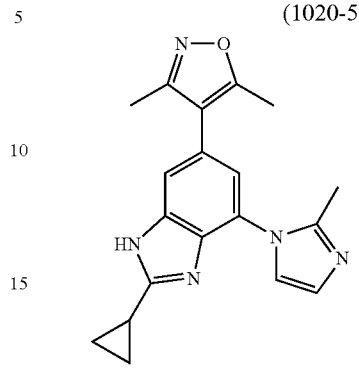

$C_{19}H_{19}N_5O$. 334.1 (M+1). $^1$H NMR (DMSO) δ 7.95 (s, 1H), 7.83 (s, 1H), 7.65 (s, 1H), 7.40 (s, 1H), 2.54 (s, 3H), 2.45 (s, 3H), 2.27 (s, 3H), 2.19 (m, 1H), 1.13-1.06 (m, 4H).

Example 55

4-(2'-Cyclopropyl-4,5,6,7-tetrahydro-1'H-1,4'-bibenzo[d]imidazol-6'-yl)-3,5-dimethylisoxazole (1020-55)

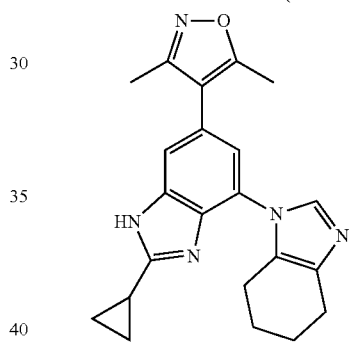

$C_{22}H_{23}N_5O$. 374.1 (M+1). $^1$H NMR (DMSO) δ 9.38 (s, 1H), 7.64 (s, 1H), 7.41 (s, 1H), 2.74 (m, 2H), 2.56 (m, 2H), 2.44 (s, 3H), 2.27 (s, 3H), 2.20 (m, 1H), 1.80 (m, 4H), 1.2-1.0 (m, 4H).

Example 56

4-(2'-Cyclopropyl-1'H-1,4'-bibenzo[d]imidazol-6'-yl)-3,5-dimethylisoxazole (1020-56)

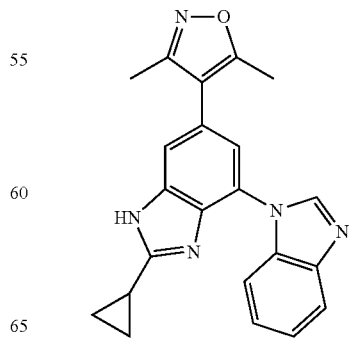

$C_{22}H_{19}N_5O$. 370.1 (M+1). $^1$H NMR (DMSO) δ 9.09 (s, 1H), 7.88 (d, J=8.0 Hz, 1H), 7.63 (s, 1H), 7.6-7.4 (m, 4H), 2.47 (s, 3H), 2.30 (s, 3H), 2.20 (m, 1H), 1.2-1.0 (m, 4H).

Example 57

4-(2-Cyclopropyl-7-(2,4-dimethylpyridin-3-yl)-1H-benzo[d]imidazol-5-yl)-3,5-dimethylisoxazole (1020-57)

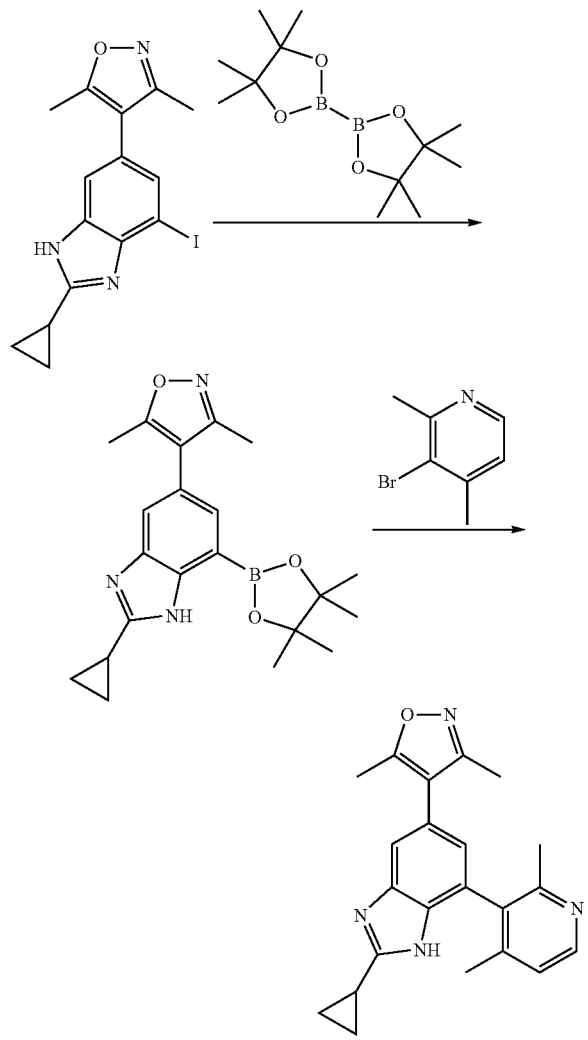

To a 10 mL Smith process vial equipped with a stir bar was added 4-(2-cyclopropyl-4-iodo-1H-benzo[d]imidazol-6-yl)-3,5-dimethylisoxazole (758 mg, 2 mmol), (Example 8, Step 4) bis(pinacolato)diboron (2.54 g, 10 mmol), [1,1'-bis(diphenylphosphino)-ferrocene]dichloropalladium(II) (146 mg, 0.2 mmol), and potassium acetate (1.96 g, 20 mmol). 1,4-dioxane was then added, and the reaction vessel was capped with a rubber septum, and evacuated and backfilled with $N_2$ three times. The reaction mixture was then heated for 18 hours at 100° C., followed by 6 hours at 110° C. The reaction mixture was then diluted with ethyl acetate (100 mL), filtered, washed with water (100 mL) followed by brine (50 mL), and dried over anhydrous magnesium sulfate. This mixture was then concentrated to dryness to give crude 4-(2-cyclopropyl-7-(4,4,5,5-tetramethyl-1,3,2-dioxaborolan-2-yl)-1H-benzo[d]imidazol-5-yl)-3,5-dimethylisoxazole. $C_{15}H_{17}BN_3O_3$. 298.1 ((M-Pinacol)+1).

Crude 4-(2-cyclopropyl-7-(4,4,5,5-tetramethyl-1,3,2-dioxaborolan-2-yl)-1H-benzo[d]imidazol-5-yl)-3,5-dimethylisoxazole (280 mg crude mixture, ~0.2 mmol) from the previous step was added to a 0.5 to 2 mL Smith process vial equipped with a stir bar. To the reaction vessel was added 3-bromo-2,4-dimethylpyridine (112 mg, 0.6 mmol), potassium carbonate (276 mg, 2 mmol), PEPPSI-IPr catalyst (13.6 mg, 0.02 mmol), 1,4-dioxane (0.8 mL) and water (0.2 mL). The reaction mixture was heated in a microwave reactor for 45 minutes at 135° C., then the organic layer was removed by syringe, filtered, and directly injected onto preparative reverse phase high performance liquid chromatography (Phenomenex Gemini C18 column, 5% to 50% gradient acetonitrile in water with 0.1% TFA) to give 4-(2-cyclopropyl-7-(2,4-dimethylpyridin-3-yl)-1H-benzo[d]imidazol-5-yl)-3,5-dimethylisoxazole (34 mg) as a TFA salt.

$C_{22}H_{22}N_4O$. 359.2 (M+1). $^1$H NMR (400 MHz, $CD_3OD$) δ 8.69 (d, J=6.2 Hz, 1H), 7.94 (d, J=6.2 Hz, 1H), 7.79 (d, J=1.4 Hz, 1H), 7.44 (d, J=1.4 Hz, 1H), 2.50 (s, 3H), 2.49-2.40 (m, 4H), 2.36 (s, 3H), 2.30 (s, 3H), 1.57-1.46 (m, 2H), 1.46-1.37 (m, 2H).

Example 58

4-(2-Cyclopropyl-7-(3-cyclopropyl-5-methyl-1H-pyrazol-4-yl)-1H-benzo[d]imidazol-5-yl)-3,5-dimethylisoxazole (1020-58)

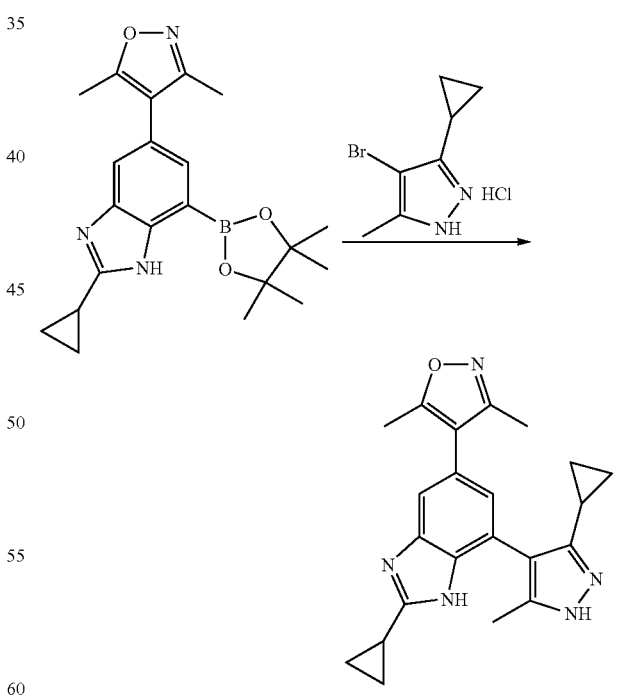

Crude 4-(2-cyclopropyl-7-(4,4,5,5-tetramethyl-1,3,2-dioxaborolan-2-yl)-1H-benzo[d]imidazol-5-yl)-3,5-dimethylisoxazole (729 mg crude mixture, ~0.5 mmol) (Example 57) was added to a 2 to 5 mL Smith process vial equipped with a stir bar. To the reaction vessel was added 4-bromo-3-cyclopropyl-5-methyl-1H-pyrazole hydrochloride (355.5 mg, 1.5 mmol), potassium carbonate (690 mg, 5 mmol), PEPPSI-IPr catalyst (34 mg, 0.05 mmol), 1,4-dioxane (2 mL) and water (0.5 mL). The reaction mixture was heated in a microwave reactor for 1 hour at 135° C., then the organic layer was removed by syringe, filtered, and directly injected onto preparative reverse phase high performance liquid chromatography (Phenomenex Gemini C18 column, 5% to 50% gradient acetonitrile in water with 0.1% TFA) to give 4-(2-cyclopropyl-7-(3-cyclopropyl-5-methyl-1H-pyrazol-4-yl)-1H-benzo[d]imidazol-5-yl)-3,5-dimethylisoxazole as a TFA salt.

$C_{22}H_{23}N_5O$. 374.2 (M+1). $^1$H NMR (400 MHz, $CD_3OD$) δ 7.64 (d, J=1.4 Hz, 1H), 7.39 (d, J=1.5 Hz, 1H), 2.53-2.39 (m, 4H), 2.29 (s, 3H), 2.23 (s, 3H), 1.87-1.70 (m, 1H), 1.58-1.48 (m, 2H), 1.48-1.40 (m, 2H), 1.02-0.73 (m, 4H).

Example 59

4-(2-Cyclopropyl-4-(3-methyl-5-phenyl-1H-pyrazol-4-yl)-1H-benzo[d]imidazol-6-yl)-3,5-dimethylisoxazole (1020-59)

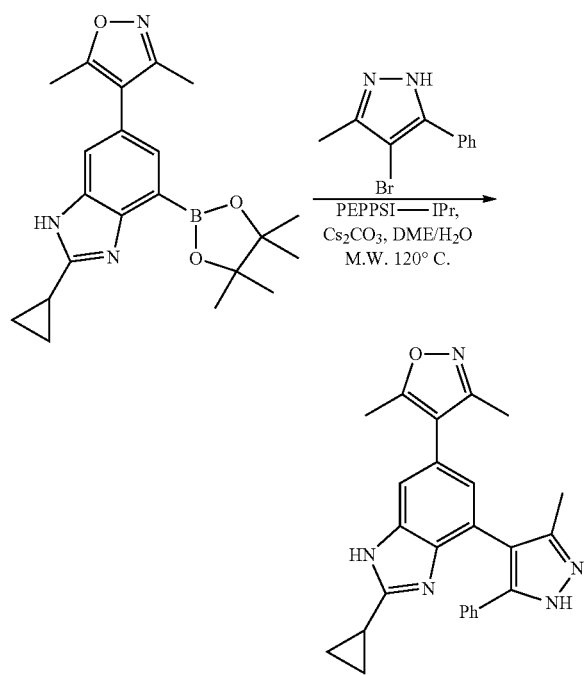

Crude 4-(2-cyclopropyl-7-(4,4,5,5-tetramethyl-1,3,2-dioxaborolan-2-yl)-1H-benzo[d]imidazol-5-yl)-3,5-dimethylisoxazole (74 mg, 0.05 mmol) (Example 57) and 4-bromo-3-methyl-5-phenyl-1H-pyrazole (36 mg, 0.15 mmol) was added to a solvent mixture of 1,2-dimethoxyethane (2 mL) and water (1 mL). To the above mixture were added PEPPSI-IPr (4 mg, 0.005 mmol) and $Cs_2CO_3$ (72 mg, 0.2 mmol). The reaction mixture was heated at 120° C. for 30 mins in microwave reactor. The reaction mixture was evaporated and the residue was purified by preparative HPLC (0-100% $CH_3CN/H_2O$) to afford 4-(2-cyclopropyl-4-(3-methyl-5-phenyl-1H-pyrazol-4-yl)-1H-benzo[d]imidazol-6-yl)-3,5-dimethylisoxazole.

$C_{25}H_{23}N_5O$. 410.3 (M+1). $^1$H NMR (400 MHz, $CD_3OD$) δ 7.61 (d, J=1.2 Hz, 1H), 7.35-7.28 (m, 5H), 7.26 (d, J=1.2 Hz, 1H), 2.41-2.39 (m, 1H), 2.33 (s, 3H), 2.31 (s, 3H), 2.13 (s, 3H), 1.51-1.48 (m, 2H), 3.34 (s, 2H).

Example 60

4-(2-Cyclopropyl-4-(3,5-dicyclopropyl-1H-pyrazol-4-yl)-1H-benzo[d]imidazol-6-yl)-3,5-dimethylisoxazole (1020-60)

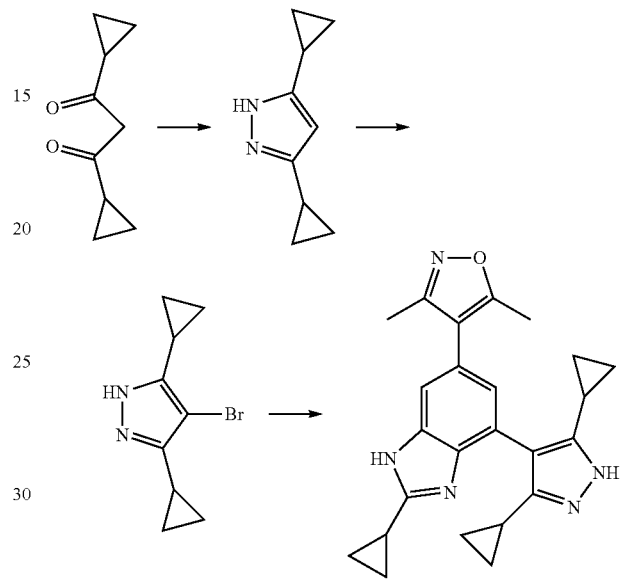

Step 1

1,3-Dicyclopropylpropane-1,3-dione (1.1 g, 7.23 mmol) was stirred at 0° C. in EtOH (25 mL) and hydrazine (0.232 g, 7.23 mmol) added slowly. After stirring at RT for 2 h, volatiles were remove, the residue taken up in EtOAc and the organic layer washed with brine and dried over sodium sulfate. Purification on silica gel (hexanes ethyl acetate 0-100%) afforded 3,5-dicyclopropyl-1H-pyrazole.

Step 2

3,5-Dicyclopropyl-1H-pyrazole (1.0 g, 6.79 mmol) was dissolved in acetic acid (10 ml) and reacted with NBS (1.209 g, 6.79 mmol). After stirring for 1 h, volatiles were removed, the residue taken up in EtOAc and the organic layer washed with brine and dried over sodium sulfate. Purification on silica gel (hexanes ethyl acetate 0-100%) afforded 4-bromo-3,5-dicyclopropyl-1H-pyrazole.

Step 3

4-Bromo-3,5-dicyclopropyl-1H-pyrazole was reacted under standard Suzuki conditions with 4-(2-cyclopropyl-4-(4,4,5,5-tetramethyl-1,3,2-dioxaborolan-2-yl)-1H-benzo[d]imidazol-6-yl)-3-methylisoxazole (see Example 59) to afford 4-(2-cyclopropyl-4-(3,5-dicyclopropyl-1H-pyrazol-4-yl)-1H-benzo[d]imidazol-6-yl)-3,5-dimethylisoxazole.

$C_{24}H_{25}N_5O$. 400.2 (M+1). $^1$H NMR (400 MHz, dmso) δ 7.61 (s, 1H), 7.34 (s, 1H), 2.45 (s, 3H), 2.26 (s, 3H), 1.71-1.59 (m, 1H), 1.48-1.33 (m, 8H), 0.74 (m, 6H).

Example 61

5-(2-Cyclopropyl-6-(3,5-dimethylisoxazol-4-yl)-1H-benzo[d]imidazol-4-yl)quinolin-2(1H)-one (1020-61)

Step 1: Preparation of 2-cyclopropyl-(3,5-dimethyl-isoxazol-4-yl)-1H-benzo[d]imidazol-4-ylboronic acid

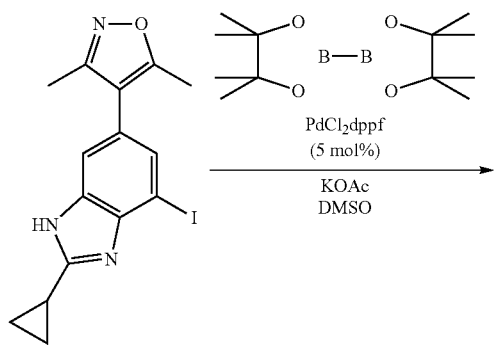

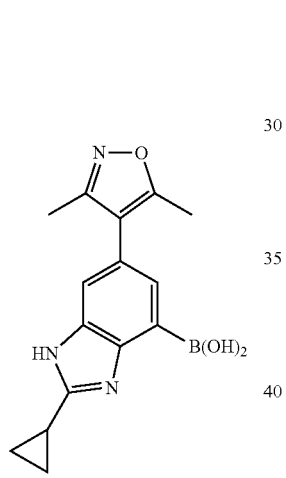

4-(2-Cyclopropyl-4-iodo-1H-benzo[d]imidazol-6-yl)-3,5-dimethylisoxazole (300.0 mg, 0.791 mmol) (Example 8, Step 4) was treated with 4,4,4',4',5,5,5',5'-octamethyl-2,2'-bi(1,3,2-dioxaborolane) (301.3 mg, 1.1865 mmol, 1.5 equiv.), KOAc (232.9 mg, 2.373 mmol, 3.0 equiv.) in the presence of PdCl$_2$dppf (28.9 mg, 0.03955 mmol, 0.05 equiv) in DMSO (5 mL) at 170° C. for 30 min. in an oil bath. To the reaction mixture were added water (30 mL) and EtOAc (70 mL). The whole was filtered through Celite (3 g) and then organic layer was separated from the filtrate. The organic layer was washed with brine (30 mL) and dried over Na$_2$SO$_4$. The solvent was removed under a reduced pressure to give the crude product. The crude product was purified by a preparative HPLC (5-95% acetonitrile: water with 0.05% trifluoroacetic acid, on a Phenomenex Luna C18 column) to give 2-cyclopropyl-6-(3,5-dimethylisoxazol-4-yl)-1H-benzo[d]imidazol-4-ylboronic acid.

$C_{15}H_{16}BN_3O_3$: MS. m/z 297.9 (M+1).

Step 2: Preparation of 5-(2-cyclopropyl-6-(3,5-dimethylisoxazol-4-yl)-1H-benzo[d]imidazol-4-yl)isoquinolin-1(2H)-one

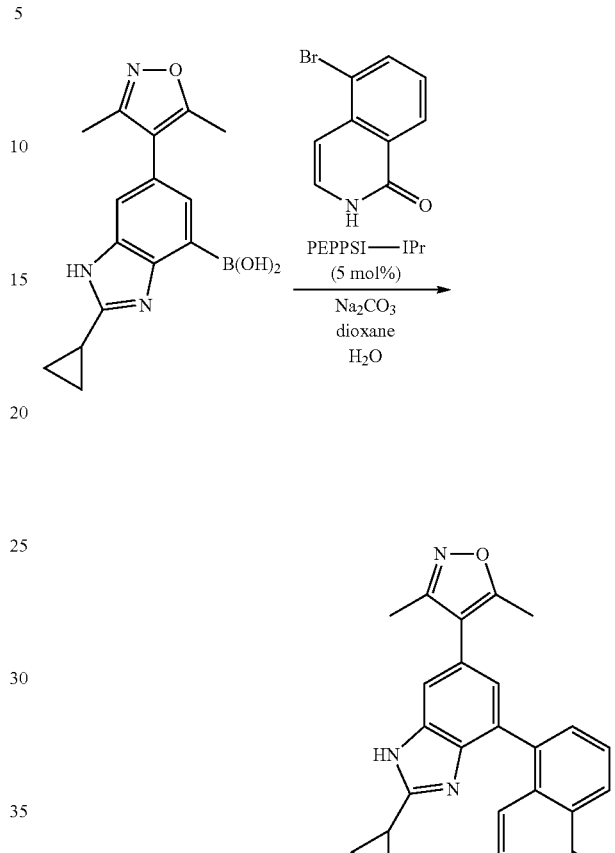

2-Cyclopropyl-6-(3,5-dimethylisoxazol-4-yl)-1H-benzo[d]imidazol-4-ylboronic acid (47.1 mg, 0.1585 mmol) was treated with 5-bromoquinolin-2(1H)-one (106.5 mg, 0.4755 mmol, 3.0 equiv.), 2M-Na$_2$CO$_3$ (aq) (1 mL) in the presence of PEPPSI-IPr (5.3 mg, 0.007925 mmol, 0.05 equiv) in 1,4-dioxane (3 mL) at 150° C. for 10 min in microwave reactor. To the reaction mixture were added water (30 mL) and EtOAc (70 mL). The whole was filtered through Celite (3 g) and then organic layer was separated from the filtrate. The organic layer was washed with brine (30 mL) and dried over Na$_2$SO$_4$. The solvent was removed under a reduced pressure to give the crude product. The crude product was purified by a preparative HPLC (5-95% acetonitrile: water with 0.05% trifluoroacetic acid, on a Phenomenex Luna C18 column) and a silica gel chromatography (MeOH:CH$_2$Cl$_2$=3:97~10:90) to give 5-(2-cyclopropyl-6-(3,5-dimethylisoxazol-4-yl)-1H-benzo[d]imidazol-4-yl)isoquinolin-1 (2H)-one.

$C_{24}H_{20}N_4O_2$. MS. m/z 396.9 (M+1). $^1$H NMR (MeOH-d$_4$) δ 8.45 (d, J=7.3 Hz, 1H), 7.81 (d, J=7.3 Hz, 1H), 7.66 (t, J=7.3, 1.5 Hz, 1H), 7.48 (s, 1H), 7.13 (d, J=7.3, 1H), 7.07 (s, 1H), 6.35 (d, J=7.3, 1H), 2.45 (s, 3H), 2.30 (s, 3H), 2.15-2.05 (m, 1H), 1.17-1.05 (m, 4H).

Example 62

5-(2-Cyclopropyl-6-(3,5-dimethylisoxazol-4-yl)-1H-benzo[d]imidazol-4-yl)-3,4-dihydroisoquinolin-1(2H)-one (1020-62)

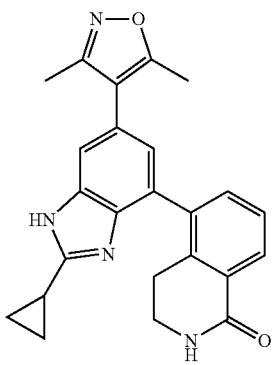 [SMILES: Cc1noc(C)c1-c1cc(-c2cccc3c2CCNC3=O)c2nc(C3CC3)[nH]c2c1]

5-(2-Cyclopropyl-6-(3,5-dimethylisoxazol-4-yl)-1H-benzo[d]imidazol-4-yl)-3,4-dihydroisoquinolin-1(2H)-one was synthesized in a similar manner as that of Example 61, Step 2, using 5-bromo-3,4-dihydroisoquinolin-1(2H)-one.

$C_{24}H_{22}N_4O_2$. MS. 399.2 (M+1). $^1$H NMR (MeOH-$d_4$) δ 8.07 (dd, J=7.7, 1.4 Hz, 1H), 7.60 (dd, J=7.7, 1.4 Hz, 1H), 7.50 (t, J=7.7 Hz, 1H), 7.43 (d, J=1.5 Hz, 1H), 7.01 (d, J=1.5 Hz, 1H), 3.41 (t, J=6.7 Hz, 2H), 2.96-2.64 (m, 2H), 2.44 (s, 3H), 2.29 (s, 3H), 2.20-2.07 (quin, J=7.0 Hz, 1H), 1.20-1.07 (d, J=7.0 Hz, 4H).

Example 63

5-(2-Cyclopropyl-6-(3,5-dimethylisoxazol-4-yl)-1H-benzo[d]imidazol-4-yl)quinolin-2(1H)-one (1020-63)

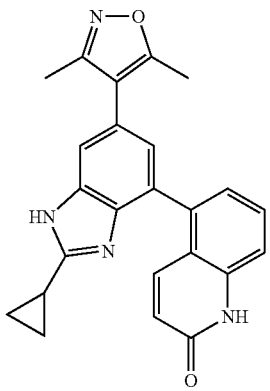 [SMILES: Cc1noc(C)c1-c1cc(-c2cccc3[nH]c(=O)ccc23)c2nc(C3CC3)[nH]c2c1]

5-(2-Cyclopropyl-6-(3,5-dimethylisoxazol-4-yl)-1H-benzo[d]imidazol-4-yl)quinolin-2(1H)-one was synthesized in a similar manner as that of Example 61, Step 2, using 5-bromoquinolin-2(1H)-one.

$C_{24}H_{20}N_4O_2$. MS. 397.1 (M+1). $^1$H NMR (MeOH-$d_4$) δ 7.68 (t, J=8.0 Hz, 1H), 7.67 (d, J=8.0 Hz, 1H), 7.49 (s, 1H), 7.47 (d, J=8.0 Hz, 1H), 7.35 (d, J=8.0 Hz, 1H), 7.08 (s, 1H), 6.55 (d, J=8.0 Hz, 1H), 2.46 (s, 3H), 2.30 (s, 3H), 2.11 (quin, J=7.0 Hz, 1H), 1.13 (d, J=7.0 Hz, 4H).

Example 64

5-(2-Cyclopropyl-6-(3,5-dimethylisoxazol-4-yl)-1H-benzo[d]imidazol-4-yl)-3,4-dihydroquinolin-2(1H)-one (1020-64)

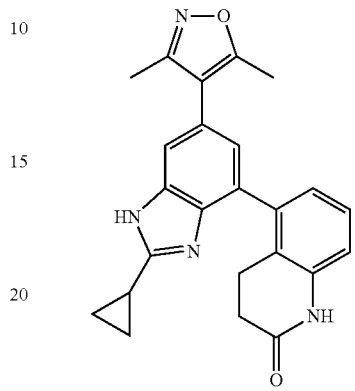

5-(2-Cyclopropyl-6-(3,5-dimethylisoxazol-4-yl)-1H-benzo[d]imidazol-4-yl)-3,4-dihydroquinolin-2(1H)-one was synthesized in a similar manner as that of Example 61, Step 2, using 5-bromo-3,4-dihydroquinolin-2(1H)-one.

$C_{24}H_{22}N_4O_2$. MS. 399.1 (M+1). $^1$H NMR (MeOH-$d_4$) δ 7.41 (br s, 1H), 7.29 (br t, J=8.0 Hz, 1H), 7.08 (d, J=8.0 Hz, 1H), 7.01-6.95 (m, 2H), 2.91-2.60 (m, 2H), 2.55-2.45 (br m, 1H), 2.43 (s, 3H), 2.28 (s, 3H), 2.16-2.07 (m, 1H), 1.12 (d, J=7.4 Hz, 4H).

Example 65

5-(2-Cyclopropyl-6-(3,5-dimethylisoxazol-4-yl)-1H-benzo[d]imidazol-4-yl)-4,6-dimethylpyrimidin-2-ol (1020-65)

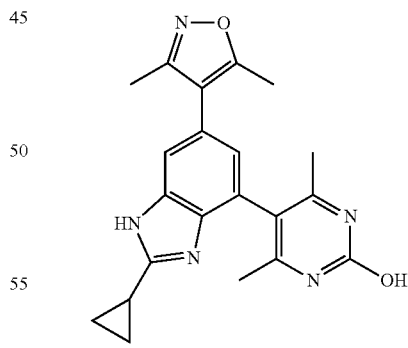

5-(2-Cyclopropyl-6-(3,5-dimethylisoxazol-4-yl)-1H-benzo[d]imidazol-4-yl)-4,6-dimethylpyrimidin-2-ol was synthesized in a similar manner as that of Example 61, Step 2, using 5-bromo-4,6-dimethylpyrimidin-2-ol.

$C_{21}H_{21}N_5O_2$. MS. 376.1 (M+1). $^1$H NMR (CD$_3$CN) δ 7.81 (d, J=1.4 Hz, 1H), 7.28 (d, J=1.4 Hz, 1H), 2.56-2.45 (m, 1H), 2.42 (s, 3H), 2.26 (s, 3H), 2.15-2.05 (m, 6H), 1.57-1.52 (m, 2H), 1.50-1.40 (m, 2H).

Example 66

5-(2-Cyclopropyl-6-(3,5-dimethylisoxazol-4-yl)-1H-benzo[d]imidazol-4-yl)-4-methylpyrimidin-2-ol (1020-66)

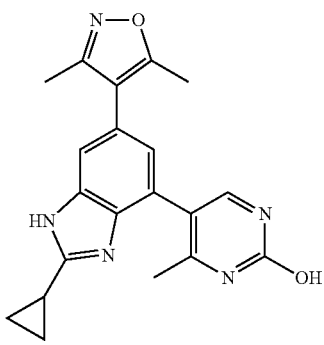 [SMILES: Cc1nc(O)ncc1-c1cc(-c2c(C)noc2C)cc2[nH]c(C3CC3)nc12]

5-(2-Cyclopropyl-6-(3,5-dimethylisoxazol-4-yl)-1H-benzo[d]imidazol-4-yl)-4-methylpyrimidin-2-ol was synthesized in a similar manner as that of Example 61, Step 2, using 5-bromo-4-methylpyrimidin-2-ol.

$C_{20}H_{19}N_5O_2$. MS. 362.1 (M+1). $^1$H NMR (CD$_3$CN) δ 8.29 (s, 1H), 7.75 (d, J=1.4 Hz, 1H), 7.34 (d, J=1.4 Hz, 1H), 2.49 (quin, J=6.7 Hz, 1H), 2.42 (s, 3H), 2.29 (s, 3H), 2.26 (s, 3H), 1.49 (d, J=6.7 Hz, 4H).

Example 67

4-(2-Cyclopropyl-6-(3,5-dimethylisoxazol-4-yl)-1H-benzo[d]imidazol-4-yl)phthalazin-1(2H)-one (1020-67)

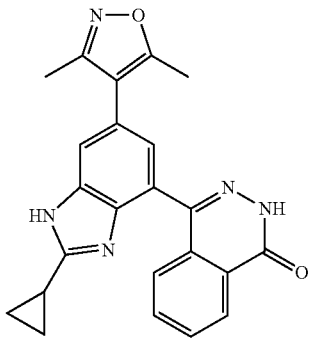 [SMILES: Cc1noc(C)c1-c1cc(-c2n[nH]c(=O)c3ccccc23)c2nc(C3CC3)[nH]c2c1]

4-(2-Cyclopropyl-6-(3,5-dimethylisoxazol-4-yl)-1H-benzo[d]imidazol-4-yl)phthalazin-1(2H)-one was synthesized in a similar manner as that of Example 61, Step 2, using 4-bromophthalazin-1 (2H)-one.

$C_{23}H_{19}N_5O_2$. MS. 398.1 (M+1). $^1$H NMR (MeOH-d$_4$) δ 8.51 (dd, J=7.5, 1.4 Hz, 1H), 7.95 (td, J=7.5, 1.4 Hz, 2H), 7.92 (td, J=7.5, 1.4 Hz, 1H), 7.77 (d, J=7.5, 1.4 Hz, 1H), 7.67 (dd, J=7.5, 1.4 Hz, 1H), 7.66 (d, 1.4 Hz, 1H), 2.49 (s, 3H), 2.48-2.40 (m, 1H), 2.33 (s, 3H), 1.58-1.49 (m, 2H), 1.44-1.35 (m, 2H).

Example 68

5'-(2-Cyclopropyl-6-(3,5-dimethylisoxazol-4-yl)-1H-benzo[d]imidazol-4-yl)spiro[cyclopropane-1,1'-isoindolin]-3'-one (1020-68)

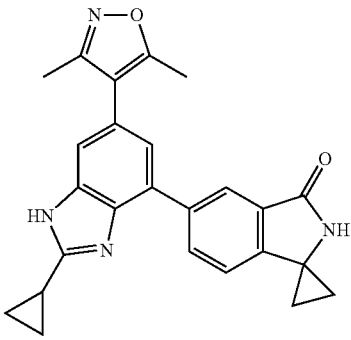 [SMILES: Cc1noc(C)c1-c1cc(-c2ccc3c(c2)C(=O)NC32CC2)c2nc(C3CC3)[nH]c2c1]

5'-(2-Cyclopropyl-6-(3,5-dimethylisoxazol-4-yl)-1H-benzo[d]imidazol-4-yl)spiro[cyclopropane-1,1'-isoindolin]-3'-one was synthesized in a similar manner as that of Example 61, Step 2, using 3'-oxospiro[cyclopropane-1,1'-isoindoline]-5'-yl trifluoromethanesulfonate.

$C_{25}H_{22}N_4O_2$. MS. 411.1 (M+1). $^1$H NMR (MeOH-d$_4$) δ 8.05 (br s, 1H), 7.90 (d, J=8.6 Hz, 1H), 7.30 (d, J=1.5 Hz, 1H), 7.27 (d, J=8.6 Hz, 1H), 7.10 (d, J=1.5 Hz, 1H), 2.35 (s, 3H), 2.20 (s, 3H), 2.08-2.16 (s, 1H), 1.58-1.50 (m, 2H), 1.50-1.47 (m, 2H), 1.11-1.02 (m, 4H).

Example 69

5-(2-Cyclopropyl-6-(3,5-dimethylisoxazol-4-yl)-1H-benzo[d]imidazol-4-yl)-1-methyl-3,4-dihydroquinolin-2(1H)-one (1020-69)

Step 1

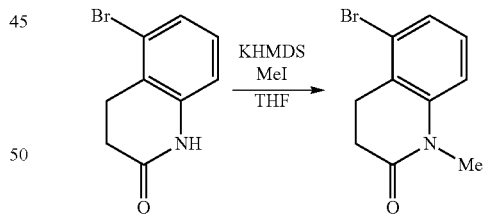

5-Bromo-3,4-dihydroquinolin-2(1H)-one (300.0 mg, 1.327 mmol) was treated with KHMDS (1.33 mL, 1.327 mmol, 1.0 equiv., 1M solution in THF) in THF (3 mL) under a nitrogen atmosphere at −78° C. for 30 min. To the reaction mixture was added a solution of MeI (367.7 mg, 2.654 mmol, 2.0 equiv.) in THF (1 mL) at the same temperature. And then the reaction was allowed to warm to room temperature and stirred for 45 min. To the reaction mixture was added water (30 mL). The whole was extracted with CH$_2$Cl$_2$ (30 mL×3). Obtained organic layer was washed with brine (30 mL) and dried over Na$_2$SO$_4$. The solvent was removed under a reduced pressure to give a crude product. The crude product was purified a silica gel column chromatography (MeOH:CH$_2$Cl$_2$=0:100~1:99) to give 5-bromo-1-methyl-3,4-dihydroquinolin-2(1H)-one.

C$_{10}$H$_{10}$BrNO: MS. m/z 240.0 (M−1), 242.0 (M+1).

Step 2: Preparation of 5-(2-cyclopropyl-6-(3,5-dimethylisoxazol-4-yl)-1H-benzo[d]imidazol-4-yl)-1-methyl-3,4-dihydroquinolin-2(1H)-one

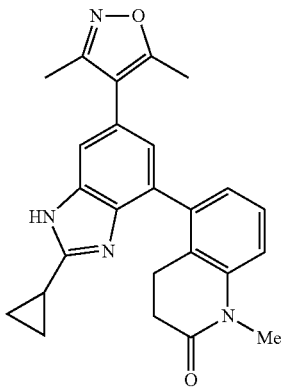 [SMILES: Cc1noc(C)c1-c1cc(-c2cccc3c2CCC(=O)N3C)c2nc(C3CC3)[nH]c2c1]

5-(2-Cyclopropyl-6-(3,5-dimethylisoxazol-4-yl)-1H-benzo[d]imidazol-4-yl)-1-methyl-3,4-dihydroquinolin-2(1H)-one was synthesized in a similar manner as that of Example 61, Step 2, using 4-bromo-2-tert-butoxypyridine.

C$_{23}$H$_{24}$N$_4$O$_2$. MS. m/z 413.2 (M+1). $^1$H NMR (MeOH-d$_4$) δ 7.63 (d, J=1.5 Hz, 1H), 7.50 (t, J=7.9 Hz, 1H), 7.36 (d, J=1.5 Hz, 1H), 7.35 (d, J=7.9 Hz, 1H), 7.19 (d, J=7.9 Hz, 1H), 3.45 (s, 3H), 2.72 (t, J=7.3 Hz, 2H), 2.55 (br t, J=7.3 Hz, 2H), 2.46 (s, 3H), 2.46-2.39 (m, 1H), 2.30 (s, 3H), 1.56-1.47 (m, 2H), 1.42-1.35 (m, 2H).

Example 70

4-(4-(2-tert-Butoxypyridin-4-yl)-2-cyclopropyl-1H-benzo[d]imidazol-6-yl)-3,5-dimethylisoxazole (1020-70)

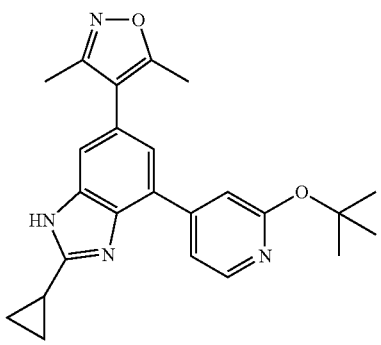 [SMILES: Cc1noc(C)c1-c1cc(-c2ccnc(OC(C)(C)C)c2)c2nc(C3CC3)[nH]c2c1]

4-(4-(2-tert-butoxypyridin-4-yl)-2-cyclopropyl-1H-benzo[d]imidazol-6-yl)-3,5-dimethylisoxazole was synthesized in a similar manner as that of Example 61, Step 2, using 4-bromo-2-tert-butoxypyridine.

C$_{24}$H$_{26}$N$_4$O$_2$. MS. m/z 403.2 (M+1). $^1$H NMR (MeOH-d$_4$) δ 8.21 (br s, 1H), 7.50-7.30 (br m, 2H), 7.30-7.10 (br m, 2H), 2.43 (s, 2H), 2.28 (s, 2H), 2.22 (quin, J=7.0 Hz, 1H), 1.61 (s, 9H), 1.16 (d, J=7.0 Hz, 4H).

Example 71

4-(2-Cyclopropyl-6-(3,5-dimethylisoxazol-4-yl)-1H-benzo[d]imidazol-4-yl)pyridin-2-ol (1020-71)

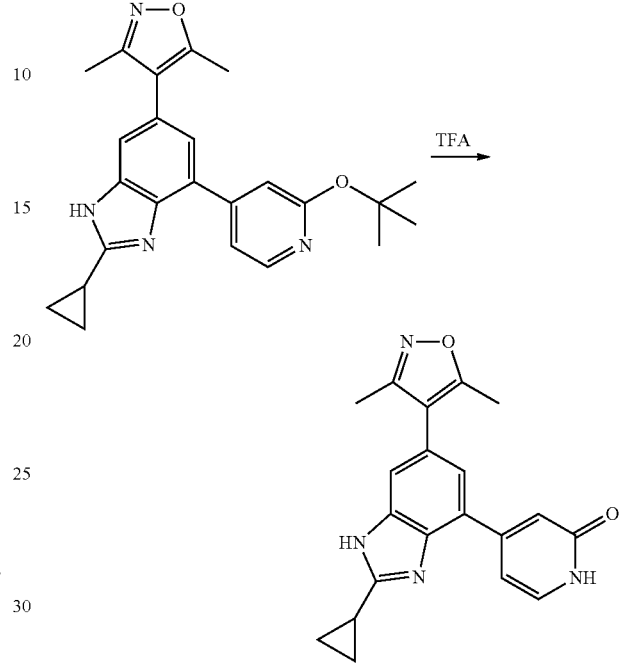

4-(4-(2-tert-Butoxypyridin-4-yl)-2-cyclopropyl-1H-benzo[d]imidazol-6-yl)-3,5-dimethylisoxazole (10.1 mg, 0.0251 mmol) was dissolved into TFA (2 mL) at room temperature. The reaction mixture was stirred at the same temperature for 1 h. The solvent was removed under a reduced pressure to give 4-(2-cyclopropyl-6-(3,5-dimethylisoxazol-4-yl)-1H-benzo[d]imidazol-4-yl)pyridin-2-ol.

C$_{20}$H$_{18}$N$_4$O$_2$. MS. m/z 347.1 (M+1). $^1$H NMR (MeOH-d$_4$) δ 7.67 (d, J=1.4 Hz, 1H), 7.65 (d, J=6.8 Hz, 0H), 7.55 (d, J=1.4 Hz, 1H), 6.83 (d, J=1.7 Hz, 1H), 6.70 (dd, J=6.8, 1.7 Hz, 1H), 2.49-2.57 (m, 1H), 2.45 (s, 3H), 2.29 (s, 3H), 1.60-1.52 (m, 1H), 1.49-1.41 (m, 1H).

Example 72

N-(4-(3,5-Dimethylisoxazol-4-yl)-2-iodo-6-nitrophenyl)-N-methylcyclopropanecarboxamide (1020-72)

Step 1: Preparation of 4-(3,5-dimethylisoxazol-4-yl)-2-iodo-N-methyl-6-nitroaniline

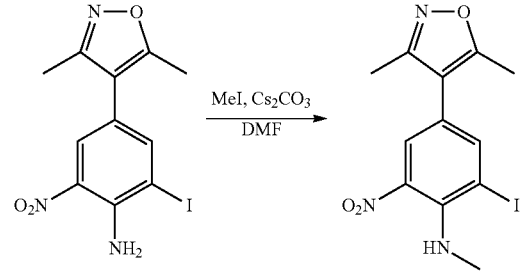

Into a flask containing 4-(3,5-dimethylisoxazol-4-yl)-2-iodo-6-nitroaniline (1000 mg, 2.78 mmol, 1 equiv) (see Example 8, Step 2) was added DMF (15 mL, 0.2 M) before adding cesium carbonate (1.4 gm, 4.17 mmol, 1.5 equiv.) and idomethane (260 µL, 4.17 mmol, 1.5 equiv). After an hour, the reaction was quenched with water and the reaction was partitioned between water and ethyl acetate. The organic layer was washed with brine and dried over sodium sulfate. Purification was carried out by flash column chromatography to furnish 4-(3,5-dimethylisoxazol-4-yl)-2-iodo-N-methyl-6-nitroaniline.

LCMS (m/z+1) 373.85. $^1$H NMR (400 MHz, cdcl3) δ 7.81 (t, J=3.0 Hz, 1H), 7.70 (d, J=2.1 Hz, 1H), 2.97 (s, 3H), 2.40 (d, J=16.8 Hz, 3H), 2.26 (d, J=14.2 Hz, 3H).

Step 2: Preparation of N-(4-(3,5-dimethylisoxazol-4-yl)-2-iodo-6-nitrophenyl)-N-methylcyclopropanecarboxamide

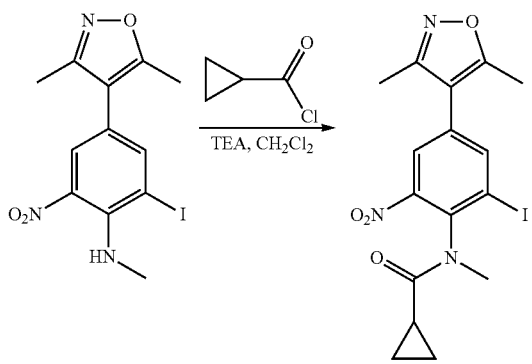

To a flask containing 4-(3,5-dimethylisoxazol-4-yl)-2-iodo-N-methyl-6-nitroaniline (300 mg, 0.8 mmol, 1 equiv.) was added methylene dichloride (8 ml, 0.1M) and TEA (335 µL, 2.42 mmol, 3 equiv.). At 0° C., cyclopropanecarbonyl chloride (110 µL, 1.21 mmol, 1.5 equiv) was added. After an hour, the reaction was complete. The reaction was extracted with EtOAc and washed with water, saturated NH$_4$Cl. After drying with MgSO$_4$, it was filtered and concentrated to dryness. The product was purified by flash column chromatography to furnish N-(4-(3,5-dimethylisoxazol-4-yl)-2-iodo-6-nitrophenyl)-N-methylcyclopropanecarboxamide.

LCMS (m/z+1) 442.06

Step 3: Preparation of 4-(2-cyclopropyl-7-iodo-1-methyl-1H-benzo[d]imidazol-5-yl)-3,5-dimethylisoxazole

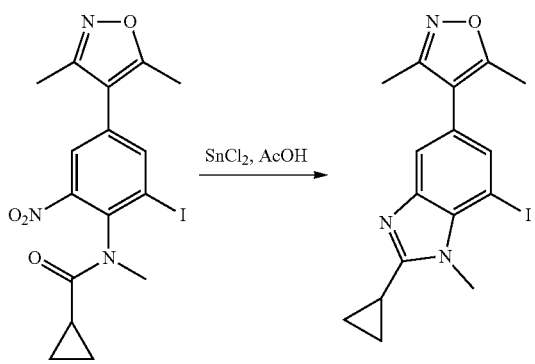 [SMILES: Cc1noc(C)c1-c1cc(I)c(N(C)C(=O)C2CC2)c([N+](=O)[O-])c1 ; Cc1noc(C)c1-c1cc(I)c2c(c1)nc(C1CC1)n2C]

Into a microwave vial containing N-(4-(3,5-dimethylisoxazol-4-yl)-2-iodo-6-nitrophenyl)-N-methylcyclopropanecarboxamide (110 mg, 0.23 mmol, 1 equiv) was added AcOH (5 mL, 0.25M) and tin (II) chloride (86 mg, 0.45 mmol, 2 equiv). The reaction was heated for 90 min at 120° C. The reaction was then stirred in 2N NaOH solution for 20 minutes before being partitioned between water and ethyl acetate. The organic layer was washed with brine and dried over sodium sulfate. The product was purified by flash column chromatography to furnish 4-(2-cyclopropyl-7-iodo-1-methyl-1H-benzo[d]imidazol-5-yl)-3,5-dimethylisoxazole.

LCMS (m/z+1) 394.05.

Step 4: Preparation of 4-(2-cyclopropyl-7-(3,5-dimethyl-1H-pyrazol-4-yl)-1-methyl-1H-benzo[d]imidazol-5-yl)-3,5-dimethylisoxazole

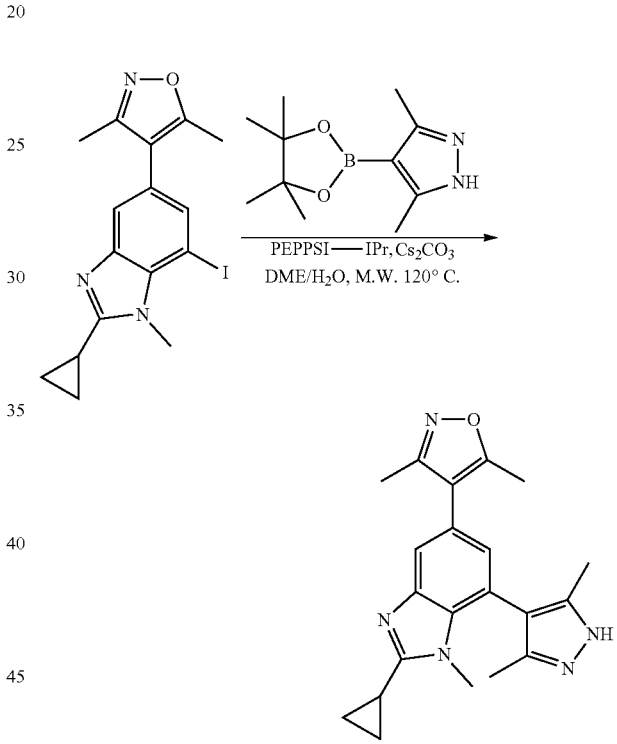

To a microwave vial containing 4-(2-cyclopropyl-7-iodo-1-methyl-1H-benzo[d]imidazol-5-yl)-3,5-dimethylisoxazole (4 mg, 0.01 mmol, 1 equiv.) was added 3,5-dimethyl-4-(4,4,5,5-tetramethyl-1,3,2-dioxaborolan-2-yl)-1H-pyrazole (6 mg, 0.025 mmol, 2.5 equiv.), Cs$_2$CO$_3$ (13 mg, 0.04 mmol, 4 equiv.) and PEPPSI™-IPr catalyst (0.8 mg, 0.02 mmol, 0.1 equiv.) and dissolved in DME-H$_2$O (20 mL, 0.2 M, 2/1, v/v). The mixture was heated to 120° C. After 1 hr, the reaction was complete. The reaction was concentrated in vacuo and purification was then carried out by reverse phase HPLC to furnish 4-(2-cyclopropyl-7-(3,5-dimethyl-1H-pyrazol-4-yl)-1-methyl-1H-benzo[d]imidazol-5-yl)-3,5-dimethylisoxazole.

LCMS (m/z+1) 362.22. $^1$H NMR (400 MHz, cd$_3$od) δ 7.44 (d, J=1.6 Hz, 1H), 6.87 (d, J=1.6 Hz, 1H), 3.54 (s, 3H), 2.40 (s, 3H), 2.25 (s, 3H), 2.15 (s, 1H), 2.10 (s, 6H), 1.37 (s, 2H), 1.19-1.07 (m, 2H).

Example 73

4-(2-Cyclopropyl-7-(1,4-dimethyl-1H-pyrazol-5-yl)-1-methyl-1H-benzo[d]imidazol-5-yl)-3,5-dimethyl-isoxazole (1020-73)

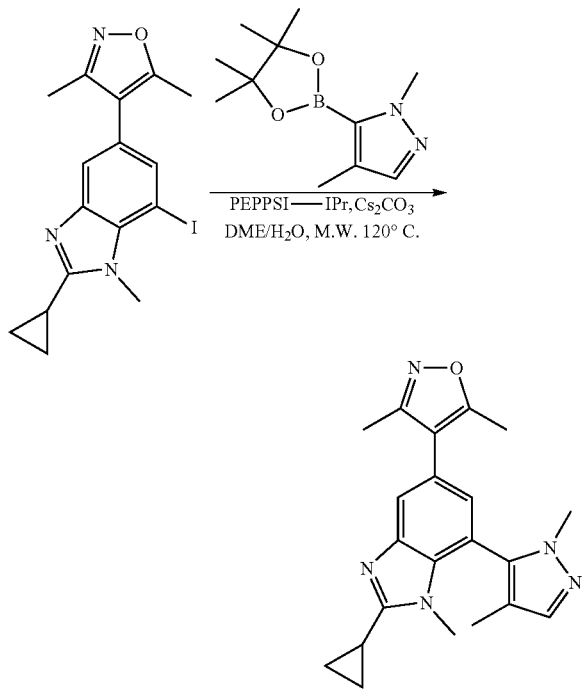

To a microwave vial containing 4-(2-cyclopropyl-7-iodo-1-methyl-1H-benzo[d]imidazol-5-yl)-3,5-dimethylisoxazole (22 mg, 0.056 mmol, 1 equiv.) was added 1,4-dimethyl-5-(4,4,5,5-tetramethyl-1,3,2-dioxaborolan-2-yl)-1H-pyrazole (31 mg, 0.14 mmol, 2.5 equiv.), $Cs_2CO_3$ (72 mg, 0.22 mmol, 4 equiv.) and PEPPSI™-IPr catalyst (4 mg, 0.006 mmol, 0.1 equiv.) and dissolved in DME-$H_2O$ (4 mL, 0.2 M, 2/1, v/v). The mixture was heated to 120° C. After 1 hr, the reaction was complete. The reaction was concentrated in vacuo and purification was then carried out by reverse phase HPLC to furnish 4-(2-cyclopropyl-7-(1,4-dimethyl-1H-pyrazol-5-yl)-1-methyl-1H-benzo[d]imidazol-5-yl)-3,5-dimethylisoxazole.

LCMS (m/z+1) 362.24. $^1$H NMR (400 MHz, cd$_3$od) δ 7.57 (d, J=1.6 Hz, 1H), 7.46 (s, 1H), 7.02 (d, J=1.6 Hz, 1H), 3.70-3.58 (m, 3H), 3.40 (s, 3H), 2.42 (s, 3H), 2.26 (s, 3H), 2.24-2.12 (m, 1H), 1.93 (s, 3H), 1.20-1.04 (m, 4H).

Example 74

4-(2-Cyclopropyl-1-methyl-7-(6-methylquinolin-5-yl)-1H-benzo[d]imidazol-5-yl)-3,5-dimethylisoxazole (1020-74)

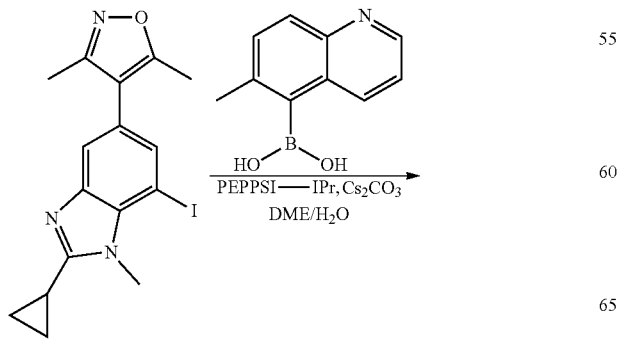

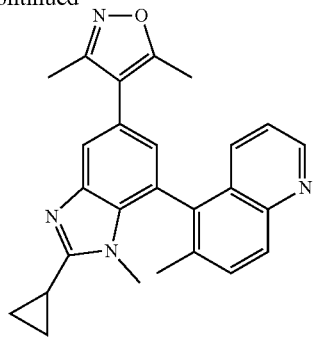

To a microwave vial containing 4-(2-cyclopropyl-7-iodo-1-methyl-1H-benzo[d]imidazol-5-yl)-3,5-dimethylisoxazole (22 mg, 0.056 mmol, 1 equiv.) was added 3,5-6-methylquinolin-5-ylboronic acid (26 mg, 0.14 mmol, 2.5 equiv.), $Cs_2CO_3$ (72 mg, 0.22 mmol, 4 equiv.) and PEPPSI™-IPr catalyst (4 mg, 0.006 mmol, 0.1 equiv.) and dissolved in DME-$H_2O$ (4 mL, 0.2 M, 2/1, v/v). The mixture was heated to 120° C. After 1 hr, the reaction was complete. The reaction was concentrated in vacuo and purification was then carried out by reverse phase HPLC to furnish 4-(2-cyclopropyl-1-methyl-7-(6-methylquinolin-5-yl)-1H-benzo[d]imidazol-5-yl)-3,5-dimethylisoxazole.

LCMS (m/z+1) 409.52. $^1$H NMR (400 MHz, cd$_3$od) δ 8.73 (d, J=4.3 Hz, 1H), 8.02 (d, J=8.6 Hz, 1H), 7.75 (d, J=8.8 Hz, 1H), 7.64 (d, J=8.4 Hz, 1H), 7.51 (d, J=1.6 Hz, 1H), 7.34 (dd, J=8.6, 4.3 Hz, 1H), 6.87 (d, J=1.5 Hz, 1H), 2.97 (s, 3H), 2.34 (s, 3H), 2.20 (d, J=9.3 Hz, 6H), 1.99 (d, J=8.6 Hz, 1H), 1.07-0.93 (m, 4H).

Example 75

4-(2-Cyclobutyl-4-(3,5-dimethyl-1H-pyrazol-4-yl)-1H-benzo[d]imidazol-6-yl)-3,5-dimethylisoxazole (1020-75)

Step 1: Preparation of 3-(3,5-dimethyl-1H-pyrazol-4-yl)-5-(3,5-dimethylisoxazol-4-yl)benzene-1,2-diamine

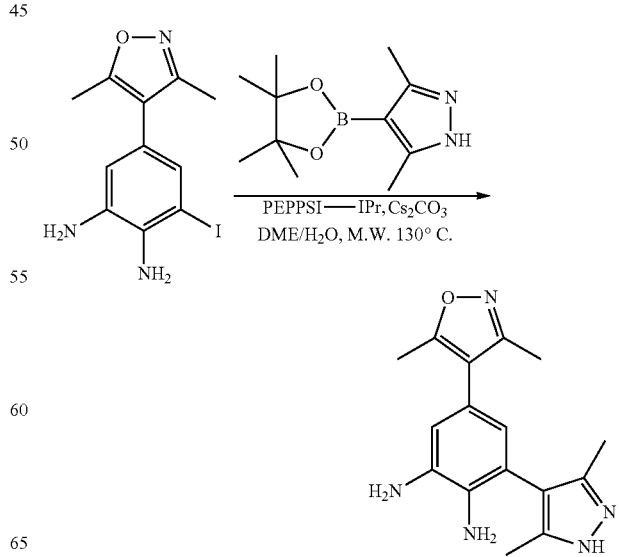

3,5-Dimethylpyrazole-4-boronic acid, pinacol ester (1.35 g, 6.08 mmol) was added to a solution of 5-(3,5-dimethylisoxazol-4-yl)-3-iodobenzene-1,2-diamine (500 mg, 1.52 mmol) in 1,2-dimethoxy ethane and water (8/4 mL). To the mixture was added cesium carbonate (2.5 g, 7.6 mmol) and PEPPSI-IPr (103 mg, 0.15 mmol). The reaction was put in microwave reactor and heated at 130° C. for 60 minutes before being evaporated under vacuum. The residue was purified by preparative HPLC (0-100% CH$_3$CN/H$_2$O) to afford 3-(3,5-dimethyl-1H-pyrazol-4-yl)-5-(3,5-dimethylisoxazol-4-yl)benzene-1,2-diamine.

C$_{16}$H$_{19}$NO$_5$. 298.4 (M+1).

Step 2: Preparation of 4-(2-cyclobutyl-4-(3,5-dimethyl-1H-pyrazol-4-yl)-1H-benzo[d]imidazol-6-yl-3,5-dimethylisoxazole

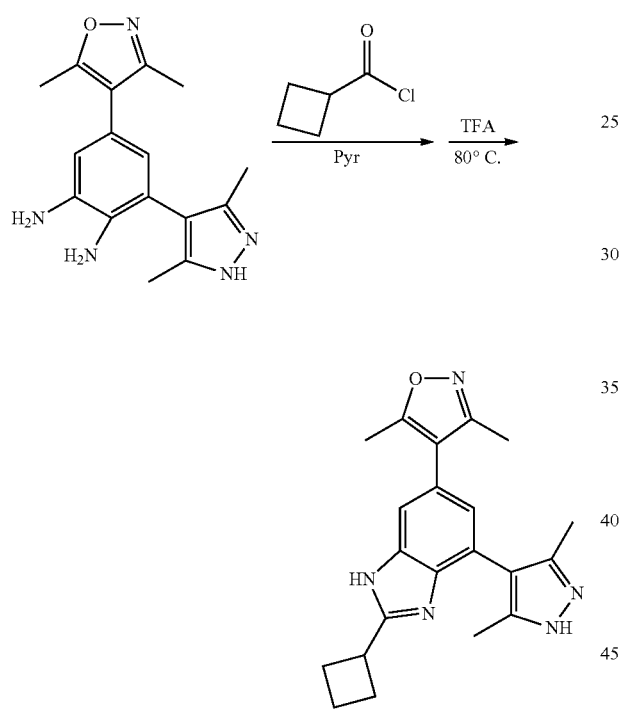

3-(3,5-dimethyl-1H-pyrazol-4-yl)-5-(3,5-dimethylisoxazol-4-yl)benzene-1,2-diamine (50 mg, 0.17 mmol) was dissolved in pyridine (1 mL). To the solution was added cyclobutyl carbonyl chloride (20 mg, 0.17 mmol). The reaction was stirred at RT for 1 h before the solvent was evaporated under vacuum and TFA (1 mL) was added and the reaction mixture was heated at 80° C. overnight. The solvent was removed under vacuum and the residue was purified by preparative HPLC (0-100% CH$_3$CN/H$_2$O) to afford 4-(2-cyclobutyl-4-(3,5-dimethyl-1H-pyrazol-4-yl)-1H-benzo[d]imidazol-6-yl)-3,5-dimethylisoxazole.

C$_{21}$H$_{23}$N$_5$O. 362.3 (M+1). $^1$H NMR (400 MHz, CD$_3$OD) δ 7.77 (d, J=1.6 Hz, 1H), 7.47 (d, J=1.6 Hz, 1H), 4.14-4.10 (m, 1H), 2.64-2.58 (m, 4H), 2.48 (s, 3H), 2.33 (s, 6H), 2.31 (s, 3H), 2.12-2.10 (m, 2H).

Examples 76 and 77

4-(2-(Difluoromethyl)-7-(3,5-dimethyl-1H-pyrazol-4-yl)-1H-benzo[d]imidazol-5-yl)-3,5-dimethylisoxazole (1020-76); and 4-(7-(3,5-Dimethyl-1H-pyrazol-4-yl)-2-methyl-1H-benzo[d]imidazol-5-yl)-3,5-dimethylisoxazole (1020-77)

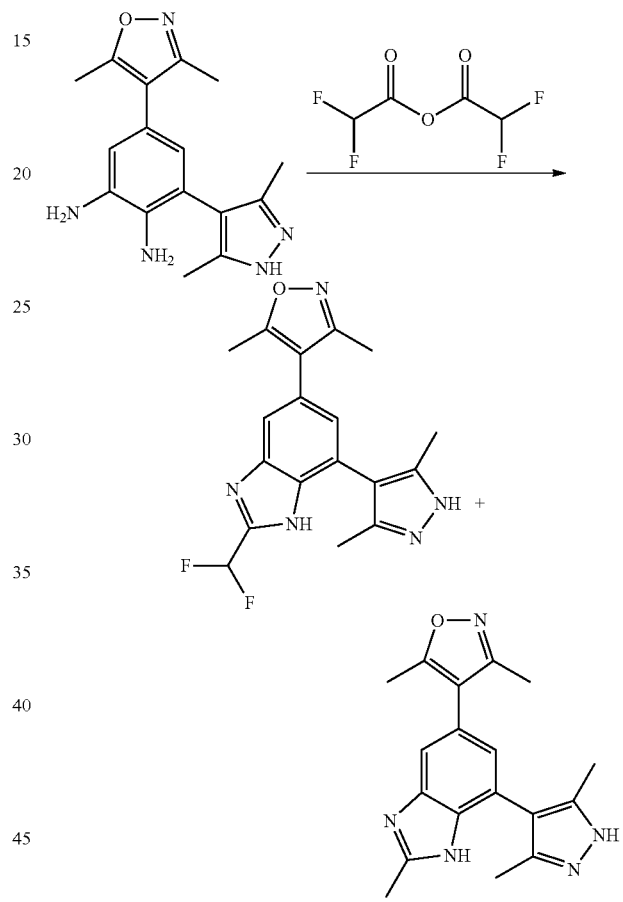

To a stirred round-bottomed flask was added 3-(3,5-dimethyl-1H-pyrazol-4-yl)-5-(3,5-dimethylisoxazol-4-yl)benzene-1,2-diamine (52.5 mg, 0.18 mmol) (see Example 75, Step 1) and methylene chloride (1 mL). To this solution was added difluoroacetic anhydride (25 μL, 0.198 mmol). This solution was allowed to stir at room temperature for 1 hour before adding 5 mL TFA. Resulting solution was refluxed 18 hours, then concentrated in vacuo. Residue was then taken up in methanol, and injected onto preparative reverse phase high performance liquid chromatography (Phenomenex Gemini C18 column, 5% to 50% gradient acetonitrile in water with 0.1% TFA) to give two products:

4-(2-(Difluoromethyl)-7-(3,5-dimethyl-1H-pyrazol-4-yl)-1H-benzo[d]imidazol-5-yl)-3,5-dimethylisoxazole:
C$_{18}$H$_{17}$F$_2$N$_5$O. 358.1 (M+1). $^1$H NMR (400 MHz, cd$_3$od) δ 7.67 (d, J=1.6 Hz, 1H), 7.27 (d, J=1.6 Hz, 1H), 7.05 (td, J=53.4, 0.8 Hz, 1H), 2.47 (s, 3H), 2.38-2.35 (m, 6H), 2.32 (s, 3H).

4-(7-(3,5-Dimethyl-1H-pyrazol-4-yl)-2-methyl-1H-benzo[d]imidazol-5-yl)-3,5-dimethylisoxazole: $C_{18}H_{19}N_5O$. 322.1 (M+1). $^1$H NMR (400 MHz, cd$_3$od) δ 7.72 (d, J=1.1 Hz, 1H), 7.40 (d, J=1.4 Hz, 1H), 2.87 (s, 3H), 2.47 (s, 3H), 2.31 (s, 3H), 2.27 (s, 6H).

Example 78

4-(2-(2,2-Difluorocyclopropyl)-7-(3,5-dimethyl-1H-pyrazol-4-yl)-1H-benzo[d]imidazol-5-yl)-3,5-dimethylisoxazole (1020-78)

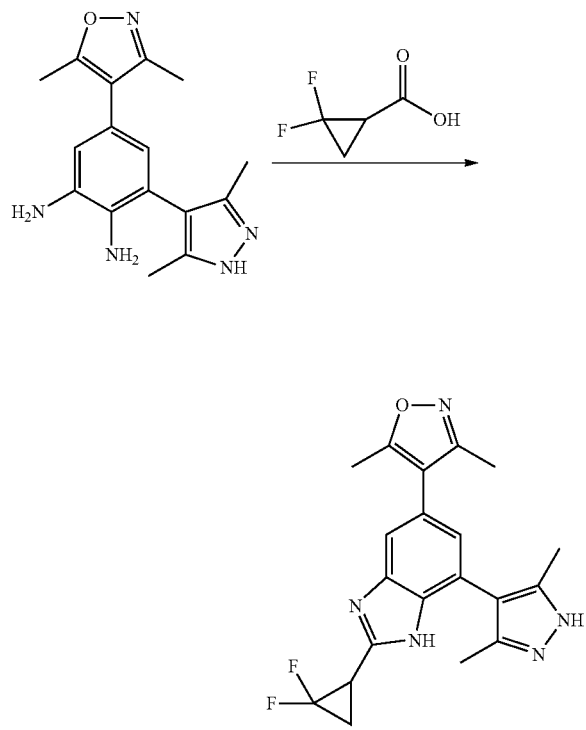

To a stirred solution of 3-(3,5-dimethyl-1H-pyrazol-4-yl)-5-(3,5-dimethylisoxazol-4-yl)benzene-1,2-diamine (52.5 mg, 0.18 mmol) (see Example 75, Step 1) in DMF (1 mL) was added 2,2-difluorocyclopropanecarboxylic acid (24.2 mg, 0.198 mmol), DIPEA (157 µL, 0.9 mmol), and HATU (150 mg, 0.396 mmol). This solution was allowed to stir 1 hr at room temperature, then 2 mL TFA was added and the solution was heated to 80° C. for 18 hours. Resulting solution was concentrated in vacuo, filtered, and purified by preparative reverse phase HPLC (Phenomenex Gemini C18 column, 5% to 50% gradient acetonitrile in water with 0.1% TFA) to give 4-(2-(2,2-difluorocyclopropyl)-7-(3,5-dimethyl-1H-pyrazol-4-yl)-1H-benzo[d]imidazol-5-yl)-3,5-dimethylisoxazole.

$C_{20}H_{19}F_2N_5O$. 384.2 (M+1). $^1$H NMR (400 MHz, CD$_3$OD) δ 7.66 (d, J=1.4 Hz, 1H), 7.35 (d, J=1.4 Hz, 1H), 3.50-3.34 (m, 1H), 2.47 (s, 3H), 2.47-2.38 (m, 2H), 2.31 (s, 3H), 2.28 (s, 6H).

Example 79

N-(Cyclopropylmethyl)-4-(3,5-dimethyl-1H-pyrazol-4-yl)-6-(3,5-dimethylisoxazol-4-yl)-1H-benzo[d]imidazol-2-amine (1020-79)

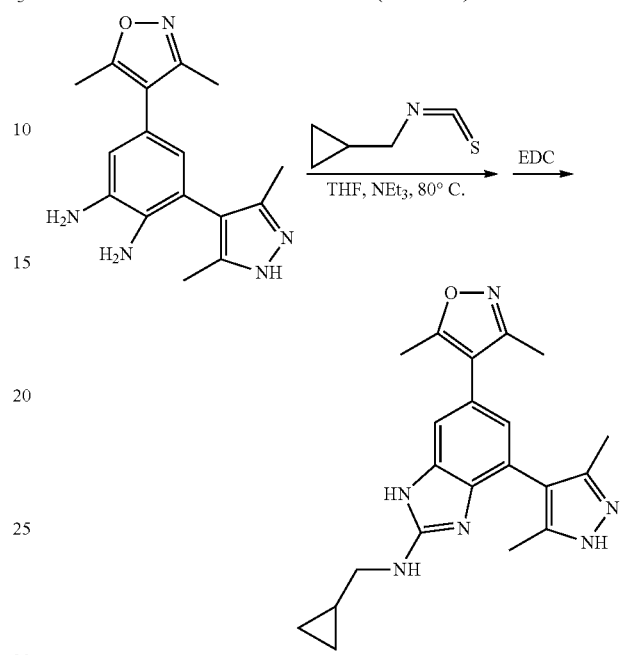

3-(3,5-Dimethyl-1H-pyrazol-4-yl)-5-(3,5-dimethylisoxazol-4-yl)benzene-1,2-diamine (20 mg, 0.07 mmol) (Example 75, Step 1) was dissolved in THF (1 mL). To the solution was added cyclopropylmethyl isothiocyanate (9 mg, 0.08 mmol) and triethylamine (93 uL). The reaction was heated at 80° C. for 3 h before 1-ethyl-3-(3-dimethylaminopropyl)-carbodiimide hydrogen chloride (30 mg, 0.16 mmol) was added and heated at 80° C. for 4 h. The solvent was then evaporated under vacuum and the residue was purified by preparative HPLC (0-100% CH$_3$CN/H$_2$O) to afford N-(cyclopropylmethyl)-4-(3,5-dimethyl-1H-pyrazol-4-yl)-6-(3,5-dimethylisoxazol-4-yl)-1H-benzo[d]imidazol-2-amine.

$C_{21}H_{24}N_6O$. 377.3 (M+1). $^1$H NMR (400 MHz, CD$_3$OD) δ 7.04 (s, 1H), 6.80 (s, 1H), 2.52-2.51 (m, 2H), 2.09 (s, 3H), 1.99 (s, 6H), 1.91 (s, 3H), 0.95-0.85 (m, 1H), 0.30-0.27 (m, 2H), 0.15-0.05 (m, 2H).

Example 80

4-(4-(3,5-Dimethyl-1H-pyrazol-4-yl)-2-(1-fluorocyclopropyl)-1H-benzo[d]imidazol-6-yl)-3,5-dimethylisoxazole (1020-80)

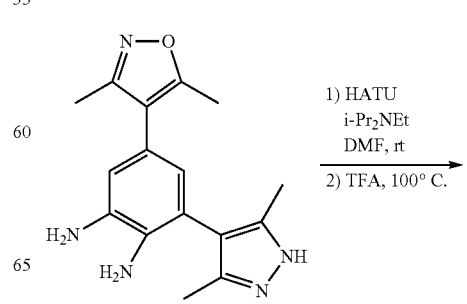

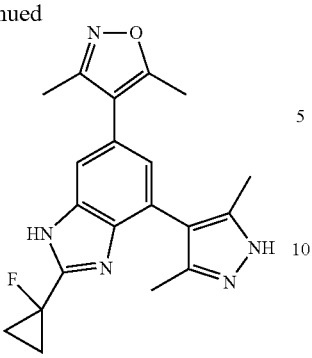

3-(3,5-Dimethyl-1H-pyrazol-4-yl)-5-(3,5-dimethylisoxazol-4-yl)benzene-1,2-diamine (20.0 mg, 0.0673 mmol) (see Example 75, Step 1) was treated with 1-fluorocyclopropanecarboxylic acid (7.0 mg, 0.0673 mmol, 1.0 equiv.), HATU (30.7 mg, 0.0808 mmol, 1.2 equiv) and i-Pr$_2$NEt (0.3 mL) in DMF (1 mL) at room temperature for 2 h. To the reaction mixture was added TFA (3 mL) and the mixture was heated at 100° C. for 15 min. After removal of TFA under a reduced pressure, the reaction mixture was quenched with brine (30 mL). The whole was extracted with AcOEt (30 mL×3). Organic layer was washed with brine (30 mL) and dried over Na$_2$SO$_4$. The solvent was removed under a reduced pressure to give the crude product. The crude product was purified by a silica gel chromatography (EtOAc:MeOH=100:0 to 90:10).

C$_{20}$H$_{21}$FN$_5$O. 366.2 (M+1). $^1$H NMR (MeOH-d$_4$) δ 7.47 (d, J=1.0 Hz, 1H), 7.05 (d, J=1.0 Hz, 1H), 2.46 (s, 3H), 2.31 (s, 3H), 2.22 (s, 6H), 1.70-1.60 (m, 2H), 1.54-1.45 (m, 2H).

Example 81

N-Cyclopropyl-4-(3,5-dimethyl-1H-pyrazol-4-yl)-6-(3,5-dimethylisoxazol-4-yl)-1H-benzo[d]imidazol-2-amine (1020-81)

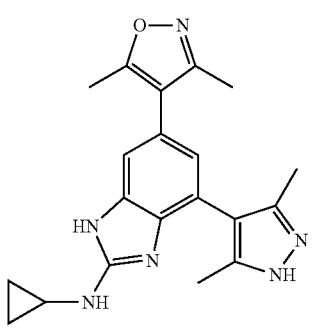 [SMILES: Cc1n[nH]c(C)c1-c1cc(-c2c(C)noc2C)cc2[nH]c(NC3CC3)nc12]

N-Cyclopropyl-4-(3,5-dimethyl-1H-pyrazol-4-yl)-6-(3,5-dimethylisoxazol-4-yl)-1H-benzo[d]imidazol-2-amine was prepared in a similar manner as Example 79, substituting isothiocyanatocyclopropane for cyclopropylmethyl isothiocyanate.

C$_{20}$H$_{22}$N$_6$O. 363.1 (M+1). $^1$H NMR (400 MHz, CD$_3$OD) δ 7.45 (d, J=1.6 Hz, 1H), 7.20 (d, J=1.6 Hz, 1H), 2.84-2.80 (m, 1H), 2.45 (s, 3H), 2.36 (s, 6H), 2.29 (s, 3H), 1.05-0.98 (m, 2H), 0.84-0.80 (m, 2H).

Example 82

4-(4-(3,5-Dimethyl-1H-pyrazol-4-yl)-2-methoxy-1H-benzo[d]imidazol-6-yl)-3,5-dimethylisoxazole (1020-82)

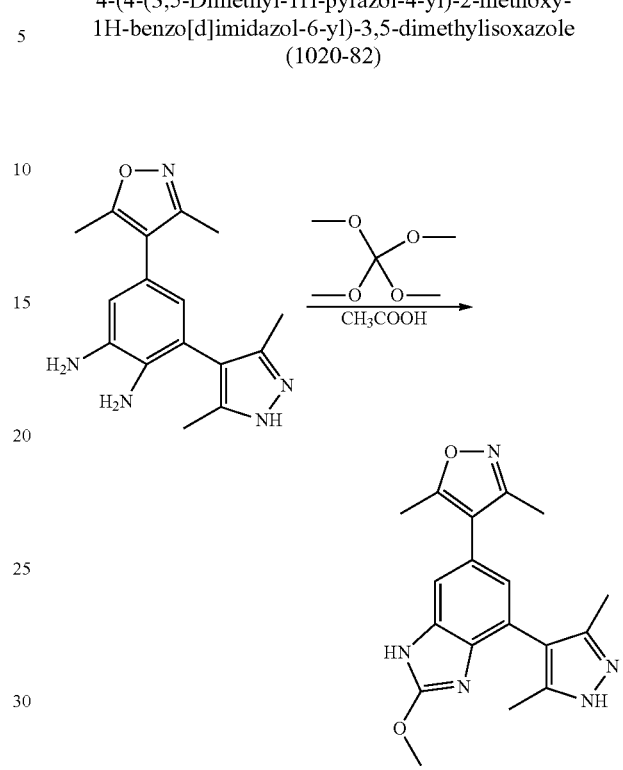

3-(3,5-Dimethyl-1H-pyrazol-4-yl)-5-(3,5-dimethylisoxazol-4-yl)benzene-1,2-diamine (60 mg, 0.2 mmol) was dissolved in acetic acid (2 mL). To the solution was added tetramethyl ortho carbonate (55 mg, 0.4 mmol). The reaction was stirred at RT for 3 h before the solvent was evaporated under vacuum and the residue was purified by preparative HPLC (0-100% CH$_3$CN/H$_2$O) to afford 4-(4-(3,5-dimethyl-1H-pyrazol-4-yl)-2-methoxy-1H-benzo[d]imidazol-6-yl)-3,5-dimethylisoxazole (8 mg, 12%).

C$_{11}$H$_{19}$N$_5$O$_2$. 338.3 (M+1). $^1$H NMR (400 MHz, CD$_3$OD) δ 7.08 (d, J=1.6 Hz, 1H), 6.91 (d, J=1.6 Hz, 1H), 2.42 (s, 3H), 2.35 (s, 6H), 2.34 (s, 3H), 2.27 (s, 3H).

Example 83

3,5-Dimethyl-4-(4-(6-methylquinolin-5-yl)-1H-benzo[d]imidazol-6-yl)isoxazole (1020-83)

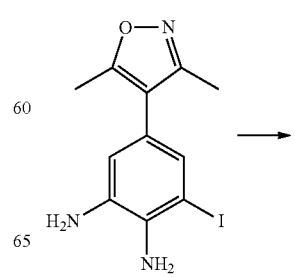

-continued

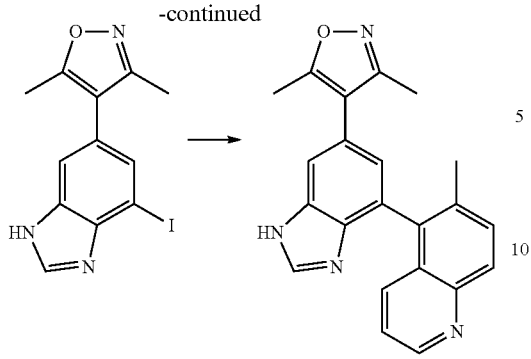

Step 1

5-(3,5-Dimethylisoxazol-4-yl)-3-iodobenzene-1,2-diamine (1.39 g) was dissolved in formic acid and heated to reflux for 15 min. Volatiles were removed, the residue taken up in EtOAc and the organic layer washed with brine and dried over sodium sulfate. Purification on silica gel (hexanes ethyl acetate 0-100%) afforded 4-(4-iodo-1H-benzo[d]imidazol-6-yl)-3,5-dimethylisoxazole.

Step 2

4-(4-Iodo-1H-benzo[d]imidazol-6-yl)-3,5-dimethylisoxazole (0.1 g, 0.3 mmol) was reacted with (6-methylquinolin-5-yl)boronic acid (0.275 g, 1.47 mmol), PEPPSI-IPr catalyst (0.02 g, 0.03 mmol) and $Cs_2CO_3$ (0.3 g, 0.9 mmol) in dioxane/water (4/2 ml, degassed with Argon) at 130° C. for 30 min in a microwave reactor. The aqueous layer was discarded, volatiles were removed and the residue was purified via preparatory HPLC (5-100%, $H_2O$-MeCN, 0.1% HCl) to afford 3,5-dimethyl-4-(4-(6-methylquinolin-5-yl)-1H-benzo[d]imidazol-6-yl)isoxazole.

$C_{22}H_{18}N_4O$. 355.1 (M+1). 1H NMR (400 MHz, dmso) δ 9.41 (s, 1H), 9.07 (d, J=3.7 Hz, 1H), 8.32 (d, J=8.8 Hz, 1H), 8.04 (d, J=8.8 Hz, 1H), 7.96 (d, J=1.4 Hz, 1H), 7.65 (dd, J=8.5, 4.8 Hz, 1H), 7.50 (d, J=1.2 Hz, 1H), 2.46 (s, 3H), 2.28 (d, J=3.0 Hz, 6H).

Example 84

4-(4-(2,4-Dimethylpyridin-3-yl)-1H-benzo[d]imidazol-6-yl)-3,5-dimethylisoxazole (1020-84)

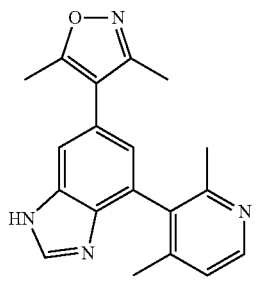 [SMILES: Cc1ccnc(C)c1-c1cc(-c2c(C)noc2C)cc2[nH]cnc12]

Compound (1020-84) was synthesized in a similar manner as that of Example 83, Step 2, using (2,4-dimethylpyridin-3-yl)boronic acid.

$C_{19}H_{18}N_4O$. 319.2.1 (M+1). 1H NMR (400 MHz, dmso) δ 9.43 (s, 1H), 9.09 (d, J=3.7 Hz, 1H), 8.34 (d, J=8.8 Hz, 1H), 8.05 (d, J=8.8 Hz, 1H), 7.98 (d, J=1.4 Hz, 1H), 7.67 (dd, J=8.5, 4.8 Hz, 1H), 7.52 (d, J=1.2 Hz, 1H), 2.48 (s, 3H), 2.30 (d, J=3.0 Hz, 6H).

Example 85

4-(4-(1,4-Dimethyl-1H-pyrazol-5-yl)-1H-benzo[d]imidazol-6-yl)-3,5-dimethylisoxazole (1020-85)

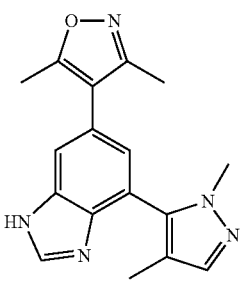 [SMILES: Cc1cnn(C)c1-c1cc(-c2c(C)noc2C)cc2[nH]cnc12]

Compound (1020-85) was synthesized in a similar manner as that of Example 83, Step 2, using (1,4-dimethyl-1H-pyrazol-5-yl)boronic acid, pinacol ester.

$C_{17}H_{17}N_5O$. 308.1 (M+1) 1H NMR (400 MHz, dmso) δ 9.09 (s, 1H), 9.09 (s, 1H), 7.83 (s, 1H), 7.83 (s, 1H), 7.45 (s, 1H), 7.45 (s, 1H), 7.40 (s, 1H), 7.40 (s, 1H), 3.70 (s, 3H), 2.47 (s, 3H), 2.29 (s, 3H), 1.95 (s, 3H).

Example 86

3,5-Dimethyl-4-(2-methyl-4-(6-methylquinolin-5-yl)-1H-benzo[d]imidazol-6-yl)isoxazole (1020-86)

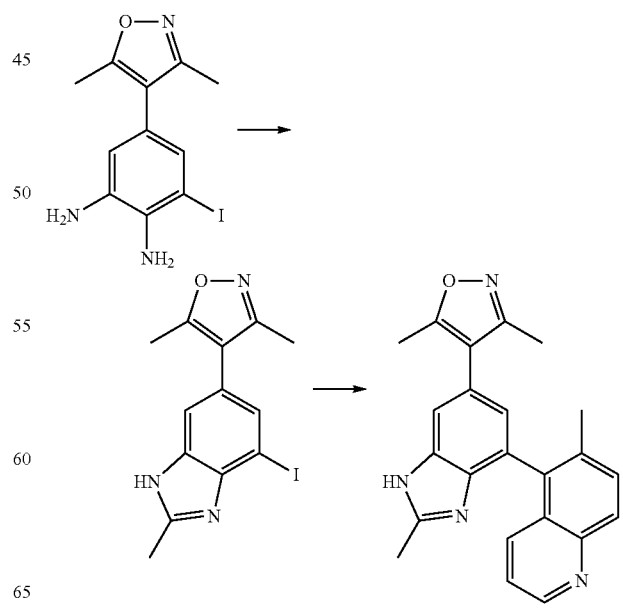

Step 1

4-(4-Iodo-2-methyl-1H-benzo[d]imidazol-6-yl)-3,5-dimethylisoxazole (1.43 g, >95%) was formed using acetic acid in Example 83, Step 1, and refluxing for 12 h.

Step 2

The product of Step 1 was used in the same procedure as that of Example 83, Step 2 to afford 3,5-dimethyl-4-(2-methyl-4-(6-methylquinolin-5-yl)-1H-benzo[d]imidazol-6-yl)isoxazole.

$C_{23}H_{20}N_4O$. 368.8. (M+1) 1H NMR (400 MHz, cd3cn) δ 9.56 (d, J=5.2 Hz, 1H), 8.93 (d, J=8.9 Hz, 1H), 8.84 (d, J=8.5 Hz, 1H), 8.63 (d, J=8.8 Hz, 1H), 8.49 (d, J=1.4 Hz, 1H), 8.31 (dd, J=8.6, 5.2 Hz, 1H), 7.98 (d, J=1.4 Hz, 1H), 3.28 (s, 3H), 3.01 (s, 3H), 2.91 (s, 3H), 2.85 (s, 3H).

Example 87

4-(4-(2,4-Dimethylpyridin-3-yl)-2-methyl-1H-benzo[d]imidazol-6-yl)-3,5-dimethylisoxazole (1020-87)

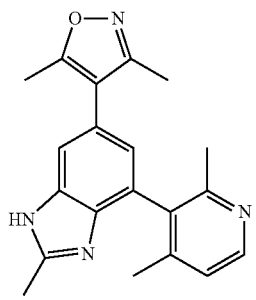 [SMILES: Cc1nc2c(-c3c(C)ccnc3C)cc(-c3c(C)noc3C)cc2[nH]1]

Compound (1020-87) was prepared by following Example 86, Step 1, to make the intermediate compound and using that compound in a similar manner as that of Example 84 to make the final product.

$C_{20}H_{20}N_4O$. 332.1 (M+1). 1H NMR (400 MHz, cd3cn) δ 9.10 (s, 1H), 8.84 (d, J=1.6 Hz, 1H), 8.35 (d, J=1.3 Hz, 1H), 7.94 (d, J=1.4 Hz, 1H), 4.74 (s, 5H), 3.31 (s, 3H), 3.05 (s, 6H), 2.96 (s, 3H), 2.79 (s, 3H).

Example 88

3,5-Dimethyl-4-(2-(1-methyl-1H-pyrazol-4-yl)-4-(6-methylquinolin-5-yl)-1H-benzo[d]imidazol-6-yl)isoxazole (1020-88)

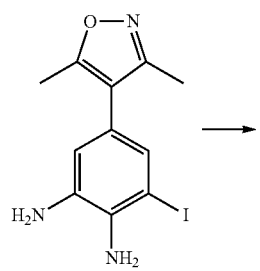

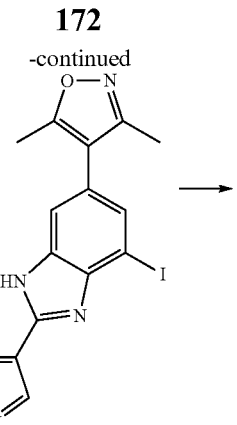

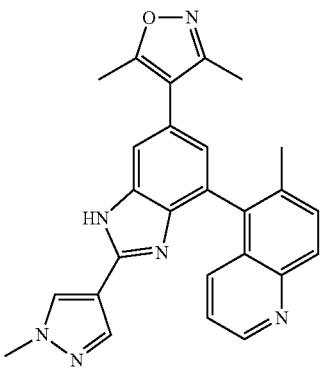

Step 1

5-(3,5-Dimethylisoxazol-4-yl)-3-iodobenzene-1,2-diamine (0.1 g, 0.336 mmol)) was dissolved in acidic acid (4 ml) and stirred at RT with 1-methyl-1H-pyrazole-4-carbonyl chloride (0.048 g, 0.336 mmol) for 24 h. Volatiles were remove and the residue purified via preparatory HPLC (5-100%, H₂O-MeCN, 0.1% HCl) to afford the 4-(4-iodo-2-(1-methyl-1H-pyrazol-4-yl)-1H-benzo[d]imidazol-6-yl)-3,5-dimethylisoxazole.

Step 2

Compound (1020-88) was made by using the product of Step 1 and (6-methylquinolin-5-yl)boronic acid in a manner similar to that of Example 83, Step 2.

$C_{26}H_{22}N_6O$. 435.21 (M+1). ¹H NMR (400 MHz, dmso) δ 8.94 (d, J=4.2 Hz, 1H), 8.43 (s, 1H), 8.15 (d, J=4.3 Hz, 2H), 7.93 (d, J=8.7 Hz, 1H), 7.81 (d, J=7.0 Hz, 2H), 7.50 (dd, J=8.6, 4.4 Hz, 1H), 7.27 (s, 1H), 3.92 (s, 3H), 2.47 (s, 17H), 2.47 (s, J=12.2 Hz, 3H), 2.30 (s, 3H), 2.29 (s, 3H).

Example 89

1-(6-(3,5-dimethylisoxazol-4-yl)-4-(6-methylquinolin-5-yl)-1H-benzo[d]imidazol-2-yl)propane-1,3-diol (1020-89)

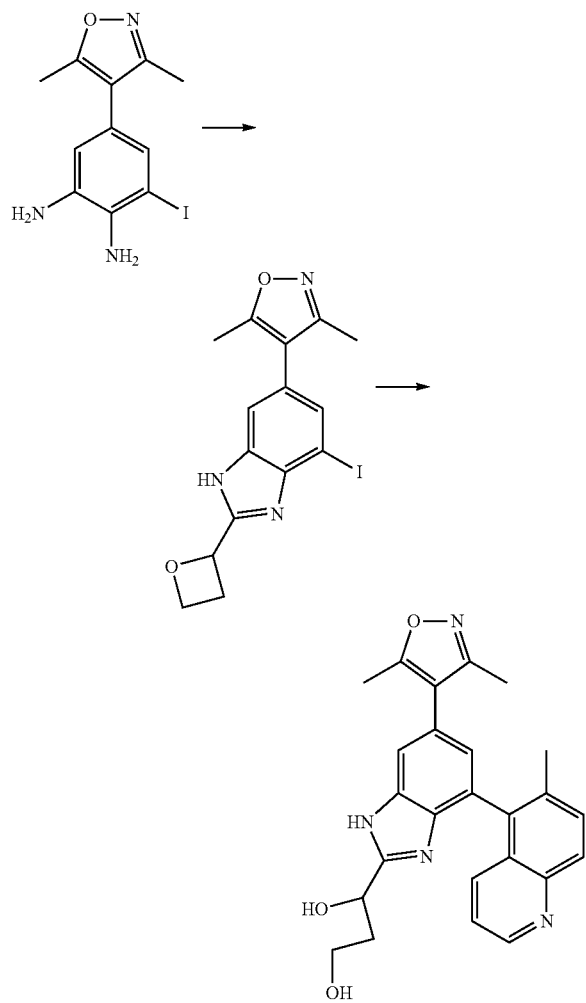

Step 1

2-Oxetane carboxylic acid (0.77 g, 2.36 mmol) and CDI (0.858 g, 3.45 mmol) were dissolved in MeCN (4 ml) and stirred for 30 min at RT. 5-(3,5-dimethylisoxazol-4-yl)-3-iodobenzene-1,2-diamine (0.77 g, 2.36 mmol) in MeCN (4 ml) was added at the solution stirred for 4 days at RT and 1 days at 70° C. Volatiles were remove and the residue purified via preparatory HPLC (5-100%, H₂O-MeCN, 0.1% HCl) to afford 4-(4-iodo-2-(oxetan-2-yl)-1H-benzo[d]imidazol-6-yl)-3,5-dimethylisoxazole.

Step 2

The method described in Example 83, Step 2, using the product of Step 1 and (6-methylquinolin-5-yl)boronic acid was used to afford compound (1020-89).

$C_{25}H_{24}N_4O_3$. 429.2 (M+1). ¹H NMR (400 MHz, dmso) δ 9.09 (d, J=4.7 Hz, 1H), 8.22 (d, J=8.9 Hz, 1H), 8.07 (d, J=8.1 Hz, 1H), 8.01 (d, J=8.7 Hz, 1H), 7.80-7.71 (m, 1H), 7.30 (s, 1H), 6.87 (s, 1H), 2.48-2.45 (m, 2H), 2.39 (s, 3H), 2.32 (s, 3H), 2.30-2.25 (m, 3H), 2.23 (s, 3H).

Example 90

5-(3,5-Dimethylisoxazol-4-yl)-3-(6-methylquinolin-5-yl)benzene-1,2-diamine (1020-90)

Step 1: Preparation of 5-(3,5-dimethylisoxazol-4-yl)-3-(6-methylquinolin-5-yl)benzene-1,2-diamine

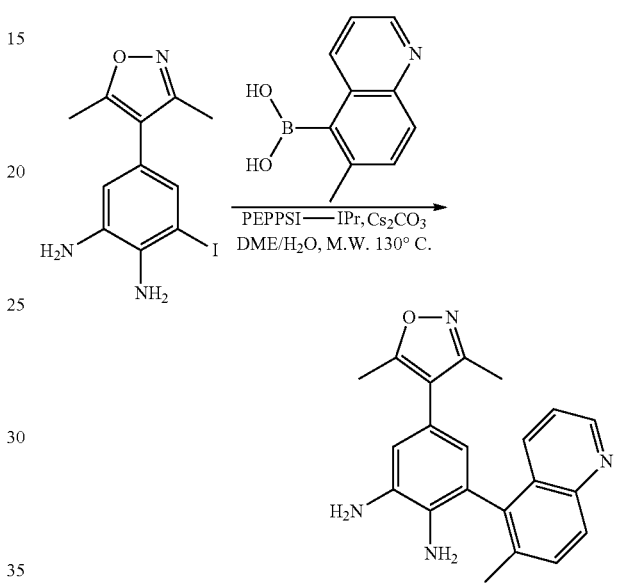

(6-Methyl-5-quinolinyl)boronic acid (0.91 g, 4.8 mmol) was added to a solution of 5-(3,5-dimethylisoxazol-4-yl)-3-iodobenzene-1,2-diamine (1 g, 3 mmol) in 1,2-dimethoxy ethane and water (10/5 mL). To the mixture was added cesium carbonate (2.9 g, 9 mmol) and PEPPSI-IPr (200 mg, 0.3 mmol). The reaction was put in microwave reactor and heated at 130° C. for 120 minutes before the solvent was evaporated under vacuum. The residue was purified by preparative HPLC (0-100% CH₃CN/H₂O) to afford 5-(3,5-dimethylisoxazol-4-yl)-3-(6-methylquinolin-5-yl)benzene-1,2-diamine.

$C_{21}H_{20}N_4O$. 345.18 (M+1).

Step 2: Preparation of 4-(2-methoxy-4-(6-methylquinolin-5-yl)-1H-benzo[d]imidazol-6-yl)-3,5-dimethylisoxazole

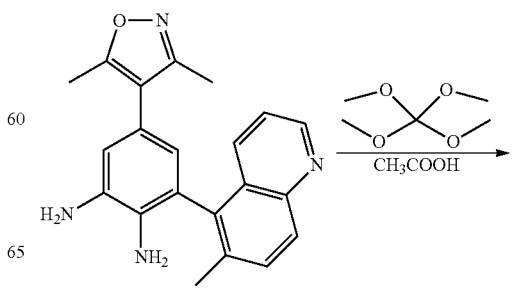

-continued

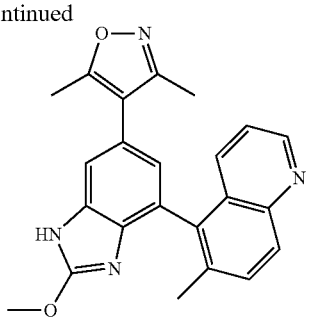

5-(3,5-Dimethylisoxazol-4-yl)-3-(6-methylquinolin-5-yl) benzene-1,2-diamine (60 mg) was dissolved in acetic acid (1 mL) and to the solution was added tetramethyl orthocarbonate (1 ml). The reaction was stirred at RT for 30 mins. The solvent was then evaporated under vacuum and the residue was purified by preparative HPLC (0-100% $CH_3CN/H_2O$) to afford 4-(2-methoxy-4-(6-methylquinolin-5-yl)-1H-benzo[d]imidazol-6-yl)-3,5-dimethylisoxazole.

$C_{23}H_{20}N_4O_2$. 385.2 (M+1). $^1$H NMR (400 MHz, $CD_3OD$) δ 9.09 (dd, J=5.1, 1.3 Hz, 1H), 8.45 (t, J=8.6 Hz, 1H), 8.24 (d, J=8.8 Hz, 1H), 8.18-8.12 (m, 1H), 7.88-7.77 (m, 1H), 7.51 (t, J=1.7 Hz, 1H), 7.05 (dd, J=7.4, 1.6 Hz, 1H), 4.06 (s, 3H), 2.53 (s, 3H), 2.44 (s, 3H), 2.34 (s, 3H).

Example 91

4-(2-Ethoxy-4-(6-methylquinolin-5-yl)-1H-benzo[d]imidazol-6-yl)-3,5-dimethylisoxazole (1020-91)

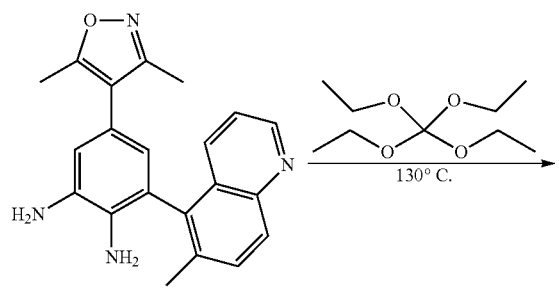

5-(3,5-Dimethylisoxazol-4-yl)-3-(6-methylquinolin-5-yl) benzene-1,2-diamine (100 mg) was added to tetraethyl orthocarbonate (1.2 ml). The reaction was stirred at 130° C. overnight. The solvent was then evaporated under vacuum and the residue was purified by preparative HPLC (0-100% $CH_3CN/H_2O$) to afford 4-(2-ethoxy-4-(6-methylquinolin-5-yl)-1H-benzo[d]imidazol-6-yl)-3,5-dimethylisoxazole.

$C_{24}H_{22}N_4O_2$. 399.2 (M+1). $^1$H NMR (400 MHz, CD3OD) δ 8.77 (dd, J=2.8 Hz, 1H), 8.05 (d, J=8.4 Hz, 1H), 7.83-7.80 (m, 2H), 7.42-7.38 (m, 2H), 6.92 (s, 1H), 4.46 (bs, 2H), 2.45 (s, 3H), 2.32 (s, 3H), 2.29 (s, 3H), 1.39 (s, 3H).

Example 92

3,5-Dimethyl-4-(4-(6-methylquinolin-5-yl)-2-(trifluoromethyl)-1H-benzo[d]imidazol-6-yl)isoxazole (1020-92)

Step 1

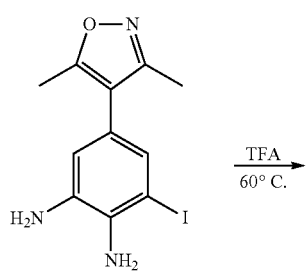

5-(3,5-Dimethylisoxazol-4-yl)-3-iodobenzene-1,2-diamine (500 mg) was dissolved in TFA (5 ml). The reaction was stirred at 60° C. overnight before solvent was evaporated. The residue was used as crude material (4-(4-iodo-2-(trifluoromethyl)-1H-benzo[d]imidazol-6-yl)-3,5-dimethylisoxazole.

$C_{13}H_9F_3IN_3O$. 408.1 (M+1).

Step 2

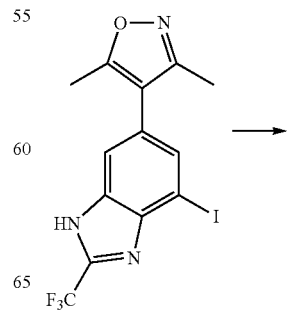

-continued

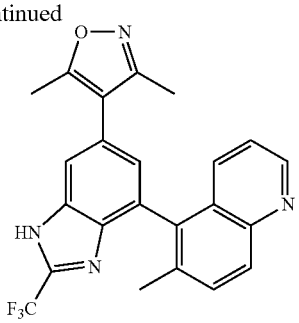

(6-Methyl-5-quinolinyl)boronic acid (90 mg, 0.48 mmol) was added to a solution of 4-(4-iodo-2-(trifluoromethyl)-1H-benzo[d]imidazol-6-yl)-3,5-dimethylisoxazole (50 mg, 0.12 mmol) in 1,2-dimethoxy ethane and water (2/1 mL). To the mixture was added cesium carbonate (196 mg, 0.6 mmol) and PEPPSI-IPr (8 mg, 0.012 mmol). The reaction was put in microwave reactor and heated at 130° C. for 120 minutes before the solvent was evaporated under vacuum. The residue was purified by preparative HPLC (0-100% $CH_3CN/H_2O$) to afford 3,5-dimethyl-4-(4-(6-methylquinolin-5-yl)-2-(trifluoromethyl)-1H-benzo[d]imidazol-6-yl) isoxazole.

$C_{23}H_{17}F_3N_4O$. 423.1 (M+1). $^1$H NMR (400 MHz, $CD_3OD$) δ 9.04 (d, J=4.4 Hz, 1H), 8.28 (d, J=8.4 Hz, 1H), 8.24 (d, J=8.8 Hz, 1H), 8.12 (d, J=8.8 Hz, 1H), 7.84 (s, 1H), 7.75 (dd, J=8.5, 5.0 Hz, 1H), 7.35 (d, J=1.3 Hz, 1H), 2.49 (s, 3H), 2.37 (s, 3H), 2.33 (s, 3H).

Compounds (1020-93), (1020-94), and (1020-95) were prepared in a similar manner as that of Example 92, substituting the appropriate commercial boronic acid or boronate ester for (6-Methyl-5-quinolinyl)boronic acid:

Example 93

5-(6-(3,5-Dimethylisoxazol-4-yl)-2-(trifluoromethyl)-1H-benzo[d]imidazol-4-yl)-3,4-dihydroquinolin-2(1H)-one (1020-93)

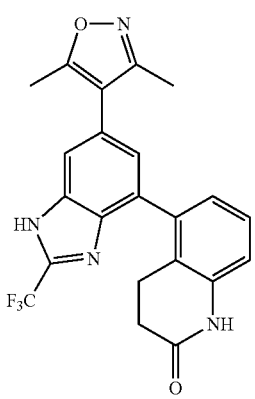 [SMILES: Cc1noc(C)c1-c1cc(-c2cccc3c2CCC(=O)N3)c2nc(C(F)(F)F)[nH]c2c1]

$C_{22}H_{17}F_3N_4O_2$. 427.1 (M+1). $^1$H NMR (400 MHz, $CD_3OD$) δ 7.68 (d, J=1.5 Hz, 1H), 7.32 (t, J=7.8 Hz, 1H), 7.25 (d, J=1.5 Hz, 1H), 7.11 (d, J=6.8 Hz, 1H), 7.01 (d, J=7.2 Hz, 1H), 2.76 (s, 2H), 2.50 (d, J=7.5 Hz, 2H), 2.47 (s, 3H), 2.32 (s, 3H).

Example 94

4-(4-(1,4-Dimethyl-1H-pyrazol-5-yl)-2-(trifluoromethyl)-1H-benzo[d]imidazol-6-yl)-3,5-dimethylisoxazole (1020-94)

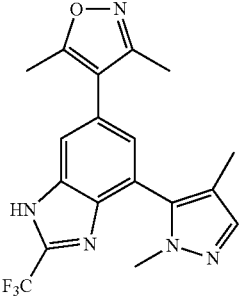 [SMILES: Cc1cnn(C)c1-c1cc(-c2c(C)noc2C)cc2[nH]c(C(F)(F)F)nc12]

$C_{18}H_{16}F_3N_5O$. 376.1 (M+1). $^1$H NMR (400 MHz, $CD_3OD$) δ 7.86 (s, 1H), 7.80 (s, 1H), 7.43 (s, 1H), 3.30 (s, 3H), 2.47 (s, 3H), 2.31 (s, 3H), 2.07 (s, 3H).

Example 95

3,5-Dimethyl-4-(4-(quinolin-5-yl)-2-(trifluoromethyl)-1H-benzo[d]imidazol-6-yl)isoxazole (1020-95)

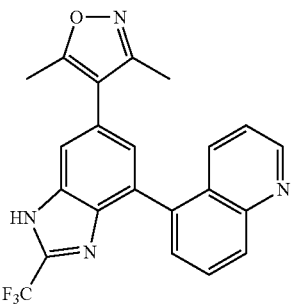 [SMILES: Cc1noc(C)c1-c1cc(-c2cccc3ncccc23)c2nc(C(F)(F)F)[nH]c2c1]

$C_{22}H_{15}F_3N_4O$. 409.1 (M+1). $^1$H NMR (400 MHz, $CD_3OD$) δ 9.03 (dd, J=5.0, 1.3 Hz, 1H), 8.49 (d, J=8.5 Hz, 1H), 8.21 (d, J=8.6 Hz, 1H), 8.12-8.04 (m, 1H), 7.90 (d, J=7.2 Hz, 1H), 7.75-7.72 (m, 1H), 7.71 (d, J=1.4 Hz, 1H), 7.38 (d, J=1.5 Hz, 1H), 2.40 (s, 3H), 2.24 (s, 3H).

Example 96

4-(3,5-Dimethyl-1H-pyrazol-4-yl)-6-(3,5-dimethylisoxazol-4-yl)-1H-benzo[d]imidazol-2-amine (1020-96)

Step 1: Preparation of 6-(3,5-dimethylisoxazol-4-yl)-4-iodo-1H-benzo[d]imidazol-2-amine

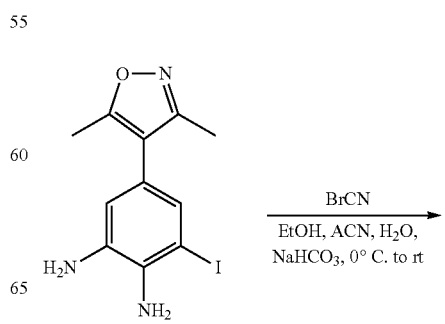

-continued

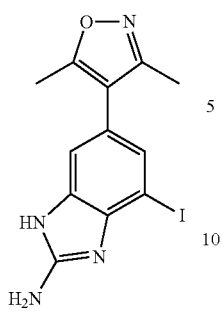

5-(3,5-dimethylisoxazol-4-yl)-3-iodobenzene-1,2-diamine (1.5 g, 4.6 mmol) was dissolved in a mixture of ethanol (10 mL) and acetonitrile (10 mL). To this solution was then added water (10 mL) followed by solid sodium bicarbonate (0.77 g, 9.2 mmol). Mixture was then stirred under nitrogen and cooled to 0° C. before adding cyanogen bromide (0.97 g, 9.2 mmol). Reaction was allowed to then warm to room temperature and stir overnight. Next day reaction solvents were removed and ethanol (100 mL) was added. Suspension was sonicated, then the solids filtered off. Solution was rotavapped dry then purified by silica gel chromatography (rf=0.5 in 10% methanol in dichloromethane) affording 6-(3,5-dimethylisoxazol-4-yl)-4-iodo-1H-benzo[d]imidazol-2-amine as a brown solid.

$C_{12}H_{11}IN_4O$. 355.0 (M+1). $^1$H NMR (400 MHz, DMSO-$d_6$) δ 11.03 (s, 1H), 7.21 (s, 1H), 7.06 (d, J=1.5 Hz, 1H), 6.56 (s, 2H), 2.37 (s, 3H), 2.19 (s, 3H).

Step 2

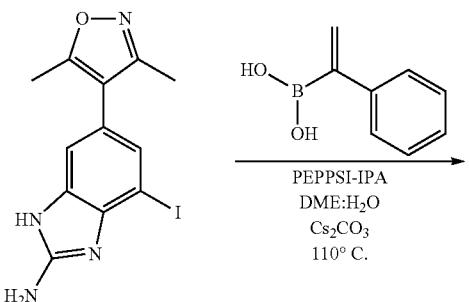

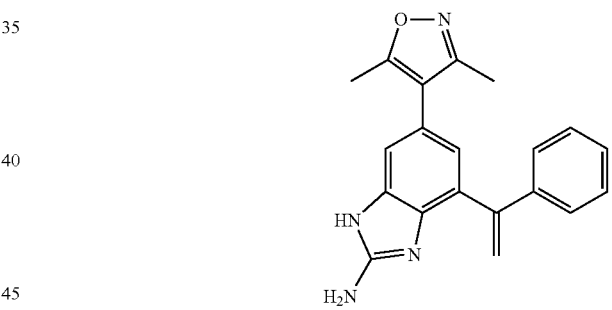

A suspension of 6-(3,5-dimethylisoxazol-4-yl)-4-iodo-1H-benzo[d]imidazol-2-amine (150 mg, 0.425 mmol), 3,5-dimethyl-4-(4,4,5,5-tetramethyl-1,3,2-dioxaborolan-2-yl)-1H-pyrazole (170 mg, 0.765 mmol), caesium carbonate (415 mg, 1.28 mmol) and PEPPSI™-IPr™ (30 mg, 0.043 mmol) in 12 mL DME:H$_2$O (2:1) was heated by microwave in a sealed vessel at 110° C. for 90 minutes. The reaction was then cooled and partitioned between water and ethyl acetate. The organic layer was washed with brine and dried over sodium sulfate. Purification on silica gel (rf=0.5 in 25% methanol in dichloromethane) afforded 4-(3,5-dimethyl-1H-pyrazol-4-yl)-6-(3,5-dimethylisoxazol-4-yl)-1H-benzo[d]imidazol-2-amine as an off-white solid.

$C_{17}H_{18}N_6O$. 323.2 (M+1). $^1$H NMR (DMSO) δ 6.99 (s, 1H), 6.63 (s, 1H), 6.09 (br, 2H), 2.38 (s, 3H), 2.21 (s, 3H), 2.11 (s, 6H).

Example 97

6-(3,5-Dimethylisoxazol-4-yl)-4-(1-phenylvinyl)-1H-benzo[d]imidazol-2-amine (1020-97)

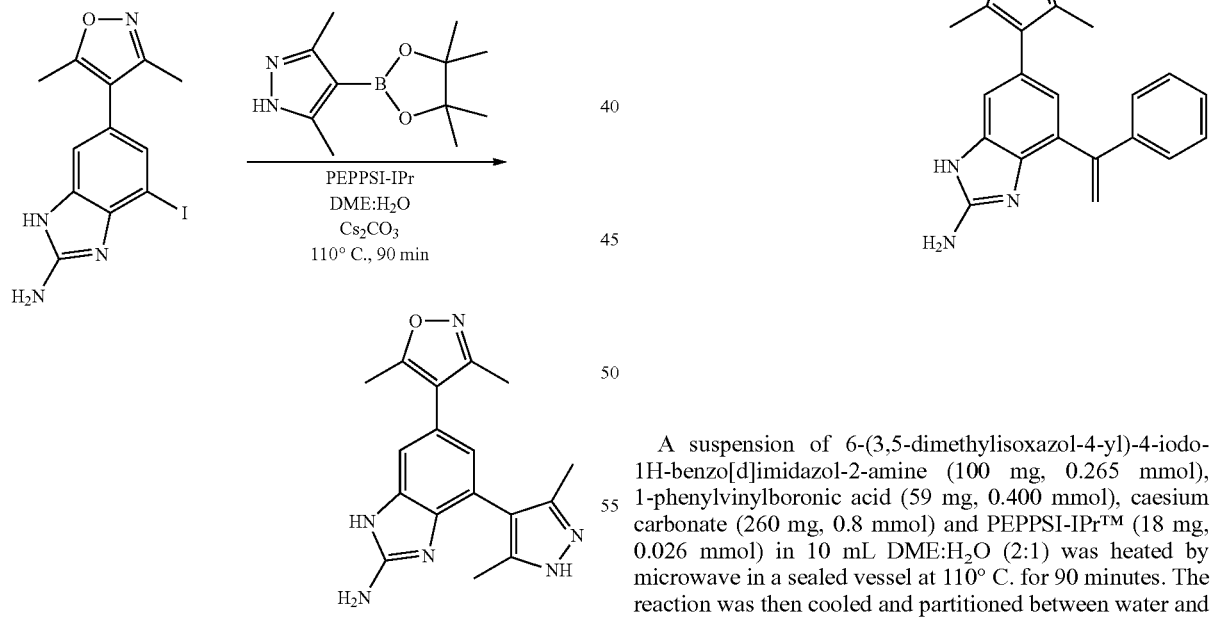

A suspension of 6-(3,5-dimethylisoxazol-4-yl)-4-iodo-1H-benzo[d]imidazol-2-amine (100 mg, 0.265 mmol), 1-phenylvinylboronic acid (59 mg, 0.400 mmol), caesium carbonate (260 mg, 0.8 mmol) and PEPPSI-IPr™ (18 mg, 0.026 mmol) in 10 mL DME:H$_2$O (2:1) was heated by microwave in a sealed vessel at 110° C. for 90 minutes. The reaction was then cooled and partitioned between water and ethyl acetate. The organic layer was washed with brine and dried over sodium sulfate. Purification on silica gel (rf=0.5 in 20% methanol in dichloromethane) afforded 6-(3,5-dimethylisoxazol-4-yl)-4-(1-phenylvinyl)-1H-benzo[d]imidazol-2-amine as an off-white solid.

$C_{20}H_{18}N_4O$. 331.2 (M+1). $^1$H NMR (MeOD) δ 7.36-7.31 (m, 4H), 7.10 (s, 1H), 6.69 (s, 1H), 5.79 (s, 1H), 5.55 (s, 1H), 2.35 (s, 3H), 2.20 (s, 3H).

Example 98

6-(3,5-Dimethylisoxazol-4-yl)-4-(1-phenylethyl)-1H-benzo[d]imidazol-2-amine (1020-98)

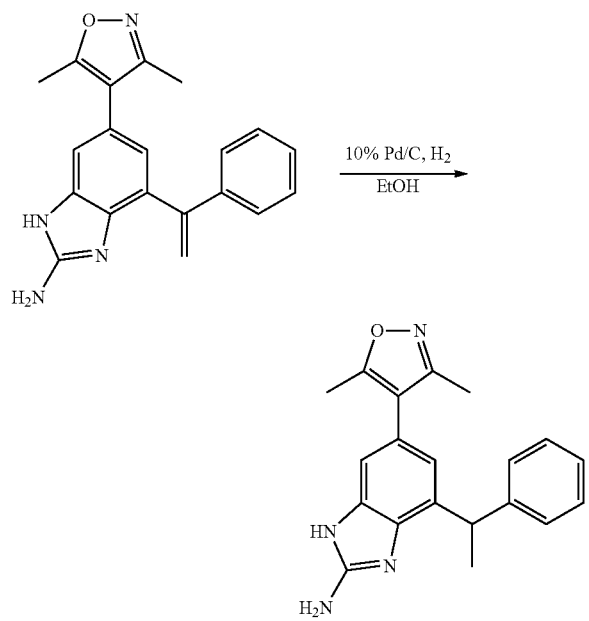

A suspension of 6-(3,5-dimethylisoxazol-4-yl)-4-(1-phenylvinyl)-1H-benzo[d]imidazol-2-amine (40 mg, 0.121 mmol) and 10% palladium on carbon (10 mg) in 5 mL ethanol was purged with hydrogen gas and allowed to stir for 2 hours. The reaction was then filtered and the solvents evaporated. Purification on silica gel (rf=0.5 in 20% methanol in dichloromethane) afforded 6-(3,5-dimethylisoxazol-4-yl)-4-(1-phenylethyl)-1H-benzo[d]imidazol-2-amine as a pale solid.

$C_{20}H_{20}N_4O$. 333.2 (M+1). $^1$H NMR (MeOD) δ 7.31-7.23 (m, 5H), 6.97 (s, 1H), 6.68 (s, 1H), 4.56 (q, 1H, J=7.2 Hz), 2.31 (s, 3H), 2.15 (s, 3H), 1.67 (d, 3H, J=7.2 Hz).

Example 99

4-(4-(1,4-Dimethyl-1H-pyrazol-5-yl)-2-methoxy-1H-benzo[d]imidazol-6-yl)-3,5-dimethylisoxazole (1020-99)

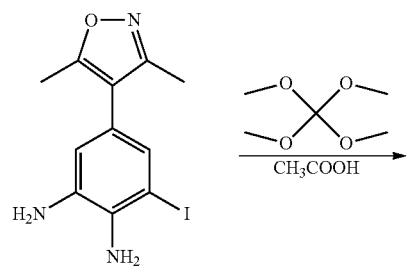

Step 1: 4-(4-Iodo-2-methoxy-1H-benzo[d]imidazol-6-yl)-3,5-dimethylisoxazole

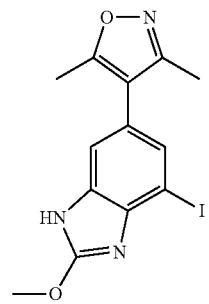

5-(3,5-Dimethylisoxazol-4-yl)-3-iodobenzene-1,2-diamine (100 mg) was dissolved in acetic acid (2 ml) and to the solution was added to tetramethyl orthocarbonate (0.08 ml). The reaction was stirred at RT for 30 mins. The solvent was then evaporated under vacuum and the residue was purified by silica gel column chromatography (0-60% EtOAc/Hexane) to afford 4-(4-iodo-2-methoxy-1H-benzo[d]imidazol-6-yl)-3,5-dimethylisoxazole.

C13H12IN3O2. 370.1 (M+1). 1H NMR (400 MHz, CD3OD) δ 7.41 (s, 1H), 7.22 (s, 1H), 4.19 (s, 3H), 2.41 (s, 3H), 2.23 (s, 3H).

Step 2

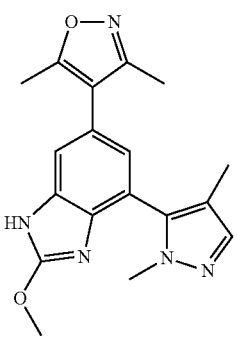 [SMILES: COc1nc2c(-c3c(C)cnn3C)cc(-c3c(C)noc3C)cc2[nH]1]

4-(4-(1,4-Dimethyl-1H-pyrazol-5-yl)-2-methoxy-1H-benzo[d]imidazol-6-yl)-3,5-dimethylisoxazole was synthesized by reacting 4-(4-iodo-2-methoxy-1H-benzo[d]imidazol-6-yl)-3,5-dimethylisoxazole with 3,5-dimethylpyrazole-4-boronic acid, pinacol ester using similar conditions as described in Example 75, Step 1.

$C_{18}H_{19}N_5O_2$. 338.1 (M+1). $^1$H NMR (400 MHz, CD$_3$OD) δ 7.32-7.25 (m, 2H), 6.89 (d, J=1.3 Hz, 1H), 4.03 (s, 3H), 3.63 (s, 3H), 2.34 (s, 3H), 2.19 (s, 3H), 1.89 (s, 3H).

Example 100

N-(Cyclopropylmethyl)-4,6-bis(3,5-dimethylisoxazol-4-yl)-1H-benzo[d]imidazol-2-amine (1020-100)

Step 1: Preparation of 2,4-bis(3,5-dimethylisoxazol-4-yl)-6-nitroaniline

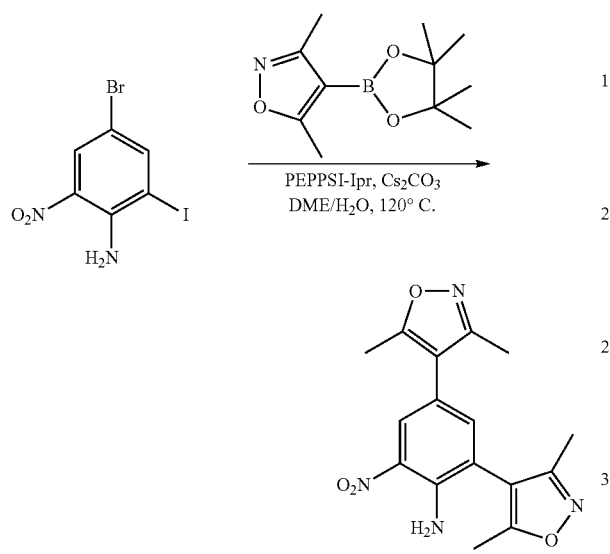

4-bromo-2-iodo-6-nitroaniline (150 mg, 0.44 mmol) and 3,5-Dimethylisoxazole-4-boronic acid pinacol ester (390 g, 1.75 mmol) was added to a solvent mixture of 1,2-dimethoxyethane (2 ml) and water (1 ml). To the above mixture were added PEPPSI-Ipr (30 mg, 0.04 mmol) and $Cs_2CO_3$ (0.86 g, 2.64 mmol). The reaction mixture was heated at 120° C. in microwave reactor for 2 hs. The reaction mixture was then diluted with EtOAc (100 ml), washed with bring (50 ml, 2 times). The organic solvent was evaporated and the residue was dissolved in DCM and purified with combi-flash column chromatography (product came out at 25% MeOH/DCM) to afford 2,4-bis(3,5-dimethylisoxazol-4-yl)-6-nitroaniline.

$C_{16}H_{16}N_4O_4$. 329.2 (M+1).

Step 2: Preparation of 3,5-bis(3,5-dimethylisoxazol-4-ylbenzene-1,2-diamine

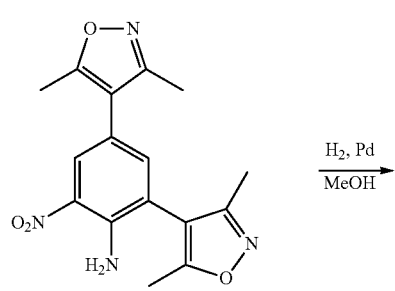

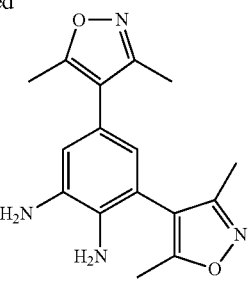

2,4-Bis(3,5-dimethylisoxazol-4-yl)-6-nitroaniline (0.1 g, 0.3 mmol) was added to MeOH (5 ml), To the solution was added Pd (10% on carbon, 100 mg). Then the flask was charged with $H_2$ balloon. The reaction was completed in 2 h. The reaction mixture was filtered, solvent was evaporated. The residue was then purified with Prep HPLC (0-100% $CH_3CN/H_2O$) to afford 3,5-bis(3,5-dimethylisoxazol-4-yl)benzene-1,2-diamine.

$C_{16}H_{18}N_4O_2$ 299.1 (M+1).

Step 3: Preparation of N-(cyclopropylmethyl-4,6-bis(3,5-dimethylisoxazol-4-yl)-1H-benzo[d]imidazol-2-amine

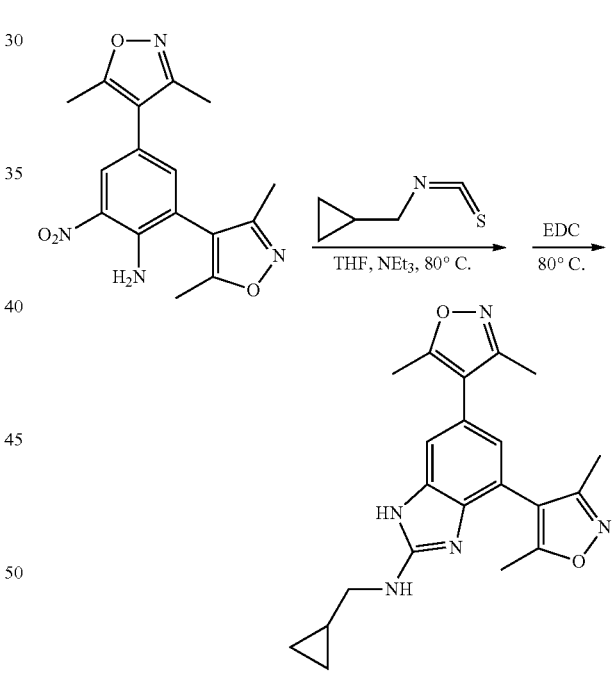

3,5-bis(3,5-dimethylisoxazol-4-yl)benzene-1,2-diamine (27 mg, 0.07 mmol) was dissolved in THF (1 mL). To the solution was added cyclopropylmethyl isothiocyanate (12 mg, 0.08 mmol) and triethylamine (130 uL). The reaction was heated at 80° C. for 3 h before 1-ethyl-3-(3-dimethylaminopropyl)carbodiimide hydrogen chloride (20 mg, 0.08 mmol) was added and heated at 80° C. for 4 h. The solvent was then evaporated under vacuum and the residue was purified with Prep HPLC (0-100% $CH_3CN/H_2O$) to afford compound (1020-106).

$C_{21}H_{23}N_5O_2$. 378.2 (M+1). $^1H$ NMR (400 MHz, $CD_3OD$) δ 7.00 (s, 1H), 6.78 (s, 1H), 2.98-2.96 (m, 2H), 2.08 (s, 3H), 2.01 (s, 3H), 1.92 (s, 6H), 1.85 (s, 3H), 0.85-0.75 (m, 1H), 0.32-0.27 (m, 2H), 0.03-0.01 (m, 2H).

Example 101

Methyl 2-cyclopropyl-6-(3,5-dimethylisoxazol-4-yl)-1H-benzo[d]imidazole-4-carboxylate (1020-101)

Step 1

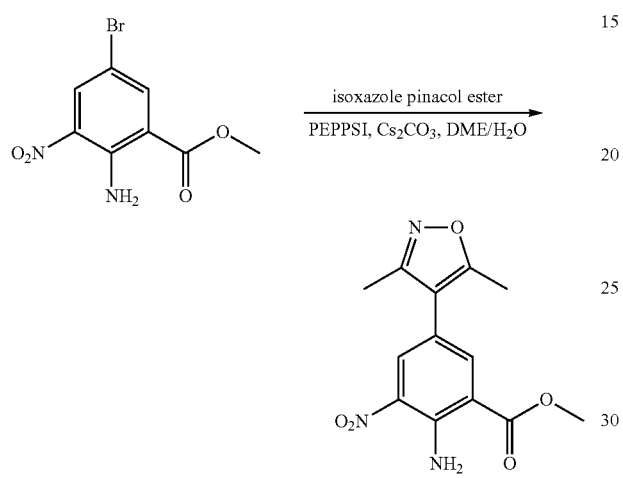

To a flask containing methyl 2-amino-5-bromo-3-nitrobenzoate (4.0 g, 14.5 mmol, 1 equiv.) was added 3,5-Dimethylisoxazole-4-boronic acid pinacol ester (4866 mg, 21.8 mmol, 1.5 equiv.), $Cs_2CO_3$ (14.2 gm, 43.6 mmol, 3 equiv.) and PEPPSI™-IPr catalyst (495 mg, 0.72 mmol, 0.05 equiv.) and dissolved in DME-$H_2O$ (70 mL, 0.2 M, 2/1, v/v). The mixture was heated to 105° C. After 3 hr, the reaction was complete. After cooling, the reaction was extracted with EtOAc and washed with water, saturated $NH_4Cl$. After drying with $MgSO_4$, it was filtered and concentrated to dryness. The resulting solid was washed with EtOAc. A mustard yellow solid was obtained as methyl 2-amino-5-(3,5-dimethylisoxazol-4-yl)-3-nitrobenzoate.

LCMS (m/z+1) 291.96. $^1$H NMR (400 MHz, dmso) δ 8.34 (s, 2H), 8.24 (d, J=2.2 Hz, 1H), 8.11 (d, J=2.2 Hz, 1H), 3.84 (s, 3H), 2.35 (s, 3H), 2.17 (s, 3H).

Step 2

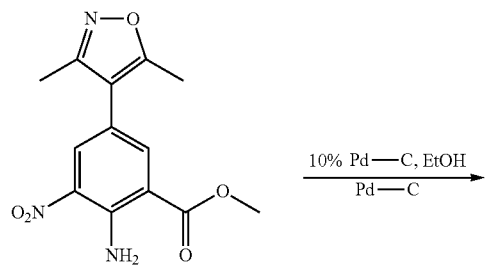

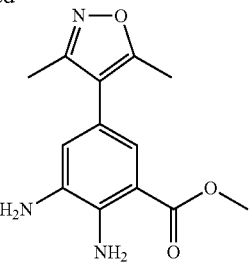

To a flask containing methyl 2-amino-5-(3,5-dimethylisoxazol-4-yl)-3-nitrobenzoate (1.55 gm, 5.32 mmol, 1 equiv) was added 10% Pd—C (600 mg) and EtOH (40 mL) and stirred under hydrogen. After 2 hr, the reaction appears complete. The reaction was degassed and the reaction filtered and washed with methanol. The filtrate was concentrated in vacuo to furnish methyl 2,3-diamino-5-(3,5-dimethylisoxazol-4-yl)benzoate. It was used in Step 3 without further purification.

LCMS (m/z+1) 262.03. $^1$H NMR (400 MHz, dmso) δ 6.99 (d, J=2.0 Hz, 1H), 6.66 (d, J=2.0 Hz, 1H), 6.31 (s, 2H), 4.91 (s, 2H), 3.74 (s, 3H), 2.30 (s, 3H), 2.12 (s, 3H).

Step 3

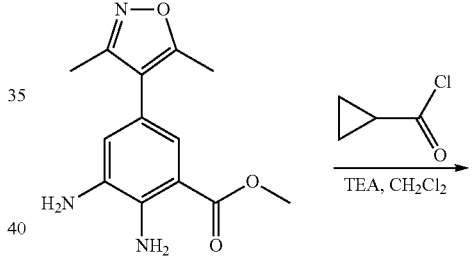

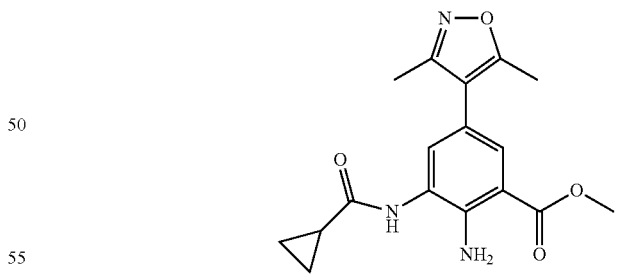

To a flask containing methyl 2,3-diamino-5-(3,5-dimethylisoxazol-4-yl)benzoate (750 mg, 2.9 mmol, 1 equiv.) was added THF (30 ml, 0.1M) and TEA (1.2 mL, 8.6 mmol, 3 equiv.). At 0° C., cyclopropanecarbonyl chloride (315 μL, 3.4 mmol, 1.1 equiv) was added. After an hour, the reaction was complete. The reaction was extracted with EtOAc and washed with water, saturated $NH_4Cl$. After drying with $MgSO_4$, it was filtered and concentrated to dryness and used in the next reaction as crude methyl 2-amino-3-(cyclopropanecarboxamido)-5-(3,5-dimethylisoxazol-4-yl)benzoate.

Step 4

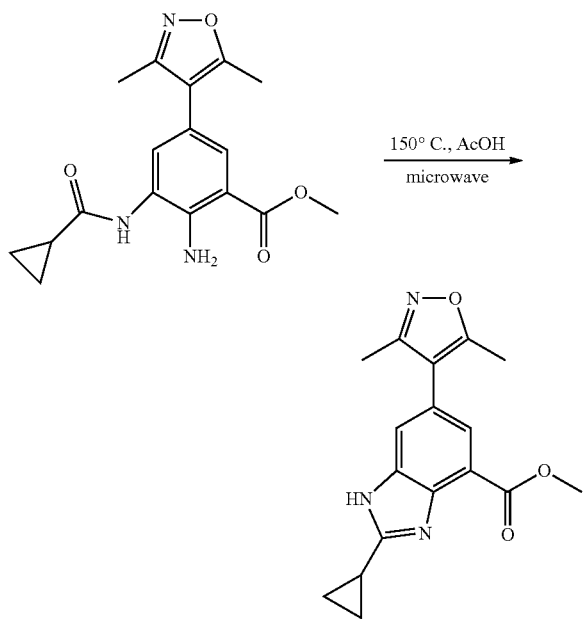

Into a microwave vial was placed methyl 2-amino-3-(cyclopropanecarboxamido)-5-(3,5-dimethylisoxazol-4-yl) benzoate was added acetic acid (10 mL) and heated in the microwave for 150° C. for 30 minutes. The reaction was concentrated down and extracted with EtOAc and washed with water (3×), saturated NaHCO$_3$ and brine. After drying with MgSO$_4$, it was filtered and concentrated to dryness and used in the next reaction as crude. The product was purified by silica gel chromatography with hexanes-EtOAc, resulting in a light-brown powder.

LCMS (m/z+1) 312.04. $^1$H NMR (400 MHz, dmso) δ 12.47 (s, 1H), 7.71 (d, J=1.4 Hz, 1H), 7.58 (d, J=1.6 Hz, 1H), 3.93 (s, 3H), 2.35 (s, 3H), 2.17 (s, 3H), 1.06 (t, J=6.9 Hz, 5H).

Example 102

(2-Cyclopropyl-6-(3,5-dimethylisoxazol-4-yl)-1H-benzo[d]imidazol-4-yl)diphenylmethanol (1020-102)

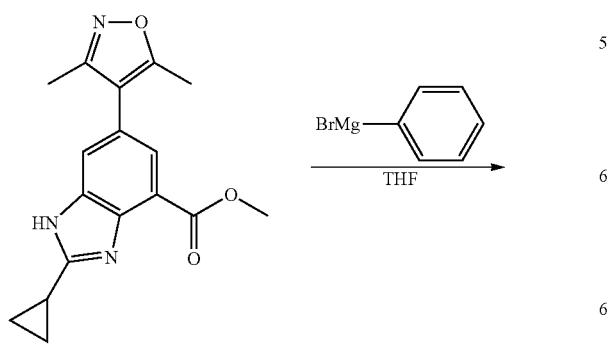

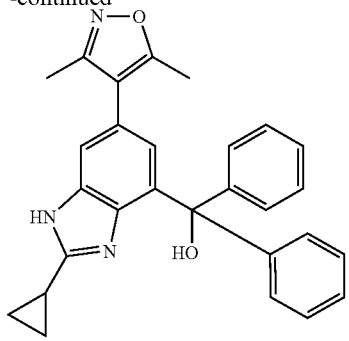

Methyl 2-cyclopropyl-6-(3,5-dimethylisoxazol-4-yl)-1H-benzo[d]imidazole-4-carboxylate (Example 101, Step 4) was treated with PhMgBr (2.9 M MeTHF solution, Aldrich, 1.24 mL, 3.531 mmol, 11 equiv.) in THF (3 mL) at 0° C. to room temperature for 20 h. The reaction mixture was quenched with brine (30 mL). The whole was extracted with AcOEt (30 mL×3). Organic layer was washed with brine (30 mL) and dried over Na$_2$SO$_4$. The solvent was removed under a reduced pressure to give the crude product. The crude product was purified by a silica gel chromatography (hexane:EtOAc=1:1).

C$_{28}$H$_{26}$N$_3$O$_2$. 436.2 (M+1). $^1$H NMR (MeOH-d$_4$) δ 7.40-7.24 (m, 12H), 2.60 (s, 3H), 2.24-2.14 (m, 1H), 2.08 (s, 3H), 1.14-1.06 (m, 4H).

Example 103

(2-cyclopropyl-6-(3,5-dimethylisoxazol-4-yl)-1H-benzo[d]imidazol-4-yl)di(thiazol-2-yl)methanol (1020-103)

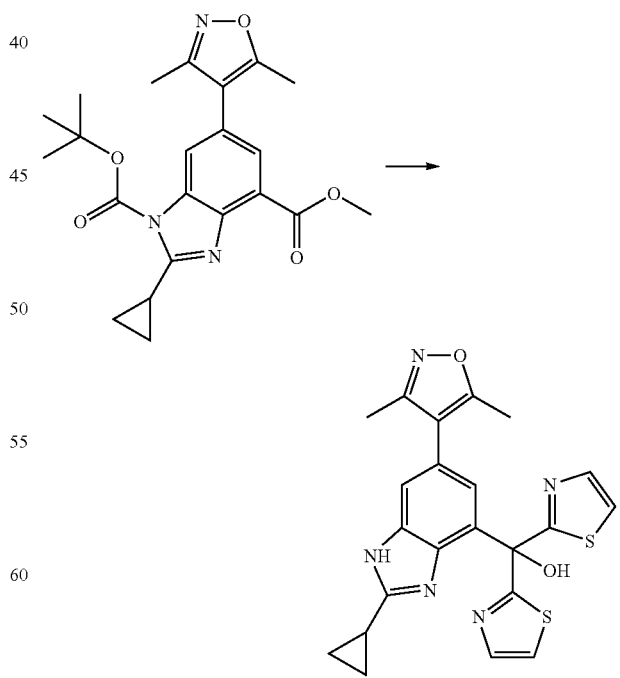

Thiazole (62 mg, 0.73 mmol) was dissolved in 5 ml THF, the reaction flask was then put in dry ice-acetone bath to lower temperature to −78° C., to the clear solution was added nBuLi (0.29 ml, 2.5 M in hexane). The reaction mixture was stirred at −78° C. for 1 h, then to the reaction mixture was added 1-tert-butyl 4-methyl 2-cyclopropyl-6-(3,5-dimethylisoxazol-4-yl)-1H-benzo[d]imidazole-1,4-dicarboxylate in 2 ml THF at −78° C. Reaction temperature was slowly raised to RT and stirred overnight. The reaction was quenched with water, solvent was evaporated, the residue was purified with Prep HPLC with 0.1% TFA modifier to afford 10 mg product (2-cyclopropyl-6-(3,5-dimethylisoxazol-4-yl)-1H-benzo[d]imidazol-4-yl)di(thiazol-2-yl)methanol.

$C_{22}H_{19}N_5O_2S_2$. 450.0 (M+1). $^1$H NMR (400 MHz, CD$_3$OD) δ 7.75 (d, J=2.8 Hz, 2H), 7.58 (d, J=3.2 Hz, 2H), 7.43 (s, 2H), 2.58-2.54 (m, 1H), 2.26 (s, 3H), 2.08 (s, 3H), 1.47-1.42 (m, 2H), 1.32-1.29 (m, 2H).

Example 104

(2-cyclopropyl-6-(3,5-dimethylisoxazol-4-yl)-1H-benzo[d]imidazol-4-yl)di(pyridin-2-yl)methanol (1020-104)

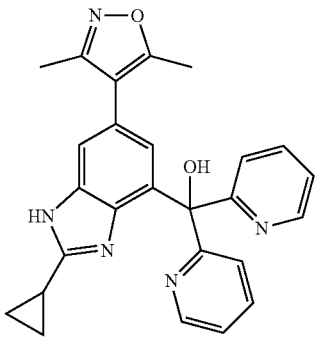 [SMILES: Cc1noc(C)c1-c1cc(C(O)(c2ccccn2)c2ccccn2)c2nc(C3CC3)[nH]c2c1]

Compound (1020-104) was made in a similar manner as that of Example 103, using 3-bromopyridine in 2-methyl-THF.

$C_{26}H_{23}N_5O_2$ 438.1 (M+1). $^1$H NMR (400 MHz, DMSO-d$_6$) δ 8.55 (ddd, J=5.0, 1.8, 0.9 Hz, 2H), 7.91 (td, J=7.8, 1.8 Hz, 2H), 7.66 (dt, J=8.1, 1.0 Hz, 2H), 7.54 (d, J=1.5 Hz, 1H), 7.40 (ddd, J=7.6, 4.9, 1.1 Hz, 2H), 7.06 (d, J=1.5 Hz, 1H), 2.70-2.55 (m, 1H), 2.31 (s, 3H), 2.11 (s, 3H), 1.48-1.22 (m, 4H).

Example 105

(2-cyclopropyl-6-(3,5-dimethylisoxazol-4-yl)-1H-benzo[d]imidazol-4-yl)di(pyrazin-2-yl)methanol (1020-105)

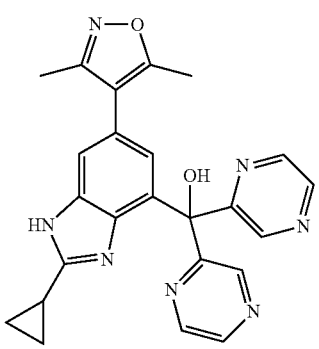 [SMILES: Cc1noc(C)c1-c1cc(C(O)(c2cnccn2)c2cnccn2)c2nc(C3CC3)[nH]c2c1]

Butyllithium (1.6 M in hexanes, 0.61 mL, 1 mmol) was added to a solution of 2,2,6,6-tetramethylpiperidine (0.18 mL, 1.1 mmol) in THF (5 mL) at 0° C. After stirring for 5 minutes, the reaction was cooled to −78° C. and pyrazine (78 mg) was added. The reaction mixture was stirred for 5 minutes and a solution of 1-tert-butyl 4-methyl 2-cyclopropyl-6-(3,5-dimethylisoxazol-4-yl)-1H-benzo[d]imidazole-1,4-dicarboxylate (80 mg, 0.19 mmol) was added The reaction mixture was allowed to warm to room temperature and quenched with 1M HCl, neutralized with sodium bicarbonate solution, extracted with ethyl acetate and purified by reverse-phase HPLC to give the desired product.

$C_{24}H_{21}N_7O_2$ 440.2 (M+1). $^1$H NMR (400 MHz, DMSO-d$_6$) δ 8.90 (d, J=1.5 Hz, 2H), 8.61 (d, J=2.5 Hz, 2H), 8.56 (dd, J=2.5, 1.5 Hz, 2H), 7.54 (s, 1H), 6.94 (s, 1H), 2.55 (m, 1H), 2.29 (s, 3H), 2.09 (s, 3H), 1.27 (m, 4H).

Example 106

(2-cyclopropyl-6-(3,5-dimethylisoxazol-4-yl)-1H-benzo[d]imidazol-4-yl)(pyridin-2-yl)(thiazol-2-yl)methanol (1020-106)

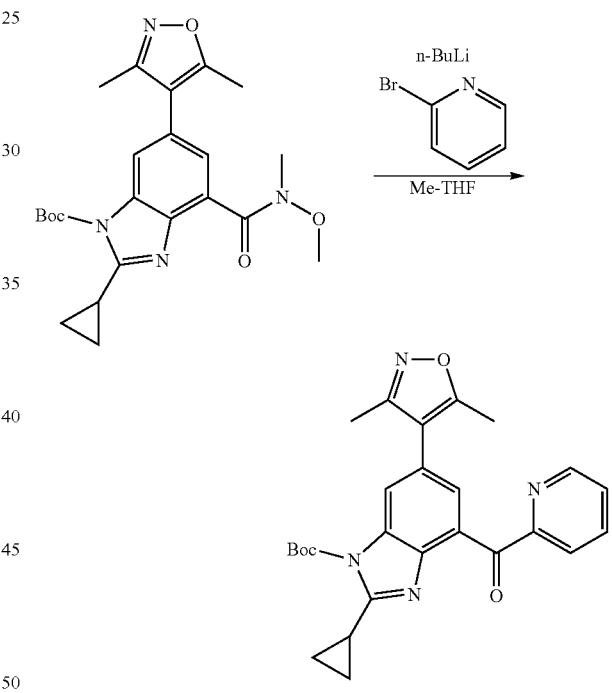

Step 1

2-bromopyridine (0.87 mL, 9.0 mmol) was dissolved in MeTHF (30 mL) and cooled to −78° C. n-BuLi (6.2 mL, 10.0 mmol, 1.6 M) was added dropwise and the reaction was allowed to stir for 1 hour at −78° C. tert-butyl 2-cyclopropyl-6-(3,5-dimethylisoxazol-4-yl)-4-(methoxy(methyl)carbamoyl)-1H-benzo[d]imidazole-1-carboxylate (2.0 g, 5.0 mmol) in MeTHF was added and the reaction was allowed to come to 0° C. and stir for 15 minutes before being quenched with water. Reaction was diluted with EtOAc, washed twice with brine, concentrated, and purified by silica gel chromatography to give tert-butyl 2-cyclopropyl-6-(3,5-dimethylisoxazol-4-yl)-4-picolinoyl-1H-benzo[d]imidazole-1-carboxylate (1.2 g, 57%) as a pale yellow powder.

191

Step 2

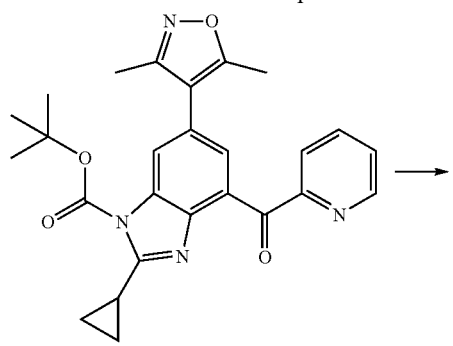

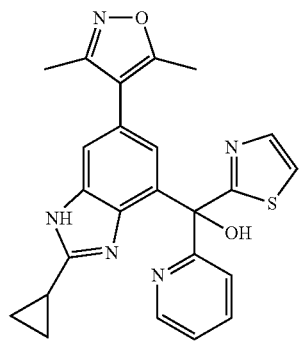

Thiazole (39 mg, 0.46 mmol) was dissolved in 5 ml THF, the reaction flask was then put in dry ice-acetone bath to lower temperature to −78° C., to the clear solution was added nBuLi (0.18 ml, 2.5 M in hexane). The reaction mixture was stirred at −78° C. for 1 h, then to the reaction mixture was added tert-butyl 2-cyclopropyl-6-(3,5-dimethylisoxazol-4-yl)-4-picolinoyl-1H-benzo[d]imidazole-1-carboxylate (35 mg, 0.076 mmol) in 2 ml THF at −78° C. Reaction temperature was slowly raised to RT and stirred overnight. The reaction was quenched with water, solvent was evaporated, the residue was purified with Prep HPLC with 0.1% TFA modifier to afford 20 mg product (2-cyclopropyl-6-(3,5-dimethylisoxazol-4-yl)-1H-benzo[d]imidazol-4-yl)(pyridin-2-yl)(thiazol-2-yl)methanol.

$C_{24}H_{21}N_5O_2S$. 444.1 (M+1). $^1H$ NMR (400 MHz, $CD_3OD$) δ 8.56 (d, J=3.2 Hz, 1H), 7.80 (t, J=4.8 Hz, 2H), 7.78 (d, J=2.8 Hz, 1H), 7.70 (d, J=3.2 Hz, 1H), 7.60 (d, J=2.8 Hz, 1H), 7.42 (d, J=2.8 Hz, 1H), 7.38-7.35 (m, 1H), 2.68-2.56 (m, 1H), 2.33 (s, 3H), 2.15 (s, 3H), 1.48-1.42 (m, 2H), 1.38-1.30 (m, 2H).

Example 107

(2-cyclopropyl-6-(3,5-dimethylisoxazol-4-yl)-1H-benzo[d]imidazol-4-yl)(pyridin-2-yl)(pyridin-3-yl)methanol (1020-107)

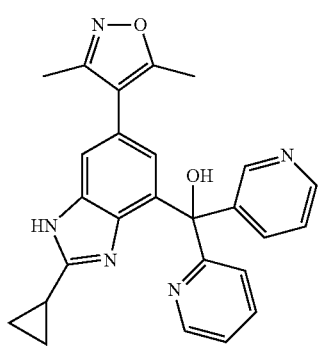 [SMILES: Cc1noc(C)c1-c1cc(C(O)(c2cccnc2)c2ccccn2)c2nc(C3CC3)[nH]c2c1]

192

Compound 1020-107 was made in a similar manner as that of Example 106, using 3-bromopyridine as the aryl bromide.

$C_{26}H_{23}N_5O_2$ 438.2 (M+1). $^1H$ NMR (400 MHz, DMSO-$d_6$) δ 8.78-8.59 (m, 2H), 8.59-8.50 (m, 1H), 8.02 (d, J=8.2 Hz, 1H), 7.96 (td, J=7.8, 1.8 Hz, 1H), 7.85 (d, J=8.1 Hz, 1H), 7.78 (br, 1H), 7.64 (t, J=6.7 Hz, 1H), 7.56 (d, J=1.5 Hz, 1H), 7.41 (ddd, J=7.4, 4.8, 1.1 Hz, 1H), 6.85 (d, J=1.5 Hz, 1H), 2.57 (s, 1H), 2.29 (s, 3H), 2.09 (s, 3H), 1.48-1.10 (m, 4H).

Example 108

(2-cyclopropyl-6-(3,5-dimethylisoxazol-4-yl)-1H-benzo[d]imidazol-4-yl)(pyridin-2-yl)(pyrimidin-2-yl)methanol (1020-108)

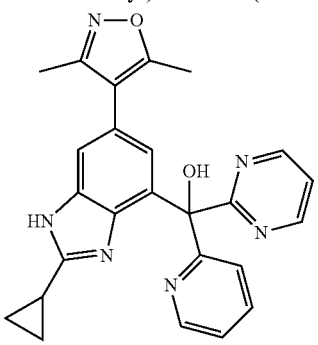

Butyllithium (1.6 M in hexanes, 0.2 mL, 0.32 mmol) was added dropwise to a solution 2-bromopyrimidine (47 mg, 0.3 mmol) in dichloromethane (5 mL) at −78° C. After stirring for 15 minutes a solution of tert-butyl 6-(3,5-dimethylisoxazol-4-yl)-2-ethoxy-4-picolinoyl-1H-benzo[d]imidazole-1-carboxylate (45 mg, 0.1 mmol) in dichloromethane (1 mL) was added. The reaction mixture was allowed to warm to room temperature and quenched with 1M HCl, neutralized with sodium bicarbonate solution, extracted with ethyl acetate and purified by reverse-phase HPLC to give the desired product.

$C_{25}H_2N_6O_2$ 439.1 (M+1). $^1H$ NMR (400 MHz, DMSO-$d_6$) δ 8.82 (d, J=4.9 Hz, 2H), 8.55-8.35 (m, 1H), 7.91 (td, J=7.6, 1.6 Hz, 1H), 7.78 (d, J=8.0 Hz, 1H), 7.54 (d, J=1.5 Hz, 1H), 7.49 (t, J=4.9 Hz, 1H), 7.41-7.31 (m, 1H), 7.09 (d, J=1.5 Hz, 1H), 2.69-2.58 (m, 1H), 2.31 (s, 3H), 2.11 (s, 3H), 1.52-1.19 (m, 4H).

Example 109

(2-cyclopropyl-6-(3,5-dimethylisoxazol-4-yl)-1H-benzo[d]imidazol-4-yl)(pyridin-2-yl)(pyrimidin-5-yl)methanol (1020-109)

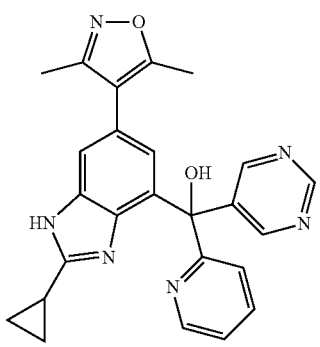 [SMILES: Cc1noc(C)c1-c1cc(C(O)(c2cncnc2)c2ccccn2)c2nc(C3CC3)[nH]c2c1]

Compound 1020-109 was made in a similar manner as that of Example 108, using 5-bromopyrimidine in place of 2-bromopyrimidine, and in 2-methylTHF instead of dichloromethane.

$C_{25}H_{22}N6O_2$ 439.1 (M+1). $^1$H NMR (400 MHz, DMSO-$d_6$) δ 9.09 (s, 1H), 8.72 (s, 2H), 8.59-8.55 (m, 1H), 7.93 (dd, J=7.7, 1.8 Hz, 1H), 7.86 (d, J=8.0 Hz, 1H), 7.52 (d, J=1.6 Hz, 1H), 7.39 (dd, J=7.6, 4.9 Hz, 1H), 6.84 (s, 1H), 2.55 (s, 1H), 2.27 (s, 3H), 2.07 (s, 3H), 1.31 (m, 4H).

Example 110

(2-cyclopropyl-6-(3,5-dimethylisoxazol-4-yl)-1H-benzo[d]imidazol-4-yl)(pyridazin-3-yl)(pyridin-2-yl)methanol (1020-110)

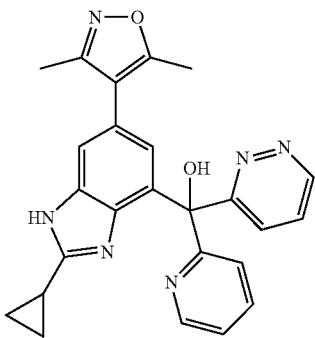 [SMILES: Cc1noc(C)c1-c1cc(C(O)(c2ccccn2)c2cccnn2)c2nc(C3CC3)[nH]c2c1]

Butyllithium (1.6 M in hexanes, 2.15 mL, 3.4 mmol) was added to a solution of 2,2,6,6-tetramethylpiperidine (0.68 mL, 4.0 mmol) in MeTHF (20 mL) at 0° C. After stirring for 5 minutes, the reaction was cooled to −78° C. and pyridazine (275 mg, 3.4 mmol) was added. The reaction mixture was stirred for 5 minutes and a solution of tert-butyl 6-(3,5-dimethylisoxazol-4-yl)-4-picolinoyl-1H-benzo[d]imidazole-1-carboxylate (525 mg, 1.15 mmol) in MeTHF (5 mL) was added. The reaction mixture was allowed to warm to room temperature and quenched with 1M HCl, neutralized with sodium bicarbonate solution, extracted with ethyl acetate and purified by reverse-phase HPLC to give the desired product.

$C_{25}H_{22}N6O_2$ 439.1 (M+1). $^1$H NMR (400 MHz, DMSO-$d_6$) δ 9.18 (dd, J=4.7, 1.8 Hz, 1H), 8.63-8.46 (m, 1H), 7.93 (td, J=7.8, 1.8 Hz, 1H), 7.87-7.66 (m, 3H), 7.57 (d, J=1.5 Hz, 1H), 7.40 (ddd, J=7.5, 4.8, 1.1 Hz, 1H), 6.99 (d, J=1.9 Hz, 1H), 2.62 (t, J=4.9 Hz, 1H), 2.29 (s, 3H), 2.09 (s, 3H), 1.54-1.25 (m, 4H).

Example 111

(2-cyclopropyl-6-(3,5-dimethylisoxazol-4-yl)-1H-benzo[d]imidazol-4-yl)(pyrazin-2-yl)(pyridin-2-yl)methanol (1020-111)

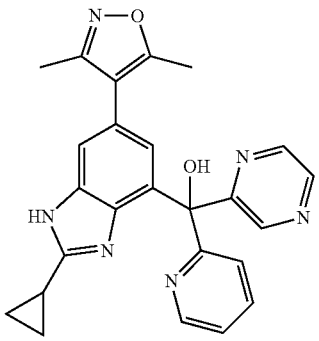 [SMILES: Cc1noc(C)c1-c1cc(C(O)(c2ccccn2)c2cnccn2)c2nc(C3CC3)[nH]c2c1]

Compound 1020-111 was made in a similar manner as that of Example 108, using pyrazine in place of pyridazine.

$C_{25}H_{22}N_6O_2$ 439.1 (M+1). $^1$H NMR (400 MHz, DMSO-$d_6$) δ 8.79 (d, J=1.5 Hz, 1H), 8.59 (d, J=2.5 Hz, 1H), 8.57-8.55 (m, 1H), 8.53 (d, J=4.7 Hz, 1H), 7.91 (t, J=7.7 Hz, 1H), 7.72 (d, J=8.0 Hz, 1H), 7.53 (d, J=1.5 Hz, 1H), 7.39 (dd, J=7.4, 4.9 Hz, 1H), 6.97 (s, 1H), 2.60 (m, 1H), 2.30 (s, 3H), 2.10 (s, 3H), 1.33 (d, J=25.6 Hz, 4H).

Example 112

(2-cyclopropyl-6-(3,5-dimethylisoxazol-4-yl)-1H-benzo[d]imidazol-4-yl)(phenyl)(pyridin-3-yl)methanol (1020-112)

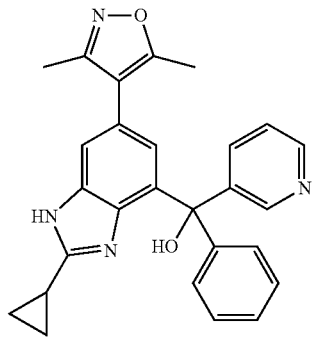 [SMILES: Cc1noc(C)c1-c1cc(C(O)(c2ccccc2)c2cccnc2)c2nc(C3CC3)[nH]c2c1]

Step 1

Phenylmagnesium chloride in THF (2M, 3 mL) was added to a solution of 2-cyclopropyl-6-(3,5-dimethylisoxazol-4-yl)-N-methoxy-N-methyl-1H-benzo[d]imidazole-4-carboxamide in NMP (6 mL) and the reaction mixture was stirred for 15 min, quenched with sodium bicarbonate solution and extracted using ethyl acetate. Purification by silica gel chromatography gave (2-cyclopropyl-6-(3,5-dimethylisoxazol-4-yl)-1H-benzo[d]imidazol-4-yl)(phenyl)methanone.

Step 2

A solution of 3-pyridylmagnesium bromide (2 equiv) and (2-cyclopropyl-6-(3,5-dimethylisoxazol-4-yl)-1H-benzo[d]imidazol-4-yl)(phenyl)methanone (30 mg) was stirred at room temperature for 15 min. The reaction mixture was quenched with 1M HCl solution, concentrated and purified by reverse-phase HPLC to give the desired product.

$C_{27}H_{24}N_4O_2$ 437.1 (M+1). $^1$H NMR (400 MHz, DMSO-$d_6$) δ 8.67-8.50 (m, 2H), 7.81 (s, 1H), 7.53 (d, J=7.4 Hz, 3H), 7.49-7.21 (m, 5H), 6.62 (s, 1H), 2.25 (s, 3H), 2.05 (s, 3H), 1.31 (m, 5H).

Example 113

(2-cyclopropyl-6-(3,5-dimethylisoxazol-4-yl)-1H-benzo[d]imidazol-4-yl)(phenyl)(pyridin-2-yl)methanol (1020-113)

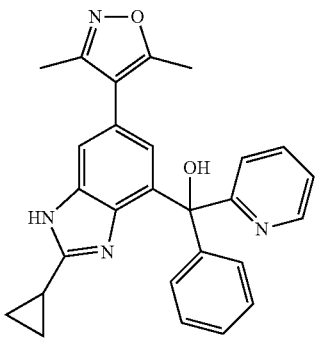 [SMILES: Cc1noc(C)c1-c1cc(C(O)(c2ccccc2)c2ccccn2)c2nc(C3CC3)[nH]c2c1]

Compound 1020-113 was made in a similar manner as that of Example 112, using 2-pyridylmagnesium bromide in place of 3-pyridylmagnesium bromide.

$C_{27}H_{24}N_4O_2$ 437.1 (M+1). $^1$H NMR (400 MHz, DMSO-d) δ 8.59-8.47 (m, 1H), 7.89 (dd, J=7.6, 1.8 Hz, 1H), 7.79-7.59 (m, 1H), 7.53-7.46 (m, 1H), 7.39-7.23 (m, 5H), 6.83 (d, J=1.4 Hz, 1H), 2.27 (s, 3H), 2.07 (s, 3H), 1.47-1.17 (m, 5H).

Example 114

(2-cyclopropyl-6-(3,5-dimethylisoxazol-4-yl)-1H-benzo[d]imidazol-4-yl)(6-methylpyridin-2-yl)(tetrahydrofuran-2-yl)methanol (1020-114)

Step 1

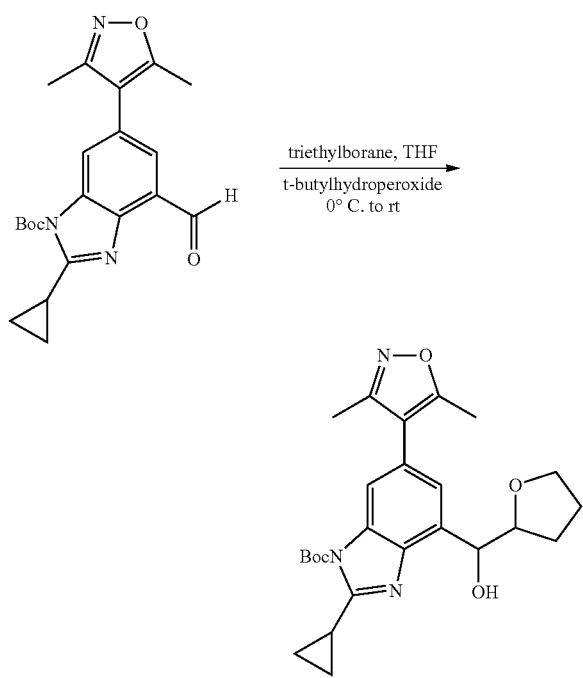

Into a flask containing tert-butyl 2-cyclopropyl-6-(3,5-dimethylisoxazol-4-yl)-4-formyl-1H-benzo[d]imidazole-1-carboxylate (280 mg, 0.73 mmol, 1 equiv.) is added THF (10 mL) and cooled to 0° C. before adding triethylborane (8.8 mL, 8.8 mmol, 12 equiv., 1 M THF). Tert-butylhydroperoxide (0.8 mL, 4.4 mmol, 6 equiv., 6 M decanes) is added slowly to the reaction mixture and the reaction allowed to warm up slowly to room temperature. After completion, the reaction was quenched with NH$_4$OH solution (5 mL) and extracted with EtOAc and washed with water (spiked with a solution of FeSO$_4$.H$_2$SO$_4$.H$_2$0 (2 mL)) and then with saturated NH$_4$Cl. After drying with MgSO$_4$, it was filtered and concentrated to dryness. Purification was carried out by flash column chromatography to furnish tert-butyl 2-cyclopropyl-6-(3,5-dimethylisoxazol-4-yl)-4-(hydroxy(tetrahydrofuran-2-yl)methyl)-1H-benzo[d]imidazole-1-carboxylate (175 mg, y. 53%, dr 3:2). LCMS (m/z+1) 454.34.

Step 2

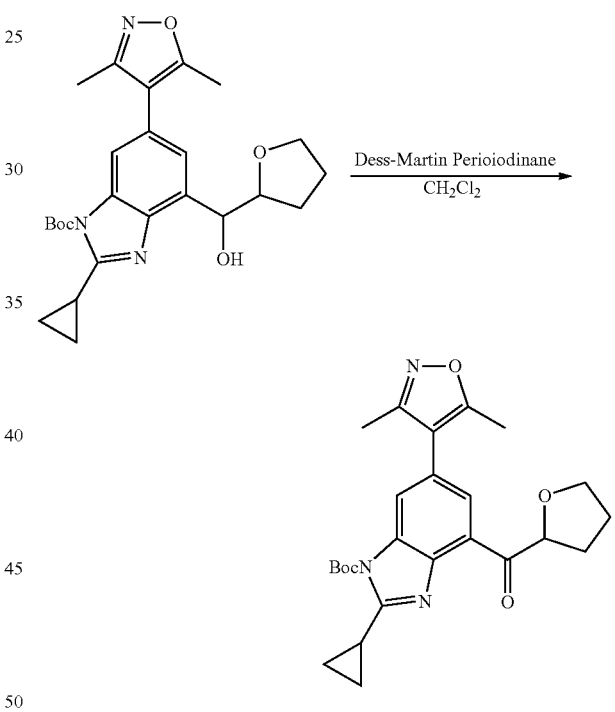

Into a flask containing tert-butyl 2-cyclopropyl-6-(3,5-dimethylisoxazol-4-yl)-4-(hydroxy(tetrahydrofuran-2-yl)methyl)-1H-benzo[d]imidazole-1-carboxylate (660 mg, 1.82 mmol, 1 equiv.) is added DCM (40 mL) and Dess-Martin periodinane (802 mg, 2.4 mmol, 1.3 equiv.). After completion, the reaction was quenched with sodium thiosulfate solution and allowed to stir for several minutes. It was extracted with DCM and washed with water and saturated NH$_4$Cl. After drying with MgSO$_4$, it was filtered and concentrated to dryness. Purification was carried out by flash column chromatography to furnish tert-butyl 2-cyclopropyl-6-(3,5-dimethylisoxazol-4-yl)-4-(hydroxy(tetrahydrofuran-2-yl)methyl)-1H-benzo[d]imidazole-1-carboxylate (175 mg, y. 53%).

LCMS (m/z+1) 452.23.

Step 3

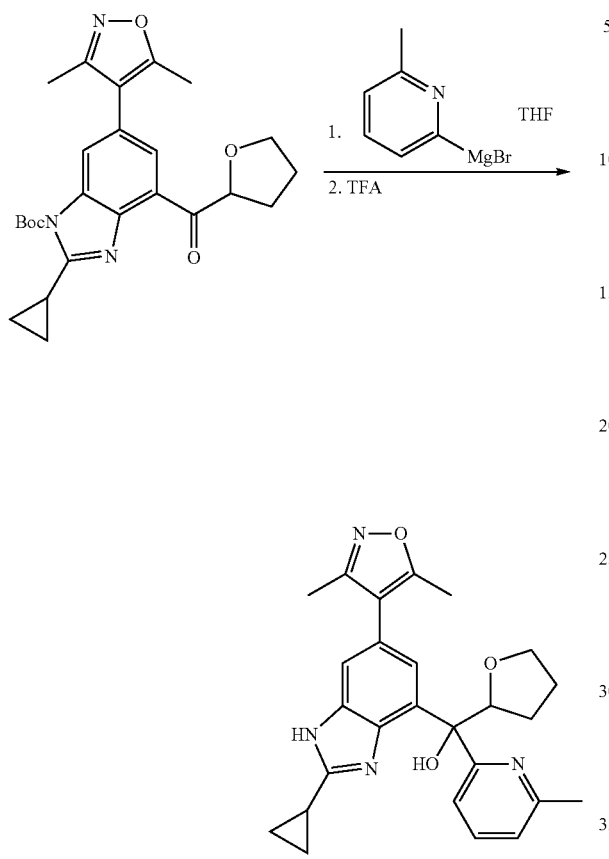

Into a flask containing tert-butyl 2-cyclopropyl-6-(3,5-dimethylisoxazol-4-yl)-4-(hydroxy(tetrahydrofuran-2-yl)methyl)-1H-benzo[d]imidazole-1-carboxylate (60 mg, 0.13 mmol, 1 equiv.) is added THF (5 mL) and to it is added (6-methylpyridin-2-yl)magnesium bromide (3.2 mL, 0.80 mmol, 6 equiv., 0.25 M THF, Rieke Metals). After completion, the reaction was quenched and extracted with EtOAc and washed with water, saturated NH₄Cl. After drying with MgSO₄, it was filtered and concentrated to dryness. To the crude material is added TFA (5 mL) and allowed to stir for 30 min. After the reaction was complete, it was concentrated in vacuo. Purification was carried out by reverse phase HPLC to furnish (2-cyclopropyl-6-(3,5-dimethylisoxazol-4-yl)-1H-benzo[d]imidazol-4-yl)(6-methylpyridin-2-yl)(tetrahydrofuran-2-yl)methanol as a mixture of enantiomers.

1H NMR (400 MHz, Methanol-d4) δ 7.62 (d, J=5.2 Hz, 1H), 7.37 (t, J=1.6 Hz, 1H), 7.28 (s, 0H), 7.11 (dd, J=6.1, 2.9 Hz, 1H), 5.34 (t, J=7.2 Hz, 1H), 3.89 (q, J=6.9 Hz, 1H), 3.79 (t, J=6.8 Hz, 1H), 2.58 (s, 2H), 2.38 (d, J=1.4 Hz, 2H), 2.34-2.26 (m, 1H), 2.22 (d, J=1.4 Hz, 2H), 2.01-1.69 (m, 3H), 1.16 (t, J=5.7 Hz, 2H).
LCMS (m/z+1) 445.23

Example 115

(2-cyclopropyl-6-(3,5-dimethylisoxazol-4-yl)-1H-benzo[d]imidazol-4-yl)(pyridazin-3-yl)(tetrahydrofuran-2-yl)methanol (1020-115)

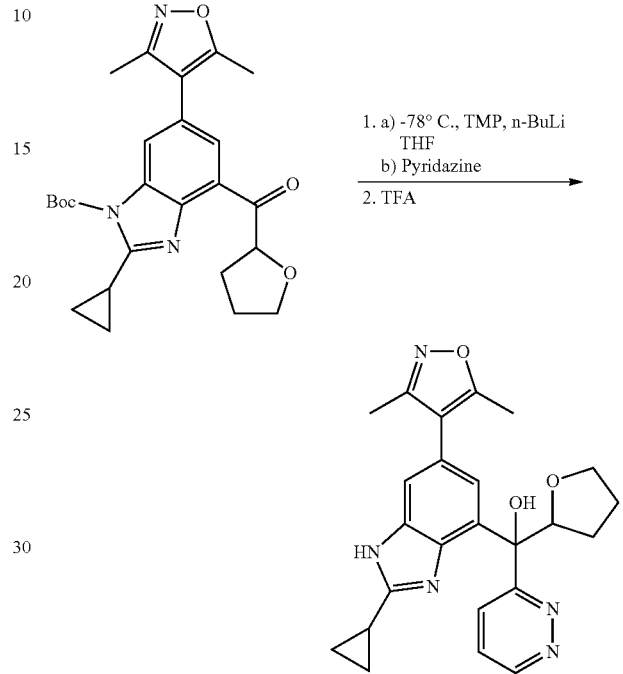

In a flame-dried flask containing THF and 2,2,6,6-Tetramethylpiperidine (0.12 mL, 4.4 equiv.) at −78° C., n-BuLi (0.42 mL, 4.0 equiv.) was added dropwise. After 15 minutes of stirring, Pyridazine (0.07 mL, 6 equiv.) was added. The solution was allowed to stir for 15 minutes, followed by the addition of tert-butyl 2-cyclopropyl-6-(3,5-dimethylisoxazol-4-yl)-4-(tetrahydrofuran-2-carbonyl)-1H-benzo[d]imidazole-1-carboxylate (75 mg, 1 equiv.). The reaction was allowed to stir for 30 minutes at −78° C., then removed from cold bath and allowed to warm to room temperature. Once complete, the solution was quenched with DI H₂O and extracted three times with EtOAc. The combined organic layers were washed with saturated NaCl, dried over sodium sulfate, filtered and concentrated in vacuo. To the crude material was added TFA (5 mL) and allowed to stir for 30 minutes. Once complete, the solution was concentrated in vacuo. Purification was carried out by reverse phase HPLC to afford (2-cyclopropyl-6-(3,5-dimethylisoxazol-4-yl)-1H-benzo[d]imidazol-4-yl)(pyridazin-3-yl)(tetrahydrofuran-2-yl)methanol (23 mg, 33% yield as a mixture of enantiomers). Enantiomers were resolved using a Chiralpak AD-H column (Heptane:IPA, 70:30)

$C_{24}H_{25}N_5O_3$. M.S 432.2 (M+1) ¹H NMR (400 MHz, MeOH-d₄) δ 9.02 (d, J=4.9 Hz, 1H), 8.16 (d, J=8.5 Hz, 1H), 7.65 (dd, J=8.7, 4.9 Hz, 1H), 7.29 (s, 2H), 5.48 (t, J=7.2 Hz, 1H), 3.99-3.87 (m, 2H), 3.78 (dd, J=13.6, 7.2 Hz, 1H), 3.34-3.27 (m, 1H), 2.33 (s, 3H), 2.27 (dd, J=13.0, 6.6 Hz, 1H), 2.17 (s, 3H), 1.95 (dqd, J=26.1, 11.6, 7.5 Hz, 4H), 1.78 (qd, J=11.3, 5.6 Hz, 1H), 1.14 (d, J=6.1 Hz, 2H).

Example 116

(2-Cyclopropyl-6-(3,5-dimethylisoxazol-4-yl)-1H-benzo[d]imidazol-4-yl)dipyridin-3-ylmethanol (1020-116)

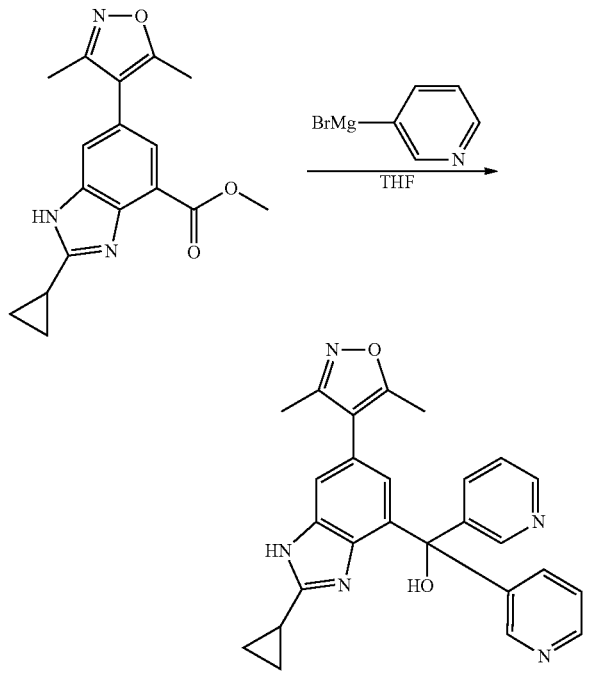

Methyl 2-cyclopropyl-6-(3,5-dimethylisoxazol-4-yl)-1H-benzo[d]imidazole-4-carboxylate (Example 107, Step 4) was treated with 3-pyridine magnesiumbromide (0.25 M MeTHF solution, Novel, 5.6 mL, 1.42 mmol, 8.8 equiv.) in THF (3 mL) at room temperature for 16 h. The reaction mixture was quenched with water (30 mL). The whole was extracted with AcOEt (30 mL×3). Organic layer was washed with brine (30 mL) and dried over $Na_2SO_4$. The solvent was removed under a reduced pressure to give the crude product. The crude product was purified by a preparative HPLC (5-95% acetonitrile: water with 0.05% trifluoroacetic acid, on a Phenomenex Luna $C_{18}$ column).

$C_{26}H_{24}N_5O_2$. 438.2 (M+1). $^1$H NMR (MeOH-$d_4$) δ 8.81 (s, 2H), 8.77 (d, J=5.0 Hz, 2H), 8.27 (d, J=8.3 Hz, 2H), 7.84 (dd, J=8.3, 5.0 Hz, 2H), 7.62 (d, J=1.0 Hz, 1H), 6.94 (d, J=1.0 Hz, 1H), 2.60-2.50 (m, 1H), 2.31 (s, 3H), 2.13 (s, 3H), 1.55-1.47 (m, 2H), 1.40-1.34 (m, 2H).

Examples 117-118

1-(2-Cyclopropyl-6-(3,5-dimethylisoxazol-4-yl)-1H-benzo[d]imidazol-4-yl)propan-1-ol (1020-117); and 3-(2-cyclopropyl-6-(3,5-dimethylisoxazol-4-yl)-1H-benzo[d]imidazol-4-yl)pentan-3-ol (1020-118)

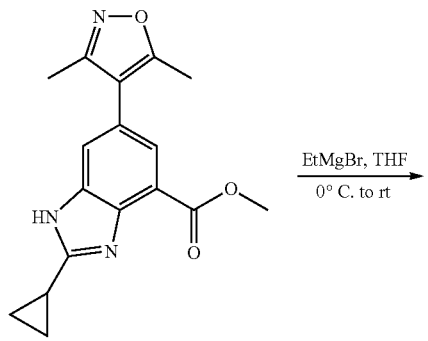

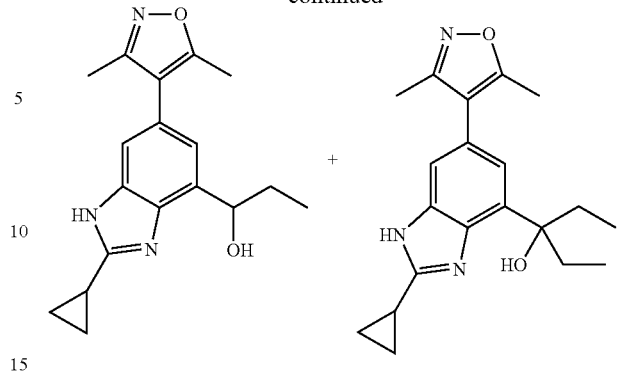

Into a flask containing methyl 2-cyclopropyl-6-(3,5-dimethylisoxazol-4-yl)-1H-benzo[d]imidazole-4-carboxylate (60 mg, 0.19 mmol, 1 equiv) (Example 107, Step 4) was added THF (4 mL, 0.05 M) before being cooled to 0° C. Ethylmagnesium bromide (0.39 mL, 1.15 mmol, 6 equiv., 3M Hexanes) was added slowly and the reaction was allowed to warm up to room temperature. After the starting material was consumed, the reaction was partitioned between water and ethyl acetate. The organic layer was washed with brine and dried over sodium sulfate. Purification was carried out by reverse phase HPLC to give two products:

1-(2-Cyclopropyl-6-(3,5-dimethylisoxazol-4-yl)-1H-benzo[d]imidazol-4-yl)propan-1-ol: LCMS (m/z+1) 312.03. $^1$H NMR (400 MHz, cd$_3$od) δ 7.74 (d, J=1.5 Hz, 1H), 7.64 (s, 1H), 4.83 (s, 14H), 4.01 (s, 4H), 3.29 (dt, J=3.2, 1.6 Hz, 26H), 3.11 (s, 2H), 2.42-2.20 (m, 10H), 1.22-1.10 (m, 6H);

3-(2-Cyclopropyl-6-(3,5-dimethylisoxazol-4-yl)-1H-benzo[d]imidazol-4-yl)pentan-3-ol: LCMS (m/z+1) 339.07. $^1$H NMR (400 MHz, cdcl$_3$) δ 7.38 (s, 1H), 6.71 (s, 1H), 2.38 (d, J=5.8 Hz, 3H), 2.24 (d, J=7.2 Hz, 3H), 2.10 (s, 1H), 1.99 (dd, J=14.4, 7.4 Hz, 2H), 1.90 (td, J=14.7, 7.4 Hz, 2H), 1.46 (s, 2H), 1.30 (s, 2H), 1.17 (s, 1H), 0.84 (t, J=7.4 Hz, 6H).

Example 119

4-(2-Cyclopropyl-4-(pent-2-en-3-yl)-1H-benzo[d]imidazol-6-yl)-3,5-dimethylisoxazole (1020-119)

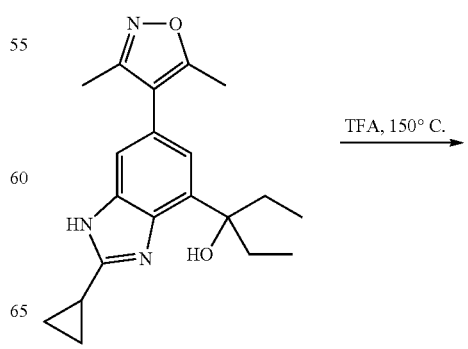

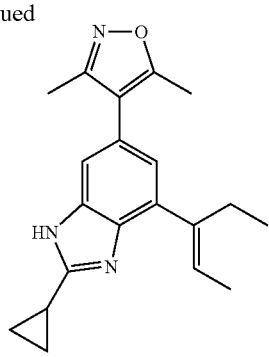

Into a microwave vial was placed 3-(2-cyclopropyl-6-(3,5-dimethylisoxazol-4-yl)-1H-benzo[d]imidazol-4-yl)pentan-3-ol (25 mg, 0.074 mmol, 1 equiv) (Example 111) and TFA (4 ml). The reaction was subjected to microwave irradiation at 150° C. for 30 minutes. Following completion of reaction, the mixture was concentrated in vacuo and the reaction was partitioned between water and ethyl acetate. The organic layer was washed with saturated NaHCO₃ solution and brine and dried over sodium sulfate. Purification was carried out by reverse phase HPLC to furnish 4-(2-cyclopropyl-4-(pent-2-en-3-yl)-1H-benzo[d]imidazol-6-yl)-3,5-dimethylisoxazole (10.3 mg, 44%). This compound was isolated as a mixture of E/Z isomers.

LCMS (m/z+1) 322.20. $^1$H NMR (400 MHz, cdcl$_3$) δ 7.34 (s, 1H), 6.91 (s, 1H), 5.82 (dd, J=2.2, 6.8 Hz, 1H), 2.58 (d, J=7.6 Hz, 2H), 2.38 (s, 3H), 2.25 (s, 3H), 2.08 (m, 1H), 1.87 (d, J=6.8 Hz, 1H), 1.26 (m, 2H), 1.15 (m, 2H), 0.97 (m, 4H).

Example 120

4-(2-Cyclopropyl-4-(pentan-3-yl)-1H-benzo[d]imidazol-6-yl)-3,5-dimethylisoxazole (1020-120)

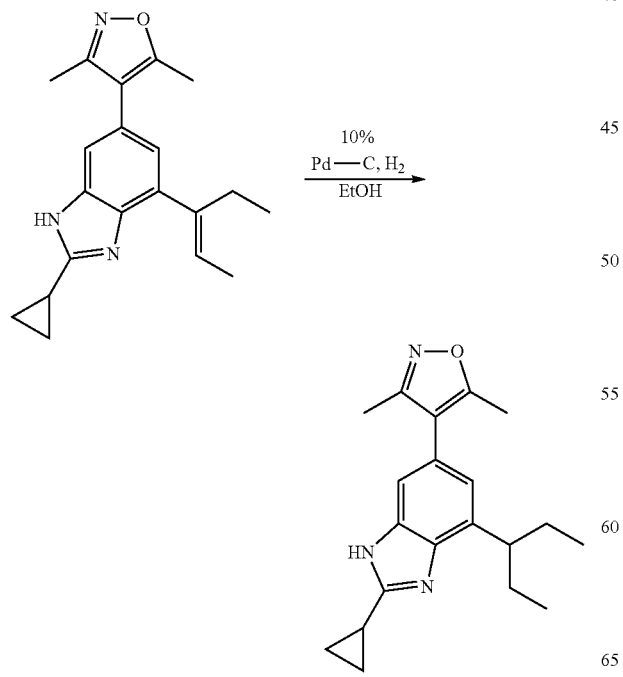

Into a flask containing 4-(2-cyclopropyl-4-(pent-2-en-3-yl)-1H-benzo[d]imidazol-6-yl)-3,5-dimethylisoxazole (20 mg, 0.062 mmol, 1 equiv.) (Example 112) was added Pd—C (30 mg, 10%) and ethanol (5 mL). The suspension was stirred under a hydrogen atmosphere for an hour. After the solid was filtered off and the filtrate was concentrated in vacuo. Purification was carried out by reverse phase HPLC to furnish 4-(2-cyclopropyl-4-(pentan-3-yl)-1H-benzo[d]imidazol-6-yl)-3,5-dimethylisoxazole.

LCMS (m/z+1) 324.22. $^1$H NMR (400 MHz, cd$_3$od) δ 7.21 (s, 1H), 6.88 (s, 1H), 2.38 (s, 3H), 2.23 (s, 3H), 2.18 (s, 1H), 1.93-1.78 (m, 3H), 1.78-1.63 (m, 3H), 1.13 (d, J=7.4 Hz, 5H), 0.80 (t, J=7.4 Hz, 7H).

Examples 121-122

Cyclopentyl(2-cyclopropyl-6-(3,5-dimethylisoxazol-4-yl)-1H-benzo[d]imidazol-4-yl)methanol (1020-121); and Dicyclopentyl(2-cyclopropyl-6-(3,5-dimethylisoxazol-4-yl)-1H-benzo[d]imidazol-4-yl)methanol (1020-122)

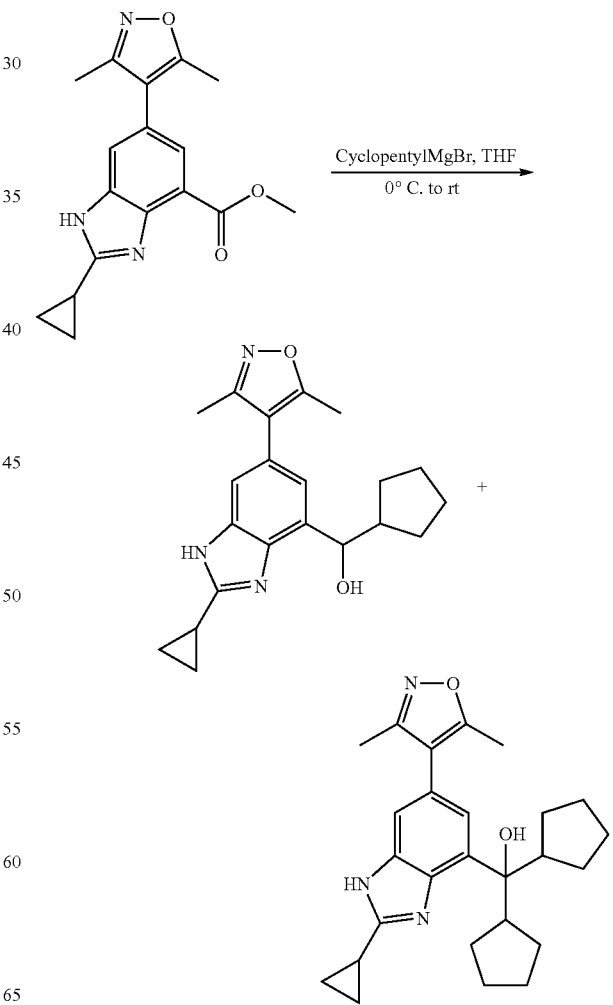

203

Into a flask containing methyl 2-cyclopropyl-6-(3,5-dimethylisoxazol-4-yl)-1H-benzo[d]imidazole-4-carboxylate (45 mg, 0.14 mmol, 1 equiv) (Example 107, Step 4) was added THF (4 mL, 0.05 M) before being cooled to 0° C. Cyclopentylmagnesium bromide (0.29 mL, 1.15 mmol, 4 equiv., 2M Diethyl ether) was added slowly and the reaction was allowed to warm up to room temperature. After the starting material was consumed, the reaction was partitioned between water and ethyl acetate. The organic layer was washed with brine and dried over sodium sulfate. Purification was carried out by reverse phase HPLC to furnish two products:

Cyclopentyl(2-cyclopropyl-6-(3,5-dimethylisoxazol-4-yl)-1H-benzo[d]imidazol-4-yl)methanol: LCMS (m/z+1) 352.02. $^1$H NMR (400 MHz, cd$_3$od) δ 7.26 (s, 1H), 6.88 (s, 1H), 2.57 (s, 2H), 2.38 (s, 3H), 2.22 (s, 5H), 1.83 (s, 3H), 1.47 (s, 5H), 1.12 (d, J=7.2 Hz, 5H).

Dicyclopentyl(2-cyclopropyl-6-(3,5-dimethylisoxazol-4-yl)-1H-benzo[d]imidazol-4-yl)methanol: LCMS (m/z+1) 420.03. $^1$H NMR (400 MHz, cd$_3$od) δ 7.26 (s, 1H), 7.08 (s, 1H), 2.46-2.31 (m, 4H), 2.31-2.15 (m, 4H), 1.84 (s, 1H), 1.77-1.45 (m, 58H), 1.33 (dd, J=19.7, 11.9 Hz, 7H), 1.13 (d, J=7.8 Hz, 6H).

Examples 123-124

(S)-Cyclopentyl(2-cyclopropyl-6-(3,5-dimethylisoxazol-4-yl)-1H-benzo[d]imidazol-4-yl)methanol (1020-123) and (R)-Cyclopentyl(2-cyclopropyl-6-(3,5-dimethylisoxazol-4-yl)-1H-benzo[d]imidazol-4-yl)methanol (1020-124)

204

-continued

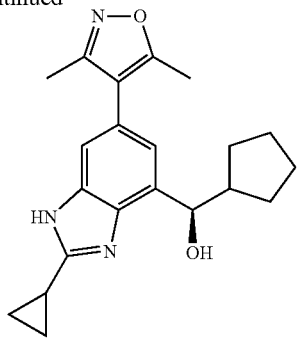

The enantiomers of compound 1020-121 were separated by chiral column (DAICEL Chirapak-IC, heptane:EtOH (80:20)).

(S)-Cyclopentyl(2-cyclopropyl-6-(3,5-dimethylisoxazol-4-yl)-1H-benzo[d]imidazol-4-yl)methanol: LCMS (m/z+1) 352.02. $^1$H NMR (400 MHz, cd$_3$od) S 7.26 (s, 1H), 6.88 (s, 1H), 2.57 (s, 2H), 2.38 (s, 3H), 2.22 (s, 5H), 1.83 (s, 3H), 1.47 (s, 5H), 1.12 (d, J=7.2 Hz, 5H).

(R)-Cyclopentyl(2-cyclopropyl-6-(3,5-dimethylisoxazol-4-yl)-1H-benzo[d]imidazol-4-yl)methanol: LCMS (m/z+1) 352.02. $^1$H NMR (400 MHz, cd$_3$od) δ 7.26 (s, 1H), 6.88 (s, 1H), 2.57 (s, 2H), 2.38 (s, 3H), 2.22 (s, 5H), 1.83 (s, 3H), 1.47 (s, 5H), 1.12 (d, J=7.2 Hz, 5H).

Examples 125-126

1-(2-Cyclopropyl-6-(3,5-dimethylisoxazol-4-yl)-1H-benzo[d]imidazol-4-yl)-2-methylpropan-1-ol (1020-125); and 3-(2-Cyclopropyl-6-(3,5-dimethylisoxazol-4-yl)-1H-benzo[d]imidazol-4-yl)-2,4-dimethylpentan-3-ol (1020-126)

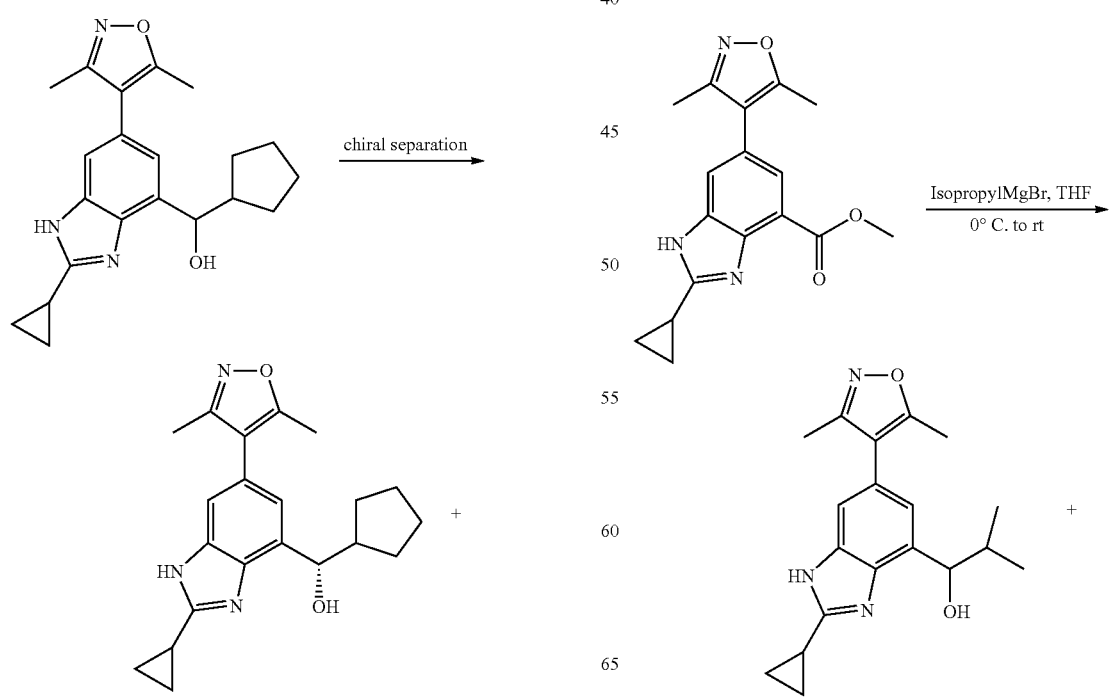

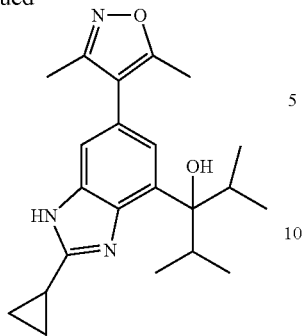

Into a flask containing methyl 2-cyclopropyl-6-(3,5-dimethylisoxazol-4-yl)-1H-benzo[d]imidazole-4-carboxylate (40 mg, 0.13 mmol, 1 equiv) (Example 107, Step 4) was added THF (4 mL, 0.05 M) before being cooled to 0° C. Isopropylmagnesium bromide (0.60 mL, 0.77 mmol, 6 equiv., 2M Diethyl ether) was added slowly and the reaction was allowed to warm up to room temperature. After the starting material was consumed, the reaction was partitioned between water and ethyl acetate. The organic layer was washed with brine and dried over sodium sulfate. Purification was carried out by reverse phase HPLC to furnish two products:

1-(2-Cyclopropyl-6-(3,5-dimethylisoxazol-4-yl)-1H-benzo[d]imidazol-4-yl)-2-methylpropan-1-ol: LCMS (m/z+1) 326.01. $^1$H NMR (400 MHz, cdcl$_3$) δ 7.36 (s, 1H), 6.81 (s, 1H), 4.70 (d, J=6.6 Hz, 1H), 2.36 (s, 3H), 2.22 (s, 3H), 2.14 (dd, J=13.2, 6.9 Hz, 3H), 1.26 (d, J=18.0 Hz, 4H), 1.15 (d, J=6.7 Hz, 2H), 1.05 (d, J=6.6 Hz, 4H), 0.88 (d, J=6.8 Hz, 5H).

3-(2-Cyclopropyl-6-(3,5-dimethylisoxazol-4-yl)-1H-benzo[d]imidazol-4-yl)-2,4-dimethylpentan-3-ol: LCMS (m/z+1) 368.03. $^1$H NMR (400 MHz, cdcl$_3$) δ 7.45 (s, 1H), 6.80 (s, 1H), 2.49-2.28 (m, 6H), 2.21 (d, J=15.9 Hz, 4H), 1.36 (s, 2H), 1.27-1.10 (m, 3H), 0.85 (dt, J=18.2, 9.1 Hz, 12H).

Example 127

4-(2-Cyclopropyl-6-(3,5-dimethylisoxazol-4-yl)-1H-benzo[d]imidazol-4-yl)heptan-4-ol (1020-127)

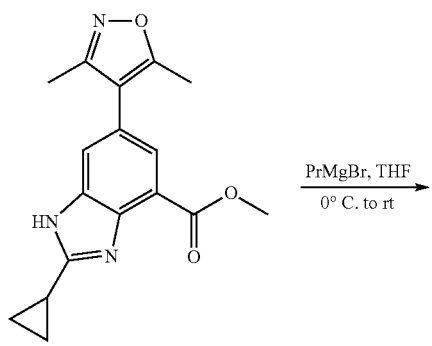

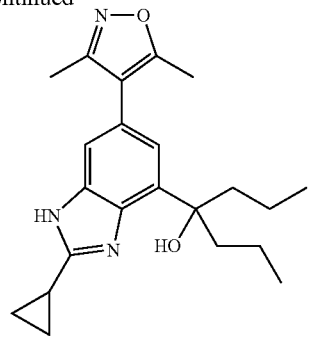

Into a flask containing methyl 2-cyclopropyl-6-(3,5-dimethylisoxazol-4-yl)-1H-benzo[d]imidazole-4-carboxylate (50 mg, 0.16 mmol, 1 equiv) (Example 101, Step 4) was added THF (3 mL, 0.05 M) before being cooled to 0° C. Isopropylmagnesium bromide (0.53 mL, 1.15 mmol, 6 equiv., 27% THF) was added slowly and the reaction was allowed to warm up to room temperature. After the starting material was consumed, the reaction was partitioned between water and ethyl acetate. The organic layer was washed with brine and dried over sodium sulfate. Purification was carried out by reverse phase HPLC to furnish 4-(2-cyclopropyl-6-(3,5-dimethylisoxazol-4-yl)-1H-benzo[d]imidazol-4-yl)heptan-4-ol.

LCMS (m/z+1) 368.22. $^1$H NMR (400 MHz, cdcl$_3$) δ 7.38 (s, 1H), 6.71 (s, 1H), 2.38 (d, J=5.8 Hz, 3H), 2.24 (d, J=7.2 Hz, 3H), 2.10 (s, 1H), 1.99 (dd, J=14.4, 7.4 Hz, 2H), 1.90 (td, J=14.7, 7.4 Hz, 2H), 1.46 (s, 2H), 1.30 (s, 2H), 1.17 (s, 1H), 0.84 (t, J=7.4 Hz, 6H).

Example 128

4-(2-Cyclopropyl-4-(hept-3-en-4-yl)-1H-benzo[d]imidazol-6-yl)-3,5-dimethylisoxazole (1020-128)

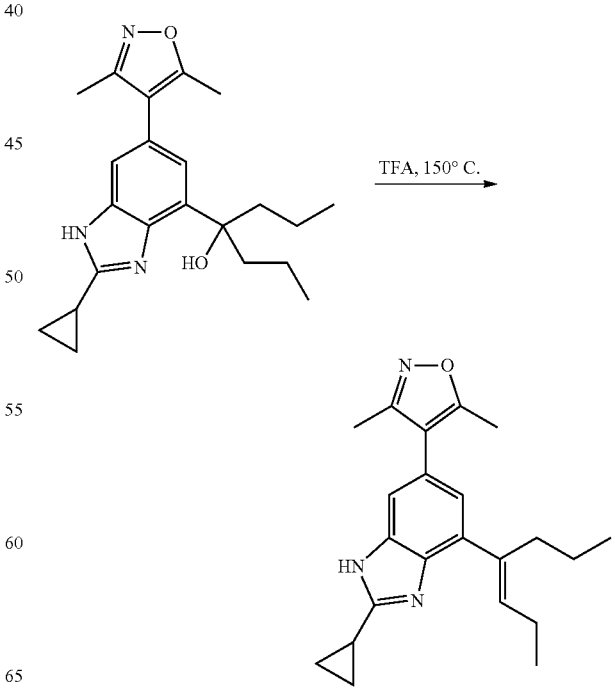

Into a microwave vial was placed 4-(2-cyclopropyl-6-(3,5-dimethylisoxazol-4-yl)-1H-benzo[d]imidazol-4-yl)heptan-4-ol (24 mg, 0.068 mmol, 1 equiv) (Example 120) and TFA (4 ml). The reaction was subjected to microwave irradiation at 150° C. for 30 minutes. Following completion of reaction, the mixture was concentrated in vacuo and the reaction was partitioned between water and ethyl acetate. The organic layer was washed with saturated NaHCO3 solution and brine and dried over sodium sulfate. Purification was carried out by reverse phase HPLC to furnish 4-(2-cyclopropyl-4-(hept-3-en-4-yl)-1H-benzo[d]imidazol-6-yl)-3,5-dimethylisoxazole as a mixture of E/Z isomers.

LCMS (m/z+1) 350.21. $^1$H NMR (400 MHz, cd$_3$od) δ 7.28 (s, 1H), 7.24 (d, J=1.4 Hz, 1H), 6.88 (d, J=1.5 Hz, 1H), 6.77 (d, J=1.5 Hz, 1H), 5.68 (dd, J=15.7, 8.5 Hz, 2H), 2.61 (t, J=7.4 Hz, 2H), 2.55-2.39 (m, 2H), 2.39-2.28 (m, 4H), 2.28-2.10 (m, 5H), 1.85 (dd, J=15.0, 7.6 Hz, 1H), 1.31 (dt, J=14.9, 7.4 Hz, 3H), 1.20-1.01 (m, 7H), 0.88 (dt, J=13.1, 7.5 Hz, 5H).

Example 129

4-(2-Cyclopropyl-4-(heptan-4-yl)-1H-benzo[d]imidazol-6-yl)-3,5-dimethylisoxazole (1020-129)

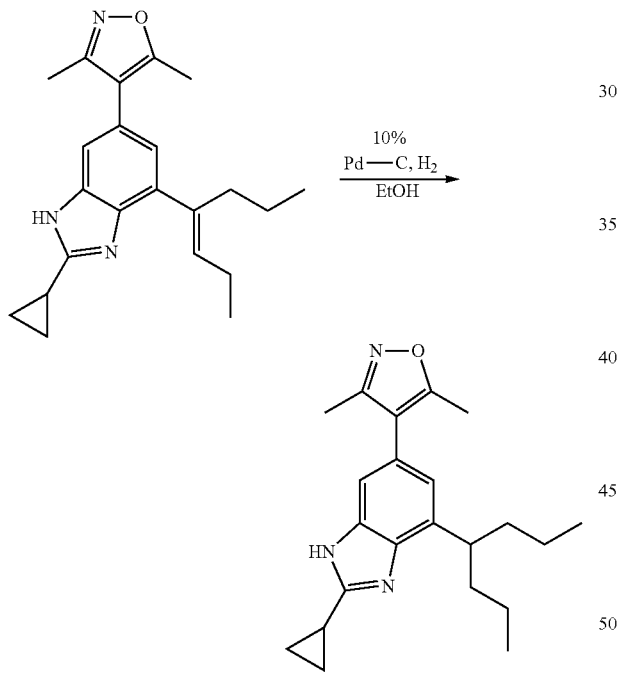

Into a flask containing 4-(2-cyclopropyl-4-(hept-3-en-4-yl)-1H-benzo[d]imidazol-6-yl)-3,5-dimethylisoxazole (16 mg, 0.045 mmol, 1 equiv.) (Example 121) was added Pd—C (30 mg, 10% Pd—C) and ethanol (5 mL). The suspension was stirred under a hydrogen atmosphere for an hour. After the solid was filtered off and the filtrate was concentrated in vacuo. Purification was carried out by reverse phase HPLC to furnish 4-(2-cyclopropyl-4-(heptan-4-yl)-1H-benzo[d]imidazol-6-yl)-3,5-dimethylisoxazole.

LCMS (m/z+1) 352.26. $^1$H NMR (400 MHz, cd$_3$od) δ 7.19 (s, 1H), 6.89 (s, 1H), 3.18 (s, 1H), 2.39 (s, 3H), 2.21 (d, J=10.4 Hz, 3H), 2.18 (d, J=7.0 Hz, 1H), 1.72 (dd, J=15.2, 7.4 Hz, 4H), 1.37-1.17 (m, 3H), 1.12 (dd, J=14.5, 6.7 Hz, 6H), 0.84 (t, J=7.4 Hz, 7H).

Example 130-131

Methyl 2-cyclopropyl-6-(3,5-dimethylisoxazol-4-yl)-1-methyl-1H-benzo[d]imidazole-4-carboxylate (1020-130); and Methyl 2-cyclopropyl-5-(3,5-dimethylisoxazol-4-yl)-1-methyl-1H-benzo[d]imidazole-7-carboxylate (1020-131)

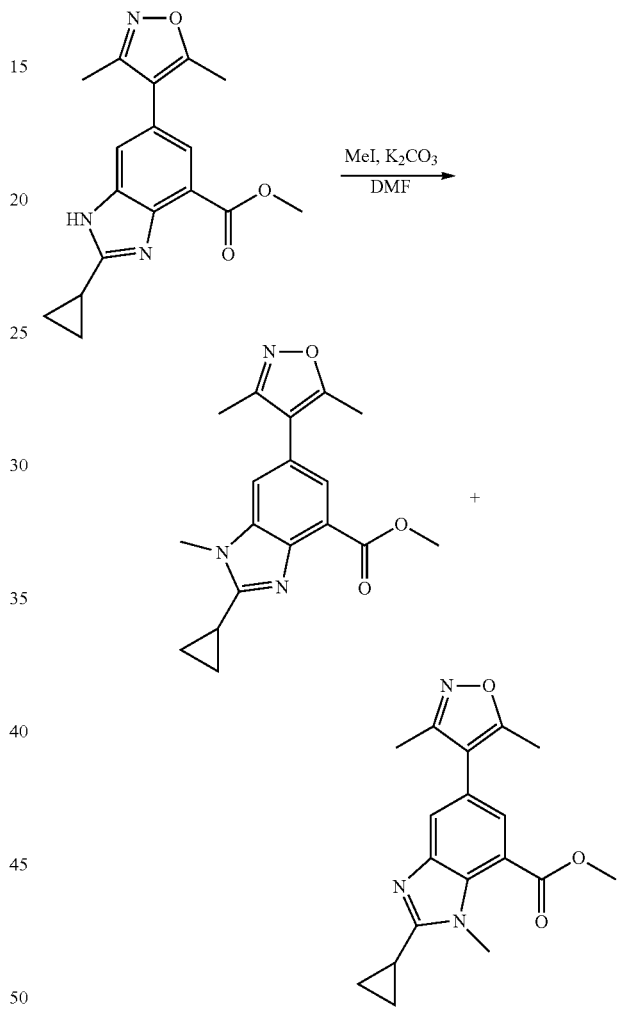

Into a flask containing methyl 2-cyclopropyl-6-(3,5-dimethylisoxazol-4-yl)-1H-benzo[d]imidazole-4-carboxylate (500 mg, 1.60 mmol, 1 equiv.) (Example 107, Step 4) was added DMF (16, 0.1 M) and cesium carbonate (1560 mg, 4.81 mmol, 3 equiv.). To this was then added iodomethane (0.30 mL, 4.81 mmol, 3 equiv.). The reaction was allowed to stir overnight and showed consumption of starting material. After the starting material was consumed, the reaction was partitioned between water and ethyl acetate. The organic layer was washed with brine and dried over sodium sulfate. Purification on silica gel (rf=0.3 in 20% ethyl acetate in hexanes) separated the two isomers (1:1 ratio):

Methyl 2-cyclopropyl-6-(3,5-dimethylisoxazol-4-yl)-1-methyl-1H-benzo[d]imidazole-4-carboxylate: LCMS (m/z+1) 326.16. $^1$H NMR (400 MHz, cd3od) δ 7.72 (d, J=1.6 Hz, 9H), 7.64 (d, J=1.6 Hz, 8H), 3.95 (d, J=4.2 Hz, 52H), 2.41 (s, 27H), 2.34-2.16 (m, 37H), 1.34-1.22 (m, 19H), 1.22-1.08 (m, 22H).

Methyl 2-cyclopropyl-5-(3,5-dimethylisoxazol-4-yl)-1-methyl-1H-benzo[d]imidazole-7-carboxylate: LCMS (m/z+1) 326.16. $^1$H NMR (400 MHz, cd$_3$od) δ 7.63 (d, J=1.6 Hz, 1H), 7.61 (d, J=1.6 Hz, 1H), 4.03 (s, 3H), 3.97 (s, 3H), 2.41 (d, J=15.6 Hz, 3H), 2.31-2.17 (m, 4H), 1.19 (dt, J=8.2, 2.9 Hz, 2H), 1.16-1.08 (m, 2H).

Example 132

3-(2-Cyclopropyl-6-(3,5-dimethylisoxazol-4-yl)-1-methyl-1H-benzo[d]imidazol-4-yl)pentan-3-ol (1020-132)

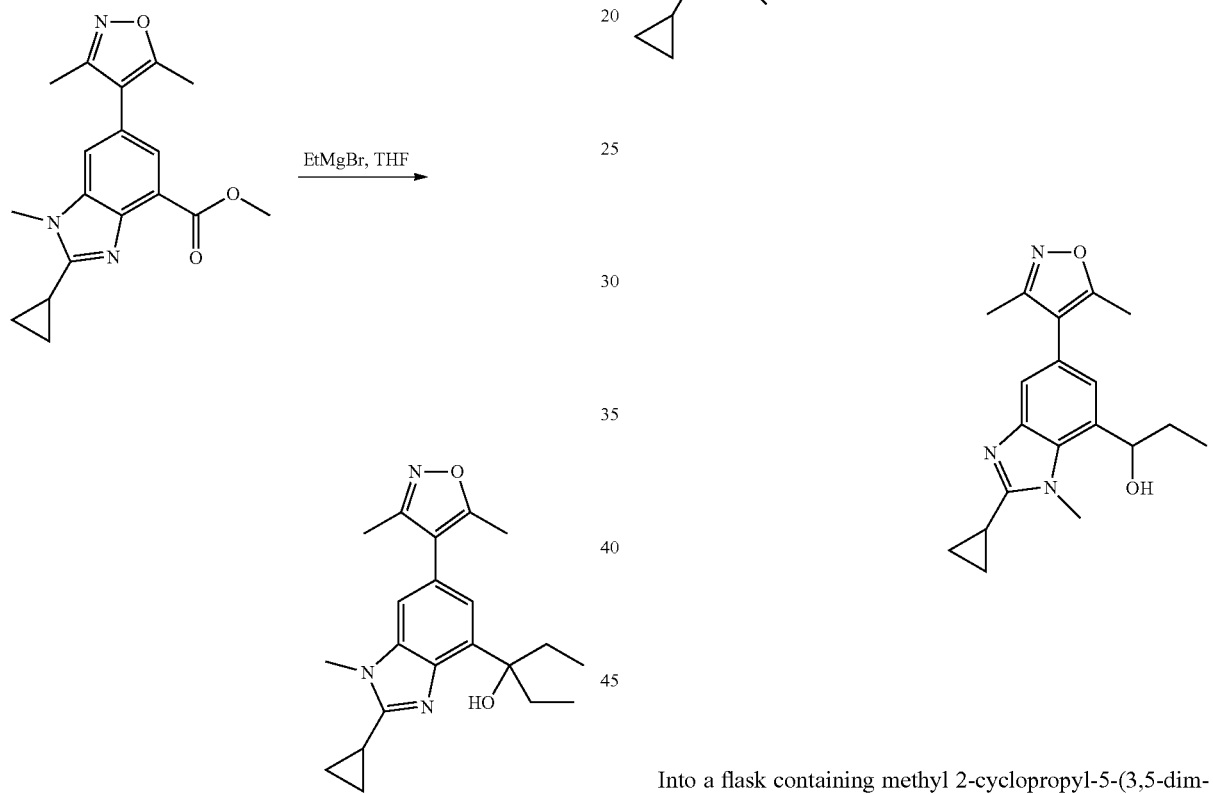

Into a flask containing methyl 2-cyclopropyl-6-(3,5-dimethylisoxazol-4-yl)-1-methyl-1H-benzo[d]imidazole-4-carboxylate (35 mg, 0.11 mmol, 1 equiv) (Example 130) was added THF (4 mL, 0.05 M) before being cooled to 0° C. Ethylmagnesium bromide (0.22 mL, 1.15 mmol, 6 equiv., 3M hexanes) was added slowly and the reaction was allowed to warm up to room temperature. After the starting material was consumed, the reaction was partitioned between water and ethyl acetate. The organic layer was washed with brine and dried over sodium sulfate. Purification was carried out by reverse phase HPLC to afford the title compound.

LCMS (m/z+1) 354.00. $^1$H NMR (400 MHz, cd$_3$od) δ 7.22 (d, J=1.3 Hz, 1H), 6.92 (d, J=1.3 Hz, 1H), 3.88 (s, 3H), 2.40 (s, 3H), 2.23 (d, J=10.0 Hz, 3H), 2.18 (td, J=8.0, 4.0 Hz, 1H), 2.08 (dq, J=14.8, 7.4 Hz, 2H), 1.86 (dq, J=14.6, 7.4 Hz, 2H), 1.23-0.99 (m, 4H), 0.72 (t, J=7.4 Hz, 6H).

Example 133

1-(2-Cyclopropyl-5-(3,5-dimethylisoxazol-4-yl)-1-methyl-1H-benzo[d]imidazol-7-yl)propan-1-ol (1020-133)

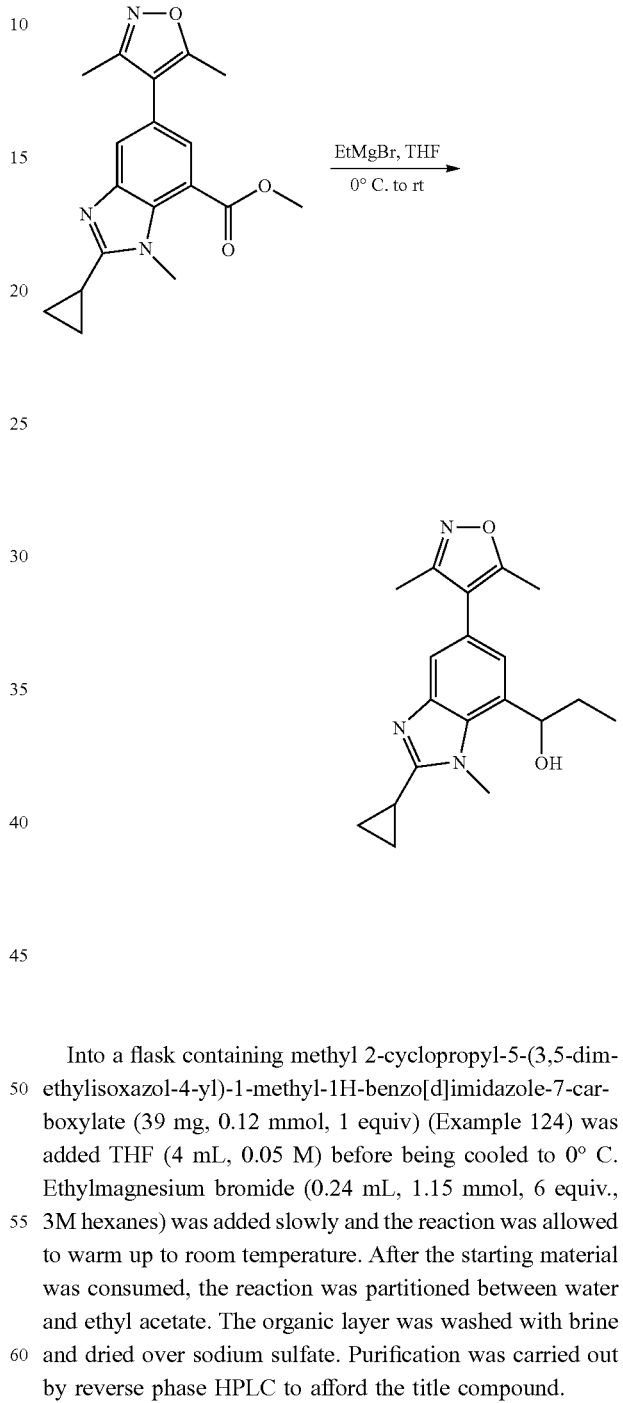

Into a flask containing methyl 2-cyclopropyl-5-(3,5-dimethylisoxazol-4-yl)-1-methyl-1H-benzo[d]imidazole-7-carboxylate (39 mg, 0.12 mmol, 1 equiv) (Example 124) was added THF (4 mL, 0.05 M) before being cooled to 0° C. Ethylmagnesium bromide (0.24 mL, 1.15 mmol, 6 equiv., 3M hexanes) was added slowly and the reaction was allowed to warm up to room temperature. After the starting material was consumed, the reaction was partitioned between water and ethyl acetate. The organic layer was washed with brine and dried over sodium sulfate. Purification was carried out by reverse phase HPLC to afford the title compound.

LCMS (m/z+1) 326.22. $^1$H NMR (400 MHz, cd$_3$od) δ 7.35 (d, J=1.6 Hz, 7H), 7.23 (d, J=1.4 Hz, 8H), 5.30 (dd, J=7.4, 5.8 Hz, 9H), 4.17 (s, 22H), 2.39 (s, 20H), 2.31-2.20 (m, 23H), 2.20-2.13 (m, 7H), 2.02-1.80 (m, 18H), 1.23-0.97 (m, 53H).

Example 134

3-(2-Amino-6-(3,5-dimethylisoxazol-4-yl)-1H-benzo[d]imidazol-4-yl)pentan-3-ol (1020-134)

Step 1

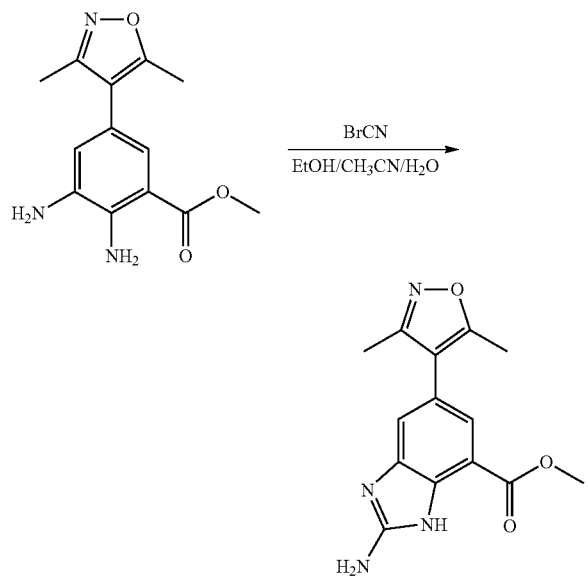

Into a flask containing methyl 2,3-diamino-5-(3,5-dimethylisoxazol-4-yl)benzoate (155 mg, 0.59 mmol, 1 equiv.) was added EtOH (2 mL), H$_2$O (2 mL) and CH$_3$CN (2 mL) before cyanogen bromide (75 mg, 0.71 mmol, 1.2 equiv.) was added. After an hour, at room temperature, the reaction was then warmed 65° C. After the reaction was complete, it was concentrated in vacuo and then washed with dilute sodium bicarbonate solution. A precipitate formed and was filtered and washed with water and warm ethanol to afford the product.

LCMS (m/z+1) 286.96. $^1$H NMR (400 MHz, cd$_3$od) δ 7.41 (d, J=1.4 Hz, 1H), 7.25 (d, J=1.4 Hz, 1H), 3.90 (s, 3H), 2.31 (s, 3H), 2.15 (s, 3H), 1.94 (s, 1H).

Step 2

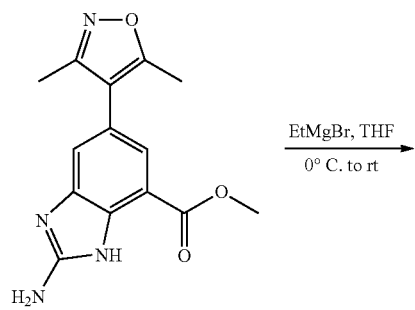

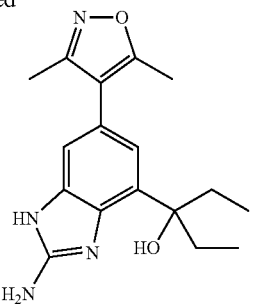

Into a flask containing methyl 2-amino-5-(3,5-dimethyl-isoxazol-4-yl)-1H-benzo[d]imidazole-7-carboxylate (30 mg, 0.09 mmol, 1 equiv) (Example 127) was added THF (4 mL, 0.05 M) before being cooled to 0° C. Ethylmagnesium bromide (0.29 mL, 0.88 mmol, 10 equiv., 3M Hexanes) was added slowly and the reaction was allowed to warm up to room temperature. After the starting material was consumed, the reaction was partitioned between water and ethyl acetate. The organic layer was washed with brine and dried over sodium sulfate. Purification was carried out by reverse phase HPLC to afforded the title compound.

LCMS (m/z+1) 314.91. $^1$H NMR (400 MHz, cd$_3$od) δ 7.00 (d, J=1.4 Hz, 2H), 6.67 (d, J=1.3 Hz, 2H), 2.38 (d, J=2.9 Hz, 6H), 2.22 (d, J=3.1 Hz, 6H), 2.05-1.91 (m, 4H), 1.91-1.72 (m, 5H), 0.79 (dd, J=9.1, 5.7 Hz, 13H).

Example 135

4,4'-(2-Cyclopropyl-1H-benzo[d]imidazole-4,6-diyl)bis(3,5-dimethylisoxazole) (1020-135)

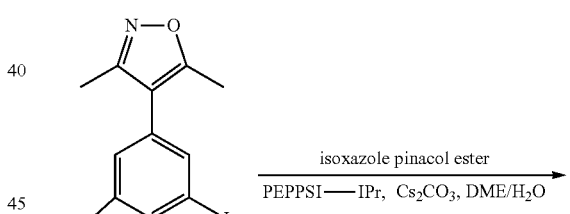

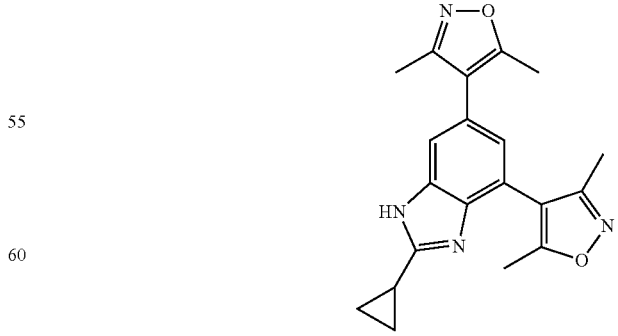

To a flask containing 4-(2-cyclopropyl-4-iodo-1H-benzo[d]imidazol-6-yl)-3,5-dimethylisoxazole (650 mg, 1.7 mmol, 1 equiv.) (Example 8, Step 5) was added 3,5-Dimethylisoxazole-4-boronic acid pinacol ester (840 mg, 3.8 mmol, 2.2 equiv.), $Cs_2CO_3$ (1.67 gm, 5.1 mmol, 3 equiv.) and PEPPSI™-IPr catalyst (120 mg, 0.2 mmol, 0.1 equiv.) and dissolved in DME-$H_2O$ (20 mL, 0.2 M, 2/1, v/v). The mixture was heated to 125° C. After 3 hr, the reaction was complete. After cooling, the reaction was extracted with EtOAc and washed with water, saturated $NH_4Cl$. After drying with $MgSO_4$, it was filtered and concentrated to dryness. The resulting solid was washed with EtOAc. A mustard yellow solid was obtained as the title compound.

LCMS (m/z+1) 349.13. $^1H$ NMR (400 MHz, $cd_3od$) δ 7.39 (s, 2H), 6.99 (d, J=1.5 Hz, 2H), 3.64 (s, 2H), 2.42 (s, 6H), 2.35 (s, 6H), 2.26 (s, 6H), 2.20 (s, 6H), 2.15 (s, 3H), 1.15 (s, 9H).

Example 136

1-(2-Cyclopropyl-6-(3,5-dimethylisoxazol-4-yl)-1H-benzo[d]imidazol-4-yl)-5-methylpyrrolidin-2-one (1020-136)

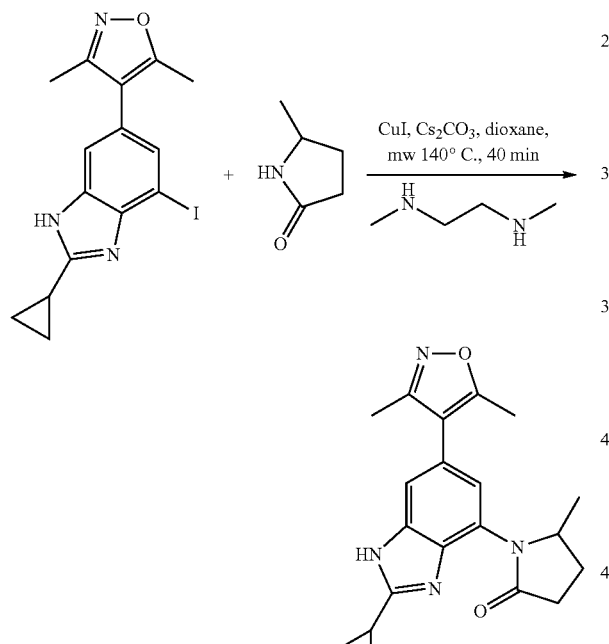

To a mixture of 4-(2-cyclopropyl-4-iodo-1H-benzo[d]imidazol-6-yl)-3,5-dimethylisoxazole (30 mg, 0.08 mmol) (Example 8, Step 4), 5-methylpyrrolidin-2-one (100 mg, 1.00 mmol), copper(I) iodide (15 mg, 0.08 mmol), cesium carbonate (163 mg, 0.50 mmol) in 1,4-dioxane (2 mL) under nitrogen was added N,N-dimethylethane-1,2-diamine (14 mg, 0.16 mmol). The reaction mixture in a microwave vial was purged with dry nitrogen, capped, heated to 140° C. in a microwave reactor for about 40 minutes. The mixture was cooled, diluted with ethyl acetate (10 mL), filtered through a layer of celite, then partitioned between water and ethyl acetate, the aqueous phase was extracted with ethyl acetate twice, and the combined organic phase was washed with 1M aqueous K2CO3, 30% aqueous ammonium chloride, brine, dried and concentrated. The crude product was purified by reverse phase HPLC eluting with 0.1% TFA-containing acetonitrile/water to afford the title compound.

$C_{20}H_{22}N_4O_2$. 351.2 (M+1). $^1H$ NMR (DMSO-$d_6$) δ 7.54 (s, 1H), 7.32 (s, 1H), 4.55 (m, 1H), 2.59 (m, 2H), 2.40-2.51 (m, 6H), 2.28 (s, 3H), 1.83 (m, 1H), 1.39 (m, 4H), 1.14 (d, J=6.2 Hz, 3H).

Example 137

1-(2-Cyclopropyl-6-(3,5-dimethylisoxazol-4-yl)-1H-benzo[d]imidazol-4-yl)-5-ethylpyrrolidin-2-one (1020-137)

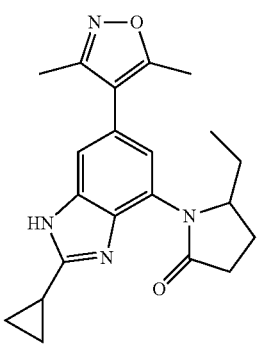 [SMILES: CCC1CCC(=O)N1c1cc(-c2c(C)noc2C)cc2[nH]c(C3CC3)nc12]

Compound 1020-137 was synthesized from 4-(2-cyclopropyl-4-iodo-1H-benzo[d]imidazol-6-yl)-3,5-dimethylisoxazole and 5-ethylpyrrolidin-2-one, using similar conditions as described in Example 136.

$C_{21}H_{24}N_4O_2$. 365.2 (M+1). $^1H$ NMR (DMSO-d6) δ 7.47 (s, 1H), 7.25 (s, 1H), 4.87 (m, 1H), 2.59 (m, 2H), 2.45 (s, 3H), 2.30-2.43 (m, 3H), 2.27 (s, 3H), 1.80-2.00 (m, 1H), 1.54 (m, 1H), 1.20-1.45 (m, 5H), 0.85 (t, J=7.4 Hz, 3H).

Example 138

(S)-1-(2-Cyclopropyl-6-(3,5-dimethylisoxazol-4-yl)-1H-benzo[d]imidazol-4-yl)-5-(trifluoromethyl)pyrrolidin-2-one (1020-138)

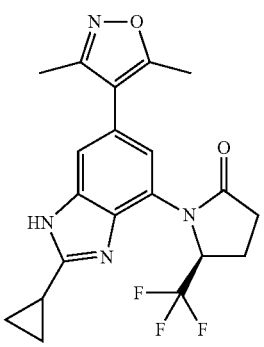 [SMILES: Cc1noc(C)c1-c1cc(N2C(=O)CC[C@H]2C(F)(F)F)c2nc(C3CC3)[nH]c2c1]

Compound 1020-138 was synthesized from 4-(2-cyclopropyl-4-iodo-1H-benzo[d]imidazol-6-yl)-3,5-dimethylisoxazole and 5-trifluoromethylpyrrolidin-2-one using similar conditions as described in Example 136.

$C_{20}H_{19}F_3N_4O_2$. 405.1 (M+1). $^1H$ NMR (DMSO-d6) δ 7.47 (s, 1H), 7.32 (s, 1H), 5.60 (m, 1H), 2.52-2.80 (m, 2H), 2.48-2.50 (m, 4H), 2.40-2.47 (m, 6H), 1.23 (m, 4H).

Example 139

2-Amino-N-cyclopentyl-6-(3,5-dimethylisoxazol-4-yl)-1H-benzo[d]imidazole-4-sulfonamide (1020-139)

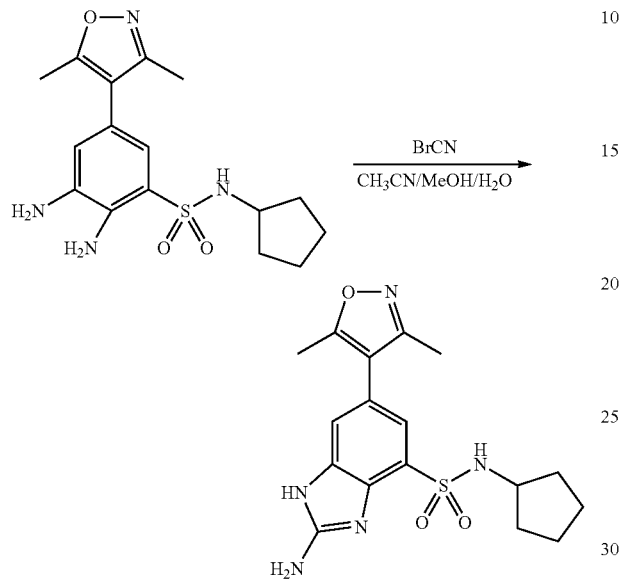

2,3-diamino-N-cyclopentyl-5-(3,5-dimethylisoxazol-4-yl)benzenesulfonamide (17 mg, 0.05 mmol) (Example 1, Step 8) was dissolved in MeOH (1 mL). The solution was added slowly to a stirred solution of 5M BrCN in acetonitrile (11 ul) in water (1 mL). The reaction was stirred at RT for 1 h before being evaporated under vacuum. The residue was purified with Prep HPLC (0-100% CH3CN/H2O) to afford the title compound.

$C_{17}H_{21}N_5O_3S$. 376.0 (M+1). $^1$H NMR (400 MHz, CD$_3$OD) δ 7.57 (s, 1H), 7.53 (s, 1H), 3.67-3.63 (m, 1H), 2.42 (s, 3H), 2.21 (s, 3H), 1.78-1.61 (m, 4H), 1.50-1.38 (m, 4H).

Example 140

N-Cyclopentyl-6-(3,5-dimethylisoxazol-4-yl)-2-(hydroxymethyl)-1H-benzo[d]imidazole-4-sulfonamide (1020-140)

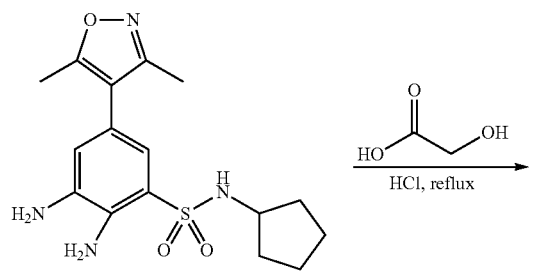

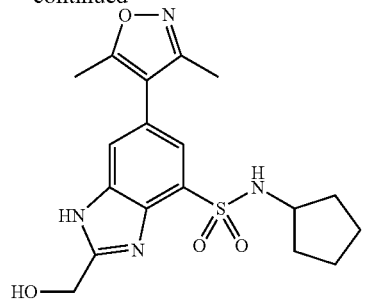

2,3-Diamino-N-cyclopentyl-5-(3,5-dimethylisoxazol-4-yl)benzenesulfonamide (20 mg, 0.06 mmol) (Example 1, Step 8) was dissolved in 4N HCl (2 mL). To the above solution was added glycolic acid (13 mg, 017 mmol). The reaction was refluxed overnight before being evaporated under vacuum. The residue was purified with Prep HPLC (0-100% CH3CN/H2O) to afford the title compound.

$C_{15}H_{22}N_4O_4S$. 391.1 (M+1). $^1$H NMR (400 MHz, CD$_3$OD) δ 7.88 (s, 1H), 7.81 (s, 1H), 5.08 (s, 2H), 3.68-3.65 (m, 1H), 2.46 (s, 3H), 2.29 (s, 3H), 1.73-1.61 (m, 4H), 1.49-1.46 (m, 4H).

Example 141

2-Benzyl-N-cyclopentyl-6-(3,5-dimethylisoxazol-4-yl)-1H-benzo[d]imidazole-4-sulfonamide (1020-141)

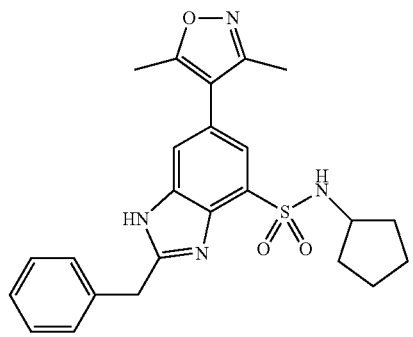 [SMILES: Cc1noc(C)c1-c1cc(S(=O)(=O)NC2CCCC2)c2nc(Cc3ccccc3)[nH]c2c1]

Compound 1020-141 was prepared in a similar manner as that of Example 7 by reacting 2,3-diamino-N-cyclopentyl-5-(3,5-dimethylisoxazol-4-yl)benzenesulfonamide (20 mg, 0.06 mmol) (Example 1, Step 8) with 2-phenylacetic acid.

$C_{24}H_{26}N_4O_3S$. 451.2 (M+1). $^1$H NMR (400 MHz, CD$_3$OD) δ 7.66 (s, 1H), 7.58 (s, 1H), 7.49-7.32 (m, 5H), 3.85 (s, 2H), 3.64-3.62 (m, 1H), 2.44 (s, 3H), 2.24 (s, 3H), 1.75-1.62 (m, 4H), 1.58-1.44 (m, 4H).

Compounds 1020-142, 1020-143, 1020-144, 1020-145, 1020-146, 1020-147, and 1020-148, were prepared in a similar fashion as N-cyclopentyl-2-(cyclopropylmethyl-amino)-6-(3,5-dimethylisoxazol-4-yl)-1H-benzo[d]imidazole-4-sulfonamide (Example 1) by substituting the appropriate commercial isothiocyanate in Example 1, Step 9:

Example 142

N-Cyclopentyl-6-(3,5-dimethylisoxazol-4-yl)-2-(phenylamino)-1H-benzo[d]imidazole-4-sulfonamide (1020-142)

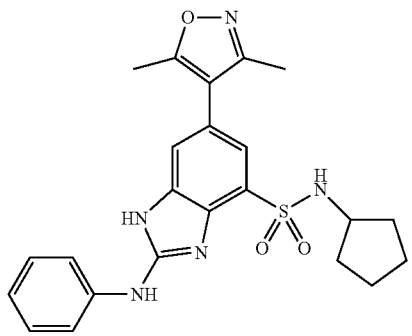 [SMILES: Cc1noc(C)c1-c1cc(S(=O)(=O)NC2CCCC2)c2nc(Nc3ccccc3)[nH]c2c1]

$C_{23}H_{25}N_5O_3S$. 452.2 (M+1). $^1$H NMR (400 MHz, CD$_3$OD) δ 7.57-7.51 (m, 6H), 7.40-7.36 (m, 1H), 3.68-3.65 (m, 1H), 2.42 (s, 3H), 2.26 (s, 3H), 1.79-1.62 (m, 4H), 1.52-1.44 (m, 4H).

Example 143

2-(Benzylamino)-N-cyclopentyl-6-(3,5-dimethylisoxazol-4-yl)-1H-benzo[d]imidazole-4-sulfonamide (1020-143)

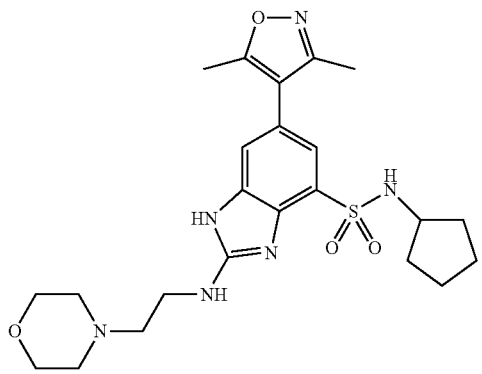 [SMILES: Cc1noc(C)c1-c1cc(S(=O)(=O)NC2CCCC2)c2nc(NCCN3CCOCC3)[nH]c2c1]

$C_{24}H_{27}N_5O_3S$. 466.2 (M+1). $^1$H NMR (400 MHz, CD$_3$OD) δ 7.56 (s, 1H), 7.51 (s, 1H), 7.48-7.34 (m, 5H), 4.74 (s, 2H), 3.65-3.62 (m, 1H), 2.42 (s, 3H), 2.24 (s, 3H), 1.79-1.64 (m, 4H), 1.58-1.48 (m, 4H).

Example 144

N-Cyclopentyl-6-(3,5-dimethylisoxazol-4-yl)-2-(2-morpholinoethylamino)-1H-benzo[d]imidazole-4-sulfonamide (1020-144)

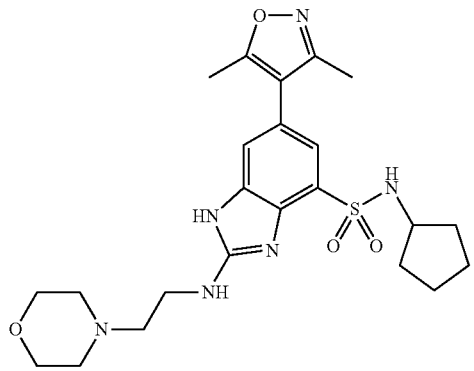 [SMILES: Cc1noc(C)c1-c1cc(S(=O)(=O)NC2CCCC2)c2nc(NCCN3CCOCC3)[nH]c2c1]

$C_{23}H_{32}N_6O_4S$. 489.2 (M+1). $^1$H NMR (400 MHz, CD$_3$OD) δ 7.61 (s, 1H), 7.59 (s, 1H), 4.74 (s, 2H), 4.08-4.01 (m, 6H), 3.67-3.64 (m, 1H), 3.60-3.48 (m, 6H), 2.44 (s, 3H), 2.27 (s, 3H), 1.74-1.64 (m, 4H), 1.51-1.42 (m, 4H).

Example 145

N-Cyclopentyl-2-(cyclopropylamino)-6-(3,5-dimethylisoxazol-4-yl)-1H-benzo[d]imidazole-4-sulfonamide (1020-145)

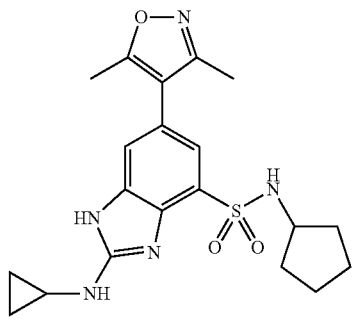 [SMILES: Cc1noc(C)c1-c1cc(S(=O)(=O)NC2CCCC2)c2nc(NC3CC3)[nH]c2c1]

$C_{20}H_{25}N_5O_3S$. 416.1 (M+1). $^1$H NMR (400 MHz, CD$_3$OD) δ 7.68 (s, 1H), 7.52 (s, 1H), 3.68-3.57 (m, 1H), 2.42 (s, 3H), 2.28 (s, 3H), 2.05-1.58 (m, 4H), 1.49-1.39 (m, 4H), 1.35-1.20 (m, 1H). 0.35-0.24 (m, 2H), 0.18-0.15 (m, 2H).

Example 146

N-Cyclopentyl-6-(3,5-dimethylisoxazol-4-yl)-2-((tetrahydrofuran-2-yl)methylamino)-1H-benzo[d]imidazole-4-sulfonamide (1020-146)

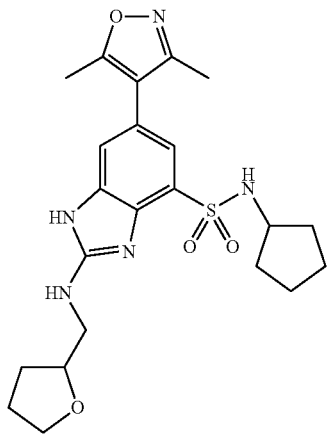 [SMILES: Cc1noc(C)c1-c1cc(S(=O)(=O)NC2CCCC2)c2nc(NCC3CCCO3)[nH]c2c1]

$C_{22}H_{29}N_5O_4S$. 460.1 (M+1). $^1$H NMR (400 MHz, CD$_3$OD) δ 7.67 (s, 1H), 7.58 (s, 1H), 3.81-3.75 (m, 2H), 3.45-3.37 (m, 2H), 3.00-2.95 (m, 1H), 2.43 (s, 3H), 2.28 (s, 3H), 2.05-1.58 (m, 8H), 1.49-1.39 (m, 4H).

Example 147

N-Cyclopentyl-6-(3,5-dimethylisoxazol-4-yl)-2-(2-methoxyethylamino)-1H-benzo[d]imidazole-4-sulfonamide (1020-147)

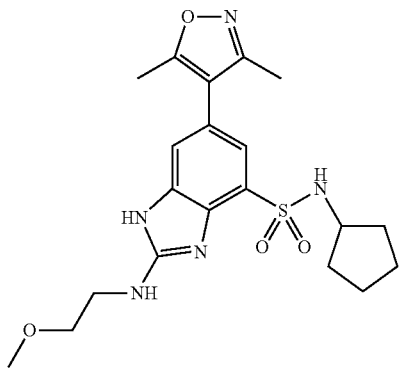 [SMILES: COCCNc1nc2c(S(=O)(=O)NC3CCCC3)cc(-c3c(C)noc3C)cc2[nH]1]

$C_{19}H_{27}N_5O_4S$. 434.2 (M+1). $^1$H NMR (400 MHz, CD$_3$OD) δ 7.78 (s, 1H), 7.62 (s, 1H), 3.60-3.48 (m, 3H), 2.43 (s, 3H), 2.27 (s, 3H), 2.02-1.59 (m, 4H), 1.48-1.32 (m, 4H).

Example 148

N-Cyclopropyl-6-(3,5-dimethylisoxazol-4-yl)-2-(2,2,2-trifluoroethylamino)-1H-benzo[d]imidazole-4-sulfonamide (1020-148)

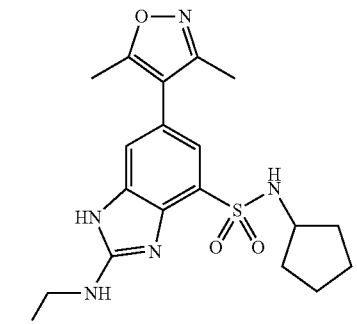

$C_{19}H_{22}F_3N_5O_3S$. 458.1 (M+1). 1H NMR (400 MHz, CD$_3$OD) δ 7.72 (s, 1H) 7.58 (s, 1H), 3.60-3.58 (m, 3H), 2.43 (s, 3H), 2.25 (s, 3H), 2.08-1.54 (m, 4H), 1.48-1.32 (m, 4H).

Examples 149 or 150

(R)-4-(2-cyclopropyl-4-(6-methylquinolin-5-yl)-1H-benzo[d]imidazol-6-yl)-3,5-dimethylisoxazole (1020-129)

and (S)-4-(2-cyclopropyl-4-(6-methylquinolin-5-yl)-1H-benzo[d]imidazol-6-yl)-3,5-dimethylisoxazole (1020-150)

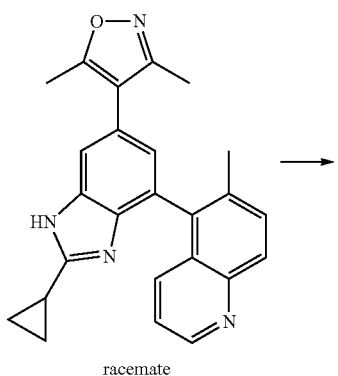

racemate

-continued

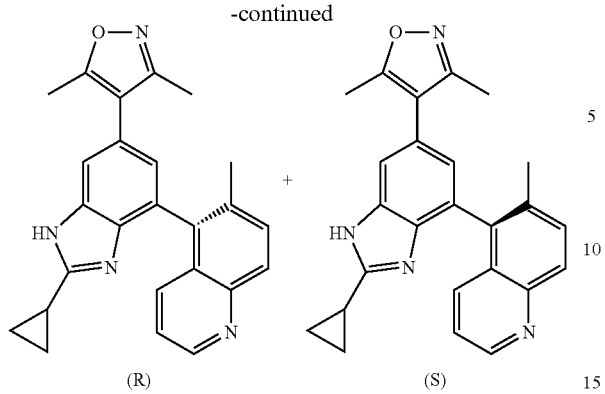

4-(2-cyclopropyl-4-(6-methylquinolin-5-yl)-1H-benzo[d]imidazol-6-yl)-3,5-dimethylisoxazole from Example 18 was optically resolved by DAICEL, Chiralapk IC, EtOAc/hexane/diethylamine=70:30:0.1.

(R)-4-(2-cyclopropyl-4-(6-methylquinolin-5-yl)-1H-benzo[d]imidazol-6-yl)-3,5-dimethylisoxazole (1020-149): retention time 5.46 min, 99.8% e.e. (entantiomeric excess).

(S)-4-(2-cyclopropyl-4-(6-methylquinolin-5-yl)-1H-benzo[d]imidazol-6-yl)-3,5-dimethylisoxazole (1020-150): retention time 5.87 min, 99.2% e.e.

Example 151

(S)-5-(2-cyclopropyl-6-(3,5-dimethylisoxazol-4-yl)-1H-benzo[d]imidazol-4-yl)-6-methylquinoline 1-oxide (1020-151)

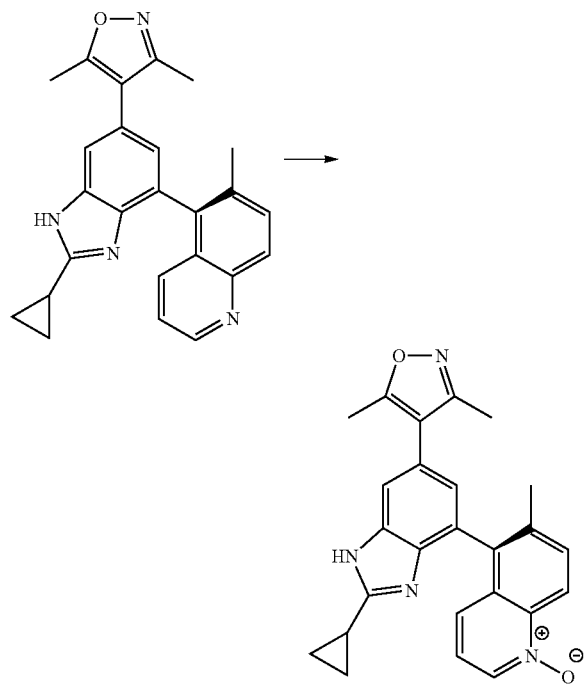

(S)-4-(2-Cyclopropyl-4-(6-methylquinolin-5-yl)-1H-benzo[d]imidazol-6-yl)-3,5-dimethylisoxazole (0.015 g) was subjected to MCPBA (0.016 g) in MeOH/DCM (1/1 ml) and stirred at RT for 24 h. Volatiles were removed and the residue purified by reverse phase HPLC (5-95% MeCN in water, 0.1% TFA) to afford (S)-5-(2-cyclopropyl-6-(3,5-dimethylisoxazol-4-yl)-1H-benzo[d]imidazol-4-yl)-6-methylquinoline 1-oxide.

LCMS (m/z+1) 411.22. $^1$H NMR (400 MHz, DMSO-d6) δ 8.58 (d, J=8.9 Hz, 1H), 8.53 (d, J=6.0 Hz, 1H), 7.84 (d, J=9.1 Hz, 2H), 7.55 (s, 2H), 7.35-7.23 (m, 1H), 7.11 (d, J=8.8 Hz, 1H), 7.01 (s, 1H), 2.42 (s, 3H), 2.24 (s, 2H), 2.21 (s, 2H).

Example 152

5-(2-cyclopropyl-5-(3,5-dimethylisoxazol-4-yl)-1-methyl-1H-benzo[d]imidazol-7-yl)-6-methylquinoline 1-oxide (1020-152)

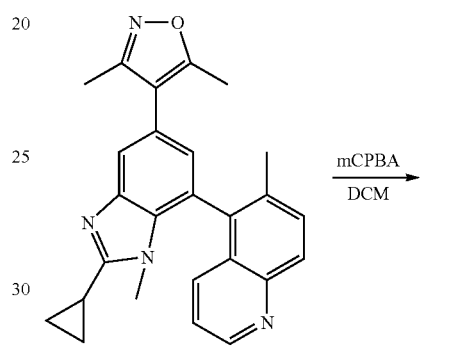

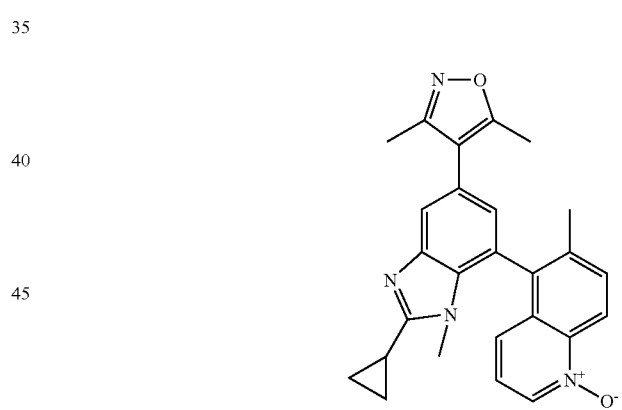

Into a flask containing 4-(2-cyclopropyl-1-methyl-7-(6-methylquinolin-5-yl)-1H-benzo[d]imidazol-5-yl)-3,5-dimethylisoxazole (120 mg, 0.29 mmol, 1 equiv. from Example 74) in DCM (5 mL) is added mCPBA (130 mg, 0.59 mmol, 2 equiv., 77%). After completion, the reaction was quenched with water and extracted with DCM and washed with water, saturated NH$_4$Cl. After drying with MgSO4, it was filtered and concentrated to dryness. Purification was carried out by reverse phase HPLC to 5-(2-cyclopropyl-5-(3,5-dimethylisoxazol-4-yl)-1-methyl-1H-benzo[d]imidazol-7-yl)-6-methylquinoline 1-oxide.

LCMS (m/z+1) 425.34. $^1$H NMR (400 MHz, Methanol-d4) δ 8.75 (d, J=6.8 Hz, 1H), 8.62 (d, J=4.2 Hz, 1H), 7.90 (d, J=5.2 Hz, 1H), 7.60 (s, 1H), 7.55-7.40 (M, 2H), 7.00 (s, 1H), 3.29 (s, 3H), 2.32 (s, 3H), 2.27 (s, 3H), 2.15-2.00 (m, 1H), 1.19-1.02 (m, 4H).

Example 153

5-(2-cyclopropyl-6-(3,5-dimethylisoxazol-4-yl)-1H-benzo[d]imidazol-4-yl)-6-methylquinolin-2(1H)-one
(1020-153)

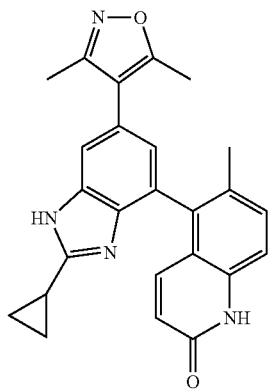 [SMILES: Cc1ccc2[nH]c(=O)ccc2c1-c1cc(-c2c(C)noc2C)cc2[nH]c(C3CC3)nc12]

5-(2-cyclopropyl-6-(3,5-dimethylisoxazol-4-yl)-1H-benzo[d]imidazol-4-yl)-6-methylquinolin-2(1H)-one was synthesized in a similar manner as that of Example 61, Step 2, using 5-bromo-6-methylquinolin-2(1H)-one.

$C_{25}H_{22}N_4O_2$. MS. 411.1 (M+1). $^1$H NMR (MeOH-$d_4$) δ 7.59 (d, J=8.5 Hz, 1H), 7.50 (s, 1H), 7.41 (d, J=8.5 Hz, 1H), 7.405 (d, J=9.8 Hz, 1H), 6.96 (d, J=1.5 Hz, 1H), 6.47 (d, J=9.8 Hz, 1H), 2.45 (s, 3H), 2.30 (s, 3H), 2.15 (s, 3H), 2.09 (quin, J=6.7 Hz, 1H), 1.18-1.06 (m, 4H).

Example 154

5-(2-cyclopropyl-6-(3,5-dimethylisoxazol-4-yl)-1H-benzo[d]imidazol-4-yl)-4-methylpyridin-2(1H)-one
(1020-154)

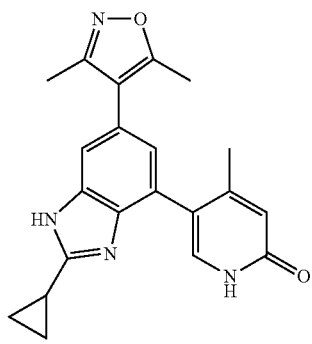 [SMILES: Cc1cc(=O)[nH]cc1-c1cc(-c2c(C)noc2C)cc2[nH]c(C3CC3)nc12]

5-(2-cyclopropyl-6-(3,5-dimethylisoxazol-4-yl)-1H-benzo[d]imidazol-4-yl)-4-methylpyridin-2(1H)-one was synthesized in a similar manner as that of Example 61, Step 2, using 5-bromo-4-methylpyridin-2(1H)-one.

$C_{21}H_{20}N_4O_2$. MS. 361.1 (M+1). $^1$H NMR (MeOH-$d_4$) δ 7.33 (s, 1H), 7.32 (d, J=1.5 Hz, 1H), 6.89 (d, J=1.5 Hz, 1H), 6.48 (br s, 1H), 2.33 (s, 3H), 2.17 (s, 3H), 2.11-2.01 (m, 1H), 2.01 (s, 3H), 1.11-1.00 (m, 4H).

Example 155

4-(2-cyclopropyl-6-(3,5-dimethylisoxazol-4-yl)-1H-benzo[d]imidazol-4-yl)-5-methylpyridin-2(1H)-one
(1020-155)

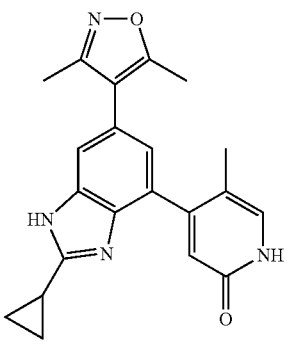 [SMILES: Cc1c[nH]c(=O)cc1-c1cc(-c2c(C)noc2C)cc2[nH]c(C3CC3)nc12]

4-(2-cyclopropyl-6-(3,5-dimethylisoxazol-4-yl)-1H-benzo[d]imidazol-4-yl)-5-methylpyridin-2(1H)-one was synthesized in a similar manner as that of Example 61, Step 2, using 4-bromo-5-methylpyridin-2(1H)-one.

$C_{21}H_{20}N_4O_2$. MS. 361.1 (M+1). $^1$H NMR (MeOH-$d_4$) δ 7.33 (s, 1H), 7.32 (d, J=1.5 Hz, 1H), 6.89 (d, J=1.5 Hz, 1H), 6.48 (br s, 1H), 2.33 (s, 3H), 2.17 (s, 3H), 2.11-2.01 (m, 1H), 2.01 (s, 3H), 1.11-1.00 (m, 4H).

Example 156

5-(2-cyclopropyl-6-(3,5-dimethylisoxazol-4-yl)-1H-benzo[d]imidazol-4-yl)-6-methylpyridin-2(1H)-one
(1020-156)

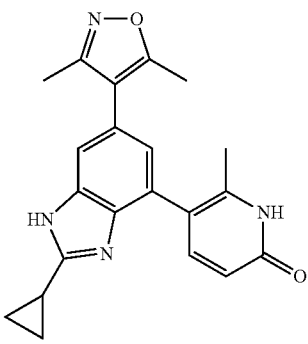 [SMILES: Cc1noc(C)c1-c1cc(-c2ccc(=O)[nH]c2C)c2nc(C3CC3)[nH]c2c1]

5-(2-cyclopropyl-6-(3,5-dimethylisoxazol-4-yl)-1H-benzo[d]imidazol-4-yl)-6-methylpyridin-2(1H)-one was synthesized in a similar manner as that of Example 61, Step 2, using 5-bromo-6-methylpyridin-2(1H)-one.

$C_{21}H_{20}N_4O_2$. MS. 361.1 (M+1). $^1$H NMR (MeOH-$d_4$) δ 7.61 (d, J=9.2 Hz, 1H), 7.41 (d, J=1.5 Hz, 1H), 7.01 (d, J=1.5 Hz, 1H), 6.51 (d, J=9.2 Hz, 1H), 2.43 (s, 3H), 2.28 (s, 3H), 2.21 (s, 3H), 2.19-2.14 (m, 1H), 1.20-1.13 (m, 4H).

Example 157

3,5-dimethyl-4-(4-(6-methylquinolin-5-yl)-2-(oxetan-3-yl)-1H-benzo[d]imidazol-6-yl)isoxazole (1020-157)

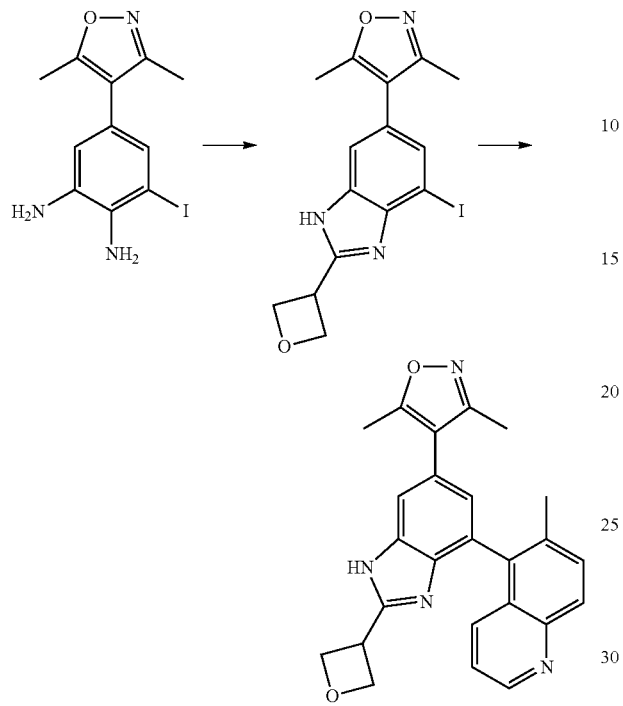

3,5-Dimethyl-4-(4-(6-methylquinolin-5-yl)-2-(oxetan-3-yl)-1H-benzo[d]imidazol-6-yl)isoxazole was synthesized in a similar fashion as that of Example 88, Steps 1-2 replacing 1-methyl-1H-pyrazole-4-carbonyl chloride with oxetane-3-carbonyl chloride.

Step 1: 4-(4-iodo-2-(oxetan-3-yl)-1H-benzo[d]imidazol-6-yl)-3,5-dimethylisoxazole LCMS (m/z+1) 396.0.

Step 2: 35-Dimethyl-4-(4-(6-methylquinolin-5-yl)-2-(oxetan-3-yl)-1H-benzo[d]imidazol-6-yl)isoxazole LCMS (m/z+1) 411.1.

Example 158

3,5-dimethyl-4-(1-methyl-7-(6-methylquinolin-5-yl)-2-(trifluoromethyl)-1H-benzo[d]imidazol-5-yl)isoxazole

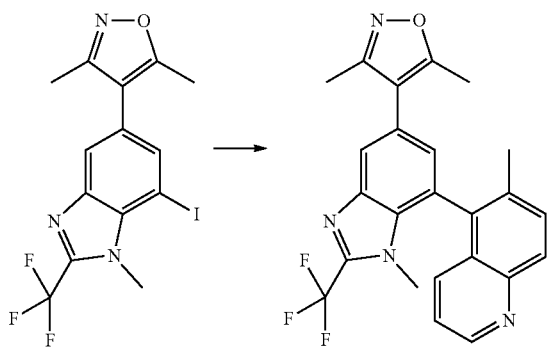 [SMILES: Cc1noc(C)c1-c1cc(I)c2c(c1)nc(C(F)(F)F)n2C ; Cc1ccc2ncccc2c1-c1cc(-c2c(C)noc2C)cc2nc(C(F)(F)F)n(C)c12]

To a microwave vial containing 4-(7-iodo-1-methyl-2-(trifluoromethyl)-1H-benzo[d]imidazol-5-yl)-3,5-dimethylisoxazole (80 mg, 0.19 mmol, 1 equiv.) was added 3,5-6-methylquinolin-5-ylboronic acid (106 mg, 0.57 mmol, 3 equiv.), $Cs_2CO_3$ (371 mg, 1.14 mmol, 6 equiv.) and PEPPSI™-IPr catalyst (51 mg, 0.076 mmol, 0.4 equiv.) and dissolved in DME-$H_2O$ (10 mL, 0.2 M, 2/1, v/v). The mixture was heated to 140° C. for 30 min. The reaction was extracted with EtOAc and washed with water, saturated $NH_4Cl$. After drying with $MgSO_4$, it was filtered and concentrated to dryness. The resulting solid was washed with EtOAc. Purification was carried out by reverse phase HPLC to furnish 3,5-dimethyl-4-(1-methyl-7-(6-methylquinolin-5-yl)-2-(trifluoromethyl)-1H-benzo[d]imidazol-5-yl)isoxazole.

LCMS (m/z+1) 437.50. $^1$H NMR (400 MHz, Methanol-d4) δ 8.85 (d, 1H), 8.10 (d, J=5.8 Hz, 1H), 7.90 (d, J=5.2 Hz, 1H), 7.82 (d, J=5.8 Hz, 1H), 7.78 (d, J=8.2 Hz, 1H), 7.43 (d, J=8.2 Hz, 1H), 7.20 (d, J=4.8 Hz, 1H), 3.29 (s, 3H), 2.46 (s, 3H), 2.30 (s, 3H).

Example 159

4-(2-cyclopropyl-4-(3,5-dimethyl-1H-pyrazol-4-yl)-1-methyl-1H-benzo[d]imidazol-6-yl)-3,5-dimethylisoxazole (1020-159)

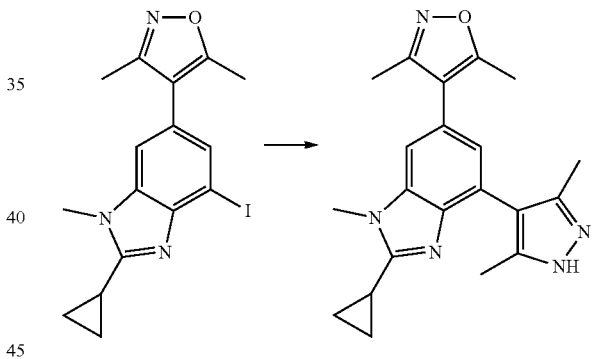

To a microwave vial containing 4-(2-cyclopropyl-4-iodo-1-methyl-1H-benzo[d]imidazol-6-yl)-3,5-dimethylisoxazole (125 mg, 0.32 mmol, 1 equiv.) was 3,5-dimethyl-4-(4,4,5,5-tetramethyl-1,3,2-dioxaborolan-2-yl)-1H-pyrazole (140 mg, 0.64 mmol, 2 equiv.), $Cs_2CO_3$ (310 mg, 0.95 mmol, 3 equiv.) and PEPPSI™-IPr catalyst (22 mg, 0.031 mmol, 0.1 equiv.) and dissolved in DME-$H_2O$ (5 mL, 0.2 M, 2/1, v/v). The mixture was heated to 140° C. for 30 min. The reaction was extracted with EtOAc and washed with water, saturated $NH_4Cl$. After drying with $MgSO_4$, it was filtered and concentrated to dryness. The resulting solid was washed with EtOAc. Purification was carried out by reverse phase HPLC to furnish 4-(2-cyclopropyl-4-(3,5-dimethyl-1H-pyrazol-4-yl)-1-methyl-1H-benzo[d]imidazol-6-yl)-3,5-dimethylisoxazole.

LCMS (m/z+1) 362.21. $^1$H NMR (400 MHz, Methanol-d4) δ 7.73 (d, J=1.2 Hz, 1H), 6.95 (d, J=1.2 Hz, 1H), 3.92 (s, 3H), 2.43 (s, 3H), 2.29 (s, 3H), 2.18 (S, 3), 2.19 (s, 3H), 2.20-2.15 (m, 1H), 1.15-1.05 (m, 4H).

Example 160

4-(2-cyclopropyl-4-(prop-1-yn-1-yl)-1H-benzo[d]imidazol-6-yl)-3,5-dimethylisoxazole

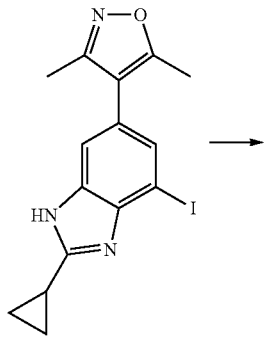

To a microwave vial containing 4-(2-cyclopropyl-4-iodo-1H-benzo[d]imidazol-6-yl)-3,5-dimethylisoxazole (200 mg, 0.53 mmol, 1 equiv.) was added tributyl(prop-1-yn-1-yl)stannane (245 μL, 0.79 mmol, 1.5 equiv.), Pd(PPh$_3$)$_4$ (61 mg, 0.051 mmol, 0.1 equiv.) and dissolved in THF (10 mL). The mixture was heated to 120° C. for 30 min. The reaction was extracted with EtOAc and washed with water, saturated NH$_4$Cl. After drying with MgSO$_4$, it was filtered and concentrated to dryness. Purification was carried out by reverse phase HPLC to furnish 4-(2-cyclopropyl-4-(prop-1-yn-1-yl)-1H-benzo[d]imidazol-6-yl)-3,5-dimethylisoxazole.

LCMS (m/z+1) 292.11. $^1$H NMR (400 MHz, Methanol-d4) δ 7.23 (s, 1H), 7.05 (d, J=1.2 Hz, 1H), 2.37 (s, 3H), 2.21 (s, 3H), 2.20-2.15 (m, 1H), 2.13 (s, 3H), 1.15-1.05 (m, 4H).

Example 161

N-(6-(3,5-dimethylisoxazol-4-yl)-4-(6-methylquinolin-5-yl)-1H-benzo[d]imidazol-2-yl)cyclopropanesulfonamide (1020-161)

Step 1: Preparation of N-cyanocyclopropanesulfonamide calcium salt

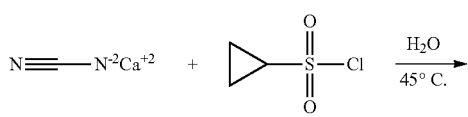

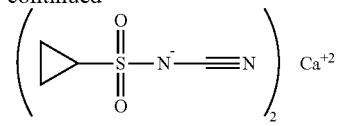

Cyclopropanesulfonyl Chloride (1.09 ml, 10.14 mmol) was added dropwise to a suspension of Calcium Cyanamide (0.89 g, 11.15 mmol) in 25 mL of distilled water under stirring at 45° C. The mixture was stirred for 3 hours at that temperature and filtered, collecting the filtrate for subsequent use.

Step 2: Preparation of N-(6-(3,5-dimethylisoxazol-4-yl)-4-iodo-1H-benzo[d]imidazol-2-yl)cyclopropanesulfonamide

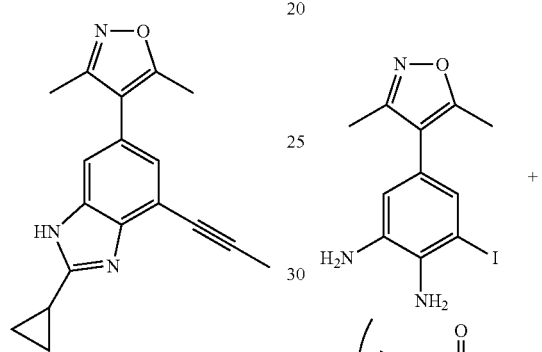

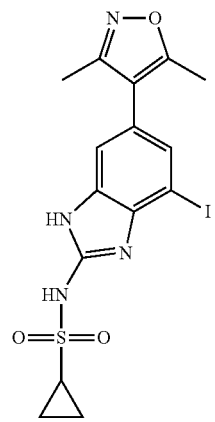

5-(3,5-dimethylisoxazol-4-yl)-3-iodobenzene-1,2-diamine (750 mg, 2.28 mmol) in 15 mL of solvent (2-Propanol:acetic acid, conc (36%) HCl—10:1:1) was added 25 mL of aqueous calcium sulfonyl cyanamide salt. Reaction was heated to 90° C. for 2 days in a sealed tube.

After 2 days reaction was cooled and diluted 1× with water then placed on ice. Precipitates formed which were subsequently filtered and collected to afford N-(6-(3,5-dimethylisoxazol-4-yl)-4-iodo-1H-benzo[d]imidazol-2-yl)cyclopropanesulfonamide (215 mg, 21%).

LCMS (m/z+1) 459.1

Step 3: Preparation of N-(6-(3,5-dimethylisoxazol-4-yl)-4-(6-methylquinolin-5-yl)-1H-benzo[d]imidazol-2-yl)cyclopropanesulfonamide

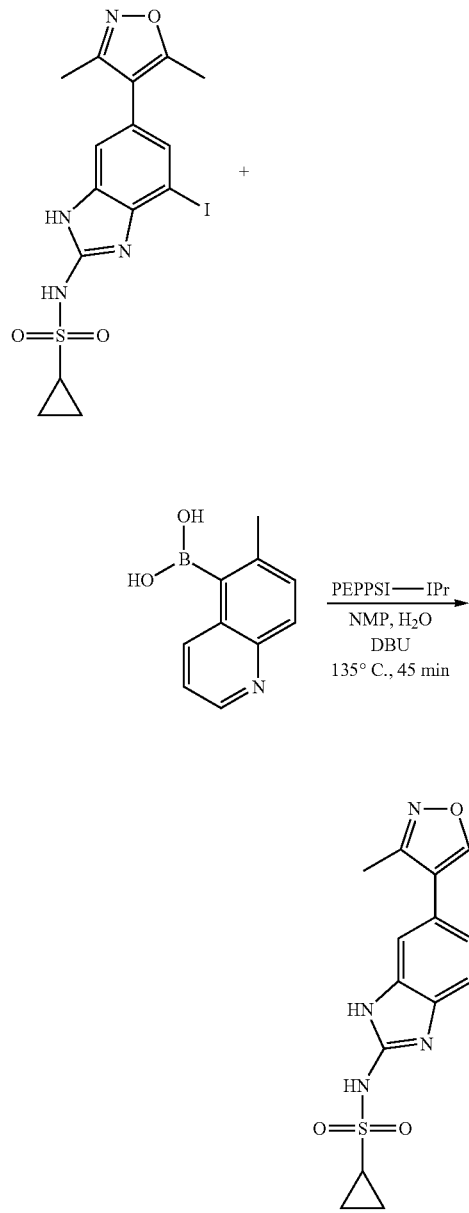

In a microwave vial were combined N-(6-(3,5-dimethylisoxazol-4-yl)-4-iodo-1H-benzo[d]imidazol-2-yl)cyclopropanesulfonamide (50 mg, 0.11 mmol), (6-methylquinolin-5-yl)boronic acid (61.21 mg, 0.33 mmol), 1,8-Diazabicyclo[5.4.0]undec-7-ene (0.1 ml, 0.65 mmol), PEPPSI-IPr catalyst (2.48 mg, 0.005 mmol) and 9 mL NMP/H$_2$O (2:1 by volume) and heated to 135° C. for 45 minutes. After cooling, the reaction diluted in EtAc and aqueous ammonium chloride, was then extracted 3× with EtAc, organics were washed with water and then brine. Organics were then dried over sodium sulphate, filtered and concentrated to dryness. Purification was carried out first by silica gel chromatography (DCM/EtAc as the eluent) followed by reverse phase HPLC to furnish N-(6-(3,5-dimethylisoxazol-4-yl)-4-(6-methylquinolin-5-yl)-1H-benzo[d]imidazol-2-yl)cyclopropanesulfonamide.

LCMS (m/z+1) 474.3. $^1$H NMR (400 MHz, DMSO-d6) δ 11.74 (s, 1H), 8.87 (dd, J=4.1, 1.6 Hz, 1H), 8.06 (d, J=8.5 Hz, 1H), 7.79 (d, J=8.7 Hz, 1H), 7.72-7.59 (m, 1H), 7.53-7.32 (m, 2H), 7.03 (d, J=1.6 Hz, 1H), 2.63-2.58 (m, 1H), 2.46 (s, 3H), 2.28 (s, 6H), 1.38 (d, J=3.8 Hz, 1H), 0.94 (dt, J=5.2, 2.9 Hz, 2H), 0.88 (dt, J=8.1, 3.0 Hz, 3H).

Example 162

N-(4-(3,5-dimethyl-1H-pyrazol-4-yl)-6-(3,5-dimethylisoxazol-4-yl)-1H-benzo[d]imidazol-2-yl)cyclopropanesulfonamide (1020-162)

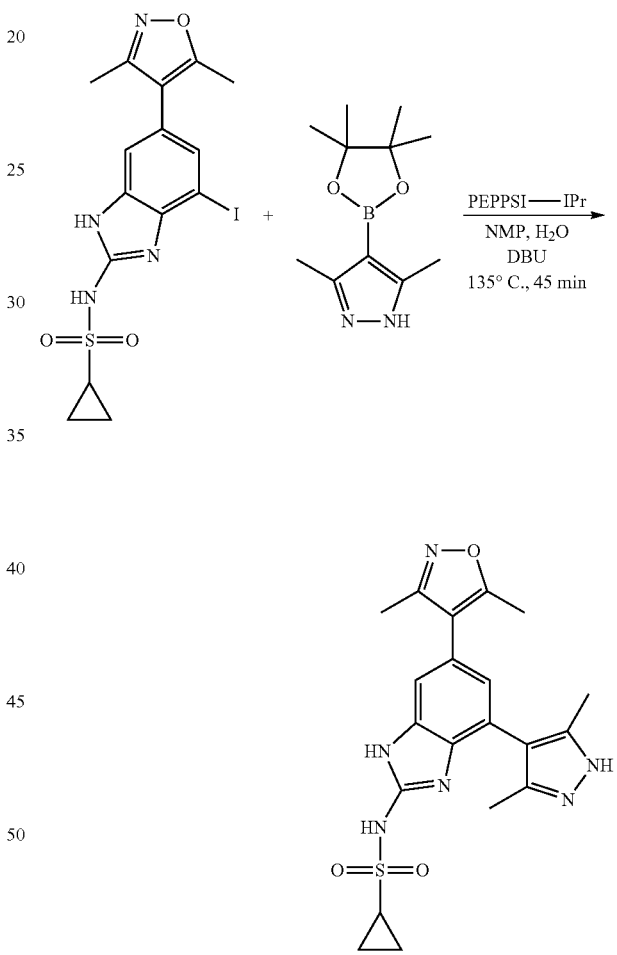

N-(4-(3,5-dimethyl-1H-pyrazol-4-yl)-6-(3,5-dimethylisoxazol-4-yl)-1H-benzo[d]imidazol-2-yl)cyclopropanesulfonamide was prepared using 3,5-dimethyl-4-(4,4,5,5-tetramethyl-1,3,2-dioxaborolan-2-yl)-1H-pyrazole in a similar fashion to N-(6-(3,5-dimethylisoxazol-4-yl)-4-(6-methylquinolin-5-yl)-1H-benzo[d]imidazol-2-yl)cyclopropanesulfonamide Example 161, step 3.

LCMS (m/z+1) 427.2. $^1$H NMR (400 MHz, DMSO-d6) δ 12.39 (s, 1H), 11.66 (s, 2H), 7.30 (d, J=1.6 Hz, 1H), 6.92 (d, J=1.6 Hz, 1H), 2.68-2.59 (m, 1H), 2.45 (s, 3H), 2.27 (s, 3H), 2.13 (s, 6H), 1.01-0.84 (m, 4H).

Example 163

N-(6-(3,5-dimethylisoxazol-4-yl)-4-(2-phenylpyridin-3-yl)-1H-benzo[d]imidazol-2-yl)cyclopropanesulfonamide (1020-163)

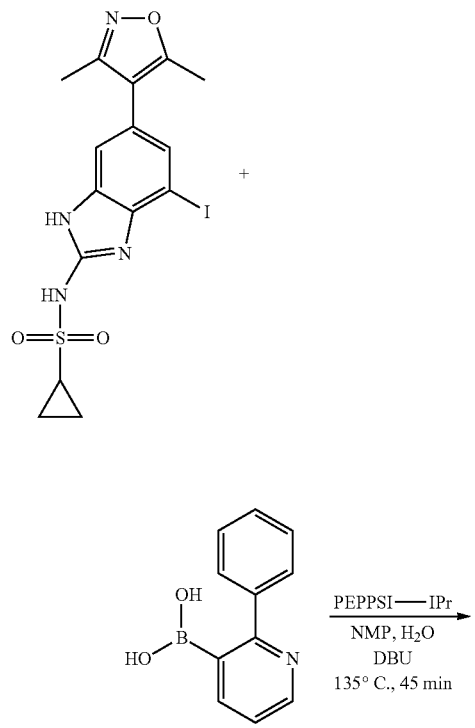

N-(6-(3,5-dimethylisoxazol-4-yl)-4-(2-phenylpyridin-3-yl)-1H-benzo[d]imidazol-2-yl)cyclopropanesulfonamide was prepared using (2-phenylpyridin-3-yl)boronic acid in a similar fashion to N-(6-(3,5-dimethylisoxazol-4-yl)-4-(6-methylquinolin-5-yl)-1H-benzo[d]imidazol-2-yl)cyclopropanesulfonamide Example 161, step 3.

LCMS (m/z+1) 486.3. $^1$H NMR (400 MHz, DMSO-d6) δ 11.95 (d, J=4.8 Hz, 1H), 11.65 (s, 0H), 8.74 (dd, J=4.7, 1.7 Hz, 1H), 7.94 (dd, J=7.8, 1.7 Hz, 1H), 7.51 (dd, J=7.7, 4.8 Hz, 1H), 7.39-7.31 (m, 2H), 7.26 (dt, J=4.3, 2.9 Hz, 4H), 6.71 (d, J=1.6 Hz, 1H), 2.66-2.57 (m, 1H), 2.14 (s, 3H), 1.97 (s, 3H), 1.00-0.84 (m, 4H).

Example 164

N-(6-(3,5-dimethylisoxazol-4-yl)-4-(6-methylquinolin-5-yl)-1H-benzo[d]imidazol-2-yl)ethanesulfonamide (1020-164)

Step 1: Preparation of N-(6-(3,5-dimethylisoxazol-4-yl)-4-iodo-1H-benzo[d]imidazol-2-yl)ethanesulfonamide

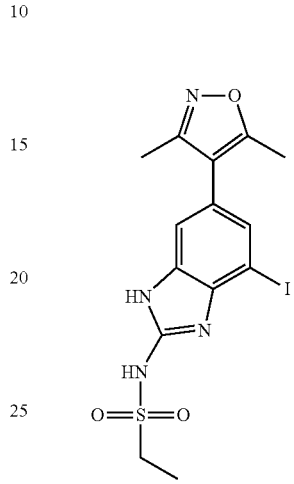

Preparation of N-(6-(3,5-dimethylisoxazol-4-yl)-4-iodo-1H-benzo[d]imidazol-2-yl)ethanesulfonamide was accomplished in a similar fashion as N-(6-(3,5-dimethylisoxazol-4-yl)-4-iodo-1H-benzo[d]imidazol-2-yl)cyclopropanesulfonamide by using ethanesulfonyl chloride, Example 161, steps 1-2.

LCMS (m/z+1) 447.0.

Step 2: Preparation of N-(6-(3,5-dimethylisoxazol-4-yl)-4-(6-methylquinolin-5-yl)-1H-benzo[d]imidazol-2-yl)ethanesulfonamide

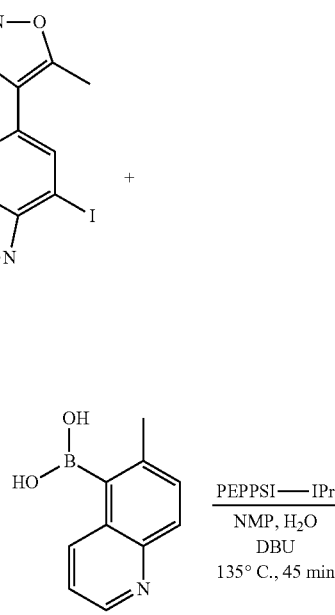

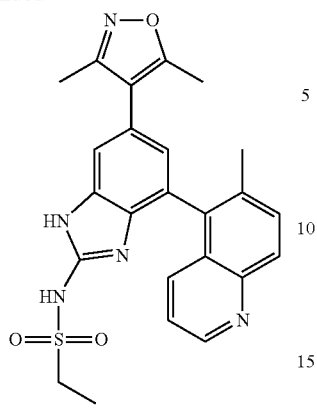

In a microwave vial were combined N-(6-(3,5-dimethylisoxazol-4-yl)-4-iodo-1H-benzo[d]imidazol-2-yl)ethanesulfonamide (50 mg, 0.11 mmol), 6-methylquinolin-5-ylboronic acid (83.81 mg, 0.45 mmol), 1,8-Diazabicyclo[5.4.0]undec-7-ene (0.1 ml, 0.67 mmol), PEPPSI-IPr catalyst (7.64 mg, 0.01 mmol) and 9 mL NMP/H₂O (2:1 by volume) and heated to 135° C. for 45 minutes. After cooling, the reaction diluted in EtAc and aqueous ammonium chloride, was then extracted 3× with EtAc, organics were washed with water and then brine then dried over sodium sulfate, filtered and concentrated to dryness. Purification was carried out first by silica gel chromatography (DCM/EtAc as the eluent) followed by reverse phase HPLC to furnish N-(6-(3,5-dimethylisoxazol-4-yl)-4-(6-methylquinolin-5-yl)-1H-benzo[d]imidazol-2-yl)ethanesulfonamide.

LCMS (m/z+1) 462.3. ¹H NMR (400 MHz, DMSO-d6) δ 11.60 (s, 2H), 8.83 (dd, J=4.2, 1.6 Hz, 1H), 8.01 (d, J=8.7 Hz, 1H), 7.75 (d, J=8.7 Hz, 1H), 7.64 (ddd, J=8.5, 1.6, 0.9 Hz, 1H), 7.47-7.36 (m, 2H), 6.98 (d, J=1.6 Hz, 1H), 2.95 (q, J=7.3 Hz, 2H), 2.41 (s, 3H), 2.24 (s, 6H), 1.18 (t, J=7.3 Hz, 3H).

Example 165

N-(4,6-bis(3,5-dimethylisoxazol-4-yl)-1H-benzo[d]imidazol-2-yl)ethanesulfonamide (1020-165)

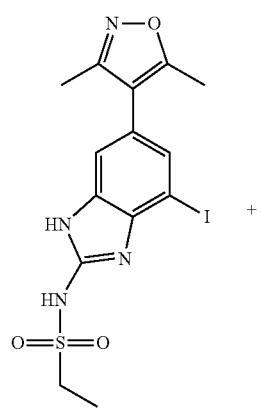

+

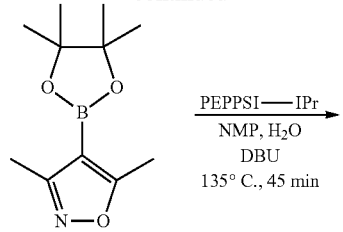

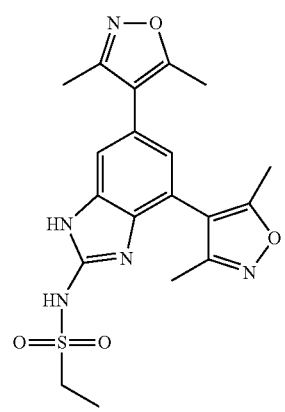

N-(4,6-bis(3,5-dimethylisoxazol-4-yl)-1H-benzo[d]imidazol-2-yl)ethanesulfonamide was prepared using 3,5-dimethyl-4-(4,4,5,5-tetramethyl-1,3,2-dioxaborolan-2-yl)isoxazole in a similar fashion to N-(6-(3,5-dimethylisoxazol-4-yl)-4-(6-methylquinolin-5-yl)-1H-benzo[d]imidazol-2-yl)ethanesulfonamide, Example 164, step 2.

LCMS (m/z+1) 416.2. ¹H NMR (400 MHz, DMSO-d6) δ 11.97 (s, 1H), 11.70 (s, 1H), 7.37 (d, J=1.6 Hz, 1H), 7.03 (d, J=1.6 Hz, 1H), 3.02 (q, J=7.3 Hz, 2H), 2.43 (s, 3H), 2.31 (s, 3H), 2.25 (s, 3H), 2.15 (s, 3H), 1.23 (t, J=7.3 Hz, 3H).

Example 166

N-(6-(3,5-dimethylisoxazol-4-yl)-4-(2-phenylpyridin-3-yl)-1H-benzo[d]imidazol-2-yl)ethanesulfonamide (1020-166)

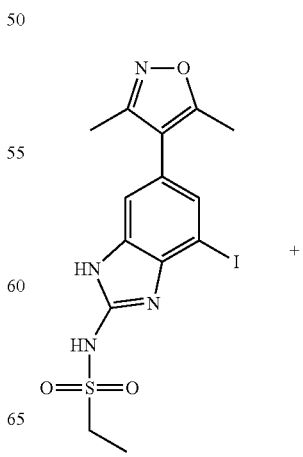

+

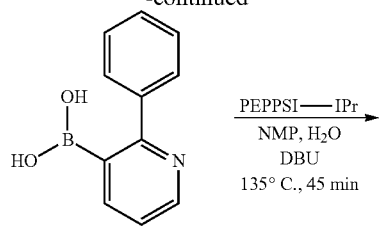

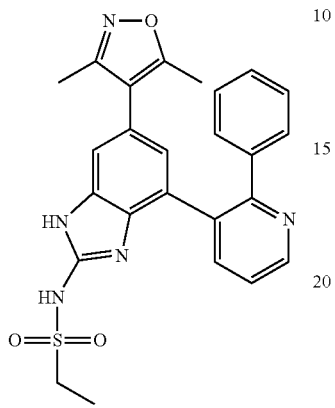

N-(6-(3,5-dimethylisoxazol-4-yl)-4-(2-phenylpyridin-3-yl)-1H-benzo[d]imidazol-2-yl)ethanesulfonamide was prepared using (2-phenylpyridin-3-yl)boronic acid in a similar fashion to N-(6-(3,5-dimethylisoxazol-4-yl)-4-(6-methylquinolin-5-yl)-1H-benzo[d]imidazol-2-yl)ethanesulfonamide, Example 164, step 2.

LCMS (m/z+1) 474.3.

$^1$H NMR (400 MHz, DMSO-d6) δ 11.84 (s, 0H), 11.67-11.60 (m, 1H), 8.71 (dd, J=4.8, 1.6 Hz, 1H), 7.91 (dd, J=7.8, 1.7 Hz, 1H), 7.48 (dd, J=7.7, 4.8 Hz, 1H), 7.35-7.28 (m, 2H), 7.26-7.19 (m, 4H), 6.70 (d, J=1.6 Hz, 1H), 2.97 (q, J=7.3 Hz, 2H), 2.12 (s, 3H), 1.95 (s, 3H), 1.20 (t, J=7.4 Hz, 3H).

Example 167

N-(6-(3,5-dimethylisoxazol-4-yl)-4-(6-methylquinolin-5-yl)-1H-benzo[d]imidazol-2-yl)propane-2-sulfonamide (1020-167)

Step 1: Preparation of N-(6-(3,5-dimethylisoxazol-4-yl)-4-iodo-1H-benzo[d]imidazol-2-yl)propane-2-sulfonamide

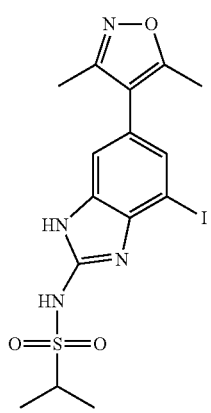 [SMILES: Cc1noc(C)c1-c1cc(I)c2nc(NS(=O)(=O)C(C)C)[nH]c2c1]

Preparation of N-(6-(3,5-dimethylisoxazol-4-yl)-4-iodo-1H-benzo[d]imidazol-2-yl)propane-2-sulfonamide was accomplished in a similar fashion to N-(6-(3,5-dimethylisoxazol-4-yl)-4-iodo-1H-benzo[d]imidazol-2-yl)cyclopropanesulfonamide by using propane-2-sulfonyl chloride, Example 161, steps 1-2.

LCMS (m/z+1) 461.1.

Step 2: Preparation of N-(6-(3,5-dimethylisoxazol-4-yl)-4-iodo-1H-benzo[d]imidazol-2-yl)propane-2-sulfonamide

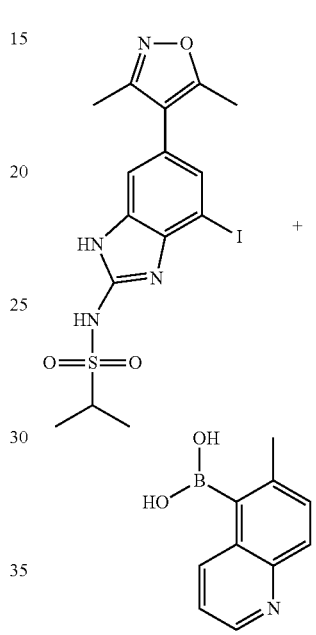

+

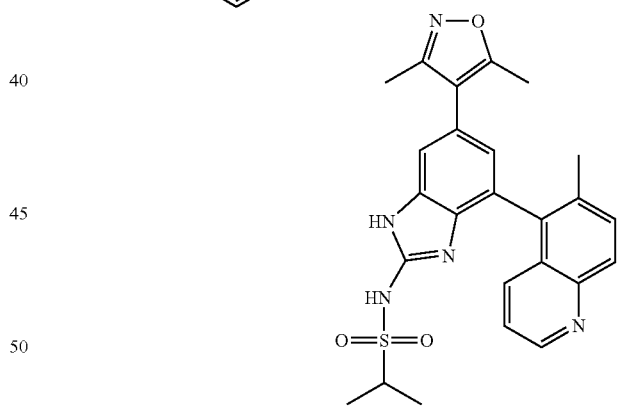

In a microwave vial were combined N-(6-(3,5-dimethylisoxazol-4-yl)-4-iodo-1H-benzo[d]imidazol-2-yl)propane-2-sulfonamide (50 mg, 0.11 mmol), 6-methylquinolin-5-ylboronic acid (81.25 mg, 0.43 mmol), 1,8-Diazabicyclo[5.4.0]undec-7-ene (0.1 ml, 0.67 mmol), PEPPSI-IPr catalyst (7.64 mg, 0.01 mmol) and 9 mL NMP/H$_2$O (2:1 by volume) and heated to 135° C. for 45 minutes. After cooling, the reaction diluted in EtAc and aqueous ammonium chloride, was then extracted 3× with EtAc, organics were washed with water and then brine. Organics were then dried over sodium sulphate, filtered and concentrated to dryness. Purification was carried out first by silica gel chromatography (DCM/EtAc as the eluent) followed by reverse phase HPLC to furnish N-(6-(3,5-dimethylisoxazol-4-yl)-4-(6-methylquinolin-5-yl)-1H-benzo[d]imidazol-2-yl)propane-2-sulfonamide.

LCMS (m/z+1) 476.2. $^1$H NMR (400 MHz, DMSO-d6) δ 11.69 (s, 2H), 8.87 (dd, J=4.1, 1.6 Hz, 1H), 8.05 (d, J=8.7 Hz, 1H), 7.79 (d, J=8.7 Hz, 1H), 7.72-7.65 (m, 1H), 7.51-7.40 (m, 2H), 7.02 (d, J=1.7 Hz, 1H), 3.09 (p, J=6.7 Hz, 1H), 2.45 (s, 3H), 2.28 (s, 6H), 1.24 (d, J=6.8 Hz, 6H).

Example 168

N-(4,6-bis(3,5-dimethylisoxazol-4-yl)-1H-benzo[d]imidazol-2-yl)propane-2-sulfonamide (1020-168)

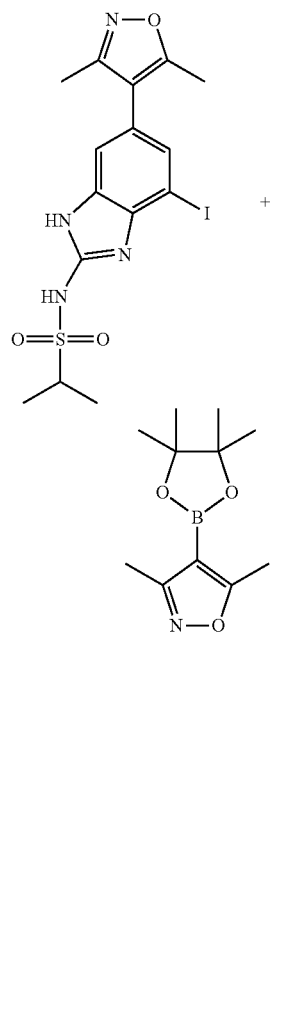

N-(4,6-bis(3,5-dimethylisoxazol-4-yl)-1H-benzo[d]imidazol-2-yl)propane-2-sulfonamide was prepared using 3,5-dimethyl-4-(4,4,5,5-tetramethyl-1,3,2-dioxaborolan-2-yl)isoxazole in a similar fashion to N-(6-(3,5-dimethyl isoxazol-4-yl)-4-(6-methylquinolin-5-yl)-1H-benzo[d]imidazol-2-yl)propane-2-sulfonamide, Example 167, step 2.

LCMS (m/z+1) 430.2. $^1$H NMR (400 MHz, DMSO-d6) δ 11.97 (s, 1H), 11.67 (s, 1H), 7.37 (d, J=1.6 Hz, 1H), 7.03 (d, J=1.6 Hz, 1H), 3.13 (p, J=6.7 Hz, 1H), 2.43 (s, 3H), 2.31 (s, 3H), 2.25 (s, 3H), 2.15 (s, 3H), 1.26 (d, J=6.7 Hz, 6H).

Example 169

N-(6-(3,5-d methylisoxazol-4-yl)-4-(2-phenylpyridin-3-yl)-1H-benzo[d]imidazol-2-yl)propane-2-sulfonamide (1020-169)

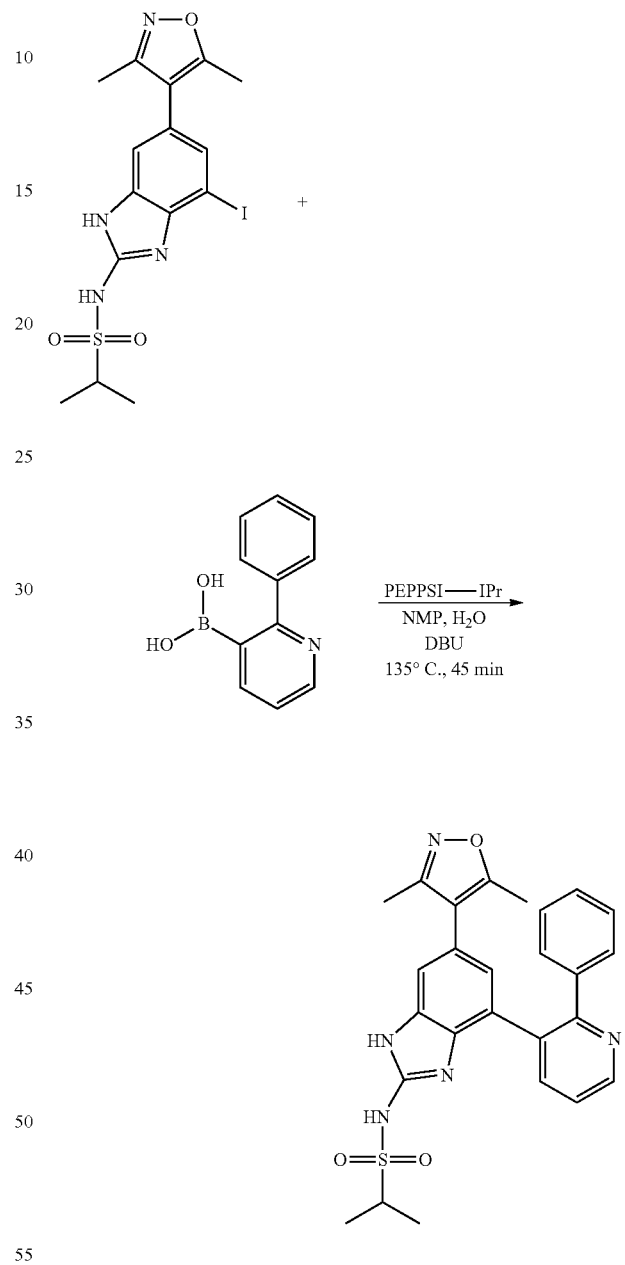

N-(6-(3,5-dimethylisoxazol-4-yl)-4-(2-phenylpyridin-3-yl)-1H-benzo[d]imidazol-2-yl)propane-2-sulfonamide was prepared using (2-phenylpyridin-3-yl)boronic acid in a similar fashion to N-(6-(3,5-dimethylisoxazol-4-yl)-4-(6-methylquinolin-5-yl)-1H-benzo[d]imidazol-2-yl)propane-2-sulfonamide, Example 167, step 2.

LCMS (m/z+1) 488.4. $^1$H NMR (400 MHz, DMSO-d6) δ 11.85 (s, 1H), 11.61 (s, 1H), 8.75 (dd, J=4.8, 1.7 Hz, 1H), 7.95 (dd, J=7.8, 1.7 Hz, 1H), 7.52 (dd, J=7.7, 4.8 Hz, 1H), 7.38-7.31 (m, 2H), 7.25 (dt, J=5.7, 2.2 Hz, 4H), 6.76 (d, J=1.7 Hz, 1H), 3.10 (p, J=6.8 Hz, 1H), 2.17 (s, 3H), 2.00 (s, 3H), 1.25 (d, J=6.7 Hz, 6H).

Example 170

N-(6-(3,5-dimethylisoxazol-4-yl)-4-(6-methylquinolin-5-yl)-1H-benzo[d]imidazol-2-yl)methanesulfonamide (1020-170)

Step 1: Preparation of N-(6-(3,5-dimethylisoxazol-4-yl)-4-iodo-1H-benzo[d]imidazol-2-yl)methanesulfonamide

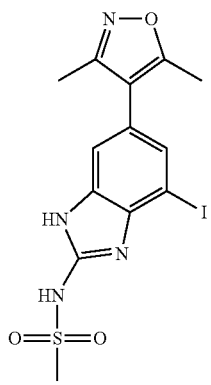 [SMILES: Cc1noc(C)c1-c1cc(I)c2nc(NS(C)(=O)=O)[nH]c2c1]

Preparation of N-(6-(3,5-dimethylisoxazol-4-yl)-4-iodo-1H-benzo[d]imidazol-2-yl)methanesulfonamide was accomplished in a similar fashion to N-(6-(3,5-dimethylisoxazol-4-yl)-4-iodo-1H-benzo[d]imidazol-2-yl)cyclopropanesulfonamide by using methanesulfonyl chloride, Example 161, steps 1-2.

LCMS (m/z+1) 433.0.

Step 2: N-(6-(3,5-dimethylisoxazol-4-yl)-4-(6-methylquinolin-5-yl)-1H-benzo[d]imidazol-2-yl)methanesulfonamide

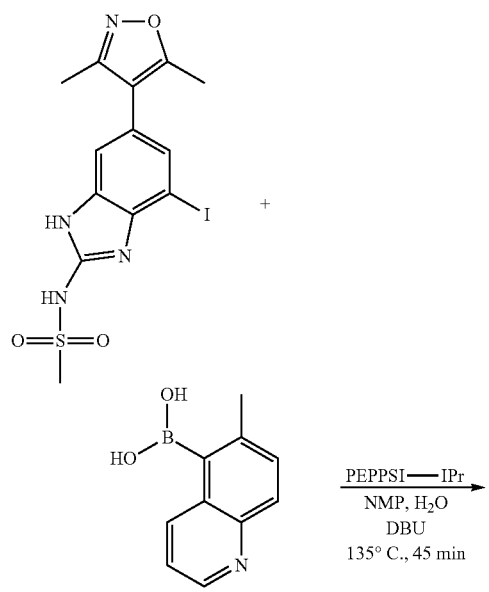

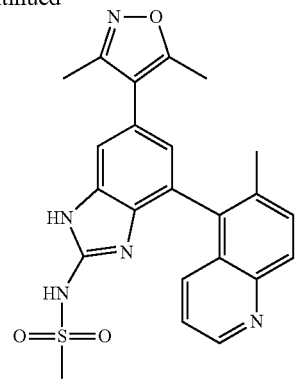

In a microwave vial were combined N-(6-(3,5-dimethylisoxazol-4-yl)-4-iodo-1H-benzo[d]imidazol-2-yl)methanesulfonamide (90 mg, 0.21 mmol), 6-methylquinolin-5-ylboronic acid (116.81 mg, 0.62 mmol), 1,8-Diazabicyclo[5.4.0]undec-7-ene, PEPPSI-IPr catalyst (4.73 mg, 0.01 mmol) and 15 mL NMP/H$_2$O (2:1 by volume) and heated to 135° C. for 45 minutes. After cooling, the reaction diluted in EtAc and aqueous ammonium chloride, was then extracted 3× with EtAc, organics were washed with water and then brine. Organics were then dried over sodium sulphate, filtered and concentrated to dryness. Purification was carried out first by silica gel chromatography (DCM/EtAc as the eluent) followed by reverse phase HPLC to furnish N-(6-(3,5-dimethylisoxazol-4-yl)-4-(6-methylquinolin-5-yl)-1H-benzo[d]imidazol-2-yl)methanesulfonamide.

LCMS (m/z+1) 448.2. $^1$H NMR (400 MHz, DMSO-d6) δ 11.64 (s, 2H), 8.84 (dd, J=4.2, 1.6 Hz, 1H), 8.03 (d, J=8.7 Hz, 1H), 7.76 (d, J=8.7 Hz, 1H), 7.70-7.60 (m, 1H), 7.41 (dd, J=8.5, 4.0 Hz, 2H), 6.95 (s, 1H), 2.90 (s, 3H), 2.43 (s, 3H), 2.26 (d, J=1.4 Hz, 6H).

Example 171

N-(6-(3,5-dimethylisoxazol-4-yl)-4-(2-phenylpyridin-3-yl)-1H-benzo[d]imidazol-2-yl)methanesulfonamide (1020-171)

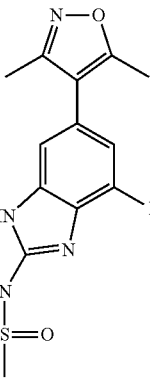

-continued

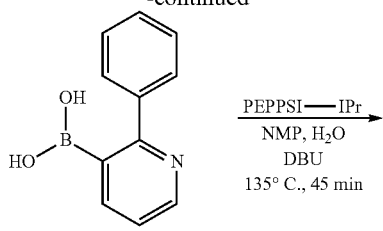

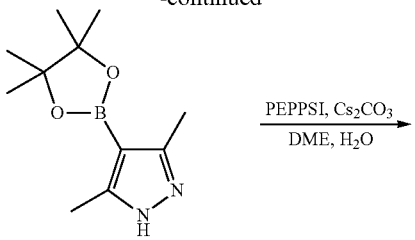

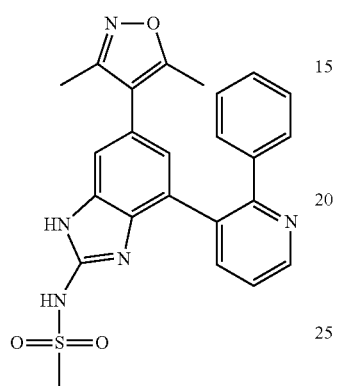

N-(6-(3,5-dimethylisoxazol-4-yl)-4-(2-phenylpyridin-3-yl)-1H-benzo[d]imidazol-2-yl)methanesulfonamide was prepared using (2-phenylpyridin-3-yl)boronic acid in a similar fashion to N-(6-(3,5-dimethylisoxazol-4-yl)-4-(6-methylquinolin-5-yl)-1H-benzo[d]imidazol-2-yl)methanesulfonamide, Example 170, step 2.

LCMS (m/z+1) 460.3. $^1$H NMR (400 MHz, DMSO-d6) δ 11.90 (s, 1H), 11.72 (s, 1H), 8.75 (dd, J=4.8, 1.6 Hz, 1H), 7.94 (dd, J=7.8, 1.7 Hz, 1H), 7.52 (dd, J=7.8, 4.8 Hz, 1H), 7.39-7.23 (m, 7H), 6.70 (d, J=1.6 Hz, 1H), 2.95 (s, 3H), 2.13 (s, 3H), 1.96 (s, 3H).

Example 172

N-(4-(3,5-dimethyl-1H-pyrazol-4-yl)-6-(3,5-dimethylisoxazol-4-yl)-1H-benzo[d]imidazol-2-yl)methanesulfonamide (1020-172)

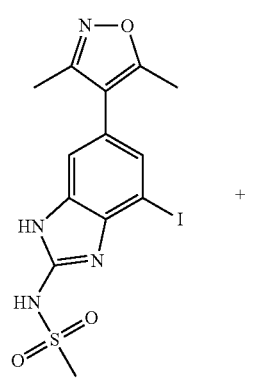

+

In a microwave vial containing N-(6-(3,5-dimethylisoxazol-4-yl)-4-iodo-1H-benzo[d]imidazol-2-yl)methanesulfonamide (50 mg, 0.12 mmol), PEPPSI (16 mg, 0.023 mmol), 3,5-dimethyl-4-(4,4,5,5-tetramethyl-1,3,2-dioxaborolan-2-yl)-1H-pyrazole (77 mg, 0.35 mmol), and cesium carbonate (226 mg, 0.69 mmol) was added 2 mL of DME and 1 mL of DI water. The vial was placed in a microwave and heated to 130° C. for 30 minutes. Once complete, Once complete, the solution was quenched with DI H$_2$O and extracted three times with EtOAc. The combined organic layers were washed with saturated NaCl, dried over sodium sulfate, filtered and concentrated in vacuo. Purification was carried out by reverse phase HPLC to afford N-(4-(3,5-dimethyl-1H-pyrazol-4-yl)-6-(3,5-dimethylisoxazol-4-yl)-1H-benzo[d]imidazol-2-yl)methanesulfonamide.

C$_{18}$H$_{20}$N$_6$O$_3$S. MS. m/z 401.5 (M+1). $^1$H NMR (400 MHz, cd$_3$od) δ 7.25 (d, J=1.5 Hz, 1H), 6.94 (s, 1H), 3.02 (s, 3H), 2.44 (s, 3H), 2.28 (s, 3H), 2.19 (s, 6H).

Example 173

Preparation of N-(4,6-bis(3,5-dimethylisoxazol-4-yl)-1H-benzo[d]imidazol-2-yl)methanesulfonamide (1020-173)

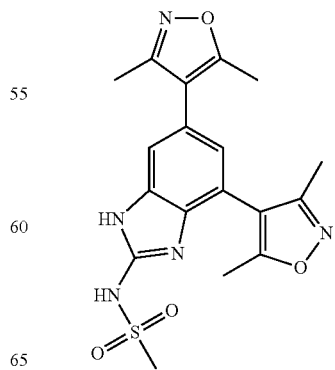

N-(4,6-bis(3,5-dimethylisoxazol-4-yl)-1H-benzo[d]imidazol-2-yl)methanesulfonamide was synthesized in a similar fashion as that of Example 172, substituting 3,5-dimethyl-4-(4,4,5,5-tetramethyl-1,3,2-dioxaborolan-2-yl)-1H-pyrazole for 3,5-dimethyl-4-(4,4,5,5-tetramethyl-1,3,2-dioxaborolan-2-yl)isoxazole.

$C_{18}H_{19}N_5O_4S$. MS m/z 402.1 (M+1). $^1$H NMR (400 MHz, cd$_3$od) δ 7.30 (d, J=1.4 Hz, 1H), 6.97 (d, J=1.3 Hz, 1H), 3.03 (s, 3H), 2.43 (s, 3H), 2.36 (s, 3H), 2.28 (s, 3H), 2.21 (s, 3H).

Example 174

N-(6-(3,5-dimethylisoxazol-4-yl)-4-(6-methylquinolin-5-yl)-1H-benzo[d]imidazol-2-yl)benzenesulfonamide (1020-174)

Step 1: Preparation of N-(6-(3,5-dimethylisoxazol-4-yl)-4-iodo-1H-benzo[d]imidazol-2-yl)benzenesulfonamide

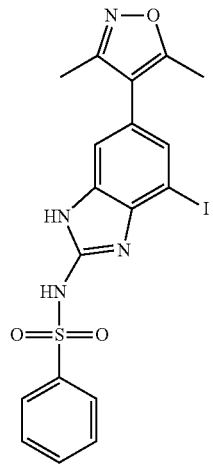 [SMILES: Cc1noc(C)c1-c1cc(I)c2nc(NS(=O)(=O)c3ccccc3)[nH]c2c1]

Preparation of N-(6-(3,5-dimethylisoxazol-4-yl)-4-iodo-1H-benzo[d]imidazol-2-yl)benzenesulfonamide was accomplished in a similar fashion to N-(6-(3,5-dimethylisoxazol-4-yl)-4-iodo-1H-benzo[d]imidazol-2-yl)cyclopropanesulfonamide by using benzenesulfonyl chloride, Example 161, steps 1-2.

LCMS (m/z+1) 495.1.

Step 2: N-(6-(3,5-dimethylisoxazol-4-yl)-4-(6-methylquinolin-5-yl)-1H-benzo[d]imidazol-2-yl)benzenesulfonamide

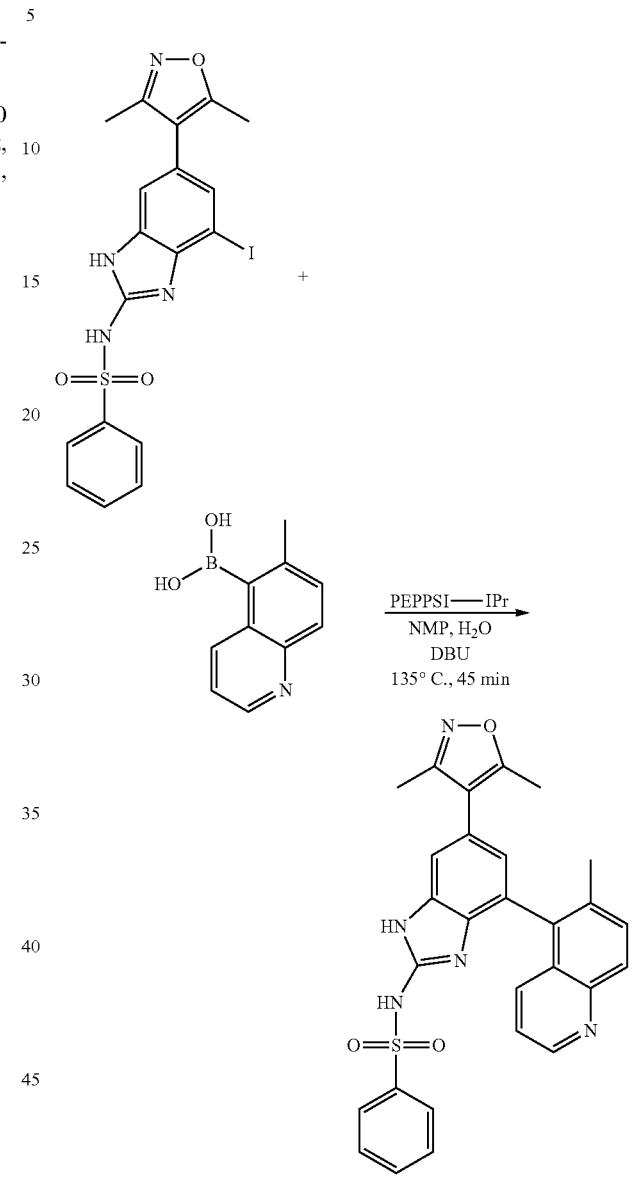

In a microwave vial were combined N-(6-(3,5-dimethylisoxazol-4-yl)-4-iodo-1H-benzo[d]imidazol-2-yl)benzenesulfonamide (50 mg, 0.11 mmol), 6-methylquinolin-5-ylboronic acid (83.81 mg, 0.45 mmol), 1,8-Diazabicyclo[5.4.0]undec-7-ene (0.1 ml, 0.67 mmol), PEPPSI-IPr catalyst (7.64 mg, 0.01 mmol) and 9 mL NMP/H$_2$O (2:1 by volume) and heated to 135° C. for 45 minutes. After cooling, the reaction diluted in EtAc and aqueous ammonium chloride, was then extracted 3× with EtAc, organics were washed with water and then brine. Organics were then dried over sodium sulphate, filtered and concentrated to dryness. Purification was carried out first by silica gel chromatography (DCM/EtAc as the eluent) followed by reverse phase HPLC to furnish N-(6-(3,5-dimethylisoxazol-4-yl)-4-(6-methylquinolin-5-yl)-1H-benzo[d]imidazol-2-yl)benzenesulfonamide.

LCMS (m/z+1) 510.3. $^1$H NMR (400 MHz, DMSO-d6) δ 11.90 (s, 2H), 8.84 (dd, J=4.2, 1.6 Hz, 1H), 8.03 (d, J=8.7

Hz, 1H), 7.91-7.79 (m, 2H), 7.76 (d, J=8.7 Hz, 1H), 7.64 (dt, J=8.4, 1.3 Hz, 1H), 7.60-7.44 (m, 4H), 7.39 (dd, J=8.6, 4.2 Hz, 1H), 7.02 (s, 1H), 2.44 (s, 3H), 2.27 (s, 3H), 2.23 (s, 3H).

Example 175

N-(6-(3,5-dimethylisoxazol-4-yl)-4-(6-methylquinolin-5-yl)-1H-benzo[d]imidazol-2-yl)-3,3,3-trifluoropropane-1-sulfonamide (1020-175)

Step 1: Preparation of N-(6-(3,5-dimethylisoxazol-4-yl)-4-iodo-1H-benzo[d]imidazol-2-yl)-3,3,3-trifluoropropane-1-sulfonamide

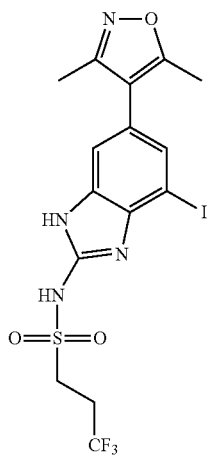 [SMILES: Cc1noc(C)c1-c1cc(I)c2nc(NS(=O)(=O)CCC(F)(F)F)[nH]c2c1]

Preparation of N-(6-(3,5-dimethylisoxazol-4-yl)-4-iodo-1H-benzo[d]imidazol-2-yl)-3,3,3-trifluoropropan-1-sulfonamide was accomplished in a similar fashion to N-(6-(3,5-dimethylisoxazol-4-yl)-4-iodo-1H-benzo[d]imidazol-2-yl)cyclopropanesulfonamide by using 3,3,3-trifluoropropane-1-sulfonyl chloride, Example 161, steps 1-2.

LCMS (m/z+1) 515.0.

Step 2: Preparation of N-(6-(3,5-dimethylisoxazol-4-yd)-4-(6-methylquinolin-5-yl)-1H-benzo[d]imidazol-2-yl)-3,3,3-trifluoropropane-1-sulfonamide

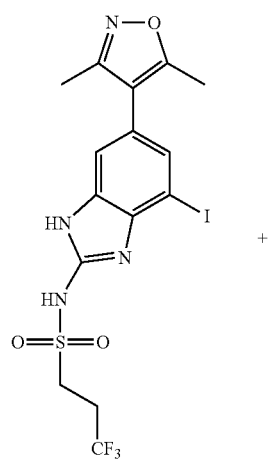

+

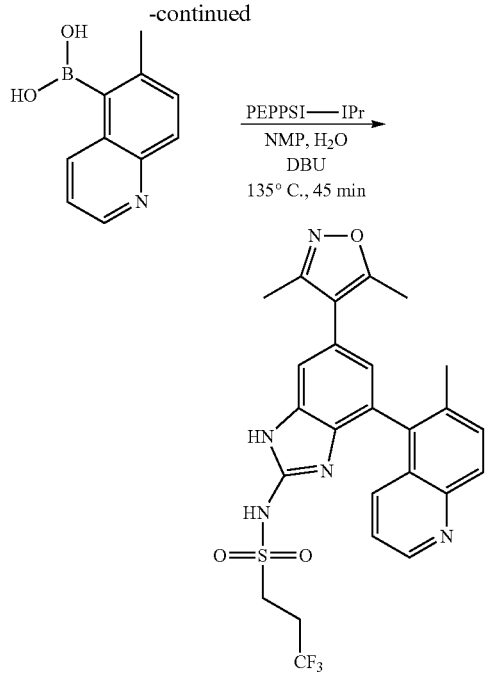

In a microwave vial were combined N-(6-(3,5-dimethylisoxazol-4-yl)-4-iodo-1H-benzo[d]imidazol-2-yl)-3,3,3-trifluoropropane-1-sulfonamide (50 mg, 0.1 mmol), 6-methylquinolin-5-ylboronic acid (72.73 mg, 0.39 mmol), 1,8-Diazabicyclo[5.4.0]undec-7-ene (0.09 ml, 0.58 mmol), PEPPSI-IPr catalyst (6.63 mg, 0.01 mmol) and 9 mL NMP/H$_2$O (2:1 by volume) and heated to 135° C. for 45 minutes. After cooling, the reaction diluted in EtAc and aqueous ammonium chloride, was then extracted 3× with EtAc, organics were washed with water and then brine. Organics were then dried over sodium sulphate, filtered and concentrated to dryness. Purification was carried out first by silica gel chromatography (DCM/EtAc as the eluent) followed by reverse phase HPLC to furnish N-(6-(3,5-dimethylisoxazol-4-yl)-4-(6-methylquinolin-5-yl)-1H-benzo[d]imidazol-2-yl)-3,3,3-trifluoropropane-1-sulfonamide.

LCMS (m/z+1) 530.3. $^1$H NMR (400 MHz, DMSO-d6) δ 11.87 (s, 1H), 11.81 (s, 1H), 8.83 (dd, J=4.3, 1.6 Hz, 1H), 8.02 (d, J=8.7 Hz, 1H), 7.75 (d, J=8.7 Hz, 1H), 7.68-7.60 (m, 1H), 7.47-7.35 (m, 2H), 7.01 (s, 1H), 3.25-3.16 (m, 2H), 2.71-2.59 (m, 2H), 2.42 (s, 3H), 2.24 (s, 6H). $^{19}$F NMR (376 MHz, DMSO-d6) δ −64.98 (t, J=11.1 Hz).

Example 176

N-(5-(3,5-dimethylisoxazol-4-yl)-1-methyl-7-(6-methylquinolin-5-yl)-1H-benzo[d]imidazol-2-yl)methanesulfonamide (1020-176)

Step 1: Preparation of 2-chloro-4-(3,5-dimethylisoxazol-4-yl-N-methyl-6-nitroaniline

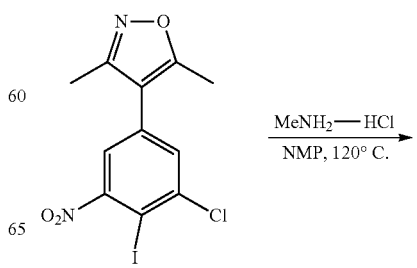

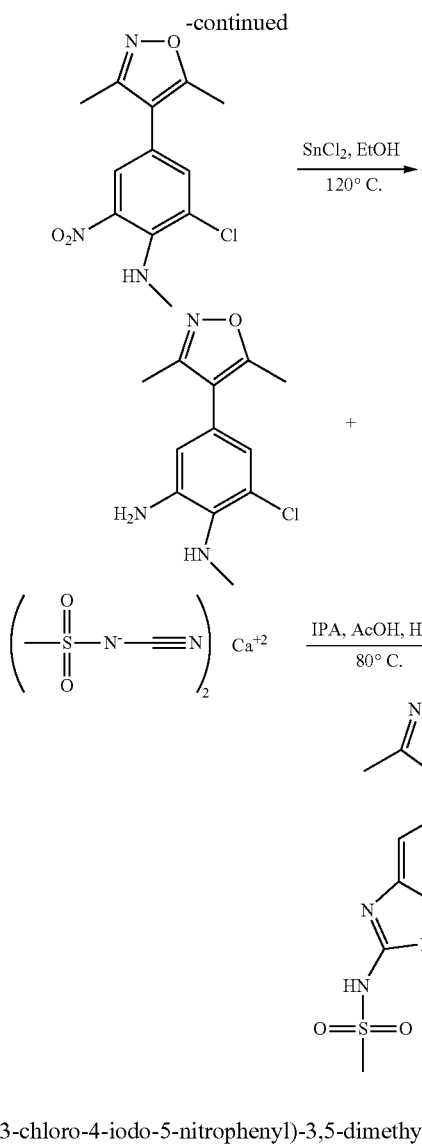

4-(3-chloro-4-iodo-5-nitrophenyl)-3,5-dimethylisoxazole (4 g, 10.57 mmol) was taken up in 1-methyl-2-pyrrolidinone (10 ml) in a sealed vessel. To this was added methylamine hydrochloride (1.43 g, 21.13 mmol) and triethylamine (5.89 ml, 42.27 mmol). The vessel was capped and stirred at 120° C. for 1 day. Reaction was then cooled to room temperature and the crude mixture was diluted in EtAc and aqueous ammonium chloride and extracted 3× with EtAc. Organics were washed with ammonium chloride, water then brine, dried over sodium sulfate and evaporated to dryness under reduced pressure to afford 2-chloro-4-(3,5-dimethylisoxazol-4-yl)-N-methyl-6-nitroaniline as a very dark red oil.
LCMS (m/z+1) 281.9

Step 2: Preparation of 6-chloro-4-(3,5-dimethylisoxazol-4-yl)-N1-methylbenzene-1,2-diamine 2-chloro-4-(3,5-dimethylisoxazol-4-yl)-N-methyl-6-nitroaniline (3.3 g, 11.7 mmol), stannous chloride (6.66 g, 35.1 mmol) were mixed in 100 mL ethanol in a pressure sealed vessel and heated to 120° C. for 1 hour. Reaction was then cooled to room temperature before being poured into stirring EtAc/1N NaOH for 20 minutes. Reaction was then extracted 3× with EtAc, washed with 1N NaOH, water 2× and brine. Organics were then dried over sodium sulfate and solvents removed under reduced pressure. Crude material was purified by silica gel chromatography, with Hex/EtAc as the eluent to provide 6-chloro-4-(3,5-dimethylisoxazol-4-yl)-N1-methylbenzene-1,2-diamine as a dark yellow solid.
LCMS (m/z+1) 252.2

Step 3: Preparation of N-(7-chloro-5-(3,5-dimethyl-isoxazol-4-yl)-1-methyl-1H-benzo[d]imidazol-2-yl) methanesulfonamide from 6-chloro-4-(3,5-dimethyl-isoxazol-4-yl)-N1-methylbenzene-1,2-diamine Preparation of N-(7-chloro-5-(3,5-dimethylisoxazol-4-yl)-1-methyl-1H-benzo[d]imidazol-2-yl)methanesulfonamide from 6-chloro-4-(3,5-dimethylisoxazol-4-yl)-N1-methylbenzene-1,2-diamine (420 mg, 1.67 mmol) was accomplished in a similar fashion to N-(6-(3,5-dimethylisoxazol-4-yl)-4-iodo-1H-benzo[d]imidazol-2-yl)cyclopropanesulfonamide by using methanesulfonyl cyanamide, Example 161, steps 1-2.
LCMS (m/z+1) 355.1

Step 4: Preparation of N-(5-(3,5-dimethylisoxazol-4-yl)-1-methyl-7-(6-methylquinolin-5-yl)-1H-benzo[d]imidazol-2-yl)methanesulfonamide

249

Preparation of N-(5-(3,5-dimethylisoxazol-4-yl)-1-methyl-7-(6-methylquinolin-5-yl)-1H-benzo[d]imidazol-2-yl)methanesulfonamide was done in a similar manner as the preparation of N-(6-(3,5-dimethylisoxazol-4-yl)-4-(6-methylquinolin-5-yl)-1H-benzo[d]imidazol-2-yl)cyclopropanesulfonamide by using N-(7-chloro-5-(3,5-dimethylisoxazol-4-yl)-1-methyl-1H-benzo[d]imidazol-2-yl)methanesulfonamide as the starting material and heating the reaction to 160° C. for 45 minutes.

LCMS (m/z+1) 462.3. ¹H NMR (400 MHz, DMSO-d6) δ 11.96 (s, 1H), 8.90 (dd, J=4.2, 1.6 Hz, 1H), 8.11 (d, J=8.7 Hz, 1H), 7.83 (d, J=8.7 Hz, 1H), 7.68 (dt, J=8.5, 1.2 Hz, 1H), 7.58 (d, J=1.6 Hz, 1H), 7.47 (dd, J=8.5, 4.2 Hz, 1H), 6.99 (d, J=1.6 Hz, 1H), 2.99 (s, 3H), 2.57 (s, 3H), 2.45 (s, 3H), 2.28 (d, J=8.4 Hz, 6H).

Example 177

N-benzyl-6-(3,5-dimethylisoxazol-4-yl)-4-iodo-1H-benzo[d]imidazol-2-amine (1020-177)

Step 1: Preparation of 6-(3,5-dimethylisoxazol-4-yl)-4-iodo-1H-benzo[d]imidazol-2(3H)-one 5-(3,5-dimethylisoxazol-4-yl)-3-iodobenzene-1,2-diamine (2.5 g, 7.6 mmol) and 1,1'-carbonyldiimidazole (2.71 g, 16.72 mmol) were added to tetrahydrofuran (75 ml) in a sealed vessel and heated to 105° C. overnight white stirring. Reaction was cooled then diluted in EtAc/H₂O and extracted 4× with EtAc. Organics were washed with water, brine and dried over sodium sulfate. Solvents were removed under reduced pressure, then triturated with minimal EtAc and filtered to provide solids. Process was repeated and solids combined to afford 6-(3,5-dimethylisoxazol-4-yl)-4-iodo-1H-benzo[d]imidazol-2(3H)-one.

LCMS (m/z+1) 356.0.

Step 2: Preparation of 4-(2-chlor-4-iodo-1H-benzo[d]imidazol-6-yl)-3,5-dimethylisoxazole 6-(3,5-dimethylisoxazol-4-yl)-4-iodo-1H-benzo[d]imidazol-2(3H)-one (4.5 g, 12.67 mmol) was taken up in 100 mL

250

POCl₃ and heated to 105° C. overnight. Next day POCl₃ was removed under reduced pressure. Resulting residue was azeoptroped 2× with DCM then to afford a yellowish brown solid. Crude mixture was diluted in EtAc and water and extracted 3× with EtAc. Organics were washed with water then aq. sodium bicarbonate, brine. Organics were then dried over sodium sulfate and evaporated to dryness under reduced pressure to afford 4-(2-chloro-4-iodo-1H-benzo[d]imidazol-6-yl)-3,5-dimethylisoxazole.

LCMS (m/z+1) 374.0/376.0.

Step 3: N-benzyl-6-(3,5-dimethylisoxazol-4-yl)-4-iodo-1H-benzo[d]imidazol-2-amine

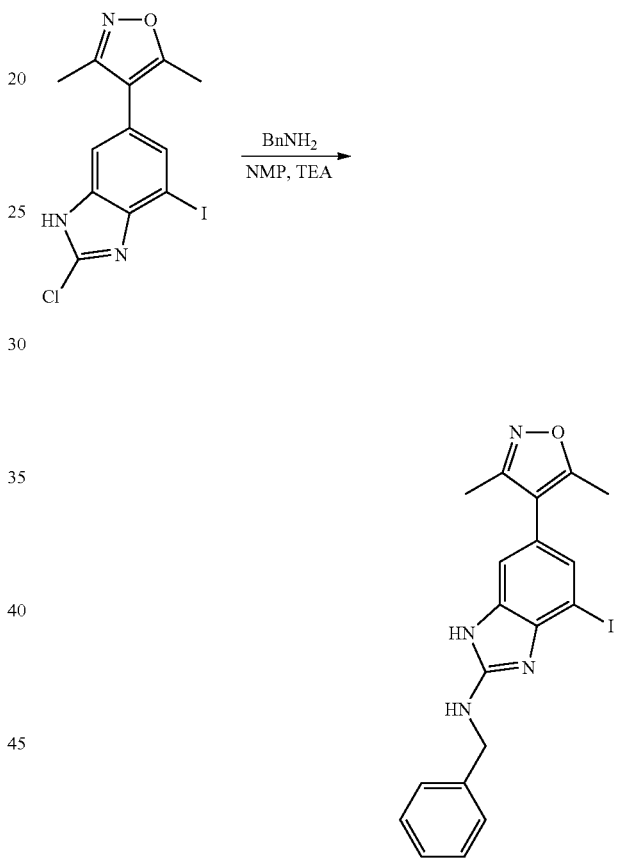

4-(2-chloro-4-iodo-1H-benzo[d]imidazol-6-yl)-3,5-dimethylisoxazole (800 mg, 2.14 mmol) was dissolved in 1-methyl-2-pyrrolidinone (25 ml) and to this was added benzylamine (1.88 ml, 17.14 mmol) and triethylamine (1 mL, 7.17 mmol. Reaction was scaled in a pressure vessel and heated to 120° C. for 1 day. Ath this point reaction was cooled, then diluted in EtAc/aq. ammonium chloride, extracted 3× with EtAc, washed with ammonium chloride 2×, water 2×, brine, then dried over sodium sulfate before evaporating to dryness under reduced pressure. Residue was purified by flash chromatography using Hex/EtAc as the eluent to afford N-benzyl-6-(3,5-dimethylisoxazol-4-yl)-4-iodo-1H-benzo[d]imidazol-2-amine.

.LCMS (m/z+1) 445.1. ¹H NMR (400 MHz, Methanol-d4) δ 7.34 (ddd, J=33.2, 23.7, 7.0 Hz, 5H), 7.13-7.06 (m, 1H), 4.63 (s, 2H), 2.39 (s, 3H), 2.23 (s, 3H).

Example 178

4-(2-ethoxy-4-(1-methyl-4-phenyl-1H-pyrazol-5-yl)-1H-benzo[d]imidazol-6-yl)-3,5-dimethylisoxazole (1020-178)

Step 1

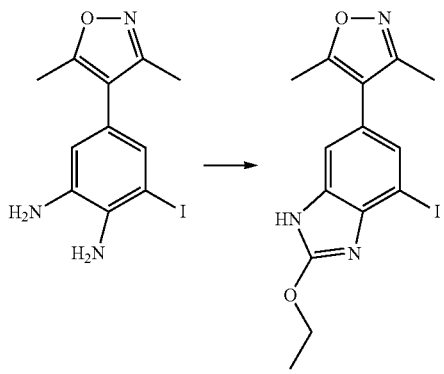 [SMILES: Cc1noc(C)c1-c1cc(N)c(N)c(I)c1 ; CCOc1nc2c(I)cc(-c3c(C)noc3C)cc2[nH]1]

5-(3,5-dimethylisoxazol-4-yl)-3-iodobenzene-1,2-diamine (1 g, 3 mmol) was dissolved in tetraethylorthocarbonate (2 mL). The reaction mixture was then heated at 130° C. overnight. The solvent was then evaporated and the residue was purified with combi-flash column chromatography to afford 1.1 g of 4-(2-ethoxy-4-iodo-1H-benzo[d]imidazol-6-yl)-3,5-dimethylisoxazole.

$C_{14}H_{14}N_3O_2$. 384.1 (M+1).

Step 2

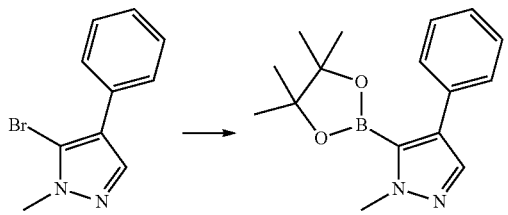 [SMILES: Cn1ncc(-c2ccccc2)c1Br ; Cn1ncc(-c2ccccc2)c1B1OC(C)(C)C(C)(C)O1]

5-Bromo-1-methyl-4-phenyl-1H-pyrazole (87 mg, 0.37 mmol) and 3,5-Dimethylisoxazole-4-boronic acid pinacol ester (373 mg, 1.47 mmol) was added to a 1,4-dioxane (2 ml). To the above mixture were added Pd(dppf)Cl$_2$ (27 mg, 0.037 mmol) and potassium acetate (181 mg, 1.85 mmol). The reaction mixture was heated at 100° C. for 2 h. The reaction mixture was then diluted with EtOAc (100 ml), washed with bring (50 ml×2). The organic solvent was evaporated and the residue was dissolved in DCM and purified with combi-flash column chromatography (product came out at 45% EtOAc/Hexane) to afford 1-methyl-4-phenyl-5-(4,4,5,5-tetramethyl-1,3,2-dioxaborolan-2-yl)-1H-pyrazole.

$C_{16}H_{21}BN_2O_2$. 285.3 (M+1).

Step 3

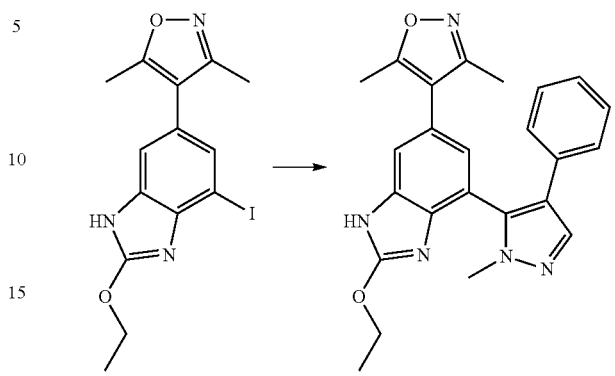

4-(2-ethoxy-4-iodo-1H-benzo[d]imidazol-6-yl)-3,5-dimethylisoxazole (100 mg, 0.26 mmol) and 1-methyl-4-phenyl-5-(4,4,5,5-tetramethyl-1,3,2-dioxaborolan-2-yl)-1H-pyrazole (37 mg, 0.13 mmol) were added to a solvent mixture of 1,2-dimethoxyethane (2 ml) and water (1 ml). To the above mixture were added PEPPSI-Ipr (18 mg, 0.026 mmol) and Cs2CO3 (127 mg, 0.39 mmol). The reaction mixture was heated at 130° C. in microwave reactor for 30 mins. The reaction mixture was then filtered and organic solvent was evaporated and the residue was purified with Prep HPLC (0-100% CH$_3$CN/H$_2$O) to afford 4-(2-ethoxy-4-(1-methyl-4-phenyl-1H-pyrazol-5-yl)-1H-benzo[d]imidazol-6-yl)-3,5-dimethylisoxazole.

$C_{24}H_{23}N_5O_2$. 414.5 (M+1). $^1$H NMR (400 MHz, CD$_3$OD) δ 8.20 (s, 1H), 7.91 (s, 1H), 7.64 (d, J=7.6 Hz, 2H), 7.55 (d, J=7.6 Hz, 2H), 6.94 (s, 1H), 6.86 (s, 1H), 3.87 (s, 3H), 4.18 (q, J=8.0 Hz, 2H), 2.39 (s, 3H), 2.22 (s, 3H), 1.22 (t, J=8.0 Hz, 3H).

Example 179

4-(2-isopropoxy-1-methyl-7-(6-methylquinolin-5-yl)-1H-benzo[d]imidazol-5-yl)-3,5-dimethylisoxazole (1020-179)

Step 1

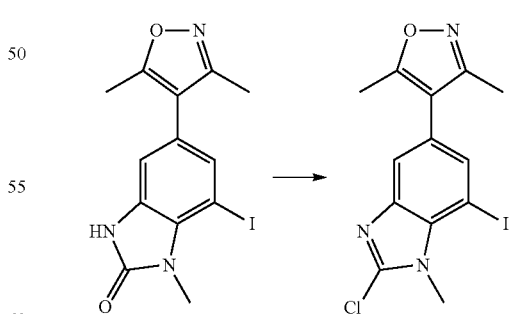

5-(3,5-dimethylisoxazol-4-yl)-7-iodo-1-methyl-1H-benzo[d]imidazol-2(3H)-one (48 mg, 0.13 mmol) was added to POCl$_3$ (0.1 mL) in round bottom flask and heated at 80° C. overnight. POCl$_3$ was then evaporated; the residue was dissolved in EtOAc, washed with NaHCO$_3$, dried organic layer over MgSO$_4$, filtered, and then evaporated. The residue

253 was dried over high vacuum pump to afford 69 mg of crude 4-(2-chloro-7-iodo-1-methyl-1H-benzo[d]imidazol-5-yl)-3,5-dimethylisoxazole.

$C_{13}H_{11}ClN_3O$. 388.1 (M+1).

Step 2

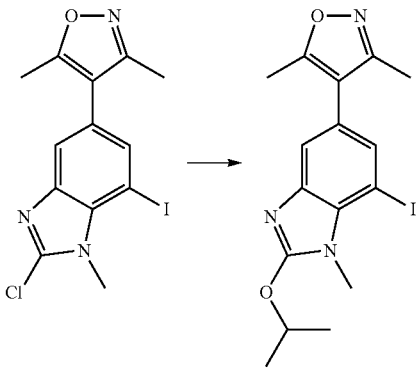 [SMILES: Cc1noc(C)c1-c1cc(I)c2c(c1)nc(Cl)n2C ; Cc1noc(C)c1-c1cc(I)c2c(c1)nc(OC(C)C)n2C]

4-(2-Chloro-7-iodo-1-methyl-1H-benzo[d]imidazol-5-yl)-3,5-dimethylisoxazole (46 mg, 0.12 mmol) was dissolved in isopropanol (2 mL), to the solution was added sodium isoproponoxide (195 mg, 2.4 mmol) and the reaction mixture was heated at 80° C. for 2 h. The solvent was then evaporated and the residue was purified with Prep HPLC to afford 14 mg of 4-(7-iodo-2-isopropoxy-1-methyl-1H-benzo[d]imidazol-5-yl)-3,5-dimethylisoxazole.

$C_{16}H_{18}N_3O_2$. 412.1 (M+1).

Step 3

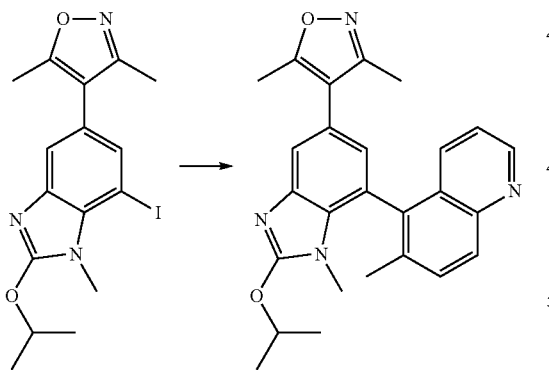

4-(7-iodo-2-isopropoxy-1-methyl-1H-benzo[d]imidazol-5-yl)-3,5-dimethylisoxazole (13 mg, 0.03 mmol) and (6-methylquinolin-5-yl)boronic acid (26 mg, 0.14 mmol) were added to a solvent mixture of 1,2-dimethoxyethane (2 ml) and water (1 ml). To the above mixture were added PEPPSI-Ipr (3 mg, 0.004 mmol) and $Cs_2CO_3$ (52 mg, 0.16 mmol). The reaction mixture was heated at 130° C. in microwave reactor for 30 mins. The reaction mixture was then filtered and organic solvent was evaporated and the residue was purified with Prep HPLC (0-100% $CH_3CN$/$H_2O$) to afford 4-(2-isopropoxy-1-methyl-7-(6-methylquinolin-5-yl)-1H-benzo[d]imidazol-5-yl)-3,5-dimethylisoxazole.

254

$C_{26}H_{26}N_4O_2$. 427.5 (M+1). $^1$H NMR (400 MHz, $CD_3OD$) δ 8.72 (d, J=4.0 Hz, 1H), 8.00 (d, J=8.8 Hz, 1H), 7.73 (d, J=8.4 Hz, 1H), 7.68 (d, J=8.0 Hz, 1H), 7.41 (s, 1H), 7.35 (d, J=4.0, 8.4 Hz, 1H), 6.78 (s, 1H), 5.20-5.16 (m, 1H), 2.62 (s, 3H), 2.35 (s, 3H), 2.22 (s, 3H), 2.19 (s, 3H), 1.37-1.34 (m, 6H).

Example 180

(4-chlorophenyl)(2-cyclopropyl-6-(3,5-dimethylisoxazol-4-yl)-1H-benzo[d]imidazol-4-yl)(pyridin-3-yl)methanol (1020-180)

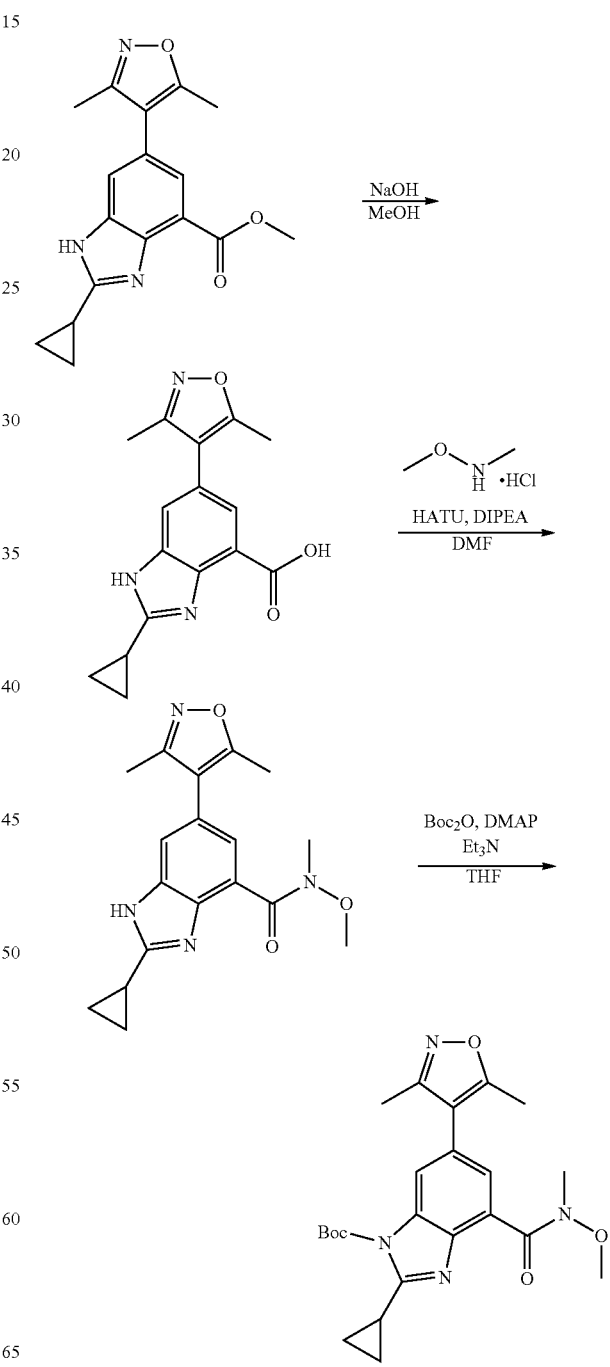

Step 1

From Example 101, step 4, methyl 2-cyclopropyl-6-(3,5-dimethylisoxazol-4-yl)-1H-benzo[d]imidazole-4-carboxylate (500 mg, 1.61 mmol) was dissolved in MeOH (5 mL) and NaOH (2M, 1.6 mL). Reaction was allowed to stir at room temperature overnight. The reaction was then neutralized to pH-7 with 1N HCl and precipitate was collected by vacuum filtration to give 2-cyclopropyl-6-(3,5-dimethylisoxazol-4-yl)-1H-benzo[d]imidazole-4-carboxylic acid (329 mg, 69%) as a white powder.

Step 2

2-cyclopropyl-6-(3,5-dimethylisoxazol-4-yl)-1H-benzo[d]imidazole-4-carboxylic acid (284 mg, 0.95 mmol) in DMF (10 mL) with HATU (581 mg, 2 mmol) for 15 mins, then added N,O-dilmethylhydroxylamine HCl salt (0.28 g, 3 mmol) and triethylamine. (0.53 ml, 4 mmol), stirred at RT overnight. Diluted with EtOAc, washed with brine, backextracted with EtOAc 4 times, evaporated organic solvent, purified with Combi-Flash column, product came out at 100% EtOAc, quantitative yield of 2-cyclopropyl-6-(3,5-dimethylisoxazol-4-yl)-N-methoxy-N-methyl-1H-benzo[d]imidazole-4-carboxamide.

Step 3

2-cyclopropyl-6-(3,5-dimethylisoxazol-4-yl)-N-methoxy-N-methyl-1H-benzo[d]imidazole-4-carboxamide (500 mg, 1.47 mmol) was dissolved in THF, to the solution was added Di-tert-butyl dicarbonate (641 mg, 2.94 mmol), N,N-Diisopropylethylamine (0.77 ml, 4.14 mmol) and 4-(Dimethylamino)pyridine (36 mg, 0.29 mmol). After stirring at RT for 30 mins, reaction was completed. Diluted with EtOAc, washed with brine, evaporated organic solvent, purified with Combi-Flash column. Product came out at 70% EtOAc/Hexane to give tert-butyl 2-cyclopropyl-6-(3,5-dimethylisoxazol-4-yl)-4-(methoxy(methyl)carbamoyl)-1H-benzo[d]imidazole-1-carboxylate (563 mg, 87%) as a white solid.

Steps 4 and 5

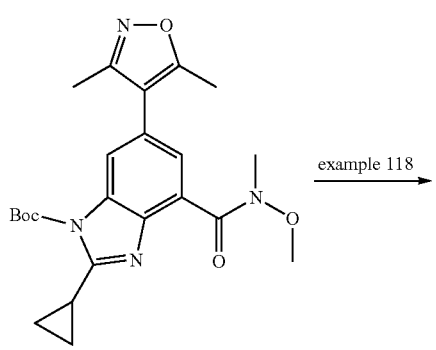

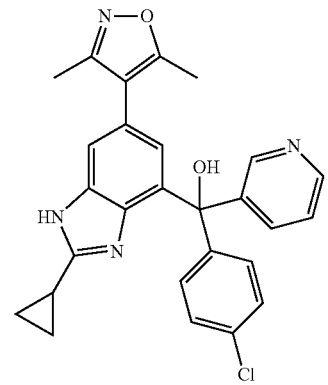

(2-cyclopropyl-6-(3,5-dimethylisoxazol-4-yl)-1H-benzo[d]imidazol-4-yl)(phenyl)(pyrimidin-5-yl)methanol was synthesized in similar fashion to Example 112 using 4-chlorophenylmagnesium chloride in place of phenylmagnesium chloride.

$C_{27}H_{23}ClN_4O_2$ 471.2 (M+1). $^1$H NMR (400 MHz, DMSO-$d_6$) δ 8.61 (dd, J=15.4, 3.5 Hz, 2H), 7.85 (s, 1H), 7.58 (d, J=8.6 Hz, 2H), 7.47 (d, J=8.6 Hz, 2H), 7.39-7.26 (m, 2H), 6.69 (s, 1H), 2.27 (s, 3H), 2.07 (s, 3H), 1.31 (d, J=27.1 Hz, 5H).

Example 181

(2-cyclopropyl-6-(3,5-dimethylisoxazol-4-yl)-1H-benzo[d]imidazol-4-yl)(pyridin-3-yl)(pyrimidin-2-yl)methanol (1020-181)

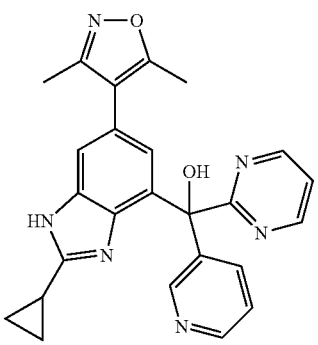 [SMILES: Cc1noc(C)c1-c1cc(C(O)(c2cccnc2)c2ncccn2)c2nc(C3CC3)[nH]c2c1]

(2-cyclopropyl-6-(3,5-dimethylisoxazol-4-yl)-1H-benzo[d]imidazol-4-yl)(phenyl)(pyrimidin-5-yl)methanol was synthesized in similar fashion to Example 112 using 3-pyridylmagneisum bromide in place of phenylmagnesium chloride in step 1 and 2-pyrimidynyllithium in step 2.

$C_{25}H_{22}N_6O_2$ 439.1 (M+1). $^1$H NMR (400 MHz, DMSO-$d_6$) δ 8.90 (d, J=4.9 Hz, 2H), 8.73 (s, 1H), 8.69-8.57 (m, 1H), 8.00 (m, 1H), 7.54 (dd, J=10.6, 5.7 Hz, 4H), 6.84 (s, 1H), 2.29 (s, 3H), 2.09 (s, 3H), 1.28 (d, J=28.3 Hz, 4H).

Example 182

(2-cyclopropyl-6-(3,5-dimethylisoxazol-4-yl)-1H-benzo[d]imidazol-4-yl)(phenyl)(pyridazin-3-yl)methanol (1020-182)

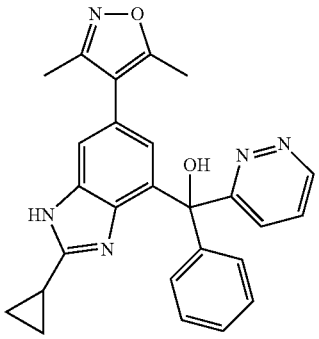 [SMILES: Cc1noc(C)c1-c1cc(C(O)(c2ccccc2)c2cccnn2)c2nc(C3CC3)[nH]c2c1]

(2-cyclopropyl-6-(3,5-dimethylisoxazol-4-yl)-1H-benzo[d]imidazol-4-yl)(phenyl)(pyrimidin-5-yl)methanol was synthesized in similar fashion to Example 112 using 2-pyridazinelithium in Step 2.

$C_{26}H_{23}N_5O_2$ 438.2 (M+1). $^1$H NMR (400 MHz, DMSO-$d_6$) δ 9.32-9.14 (m, 2H), 7.69 (s, 1H), 7.55 (s. 1H), 7.50-7.36 (m, 3H), 7.36-7.23 (m, 2H), 6.66 (s, 1H), 2.27 (s, 3H), 2.07 (s, 3H), 1.31 (s, 4H).

Example 183

(2-cyclopropyl-6-(3,5-dimethylisoxazol-4-yl)-1H-benzo[d]imidazol-4-yl)(phenyl)(pyrazin-2-yl)methanol (1020-183)

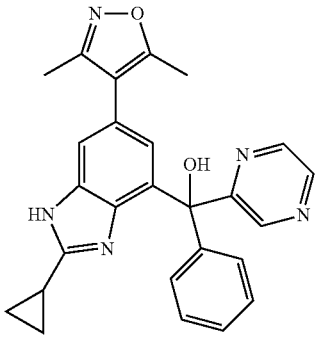 [SMILES: Cc1noc(C)c1-c1cc(C(O)(c2ccccc2)c2cncnc2)c2nc(C3CC3)[nH]c2c1]

(2-cyclopropyl-6-(3,5-dimethylisoxazol-4-yl)-1H-benzo[d]imidazol-4-yl)(phenyl)(pyrimidin-5-yl)methanol was synthesized in similar fashion to Example 112 using 2-pyrazinelithium in Step 2.

$C_{26}H_{23}N_5O_2$ 438.2 (M+1). $^1$H NMR (400 MHz, DMSO-$d_6$) δ 9.05 (d, J=1.5 Hz, 1), 8.64-8.52 (m, 2H), 7.64 (s, 1H), 7.53 (s, 1H), 7.41-7.24 (m, 6H), 6.78 (d, J=1.8 Hz, 1H), 2.60 (br, 1H), 2.28 (s, 3H), 2.07 (s, 3H), 1.34 (d, J=24.7 Hz, 4H).

Example 184

(2-cyclopropyl-6-(3,5-dimethylisoxazol-4-yl)-1H-benzo[d]imidazol-4-yl)(phenyl)(pyridin-4-yl)methanol (1020-184)

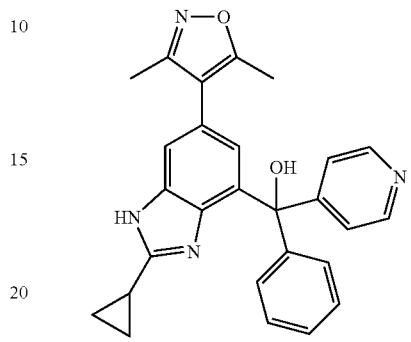

(2-cyclopropyl-6-(3,5-dimethylisoxazol-4-yl)-1H-benzo[d]imidazol-4-yl)(phenyl)(pyrimidin-5-yl)methanol was synthesized in similar fashion to Example 112 using 4-pyridinyllithium in Step 2.

$C_{27}H_{24}N_4O_2$ 438.2 (M+1). $^1$H NMR (400 MHz, DMSO-$d_6$) δ 8.70-8.64 (m, 2H), 7.61 (s, 1H), 7.54 (s, 3H), 7.45-7.34 (m, 3H), 7.32-7.25 (m, 2H), 6.61 (s, 1H), 2.55 (m, 1H) 2.26 (s, 3H), 2.06 (s, 3H), 1.32 (br, J=8.4 Hz, 2H), 1.25 (br, 2H).

Example 185

(2-cyclopropyl-6-(3,5-dimethylisoxazol-4-yl)-1H-benzo[d]imidazol-4-yl)(phenyl)(pyrimidin-5-yl)methanol (1020-185)

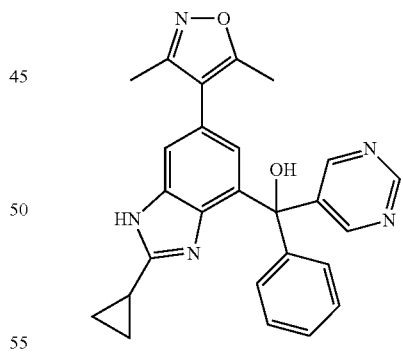

(2-cyclopropyl-6-(3,5-dimethylisoxazol-4-yl)-1H-benzo[d]imidazol-4-yl)(phenyl)(pyrimidin-5-yl)methanol was synthesized in similar fashion to Example 112 using 5-pyrimidinyllithium in Step 2.

$C_{26}H_{23}N_5O_2$ 438.2 (M+1). $^1$H NMR (400 MHz, DMSO-d) δ 9.15 (s, 1H), 8.67 (s, 2H), 7.55 (d, J=1.8 Hz, 2H), 7.47-7.23 (m, 6H), 6.72 (d, J=1.5 Hz, 1H), 2.58 (m, 1H), 2.25 (s, 3H), 2.05 (s, 3H), 1.32 (d, J=24.4 Hz, 4H).

Example 186

(2-cyclopropyl-6-(3,5-dimethylisoxazol-4-yl)-1H-benzo[d]imidazol-4-yl)di(pyridin-4-yl)methanol (1020-186)

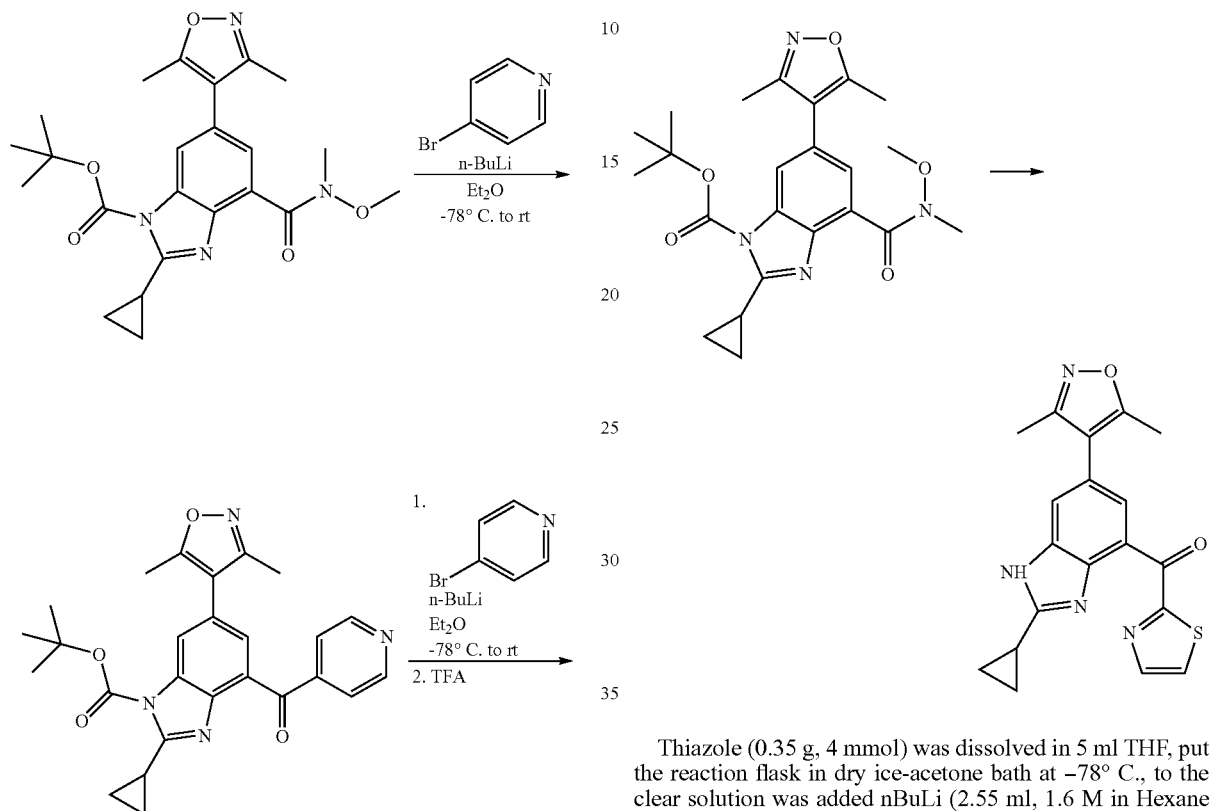

(2-cyclopropyl-6-(3,5-dimethylisoxazol-4-yl)-1H-benzo[d]imidazol-4-yl)di(pyridin-4-yl)methanol was synthesized using 4-bromopyridine in ether in a similar fashion to Example 112, steps 1-2.

$C_{26}H_{23}N_5O_2$. MS. 438.1 (M+1). $^1$H NMR (MeOH-d$_4$) δ 8.82 (d, J=6.4 Hz, 2H), 7.90 (d, J=5.2 Hz, 2H), 7.64 (s, 1H), 6.95 (s, 1H), 2.56 (td, J=8.6, 4.3 Hz, 1H), 2.33 (s, 3H), 2.14 (s, 3H), 1.57-1.47 (m, 2H), 1.42-1.34 (m, 2H).

Example 187

(2-cyclopropyl-6-(3,5-dimethylisoxazol-4-yl)-1H-benzo[d]imidazol-4-yl)(pyridazin-3-yl)(thiazol-2-yl)methanol (1020-187)

Step 1

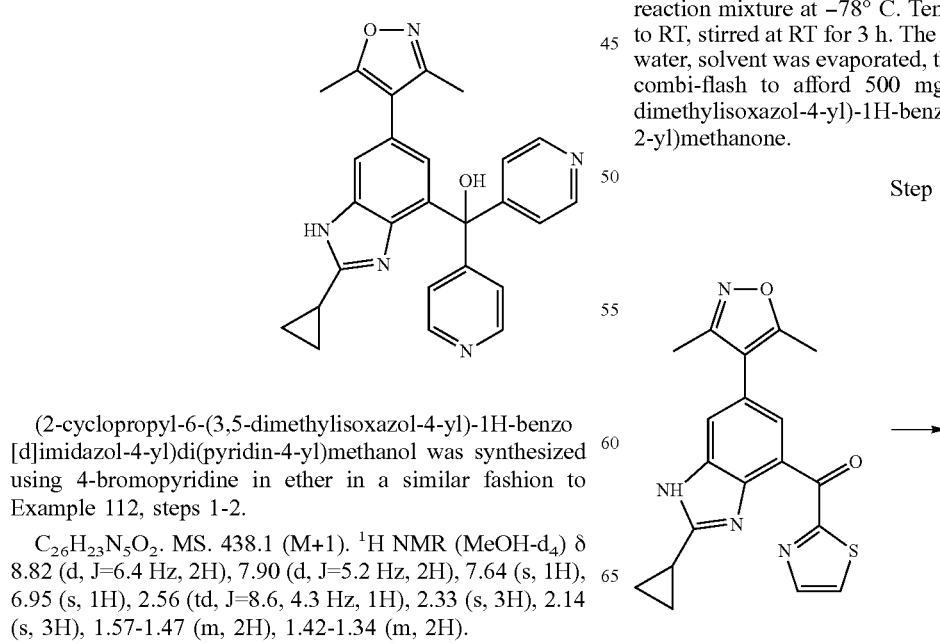

Thiazole (0.35 g, 4 mmol) was dissolved in 5 ml THF, put the reaction flask in dry ice-acetone bath at −78° C., to the clear solution was added nBuLi (2.55 ml, 1.6 M in Hexane the reaction mixture was stirred at −78° C. for 1 h, then added the solution of tert-butyl 2-cyclopropyl-6-(3,5-dimethylisoxazol-4-yl)-4-(methoxy(methyl)carbamoyl)-1H-benzo[d]imidazole-1-carboxylate in 2 ml THF to the above reaction mixture at −78° C. Temperature was slowly raised to RT, stirred at RT for 3 h. The reaction was quenched with water, solvent was evaporated, the residue was purified with combi-flash to afford 500 mg of (2-cyclopropyl-6-(3,5-dimethylisoxazol-4-yl)-1H-benzo[d]imidazol-4-yl)(thiazol-2-yl)methanone.

Step 2

-continued

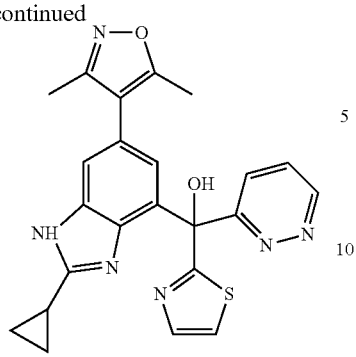

Pyridazine (52 mg, 0.65 mmol) was dissolved in 2 ml THF, put the reaction flask in dry ice-acetone bath at −78° C., to the clear solution was added TMP-MgCl—LiCl (0.365 ml, 1.0 M in Hexane/toluene), let Temperature warm up to 0° C. The reaction mixture was stirred at 0° C. for 30 mins, to the reaction mixture was added (2-cyclopropyl-6-(3,5-dimethylisoxazol-4-yl)-1H-benzo[d]imidazol-4-yl)(thiazol-2-yl)methanone (50 mg, 0.1 mmol) in THF at 0° C. and stirred for 1 h and then stirred at RT overnight. The reaction was quenched with water, extracted with EtOAc, evaporated organic solvent, then purified with Prep HPLC. Then added 1 ml TFA to the pure HPLC fraction of product and evaporated solvent at 50° C., the residue was purified again with Prep HPLC to afford 13 mg of (2-cyclopropyl-6-(3,5-dimethylisoxazol-4-yl)-1H-benzo[d]imidazol-4-yl)(pyridazin-3-yl)(thiazol-2-yl)methanol.

$C_{23}H_{20}N_6O_2S$. 445.1 (M+1). $^1$H NMR (400 MHz, $CD_3OD$) δ 9.44 (d, J=2.4 Hz, 1H), 9.29-9.17 (m, 1H), 8.07-7.82 (m, 2H), 7.73 (d, J=3.2 Hz, 1H), 7.58 (d, J=1.6 Hz, 1H), 7.41 (d, J=1.6 Hz, 1H), 2.63 (tt, J=8.4, 6.0 Hz, 1H), 2.35 (s, 3H), 2.17 (s, 3H), 1.64-1.47 (m, 2H), 1.50-1.32 (m, 2H).

Example 188

(2-cyclopropyl-6-(3,5-dimethylisoxazol-4-yl)-1H-benzo[d]imidazol-4-yl)(3,5-dimethylisoxazol-4-yl)(pyridin-3-yl)methanol (1020-188)

Step 1: tert-butyl 2-cyclopropyl-6-(3,5-dimethylisoxazol-4-yl)-4-nicotinoyl-1H-benzo[d]imidazole-1-carboxylate

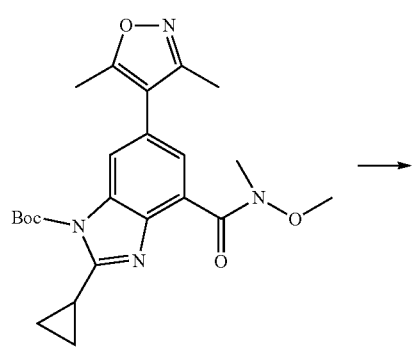

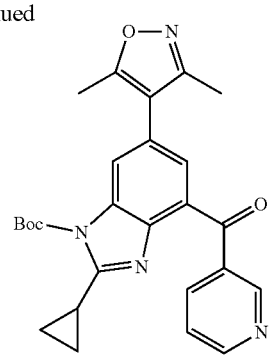

To a solution of tert-butyl 2-cyclopropyl-6-(3,5-dimethylisoxazol-4-yl)-4-(methoxy(methyl)carbamoyl)-1H-benzo[d]imidazole-1-carboxylate (300 mg, 0.68 mmol) in THF (30 mL) was added a solution of 3-pyridinylMgCl (2 eq) and the solution was stirred at room temperature for h. To the solution was added 3-pyridinylMgCl (2 eq) and the solution was stirred at room temperature for 20 min. Additional 0.25 mmol of 3-pyridinylMgCl was added and the solution was stirred at room temperature for 1.5 h. Aq. NH$_4$Cl was added and the mixture was extracted with EtOAc (200 mL). The organic solution was washed with brine and dried over Na$_2$SO$_4$. Solvent was removed and the residue was purified by silica gel column chromatography (0-100% EtOAc in hexane) to give tert-butyl 2-cyclopropyl-6-(3,5-dimethylisoxazol-4-yl)-4-nicotinoyl-1H-benzo[d]imidazole-1-carboxylate.

$C_{26}H_{26}N_4O_4$. MS. m/z 459.0. $^1$H NMR (Chloroform-d) δ 8.92 (dd, J=2.2, 0.9 Hz, 1H), 8.79 (dd, J=5.0, 1.7 Hz, 1H), 8.25 (d, J=8.0 Hz, 1H), 8.07 (d, J=1.6 Hz, 1H), 7.57 (d, J=1.6 Hz, 1H), 7.50 (m, 1H), 2.76 (ddd, J=8.0, 5.0, 2.8 Hz, 1H), 2.46 (s, 3H), 2.32 (s, 3H), 1.73 (s, 9H), 1.08-0.95 (m, 4H).

Step 2: (2-cyclopropyl-6-(3,5-dimethylisoxazol-4-yl)-1H-benzo[d]imidazol-4-yl)(3,5-dimethylisoxazol-4-yl)(pyridin-3-ylmethanol

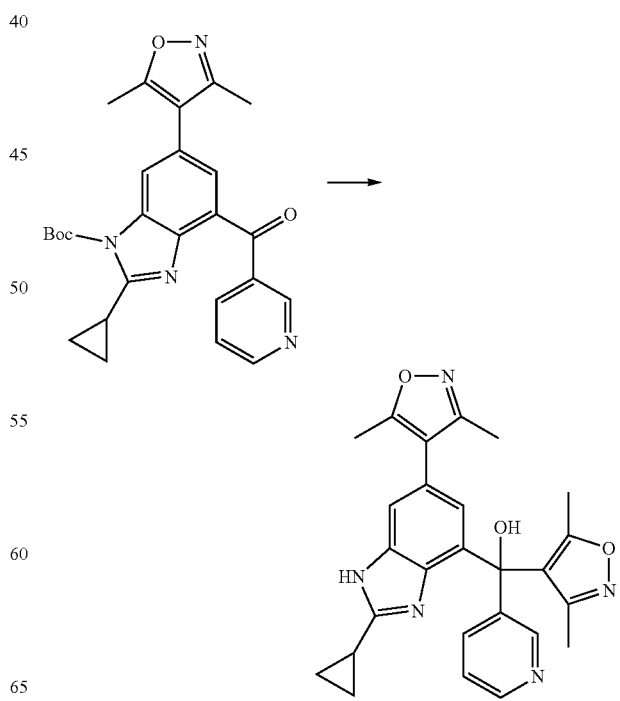

To a solution of 3,5-dimethylisooxazole (446 mg, 2 mmol) in THF (5 mL) was added butyllithium (96 mg, 1.5 mmol, 1.6 M in THF) and the solution was stirred at −78° C. for 1 h. To the solution was added a solution of tert-butyl 2-cyclopropyl-6-(3,5-dimethylisoxazol-4-yl)-4-nicotinoyl-1H-benzo[d]imidazole-1-carboxylate (69 mg, 0.15 mmol) in THF (3 mL) at −78° C. and the solution was stirred at room temperature for 5 h. H$_2$O (0.5 mL) was added and the solution was stirred at room temperature for 20 h. EtOAc (100 mL) was added. The organic solution was washed with brine and dried over Na$_2$SO$_4$. Solvent was removed and the residue was purified by silica gel column chromatography (0-5% MeOH/CH$_2$Cl$_2$) to give (2-cyclopropyl-6-(3,5-dimethylisoxazol-4-yl)-1H-benzo[d]imidazol-4-yl)(3,5-dimethylisoxazol-4-yl)(pyridin-3-yl)methanol.

C$_{26}$H$_{25}$N$_5$O$_3$. MS m/z 456.2 (M+1). $^1$H NMR (Methanol-d$_4$) δ 8.59 (d, J=2.6 Hz, 1H), 8.52 (dd, J=5.0, 1.5 Hz, 1H), 7.85 (ddd, J=8.1, 2.3, 1.5 Hz, 1H), 7.51-7.34 (m, 2H), 6.43 (d, J=1.5 Hz, 1H), 2.28 (s, 3H), 2.25-2.15 (m, 1H), 2.11 (s, 3H), 1.92 (s, 3H), 1.53 (s, 3H), 1.17-1.06 (m, 4H).

Example 189

(2-cyclopropyl-6-(3,5-dimethylisoxazol-4-yl)-1H-benzo[d]imidazol-4-yl)(pyridin-3-yl)(thiazol-2-yl)methanol (1020-189)

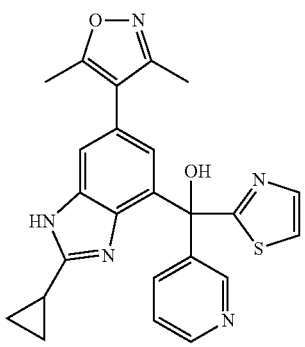 [SMILES: Cc1noc(C)c1-c1cc(C(O)(c2cccnc2)c2nccs2)c2nc(C3CC3)[nH]c2c1]

(2-cyclopropyl-6-(3,5-dimethylisoxazol-4-yl)-1H-benzo[d]imidazol-4-yl)(pyridin-3-yl)(thiazol-2-yl)methanol was synthesized using thiazole in a similar fashion as Example 188.

(2-cyclopropyl-6-(3,5-dimethylisoxazol-4-yl)-1H-benzo[d]imidazol-4-yl)(pyridin-3-yl)(thiazol-2-yl)methanol: C$_{24}$H$_{21}$N$_5$O$_2$S. MS m/z 444.1 (M+1). $^1$H NMR (Methanol-d$_4$) δ 8.64 (d, J=2.3 Hz, 1H), 8.44 (dd, J=4.6, 1.6 Hz, 1H), 7.92 (dt, J=8.4, 1.9 Hz, 1H), 7.81 (d, J=3.0 Hz, 1H), 7.59 (d, J=3.3 Hz, 1H), 7.39 (dd, J=8.1, 4.8 Hz, 1H), 6.94 (s, 1H), 2.32 (s, 3H), 2.20 (s, 1H), 2.15 (s, 3H), 1.10 (d, J=8.1 Hz, 4H).

Example 190

(2-cyclopropyl-6-(3,5-dimethylisoxazol-4-yl)-1H-benzo[d]imidazol-4-yl)(oxazol-2-yl)(pyridin-3-yl)methanol (1020-190)

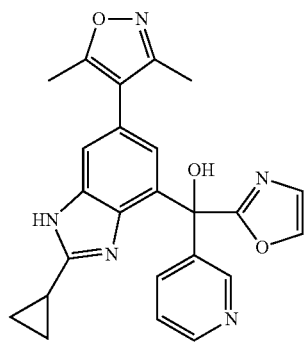 [SMILES: Cc1noc(C)c1-c1cc(C(O)(c2cccnc2)c2ncco2)c2nc(C3CC3)[nH]c2c1]

(2-cyclopropyl-6-(3,5-dimethylisoxazol-4-yl)-1H-benzo[d]imidazol-4-yl)(oxazol-2-yl)(pyridin-3-yl)methanol was synthesized using oxazole in a similar fashion as Example 188.

(2-cyclopropyl-6-(3,5-dimethylisoxazol-4-yl)-1H-benzo[d]imidazol-4-yl)(oxazol-2-yl)(pyridin-3-yl)methanol: C$_{24}$H$_{21}$N$_5$O$_3$. MS m/z 428.1 (M+1). $^1$H NMR (Methanol-d$_4$) δ 8.66 (t, J=1.6 Hz, 1H), 8.52-8.41 (m, 1H), 8.10-7.84 (m, 2H), 7.42 (dd, J=8.1, 4.8 Hz, 2H), 7.22 (s, 1H), 6.56 (s, 1H), 2.32 (s, 3H), 2.19 (s, 1H), 2.15 (s, 3H), 1.09 (d, J=7.9 Hz, 4H).

Example 191

1-(2-cyclopropyl-6-(3,5-dimethylisoxazol-4-yl)-1H-benzo[d]imidazol-4-yl)-1,2-di(pyridin-3-yl)ethanol (1020-191)

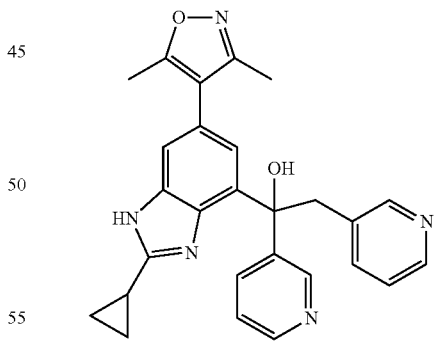

1-(2-cyclopropyl-6-(3,5-dimethylisoxazol-4-yl)-1H-benzo[d]imidazol-4-yl)-1,2-di(pyridin-3-yl)ethanol was synthesized using 3-picoline in a similar fashion as Example 188.

1-(2-cyclopropyl-6-(3,5-dimethylisoxazol-4-yl)-1H-benzo[d]imidazol-4-yl)-1,2-di(pyridin-3-yl)ethanol: C$_{27}$H$_{25}$N$_5$O$_2$. MS m/z 452.1 (M+1). $^1$H NMR (Methanol-d$_4$) δ 8.93 (d, J=2.2 Hz, 1H), 8.77-8.63 (m, 2H), 8.55-8.44 (m, 2H), 8.14 (dd, J=8.1, 1.7 Hz, 1H), 7.84 (ddd, J=15.5, 8.2, 5.4 Hz, 2H), 7.55 (dd, J=10.0, 1.3 Hz, 2H), 4.14 (d, J=2.2 Hz, 2H), 2.50 (dd, J=8.8, 1.9 Hz, 1H), 2.40 (s, 3H), 2.23 (s, 3H), 1.56-1.42 (m, 2H), 1.32 (td, J=6.9, 6.3, 3.9 Hz, 2H).

Example 192

(2-cyclopropyl-6-(3,5-dimethylisoxazol-4-yl)-1H-benzo[d]imidazol-4-yl)(6-methylpyridin-2-yl)(pyridazin-3-yl)methanol (1020-192)

Step 1: Preparation of tert-butyl 2-cyclopropyl-6-(3,5-dimethylisoxazol-4-yl-4-(pyridazino-3-carbonyl)-1H-benzo[d]imidazole-1-carboxylate

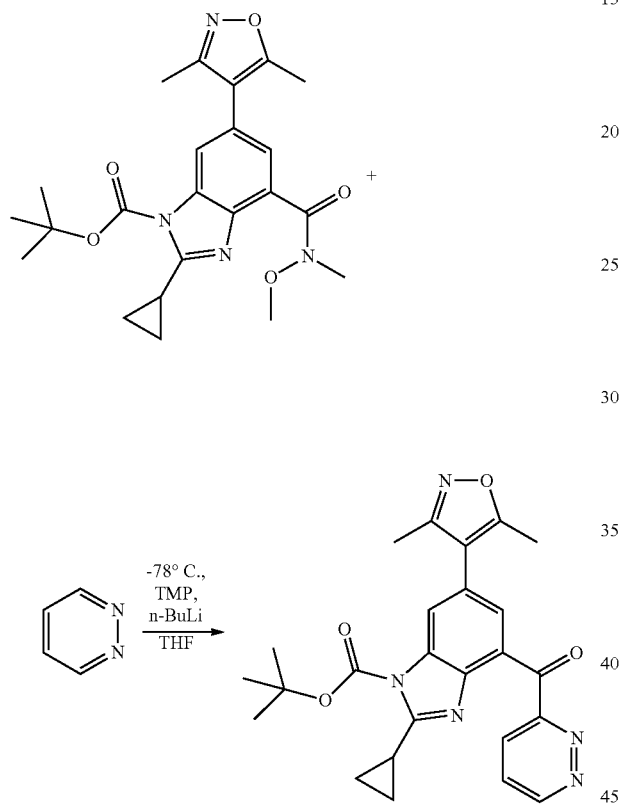

To a flame dried flask containing THF and 2,2,6,6-Tetramethylpiperidine (1.6 mL, 9.6 mmol.) at −78° C., n-BuLi (5.9 mL, 9.5 mmol, 1.6 M) was added dropwise. After 15 minutes of stirring, Pyridazine (0.66 mL, 9.1 mmol) was added. The solution was allowed to stir for 15 minutes, followed by the addition of tert-butyl 2-cyclopropyl-6-(3,5-dimethylisoxazol-4-yl)-4-(methoxy(methyl)carbamoyl)-1H-benzo[d]imidazole-1-carboxylate (500 mg, 1.1 mmol). The solution was allowed to stir for 30 minutes, then was removed from the cold bath to warm to room temperature. Once complete, the solution was quenched with DI H₂O and extracted three times with EtOAc. The combined organic layers were washed with saturated NaCl, dried over sodium sulfate, filtered and concentrated in vacuo. To the crude product was added 5 mL of TFA and was allowed to stir for 30 minutes. The solution was concentrated in vacuo and was purified via flash column chromatography to afford tert-butyl 2-cyclopropyl-6-(3,5-dimethylisoxazol-4-yl)-4-(pyridazine-3-carbonyl)-1H-benzo[d]imidazole-1-carboxylate (270 mg, 52% yield).

$C_{25}H_{25}N_5O_4$. MS. m/z 460.5 (M+1).

Step 2: Preparation of (2-cyclopropyl-6-(3,5-dimethylisoxazol-4-yl)-1H-benzo[d]imidazol-4-yl)(6-methylpyridin-2-yl(pyridazin-3-yl)methanol

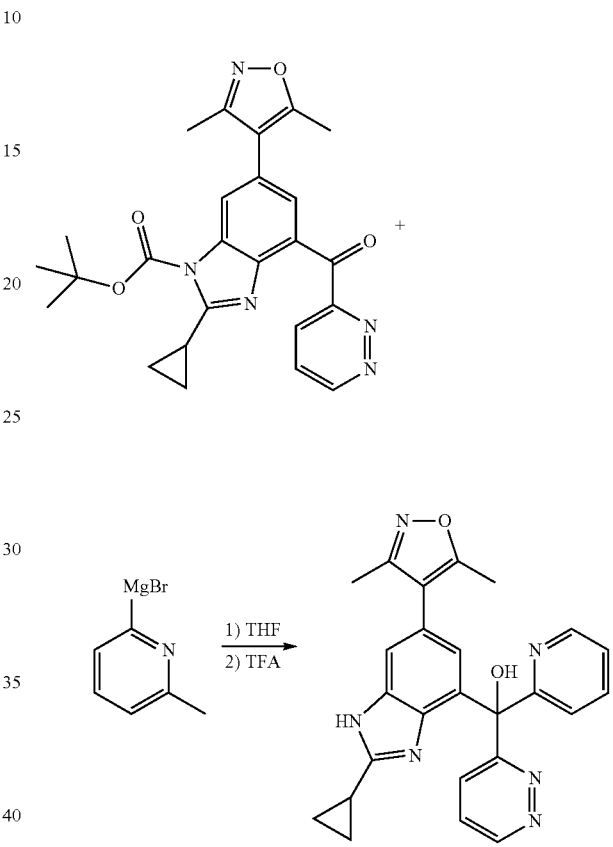

To a flame dried flask containing tert-butyl 2-cyclopropyl-6-(3,5-dimethylisoxazol-4-yl)-4-(pyridazine-3-carbonyl)-1H-benzo[d]imidazole-1-carboxylate (50 mg, 0.11 mmol) was added (6-methylpyridin-2-yl)magnesium bromide (1.3 mL, 0.33 mmol, 0.25 M). The reaction was allowed to stir for 30 minutes. Once complete, the solution was quenched with DI H₂O and extracted three times with EtOAc. The combined organic layers were washed with saturated NaCl, dried over sodium sulfate, filtered and concentrated in vacuo. To the crude product was added 5 mL of TFA and was allowed to stir for 30 minutes. The solution was concentrated in vacuo and was purified via flash column chromatography to afford (2-cyclopropyl-6-(3,5-dimethylisoxazol-4-yl)-1H-benzo[d]imidazol-4-yl)(6-methylpyridin-2-yl)(pyridazin-3-yl)methanol.

$C_{26}H_{24}N_6O_2$. MS. m/z 443.5 (M+1). ¹H NMR (400 MHz, cd₃od) δ 9.09 (d, J=3.9 Hz, 1H), 8.03 (d, J=7.6 Hz, 1H), 7.76-7.63 (m, 2H), 7.37 (d, J=8.6 Hz, 2H), 7.20 (d, J=7.6 Hz, 1H), 6.73 (d, J=1.3 Hz, 1H), 2.51 (s, 3H), 2.31 (s, 3H), 2.16 (d, J=9.4 Hz, 1H), 2.14 (s, 3H), 1.09 (d, J=7.1 Hz, 4H).

Example 193

Preparation of (2-cyclopropyl-6-(3,5-dimethylisoxazol-4-yl)-1H-benzo[d]imidazol-4-yl)(3-methylpyridin-2-yl)(phenyl)methanol (1020-193)

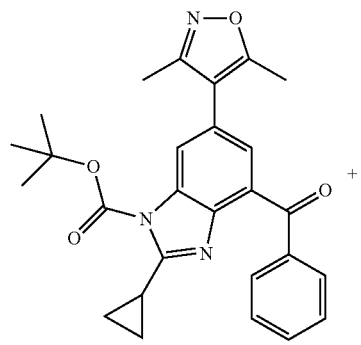

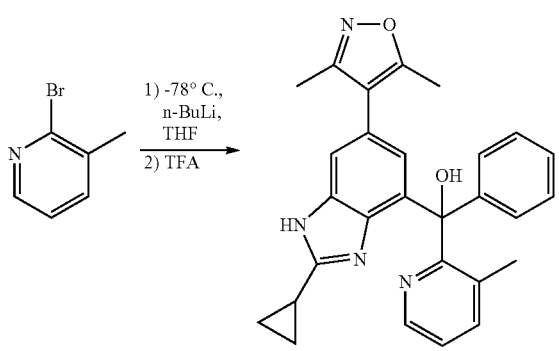

Using the intermediate from Example 112, step 1, to a flame dried flask containing THF and 2-bromo-3-methylpyridine (56 mg, 0.33 mmol) was added n-BuLi (0.41 mL, 6.6 mmol) dropwise at −78° C. The solution was allowed to stir for 15 minutes, followed by the addition of tert-butyl 4-benzoyl-2-cyclopropyl-6-(3,5-dimethylisoxazol-4-yl)-1H-benzo[d]imidazole-1-carboxylate (50 mg, 0.11 mmol) in 2 mL of THF. The solution was allowed to warm to room temperature. Once complete, the solution was quenched with DI H$_2$O and extracted three times with EtOAc. The combined organic layers were washed with saturated NaCl, dried over sodium sulfate, filtered and concentrated in vacuo. To the crude product was added 5 mL of TFA and was allowed to stir for 30 minutes. The solution was concentrated in vacuo and was purified via reverse phase HPLC to afford (2-cyclopropyl-6-(3,5-dimethylisoxazol-4-yl)-1H-benzo[d]imidazol-4-yl)(3-methylpyridin-2-yl)(phenyl) methanol.

C$_{28}$H$_{26}$N$_4$O$_2$. MS. m/z 451.5 (M+1). $^1$H NMR (400 MHz, cd$_3$od) δ 8.39 (s, 1H), 7.62 (d, J=7.5 Hz, 1H), 7.46-7.27 (m, 6H), 7.22 (s, 2H), 6.32 (s, 1H), 2.25 (s, 3H), 2.12 (d, J=18.5 Hz, 2H), 2.06 (s, 3H), 1.92 (s, 3H), 1.08 (d, J=8.1 Hz, 4H).

Example 194

Preparation of (2-cyclopropyl-6-(3,5-dimethylisoxazol-4-yl)-1H-benzo[d]imidazol-4-yl)(phenyl)methanone (1020-194)

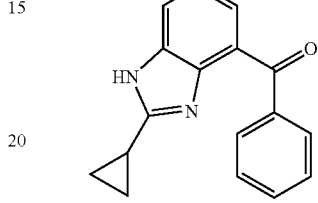

(2-cyclopropyl-6-(3,5-dimethylisoxazol-4-yl)-1H-benzo[d]imidazol-4-yl)(phenyl)methanone was obtained from Example 193. In this case, deprotected starting material was recovered and characterized.

C$_{22}$H$_{19}$N$_3$O$_2$. MS. m/z 358.4 (M+1). $^1$H NMR (400 MHz, cd$_3$od) δ 7.83 (d, J=7.2 Hz, 2H), 7.67 (dd, J=18.5, 11.1 Hz, 2H), 7.56 (t, J=7.6 Hz, 2H), 7.37 (s, 1H), 2.40 (s, 3H), 2.34 (s, 1H), 2.24 (s, 3H), 1.21 (d, J=8.1 Hz, 4H).

Example 195

Preparation of (2-cyclopropyl-6-(3,5-dimethylisoxazol-4-yl)-1H-benzo[d]imidazol-4-yl)(4-methylpyridin-2-yl)(phenyl)methanol (1020-195)

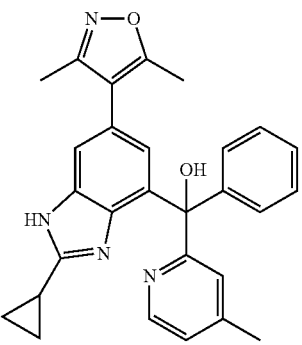 [SMILES: Cc1ccnc(C(O)(c2ccccc2)c2cc(-c3c(C)noc3C)cc3[nH]c(C4CC4)nc23)c1]

(2-cyclopropyl-6-(3,5-dimethylisoxazol-4-yl)-1H-benzo[d]imidazol-4-yl)(4-methylpyridin-2-yl)(phenyl)methanol was synthesized in a similar fashion as Example 193, substituting 2-bromo-3-methylpyridine for 2-bromo-4-methylpyridine.

C$_{28}$H$_{26}$N$_4$O$_2$. MS. m/z 451.5 (M+1). $^1$H NMR (400 MHz, dmso) δ 8.33 (d, J=37.9 Hz, 1H), 7.77 (d, J=51.4 Hz, 1H), 7.49-7.03 (m, 8H), 6.78 (d, J=63.4 Hz, 1H), 6.44 (s, 1H), 2.09 (s, 1H), 0.95 (s, 4H).

Example 196

Preparation of (2-cyclopropyl-6-(3,5-dimethylisoxazol-4-yl)-1H-benzo[d]imidazol-4-yl)(5-methylpyridin-2-yl)(phenyl)methanol (1020-196)

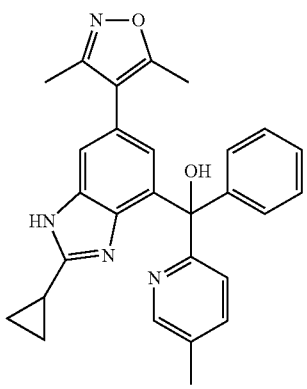 [SMILES: Cc1ccc(C(O)(c2ccccc2)c2cc(-c3c(C)noc3C)cc3[nH]c(C4CC4)nc23)nc1]

(2-cyclopropyl-6-(3,5-dimethylisoxazol-4-yl)-1H-benzo[d]imidazol-4-yl)(5-methylpyridin-2-yl)(phenyl)methanol was synthesized in a similar fashion as Example 193, substituting 2-bromo-3-methylpyridine for 2-bromo-5-methylpyridine.

$C_{28}H_{26}N_4O_2$. MS. m/z 451.5 (M+1). $^1$H NMR (400 MHz, cd$_3$od) δ 8.33 (s, 1H), 7.61 (dd, J=8.2, 2.3 Hz, 1H), 7.45-7.19 (m, 7H), 6.33 (s, 1H), 2.52 (s, 3H), 2.26 (s, 3H), 2.17 (d, J=82 Hz, 1H), 2.08 (s, 3H), 2.00 (s, 1H), 1.11 (dd, J=18.3, 7.0 Hz, 4H).

Example 197

Preparation of (2-cyclopropyl-6-(3,5-dimethylisoxazol-4-yl)-1H-benzo[d]imidazol-4-yl)(2-methylpyridin-3-yl)(phenyl)methanol (1020-197)

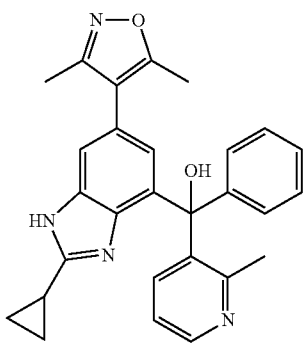 [SMILES: Cc1ncccc1C(O)(c1ccccc1)c1cc(-c2c(C)noc2C)cc2[nH]c(C3CC3)nc12]

(2-cyclopropyl-6-(3,5-dimethylisoxazol-4-yl)-1H-benzo[d]imidazol-4-yl)(2-methylpyridin-3-yl)(phenyl)methanol was synthesized in a similar fashion as Example 193, substituting 2-bromo-3-methylpyridine for 3-bromo-2-methylpyridine.

$C_{28}H_{26}N_4O_2$. MS. m/z 451.5 (M+1). $^1$H NMR (400 MHz, dmso) δ 8.33 (d, J=3.6 Hz, 1H), 7.65 (s, 1H), 7.31 (dt, J=16.0, 7.6 Hz, 5H), 7.02 (s, 1H), 6.78 (s, 1H), 6.15 (s, 1H), 2.28 (s, 3H), 2.19 (s, 3H), 1.98 (s, 3H), 1.10-0.89 (m, 4H).

Example 198

1-(2-cyclopropyl-6-(3,5-dimethylisoxazol-4-yl)-1H-benzo[d]imidazol-4-yl)-1-(5-fluoro-6-methylpyridin-2-yl)-2-methylpropan-1-ol (1020-198)

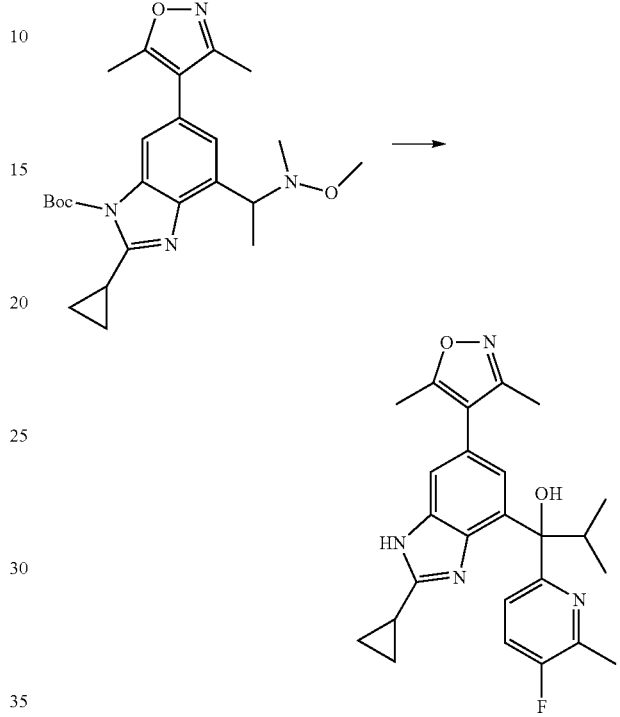

Step 1

To a solution of 2-bromo-5-fluoro-6-methyl-pyridine (345 mg, 1.82 mmol) in toluene (4 mL) was added iPrMgCl/LiCl (0.187 g, 1.8 mmol, 1M in THF) and the solution was stirred at room temperature for 4 h. To the solution was added tert-butyl 2-cyclopropyl-6-(3,5-dimethylisoxazol-4-yl)-4-(methoxy(methyl)carbamoyl)-1H-benzo[d]imidazole-1-carboxylate (100 mg, 0.227 mmol) in THF (2 mL) and the solution was stirred at room temperature for 1 h. EtOAc (100 mL) was added and the solution was washed with aq NH$_4$Cl and brine, dried over Na$_2$SO$_4$. Solvent was removed and the residue was purified by silica gel column chromatography (0-10% MeOH in CH$_2$Cl$_2$), then 0-60% EtOAc in hexane) to give ketone intermediate (30 mg) which was dissolved in 2-methyl-THF (2 mL) for the next reaction.

Step 2

To a solution of 2-bromo-5-fluoro-6-methyl-pyridine (93 mg, 0.49 mmol) in toluene (4 mL) was added iPrMgCl/LiCl (50 mg, 0.49 mmol, 1M in THF) and the solution was stirred at room temperature for 4 h. To the solution was added a solution of ketone prepared above and the solution was stirred at room temperature for 1 h. EtOAc (100 mL) was added and the solution was washed with aq NH$_4$Cl and dried over Na$_2$SO$_4$. Solvent was removed and the residue was purified by silica gel column chromatography (0-10% MeOH in CH2Cl2 then 0-60% EtOAc in hexanes) to give N-Boc protected product which was dissolved in THF (2 mL), TFA (2 mL) and waster (0.1 mL). The solution was heated at 50° C. for 1 h. Solvent was removed and the residue was purified by HPLC to give 1-(2-cyclopropyl-6-(3,5-dimethylisoxazol-4-yl)-1H-benzo[d]imidazol-4-yl)-1-(5-fluoro-6-methylpyridin-2-yl)-2-methylpropan-1-ol.

$C_{25}H_{27}FN_4O_2$. MS m/z 435.2 (M+1). $^1$H NMR (Methanol-$d_4$) δ 7.72 (ddd, J=8.7, 3.6, 0.8 Hz, 1H), 7.65 (d, J=1.4 Hz, 1H), 7.48 (t, J=8.9 Hz, 1H), 7.40 (d, J=1.4 Hz, 1H), 3.18 (p, J=6.7 Hz, 1H), 2.67 (tt, J=8.5, 5.0 Hz, 1H), 2.51 (d, J=2.9 Hz, 3H), 2.40 (s, 3H), 2.24 (s, 3H), 1.61-1.49 (m, 2H), 1.40 (dddd, J=14.2, 7.4, 5.6, 3.9 Hz, 2H), 0.94 (d, J=6.8 Hz, 3H), 0.81 (d, J=6.6 Hz, 3H).

Example 199

(2-cyclopropyl-6-(3,5-dimethylisoxazol-4-yl)-1H-benzo[d]imidazol-4-yl)(pyridazin-3-yl)(thiazol-2-yl)methanol (1020-199)

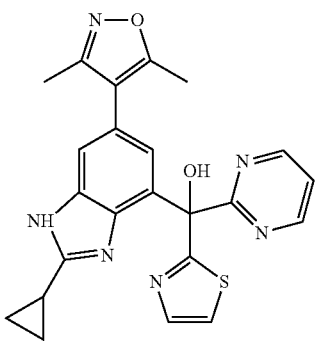 [SMILES: Cc1noc(C)c1-c1cc(C(O)(c2ncccn2)c2nccs2)c2nc(C3CC3)[nH]c2c1]

(2-cyclopropyl-6-(3,5-dimethylisoxazol-4-yl)-1H-benzo[d]imidazol-4-yl)(pyridazin-3-yl)(thiazol-2-yl)methanol was synthesized in a similar fashion to Example 198.

$C_{23}H_{20}N_6O_2S$. 445.1 (M+1). $^1$H NMR (400 MHz, CD$_3$OD) δ 8.86 (d, J=2.4 Hz, 1H), 7.79-7.77 (m, 1H), 7.74-7.72 (m, 1H), 7.64 (d, J=2.8 Hz, 1H), 7.58 (d, J=1.6 Hz, 1H), 7.51 (d, J=1.6 Hz, 1H), 7.44-7.42 (m, 1H), 5.68 (s, 1H), 2.58-2.47 (m, 1H), 2.38 (s, 3H), 2.21 (s, 3H), 1.55-1.53 (m, 2H), 1.44-1.42 (m, 2H).

Example 200

(2-cyclopropyl-6-(3,5-dimethylisoxazol-4-yl)-1H-benzo[d]imidazol-4-yl)(2,6-dimethylpyridin-3-yl)(pyridin-3-yl)methanol (1020-200)

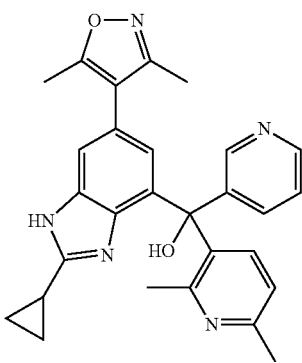 [SMILES: Cc1ccc(C(O)(c2cccnc2)c2cc(-c3c(C)noc3C)cc3[nH]c(C4CC4)nc23)c(C)n1]

(2-cyclopropyl-6-(3,5-dimethylisoxazol-4-yl)-1H-benzo[d]imidazol-4-yl)(2,6-dimethylpyridin-3-yl)(pyridin-3-yl)methanol was synthesized in a similar fashion to Example 198.

$C_{28}H_{27}N_5O_2$. 466.2 (M+1). $^1$H NMR (400 MHz, CD$_3$OD) δ 8.41 (d, J=3.6 Hz, 2H), 7.69 (d, J=8.0 Hz, 1H), 7.38-7.35 (m, 1H), 7.31 (bs, 1H), 6.88 (bs, 2H), 6.18 (d, J=1.6 Hz, 1H), 2.41 (s, 3H), 2.33 (s, 3H), 2.17 (s, 3H), 2.13-2.04 (m, 1H), 1.98 (s, 3H), 1.13-1.01 (m, 4H).

Example 201 cyclopropyl(2-cyclopropyl-6-(3,5-dimethylisoxazol-4-yl)-1H-benzo[d]imidazol-4-yl)(pyridin-3-yl)methanol (1020-201)

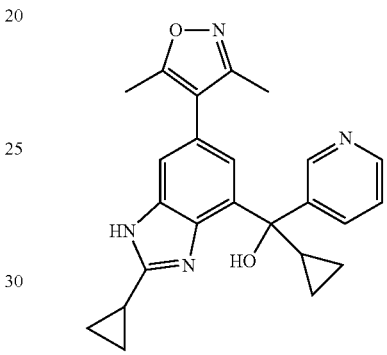

cyclopropyl(2-cyclopropyl-6-(3,5-dimethylisoxazol-4-yl)-1H-benzo[d]imidazol-4-yl)(pyridin-3-yl)methanol was synthesized in a similar fashion to Example 198.

$C_{24}H_{24}N_4O_2$. 401.1 (M+1). $^1$H NMR (400 MHz, CD$_3$OD) δ 8.97 (d, J=2.0 Hz, 1H), 8.70 (dd, J=1.2, 6.4 Hz, 1H), 8.42 (tt, J=1.6, 8.0 Hz, 1H), 7.84 (dd, J=1.6, 8.4 Hz, 1H), 7.55-7.52 (m, 2H), 2.58-2.51 (m, 1H), 2.41 (s, 3H), 2.24 (s, 3H), 1.88-1.83 (m, 1H), 1.53-1.49 (m, 2H), 1.38-1.36 (m, 2H), 0.74-0.65 (m, 4H).

Example 202

(2-cyclopropyl-6-(3,5-dimethylisoxazol-4-yl)-1H-benzo[d]imidazol-4-yl)(6-methylpyridin-2-yl)(phenyl)methanol (1020-202)

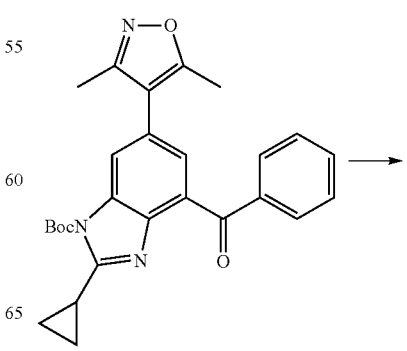

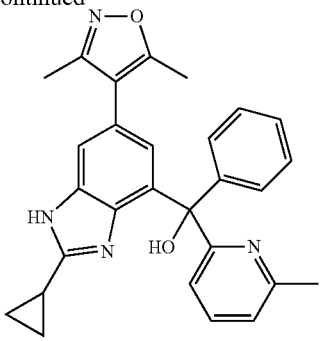

Into a flask containing tert-butyl 4-benzoyl-2-cyclopropyl-6-(3,5-dimethylisoxazol-4-yl)-1H-benzo[d]imidazole-1-carboxylate (50 mg, 0.11 mmol, 1 equiv.) is added THF (5 mL) and to it is added (6-methylpyridin-2-yl)magnesium bromide (2.6 mL, 0.66 mmol, 6 equiv., 0.25 M THF, Rieke Metals). After completion, the reaction was quenched and extracted with EtOAc and washed with water, saturated NH₄Cl. After drying with MgSO₄, it was filtered and concentrated to dryness. To the crude material is added TFA (5 mL) and allowed to stir for 30 min. After the reaction was complete, it was concentrated in vacuo. Purification was carried out by reverse phase HPLC to (2-cyclopropyl-6-(3,5-dimethylisoxazol-1-yl)-1H-benzo[d]imidazol-4-yl)(6-methylpyridin-2-yl)(phenyl)methanol (as a racemate).

LCMS (m/z+1) 467.23

Example 203

Preparation of (2-cyclopropyl-6-(3,5-dimethylisoxazol-4-yl)-1H-benzo[d]imidazol-4-yl)(3-methylpyridin-2-yl)(pyridin-2-yl)methanol (1020-203)

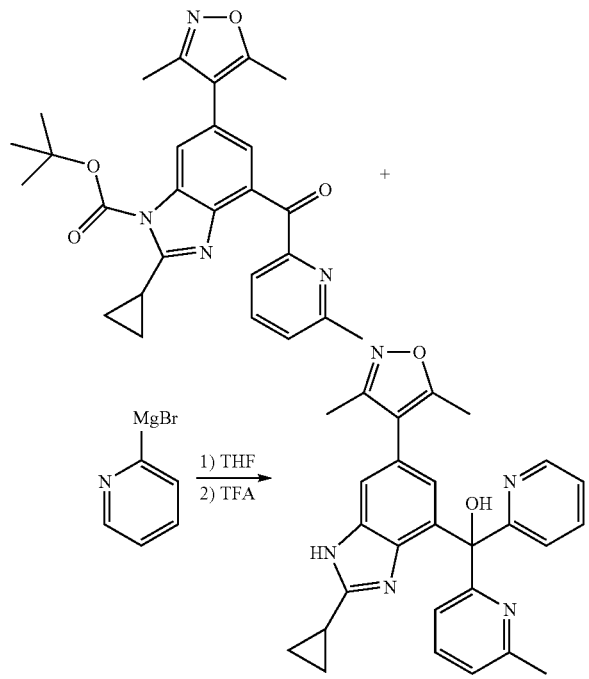

To a flame dried flask containing THF and tert-butyl 2-cyclopropyl-6-(3,5-dimethylisoxazol-4- yl)-4-(6-methylpicolinoyl)-1H-benzo[d]imidazole-1-carboxylate (45 mg, 0.095 mmol) was added (pyridin-2-yl)magnesium bromide (2.3 mL, 0.57 mmol). The solution was allowed to stir for 1 hour. Once complete, the solution was quenched with DI H₂O and extracted three times with EtOAc. The combined organic layers were washed with saturated NaCl, dried over sodium sulfate, filtered and concentrated in vacuo. To the crude product was added 5 mL of TFA and was allowed to stir for 30 minutes. The solution was concentrated in vacuo and was purified via reverse phase HPLC to afford (2-cyclopropyl-6-(3,5-dimethylisoxazol-4-yl)-1H-benzo[d]imidazol-4-yl)(6-methylpyridin-2-yl)(pyridin-2-yl)methanol.

$C_{27}H_{25}N_5O_2$. MS. m/z 452.5 (M+1). ¹H NMR (400 MHz, cd₃od) δ 8.51 (d, J=4.3 Hz, 1H), 7.80 (td, J=7.8, 1.7 Hz, 1H), 7.67-7.60 (m, 2H), 7.36 (s, 1H), 7.33-7.28 (m, 1H), 7.24 (d, J=7.8 Hz, 1H), 7.18 (d, J=7.7 Hz, 1H), 6.68 (d, J=1.4 Hz, 1H), 2.52 (s, 3H), 2.29 (d, J=6.8 Hz, 3H), 2.18 (dd, J=13.4, 7.0 Hz, 1H), 2.13 (s, 3H), 1.09 (d, J=7.9 Hz, 4H).

Example 204

(2-cyclopropyl-6-(3,5-dimethylisoxazol-4-yl)-1H-benzo[d]imidazol-4-yl)(6-methoxypyridin-3-yl)(pyridin-2-yl)methanol (1020-204)

Step 1: Tert-butyl 2-cyclopropyl-6-(3,5-dimethylisoxazol-4-yl)-4-(6-methoxynicotinoyl)-1H-benzo[d]imidazole-1-carboxylate

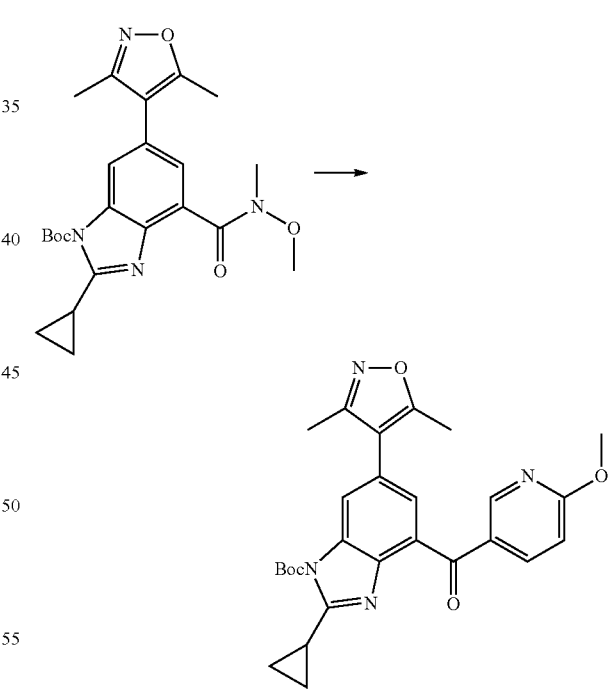

A flask containing 5-bromo-2-methoxypyridine (705 μL, 5.45 mmol, 4 equiv.) and MeTHF (10 mL) was cooled to −78° C. before BuLi (3.41 mL, 5.45 mmol, 4 equiv.) was added. After 30 min, tert-butyl 2-cyclopropyl-6-(3,5-dimethylisoxazol-4-yl)-4-(methoxy(methyl)carbamoyl)-1H-benzo[d]imidazole-1-carboxylate (600 mg, 1.36 mmol, 1 equiv.) dissolved in MeTHF (4 mL) was added to the reaction mixture. After completion, the reaction was quenched and extracted with EtOAc and washed with water, saturated NH₄Cl. After drying with MgSO₄, it was filtered and concentrated to dryness. Flash column chromatography was carried out to tert-butyl 2-cyclopropyl-6-(3,5-dimethylisoxazol-4-yl)-4-(6-methoxynicotinoyl)-1H-benzo[d]imidazole-1-carboxylate (325 mg, 49%, 7/3 EtOAc/Hex).

LCMS (m/z+1) 489.48

Step 2: (2-cyclopropyl-6-(3,5-dimethylisoxazol-4-yl)-1H-benzo[d]imidazol-4-yl)(6-methoxypyridin-3-yl)(pyridin-2-yl)methanol

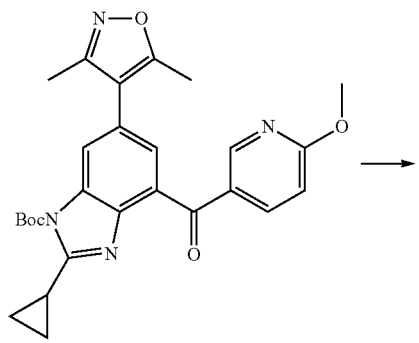

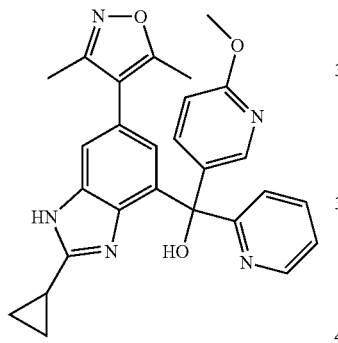

Into a flask containing 2-bromopyridine (110 μL, 1.15 mml, 8 equiv.) was added MeTHF (5 mL) and to it is added BuLi (720 μL, 1.15 mmol, 8 equiv.) slowly at −78° C. After 45 minutes, tert-butyl 2-cyclopropyl-6-(3,5-dimethylisoxazol-4-yl)-4-(6-methoxynicotinoyl)-1H-benzo[d]imidazole-1-carboxylate (70 mg, 0.14 mmol, 1 equiv.) dissolved in MeTHF (2 mL) was added slowly to the reaction. After completion, the reaction was quenched and extracted with EtOAc and washed with water, saturated NH₄Cl. After drying with MgSO₄, it was filtered and concentrated to dryness. To the crude material is added TFA (5 mL) and allowed to stir for 30 min. After the reaction was complete, it was concentrated in vacuo. Purification was carried out by reverse phase HPLC to (2-cyclopropyl-6-(3,5-dimethylisoxazol-4-yl)-1H-benzo[d]imidazol-4-yl)(6-methoxypyridin-3-yl)(pyridin-2-yl)methanol (as a racemate).

LCMS (m/z+1) 468.23. ¹H NMR (400 MHz, Methanol-d4) δ 8.62 (ddd, J=4.9, 1.8, 0.9 Hz, 1H), 7.99-7.80 (m, 2H), 7.72 (dt, J=8.1, 1.0 Hz, 1H), 7.64 (dd, J=8.8, 2.6 Hz, 1H), 7.52 (d, J=1.5 Hz, 1H), 7.42 (ddd, J=7.6, 4.9, 1.1 Hz, 1H), 7.04 (d, J=1.4 Hz, 1H), 6.83 (dd, J=8.8, 0.7 Hz, 1H), 3.91 (s, 3H), 2.67-2.49 (m, 1H), 2.33 (s, 3H), 2.15 (s, 3H), 1.52 (dd, J=8.4, 2.8 Hz, 2H), 1.45-1.26 (m, 2H). ¹⁹F NMR (377 MHz, Methanol-d4) δ −78.08.

Example 205

5-((2-cyclopropyl-6-(3,5-dimethylisoxazol-4-yl)-1H-benzo[d]imidazol-4-yl)(hydroxy)(pyridin-2-yl)methyl)pyridin-2-ol (1020-205)

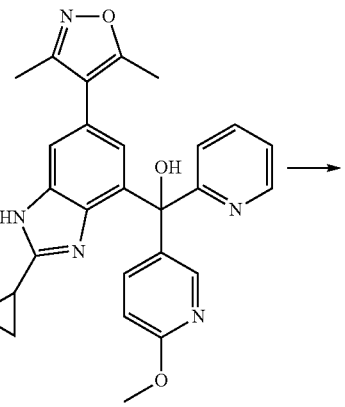

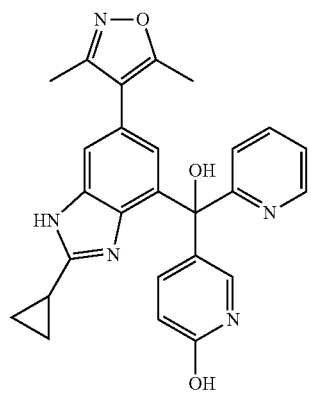

Into a microwave vial containing (2-cyclopropyl-6-(3,5-dimethylisoxazol-4-yl)-1H-benzo[d]imidazol-4-yl)(6-methoxypyridin-3-yl)(pyridin-2-yl)methanol (35 mg, 0.075 mmol, 1 equiv.) is added THF (5 mL) and to it is added HCl (1 mL, 1N). The reaction was heated to 100° C. for 30 min. After completion, the reaction was concentrated to dryness. Purification was carried out by reverse phase HPLC to furnish 5-((2-cyclopropyl-6-(3,5-dimethylisoxazol-4-yl)-1H-benzo[d]imidazol-4-yl)(hydroxy)(pyridin-2-yl)methyl)pyridin-2-ol (as a racemate).

¹H NMR (400 MHz, Methanol-d4) δ 8.61 (ddd, J=4.8, 1.8, 0.9 Hz, 1H), 7.92 (td, J=7.8, 1.8 Hz, 1H), 7.78 (dt, J=8.1, 1.0 Hz, 1H), 7.58 (dd, J=9.6, 2.8 Hz, 1H), 7.52 (d, J=1.4 Hz, 1H), 7.40 (ddd, J=7.6, 4.8, 1.1 Hz, 1H), 7.18-7.06 (m, 2H), 6.54 (d, J=9.6 Hz, 1H), 3.89 (s, 1H), 2.98 (s, 1H), 2.65 (s, 2H), 2.63-2.57 (m, 1H), 2.35 (s, 3H), 2.17 (s, 3H), 1.63-1.45 (m, 2H), 1.45-1.17 (m, 2H). ¹⁹F NMR (377 MHz, Methanol-d4) δ −77.94.

Example 206

(2-cyclopropyl-6-(3,5-dimethylisoxazol-4-yl)-1H-benzo[d]imidazol-4-yl)bis(6-fluoropyridin-3-yl)methanol (1020-206)

Step 1: Preparation of methyl 2-cyclopropyl-5-(3,5-dimethylisoxazol-4-yl)-1H-benzo[d]imidazole-7-carboxylate

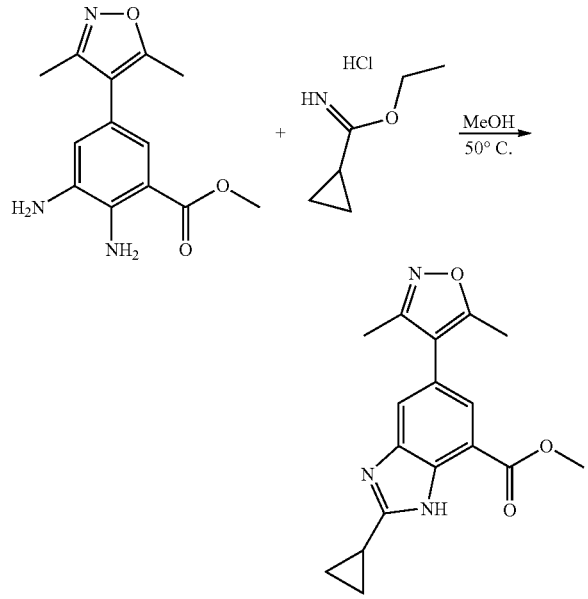

Methyl 2,3-diamino-5-(3,5-dimethylisoxazol-4-yl)benzoate (10 g, 0.038 mol) was added to MeOH (50 ml) and to this was added ethyl cyclopropanecarbimidate hydrochloride (8.6 g, 0.057 mol) and heated to 50° C. for 3 hours. Solvents were then removed under reduced pressure and residue co-evaporated with toluene (2×), dissolved in EtAc, solids filtered off and organics washed with water and then solvents removed under reduced pressure to afford methyl 2-cyclopropyl-5-(3,5-dimethylisoxazol-4-yl)-1H-benzo[d]imidazole-7-carboxylate (11.3 g, 94%).
.LCMS (m/z+1) 312.1

Step 2: Preparation of 1-tert-butyl 4-methyl 2-cyclopropyl-6-(3,5-dimethylisoxazol-4-yl)-1H-benzo[d]imidazole-1,4-dicarboxylate

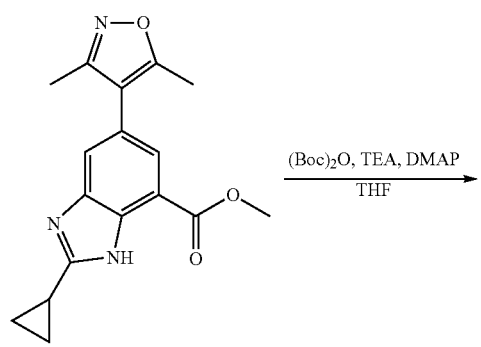

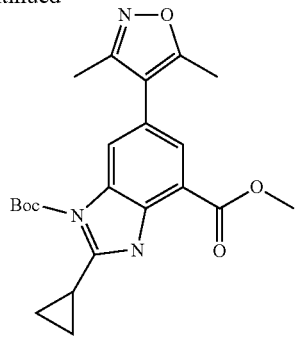

Methyl 2-cyclopropyl-6-(3,5-dimethylisoxazol-4-yl)-1H-benzo[d]imidazole-4-carboxylate (24 g, 77.09 mmol) was taken up in tetrahydrofuran (500 ml) and to this was added di-tert-butyl dicarbonate (33.65 g, 154.17 mmol), 4-(dimethylamino)pyridine (1.88 g, 15.42 mmol) and finally triethylamine (32.23 ml, 231.26 mmol). Reaction was stirred at room temperature for 2 hours under nitrogen. At this point solvents were removed under reduced pressure and the residue was diluted in EtAc/aq. ammonium chloride. Material was extracted 3× with EtAc, washed with ammonium chloride, water, brine then dried over sodium sulfate. Solvents were removed under reduced pressure and the residue purified by silica gel chromatography using Hex/EtAc as the eluent. Solvents were removed under reduced pressure to give a yellowish solid. Material was triturated in minimal Et$_2$O and filtered and air dried to provide 1-tert-butyl 4-methyl 2-cyclopropyl-6-(3,5-dimethylisoxazol-4-yl)-1H-benzo[d]imidazole-1,4-dicarboxylate a pure white solid. (28.0 g, 88%).

LCMS (m/z+1) 411.7. $^1$H NMR (400 MHz, DMSO-d6) δ 8.00 (d, J=1.7 Hz, 1H), 7.69 (d, J=1.7 Hz, 1H), 3.87 (s, 3H), 2.80 (ddd, J=8.2, 5.7, 3.1 Hz, 1H), 2.40 (s, 3H), 2.21 (s, 3H), 1.24-1.00 (m, 4H).

Step 3: Preparation of tert-butyl 4-(bis(6-fluoropyridin-3-yl)(hydroxy)methyl)-2-cyclopropyl-6-(3,5-dimethylisoxazol-4-yl)-1H-benzo[d]imidazole-1-carboxylate

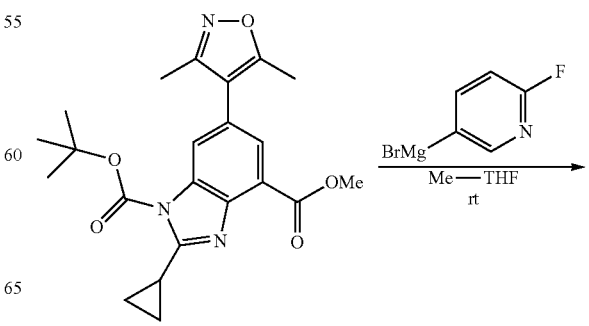

279

-continued

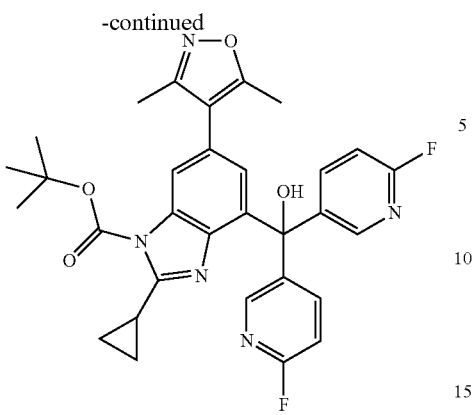

1-tert-butyl 4-methyl 2-cyclopropyl-6-(3,5-dimethylisoxazol-4-yl)-1H-benzo[d]imidazole-1,4-dicarboxylate was treated with 2-fluoropyridine-5-magnesium bromide (0.062M in Me-THF, 3.8 mL, 3.0 equiv.) at room temperature for 16 h. After an aqueous work-up, the crude material was purified by an HPLC purification to give 1-tert-butyl 4-(bis(6-fluoropyridin-3-yl)(hydroxy)methyl)-2-cyclopropyl-6-(3,5-dimethylisoxazol-4-yl)-1H-benzo[d]imidazole-1-carboxylate.

$C_{31}H_{29}F_2N_5O_4$. MS. 574.2 (M+1).

Step 4: Preparation of (2-cyclopropyl-6-(3,5-dimethylisoxazol-4-yl)-1H-benzo[d]imidazol-4-yl)bis(6-fluoropyridin-3-yl)methanol

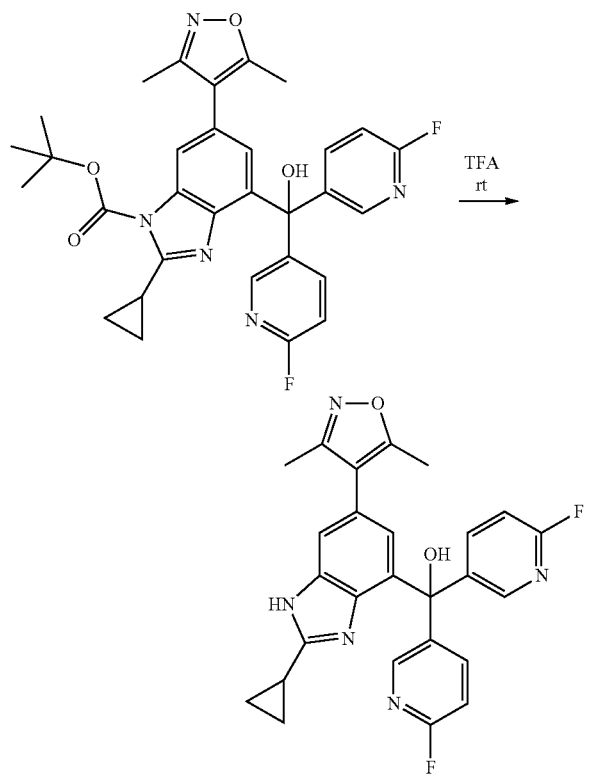

1-tert-butyl 4-(bis(6-fluoropyridin-3-yl)(hydroxy)methyl)-2-cyclopropyl-6-(3,5-dimethylisoxazol-4-yl)-1H-benzo[d]imidazole-1-carboxylatem was then treated with TFA at room temperature for 1 h and 15 min. After removing TFA under a reduced pressure, the material was purified by an HPLC to give the (2-cyclopropyl-6-(3,5-dimethylisoxazol-4-yl)-1H-benzo[d]imidazol-4-yl)bis(6-fluoropyridin-3-yl)methanol.

$^1$H NMR (MeOH-d$_4$) δ 8.22 (d, J=2.6 Hz, 2H), 7.95 (td, J=8.0, 2.6 Hz, 2H), 7.57 (d, J=1.6 Hz, 1H), 7.13 (dd, J=8.0, 2.6 Hz, 2H), 6.88 (d, J=1.6 Hz, 1H), 2.64-2.56 (m, 1H), 2.32 (s, 3H), 2.14 (s, 3H), 1.58-1.50 (m, 2H), 1.42-1.36 (m, 2H).

Example 207 and 208

(2-cyclopropyl-6-(3,5-dimethylisoxazol-4-yl)-1H-benzo[d]imidazol-4-yl)bis(4-fluorophenyl)methanol (1020-207) and (2-cyclopropyl-6-(3,5-dimethylisoxazol-4-yl)-1H-benzo[d]imidazol-4-yl)(4-fluorophenyl)methanone (1020-208)

The above two compounds were synthesized in a similar manner as that of Example 206, Steps 3-4, using 4-fluorophenyl magnesium bromide.

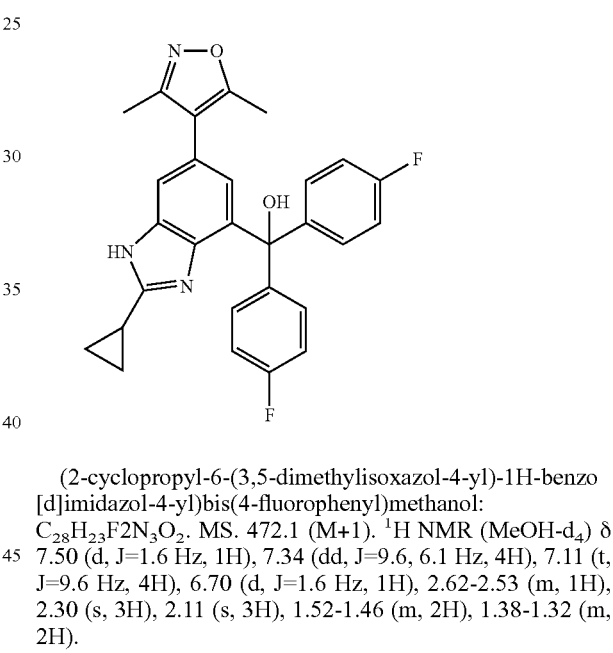

(2-cyclopropyl-6-(3,5-dimethylisoxazol-4-yl)-1H-benzo[d]imidazol-4-yl)bis(4-fluorophenyl)methanol:
$C_{28}H_{23}F2N_3O_2$. MS. 472.1 (M+1). $^1$H NMR (MeOH-d$_4$) δ 7.50 (d, J=1.6 Hz, 1H), 7.34 (dd, J=9.6, 6.1 Hz, 4H), 7.11 (t, J=9.6 Hz, 4H), 6.70 (d, J=1.6 Hz, 1H), 2.62-2.53 (m, 1H), 2.30 (s, 3H), 2.11 (s, 3H), 1.52-1.46 (m, 2H), 1.38-1.32 (m, 2H).

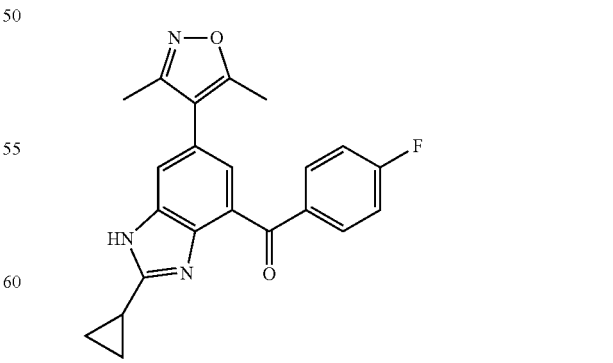

(2-cyclopropyl-6-(3,5-dimethylisoxazol-4-yl)-1H-benzo[d]imidazol-4-yl)(4-fluorophenyl)methanone:
$C_{22}H_{18}FN_3O_2$. MS. 376.1 (M+1). $^1$H NMR (MeOH-d$_4$) δ

7.99 (dd, J=9.6, 6.1 Hz, 2H), 7.85 (d, J=1.6 Hz, 1H), 7.68 (d, J=1.6 Hz, 1H), 7.35 (t, J=9.6 Hz, 2H), 2.56-2.64 (m, 1H), 2.44 (s, 3H), 2.28 (s, 3H), 1.61-1.54 (m, 2H), 1.50-1.44 (m, 2H).

Example 209

(2-cyclopropyl-6-(3,5-dimethylisoxazol-4-yl)-1H-benzo[d]imidazol-4-yl)(6-methylpyridazin-3-yl)methanone (1020-209)

Step 1: Preparation of tert-butyl 2-cyclopropyl-6-(3,5-dimethylisoxazol-4-yl)-4-(6 methylpyridazine-3-carbonyl)-1H-benzo[d]imidazole-1-carboxylate

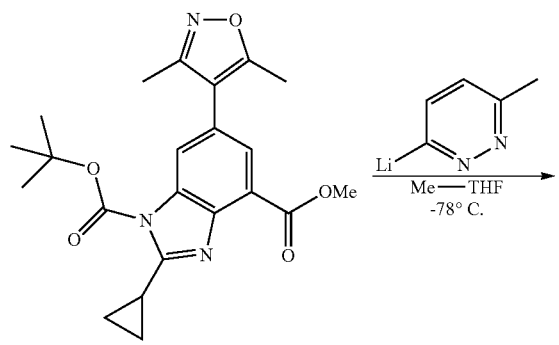

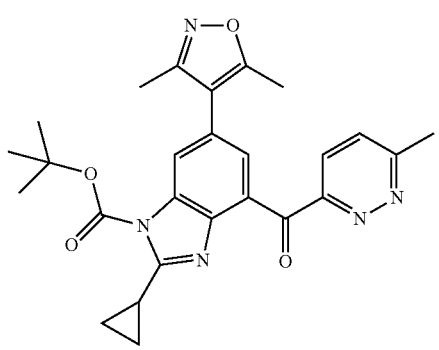

To a solution of tetramethylpiperidine (68.7 mg, 0.486 mmol, 4 equiv) in Me-THF (1 mL) was treated with BuLi (1.4 M in hexane, 0.49 mL, 0.486 mmol, 4 equiv) at −78° C. After 15 min to the solution was added 3-methylpyridazine (57.2 mg, 0.608 mmol, 5 equiv) in Me-THF (3 mL). After 1 h stirring, 1-tert-butyl 4-methyl 2-cyclopropyl-6-(3,5-dimethylisoxazol-4-yl)-1H-benzo[d]imidazole-1,4-dicarboxylate (50.0 mg, 0.122 mmol) was added at −78° C. After an aqueous work-up, The crude mixture was purified by a column chromatography and Preparative HPLC to give tert-butyl 2-cyclopropyl-6-(3,5-dimethylisoxazol-4-yl)-4-(6-methylpyridazine-3-carbonyl)-1H-benzo[d]imidazole-1-carboxylate. $C_{26}H_{27}N_5O_4$. MS. 474.2 (M+1).

Step 2: Preparation of (2-cyclopropyl-6-(3,5-dimethylisoxazol-4-yl)-1H-benzo[d]imidazol-4-yl)(6-methylpyridazin-3-yl)methanone

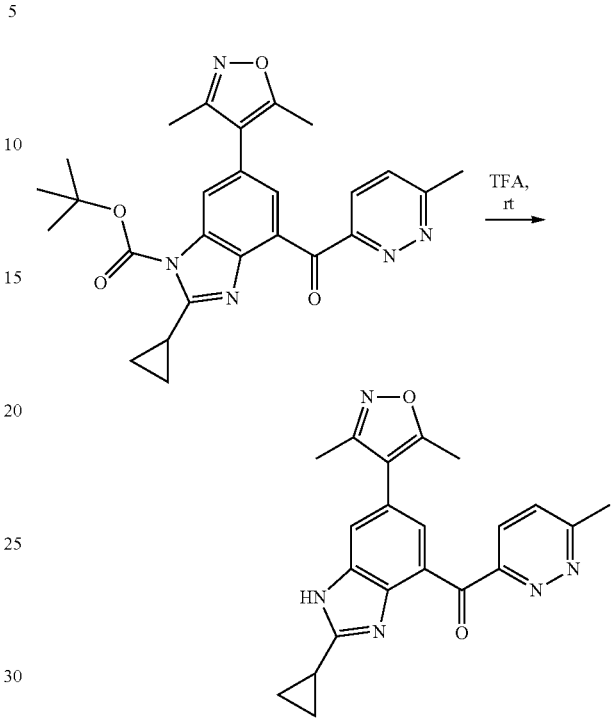

tert-Butyl 2-cyclopropyl-6-(3,5-dimethylisoxazol-4-yl)-4-(6-methylpyridazine-3-carbonyl)-1H-benzo[d]imidazole-1-carboxylate was treated with TFA at rt for 30 min to give (2-cyclopropyl-6-(3,5-dimethylisoxazol-4-yl)-1H-benzo[d]imidazol-4-yl)(6-methylpyridazin-3-yl)methanone.
$C_{21}H_{19}FN_5O_2$. MS. 374.2 (M+1). $^1$H NMR (MeOH-$d_4$) δ 8.48 (s, 1H), 8.30 (d, J=8.0 Hz, 1H), 7.90 (d, J=8.0 Hz, 1H), 7.88 (s, 1H), 2.84 (s, 3H), 2.64-2.56 (m, 1H), 2.49 (s, 3H), 2.33 (s, 3H), 1.60-1.40 (m, 4H).

Example 210

3-((2-cyclopropyl-6-(3,5-dimethylisoxazol-4-yl)-1H-benzo[d]imidazol-4-yl)(hydroxy)(pyridin-3-yl)methyl)pyridine 1-oxide (1020-210)

Step 1

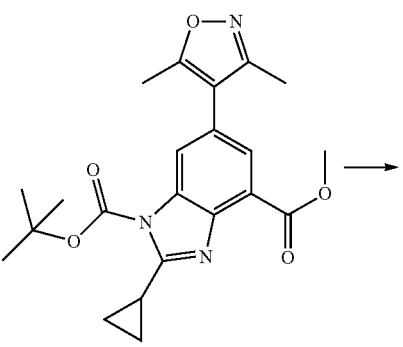

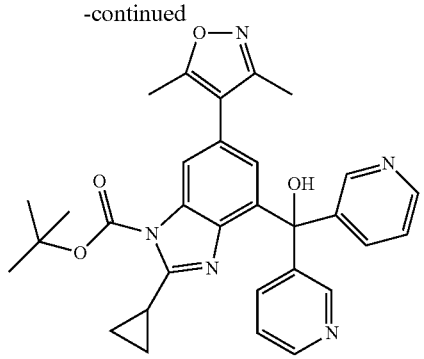

1-tert-Butyl 4-methyl 2-cyclopropyl-6-(3,5-dimethylisoxazol-4-yl)-1H-benzo[d]imidazole-1,4-dicarboxylate (0.15 g) was reacted with 3-MgCl-pyrdine (excess, Novel, 0.25 M) in THF (3 ml) at RT and stirred for 20 min. After adding MeOH (1 mL), volatiles were removed and the residue purified by reverse phase HPLC (5-95% MeCN in water, 0.1% TFA) to afford tert-butyl 2-cyclopropyl-6-(3,5-dimethylisoxazol-4-yl)-4-(hydroxydi(pyridin-3-yl)methyl)-1H-benzo[d]imidazole-1-carboxylate.

LCMS (m/z+1) 438.2 (fragment parent—Boc)

Step 2

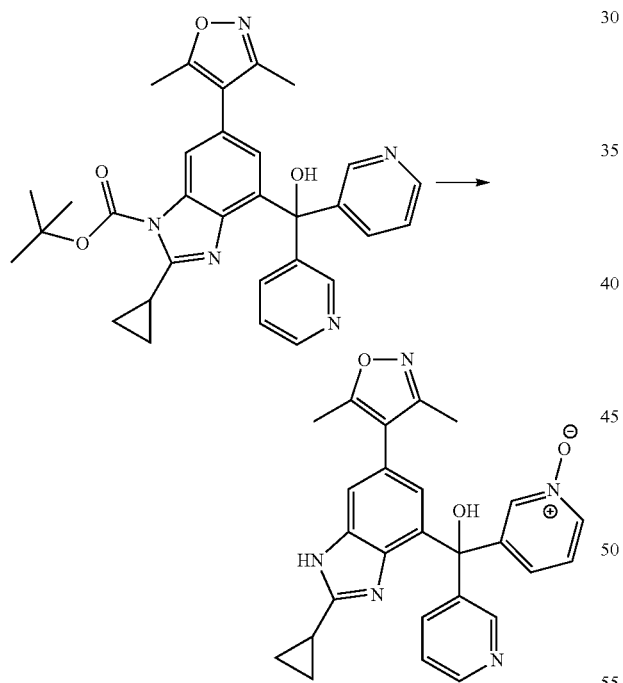

The substrate (0.057 g) was subjected to MCPBA (0.037 g) in MeOH/DCM (1/1 ml) and stirred at RT for 3 h. Volatiles were removed, the residue dissolved in TFA and stirred for 1 h. Volatiles were removed and the residue purified by reverse phase HPLC (5-95% MeCN in water, 0.1% TFA) to afford 3-((2-cyclopropyl-6-(3,5-dimethylisoxazol-4-yl)-1H-benzo[d]imidazol-4-yl)(hydroxy)(pyridin-3-yl)methyl)pyridine 1-oxide. The bis-N-oxide was also isolated, see below.

LCMS (m/z+1) 454.0. $^1$H NMR (400 MHz, Methanol-d4) δ 8.63-8.53 (m, 1H), 8.35 (d, J=1.9 Hz, 1H), 8.31-8.23 (m, 1H), 7.89 (d, J=8.5 Hz, 1H), 7.61-7.40 (m, 2H), 6.85 (d, J=1.4 Hz, 1H), 2.49 (s, 1H), 2.24 (s, 1H), 2.06 (s, 1H), 1.43 (dd, J=8.4, 2.9 Hz, 3H), 1.32-1.23 (m, 3H).

Example 211

3,3'-((2-cyclopropyl-6-(3,5-dimethylisoxazol-4-yl)-1H-benzo[d]imidazol-4-yl)(hydroxy)methylene)bis(pyridine 1-oxide) (1020-211)

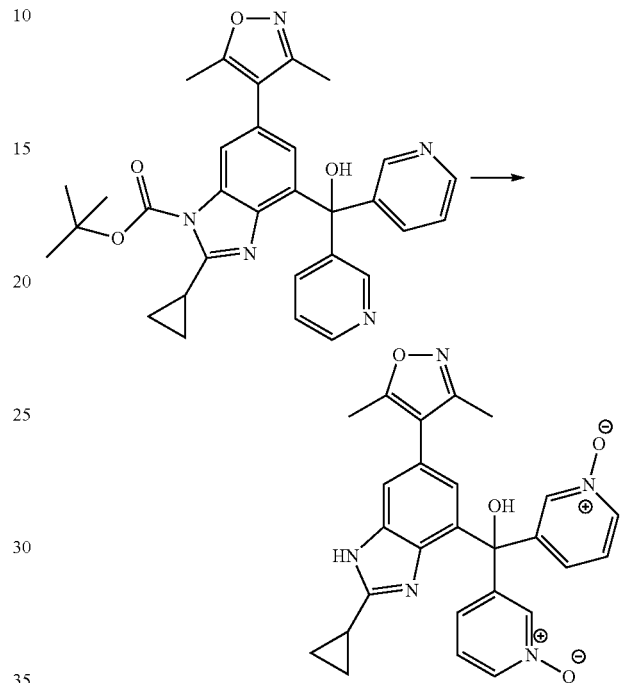

LCMS (m/z+1) 569.8. $^1$H NMR (400 MHz, Methanol-d4) δ 8.42 (t, J=1.5 Hz, 1H), 8.36 (dt, J=6.1, 1.5 Hz, 1H), 7.63-7.48 (m, 3H), 7.00 (d, J=1.4 Hz, 1H), 2.58 (s, 1H), 2.34 (s, 2H), 2.17 (s, 2H), 1.52 (dd, J=8.3, 3.0 Hz, 2H), 1.43-1.29 (m, 2H).

Example 212

(2-cyclopropyl-6-(3,5-dimethylisoxazol-4-yl)-1H-benzo[d]imidazol-4-yl)(6-methylpyridazin-3-yl)methanone (1020-212)

Step 1: Preparation of tert-butyl 2-cyclopropyl-6-(3,5-dimethylisoxazol-4-yl)-4-(2-methylisonicotinoyl)-1H-benzo[d]imidazole-1-carboxylate

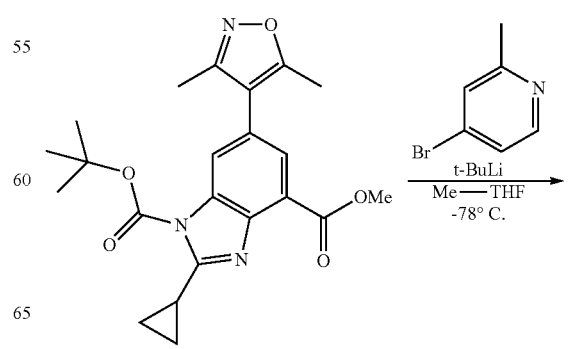

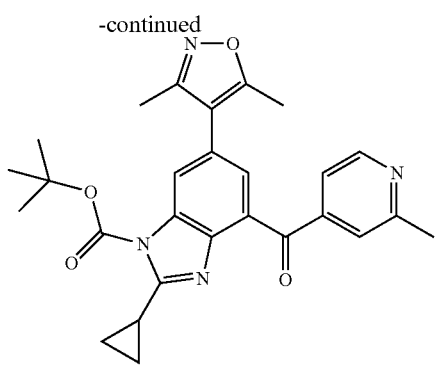

To a solution of 4-bromo-2-methylpyridine (41.8 mg, 0.243 mmol, 4 equiv) in Me-THF (1 mL) was treated with t-BuLi (1.7 M in hexane, 0.14 mL, 0.243 mmol, 4 equiv) at −78° C. After 10 min to the solution was added 1-tert-butyl 4-methyl 2-cyclopropyl-6-(3,5-dimethylisoxazol-4-yl)-1H-benzo[d]imidazole-1,4-dicarboxylate (25.0 mg, 0.061 mmol) in Me-THF (2 mL). After 1 h stirring, the reaction mixture was worked-up. The crude mixture was purified by a column chromatography (35% to 60% EtOAc/hexane) to give tert-butyl 2-cyclopropyl-6-(3,5-dimethylisoxazol-4-yl)-4-(2-methylisonicotinoyl)-1H-benzo[d]imidazole-1-carboxylate. $C_{27}H_{28}N_4O_4$. MS. 473.2 (M+1).

Step 2: Preparation of (2-cyclopropyl-6-(3,5-dimethylisoxazol-4-yl)-1H-benzo[d]imidazol-4-yl)bis(2-methylpyridin-4-yl)methanol

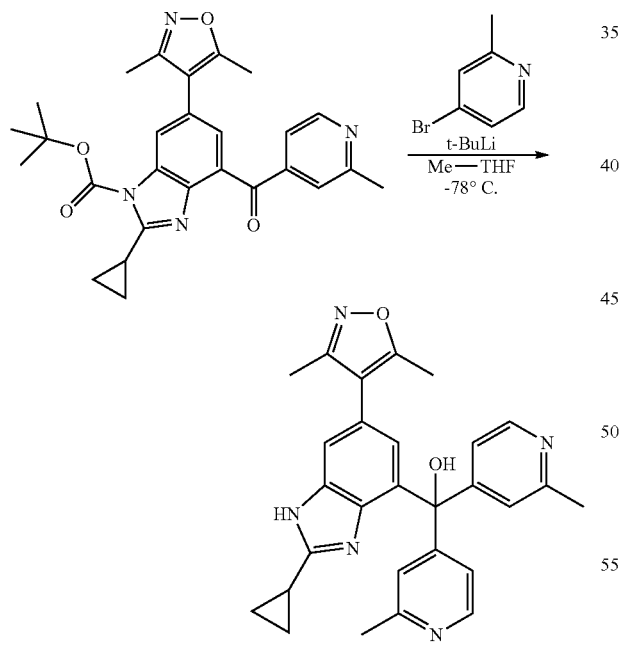

tert-butyl 2-cyclopropyl-6-(3,5-dimethylisoxazol-4-yl)-4-(2-methylisonicotinoyl)-1H-benzo[d]imidazole-1-carboxylate was re-subjected to the similar conditions to the preparation of present intermediate to give (2-cyclopropyl-6-(3,5-dimethylisoxazol-4-yl)-1H-benzo[d]imidazol-4-yl)bis(2-methylpyridin-4-yl)methanol.

$C_{28}H_{27}N_5O_2$. MS. 466.2 (M+1). $^1$H NMR (MeOH-d4) δ 8.71 (d, J=6.4 Hz, 2H), 7.93 (s, 2H), 7.84 (d, J=6.4 Hz, 2H), 7.64 (d, J=1.0 Hz, 1H), 7.00 (d, J=1.0 Hz, 1H), 2.76 (s, 6H), 2.60-2.50 (m, 1H), 2.35 (s, 3H), 2.17 (s, 3H), 1.56-1.47 (m, 2H), 1.40-1.35 (m, 2H).

Example 213

(2-cyclopropyl-6-(3,5-dimethylisoxazol-4-yl)-1H-benzo[d]imidazol-4-yl)bis(3-methylpyridin-4-yl)methanol (1020-213)

Step 1: Preparation of tert-butyl 2-cyclopropyl-6-(3,5-dimethylisoxazol-4-yl)-4-(hydroxybis(3-methylpyridin-4-yl)methyl)-1H-benzo[d]imidazole-1-carboxylate

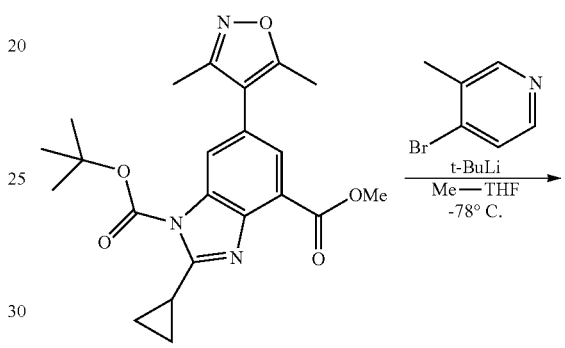

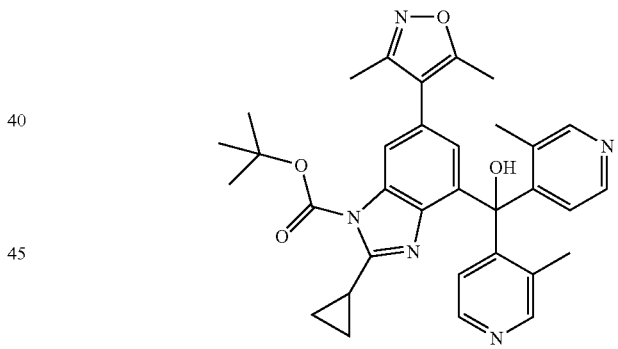

To a solution of 4-bromo-3-methylpyridine (167.2 mg, 0.972 mmol, 8 equiv) in Me-THF (1 mL) was treated with t-BuLi (1.42 M in hexane, 0.68 mL, 0.972 mmol, 8 equiv) at −78° C. After 10 min to the solution was added 1-tert-butyl 4-methyl 2-cyclopropyl-6-(3,5-dimethylisoxazol-4-yl)-1H-benzo[d]imidazole-1,4-dicarboxylate (50.0 mg, 0.122 mmol) in Me-THF (2 mL). After 1 h stirring at rt, the reaction mixture was worked-up. The crude mixture was purified by a prep-HPLC to give tert-butyl 2-cyclopropyl-6-(3,5-dimethylisoxazol-4-yl)-4-(hydroxybis(3-methylpyridin-4-yl)methyl)-1H-benzo[d]imidazole-1-carboxylate. $C_{33}H_{35}N_5O_4$. MS. 566.3 (M+1).

287

Step 2: Preparation of (2-cyclopropyl-6-(3,5-dimethylisoxazol-4-yl)-1H-benzo[d]imidazol-4-yl)bis(3-methylpyridin-4-yl)methanol

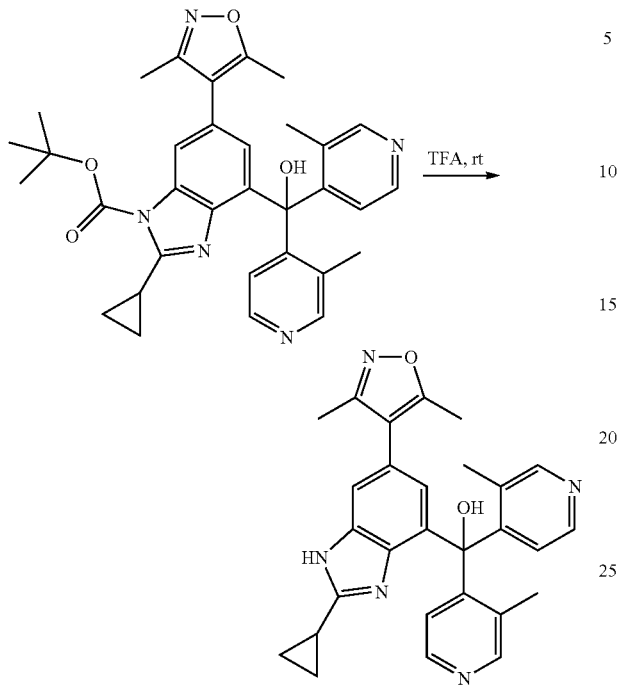

tert-butyl 2-cyclopropyl-6-(3,5-dimethylisoxazol-4-yl)-4-(hydroxybis(3-methylpyridin-4-yl)methyl)-1H-benzo[d]imidazole-1-carboxylate was treated with TFA at rt to give (2-cyclopropyl-6-(3,5-dimethylisoxazol-4-yl)-1H-benzo[d]imidazol-4-yl)bis(3-methylpyridin-4-yl)methanol.

$C_{28}H_{27}N_5O_2$. MS. 466.2 (M+1). $^1$H NMR (MeOH-$d_4$) δ 8.70 (br s, 1H), 8.58 (br s, 1H), 7.64 (d, J=1.0 Hz, 1H), 7.48 (br s, 1H), 6.61 (d, J=1.0 Hz, 1H), 2.40 (m, 1H), 2.30 (s, 6H), 2.30 (s, 3H), 2.09 (s, 3H), 1.45-1.26 (m, 4H).

Example 214

(2-cyclopropyl-6-(3,5-dimethylisoxazol-4-yl)-1H-benzo[d]imidazol-4-yl)(2,5-dimethylpyridin-4-yl)methanone (1020-214)

(2-cyclopropyl-6-(3,5-dimethylisoxazol-4-yl)-1H-benzo[d]imidazol-4-yl)(2,5-dimethylpyridin-4-yl)methanone was synthesized in a similar fashion to Example 209, steps 1-2.

Step 1

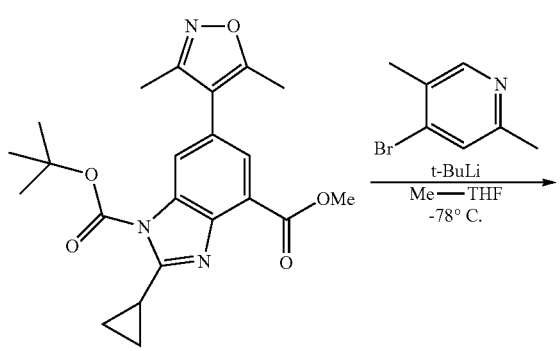

288

-continued

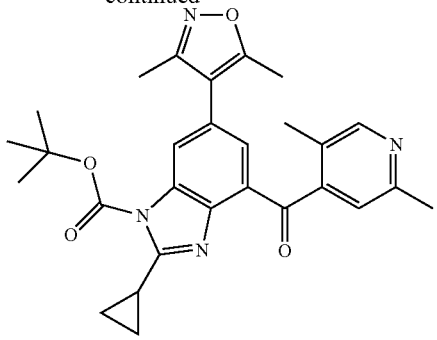

$C_{33}H_{35}N_5O_4$. MS. 566.3 (M+1).

Step 2: Preparation of (2-cyclopropyl-6-(3,5-dimethylisoxazol-4-yl)-1H benzo[d]imidazol-4-yl)(2,5-dimethylpyridin-4-yl)methanone

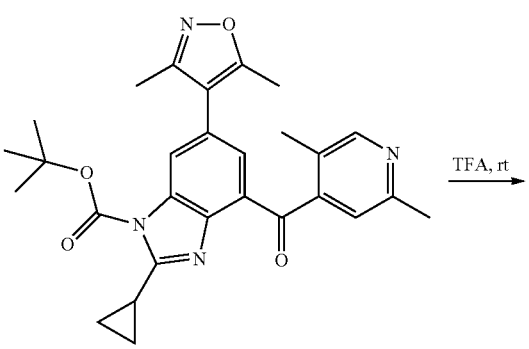

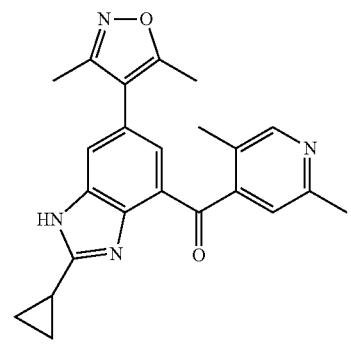

$C_{23}H_{22}N_4O_2$. MS. 378.2 (M+1). $^1$H NMR (MeOH-$d_4$) δ 8.72 (s, 1H), 7.92 (s, 1H), 7.87 (s, 1H), 7.42 (s, 1H), 2.75 (s, 3H), 2.65-2.56 (m, 1H), 2.42 (s, 3H), 2.37 (s, 3H), 2.20 (s, 3H), 1.56-1.40 (m, 4H).

Example 215

(2-cyclopropyl-6-(3,5-dimethylisoxazol-4-yl)-1H-benzo[d]imidazol-4-yl)(6-(trifluoromethyl)pyridazin-3-yl)methanone (1020-215)

(2-cyclopropyl-6-(3,5-dimethylisoxazol-4-yl)-1H-benzo[d]imidazol-4-yl)(6-(trifluoromethyl)pyridazin-3-yl)methanone was synthesized in a similar fashion to Example 209, steps 1-2.

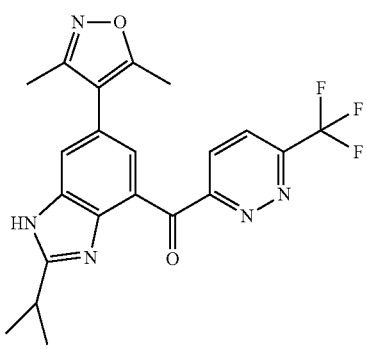 [SMILES: Cc1noc(C)c1-c1cc(C(=O)c2ccc(C(F)(F)F)nn2)c2nc(C(C)C)[nH]c2c1]

$C_{21}H_{16}F_3N_5O_2$. MS. 428.1 (M+1). $^1$H NMR (MeOH-d$_4$) δ 8.62 (d, J=8.0 Hz, 1H), 8.49 (s, 1H), 8.44 (d, J=8.0 Hz, 1H), 7.94 (s, 1H), 2.70-2.62 (m, 1H), 2.50 (s, 3H), 2.33 (s, 3H), 1.64-1.44 (m, 4H).

Example 216
(2-cyclopropyl-6-(3,5-dimethylisoxazol-4-yl)-1H-benzo[d]imidazol-4-yl)(pyridazin-3-yl)methanone (2010-216)

(2-cyclopropyl-6-(3,5-dimethylisoxazol-4-yl)-1H-benzo[d]imidazol-4-yl)(pyridazin-3-yl)methanone was synthesized in a similar fashion to Example 209, steps 1-2.

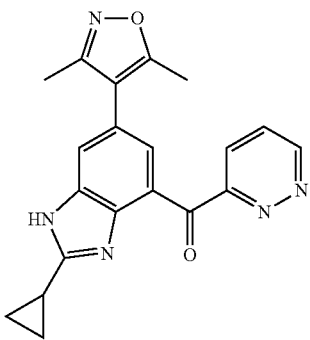 [SMILES: Cc1noc(C)c1-c1cc(C(=O)c2cccnn2)c2nc(C3CC3)[nH]c2c1]

$C_{20}H_{17}F_3N_5O_2$. MS. 360.1 (M+1). $^1$H NMR (MeOH-d$_4$) δ 9.44 (d, J=5.2 Hz, 1H), 8.52 (s, 1H), 8.43 (d, J=9.0 Hz, 1H), 8.04 (dd, J=8.6, 5.1 Hz, 2H), 7.93 (s, 1H), 2.73-2.62 (m, 1H), 2.50 (s, 3H), 2.33 (s, 3H), 1.65-1.44 (m, 4H)

Example 217
(2-cyclopropyl-6-(3,5-dimethylisoxazol-4-yl)-1H-benzo[d]imidazol-4-yl)bis(5-fluoropyridin-2-yl)methanol (2010-217)

Step 1: Preparation of tert-butyl 4-(bis(5-fluoropyridin-2-yl)(hydroxy)methyl)-2-cyclopropyl-6-(3,5-dimethylisoxazol-4-yl)-1H-benzo[d]imidazole-1-carboxylate

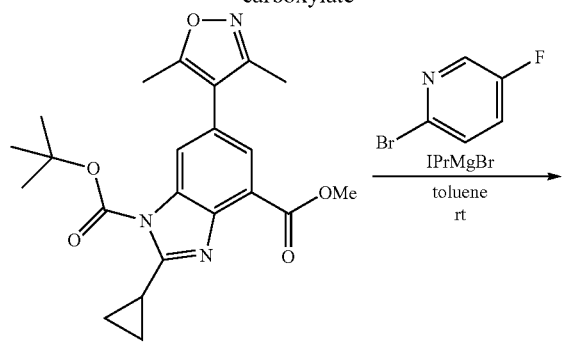

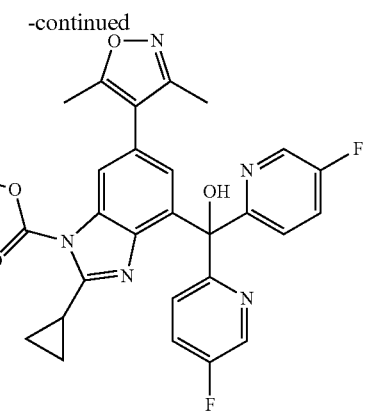

4-Fluruolo-2-bromopyridine (128.3 mg, 0.729 mmol, 10 equiv) was treated with isopropyl magnesiumbromide (2M, THF, 0.33 mL, 0.656 mmol, 9 equiv) in toluene (2 mL) at room temperature for 1 h. To the reaction mixture was added 6-(3,5-dimethylisoxazol-4-yl)-2-methyl-1H-benzo[d]imidazole-4-carboxylate (50.0 mg, 0.175 mmol) in toluene (1 mL) at room temperature. After 18 h stirring, the reaction mixture was worked-up. The crude mixture was purified by a prep-HPLC to give tert-butyl 4-(bis(5-fluoropyridin-2-yl)(hydroxy)methyl)-2-cyclopropyl-6-(3,5-dimethylisoxazol-4-yl)-1H-benzo[d]imidazole-1-carboxylate. $C_{31}H_{29}F_2N_5O_2$. MS. 574.2 (M+1).

Step 2: Preparation of (2-cyclopropyl-6-(3,5-dimethylisoxazol-4-yl)-1H-benzo[d]imidazol-4-yl)bis(5-fluoropyridin-2-yl)methanol

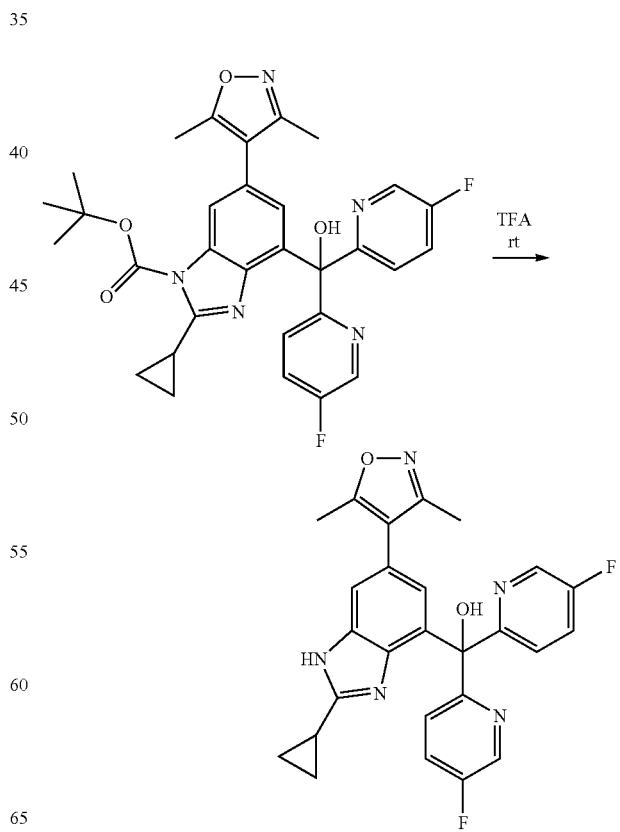

tert-Butyl 4-(bis(5-fluoropyridin-2-yl)(hydroxy)methyl)-2-cyclopropyl-6-(3,5-dimethylisoxazol-4-yl)-1H-benzo[d]imidazole-1-carboxylate was treated with TFA (3 mL) at room temperature for 1 h. After removing of TFA, the mixture was purified by a prep-HPLC and a silica gel column chromatography (50 to 100% EtOAc/hexane) to give (2-cyclopropyl-6-(3,5-dimethylisoxazol-4-yl)-1H-benzo[d]imidazol-4-yl)bis(5-fluoropyridin-2-yl)methanol.

$C_{26}H_{21}F_2N_5O_2$. MS. 474.1 (M+1). $^1$H NMR (MeOH-$d_4$) δ 8.43 (d, J=2.8 Hz, 1H), 7.72 (dd, J=8.6, 4.3 Hz, 1H), 7.64 (td, J=8.6, 2.9 Hz, 1H), 7.50 (d, J=1.5 Hz, 1H), 7.21 (d, J=1.5 Hz, 1H), 2.62-2.54 (m, 1H), 2.35 (s, 3H), 2.17 (s, 3H), 1.56-1.48 (m, 2H), 1.42-1.34 (m, 2H).

Example 218

(6-(3,5-dimethylisoxazol-4-yl)-2-methyl-1H-benzo[d]imidazol-4-yl)bis(5-fluoropyridin-2-yl)methanol (1020-218)

Step 1: Preparation of N-((3-methylisoxazol-5-yl)methyl)acetamide

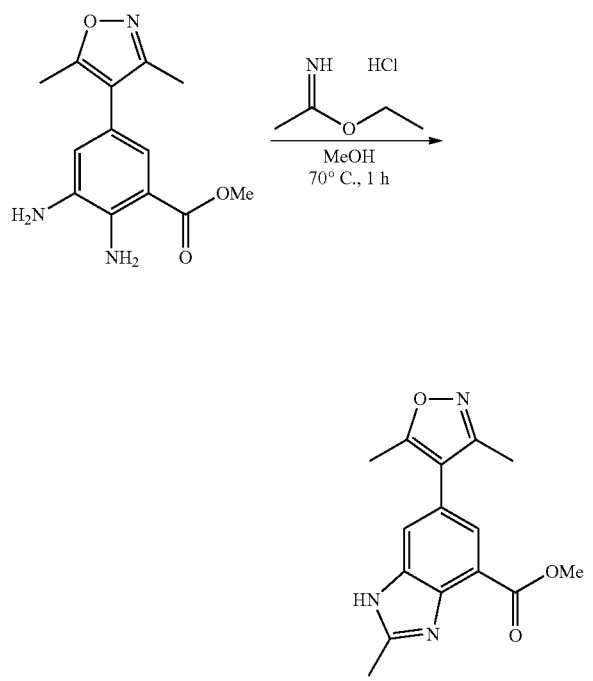

Methyl 2,3-diamino-5-(3,5-dimethylisoxazol-4-yl)benzoate (351.8 mg, 1.346 mmol) was treated with ethyl acetimidate hydrochloride in MeOH at 70° C. for 1 h. After an aqueours work-up, the crude mixture was purified by a silica-gel column chromatography (20 to 40% EtOAc/hexane) to give methyl 6-(3,5-dimethylisoxazol-4-yl)-2-methyl-1H-benzo[d]imidazole-4-carboxylate. $C_{15}H_{15}N_3O_3$. MS. 286.1 (M+1).

Step 2: Preparation of (6-(3,5-dimethylisoxazol-4-yl)-2-methyl-1H-benzo[d]imidazol-4-yl)bis(5-fluoropyridin-2-yl)methanol

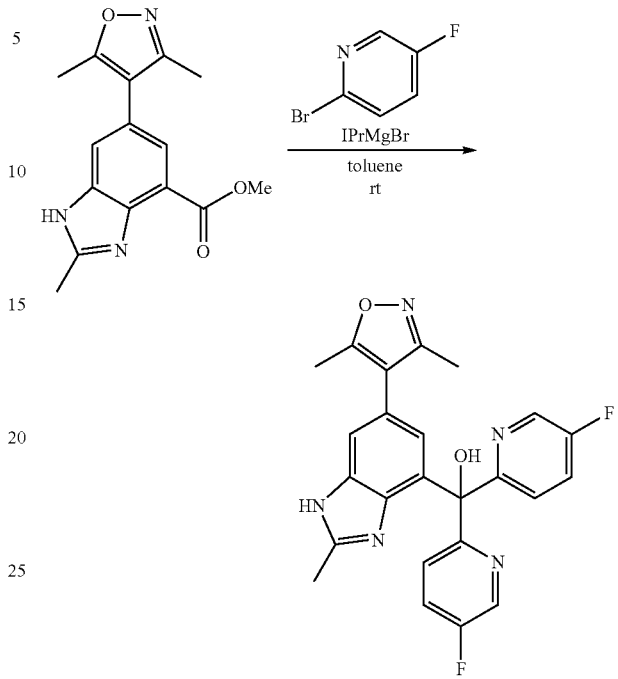

4-Fluoro-2-bromopyridine (308.4 mg, 1.753 mmol, 10 equiv) was treated with isopropyl magnesiumbromide (2M, THF, 0.789 mL, 1.58 mmol, 9 equiv) in toluene (3 mL) at room temperature for 1 h. To the reaction mixture was added 6-(3,5-dimethylisoxazol-4-yl)-2-methyl-1H-benzo[d]imidazole-4-carboxylate (50.0 mg, 0.175 mmol) at room temperature. After 2 h stirring, the reaction mixture was worked-up. The crude mixture was purified by a prep-HPLC to give (6-(3,5-dimethylisoxazol-4-yl)-2-methyl-1H-benzo[d]imidazol-4-yl)bis(5-fluoropyridin-2-yl)methanol.

$C_{24}H_{19}F_2N_5O_2$. MS. 448.1 (M+1). $^1$H NMR (MeOH-$d_4$) δ 8.42 (d, J=2.9 Hz, 1H), 7.72 (dd, J=8.5, 5.8 Hz, 1H), 7.65 (dd, J=8.5, 2.9 Hz, 1H), 7.61 (d, J=1.6 Hz, 1H), 7.25 (d, J=1.5 Hz, 1H), 2.84 (s, 2H), 2.36 (s, 2H), 2.18 (s, 2H).

Example 219

(2-cyclopropyl-6-(3,5-dimethylisoxazol-4-yl)-1H-benzo[d]imidazol-4-yl)bis(5-methylthiazol-2-yl)methanol (1020-219)

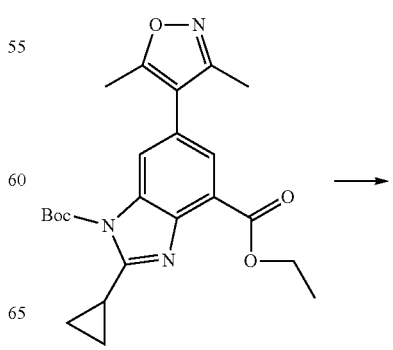

-continued

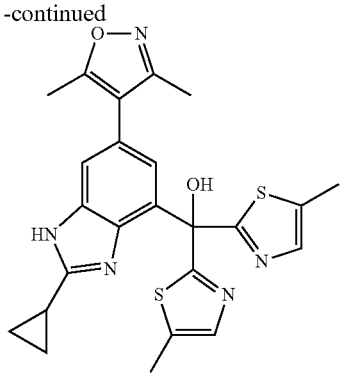

To a solution of 5-methylthiazole (170 mg, 2.0 mmol) in THF (5 mL) was added butyllithium (96 mg, 1.5 mmol) and the solution was stirred at −78° C. for 1 h. To the solution of 1-tert-butyl 4-ethyl 2-cyclopropyl-6-(3,5-dimethylisoxazol-4-yl)-1H-benzo[d]imidazole-1,4-dicarboxylate (212 mg, 0.50 mmol) in THF (5 mL) was added a solution of the lithiate prepared above at room temperature and the solution was stirred at room temperature for 4 h. Water (2 mL) was added and the solution was stirred at room temperature for 1 h. EtOAc (100 mL) was added and the organic solution was washed with brine and dried over $Na_2SO_4$. Solvent was removed and the residue was purified by silica gel column chromatography (0-50% $MeOH/CH_2Cl_2$) to give (2-cyclopropyl-6-(3,5-dimethylisoxazol-4-yl)-1H-benzo[d]imidazol-4-yl)bis(5-methylthiazol-2-yl)methanol.

$C_{24}H_{23}N_5O_2S_2$. MS m/z 478.1 (M+1). $^1$H NMR (Methanol-$d_4$) δ 7.41 (d, J=24.1 Hz, 3H), 7.12 (s, 1H), 2.49-2.40 (m, 6H), 2.34 (s, 3H), 2.26 (d, J=15.4 Hz, 1H), 2.18 (s, 3H), 1.18-1.07 (m, 4H).

Example 220

(2-cyclopropyl-6-(3,5-dimethylisoxazol-4-yl)-1H-benzo[d]imidazol-4-yl)(pyridin-2-yl)(thiazol-2-yl)methanol (1020-220)

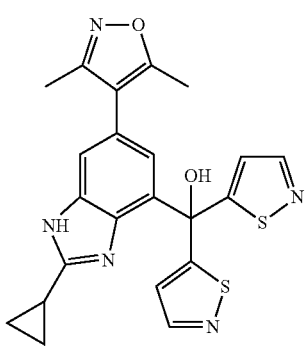 [SMILES: Cc1noc(C)c1-c1cc(C(O)(c2ccns2)c2ccns2)c2nc(C3CC3)[nH]c2c1]

(2-Cyclopropyl-6-(3,5-dimethylisoxazol-4-yl)-1H-benzo[d]imidazol-4-yl)(pyridin-2-yl)(thiazol-2-yl)methanol was synthesized in a similar fashion as Example 219.

$C_{22}H_{19}N_5O_2S_2$. 449.9 (M+1). $^1$H NMR (400 MHz, $CD_3OD$) δ 8.47 (d, J=1.6 Hz, 2H), 7.60 (d, J=1.2 Hz, 1H), 7.35 (d, J=1.6 Hz, 2H), 7.10 (d, J=1.2 Hz, 1H), 2.68-2.64 (m, 1H), 2.33 (s, 3H), 2.18 (s, 3H), 1.57-1.51 (m, 2H), 1.44-1.39 (m, 2H).

Example 221

(2-cyclopropyl-6-(3,5-dimethylisoxazol-4-yl)-1H-benzo[d]imidazol-4-yl)bis(2-methylpyridin-3-yl)methanol (1020-221)

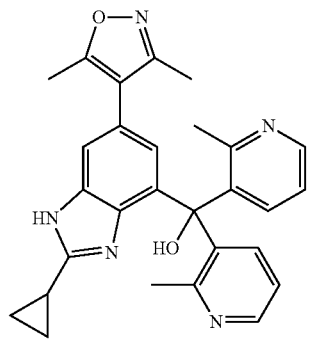 [SMILES: Cc1ncccc1C(O)(c1cccnc1C)c1cc(-c2c(C)noc2C)cc2[nH]c(C3CC3)nc12]

(2-Cyclopropyl-6-(3,5-dimethylisoxazol-4-yl)-1H-benzo[d]imidazol-4-yl)bis(2-methylpyridin-3-yl)methanol was synthesized in a similar fashion as Example 219.

$C_{28}H_{27}N_5O_2$. 466.2 (M+1). $^1$H NMR (400 MHz, $CD_3OD$) δ 8.48 (d, J=4.4 Hz, 2H), 7.42 (s, 2H), 7.36 (bs, 3H), 6.38 (s, 1H), 2.44 (s, 6H), 2.23 (s, 3H), 2.18-2.11 (m, 1H), 2.03 (s, 3H), 1.17-1.13 (m, 2H), 1.08-1.05 (m, 2H).

Example 222

(2-cyclopropyl-6-(3,5-dimethylisoxazol-4-yl)-1H-benzo[d]imidazol-4-yl)bis(2,6-dimethylpyridin-3-yl)methanol (1020-222)

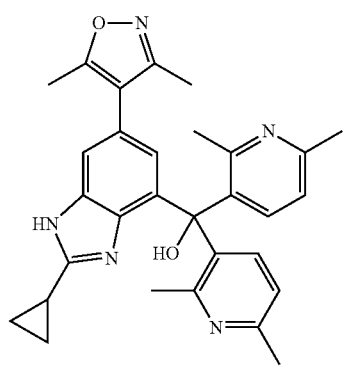 [SMILES: Cc1ccc(C(O)(c2ccc(C)nc2C)c2cc(-c3c(C)noc3C)cc3[nH]c(C4CC4)nc23)c(C)n1]

(2-Cyclopropyl-6-(3,5-dimethylisoxazol-4-yl)-1H-benzo[d]imidazol-4-yl)bis(2,6-dimethylpyridin-3-yl)methanol was synthesized in a similar fashion as Example 219.

$C_{30}H_{31}N_5O_2$. 494.3 (M+1). $^1$H NMR (400 MHz, $CD_3OD$) δ 7.87-7.85 (m, 2H), 7.60 (s, 1H), 7.58 (s, 1H), 7.55 (d, J=1.2 Hz, 1H), 6.72 (d, J=1.2 Hz, 1H), 2.75 (s, 6H), 2.64 (s, 6H), 2.33 (s, 3H), 2.22-2.18 (m, 1H), 2.14 (s, 3H), 1.25-1.21 (m, 2H), 1.10-1.09 (m, 2H).

Example 223

(2-cyclopropyl-6-(3,5-dimethylisoxazol-4-yl)-1H-benzo[d]imidazol-4-yl)bis(5-fluoropyridin-3-yl)methanol (1020-223)

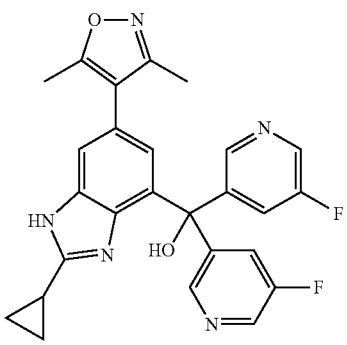 [SMILES: Cc1noc(C)c1-c1cc(C(O)(c2cncc(F)c2)c2cncc(F)c2)c2nc(C3CC3)[nH]c2c1]

(2-Cyclopropyl-6-(3,5-dimethylisoxazol-4-yl)-1H-benzo[d]imidazol-4-yl)bis(5-fluoropyridin-3-yl)methanol was synthesized in a similar fashion as Example 219.

$C_{26}H_{21}F_2N_5O_2$. 474.0 (M+1). $^1$H NMR (400 MHz, CD$_3$OD) δ 8.42 (d, J=2.8 Hz, 2H), 8.32 (t, J=1.6 Hz, 2H), 7.61-7.58 (m, 2H), 7.46 (d, J=1.6 Hz, 1H), 6.79 (d, J=1.2 Hz, 1H), 2.48-2.42 (m, 1H), 2.44 (s, 3H), 2.04 (s, 3H), 1.39-1.38 (m, 2H), 1.27-1.24 (m, 2H).

Example 224

(2-cyclopropyl-6-(3,5-dimethylisoxazol-4-yl)-7-fluoro-1H-benzo[d]imidazol-4-yl)di(pyridin-2-yl)methanol (1020-224)

Step 1: Methyl 2-cyclopropyl-6-(3,5-dimethylisoxazol-4-yl)-7-fluoro-1H-benzo[d]imidazole-4-carboxylate

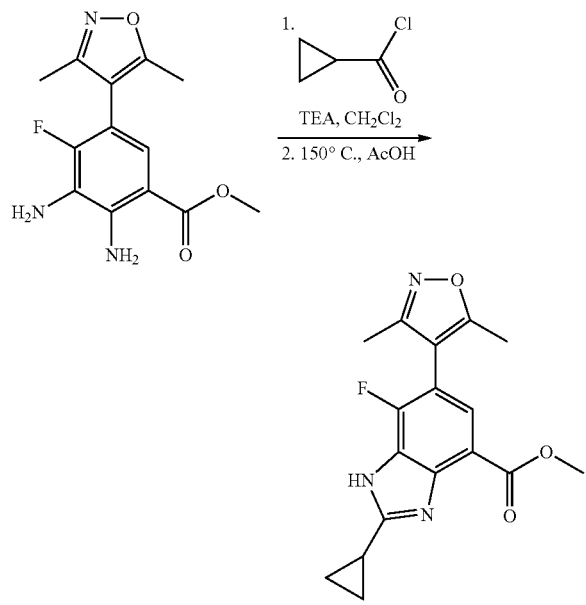

To a flask containing methyl-2,3-diamino-5-(3,5-dimethylisoxazol-4-yl)-4-fluorobenzoate (500 mg, 1.95 mmol, 1 equiv.) is added 1,2 DCE (20 ml, 0.1M) and DIPEA (1.0 mL, 5.87 mmol, 3 equiv.). At 0° C., cyclopropanecarbonyl chloride (198 μL, 3.4 mmol, 1.1 equiv.) was added. After an hour, the reaction was complete. The reaction was extracted with EtOAc and washed with water and saturated NH$_4$Cl. After drying with MgSO$_4$, it was filtered and concentrated to dryness and used in the next reaction as crude methyl 2-amino-3-(cyclopropanecarboxamido)-5-(3,5-dimethylisoxazol-4-yl)-4-fluorobenzoate.

Into a microwave vial was placed methyl 2-amino-3-(cyclopropanecarboxamido)-5-(3,5-dimethylisoxazol-4-yl)-4-fluorobenzoate and to it added acetic acid (10 mL) and heated in the microwave for 150° C. for 30 minutes. The reaction was concentrated down and extracted with EtOAc and washed with water (3×), saturated NaHCO$_3$ and brine. After drying with MgSO$_4$, it was filtered and concentrated to dryness. Silica gel chromatography was carried out with Hexanes-EtOAc to furnish methyl 2-cyclopropyl-6-(3,5-dimethylisoxazol-4-yl)-7-fluoro-1H-benzo[d]imidazole-4-carboxylate (535 mg, 85%) as a light brown powder.

LCMS (m/z+1) 330.04

Step 2: (2-cyclopropyl-6-(3,5-dimethylisoxazol-4-yl)-7-fluoro-1H-benzo[d]imidazol-4-yl)di(pyridin-2-yl)methanol

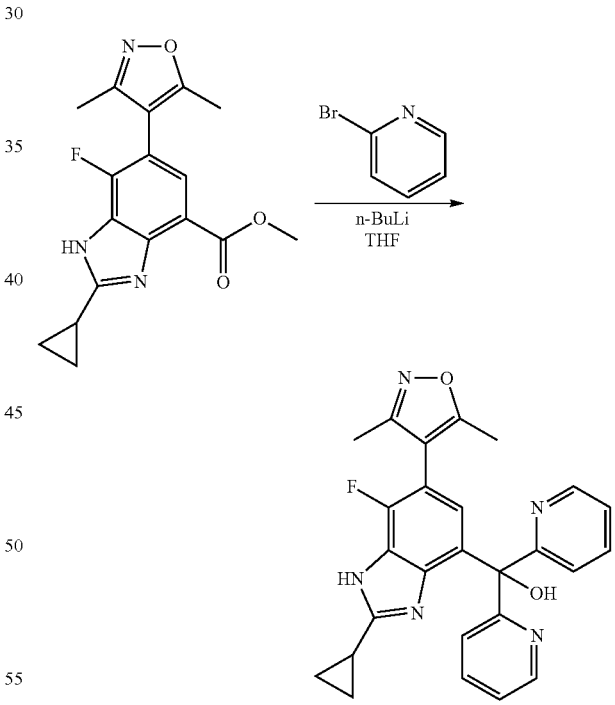

A flask containing 2-bromopridine (135 μL, 1.37 mmol, 7 equiv.) and THF (3 mL) is cooled to −78° C. before BuLi (0.86 mL, 1.37 mmol, 7 equiv.) is added. After 30 min, methyl 6-(3,5-dimethylisoxazol-4-yl)-7-fluoro-2-oxo-2,3-dihydro-1H-benzo[d]imidazole-4-carboxylate (60 mg, 0.197 mmol, 1 equiv.) dissolved in THF (2 mL) is added to the reaction mixture. After completion, the reaction was quenched and extracted with EtOAc and washed with water, saturated NH$_4$Cl. After drying with MgSO$_4$, it was filtered and concentrated to dryness. Purification was carried out by reverse phase HPLC to furnish (2-cyclopropyl-6-(3,5-dimethylisoxazol-4-yl)-7-fluoro-1H-benzo[d]imidazol-4-yl)di(pyridin-2-yl)methanol.

LCMS (m/z+1) 455.48. $^1$H NMR (400 MHz, Methanol-d4) δ 8.62 (ddd, J=5.1, 1.8, 0.9 Hz, 1H), 8.09 (ddd, J=9.5, 6.5, 1.8 Hz, 1H), 7.88 (dq, J=8.0, 1.5, 1.0 Hz, 1H), 7.58 (ddd, J=7.4, 5.0, 1.3 Hz, 1H), 6.97-6.67 (m, 0H), 2.37 (td, J=8.9, 8.4, 4.2 Hz, 1H), 2.27 (s, 1H), 2.09 (s, 2H), 1.46-1.14 (m, 2H). $^{19}$F NMR (377 MHz, Methanol-d4) δ −77.94, −132.51.

Example 225

(2-cyclopropyl-6-(3,5-dimethylisoxazol-4-yl)-5-fluoro-1H-benzo[d]imidazol-4-yl)di(pyridin-2-yl)methanol (1020-225)

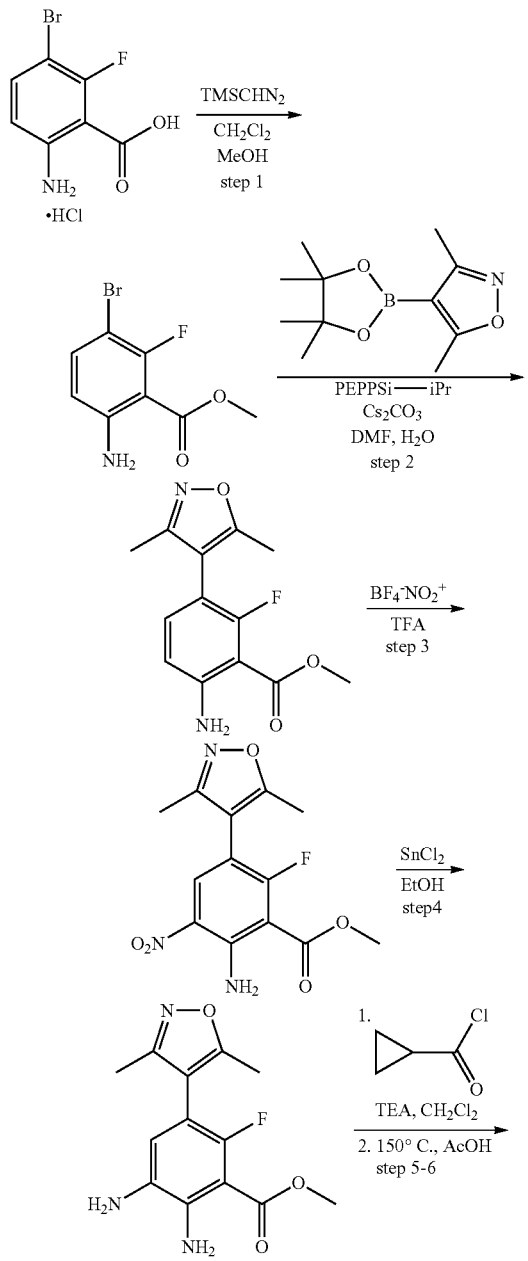

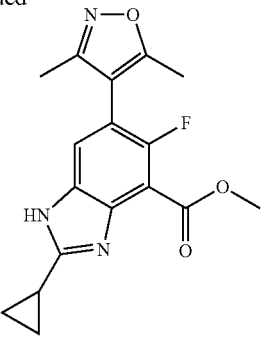

Step 1: Methyl 6-amino-3-bromo-2-fluorobenzoate

Into a flask 6-amino-3-bromo-2-fluorobenzoic acid. HCl. salt, (6000 mg, 22 mmol, 1 equiv.), DCM (75 mL) and MeOH (20 mL) is added Trimethylsilyldiazomethane (22 mL, 44 mmol, 2 equiv.) slowly over 5 min. After an hour the reaction is quenched with 1N HCL (3 mL) and concentrated in vacuo. DCM is added and the reaction is washed with a solution of sodium bicarbonate and water and NH$_4$Cl solution. After drying with MgSO$_4$, it was filtered and concentrated to dryness. The material is used as is without further purification to methyl 6-amino-3-bromo-2-fluorobenzoate.

1H NMR (400 MHz, Chloroform-d) δ 7.20 (dd, J=8.9, 7.1 Hz, 1H), 6.37-6.18 (m, 1H), 3.77 (s, 3H). $^{19}$F NMR (377 MHz, Chloroform-d) δ −99.18 (d, J=7.0 Hz).

Step 2: Methyl 6-amino-3-(3,5-dimethylisoxazol-4-yl)-2-fluorobenzoate

Methyl 6-amino-3-bromo-2-fluorobenzoate (5100 mg, 20.56 mol, 1 equiv.), 3,5-dimethylisoxazole-4-boronic acid, pinacol ester (6880 mg, 30.84 mmol, 1.5 equiv.), Pd(PH$_3$)$_4$ (1155 mg, 1.03 mmol, 0.05 equiv.), cesium carbonate (20098 mg, 61.68 mmol, 3 equiv.) in 150 mL DME:H$_2$O (2:1) were stirred and heated to 13° C. in a pressure tube. The reaction was then cooled and partitioned between water and ethyl acetate. The organic layer was washed with water then brine and dried over sodium sulfate. Purification on silica gel (Hex/EtOAc) afforded methyl 6-amino-3-(3,5-dimethylisoxazol-4-yl)-2-fluorobenzoate.

LCMS (m/z+1) 265.30. $^1$H NMR (400 MHz, Chloroform-d) δ 7.03 (dd, J=8.6, 7.6 Hz, 1H), 6.54 (dd, J=8.5, 1.1 Hz, 1H), 3.92 (s, 3H), 2.31 (d, J=0.9 Hz, 3H), 2.18 (d, J=0.9 Hz, 3H). $^{19}$F NMR (377 MHz, Chloroform-d) δ −106.99 (d, J=7.5 Hz).

Step 3 and 4: Methyl 2,3-diamino-5-(3,5-dimethylisoxazol-4-yl)-6-fluorobenzoate

Methyl 6-amino-3-(3,5-dimethylisoxazol-4-yl)-2-fluorobenzoate (1400 mg, 5.29 mmol) was dissolved in TFA (20 mL) and cooled to 0° C. under argon. To this was slowly added Nitronium tetrafluoroborate (13.7 mL, 6.89 mmol, 1.3 equiv., 0.5M sulfolane) slowly over 20 minutes. The reaction was stirred at 0° C., then after 1 hour was allowed to warm and react overnight. Reaction solvents were removed under reduced pressure and the residue taken up EtOAc and washed with aq. NaHCO$_3$, then water, brine and dried over sodium sulfate before removing solvents under reduced pressure to yield a dark red oil/liquid. This material was taken up in 20 mL ethanol and stannous (I) chloride (2.50 g, 13.25 mmol, 2.5 equiv.) and heated to 110° C. in a pressure tube. After 2 hr. the reaction was allowed to cool and to it added NaOH (10 mL, 1 N) and stirred for an additional 10 min and the solvents removed under reduced pressure. The residue was taken up EtOAc and washed with aq. NaHCO₃, then water, brine and dried over sodium sulfate before removing solvents under reduced pressure. Crude residue was purified by silica gel chromatography (Hex/EtOAc as the eluent) to afford methyl-2,3-diamino-5-(3,5-dimethyl-isoxazol-4-yl)-6-fluorobenzoate (1.63 g 41% yield) as a light coloured oil.

LCMS (m/z+1) 280.2

Step 5 and 6: tert-butyl 2-cyclopropyl-6-(3,5-dimethylisoxazol-4-yl)-4-formyl-1H-benzo[d]imidazole-1-carboxylate To a flask containing Methyl 2,3-diamino-5-(3,5-dimethylisoxazol-4-yl)-6-fluorobenzoate] (150 mg, 0.53 mmol, 1 equiv.) is added 1,2 DCE (10 ml, 0.1M) and DIPEA (0.44 mL, 1.53 mmol, 3 equiv.). At 0° C., cyclopropanecarbonyl chloride (38 µL, 0.58 mmol, 1.1 equiv.) was added. After an hour, the reaction was complete. The reaction was extracted with EtOAc and washed with water and saturated NH₄Cl. After drying with MgSO₄, it was filtered and concentrated to dryness and used in the next reaction as methyl 3-amino-2-(cyclopropanecarboxamido)-5-(3,5-dimethylisoxazol-4-yl)-6-fluorobenzoate.

Into a microwave vial was placed methyl 3-amino-2-(cyclopropanecarboxamido)-5-(3,5-dimethylisoxazol-4-yl)-6-fluorobenzoate and to it added acetic acid (10 mL) and heated in the microwave for 150° C. for 30 minutes. The reaction was concentrated down and extracted with EtOAc and washed with water (3×), saturated NaHCO₃ and brine. After drying with MgSO₄, it was filtered and concentrated to dryness. Silica gel chromatography was carried out with Hexanes-EtOAc to furnish methyl 2-cyclopropyl-6-(3,5-dimethylisoxazol-4-yl)-7-fluoro-1H-benzo[d]imidazole-4-carboxylate (97 mg, 55%) as a light brown powder.

LCMS (m/z+1) 330.04

Step 7

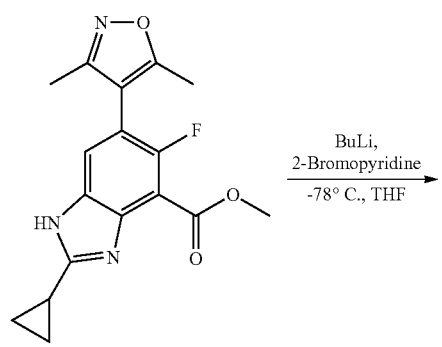

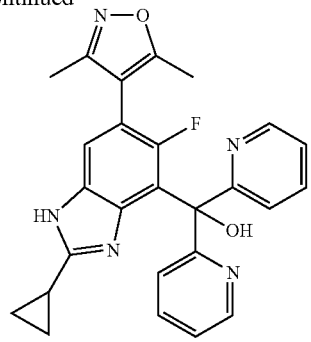

A flask containing 2-bromopridine (60 µL, 0.61 mmol, 8 equiv.) and THF (3 mL) is cooled to −78° C. before BuLi (0.38 mL, 0.61 mmol, 8 equiv.) is added. After 30 min, methyl 2-cyclopropyl-6-(3,5-dimethylisoxazol-4-yl)-5-fluoro-1H-benzo[d]imidazole-4-carboxylate (25 mg, 0.076 mmol, 1 equiv.) dissolved in THF (2 mL) is added to the reaction mixture. After completion, the reaction was quenched and extracted with EtOAc and washed with water followed by saturated NH₄Cl. After drying with MgSO₄, it was filtered and concentrated to dryness. Purification was carried out by reverse phase HPLC to furnish (2-cyclopropyl-6-(3,5-dimethylisoxazol-4-yl)-5-fluoro-1H-benzo[d]imidazol-4-yl)di(pyridin-2-yl)methanol.

LCMS (m/z+1) 455.48. $^1$H NMR (400 MHz, Methanol-d4) δ 8.63 (ddd, J=5.1, 1.9, 0.9 Hz, 1H), 8.02 (td, J=8.1, 2.0 Hz, 1H), 7.64 (dd, J=8.1, 1.2 Hz, 1H), 7.60-7.42 (m, 1H), 2.58 (d, J=4.7 Hz, 0H), 2.27 (s, 2H), 2.07 (s, 1H), 1.49 (dd, J=8.3, 3.0 Hz, 1H), 1.34 (dd, J=4.9, 2.7 Hz, 1H). $^{19}$F NMR (376 MHz, Methanol-d4) δ −77.91.

Example 226

(2-cyclopropyl-5-(3,5-dimethylisoxazol-4-yl)-1-methyl-1H-benzo[d]imidazol-7-yl)di(pyridin-2-yl)methanol (1020-226)

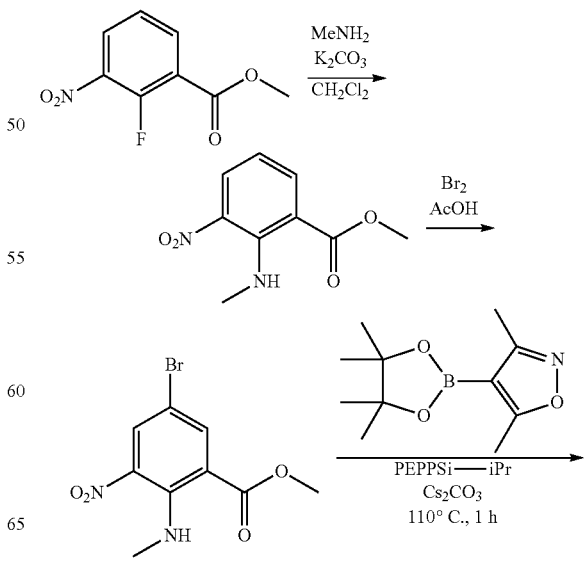

-continued

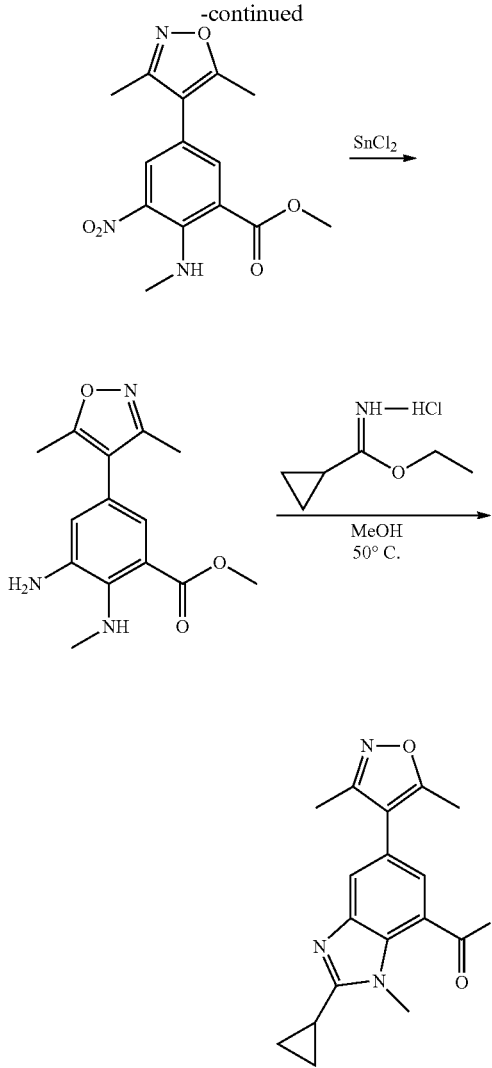

Step 1

To a stirred solution of methyl 2-fluoro-3-nitrobenzoate (1 g, 5 mmol) in DCM (10 mL), potassium carbonate (1.38 g, 10 mmol) was added at room temperature. To the reaction was then added methylamine in THF (20 mL, 40 mmol, 2M). The progress of reaction was monitored by LCMS which shows complete conversion of methyl 2-fluoro-3-nitrobenzoate, Reaction was diluted with water (50 mL) then extracted with DCM (50 mL). Organic was condensed to give methyl 2-(methylamino)-3-nitrobenzoate (1 g, 95%)

Step 2

To a stirred solution of methyl 2-(methylamino)-3-nitrobenzoate (2 g, 10 mmol) in acetic acid (14 mL) bromine (0.49 mL, 10 mmol) in acetic acid (2 mL) was added. Reaction was stirred at rt for 30 min. The reaction was complete by LCMS and then was poured on ice (~100 g). The resulting solid was filtered and dried on high vac to give methyl 5-bromo-2-(methylamino)-3-nitrobenzoate (2.6 g, 94%) as a orange solid.

Step 3

To a stirred solution of methyl 5-bromo-2-(methylamino)-3-nitrobenzoate (1.5 g, 5.2 mmol) in 1,2-deimethoxyethane (15 mL) and water (3 mL), 3,5-dimethyl-4-(4,4,5,5-tetramethyl-1,3,2-dioxaborolan-2-yl)isoxazole (2.1 g, 9.3 mmol) was added, followed by cesium carbonate (2.8 g, 8.6 mmol). After addition was completed, resulting reaction mixture was stirred at rt for 30 min. followed by degas with argon for 15 min. Then PEPPSI-IPr catalyst (0.2 g, 0.2 mmol) was added and again reaction mixture was degas with argon for another 15 min. Then resulting reaction mixture was heated to stir at 110° C. for 1 h under argon atmosphere. Reaction monitored by LCMS till completion. Reaction was cooled to rt then diluted with EtOAc (25 mL) and water (15 mL). EtOAc (25 mL) was used twice to extract product. Organic layers were combined and dried with magnesium sulfate and condensed. The resulting mixture was purified via normal phase 0-25% (EtOAc/Hexanes) to give methyl 5-(3,5-dimethylisoxazol-4-yl)-2-(methylamino)-3-nitrobenzoate (1.5 g, 38%)

Step 4

To a stirred solution of methyl 5-(3,5-dimethylisoxazol-4-yl)-2-(methylamino)-3-nitrobenzoate (0.6 g, 2 mmol) in EtOH (15 mL) stannous chloride (1.87 g, 10 mmol) was added at room temperature. Then resulting reaction mixture was heated to stir at 60° C. for 1 h under argon atmosphere reaction was monitored by LCMS to be complete. Material was condensed to a dark solid, then slurried in EtOAc. This was then filtered thru celite and condensed down to give methyl 3-amino-5-(3,5-dimethylisoxazol-4-yl)-2-(methylamino)benzoate (0.5 g 99%).

Step 5

To a stirred solution of methyl 3-amino-5-(3,5-dimethylisoxazol-4-yl)-2-(methylamino)benzoate (6.5 g, 24.0 mmol) in MeOH (125 mL), ethyl cyclopropanecarbimidate hydrochloride (4.2 g, 30 mmol) was added. The reaction was then heated to 50 C overnight. The reaction was then condensed down and coevaporated with Toluene (100 mL) to give methyl 2-cyclopropyl-5-(3,5-dimethylisoxazol-4-yl)-1-methyl-1H-benzo[d]imidazole-7-carboxylate (7.5 g, 98%)

Step 6: (2-cyclopropyl-5-(3,5-dimethylisoxazol-4-yl)-1-methyl-1H-benzo[d]imidazol-7-yl)di(pyridin-2-yl)methanol

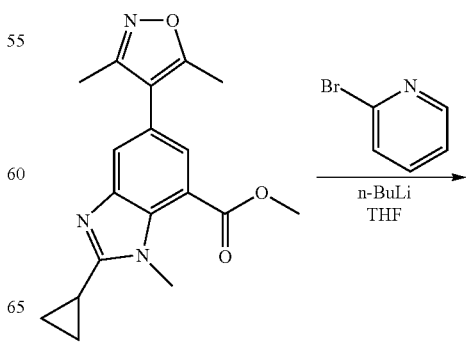

303

-continued

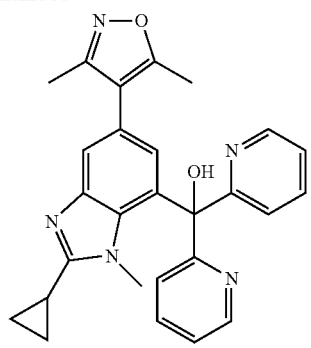

2-bromopyridine (0.18 mL, 1.84 mmol) was dissolved in THF (22 mL) and cooled to −78° C. n-BuLi (1.28 mL, 2.02 mmol, 1.6 M) was added dropwise and the reaction was allowed to stir for 30 minutes at −78° C. methyl 2-cyclopropyl-5-(3,5-dimethylisoxazol-4-yl)-1-methyl-1H-benzo[d]imidazole-7-carboxylate (150 mg, 0.46 mmol) in THF (3 mL) was added. The reaction was allowed to stir at rt for 1 hour. The reaction was monitored by LCMS and when complete it was quenched with water (50 mL) and EtOAc (50 mL) the organic layer was extracted and condensed to an light oil. The oil was purified by RPHPLC 0-50% (Acetonitrile/water) to give (2-cyclopropyl-5-(3,5-dimethylisoxazol-4-yl)-1-methyl-1H-benzo[d]imidazol-7-yl)di(pyridin-2-yl)methanol (110 mg, 54%)

$C_{27}H_{25}N_5O_2$ MS=452.21 (M+H+). $^1$H NMR (400 MHz, Methanol-d4) δ 8.58 (ddd, J=5.0, 1.8, 0.9 Hz, 2H), 7.95-7.86 (m, 2H), 7.62-7.51 (m, 3H), 7.44 (ddd, J=7.6, 4.9, 1.1 Hz, 2H), 6.50 (d, J=1.6 Hz, 1H), 3.67 (d, J=13.5 Hz, 3H), 2.42-2.34 (m, 1H), 2.25 (s, 3H), 2.07 (s, 3H), 1.46-1.39 (m, 2H), 1.32-1.23 (m, 2H).

Example 227

(2-cyclopropyl-5-(3,5-dimethylisoxazol-4-yl)-1-methyl-1H-benzo[d]imidazol-7-yl)(pyridin-2-yl)(pyrimidin-2-yl)methanol (1020-227)

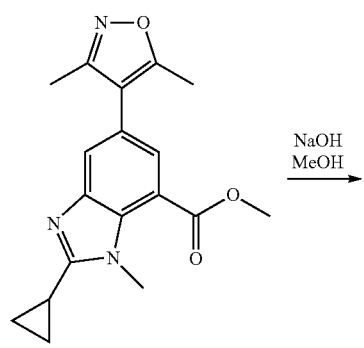

304

-continued

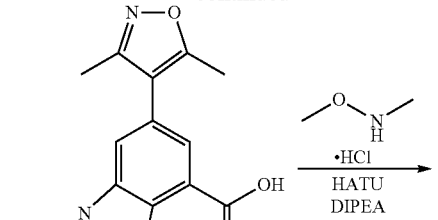

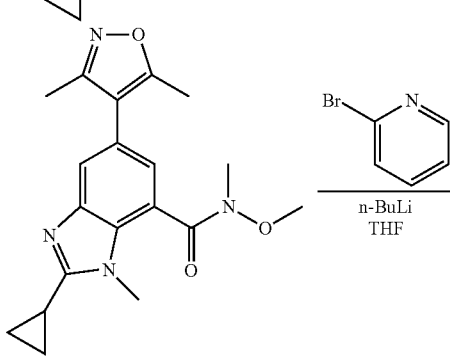

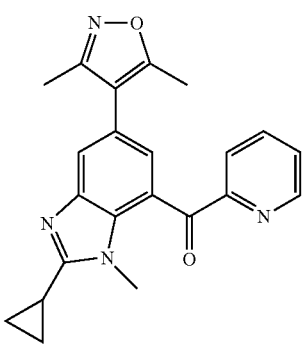

Step 1

To a stirred solution of methyl 2-cyclopropyl-5-(3,5-dimethylisoxazol-4-yl)-1-methyl-1H-benzo[d]imidazole-7-carboxylate (4.5 g, 14 mmol) in MeOH (100 mL) was added sodium hydroxide (1.2 g, 30 mmol). The reaction was heated to 40 C overnight under an atmosphere of argon. The reaction was monitored by LCMS and was complete. The reaction was then condensed down to a solid to give 2-cyclopropyl-5-(3,5-dimethylisoxazol-4-yl)-1-methyl-1H-benzo[d]imidazole-7-carboxylic acid (4.1 g, 95%)

Step 2

2-cyclopropyl-5-(3,5-dimethylisoxazol-4-yl)-1-methyl-1H-benzo[d]imidazole-7-carboxylic acid (1.2 g, 3.9 mmol) in DMF (15 mL) with HATU (1.76 g, 4.6 mmol) for 15 mins, then added N,O-dilmethylhydroxylamine HCl salt (0.56 g, 5.8 mmol) and DIPEA (3.1 mL, 22 mmol), stirred at RT overnight. Diluted with EtOAc, washed with brine, backextracted with EtOAc 4 times, evaporated organic solvent, purified with normal phase 0-100% (EtOAc/Hexanes) to give 2-cyclopropyl-5-(3,5-dimethylisoxazol-4-yl)-N-methoxy-N,1-dimethyl-1H-benzo[d]imidazole-7-carboxamide (1 g, 73%)

Step 3

2-bromopyridine (0.80 mL, 8.4 mmol) was dissolved in THF (35 mL) and cooled to −78° C. n-BuLi (6.2 mL, 10.0 mmol, 1.6 M) was added dropwise and the reaction was allowed to stir for 1 hour at −78° C. 2-cyclopropyl-5-(3,5-dimethylisoxazol-4-yl)-N-methoxy-N,1-dimethyl-1H-benzo[d]imidazole-7-carboxamide (0.5 g, 1.4 mmol) in THF (5 mL) was added and the reaction was allowed to come to 0° C. and stir for 15 minutes before being quenched with water. Reaction was diluted with EtOAc, washed twice with brine, concentrated, and purified by silica gel chromatography to give (2-cyclopropyl-5-(3,5-dimethylisoxazol-4-yl)-1-methyl-1H-benzo[d]imidazol-7-yl)(pyridin-2-yl)methanone (0.46 g, 88%)

Step 4: (2-cyclopropyl-5-(3,5-dimethylisoxazol-4-yl)-1-methyl-1H-benzo[d]imidazol-7-yl)(pyridin-2-yl)(pyrimidin-2-yl)methanol

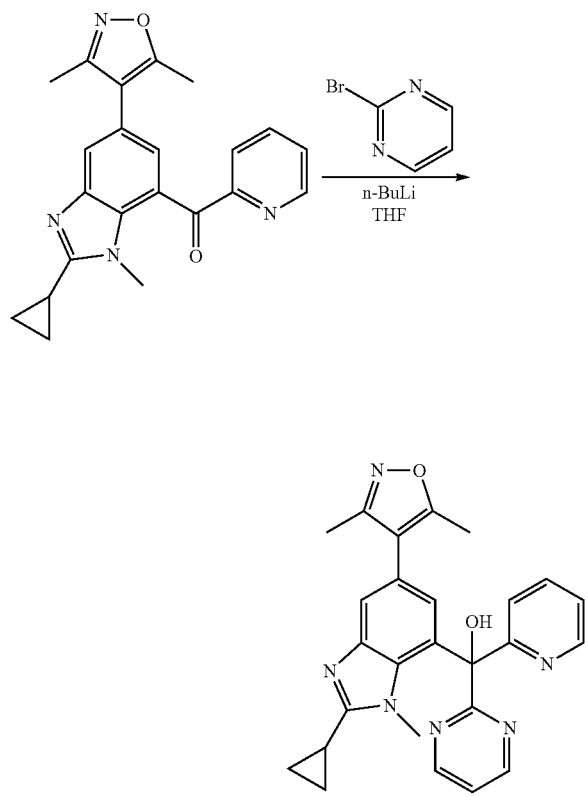 [SMILES: Cc1noc(C)c1-c1cc(C(=O)c2ccccn2)c2c(c1)nc(C1CC1)n2C ; Brc1ncccn1 ; Cc1noc(C)c1-c1cc(C(O)(c2ccccn2)c2ncccn2)c2c(c1)nc(C1CC1)n2C]

(2-cyclopropyl-5-(3,5-dimethylisoxazol-4-yl)-1-methyl-1H-benzo[d]imidazol-7-yl)(pyridin-2-yl)(pyrimidin-2-yl)methanol was synthesized using 2-bromopyrimidine and (2-cyclopropyl-5-(3,5-dimethylisoxazol-4-yl)-1-methyl-1H-benzo[d]imidazol-7-yl)(pyridin-2-yl)methanone in a similar fashion as Example No. 1

$C_{26}H_{24}N_6O_2$ MS=453.23 (M+H+). $^1$H NMR (400 MHz, Methanol-d4) δ 9.21 (dd, J=4.9, 1.6 Hz, 1H), 8.63-8.60 (m, 1H), 8.06-7.96 (m, 2H), 7.92 (td, J=7.8, 1.8 Hz, 1H), 7.87-7.78 (m, 2H), 7.62 (d, J=1.6 Hz, 1H), 7.51 (dt, J=8.0, 1.0 Hz, 1H), 7.46 (ddd, J=7.6, 4.9, 1.1 Hz, 1H), 6.53 (d, J=1.6 Hz, 1H), 3.92 (s, 1H), 3.67 (d, J=11.2 Hz, 3H), 2.47-2.33 (m, 3H), 2.26 (s, 3H), 2.08 (s, 3H), 1.49-1.36 (m, 3H), 1.28 (dt, J=6.5, 3.4 Hz, 3H).

Example 228

(2-cyclopropyl-5-(3,5-dimethylisoxazol-4-yl)-1-methyl-1H-benzo[d]imidazol-7-yl)(pyridazin-3-yl)(pyridin-2-yl)methanol (1020-228)

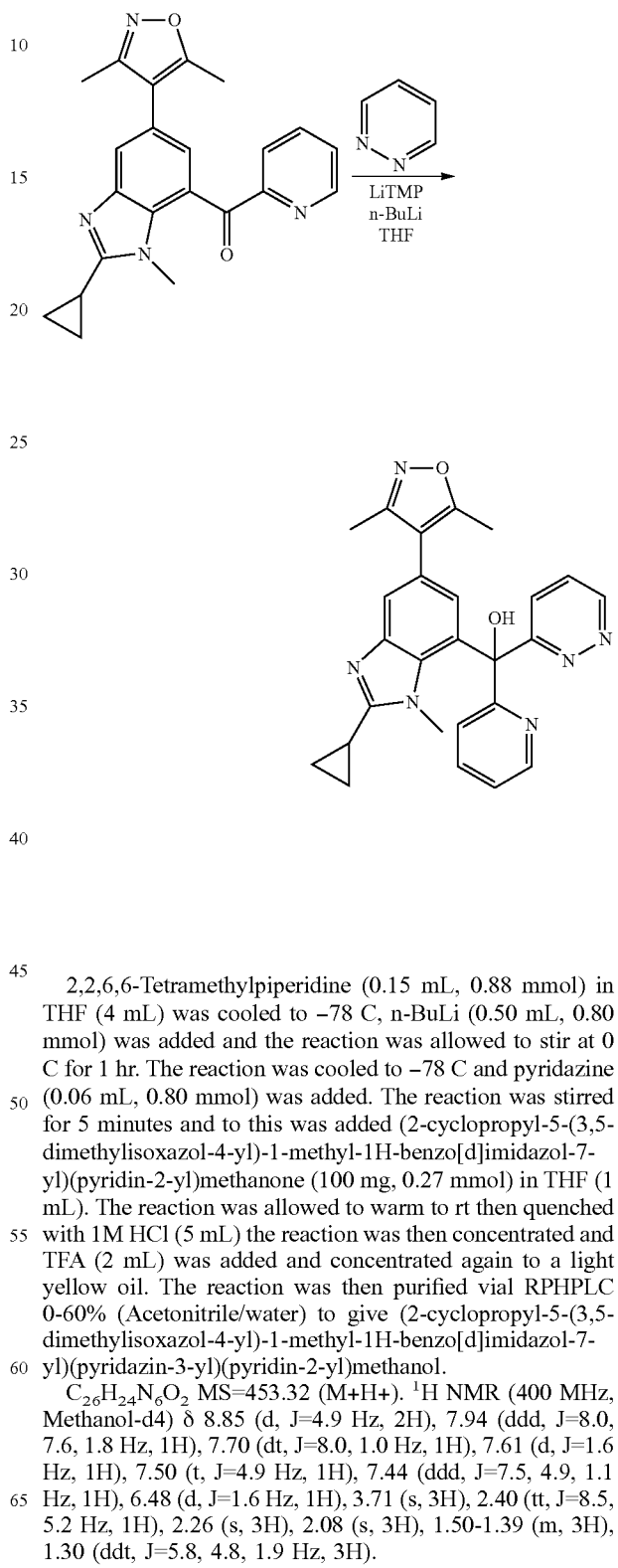

2,2,6,6-Tetramethylpiperidine (0.15 mL, 0.88 mmol) in THF (4 mL) was cooled to −78 C, n-BuLi (0.50 mL, 0.80 mmol) was added and the reaction was allowed to stir at 0 C for 1 hr. The reaction was cooled to −78 C and pyridazine (0.06 mL, 0.80 mmol) was added. The reaction was stirred for 5 minutes and to this was added (2-cyclopropyl-5-(3,5-dimethylisoxazol-4-yl)-1-methyl-1H-benzo[d]imidazol-7-yl)(pyridin-2-yl)methanone (100 mg, 0.27 mmol) in THF (1 mL). The reaction was allowed to warm to rt then quenched with 1M HCl (5 mL) the reaction was then concentrated and TFA (2 mL) was added and concentrated again to a light yellow oil. The reaction was then purified vial RPHPLC 0-60% (Acetonitrile/water) to give (2-cyclopropyl-5-(3,5-dimethylisoxazol-4-yl)-1-methyl-1H-benzo[d]imidazol-7-yl)(pyridazin-3-yl)(pyridin-2-yl)methanol.

$C_{26}H_{24}N_6O_2$ MS=453.32 (M+H+). $^1$H NMR (400 MHz, Methanol-d4) δ 8.85 (d, J=4.9 Hz, 2H), 7.94 (ddd, J=8.0, 7.6, 1.8 Hz, 1H), 7.70 (dt, J=8.0, 1.0 Hz, 1H), 7.61 (d, J=1.6 Hz, 1H), 7.50 (t, J=4.9 Hz, 1H), 7.44 (ddd, J=7.5, 4.9, 1.1 Hz, 1H), 6.48 (d, J=1.6 Hz, 1H), 3.71 (s, 3H), 2.40 (tt, J=8.5, 5.2 Hz, 1H), 2.26 (s, 3H), 2.08 (s, 3H), 1.50-1.39 (m, 3H), 1.30 (ddt, J=5.8, 4.8, 1.9 Hz, 3H).

Example 229

(2-cyclopropyl-6-(3,5-dimethylisoxazol-4-yl)-1H-benzo[d]imidazol-4-yl)di(thiophen-2-yl)methanol (1020-229)

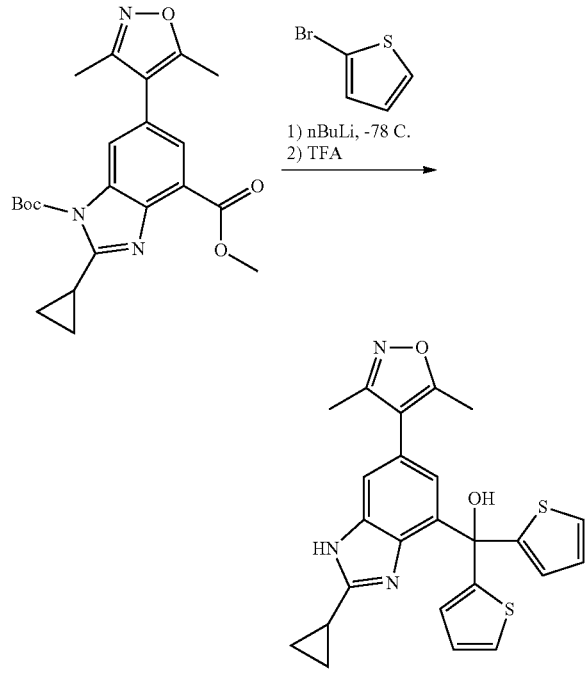

(2-cyclopropyl-6-(3,5-dimethylisoxazol-4-yl)-1H-benzo[d]imidazol-4-yl)di(thiophen-2-yl)methanol was synthesized using 1-tert-butyl 4-methyl 2-cyclopropyl-6-(3,5-dimethylisoxazol-4-yl)-1H-benzo[d]imidazole-1,4-dicarboxylate and 2-bromothiophene in a similar fashion to Example 206.

$C_{24}H_{21}N_3O_2S_2$ MS=447.80 (M+H$^+$). $^1$H NMR (400 MHz, Methanol-d$_4$) δ 7.48 (d, J=1.4 Hz, 1H), 7.44 (dd, J=5.0, 1.3 Hz, 1H), 7.04-6.94 (m, 3H), 6.90 (s, 1H), 3.75 (s, 1H), 3.65 (s, 1H), 2.32 (s, 2H), 2.14 (s, 3H), 1.45 (s, 2H), 1.34 (d, J=7.6 Hz, 3H).

Example 230

(2-cyclopropyl-6-(3,5-dimethylisoxazol-4-yl)-1H-benzo[d]imidazol-4-yl)(furan-2-yl)(pyridin-2-yl)methanol (1020-230)

The title compound was synthesized in a similar fashion as that of Example 106, step 2.

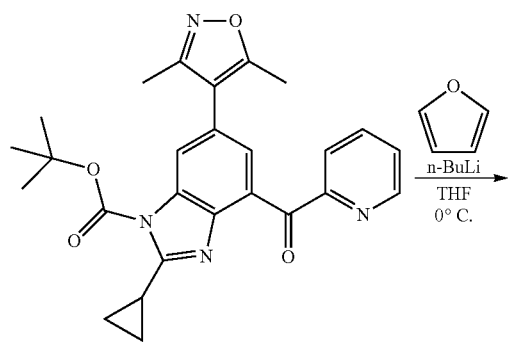

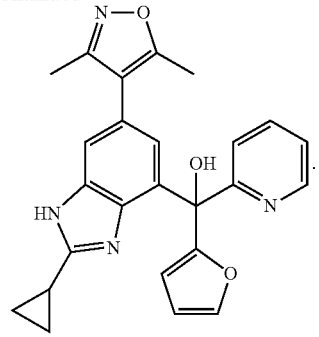

$C_{25}H_{22}N_4O_3$. MS. 427.1 (M+1). $^1$H NMR (MeOH-d$_4$) δ 8.00 (td, J=8.0, 1.9 Hz, 1H), 7.78 (d, J=8.0 Hz, 1H), 7.60 (dd, J=4.8, 1.0 Hz, 1H), 7.54 (d, J=1.9 Hz, 1H), 7.49 (ddd, J=8.0, 4.8, 1.0 Hz, 1H), 7.08 (d, J=1.9 Hz, 1H), 6.47 (dd, J=4.8, 1.6 Hz, 1H), 6.19 (dd, J=4.8, 1.0 Hz, 1H), 2.65-2.56 (m, 1H), 2.36 (s, 3H), 2.18 (s, 3H), 1.60-1.34 (m, 4H).

Example 231

(2-cyclopropyl-6-(3,5-dimethylisoxazol-4-yl)-1H-benzo[d]imidazol-4-yl)(pyridin-2-yl)(5-(trifluoromethyl)thiophen-2-yl)methanol (1020-231)

The title compound was synthesized in a similar fashion as that of Example 106, step 2.

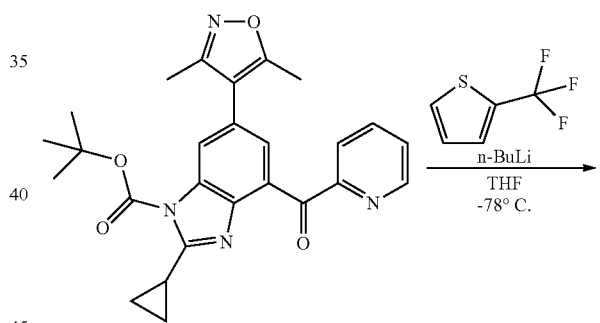

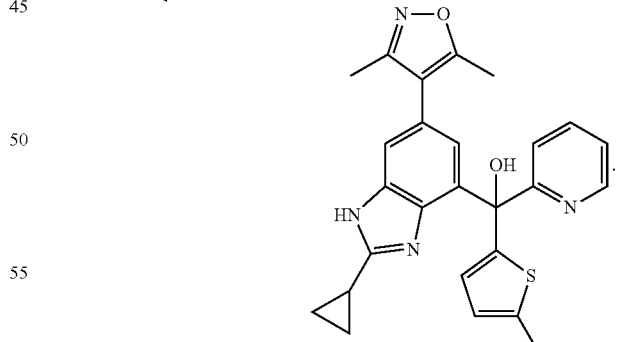

$C_{26}H_{21}F_3N_4O_2S$. MS. 511.1 (M+1). $^1$H NMR (MeOH-d$_4$) δ 8.64 (td, J=4.8 Hz, 1H), 7.92 (td, J=8.0, 1.6 Hz, 1H), 7.81 (d, J=8.0 Hz, 1H), 7.53 (d, J=1.6 Hz, 1H), 7.46-7.40 (m, 2H), 7.22 (d, J=1.6 Hz, 1H), 7.03 (d, J=4.8 Hz, 1H), 2.68-2.60 (m, 1H), 2.34 (s, 3H), 2.16 (s, 3H), 1.60-1.48 (m, 2H), 1.44-1.34 (m, 2H).

Example 232

(5-chlorothiophen-2-yl)(2-cyclopropyl-6-(3,5-dimethylisoxazol-4-yl)-1H-benzo[d]imidazol-4-yl)(pyridin-2-yl)methanol (1020-232)

The title compound was synthesized in a similar fashion as that of Example 106, step 2.

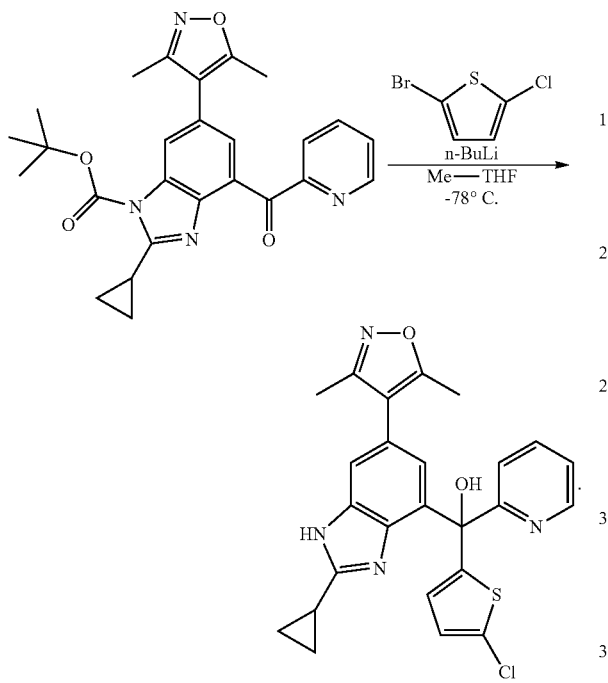

C<sub>25</sub>H<sub>21</sub>ClN<sub>4</sub>O<sub>2</sub>S. MS. 477.1 (M+1). <sup>1</sup>H NMR (MeOH-d<sub>4</sub>) δ 8.62 (d, J=4.8 Hz, 1H), 7.91 (td, J=8.0, 1.6 Hz, 1H), 7.78 (d, J=8.0 Hz, 1H), 7.52 (d, J=1.6 Hz, 1H), 7.41 (dd, J=6.7, 4.8 Hz, 1H), 7.21 (d, J=1.6 Hz, 1H), 6.88 (d, J=3.2 Hz, 1H), 6.73 (d, J=3.2 Hz, 1H), 2.67-2.58 (m, 1H), 2.36 (s, 3H), 2.18 (s, 3H), 1.60-1.48 (m, 2H), 1.44-1.34 (m, 2H).

Example 233

Benzofuran-2-yl(2-cyclopropyl-6-(3,5-dimethylisoxazol-4-yl)-1H-benzo[d]imidazol-4-yl)(pyridin-2-yl)methanol (1020-233)

The title compound was synthesized in a similar fashion as that of Example 106, step 2.

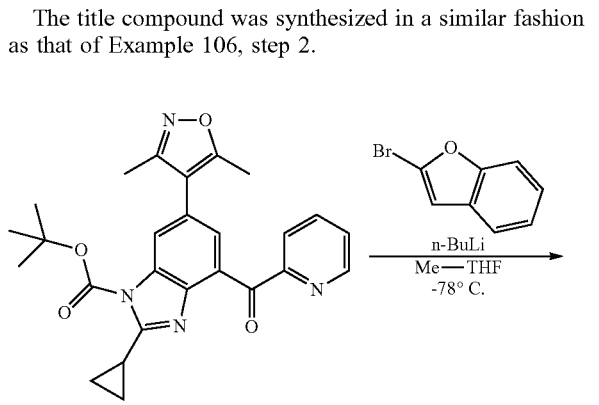

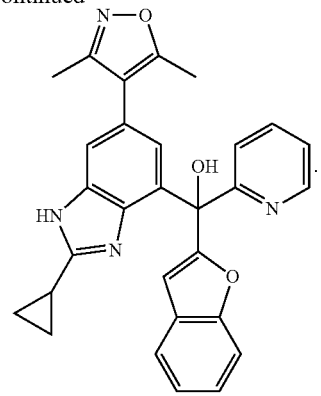

C<sub>29</sub>H<sub>24</sub>N<sub>4</sub>O<sub>3</sub>. MS. 477.2 (M+1). <sup>1</sup>H NMR (MeOH-d<sub>4</sub>) δ 8.60 (d, J=4.8 Hz, 1H), 7.96 (td, J=6.4, 1.6 Hz, 1H), 7.84 (d, J=6.4 Hz, 1H), 7.57 (d, J=6.4 Hz, 1H), 7.54 (d, J=1.6 Hz, 1H), 7.46 (dd, J=6.4, 4.8 Hz, 1H), 7.42 (d, J=6.4 Hz, 1H), 7.30 (d, J=6.4 Hz, 1H), 7.24 (d, J=6.4 Hz, 1H), 7.18 (d, J=1.6 Hz, 1H), 6.60 (s, 1H), 1.60-1.30 (m, 4H).

Example 234

(2-Cyclopropyl-6-(3,5-dimethylisoxazol-4-yl)-1H-benzo[d]imidazol-4-yl)(pyridin-2-yl)(quinolin-7-yl)methanol (1020-234)

The title compound was synthesized in a similar fashion as that of Example 106, step 2.

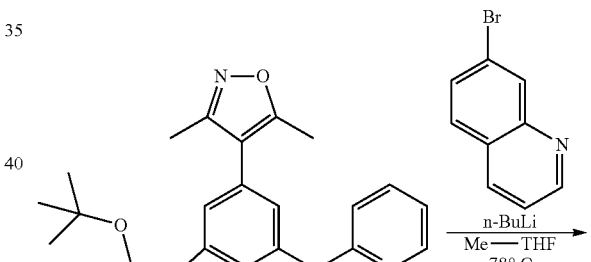

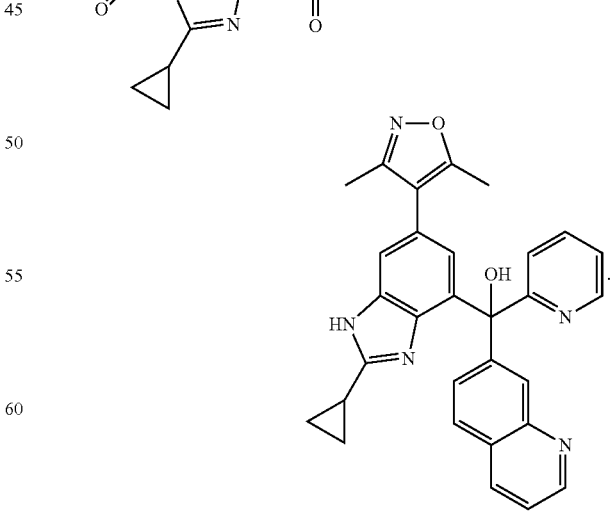

C<sub>30</sub>H<sub>25</sub>N<sub>5</sub>O<sub>2</sub>. MS. 488.2 (M+1). <sup>1</sup>H NMR (MeOH-d<sub>4</sub>) δ 8.75 (dd, J=4.3, 1.7 Hz, 1H), 8.71 (d, J=8.7 Hz, 1H), 8.66 (d, J=4.6 Hz, 1H), 8.02 (d, J=8.5 Hz, 1H), 7.81 (td, J=7.9, 1.8 Hz, 1H), 7.57 (dd, J=8.5, 7.3 Hz, 1H), 7.47-7.34 (m, 3H), 7.28 (dd, J=8.8, 4.3 Hz, 1H), 6.84 (dd, J=7.4, 1.1 Hz, 1H), 6.31 (d, J=1.5 Hz, 1H), 2.24-2.14 (m, 1H), 2.05 (s, 3H), 1.84 (s, 3H), 1.17-1.06 (m, 4H).

Example 235

(2-cyclopropyl-6-(3,5-dimethylisoxazol-4-yl)-1H-benzo[d]imidazol-4-yl)(pyridin-2-yl)(m-tolyl)methanol (1020-235)

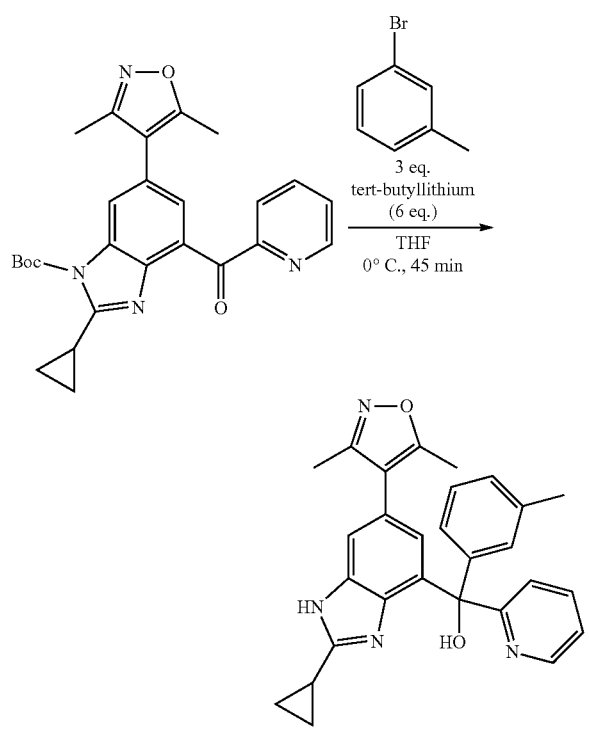

In a 2-neck, 50-mL round bottom flask, a solution of 3-bromotoluene (30 µL, 0.25 mmol) stirring in tetrahydrofuran (2 mL) was cooled to −78° C. in a dry ice/acetone bath. A 1.47 M tert-butyllithium solution in pentane (330 µL, 0.48 mmol) was added dropwise and the reaction mixture was stirred at −78° C. for 15 minutes. In a solution of 1 mL of tetrahydrofuran, tert-butyl 2-cyclopropyl-6-(3,5-dimethylisoxazol-4-yl)-4-picolinoyl-1H-benzo[d]imidazole-1-carboxylate (36.8 mg, 0.0803 mmol) was added dropwise and the reaction mixture was warmed to room temperature. The reaction was complete after fifteen minutes and quenched with brine and diluted with ethyl acetate. The organic layer was separated and saved and the aqueous layer was back-extracted three times with ethyl acetate. The organic layers were combined, dried over sodium sulfate, decanted and concentrated. The crude reaction mixture was isolated by preparatory TLC to yield the title compound (19.4, 54%).

$C_{28}H_{26}N_4O_2$. 451.2 (M+1). Rf=0.15 (1:1 Ethyl Acetate: Hexane). $^1$H NMR (400 MHz, Chloroform-d) δ 8.81 (d, J=5.5 Hz, 1H), 8.25 (t, J=8.0 Hz, 1H), 7.84 (dd, J=7.4, 5.5 Hz, 1H), 7.65 (d, J=1.4 Hz, 1H), 7.48 (d, J=7.9 Hz, 1H), 7.29-7.26 (m, 2H), 7.00 (d, J=1.9 Hz, 1H), 6.91 (dd, J=5.8, 2.4 Hz, 1H), 6.76 (d, J=1.4 Hz, 1H), 2.43 (td, J=8.5, 4.4 Hz, 1H), 2.30 (s, 3H), 2.27 (s, 3H), 2.07 (s, 3H), 1.60-1.47 (m, 2H), 1.41 (dd, J=8.5, 4.5 Hz, 2H).

Example 236 cyclopentyl(2-cyclopropyl-6-(3,5-dimethylisoxazol-4-yl)-1H-benzo[d]imidazol-4-yl)(pyridin-2-yl)methanol (1020-236)

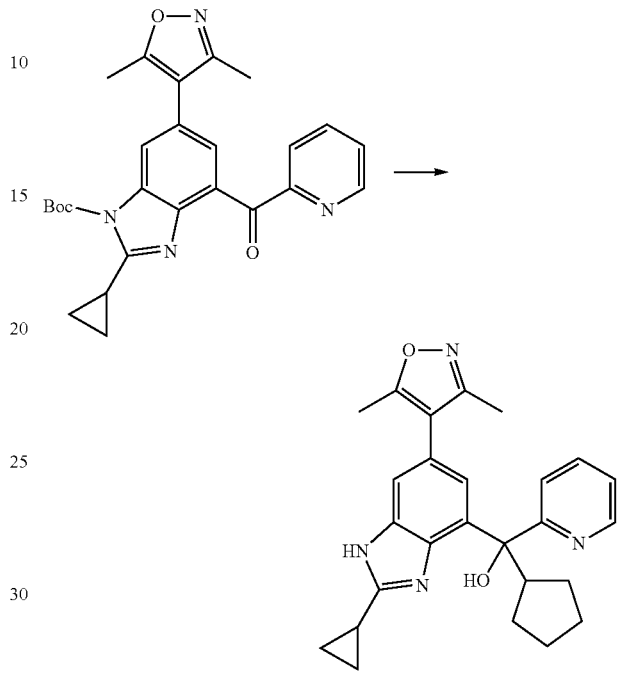

tert-Butyl 2-cyclopropyl-6-(3,5-dimethylisoxazol-4-yl)-4-picolinoyl-1H-benzo[d]imidazole-1-carboxylate (35 mg, 0.076 mmol) was dissolved in 5 ml THF, to the reaction flask was added cyclopropylmagnesium bromide at RT. The reaction mixture was stirred at RT overnight. Then it was quenched with water. To the work-up mixture was added 1 ml of TFA, heated to 70° C. for h. Then the solvent was evaporated, the residue was purified with Prep HPLC to afford cyclopentyl(2-cyclopropyl-6-(3,5-dimethylisoxazol-4-yl)-1H-benzo[d]imidazol-4-yl)(pyridin-2-yl)methanol.

$C_{26}H_{28}N_4O_2$. 429.1 (M+1). $^1$H NMR (400 MHz, CD$_3$OD) 8.49-8.48 (m, 1H), 7.78-7.76 (m, 2H), 7.57 (s, 1H), 7.31 (s, 1H), 7.27-7.24 (m, 1H), 3.40-3.36 (m, 1H), 2.55-2.52 (m, 1H), 2.30 (s, 3H), 2.13 (s, 3H), 1.58-1.50 (m, 6H), 1.44-1.42 (m, 2H), 1.18-1.08 (m, 4H).

Example 237

Cyclopropyl(2-cyclopropyl-6-(3,5-dimethylisoxazol-4-yl)-1H-benzo[d]imidazol-4-yl)(pyridin-2-yl)methanol (1020-237)

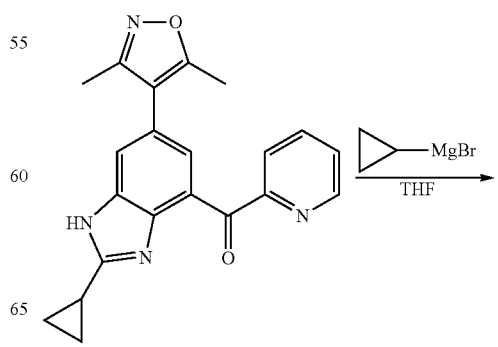

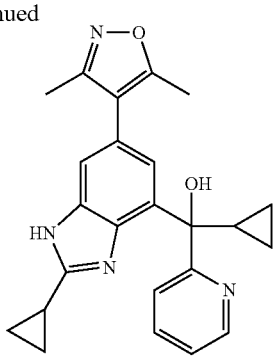

Cyclopropylmagnesium bromide (0.9 mL, 0.45 mmol) was added to a solution of (2-cyclopropyl-6-(3,5-dimethyl-isoxazol-4-yl)-1H-benzo[d]imidazol-4-yl)(pyridin-2-yl)methanone (40 mg, 0.11 mmol) in THF (1.2 mL) at room temperature and allowed to stir for 30 minutes before being quenched with water, concentrated, and purified by reverse-phase HPLC to afford cyclopropyl(2-cyclopropyl-6-(3,5-dimethylisoxazol-4-yl)-1H-benzo[d]imidazol-4-yl)(pyridin-2-yl)methanol $C_{24}H_{24}N_4O_2$ 401.4 (M+1). $^1$H NMR (400 MHz, DMSO-$d_6$) δ 8.53 (dt, J=4.8, 1.3 Hz, 1H), 7.95-7.87 (m, 2H), 7.61 (d, J=1.5 Hz, 1H), 7.49 (s, 1H), 7.36 (ddd, J=7.1, 5.0, 2.3 Hz, 1H), 2.61 (d, J=5.0 Hz, 1H), 2.42 (s, 3H), 2.23 (s, 3H), 2.17 (s, 1H), 1.42-1.24 (m, 4H), 0.70-0.40 (m, 4H).

Example 238 and 239

(R) and (S)-(2-cyclopropyl-6-(3,5-dimethylisoxazol-4-yl)-1H-benzo[d]imidazol-4-yl)(pyridin-2-yl)(pyrimidin-2-yl)methanol

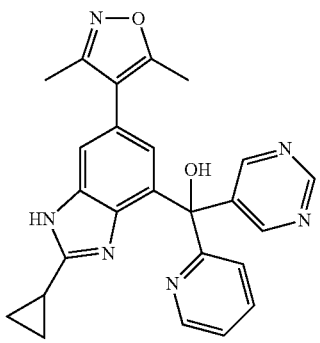 [SMILES: Cc1noc(C)c1-c1cc(C(O)(c2cncnc2)c2ccccn2)c2nc(C3CC3)[nH]c2c1]

The enantiomers described by compound 1020-108 were separated by a chiral column (DAICEL, ChiralPak AD-H, Heptane/IPA 70:30) to afford the following enantiomers.
First eluting compound is 1020-238; the second eluting compound is 1020-239.

Example 240

(2-cyclopropyl-6-(3,5-dimethylisoxazol-4-yl)-1H-benzo[d]imidazol-4-yl)(1H-imidazol-2-yl)(pyridin-2-yl)methanol (1020-240)

Step 1: Preparation of (1-(tert-butyldimethylsilyl-1H-imidazol-2-yl)(2-cyclopropyl-6-(3,5-dimethylisoxazol-4-yl)-1H-benzo[d]imidazol-4-yl)(pyridin-2-yl)methanol

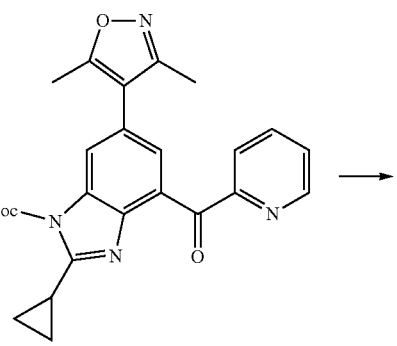

To a solution of N-TBS imidazole (16 mg, 0.087 mmol) in THF (5 mL) was added LiBu (0.044 mmol) and the solution was stirred at −78° C. for 1 h. To the solution was added tert-butyl 2-cyclopropyl-6-(3,5-dimethylisoxazol-4-yl)-4-picolinoyl-1H-benzo[d]imidazole-1-carboxylate (20 mg, 0.044 mmol) in THF (3 mL). The reaction solution was stirred at room temperature for 1 h. EtOAc (100 mL) was added and the organic solution was washed with brine and dried over $Na_2SO_4$. Solvent was removed and the residue was purified by silica gel column chromatography (0-50% MeOH/$CH_2Cl_2$) to give fraction containing (1-(tert-butyldimethylsilyl)-1H-imidazol-2-yl)(2-cyclopropyl-6-(3,5-dimethylisoxazol-4-yl)-1H-benzo[d]imidazol-4-yl)(pyridin-2-yl)methanol identified by LCMS, which was used for the next deprotection without further purification.

Step 2: (2-cyclopropyl-6-(3,5-dimethylisoxazol-4-yl)-1H-benzo[d]imidazol-4-yl)(H-imidazol-2-yl)(pyridin-2-yl)methanol

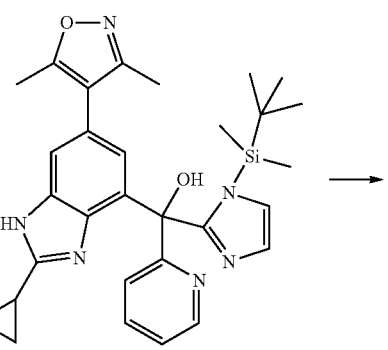

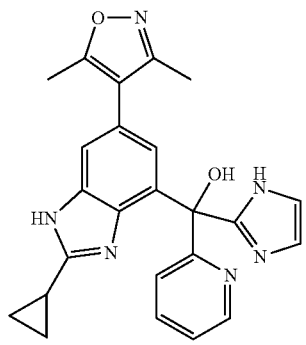

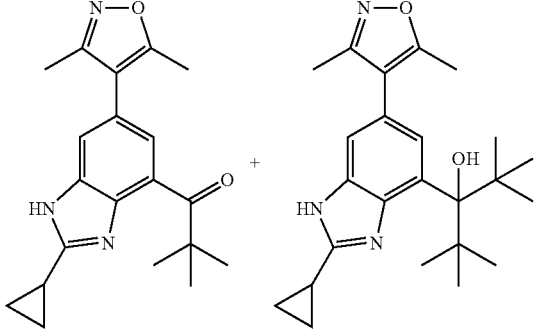

To a solution of crude (1-(tert-butyldimethylsilyl)-1H-imidazol-2-yl)(2-cyclopropyl-6-(3,5-dimethylisoxazol-4-yl)-1H-benzo[d]imidazol-4-yl)(pyridin-2-yl)methanol in THF (5 mL) was added TBAF (0.029 g, 0.11 mmol) and the solution was stirred at room temperature for 20 h. Solvent was removed and the residue was purified by HPLC to give (2-cyclopropyl-6-(3,5-dimethylisoxazol-4-yl)-1H-benzo[d]imidazol-4-yl)(1H-imidazol-2-yl)(pyridin-2-yl)methanol.

$C_{24}H_{22}N_6O_2$. MS m/z 427.1 (M+1). $^1$H NMR (Methanol-$d_4$) δ 8.76 (dd, J=2.4, 0.8 Hz, 1H), 8.71 (dd, J=5.1, 1.5 Hz, 1H), 8.15 (ddd, J=8.2, 2.4, 1.5 Hz, 1H), 7.69 (ddd, J=8.2, 5.1, 0.8 Hz, 1H), 7.65-7.50 (m, 3H), 7.12 (d, J=1.4 Hz, 1H), 2.45 (tt, J=8.4, 5.0 Hz, 1H), 2.36 (s, 3H), 2.18 (s, 3H), 1.41 (dd, J=8.4, 1.7 Hz, 2H), 1.28 (ddd, J=7.8, 3.6, 1.8 Hz, 3H).

Example 241 and 242

1-(2-cyclopropyl-6-(3,5-dimethylisoxazol-4-yl)-1H-benzo[d]imidazol-4-yl)-2,2-dimethylpropan-1-one (1020-241) and 3-(2-cyclopropyl-6-(3,5-dimethylisoxazol-4-yl)-1H-benzo[d]imidazol-4-yl)-2,2,4,4-tetramethylpentan-3-ol (1020-242)

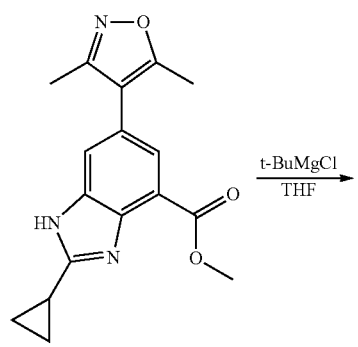

In a flame dried flask containing methyl 2-cyclopropyl-6-(3,5-dimethylisoxazol-4-yl)-1H-benzo[d]imidazole-4-carboxylate (50 mg, 0.16 mmol) in THF was added tert-Butyl Magnesium Chloride (1.6 mL, 1.6 mmol) in THF. The reaction was allowed to run for 24 hours. Once complete, the solution was quenched with DI $H_2O$ and extracted three times with EtOAc. The combined organic layers were washed with saturated NaCl, dried over sodium sulfate, filtered and concentrated in vacuo. Purification was carried out by reverse phase HPLC to afford 1-(2-cyclopropyl-6-(3,5-dimethylisoxazol-4-yl)-1H-benzo[d]imidazol-4-yl)-2,2-dimethylpropan-1-one. In some cases, the ketone, secondary, and tertiary alcohol were isolated and characterized.

Compound 1020-241: $C_{20}H_{23}N_3O_2$. MS. m/z 338.5 (M+1). $^1$H NMR (400 MHz, cd$_3$od) δ 7.73 (s, 1H), 7.59 (s, 1H), 2.43 (s, 3H), 2.27 (s, 3H), 1.28 (dd, J=30.6, 6.8 Hz, 1H), 1.17 (d, J=7.0 Hz, 4H).

Compound 1020-242: $C_{24}H_{33}N_3O_2$. MS. m/z 396.3 (M+1) $^1$H NMR (400 MHz, cd$_3$od) δ 7.29 (d, J=6.7 Hz, 1H), 7.20 (s, 1H), 2.40 (s, 1H), 2.24 (s, 3H), 2.20 (d, J=7.2 Hz, 3H), 1.36-1.26 (m, 1H), 1.13 (d, J=9.0 Hz, 23H).

Example 243

Preparation of (2-cyclopropyl-6-(3,5-dimethylisoxazol-4-yl)-1H-benzo[d]imidazol-4-yl)(6-methylpyridin-2-yl)methanone (1020-243)

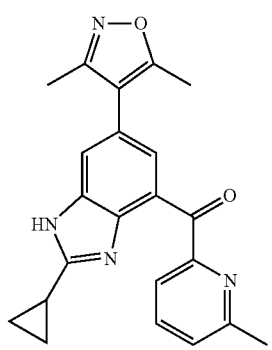 [SMILES: Cc1cccc(C(=O)c2cc(-c3c(C)noc3C)cc3[nH]c(C4CC4)nc23)n1]

(2-cyclopropyl-6-(3,5-dimethylisoxazol-4-yl)-1H-benzo[d]imidazol-4-yl)(6-methylpyridin-2-yl)methanone was synthesized in a similar fashion as that of Example 241, substituting tert-Butyl Magnesium Chloride for (6-methylpyridin-2-yl)magnesium bromide.

$C_{22}H_{20}N_4O_2$. MS. m/z 373.2 (M+1). $^1$H NMR (400 MHz, cd$_3$od) δ 7.92 (t, J=7.7 Hz, 3H), 7.83 (d, J=7.6 Hz, 1H), 7.72

(s, 1H), 7.51 (d, J=7.6 Hz, 1H), 2.61 (s, 3H), 2.44 (s, 3H), 2.35 (t, J=6.5 Hz, 1H), 2.28 (s, 2H), 1.25-1.18 (m, 4H).

Example 244

1-(2-cyclopropyl-5-(3,5-dimethylisoxazol-4-yl)-1H-benzo[d]imidazol-7-yl)-1-(pyridin-2-yl)prop-2-yn-1-ol (1020-244)

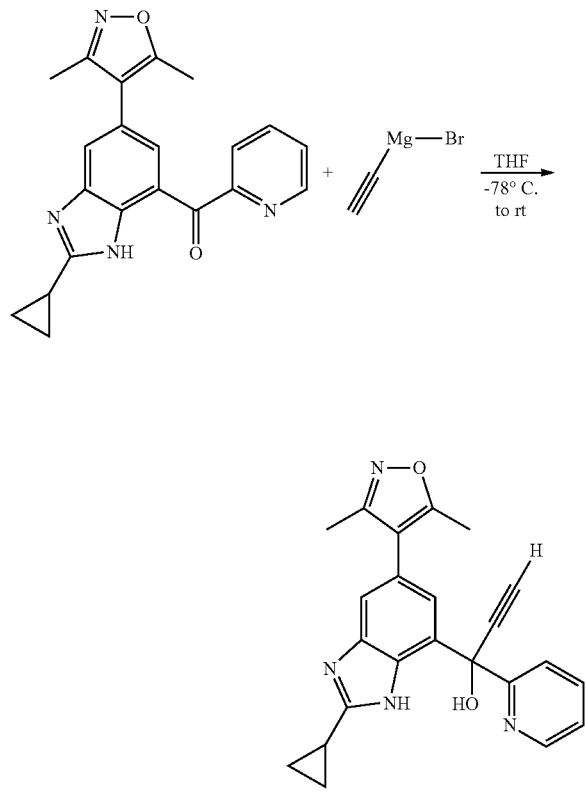

(2-cyclopropyl-6-(3,5-dimethylisoxazol-4-yl)-1H-benzo[d]imidazol-4-yl)(pyridin-2-yl)methanol (100 mg, 0.28 mmol) was dissolved in THF (10 ml) and cooled to −78° C. under argon. To this was added 0.5M ethynylmagnesium bromide (5.6 ml, 2.8 mmol) and reaction warmed to room temperature and allowed to react for 24 hours. Reaction was diluted in EtAc and aqueous ammonium chloride, extracted 3× with EtAc then washed with ammonium chloride, water, brine before drying the organics over sodium sulfate. Material was filtered and solvents removed under reduced pressure afford crude material which was purified by silica gel chromatography using Hex/EtAc as the eluent to afford 1-(2-cyclopropyl-5-(3,5-dimethylisoxazol-4-yl)-1H-benzo[d]imidazol-7-yl)-1-(pyridin-2-yl)prop-2-yn-1-ol.

.LCMS (m/z+1) 385.1. $^1$H NMR (400 MHz, DMSO-d6) δ 8.46 (dt, J=4.7, 1.3 Hz, 1H), 8.00 (d, J=8.0 Hz, 1H), 7.86 (td, J=7.7, 1.8 Hz, 1H), 7.73 (s, 1H), 7.55 (s, 1H), 7.48 (d, J=1.5 Hz, 1H), 7.29 (ddd, J=7.5, 4.8, 1.2 Hz, 1H), 3.89 (s, 1H), 2.61 (s, 1H), 2.39 (s, 3H), 2.21 (s, 3H), 1.33-1.22 (m, 4H).

Example 245

(2-cyclopropyl-6-(3,5-dimethylisoxazol-4-yl)-1H-benzo[d]imidazol-4-yl)(pyridin-2-yl)(1H-1,2,3-triazol-4-yl)methanol (1020-245)

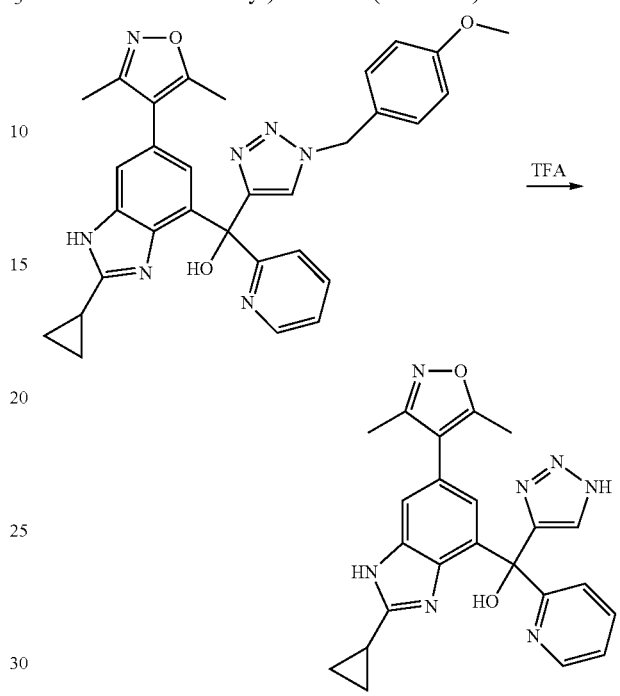

(2-cyclopropyl-6-(3,5-dimethylisoxazol-4-yl)-1H-benzo[d]imidazol-4-yl)(1-(4-methoxybenzyl)-1H-1,2,3-triazol-4-yl)(pyridin-2-yl)methanol (25 mg, 0.05 mmol) from ag-2238 was dissolved in 5 mL TFA and heated to 65° C. for 4 hours. Solvents were removed under reduced pressure and crude material was purified by reverse phase HPLC to afford (2-cyclopropyl-6-(3,5-dimethylisoxazol-4-yl)(pyridin-2-yl)(1H-1,2,3-triazol-4-yl)methanol as a TFA salt.

.LCMS (m/z+1) 428.1. $^1$H NMR (400 MHz, Methanol-d4) δ 8.58 (ddd, J=5.0, 1.8, 0.9 Hz, 1H), 7.93-7.81 (m, 2H), 7.76 (s, 1H), 7.48 (d, J=1.5 Hz, 1H), 7.38 (ddd, J=7.3, 4.8, 1.3 Hz, 1H), 7.28-7.22 (m, 1H), 2.65-2.56 (m, 1H), 2.34 (s, 3H), 2.17 (s, 3H), 1.56-1.47 (m, 2H), 1.41-1.35 (m, 2H).

Example 246

(6-bromo-3-fluoro-2-methylpyridin-4-yl)(2-cyclopropyl-6-(3,5-dimethylisoxazol-4-yl)-1H-benzo[d]imidazol-4-yl)(pyridin-2-yl)methanol (1020-246)

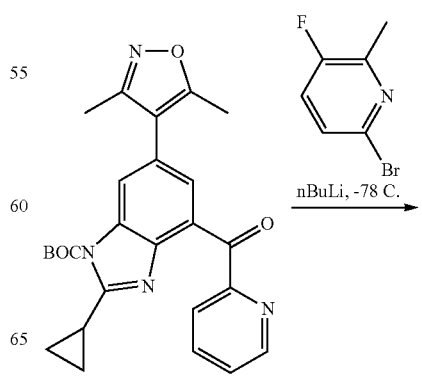

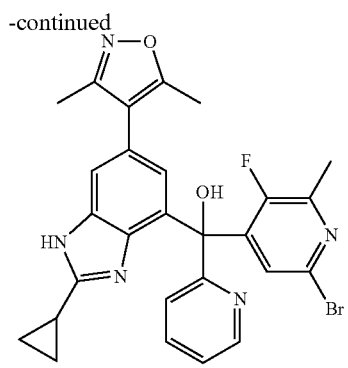

(6-Bromo-3-fluoro-2-methylpyridin-4-yl)(2-cyclopropyl-6,3,5-dimethylisoxazol-4-yl)-1H-benzo[d]imidazol-4-yl)(pyridin-2-yl)methanol was synthesized using 6-bromo-3-fluoro-2-methylpyridine and tert-butyl 2-cyclopropyl-6-(3,5-dimethylisoxazol-4-yl)-4-picolinoyl-1H-benzo[d]imidazole-1-carboxylate in a similar fashion as Example No. 5

$C_{27}H_{23}BrFN_5O_2$ MS=548.50 (M+H⁺). ¹H NMR (400 MHz, Chloroform-d) δ 8.61-8.52 (m, 1H), 7.72 (td, J=7.8, 1.7 Hz, 1H), 7.39 (d, J=16.1 Hz, 2H), 7.28 (ddd, J=7.3, 4.9, 1.0 Hz, 1H), 7.05 (d, J=4.8 Hz, 1H), 6.63 (s, 1H), 2.37 (d, J=3.2 Hz, 3H), 2.23 (s, 3H), 2.13-1.96 (m, 4H), 1.24-1.12 (m, 2H), 1.07 (dt, J=8.6, 3.4 Hz, 2H).

Example 247

(2-cyclopropyl-6-(3,5-dimethylisoxazol-4-yl)-1H-benzo[d]imidazol-4-yl)(3-fluoro-2-methylpyridin-4-yl)(pyridin-2-yl)methanol (1020-247)

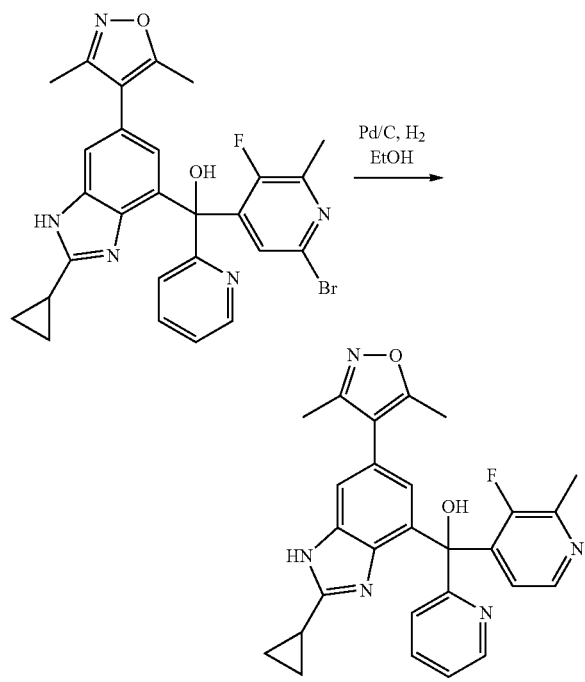

(2-Cyclopropyl-6-(3,5-dimethylisoxazol-4-yl)-1H-benzo[d]imidazol-4-yl)(3-fluoro-2-methylpyridin-4-yl)(pyridin-2-yl)methanol (40 mg, 0.07 mmol) was dissolved in EtOH (5 mL) and to the reaction was added Pd/C (20 mg). The reaction was then degassed and put under a atmosphere of Hydrogen via balloon. After 2 h the reaction was stopped and filtered through celite. EtOH was condensed down and purified via RPHPLC 0-40% (Acetonitrile/water w/0.1% TFA).

$C_{27}H_{23}BrFN_5O_2$ MS=470.25 (M+H⁺). ¹H NMR (400 MHz, Chloroform-d) δ 8.58-8.47 (m, 1H), 8.31 (d, J=5.5 Hz, 1H), 7.79 (td, J=7.8, 1.7 Hz, 1H), 7.59 (d, J=1.4 Hz, 1H), 7.43 (d, J=8.0 Hz, 1H), 7.38-7.33 (m, 1H), 7.30 (t, J=5.8 Hz, 1H), 6.79 (t, J=1.3 Hz, 1H), 2.57-2.43 (m, 4H), 2.23 (s, 3H), 2.06 (s, 3H), 1.29 (dq, J=7.9, 4.6 Hz, 2H).

Example 248

(2-cyclopropyl-6-(3,5-dimethylisoxazol-4-yl)-1H-benzo[d]imidazol-4-yl)(thiazol-2-yl)methanol (1020-248)

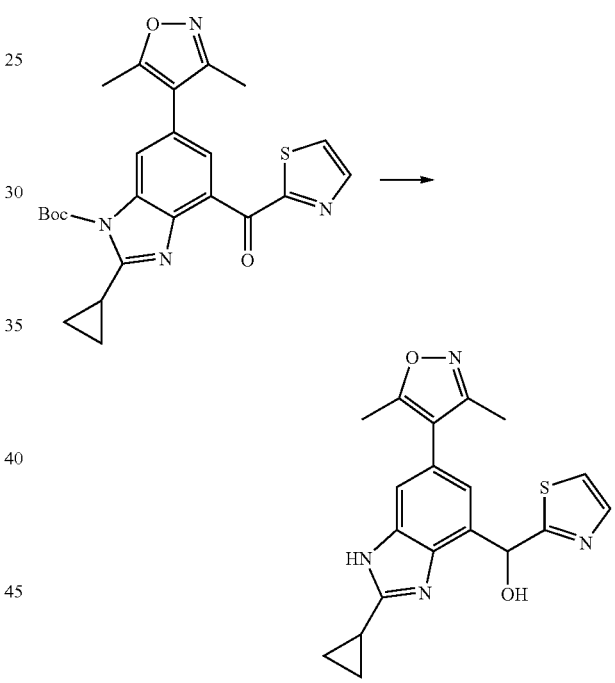

tert-Butyl 2-cyclopropyl-6-(3,5-dimethylisoxazol-4-yl)-4-(thiazole-2-carbonyl)-1H-benzo[d]imidazole-1-carboxylate in was dissolved in 2 ml MeOH, the reaction flask was then put in ice bath, to the solution was added NaBH₄ (10 mg, 0.26 mmol), slowly raised T to RT, stirred overnight. Then the reaction was quenched with NH4Cl, extracted with EtOAc to afford 170 mg crude product. Dissolved 60 mg crude product in EtOAc, added 0.5 ml TFA, heated overnight at 60° C., then evaporated solvent, the residue was purified with Prep HPLC to afford 25 mg (2-cyclopropyl-6-(3,5-dimethylisoxazol-4-yl)-1H-benzo[d]imidazol-4-yl)(thiazol-2-yl)methanol.

$C_{19}H_{18}N_4O_2S$. 367.0 (M+1). ¹H NMR (400 MHz, CD₃OD) δ 7.64 (d, J=3.2 Hz, 1H), 7.49 (d, J=3.2 Hz, 1H), 7.42 (d, J=0.9 Hz, 1H), 7.39 (s, 1H), 6.43 (s, 1H), 2.51-2.47 (m, 1H), 2.30 (s, 3H), 2.15 (s, 3H), 1.48-1.45 (m, 2H), 1.36-1.33 (m, 2H).

Example 249

4-(4-(cyclopropoxy(pyridin-2-yl)methyl)-2-cyclopropyl-1H-benzo[d]imidazol-6-yl)-3,5-dimethylisoxazole (1020-249)

Step 1

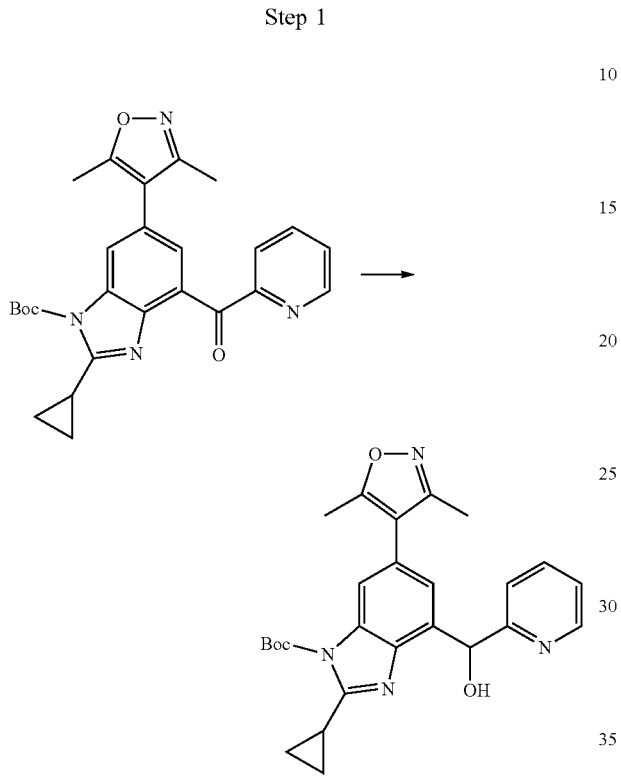

tert-Butyl 2-cyclopropyl-6-(3,5-dimethylisoxazol-4-yl)-4-picolinoyl-1H-benzo[d]imidazole-1-carboxylate (170 mg, 0.37 mmol) was dissolved in 5 ml MeOH, lowered T to 0 degree, added NaBH$_4$ (21 mg, 0.56 mmol) to the solution, slowly raised T to RT, stirred overnight. Then the reaction was quenched with NH$_4$Cl, extracted with EtOAc, evaporated organic solvent to afford 170 mg crude 4-(4-(cyclopropoxy(pyridin-2-yl)methyl)-2-cyclopropyl-1H-benzo[d]imidazol-6-yl)-3,5-dimethylisoxazole.

$C_{26}H_{28}N_4O_4$. 461.5 (M+1).

Step 2

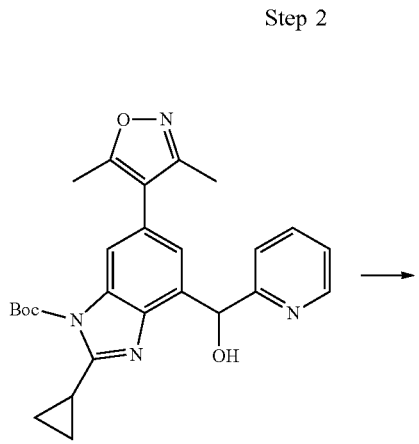

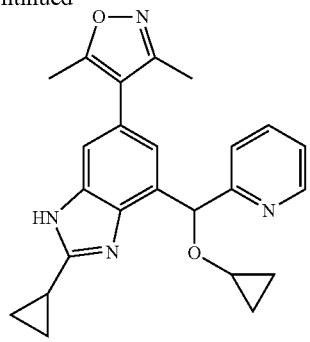

4-(4-(Cyclopropoxy(pyridin-2-yl)methyl)-2-cyclopropyl-1H-benzo[d]imidazol-6-yl)-3,5-dimethylisoxazole (32 mg, 0.09 mmol) was dissolved in 5 ml DCM, to the solution was added SOCl$_2$ (42 mg, 0.36 mmol), stirred at RT for 10 mins. Then to the reaction mixture was added cyclopropanol (41 mg, 0.7 mmol) at RT. Reaction completed instantly and was quenched with aq. NaHCO3, evaporated organic solvent, the residue was purified with Prep HPLC to afford 4-(4-(cyclopropoxy(pyridin-2-yl)methyl)-2-cyclopropyl-1H-benzo[d]imidazol-6-yl)-3,5-dimethylisoxazole.

$C_{24}H_{24}N_4O_2$. 401.1 (M+1). $^1$H NMR (400 MHz, CD$_3$OD) δ 8.82-8.81 (m, 1H), 7.90-7.88 (m, 1H), 7.86 (d, J=1.6 Hz, 1H), 7.66-7.64 (m, 1H), 7.50-7.47 (m, 2H), 6.66 (s, 1H), 3.98-3.87 (m, 1H), 2.40-2.38 (m, 1H), 2.32 (s, 3H), 2.15 (s, 3H), 2.16-2.10 (m, 2H), 1.35-1.24 (m, 8H).

Example 250

4-(4-((1H-imidazol-1-yl)(pyridin-2-yl)methyl)-2-cyclopropyl-1H-benzo[d]imidazol-6-yl)-3,5-dimethylisoxazole (1020-250)

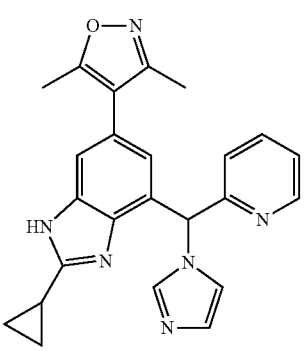 [SMILES: Cc1noc(C)c1-c1cc(C(c2ccccn2)n2ccnc2)c2nc(C3CC3)[nH]c2c1]

4-(4-((1H-imidazol-1-yl)(pyridin-2-yl)methyl)-2-cyclopropyl-1H-benzo[d]imidazol-6-yl)-3,5-dimethylisoxazole was synthesized in a similar fashion to Example 249.

$C_{24}H_{22}N_6O$. 411.0 (M+1). $^1$H NMR (400 MHz, CD$_3$OD) δ 9.01-9.00 (m, 1H), 8.66-8.65 (m, 1H), 7.94-7.89 (m, 1H), 7.71-7.70 (m, 1H), 7.58 (d, J=2.0 Hz, 2H), 7.54 (d, J=0.8 Hz, 2H), 7.52-7.46 (m, 1H), 7.01 (s, 1H), 2.35-2.32 (m, 1H), 2.31 (s, 3H), 2.14 (s, 3H), 1.34-1.24 (m, 4H).

Example 251 cyclopentyl(2-cyclopropyl-6-(3,5-dimethylisoxazol-4-yl)-1H-benzo[d]imidazol-4-yl)(pyrimidin-2-yl)methanol (1020-251)

Step 1: tert-butyl 2-cyclopropyl-6-(3,5-dimethylisoxazol-4-yl-4)pyrimidine-2-carbonyl)-1H-benzo[d]imidazole-1-carboxylate

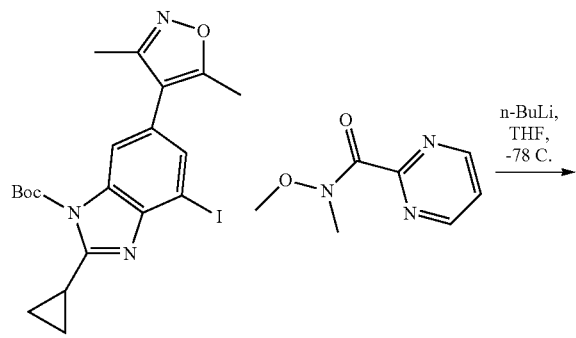

Step 2: cyclopentyl(2-cyclopropyl-6-(3,5-dimethylisoxazol-4-yl)-1H-benzo[d]imidazol-4-yl)(pyrimidin-2-yl)methanol

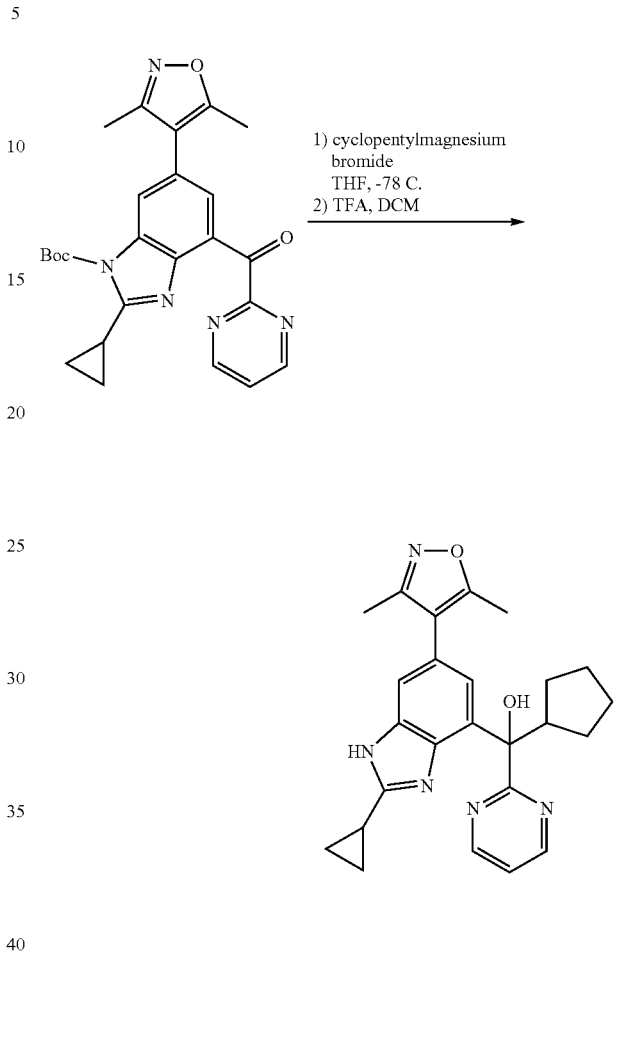

To a dry, argon purged round-bottom flask was added tert-butyl 2-cyclopropyl-6-(3,5-dimethylisoxazol-4-yl)-4-iodo-1H-benzo[d]imidazole-1-carboxylate (2.00 g 0.004 mol) in THF (75 mL), flask was placed in a −78 C bath. To the reaction was added n-Butyllithium (3.39 mL, 0.01 μmol) over a period of 2 minutes. N-methoxy-N-methylpyrimidine-2-carboxamide (1.74 g 0.01 mol) in 25 mL THF was added quickly and the reaction was allowed to stir for 10 minutes. To the reaction was added Sat. Ammonium Chloride (50 mL) followed by EtOAc (250 mL). Organic layer was washed with Sat. Brine (50 mL) then dried over Magnesium Sulfate and condensed to a dark brown oil. Material was then purified via normal phase chromatography 0-50% EtOAc/Hexanes to give tert-butyl 2-cyclopropyl-6-(3,5-dimethylisoxazol-4-yl)-4-(pyrimidine-2-carbonyl)-1H-benzo[d]imidazole-1-carboxylate which was used for the next examples.

tert-Butyl 2-cyclopropyl-6-(3,5-dimethylisoxazol-4-yl)-4-(pyrimidine-2-carbonyl)-1H-benzo[d]imidazole-1-carboxylate (100 mg, 0.21 mmol) was dissolved in THF (5 mL), reaction was cooled to 0 C. Cyclopentylmagnesium bromide (2.0M) (0.43 mL, 0.87 mmol) was added. The reaction was stirred for 30 minutes, to the reaction was added Sat. Ammonium Chloride (15 mL) followed by EtOAc (20 mL). Organic layer was washed with Sat. Brine (15 mL) then dried over Magnesium Sulfate and condensed to an yellow oil. The material was then run through a small silica plug and condensed down. This oil was then dissolved in DCM (5 mL) and TFA (1 mL) was added. The reaction was stirred for 30 mins then condensed down to a yellow oil. The residue was purified by RPHPLC (5-50% Acetonitrile/Water), affording cyclopentyl(2-cyclopropyl-6-(3,5-dimethylisoxazol-4-yl)-1H-benzo[d]imidazol-4-yl)(pyrimidin-2-yl)methanol.

$C_{25}H_{27}N_5O_2$ MS=430.23 (M+H+). $^1$H NMR (400 MHz, Chloroform-d) δ 10.83 (s, 1H), 8.77 (d, J=4.9 Hz, 2H), 7.65 (d, J=1.5 Hz, 1H), 7.42 (d, J=1.5 Hz, 1H), 5.98 (s, 1H), 3.31 (t, J=8.4 Hz, 1H), 2.40 (s, 3H), 2.27 (s, 3H), 2.11 (d, J=3.8 Hz, 2H), 1.70-1.43 (m, 6H), 1.37 (s, 1H), 1.34-1.13 (m, 7H).

Example 252

(2-cyclopropyl-6-(3,5-dimethylisoxazol-4-yl)-1H-benzo[d]imidazol-4-yl)(5-fluoropyridin-2-yl)(pyrimidin-2-yl)methanol (1020-252)

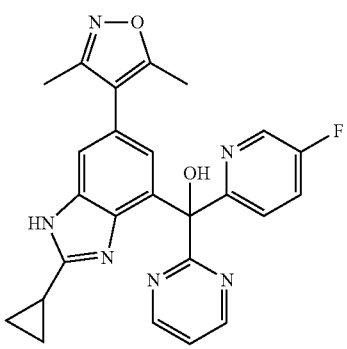 [SMILES: Cc1noc(C)c1-c1cc(C(O)(c2ccc(F)cn2)c2ncccn2)c2nc(C3CC3)[nH]c2c1]

(2-Cyclopropyl-6-(3,5-dimethylisoxazol-4-yl)-1H-benzo[d]imidazol-4-yl)(5-fluoropyridin-2-yl)(pyrimidin-2-yl)methanol was synthesized using 2-magnesiumbromide-5-fluoropyridine and tert-butyl 2-cyclopropyl-6-(3,5-dimethylisoxazol-4-yl)-4-(pyrimidine-2-carbonyl)-1H-benzo[d]imidazole-1-carboxylate in a similar fashion as Example 248 step 2.

$C_{25}H_{21}FN_6O_2$ MS=457.27 (M+H+). $^1$H NMR (400 MHz, Chloroform-d) δ 8.79 (d, J=4.8 Hz, 2H), 8.35 (d, J=2.7 Hz, 1H), 7.65-7.52 (m, 2H), 7.39 (td, J=8.4, 2.8 Hz, 1H), 7.32 (t, J=4.9 Hz, 1H), 2.39 (s, 0H), 2.35 (s, 3H), 2.27 (d, J=10.5 Hz, 0H), 2.18 (s, 2H), 1.36-1.28 (m, 2H), 1.28-1.16 (m, 2H).

Example 253

(5-chloropyridin-2-yl)(2-cyclopropyl-6-(3,5-dimethylisoxazol-4-yl)-1H-benzo[d]imidazol-4-yl)(pyrimidin-2-yl)methanol (1020-253)

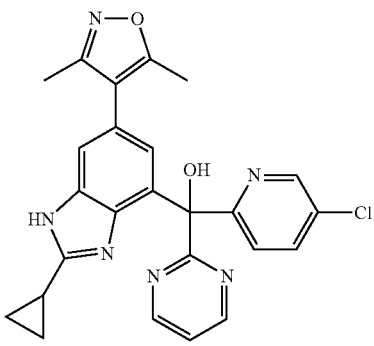 [SMILES: Cc1noc(C)c1-c1cc(C(O)(c2ccc(Cl)cn2)c2ncccn2)c2nc(C3CC3)[nH]c2c1]

(5-Chloropyridin-2-yl)(2-cyclopropyl-6-(3,5-dimethylisoxazol-4-yl)-1H-benzo[d]imidazol-4-yl)(pyrimidin-2-yl)methanol was synthesized using 2-magnesiumbromide-5-chloropyridine tert-butyl 2-cyclopropyl-6-(3,5-dimethylisoxazol-4-yl)-4-(pyrimidine-2-carbonyl)-1H-benzo[d]imidazole-1-carboxylate in a similar fashion as Example 248, step 2.

$C_{25}H_{21}ClN_6O_2$ MS=473.36 (M+H+). $^1$H NMR (400 MHz, Chloroform-d) δ 8.79 (d, J=4.9 Hz, 2H), 8.46 (d, J=2.3 Hz, 1H), 7.66 (dd, J=8.6, 2.4 Hz, 1H), 7.63-7.49 (m, 3H), 7.33 (d, J=4.9 Hz, 1H), 2.36 (s, 4H), 2.21 (s, 3H), 1.49-1.18 (m, 7H), 0.92-0.83 (m, 1H).

Example 254

(2-cyclopropyl-6-(3,5-dimethylisoxazol-4-yl)-1H-benzo[d]imidazol-4-yl)(phenyl)(pyrimidin-2-yl)methanol (1020-254)

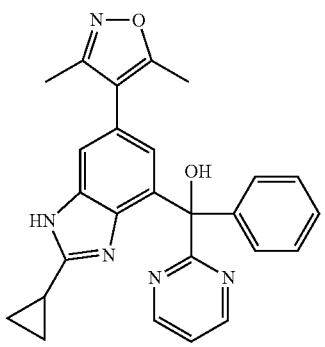 [SMILES: Cc1noc(C)c1-c1cc(C(O)(c2ccccc2)c2ncccn2)c2nc(C3CC3)[nH]c2c1]

(2-Cyclopropyl-6-(3,5-dimethylisoxazol-4-yl)-1H-benzo[d]imidazol-4-yl)(phenyl)(pyrimidin-2-yl)methanol was synthesized using phenylmagnesium bromide and tert-butyl 2-cyclopropyl-6-(3,5-dimethylisoxazol-4-yl)-4-(pyrimidine-2-carbonyl)-1H-benzo[d]imidazole-1-carboxylate in a similar fashion as Example 248, step 2.

$C_{26}H_{23}N_5O_2$ MS=438.28 (M+H$^+$). $^1$H NMR (400 MHz, Chloroform-d) δ 8.82 (d, J=4.7 Hz, 2H), 7.57 (d, J=1.6 Hz, 1H), 7.51 (d, J=1.4 Hz, 1H), 7.37 (t, J=4.6 Hz, 1H), 7.30 (d, J=3.0 Hz, 3H), 7.22 (dd, J=6.4, 2.9 Hz, 2H), 3.02 (s, 1H), 2.93 (s, 1H), 2.41 (d, J=11.9 Hz, 1H), 2.33 (s, 3H), 1.42 (d, J=5.1 Hz, 2H), 1.38-1.29 (m, 2H), 1.27 (d, J=8.7 Hz, 1H).

Example 255

(6-Bromo-3-fluoro-2-methylpyridin-4-yl)(2-cyclopropyl-6-(3,5-dimethylisoxazol-4-yl)-1H-benzo[d]imidazol-4-yl)(pyrimidin-2-yl)methanol (1020-255)

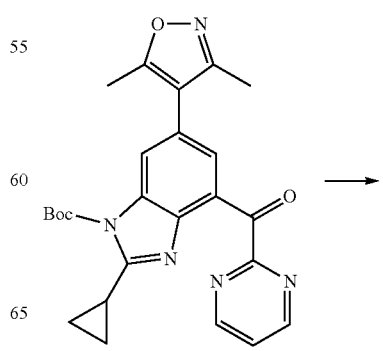

-continued

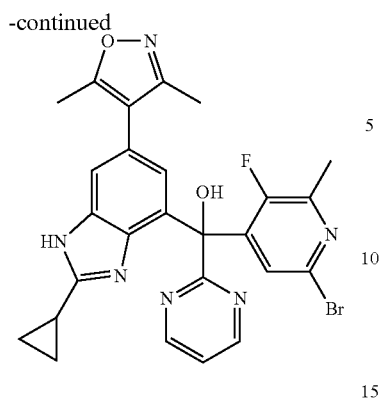

-continued

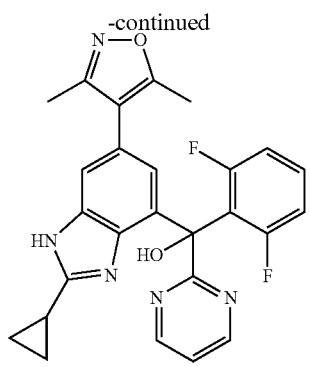

To a solution of 2-bromo-5-fluoro-6-methylpyridine (165 mg, 0.87 mmol) in THF (5 mL) was added BuLi (56 mg, 0.87 mmol, 1.6 M in hexanes) and the solution was stirred at −78° C. for 1 h. To the solution was added a solution of tert-butyl 2-cyclopropyl-6-(3,5-dimethylisoxazol-4-yl)-4-(pyrimidine-2-carbonyl)-1H-benzo[d]imidazole-1-carboxylate (100 mg, 0.22 mmol) in THF (2 mL) and the solution was stirred at −78° C. for 1 h. Aq NH$_4$Cl was added and the solution was extracted with EtOAc (200 mL). The organic solution was washed with brine and dried over Na$_2$OS$_4$. Solvent was removed and the residue was purified by silica gel column chromatography (0-10% MeOH in CH$_2$Cl$_2$) to give N-Boc protected intermediate which was dissolved in THF (2 mL), TFA (2 mL) and water (0.1 mL). The solution was heated at 50° C. for 3 h and concentrated to dryness under reduced pressure. The residue was purified by HPLC to give (6-bromo-3-fluoro-2-methylpyridin-4-yl)(2-cyclopropyl-6-(3,5-dimethylisoxazol-4-yl)-1H-benzo[d]imidazol-4-yl)(pyrimidin-2-yl)methanol.

$C_{26}H_{22}BrFN_{62}$. MS. m/z 549.5 (M+1). $^1$H NMR (Methanol-d$_4$) δ 8.86 (d, J=4.9 Hz, 2H), 7.64-7.55 (m, 2H), 7.50 (t, J=4.9 Hz, 1H), 7.13 (t, J=1.7 Hz, 1H), 2.61 (tt, J=8.4, 5.0 Hz, 1H), 2.41-2.29 (m, 6H), 2.16 (s, 3H), 1.60-1.51 (m, 2H), 1.51-1.38 (m, 2H).

Example 256 and 257

(2-Cyclopropyl-6-(3,5-dimethylisoxazol-4-yl)-1H-benzo[d]imidazol-4-yl)(2,6-difluorophenyl)(pyrimidin-2-yl)methanol (1020-256) and (2-Cyclopropyl-6-(3,5-dimethylisoxazol-4-yl)-1H-benzo[d]imidazol-4-yl)(2,4-difluorophenyl)(pyrimidin-2-yl)methanol (1020-257)

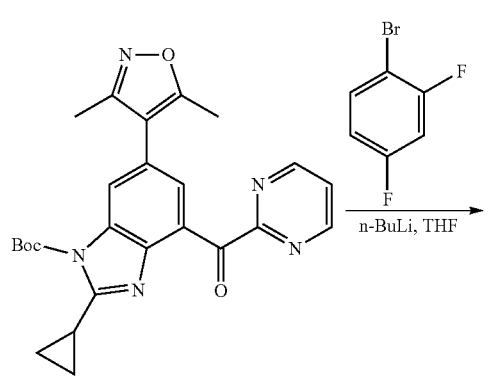

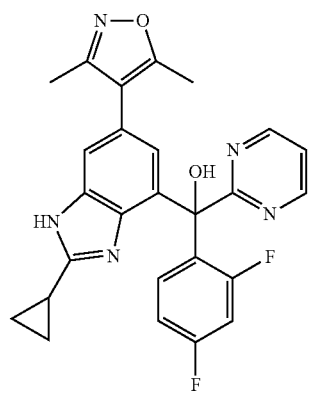

1-Bromo-2,4-difluorobenzene (520 mg, 2.70 mmol) was dissolved in THF (5 mL) and cooled to −78° C. n-BuLi (1.68 mL, 2.70 mmol, 1.6 M) was added dropwise and the reaction was allowed to stir for 30 minutes at −78° C. To the reaction was added Compound A. The reaction was allowed to stir for 30 minutes to the reaction was added Sat. Ammonium Chloride (15 mL) followed by EtOAc (20 mL). Organic layer was washed with Sat. Brine (15 mL) then dried over Magnesium Sulfate and condensed to an oil. The material was then run through a small silica plug and condensed down. This oil was then dissolved in DCM (5 mL) and TFA (1 mL) was added. The reaction was stirred for 30 minutes then condensed down to an oil. The residue was purified by normal phase chromatography (0-10%) MeOH/DCM.

(2-Cyclopropyl-6-(3,5-dimethylisoxazol-4-yl)-1H-benzo[d]imidazol-4-yl)(2,6-difluorophenyl)(pyrimidin-2-yl)methanol: $C_{26}H_{21}F_2N_5O_2$ MS=474.22 (M+H$^+$). $^1$H NMR (400 MHz, Methanol-d4) δ 8.83 (dd, J=10.2, 4.9 Hz, 2H), 7.53 (dd, J=17.4, 1.5 Hz, 1H), 7.47-7.39 (m, 3H), 6.98-6.89 (m, 2H), 2.60 (tt, J=8.4, 5.0 Hz, 1H), 2.34 (d, J=5.8 Hz, 3H), 2.16 (d, J=5.7 Hz, 3H), 1.59-1.48 (m, 2H), 1.48-1.34 (m, 2H)

(2-Cyclopropyl-6-(3,5-dimethylisoxazol-4-yl)-1H-benzo[d]imidazol-4-yl)(2,4-difluorophenyl)(pyrimidin-2-yl)methanol: $C_{26}H_{21}F_2N_5O_2$ MS=474.28 (M+H. $^1$H NMR (400 MHz, Methanol-d4) δ 8.85 (d, J=4.9 Hz, 2H), 7.54 (d, J=1.5 Hz, 1H), 7.47 (t, J=4.9 Hz, 1H), 7.29-7.23 (m, 1H), 7.22 (q, J=1.5 Hz, 1H), 6.99-6.91 (m, 2H), 2.99 (s, 0H), 2.86 (d, J=0.8 Hz, 0H), 2.59 (tt, J=8.4, 5.0 Hz, 1H), 2.34 (s, 3H), 2.15 (s, 3H), 1.57-1.49 (m, 2H), 1.43-1.37 (m, 2H).

Example 258

1-(2-cyclopropyl-6-(3,5-dimethylisoxazol-4-yl)-1H-benzo[d]imidazol-4-yl)-1-(pyridin-3-yl)ethanol (1020-258)

Step 1

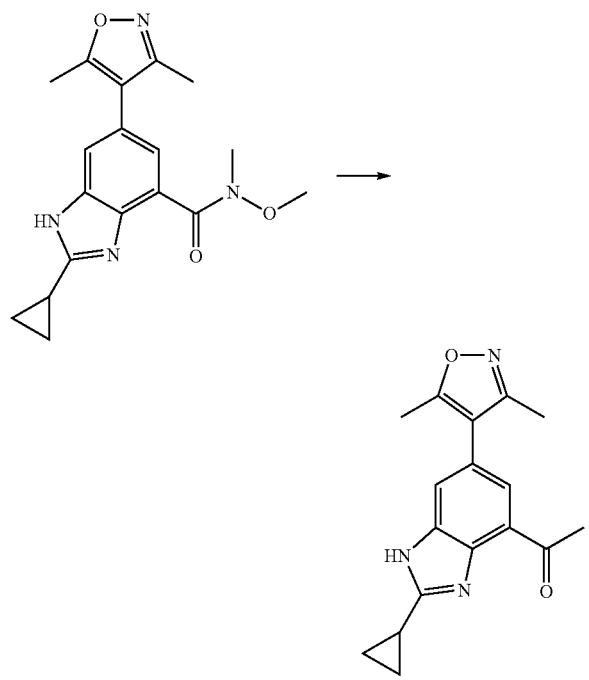

2-Cyclopropyl-6-(3,5-dimethylisoxazol-4-yl)-N-methoxy-N-methyl-1H-benzo[d]imidazole-4-carboxamide (116 mg, 0.34 mmol) was dissolved in THF (2 ml), the reaction flask was put in ice bath. To the solution was added methylmagnesium bromide (0.45 mL, 3M in THF) and stirred at 0° C. for 4 h. The reaction mixture was diluted with EtOAc, washed with brine, back-extracted with EtOAc, evaporated organic solvent to afford 116 mg of 1-(2-cyclopropyl-6-(3,5-dimethylisoxazol-4-yl)-1H-benzo[d]imidazol-4-yl)ethanone.

$C_{17}H_{17}N_3O_2$. 296.2 (M+1).

Step 2

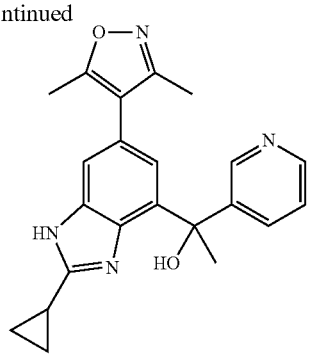

1-(2-cyclopropyl-6-(3,5-dimethylisoxazol-4-yl)-1H-benzo[d]imidazol-4-yl)ethanone (30 mg, 0.1 mmol) was dissolved in THF (1 ml), the reaction flask was put in ice bath. To the solution was added 2-pyridylmagnesium bromide (2.4 mL, 0.25M in THF) and stirred RT overnight. The reaction mixture was diluted with EtOAc, washed with brine, back-extracted with EtOAc, evaporated organic solvent and then purified with Prep HPLC to afford 1-(2-cyclopropyl-6-(3,5-dimethylisoxazol-4-yl)-1H-benzo[d]imidazol-4-yl)-1-(pyridin-3-yl)ethanol.

$C_{22}H_{22}N_4O_2$. 373.3 (M−1). $^1$H NMR (400 MHz, CD$_3$OD) 8.91 (d, J=1.6 Hz, 1H), 8.54 (dd, J=1.2, 5.2 Hz, 1H), 8.34 (tt, J=1.6, 8.0 Hz, 1H), 7.67 (dd, J=1.2, 8.0 Hz, 1H), 7.41 (d, J=1.2 Hz, 1H), 7.31 (d, J=1.6 Hz, 1H), 2.54-2.50 (m, 1H), 2.31 (s, 3H), 2.14 (s, 3H), 2.07 (s, 3H), 1.45-1.39 (m, 2H), 1.31-1.25 (m, 2H).

Example 259

4-(2-cyclopropyl-4-(1-(pyridin-3-yl)vinyl)-1H-benzo[d]imidazol-6-yl)-3,5-dimethylisoxazole (1020-259)

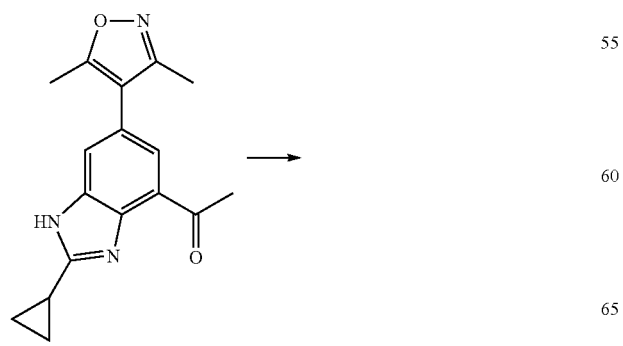

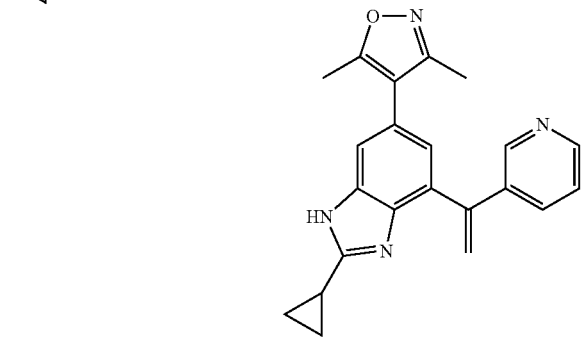

1-(2-cyclopropyl-6-(3,5-dimethylisoxazol-4-yl)-1H-benzo[d]imidazol-4-yl)-1-(pyridin-3-yl)ethanol (10 mg, 0.27 mmol) was dissolved in 2 ml of TFA, heated to 160° C. in microwave reactor for 6 h. Solvent was evaporated and the residue was purified with Prep HPLC for to afford 4-(2-cyclopropyl-4-(1-(pyridin-3-yl)vinyl)-1H-benzo[d]imidazol-6-yl)-3,5-dimethylisoxazole.

$C_{22}H_{20}N_4O$. 357.3 (M+1). $^1$H NMR (400 MHz, CD$_3$OD) 8.75 (s, 1H), 8.69 (d, J=4.8 Hz, 1H), 8.25-8.22 (m, 1H), 7.78-7.63 (m, 1H), 7.41 (d, J=1.2 Hz, 1H), 7.63 (d, J=1.2 Hz, 1H), 7.30 (d, J=1.6 Hz, 1H), 6.36 (s, 1H), 5.94 (s, 1H), 2.47-2.43 (m, 1H), 2.41 (s, 3H), 2.24 (s, 3H), 1.54-1.49 (m, 2H), 1.41-1.39 (m, 2H).

Example 260

4-(2-cyclopropyl-4-(1-(pyridin-3-yl)ethyl)-1H-benzo[d]imidazol-6-yl)-3,5-dimethylisoxazole (1020-260)

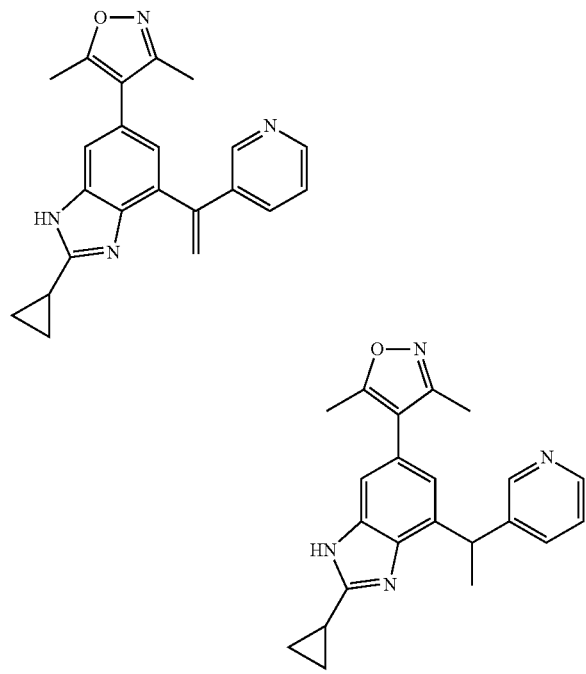

4-(2-cyclopropyl-4-(1-(pyridin-3-yl)vinyl)-1H-benzo[d]imidazol-6-yl)-3,5-dimethylisoxazole (5 mg, 0.014 mmol) was dissolved in EtOAc (2 ml). The reaction flask was degassed and to the solution as added palladium (5 mg, 10% on activated carbon). The flask as degassed again and a hydrogen balloon was put on the top of reaction flask. The reaction mixture was stirred at RT for 1 h. Then the reaction mixture was filtered, solvent was evaporated, and the residue was purified with Prep HPLC to afford 5 mg of 4-(2-cyclopropyl-4-(1-(pyridin-3-yl)ethyl)-1H-benzo[d]imidazol-6-yl)-3,5-dimethylisoxazole.

$C_{22}H_{22}N_4O$. 359.3 (M+1). $^1$H NMR (400 MHz, CD$_3$OD) 8.63 (s, 1H), 8.52 (d, J=5.2 Hz, 1H), 8.17 (d, J=8.0 Hz, 1H), 7.67 (d, J=5.2, 8.0 Hz, 1H), 7.39 (d, J=1.6 Hz, 1H), 7.18 (d, J=1.2 Hz, 1H), 4.85 (q, J=6.8 Hz, 1H), 2.39-2.28 (m, 1H), 2.28 (s, 3H), 2.11 (s, 3H), 1.78 (d, J=6.8 Hz), 1.43-1.40 (m, 2H), 1.31-1.28 (m, 2H).

Examples 261 and 262

3-((2-cyclopropyl-6-(3,5-dimethylisoxazol-4-yl)-1H-benzo[d]imidazol-4-yl)(hydroxy)(pyridin-2-yl)methyl)bicyclo[2.2.1]heptan-2-one (1020-261) and (1020-262)

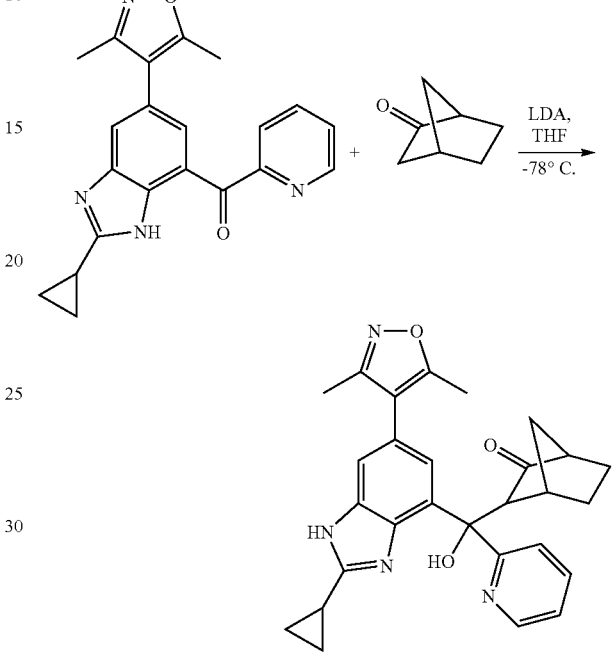

Norcamphor (494.84 mg, 4.49 mmol) was taken up in THF (40 ml) in a dry argon purged flask. Solution was cooled to −78° C. under argon. To this was added 2M lithium diisopropylamide (2.34 ml) slowly and reaction allowed to mature for 30 minutes. At this point a solution of (2-cyclopropyl-5-(3,5-dimethylisoxazol-4-yl)-1H-benzo[d]imidazol-7-yl)(pyridin-2-yl)methanone (230 mg, 0.64 mmol) in 20 mL THF was added rapidly and reaction allowed to stir at −78° C. for 10 minutes. Reaction was removed from ice bath and allowed to warm for 30 minutes. Reaction was quenched into stirring EtAc, aqueous ammonium chloride and was extracted 3× with EtAc, washed with water then brine and dried over sodium sulfate before removing solvents under reduced pressure. A portion of this material was purified by reverse phase HPLC to afford 2 diastereomers of 3-((2-cyclopropyl-6-(3,5-dimethylisoxazol-4-yl)-1H-benzo[d]imidazol-4-yl)(hydroxy)(pyridin-2-yl)methyl)bicyclo[2.2.1]heptan-2-one.

LCMS (m/z+1) 469.2

1020-261—Diastereomer "A"

$^1$H NMR (400 MHz, DMSO-d6) δ 9.21 (s, 1H), 8.71 (d, J=30.1 Hz, 2H), 8.34 (s, 1H), 8.11 (s, 1H), 7.54 (d, J=42.0 Hz, 2H), 6.77 (s, 1H), 2.89 (s, 2H), 2.39-1.81 (m, 6H), 1.53 (dd, J=31.5, 18.4 Hz, 2H), 1.36-1.06 (m, 5H), 0.89 (d, J=50.4 Hz, 3H).

1020-262—Diastereomer "B"

$^1$H NMR (400 MHz, DMSO-d6) δ 11.44 (s, 1H), 9.33 (d, J=6.1 Hz, 1H), 8.50 (t, J=7.8 Hz, 1H), 8.15 (t, J=6.9 Hz, 1H), 7.75 (d, J=8.1 Hz, 1H), 7.64 (s, 1H), 7.43 (d, J=1.5 Hz, 1H), 7.21 (s, 1H), 3.00 (d, J=3.0 Hz, 1H), 2.81 (s, 1H), 2.75 (s, 1H), 2.46 (s, 3H), 2.27 (s, 3H), 2.05 (td, J=8.0, 3.2 Hz, 2H), 1.68 (dp, J=7.3, 4.1, 3.6 Hz, 2H), 1.43-1.30 (m, 2H), 1.11 (qd, J=6.2, 3.2 Hz, 3H), 0.95 (dd, J=9.6, 4.5 Hz, 1H), 0.75 (d, J=9.0 Hz, 1H).

Example 263

3-((2-cyclopropyl-6-(3,5-dimethylisoxazol-4-yl)-1H-benzo[d]imidazol-4-yl)(hydroxy)(pyridin-2-yl)methyl)bicyclo[2.2.1]heptan-2-ol (1020-263)

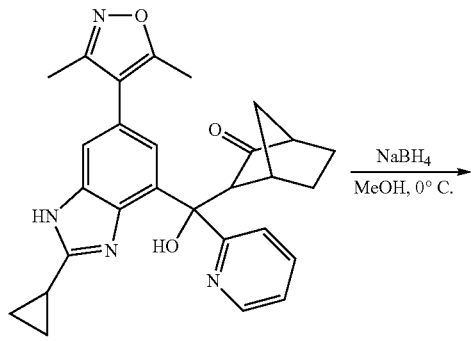

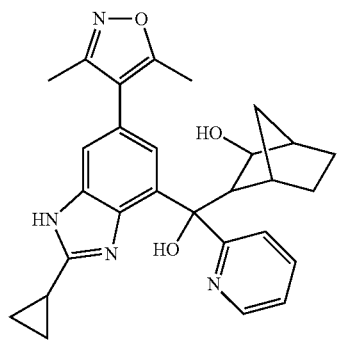

Crude 3-((2-cyclopropyl-6-(3,5-dimethylisoxazol-4-yl)-1H-benzo[d]imidazol-4-yl)(hydroxy)(pyridin-2-yl)methyl)bicyclo[2.2.1]heptan-2-one (300 mg, 0.64 mmol) 25 mL methanol and cooled to 0° C. under nitrogen. To this was added sodium borohydride (145 mg, 3.84 mmol) and reaction allowed to stir at 0° C. After 2 hours reaction was quenched into stirring EtAc, aqueous ammonium chloride and was extracted 3× with EtAC, washed with water then brine and dried over sodium sulfate before removing solvents under reduced pressure. Material was purified by silica gel chromatography using Hex/EtAc as the eluent. Material was then further purified by reverse phase HPLC to afford 3-((2-cyclopropyl-6-(3,5-dimethylisoxazol-4-yl)-1H-benzo[d]imidazol-4-yl)(hydroxy)(pyridin-2-yl)methyl)bicyclo[2.2.1]heptan-2-ol as a racemic mixture as the TFA salt.

LCMS (m/z+1) 471.2. ¹H NMR (400 MHz, Methanol-d4) δ 8.62 (ddd, J=5.1, 1.7, 0.9 Hz, 1H), 7.96-7.88 (m, 1H), 7.85 (dt, J=8.1, 1.1 Hz, 1H), 7.51 (d, J=1.4 Hz, 1H), 7.45-7.32 (m, 2H), 4.23-4.13 (m, 1H), 2.68 (tt, J=8.5, 5.0 Hz, 1H), 2.52 (dd, J=5.4, 1.8 Hz, 1H), 2.35 (s, 3H), 2.17 (s, 4H), 1.96-1.81 (m, 3H), 1.55-1.28 (m, 10H).

Example 264 and 265

2-((2-cyclopropyl-6-(3,5-dimethylisoxazol-4-yl)-1H-benzo[d]imidazol-4-yl)(hydroxy)(pyridin-2-yl)methyl)cyclopentanol (1020-264) and (1020-265)

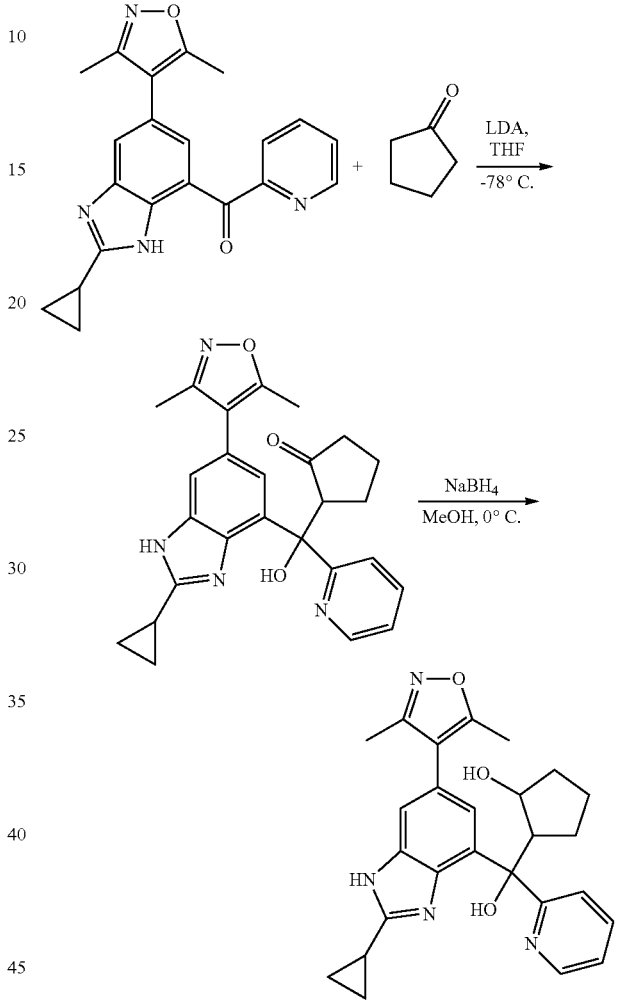

Step 1: Preparation of 2-((2-cyclopropyl-6-(3,5-dimethylisoxazol-4-yl)-1H-benzo[d]imidazol-4-yl)(hydroxy)(pyridin-2-yl)methyl)cyclopentanone Cyclopentanone (0.13 ml, 1.46 mmol) was taken up in THF (5 ml) in a dry nitrogen purged flask. Solution was cooled to −78° C. under argon. To this was added 2M lithium diisopropylamide (0.73 ml) slowly and reaction allowed to mature for 30 minutes. At this point a solution of (2-cyclopropyl-6-(3,5-dimethylisoxazol-4-yl)-1H-benzo[d]imidazol-4-yl)(pyridin-2-yl)methanol (75 mg, 0.21 mmol) in 1 mL THF was added slowly and reaction allowed to stir at −78° C. for 10 minutes. Reaction was quenched into stirring EtAc, aqueous ammonium chloride, was extracted 3× with EtAc, washed with water, brine, dried over sodium sulfate. Solvents were then removed under reduced pressure (92 mg, 100%).

LCMS (m/z+1) 443.1

Step 2: Preparation of 2-((2-cyclopropyl-6-(3,5-dimethylisoxazol-4-yl)-1H-benzo[d]imidazol-4-yl)(hydroxy)(pyridin-2-yl)methylcyclopentanol Crude 2-((2-cyclopropyl-6-(3,5-dimethylisoxazol-4-yl)-1H-benzo[d]imidazol-4-yl)(hydroxy)(pyridin-2-yl)methyl)cyclopentanone (92 mg, 0.21 mmol) was taken up in 5 ml methanol, cooled to 0° C. under nitrogen and to it added sodium borohydride (23.75 mg, 0.63 mmol). Reaction was allowed to stir for 2 hours at 0° C. Solvents were removed under reduced pressure and reaction was diluted in EtAc and aq. ammonium chloride. Reaction was then extracted 3× with EtAc, washed with water, brine, dried over sodium sulfate. Solvents were then removed under reduced pressure and the residue was purified by reverse phase HPLC to afford 2-((2-cyclopropyl-6-(3,5-dimethylisoxazol-4-yl)-1H-benzo[d]imidazol-4-yl)(hydroxy)(pyridin-2-yl)methyl)cyclopentanol as two diastereomers.

LCMS (m/z+1) 445.2

1020-264—Diastereomer "A"

$^1$H NMR (400 MHz, DMSO-d6) δ 8.53-8.39 (m, 1H), 7.92 (dt, J=8.1, 1.1 Hz, 1H), 7.79 (td, J=7.7, 1.8 Hz, 1H), 7.71 (s, 1H), 7.41 (d, J=1.5 Hz, 1H), 7.24-7.12 (m, 1H), 6.98 (s, 1H), 3.93 (dt, J=6.1, 4.3 Hz, 1), 2.68 (s, 1H), 2.41 (s, 3H), 2.23 (s, 3H), 1.83-1.07 (m, 11H).

1020-265—Diastereomer "B"

$^1$H NMR (400 MHz, DMSO-d6) δ 8.65-8.53 (m, 1H), 8.00 (dt, J=8.1, 1.1 Hz, 1H), 7.83 (td, J=7.8, 1.8 Hz, 1H), 7.53 (d, J=1.5 Hz, 1H), 7.40 (d, J=1.4 Hz, 1H), 7.27 (ddd, J=7.5, 4.8, 1.2 Hz, 1H), 6.97 (s, 1H), 3.42 (ddd, J=12.0, 8.5, 3.9 Hz, 1H), 2.73 (ddd, J=13.1, 8.3, 5.0 Hz, 1H), 2.34 (s, 3H), 2.15 (s, 3H), 2.01-1.87 (m, 1H), 1.83-1.67 (m, 2H), 1.63-1.50 (m, 2H), 1.46-1.27 (m, 6H).

Example 266

N-(4-(dicyclopentyl(hydroxy)methyl)-6-(3,5-dimethylisoxazol-4-yl)-1H-benzo[d]imidazol-2-yl)methanesulfonamide (1020-266)

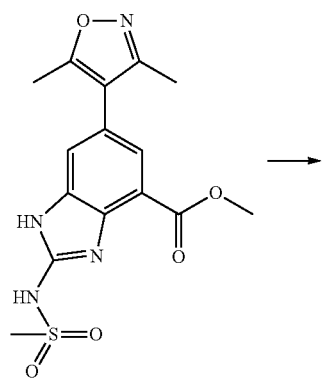

-continued

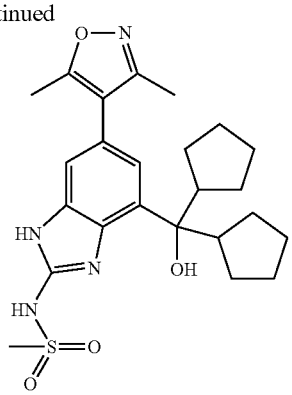

To a mixture containing methyl 6-(3,5-dimethylisoxazol-4-yl)-2-(methylsulfonamido)-1H-benzo[d]imidazole-4-carboxylate (40 mg, 0.11 mmol, 1 equiv.) and THF (3 mL) is added cylopentylmagnesium chloride (0.38 mL, 0.77 mmol, 7 equiv.) at 0° C. for 30 min. After completion, the reaction was quenched and extracted with EtOAc and washed with water, saturated NH$_4$Cl. After drying with MgSO$_4$, it was filtered and concentrated to dryness. Purification was carried out by reverse phase HPLC to furnish N-(4-(dicyclopentyl(hydroxy)methyl)-6-(3,5-dimethylisoxazol-4-yl)-1H-benzo[d]imidazol-2-yl)methanesulfonamide.

LCMS (m/z+1) 472.3. $^1$H NMR (400 MHz, DMSO-d6) δ 7.33 (s, 1H), 7.09 (s, 1H), 6.5 (s, 1H), 5.20 (bs, 1H), 2.90 (s, 3H), 2.48 (s, 3H), 2.15 (s, 3H), 1.80-1.72 (m, 2H), 1.43-1.15 (m, 16H.

Example 267

(6-(3,5-dimethylisoxazol-4-yl)-1H-benzo[d]imidazol-4-yl)di(pyridin-2-yl)methanol (1020-267)

Step 1

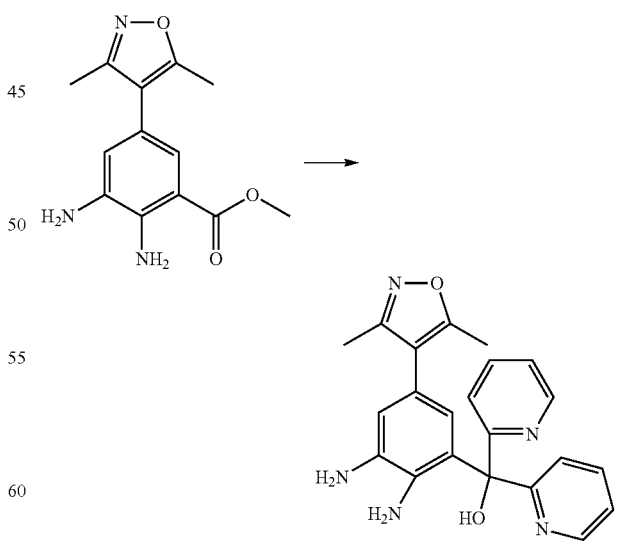

Butyllithium (1.6 M in hexanes, 21 mL, 34 mmol) was added dropwise to a solution of 2-bromopyridine (3.0 mL, 31 mmol) in MeTHF (100 mL) at −78° C. The reaction mixture was stirred for 1 hour and methyl 2,3-diamino-5-

(3,5-dimethylisoxazol-4-yl)benzoate (2 g, 7.7 mmol) in MeTHF (10 mL) was added. The reaction mixture was warmed to room temperature, and quenched with 1M HCl, neutralized with sodium bicarbonate solution, extracted with ethyl acetate and purified silica-gel chromatography (EtOAc/MeOH/NH$_4$OH) to give (2,3-diamino-5-(3,5-dimethylisoxazol-4-yl)phenyl)di(pyridin-2-yl)methanol.

$^1$H NMR (400 MHz, DMSO-d$_6$) δ 8.53 (dd, J=5.1, 1.5 Hz, 2H), 7.95 (t, J=8.0 Hz, 2H), 7.64 (d, J=8.1 Hz, 2H), 7.42 (t, J=6.1 Hz, 2H), 6.94 (s, 1H), 6.08 (s, 1H), 2.21 (s, 3H), 2.01 (s, 3H).

Step 2

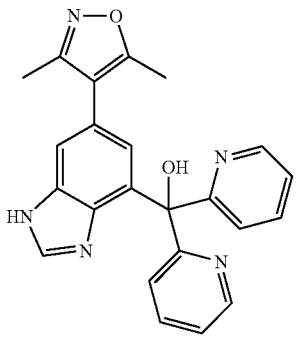 [SMILES: Cc1noc(C)c1-c1cc(C(O)(c2ccccn2)c2ccccn2)c2nc[nH]c2c1]

(2,3-diamino-5-(3,5-dimethylisoxazol-4-yl)phenyl)di(pyridin-2-yl)methanol (75 mg, 0.19 mmol) was dissolved in formic acid (1 mL) and heated to 120° C. for 3 hours. The reaction mixture was purified by reverse-phase HPLC to give the desired product.

C$_{23}$H$_{11}$N$_5$O$_2$ 398.1 (M+1). $^1$H NMR (400 MHz, DMSO-d$_6$) δ 9.22 (s, 1H), 8.51 (ddd, J=5.0, 1.7, 0.9 Hz, 2H), 7.89 (td, J=7.8, 1.8 Hz, 2H), 7.71 (d, J=1.5 Hz, 1H), 7.65 (dt, J=8.0, 1.0 Hz, 2H), 7.37 (ddd, J=7.6, 4.9, 1.1 Hz, 2H), 7.19 (d, J=1.5 Hz, 1H), 2.33 (s, 3H), 2.13 (s, 3H).

Example 268

(6-(3,5-dimethylisoxazol-4-yl)-2-methyl-1H-benzo[d]imidazol-4-yl)di(pyridin-2-yl)methanol (1020-268)

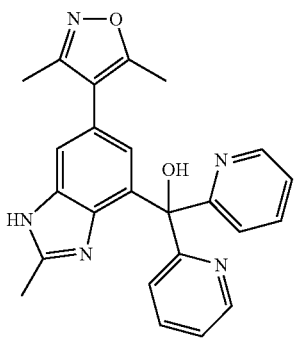 [SMILES: Cc1nc2c(C(O)(c3ccccn3)c3ccccn3)cc(-c3c(C)noc3C)cc2[nH]1]

A solution of (2,3-diamino-5-(3,5-dimethylisoxazol-4-yl)phenyl)di(pyridin-2-yl)methanol (100 mg, 0.26 mmol) and ethyl acetimidate hydrochloride (52 mg, 0.52 mmol) was heated at 50° C. for 24 hours. The reaction mixture was concentrated and purified by reverse-phase HPLC to give the desired product.

C$_{24}$H$_{21}$N$_5$O$_2$ 412.1 (M+1). $^1$H NMR (400 MHz, DMSO-d$_6$) δ 8.61-8.43 (m, 2H), 7.88 (td, J=7.7, 1.8 Hz, 2H), 7.74-7.58 (m, 3H), 7.44-7.29 (m, 2H), 7.12 (d, J=1.6 Hz, 1H), 2.77 (s, 3H), 2.32 (s, 3H), 2.12 (s, 3H).

Example 269

(6-(3,5-dimethylisoxazol-4-yl)-2-isopropyl-1H-benzo[d]imidazol-4-yl)di(pyridin-2-yl)methanol (1020-269)

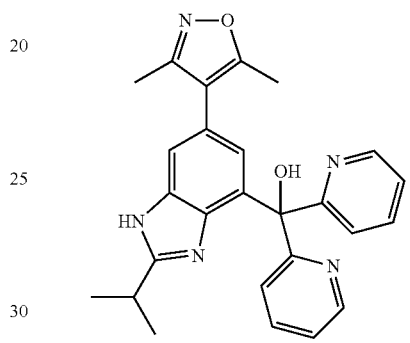

The title compound was made in a similar fashion as that of Example 268, using isopropyl acetimidate hydrochloride.

$^1$H NMR (400 MHz, DMSO-d$_6$) δ 8.63-8.44 (m, 2H), 7.88 (td, J=7.7, 1.8 Hz, 2H), 7.71-7.54 (m, 3H), 7.37 (ddd, J=7.6, 4.9, 1.2 Hz, 2H), 7.13 (d, J=1.6 Hz, 1H), 3.58 (p, J=7.0 Hz, 1H), 2.31 (s, 3H), 2.10 (s, 3H), 1.38 (d, J=7.0 Hz, 6H).

Example 270

(2-(difluoromethyl)-6-(3,5-dimethylisoxazol-4-yl)-1H-benzo[d]imidazol-4-yl)di(pyridin-2-yl)methanol (1020-270)

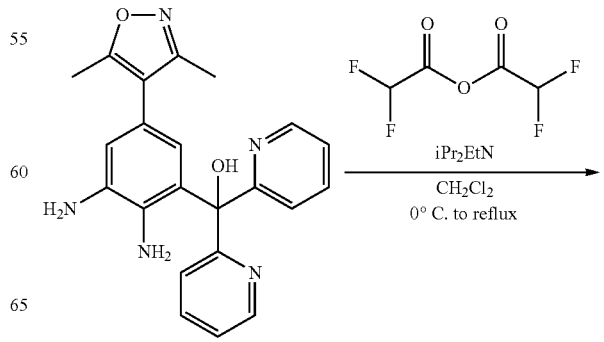

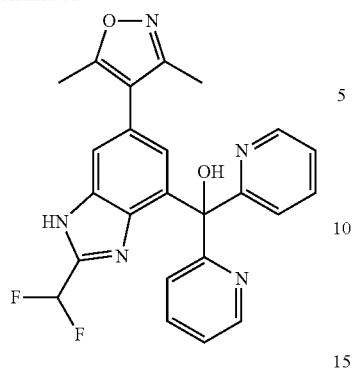

(2,3-Diamino-5-(3,5-dimethylisoxazol-4-yl)phenyl)di(pyridin-2-yl)methanol (30.0 mg, 0.049 mmol) was treated with difluoroactic anhydride (8.5 mg, 0.049 mmol) in the presence of iPr$_2$EtN (0.1 mL) in CH$_2$Cl$_2$ (3 mL) at 0° C. for 15 min. The reaction mixture was heated under a reflux conditions for 15 h. After removing the solvent under a reduced pressure, the mixture was purified by prep-HPLC to give (2-(difluoromethyl)-6-(3,5-dimethylisoxazol-4-yl)-1H-benzo[d]imidazol-4-yl)di(pyridin-2-yl)methanol.

C$_{24}$H$_{19}$F$_2$N$_5$O$_2$. MS. 448.1 (M+1). $^1$H NMR (MeOH-d$_4$) δ 8.66 (d, J=4.8 Hz, 2H), 8.23 (td, J=8.0, 1.6 Hz, 1H), 8.11 (d, J=8.0 Hz, 2H), 7.70 (ddd, J=8.0, 4.8, 1.6 Hz, 2H), 7.63 (d, J=1.6 Hz, 1H), 6.92 (d, J=1.6 Hz, 1H), 6.84 (t, J=51.2 Hz, 1H), 2.35 (s, 3H), 2.18 (s, 3H).

Example 271

(2-cyclobutyl-6-(3,5-dimethylisoxazol-4-yl)-1H-benzo[d]imidazol-4-yl)di(pyridin-2-yl)methanol (1020-271)

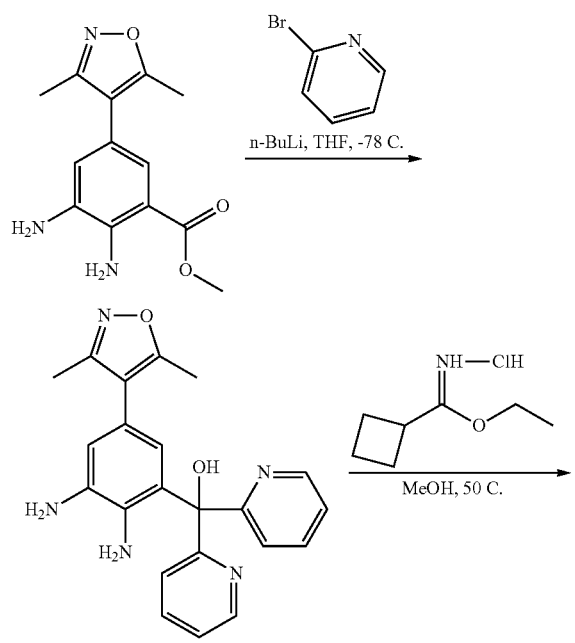

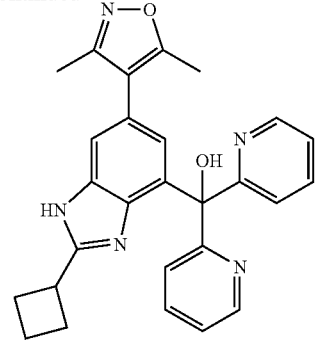

Step 1

2-bromopyridine (1.83 mL, 19 mmol) dissolved in THF (75 mL) and then cooled to −78 C. N-BuLi (12 mL, 19 mmol, 1.6M) was then added. The reaction was allowed to stir 2 minutes then (methyl 2,3-diamino-5-(3,5-dimethylisoxazol-4-yl)benzoate (1.0 g, 3.8 mmol) was added in THF (25 mL) the reaction was allowed to stir for 30 minutes. To the reaction was added Sat. Ammonium Chloride (50 mL) followed by EtOAc (100 mL). Organic layer was washed with Sat. Brine (50 mL) then dried over Magnesium Sulfate and condensed to a dark oil.

Step 2

The material was then run through a small silica plug and condensed down to get 350 mg of (2,3-diamino-5-(3,5-dimethylisoxazol-4-yl)phenyl)di(pyridin-2-yl)methanol. (2,3-diamino-5-(3,5-dimethylisoxazol-4-yl)phenyl)di(pyridin-2-yl)methanol (100 mg, 0.26 mmol) was taken and dissolved in MeOH (10 mL) and to this was added ethyl cyclobutanecarbimidate hydrochloride (64 mg, 0.39 mmol). The reaction was then heated at 50 C for 2 h. The reaction was then condensed down and purified via RPHPLC 0-50% (Acetonitrile/Water)

C$_{27}$H$_{25}$N$_5$O$_2$ MS=452.25 (M+H$^+$). $^1$H NMR (400 MHz, Chloroform-d) δ 8.56 (dt, J=4.8, 1.4 Hz, 2H), 7.78-7.70 (m, 3H), 7.63 (s, 1H), 7.32-7.19 (m, 3H), 7.10 (s, 1H), 3.83 (dd, J=16.9, 8.0 Hz, 1H), 2.49 (q, J=9.7 Hz, 4H), 2.33 (s, 3H), 2.18 (s, 4H), 1.25 (s, 1H).

Example 272

N-(6-(3,5-dimethylisoxazol-4-yl)-4-(hydroxydi(pyridin-2-yl)methyl)-1H-benzo[d]imidazol-2-yl)methanesulfonamide (1020-272)

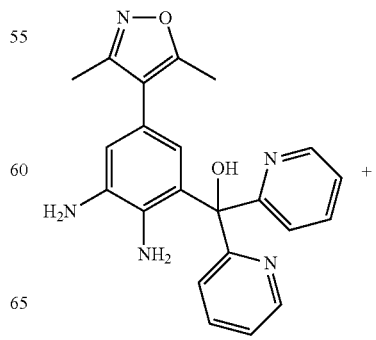

-continued

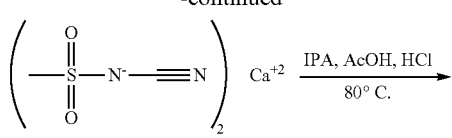

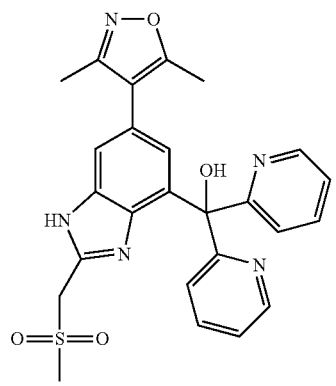

Preparation of N-(6-(3,5-dimethylisoxazol-4-yl)-4-(hydroxydi(pyridin-2-yl)methyl)-1H-benzo[d]imidazol-2-yl)methanesulfonamide from (2,3-diamino-5-(3,5-dimethylisoxazol-4-yl)phenyl)di(pyridin-2-yl)methanol was accomplished in a similar fashion to N-(6-(3,5-dimethylisoxazol-4-yl)-4-iodo-1H-benzo[d]imidazol-2-yl)methanesulfonamide. Isolated solids were then purified by reverse phase HPLC to furnish N-(6-(3,5-dimethylisoxazol-4-yl)-4-(hydroxydi(pyridin-2-yl)methyl)-1H-benzo[d]imidazol-2-yl)methanesulfonamide as a TFA salt.

LCMS (m/z+1) 491.2 $^1$H NMR (400 MHz, DMSO-d6) δ 11.96 (s, 1H), 11.31 (s, 1H), 8.50 (ddd, J=4.8, 1.7, 0.8 Hz, 2H), 7.87 (td, J=7.8, 1.9 Hz, 2H), 7.60 (d, J=8.1 Hz, 2H), 7.35 (dd, J=17.4, 5.0 Hz, 2H), 7.17 (d, J=1.5 Hz, 1H), 7.07 (s, 1H), 2.83 (9, 3H), 2.33 (s, 3H), 2.13 (s, 3H).

Example 273

(2-cyclopropyl-6-(3,5-dimethylisoxazol-4-yl)-1H-benzo[d]imidazol-4-yl)(5-methylpiperidin-3-yl)methanol (1020-273)

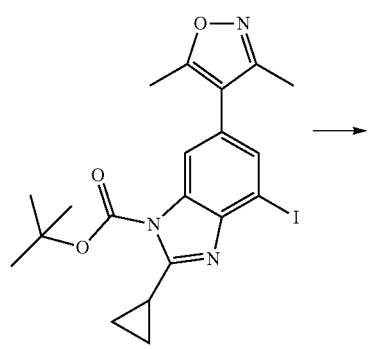

-continued

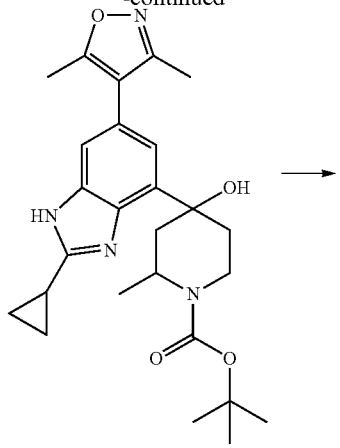

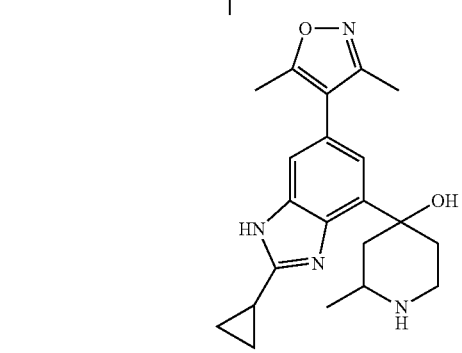

To a solution of the iodide (0.070 g) and the ketone (0.047 g) at −78 C in THF (4 ml) was added drop wise BuLi (2.5 M, hexanes, 0.1 ml) and the solution warmed to RT (step 1). After adding MeOH (1 ml), volatiles were removed, the residue dissolved in TFA, volatiles removed, and the residue purified by reverse phase HPLC (5-95% MeCN in water, 0.1% TFA) to afford (2-cyclopropyl-6-(3,5-dimethylisoxazol-4-yl)-1H-benzo[d]imidazol-4-yl)(5-methylpiperidin-3-yl)methanol (step 2).

Step 1: LCMS (m/z+1) 467.1
Step 2: LCMS (m/z+1) 367.1. $^1$H NMR (400 MHz, Methanol-d4) δ 7.43 (d, J=1.3 Hz, 1H), 7.26 (d, J=1.4 Hz, 1H), 3.54 (dtd, J=18.3, 7.6, 6.9, 4.4 Hz, 2H), 3.38 (p, J=1.6 Hz, 0H), 3.11 (ddd, J=13.2, 7.7, 3.8 Hz, 1H), 3.03 (p, J=1.6 Hz, 0H), 2.61-2.40 (m, 2H), 2.34 (s, 2H), 2.17 (s, 3H), 2.09-1.99 (m, 1H), 1.56-1.38 (m, 3H), 1.31 (dt, J=7.8, 4.8 Hz, 1H).

Example 274

(2-cyclopropyl-6-(3,5-dimethylisoxazol-4-yl)-1H-benzo[d]imidazol-4-yl)(quinuclidin-3-yl)methanol (1020-274)

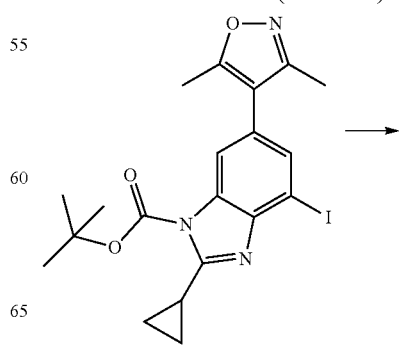

-continued

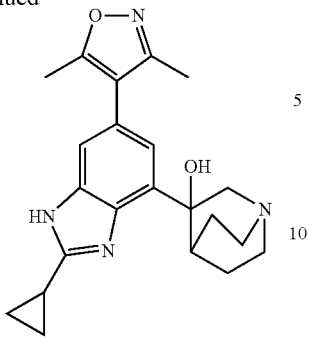

(2-Cyclopropyl-6-(3,5-dimethylisoxazol-4-yl)-1H-benzo[d]imidazol-4-yl)(quinuclidin-3-yl)methanol was synthesized in a similar fashion to Example 273 using quinuclidine-3-one.
LCMS (m/z+1) 379.3

Example 275

(2-cyclopropyl-6-(3,5-dimethylisoxazol-4-yl)-1H-benzo[d]imidazol-4-yl)(1,3-dioxolan-2-yl)methanol (1020-275)

Step 1: Preparation of tert-butyl 2-cyclopropyl-6-(3,5-dimethylisoxazol-4-yl)-4-formyl-1H-benzo[d]imidazole-1-carboxylate

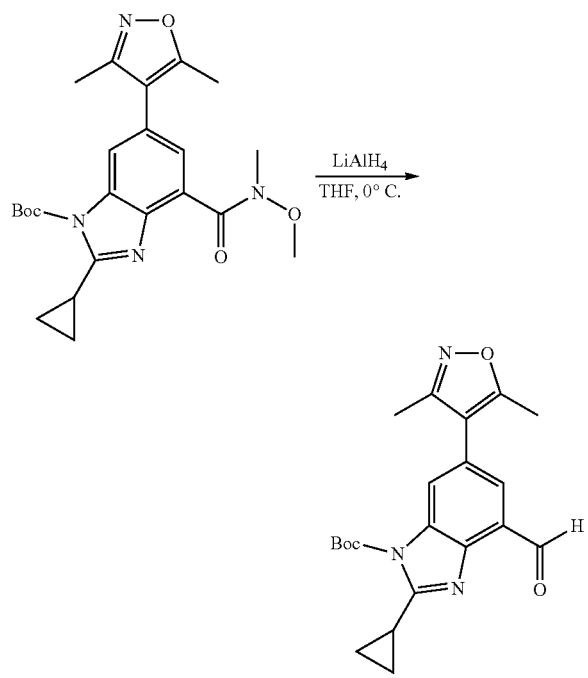

To a flame dried, nitrogen purged flask was added tert-butyl 2-cyclopropyl-6-(3,5-dimethylisoxazol-4-yl)-4-(methoxy(methyl)carbamoyl)-1H-benzo[d]imidazole-1-carboxylate (5 g, 11.35 mmol) and 20 mL THF. Reaction was stirred and cooled to −78° C. under nitrogen. To this was slowly added 1M lithium aluminum hydride in diethyl ether (18 ml, 18 mmol). Reaction was quenched into large stirring flask of EtAc, dilute ammonium chloride that was pre-cooled to 0° C. Crude suspension was filtered thru celite extracted with EtAc (3×) and organics washed with water and then brine. Organics were dried over sodium sulfate before removing solvents under reduced pressure and purifying by silica gel chromatography to afford of tert-butyl 2-cyclopropyl-6-(3,5-dimethylisoxazol-4-yl)-4-formyl-1H-benzo[d]imidazole-1-carboxylate 3.57 g (82.5%) as a yellow powder.
LCMS (m/z+1)=381.8

Step 2: Preparation of tert-butyl 4-((1,3-dioxolan-2-yl)(hydroxyl)methyl)-2-cyclopropyl-6-(3,5-dimethylisoxazol-4-yl)-1H-benzo[d]imidazole-1-carboxylate

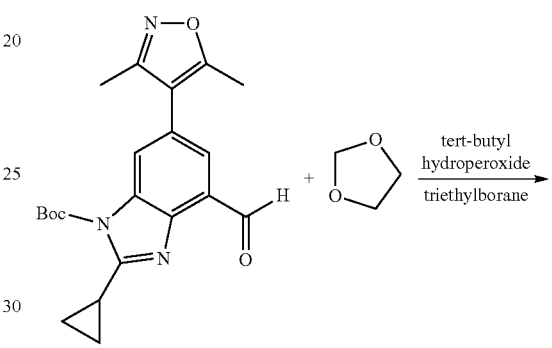

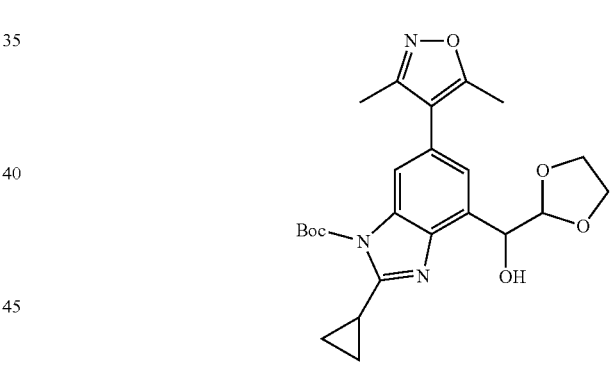

tert-butyl 2-cyclopropyl-6-(3,5-dimethylisoxazol-4-yl)-4-formyl-1H-benzo[d]imidazole-1-carboxylate (500 mg, 1.31 mmol) in 1,3-dioxolane (5 ml) was cooled to 0° C. under nitrogen. To this was added 1M triethylborane (7.87 ml) followed by 5.5M tert-butyl hydroperoxide in decane (2.38 ml). Reaction was allowed to warm and react for 3 days. To the reaction was then added NH₄OH solution (5 mL) and after stirring for 5 minutes was added FeSO₄.H₂SO₄.H₂O solution (5 mL). Solution was extracted with EtAc 3×, washed with water, added FeSO₄.H₂SO₄.H₂O solution, water, brine then dried over sodium sulfate. Solvents were removed under reduced pressure to afford tert-butyl 4-((1,3-dioxolan-2-yl)(hydroxy)methyl)-2-cyclopropyl-6-(3,5-dimethylisoxazol-4-yl)-1H-benzo[d]imidazole-1-carboxylate as a yellow film. (212 mg, 32%)
LCMS (m/z+1) 455.9

Step 3: (2-cyclopropyl-6-(3,5-dimethylisoxazol-4-yl)-1H-benzo[d]imidazol-4-yl)(1,3-dioxolan-2-yl)methanol

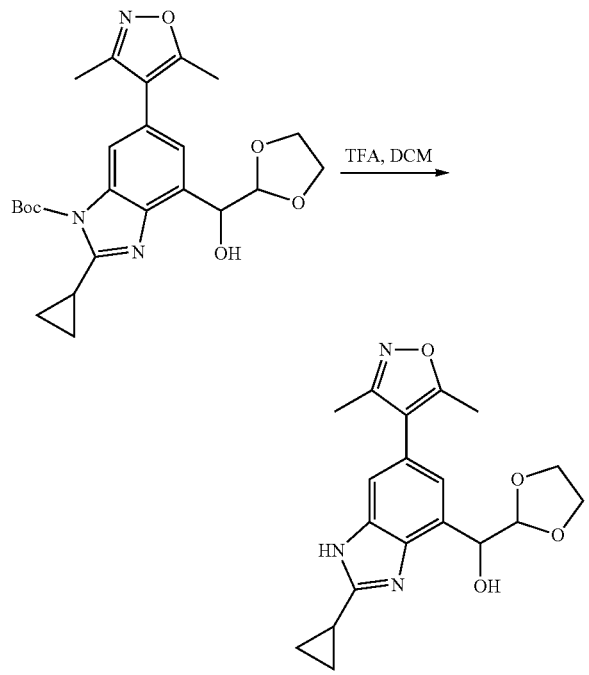

Crude tert-butyl 4-((1,3-dioxolan-2-yl)(hydroxy)methyl)-2-cyclopropyl-6-(3,5-dimethylisoxazol-4-yl)-1H-benzo[d]imidazole-1-carboxylate (53 mg, 0.116 mmol) was taken up in 5 mL DCM and to this was added 1 mL TFA and reaction stirred at rt for 3 hours. Solvents were removed under reduced pressure and crude material was purified by reverse phase HPLC to afford (2-cyclopropyl-6-(3,5-dimethylisoxazol-4-yl)-1H-benzo[d]imidazol-4-yl)(1,3-dioxolan-2-yl)methanol.

LCMS (m/z+1) 356.1. $^1$H NMR (400 MHz, DMSO-d6) δ7.46 (s, 1H), 7.34 (s, 1H), 6.24-5.93 (m, 1H), 5.08 (d, J=4.0 Hz, 1H), 5.01 (d, J=3.9 Hz, 1H), 3.87 (q, J=7.6, 7.1 Hz, 1H), 3.83-3.69 (m, 4H), 2.40 (s, 3H), 2.21 (s, 3H), 1.43-1.22 (m, 4H).

Example 276

(2-cyclopropyl-6-(3,5-dimethylisoxazol-4-yl)-1H-benzo[d]imidazol-4-yl)(1,3-dioxolan-2-yl)(2-methylpyridin-3-yl)methanol (1020-276)

Step 1: Preparation of tert-butyl 2-cyclopropyl-6-(3,5-dimethylisoxazol-4-yl)-4-(1,3-dioxolane-2-carbonyl)-1H-benzo[d]imidazole-1-carboxylate

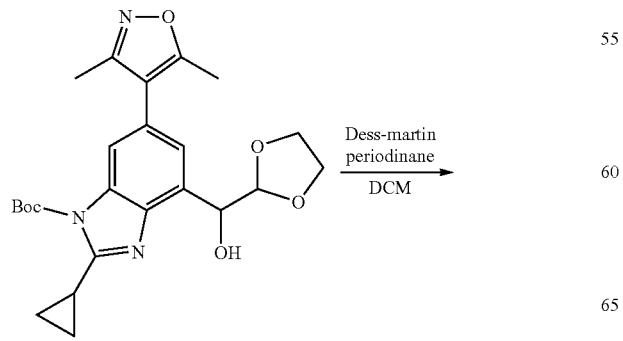

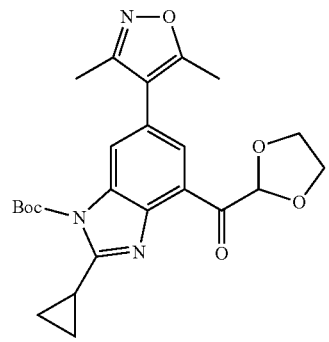

tert-butyl 4-((1,3-dioxolan-2-yl)(hydroxy)methyl)-2-cyclopropyl-6-(3,5-dimethylisoxazol-4-yl)-1H-benzo[d]imidazole-1-carboxylate (600 mg, 1.32 mmol) was taken up in 100 ml DCM and to this was added Dess-Martin periodinane (594.56 mg, 1.58 mmol) and reaction allowed to stir at room temperature under nitrogen. After 1 hour reaction was quenched with aqueous sodium thiosulfate and stirred for 15 minutes. Reaction was then extracted 3× with EtAc, washed with sodium thiosulfate, water, brine and finally dried over sodium sulfate. Solvents were removed under reduced pressure and residue was flashed on silica gel chromatography using Hex/EtAc as the eluent to afford tert-butyl 2-cyclopropyl-6-(3,5-dimethylisoxazol-4-yl)-4-(1,3-dioxolane-2-carbonyl)-1H-benzo[d]imidazole-1-carboxylate (160 mg, 27%).

LCMS (m/z+1) 453.8

Step 2: Preparation of tert-butyl 4-((1,3-dioxolan-2-yl)(hydroxy)(2-methylpyridin-3-yl)methyl)-2-cyclopropyl-6-(3,5-dimethylisoxazol-4-yl)-1H-benzo[d]imidazole-1-carboxylate

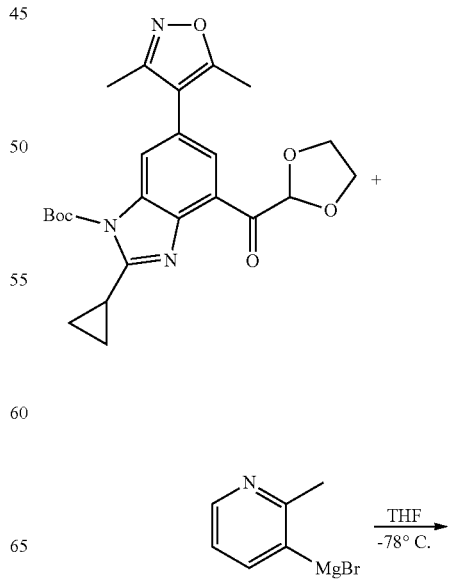

347
-continued

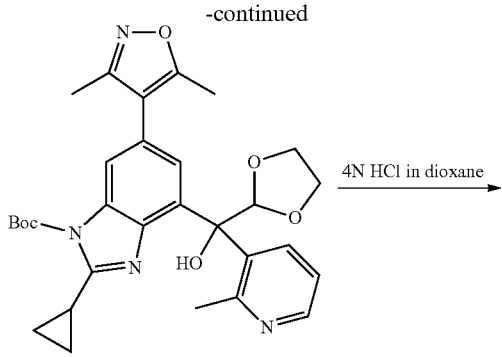

tert-butyl 2-cyclopropyl-6-(3,5-dimethylisoxazol-4-yl)-4-(1,3-dioxolane-2-carbonyl)-1H-benzo[d]imidazole-1-carboxylate (50 mg, 0.11 mmol) was taken up in THF (5 ml) and cooled to −78° C. under nitrogen. To this was added 0.25M (6-methylpyridin-2-yl)magnesium bromide (1.31 ml) over 5 minutes. Reaction was allowed to stir at −78° C. for 30 minutes. Reaction was then quenched into stirring EtAc/ammonium chloride extracted 3× with EtAc, organics were washed with ammonium chloride, water, brine then dried over sodium sulfate. Solvents were removed under reduced pressure and crude residue purified by silica gel chromatography using Hex/EtAc as the eluent to afford tert-butyl 4-((1,3-dioxolan-2-yl)(hydroxy)(2-methylpyridin-3-yl)methyl)-2-cyclopropyl-6-(3,5-dimethylisoxazol-4-yl)-1H-benzo[d]imidazole-1-carboxylate (20 mg, 34%).

LCMS (m/z+1) 546.3

Step 3: Preparation of (2-cyclopropyl-6-(3,5-dimethylisoxazol-4-yl-1H-benzo[d]imidazol-4-yl)(1,3-dioxolan-2-yl)(2-methylpyridin-3-yl)methanol tert-butyl 4-((1,3-dioxolan-2-yl)(hydroxy)(2-methylpyridin-3-yl)methyl)-2-cyclopropyl-6-(3,5-dimethylisoxazol-4-yl)-1H-benzo[d]imidazole-1-carboxylate (20 mg, 0.037 mmol) was then dissolved in 2 ml 4N HCl in dioxanes and 2 ml ethanol and heated to 75° C. for 1 hour. Solvents were removed under reduced pressure and material was purified by reverse phase HPLC to afford (2-cyclopropyl-6-(3,5-dimethylisoxazol-4-yl)-1H-benzo[d]imidazol-4-yl)(1,3-dioxolan-2-yl)(2-methylpyridin-3-yl)methanol as a mixture of diastereomers.

LCMS (m/z+1) 447.1. $^1$H NMR (400 MHz, DMSO-d6) δ 8.67 (d, J=5.7 Hz, 2H), 7.86 (td, J=14.4, 13.8, 5.4 Hz, 1H), 7.52 (s, 1H), 7.13 (s, 1H), 6.71 (s, 1H), 5.82 (s, 1H), 3.87 (dt, J=15.4, 6.2 Hz, 4H), 2.81 (s, 1H), 2.43-2.29 (m, 3H), 2.24 (s, 3H), 2.02 (s, 3H), 1.61-1.26 (m, 4H).

348

Example 277 and 278

3-((2-cyclopropyl-6-(3,5-dimethylisoxazol-4-yl)-1H-benzo[d]imidazol-4-yl)(hydroxy)methyl)bicyclo[2.2.1]heptan-2-one (1020-277) and (Z)-3-((2-cyclopropyl-6-(3,5-dimethylisoxazol-4-yl)-1H-benzo[d]imidazol-4-yl)methylene)bicyclo[2.2.1]heptan-2-one (1020-278)

Step 1: Preparation of tert-butyl 2-cyclopropyl-6-(3,5-dimethylisoxazol-4-yl)-4-(hydroxy(-3-oxobicyclo[2.2.1]heptan-2-ylmethyl)-1H-benzo[d]imidazole-1-carboxylate

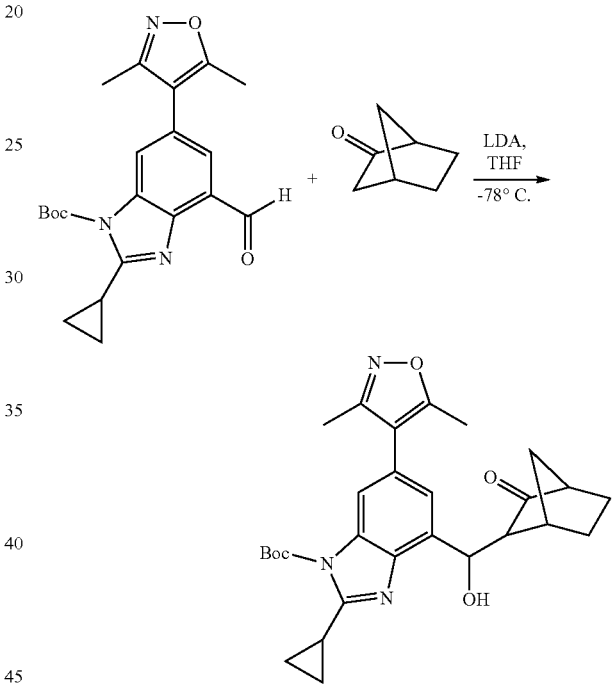

2-norbornanone (173.28 mg, 1.57 mmol) was taken up in THF (5 ml) and cooled to −78° C. under nitrogen. To this was slowly added 2M lithium diisopropylamide in THF (0.92 ml) over 5 minutes and the resulting solution was allowed to stir for 30 minutes. At this time a solution of tert-butyl 2-cyclopropyl-6-(3,5-dimethylisoxazol-4-yl)-4-formyl-1H-benzo[d]imidazole-1-carboxylate (100 mg, 0.26 mmol) in 2 mL THF was slowly added. Reaction was allowed to stir atr −78° C. for 10 minutes before being allowed to warm up. when solution was at approximately 0° C. material was quenched into stirring aqueous ammonium chloride/EtAc, extracted 3 with EtAc, then organics were washed with water, brine and dried over sodium sulfate before removing solvents under reduced pressure to afford crude tert-butyl 2-cyclopropyl-6-(3,5-dimethylisoxazol-4-yl)-4-(hydroxy(-3-oxobicyclo[2.2.1]heptan-2-yl)methyl)-1H-benzo[d]imidazole-1-carboxylate as a mixture of isomers (50 mg, 39%).

LCMS (m/z+1) 492.1

Step 2: Preparation of 3-((2-cyclopropyl-6-(3,5-dimethylisoxazol-4-yl)-1H-benzo[d]imidazol-4-yl)(hydroxy)methylbicyclo[2.2.1]heptan-2-one and (Z)-3-((2-cyclopropyl-6-(3,5-dimethylisoxazol-4-yl)-1H-benzo[d]imidazol-4-yl)methylene)bicyclo[2.2.1]heptan-2-one

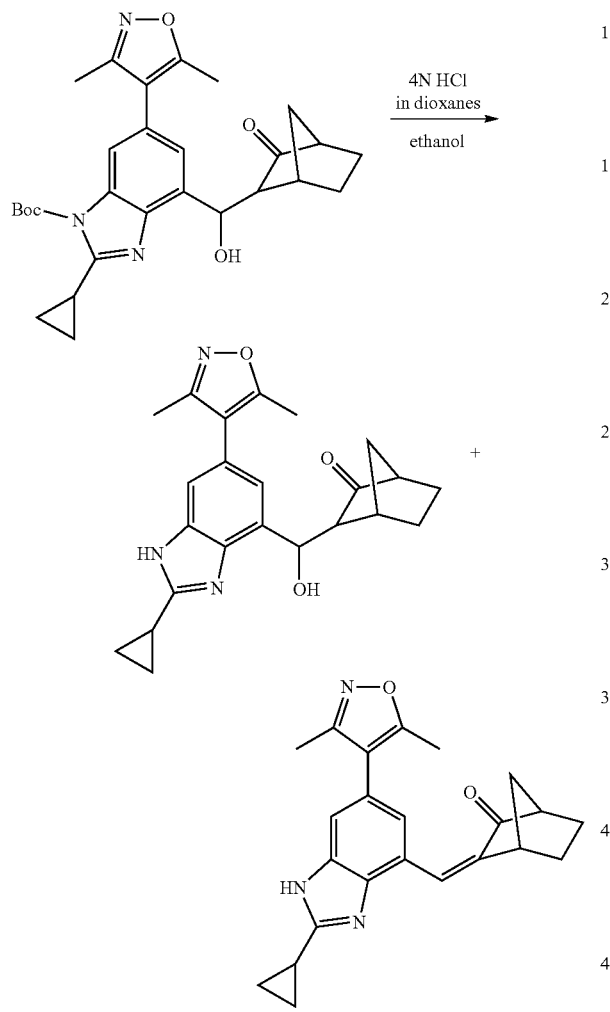

2-cyclopropyl-6-(3,5-dimethylisoxazol-4-yl)-4-(hydroxy(-3-oxobicyclo[2.2.1]heptan-2-yl)methyl))-1H-benzo[d]imidazole-1-carboxylate (50 mg, 0.1 mmol) was dissolved in 2 ml 4N HCl in dioxanes and 2 ml ethanol and heated to 50° C. for 1 hour. Solvents were removed under reduced pressure and material was purified via reverse phase HPLC to afford both 3-((2-cyclopropyl-6-(3,5-dimethylisoxazol-4-yl)-1H-benzo[d]imidazol-4-yl)methyl)bicyclo[2.2.1]heptan-2-one and (Z)-3-((2-cyclopropyl-6-(3,5-dimethylisoxazol-4-yl)-1H-benzo[d]imidazol-4-yl)methylene)bicyclo[2.2.1]heptan-2-one both as a mixture of isomers.

3-((2-cyclopropyl-6-(3,5-dimethylisoxazol-4-yl)-1H-benzo[d]imidazol-4-yl)(hydroxy)methyl)bicyclo[2.2.1]heptan-2-one: LCMS (m/z+1) 392.2. $^1$H NMR (400 MHz, DMSO-d6) δ 7.51-7.38 (m, 1H), 7.23 (s, 1H), 5.91 (s, 1H), 5.22 (d, J=5.7 Hz, 1H), 2.51 (m, 2H), 2.40 (s, 4H), 2.32 (dd, J=5.8, 2.9 Hz, 1H), 2.21 (d, J=2.2 Hz, 3H), 1.84 (d, J=10.2 Hz, 1H), 1.76-1.64 (m, 2H), 1.33 (td, J=10.9, 10.1, 4.4 Hz, 7H).

(Z)-3-((2-cyclopropyl-6-(3,5-dimethylisoxazol-4-yl)-1H-benzo[d]imidazol-4-yl)methylene)bicyclo[2.2.1]heptan-2-one: LCMS (m/z+1) 374.2. $^1$H NMR (400 MHz, DMSO-d6) δ 8.37 (d, J=7.3 Hz, 2H), 8.15 (s, 1H), 3.61-3.53 (m, 1H), 3.28 (s, 3H), 3.10 (s, 4H), 3.00-2.73 (m, 3H), 2.40-2.26 (m, 2H), 2.18 (d, J=3.7 Hz, 2H), 2.07 (d, J=7.7 Hz, 8H).

Example 279

3-((2-cyclopropyl-6-(3,5-dimethylisoxazol-4-yl)-1H-benzo[d]imidazol-4-yl)(hydroxy)methyl)bicyclo[2.2.1]heptan-2-ol (1020-279)

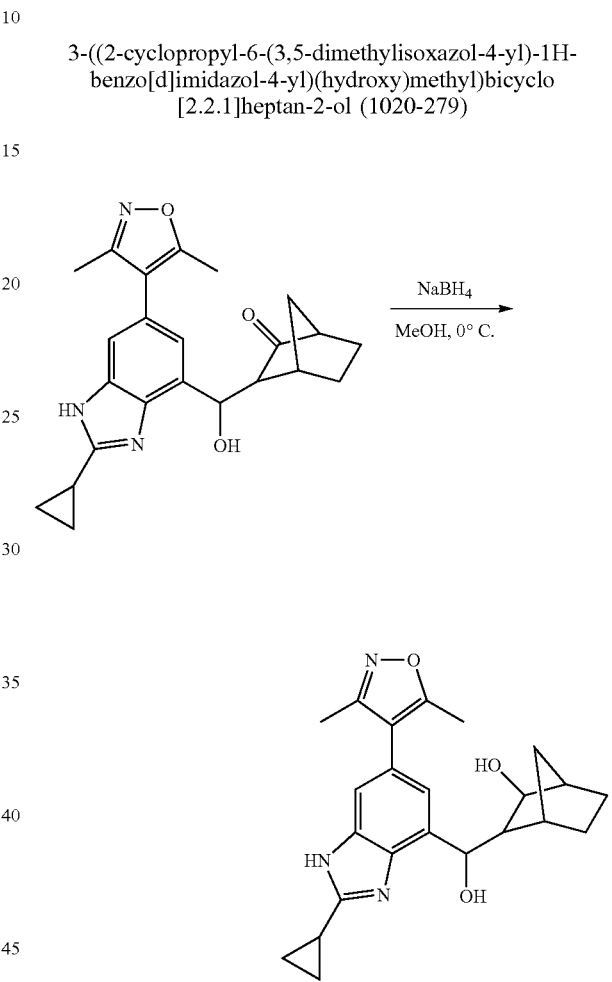

3-((2-cyclopropyl-6-(3,5-dimethylisoxazol-4-yl)-1H-benzo[d]imidazol-4-yl)(hydroxy)methyl)bicyclo[2.2.1]heptan-2-one (15 mg, 0.04 mmol) was dissolved in 1 m MeOH and cooled to 0° C. under argon. To this was added sodium borohydride (4.35 mg, 0.11 mmol) and reaction allowed to warm to room temperature for 2 hours. Solvents were removed under reduced pressure and residue was diluted in EtAc/aqueous ammonium chloride, extracted 3× with EtAc, washed with water then brine then dried over sodium sulfate before removing solvents under reduced pressure. Crude residue was purified by reverse phase HPLC to afford 3-((2-cyclopropyl-6-(3,5-dimethylisoxazol-4-yl)-1H-benzo[d]imidazol-4-yl)(hydroxy)methyl)bicyclo[2.2.1]heptan-2-ol as a mixture of isomers.

LCMS (m/z+1) 394.3. $^1$H NMR (400 MHz, DMSO-d6) δ 7.42 (s, 1H), 7.26 (s, 1H), 4.80 (d, J=8.0 Hz, 1H), 2.40 (s, 3H), 2.21 (s, 3H), 2.15-2.08 (m, 1H), 1.86-1.75 (m, 1H), 1.72 (d, J=4.0 Hz, 1H), 1.57 (d, J=9.9 Hz, 1H), 1.43 (d, J=8.7 Hz, 1H), 1.48-0.91 (m, 9H).

Example 280

2-((2-cyclopropyl-6-(3,5-dimethylisoxazol-4-yl)-1H-benzo[d]imidazol-4-yl)(hydroxy)methyl)cyclopentanol (1020-280)

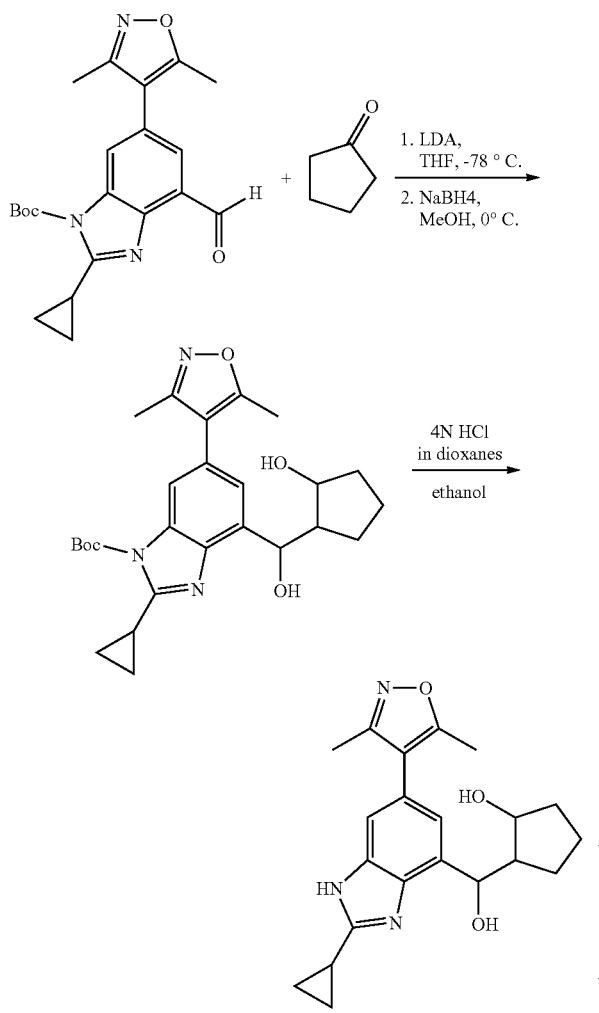

Step 1: Preparation of tert-butyl 2-cyclopropyl-6-(3,5-dimethylisoxazol-4-yl)-4-hydroxy(2-hydroxycyclopentyl)methyl)-1H-benzo[d]imidazole-1-carboxylate Cyclopentanone (0.14 ml, 1.57 mmol) was taken up in THF (5 ml) and cooled to −78° C. under argon. To this was slowly added 2M lithium diisopropylamide in THF (0.92 ml) over 5 minutes and the resulting solution was allowed to stir for 30 minutes. At this time a solution of tert-butyl 2-cyclopropyl-6-(3,5-dimethylisoxazol-4-yl)-4-formyl-1H-benzo[d]imidazole-1-carboxylate (100 mg, 0.26 mmol) in 2 mL THF was slowly added. Reaction was allowed to stir atr −78° C. for 10 minutes quenched into stirring aqueous ammonium chloride/EtAc, extracted 3× with EtAc, washed with water then brine then dried over sodium sulfate before removing solvents under reduced pressure. Material was immediately taken up in 5 mL methanol, cooled to 0° C. and had sodium borohydrode (19.83 mg, 0.52 mmol) added to it. Reaction was allowed to warm to room temperature and react for 2 hours. Solvents were removed under reduced pressure. Residue was dissolved in EtAc/aqueous ammonium chloride, extracted 3× with EtAc, washed with water then brine then dried over sodium sulfate before removing solvents under reduced pressure to provide crude tert-butyl 2-cyclopropyl-6-(3,5-dimethylisoxazol-4-yl)-4-(hydroxy(2-hydroxycyclopentyl)methyl)-1H-benzo[d]imidazole-1-carboxylate as racemic mixture of 2 diastereomers.

LCMS (m/z+1) 468.2

Step 2: Preparation of 2-((2-cyclopropyl-6-(3,5-dimethylisoxazol-4-yl)-1H-benzo[d]imidazol-4-yl)(hydroxy)methyl)cyclopentanol tert-butyl 2-cyclopropyl-6-(3,5-dimethylisoxazol-4-yl)-4-(hydroxy(2-hydroxycyclopentyl)methyl)-1H-benzo[d]imidazole-1-carboxylate (122 mg, 0.26 mmol) was taken up in ethanol (5 ml) and 2.5 mL HCl in dioxane. Mixture was then heated to 65° C. for 40 minutes. Solvents were removed under reduced pressure and residue purified by reverse phase HPLC to afford the TFA salt of 2-((2-cyclopropyl-6-(3,5-dimethylisoxazol-4-yl)-1H-benzo[d]imidazol-4-yl)(hydroxy)methyl)cyclopentanol as a racemic mixture of 4 diastereomers.

LCMS (m/z+1) 368.2. $^1$H NMR (400 MHz, DMSO-d6) δ 7.46 (dq, J=4.5, 1.4 Hz, 1H), 7.40-7.26 (m, 1H), 5.10 (d, J=9.1 Hz, 0.3H), 5.01 (d, J=9.1 Hz, 0.3H), 4.92 (d, J=9.1 Hz, 0.3H), 4.87 (d, J=9.1 Hz, 0.5H), 4.34 (t, J=3.5 Hz, 0.3H), 4.10 (dt, J=6.2, 4.3 Hz, 0.3H), 3.85 (q, J=5.3 Hz, 0.5H), 3.61 (dd, J=7.9, 4.3 Hz, 0.3H), 2.58-2.49 (m, 1H), 2.39 (d, J=1.7 Hz, 3H), 2.21 (d, J=1.5 Hz, 4H), 1.88-1.26 (m, 10H).

Example 281 and 282

(S)-(2-cyclopropyl-6-(3,5-dimethylisoxazol-4-yl)-1H-benzo[d]imidazol-4-yl)(6-methylpyridin-2-yl)((R)-tetrahydrofuran-2-yl)methanol (1020-281) and (R)-(2-cyclopropyl-6-(3,5-dimethylisoxazol-4-yl)-1H-benzo[d]imidazol-4-yl)(6-methylpyridin-2-yl)((S)-tetrahydrofuran-2-yl)methanol (1020-282)

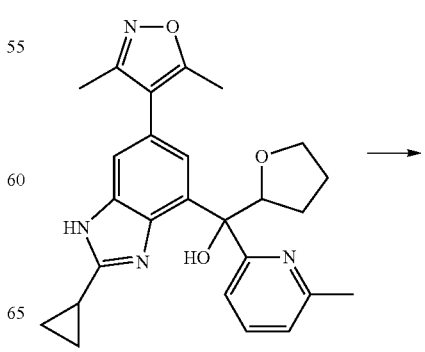

-continued

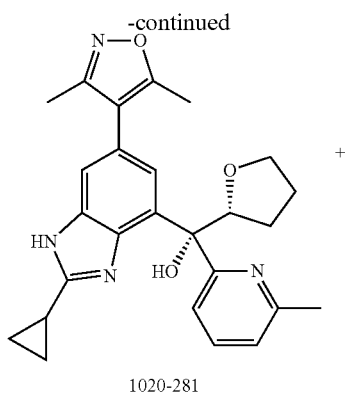

1020-281

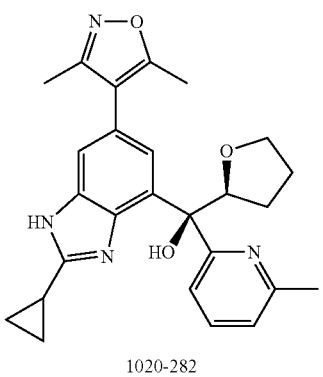

1020-282

From Example 114, the mixture was separated to provide the two enantiomers using HPLC chiral column.

LCMS (m/z+1) 445.23

Example 283 and 284

(R)-(2-cyclopropyl-6-(3,5-dimethylisoxazol-4-yl)-1H-benzo[d]imidazol-4-yl)((S)-tetrahydrofuran-2-yl)methanol (1020-283) and (R)-(2-cyclopropyl-6-(3,5-dimethylisoxazol-4-yl)-1H-benzo[d]imidazol-4-yl)(R)-tetrahydrofuran-2-yl)methanol (1020-284)

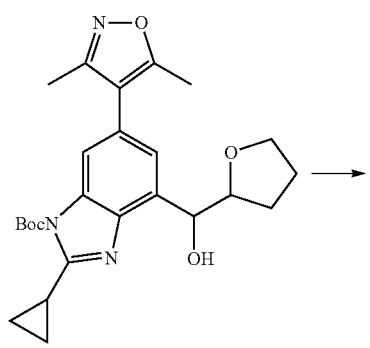

-continued

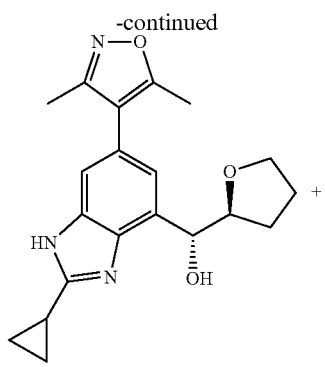

To tert-butyl 2-cyclopropyl-6-(3,5-dimethylisoxazol-4-yl)-4-(hydroxy(tetrahydrofuran-2-yl)methyl)-1H-benzo[d]imidazole-1-carboxylate (36 mg, 0.079 mmol, 1 equiv.) 1 is added TFA (5 mL) and allowed to stir for 30 min. After the reaction was complete, it was concentrated in vacuo. Purification was carried out by reverse phase HPLC to furnish a mixture of isomers. It was then separated to provide the two isomers using HPLC chiral separation to furnish (R)-(2-cyclopropyl-6-(3,5-dimethylisoxazol-4-yl)-1H-benzo[d]imidazol-4-yl)((S)-tetrahydrofuran-2-yl)methanol and (R)-(2-cyclopropyl-6-(3,5-dimethylisoxazol-4-yl)-1H-benzo[d]imidazol-4-yl)((R)-tetrahydrofuran-2-yl)methanol.

Compound 1020-283: LCMS (m/z+1) 352.46. $^1$H NMR (400 MHz, Methanol-d4) δ 7.33 (s, 1H), 7.19 (s, 1H), 5.05 (d, J=6.0 Hz, 1H), 4.27-4.18 (m, 1H), 3.89-3.80 (m, 1H), 3.78-3.60 (m, 1H), 2.41 (s, 3H), 2.27 (s, 1H), 2.28 (m, 1H), 1.49 (dd, J=8.3, 3.0 Hz, 4H), 1.34 (dd, J=4.9, 2.7 Hz, 4H). $^{19}$F NMR (376 MHz, Methanol-d4) δ -77.91.

Compound 1020-284: LCMS (m/z+1) 352.42. $^1$H NMR (400 MHz, Methanol-d$_4$) δ 7.33 (s, 1H), 7.19 (s, 1H), 5.04 (d, J=6.1 Hz, 1H), 4.31-4.15 (m, 1H), 3.96-3.82 (m, 1H), 3.79 (q, J=7.3, 6.9 Hz, 1H), 2.41 (s, 4H), 2.25 (s, 5H), 1.95-1.68 (m, 5H), 1.21 (ddt, J=10.3, 7.5, 2.6 Hz, 5H).

Example 285

Cyclopentyl(2-cyclopropyl-6-(3,5-dimethylisoxazol-4-yl)-1H-benzo[d]imidazol-4-yl)methanone (1020-285)

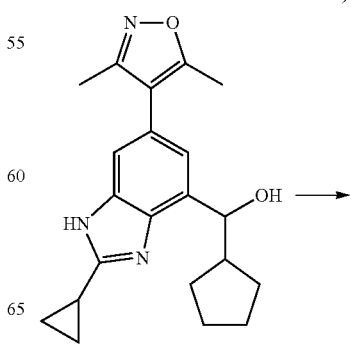

-continued

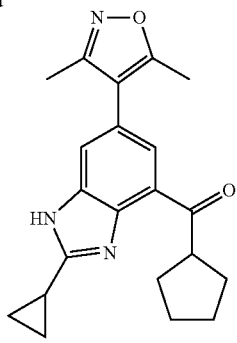

Into a flask containing cyclopentyl(2-cyclopropyl-6-(3,5-dimethylisoxazol-4-yl)-1H-benzo[d]imidazol-4-yl)methanol (25 mg, 0.07 mmol, 1 equiv.) in DCM (3 mL) is added Dess-Martin periodinane (150 mg, 0.36 mmol, 5 equiv.). The reaction was extracted with DCM and washed with water, saturated NH₄Cl. After drying with MgSO₄, it was filtered and concentrated to dryness. Purification was carried out by reverse phase HPLC to furnish cyclopentyl(2-cyclopropyl-6-(3,5-dimethylisoxazol-4-yl)-1H-benzo[d]imidazol-4-yl)methanone.

LCMS (m/z+1) 350.28. $^1$H NMR (400 MHz, Methanol-d4) δ 7.77 (s, 1H), 7.64 (s, 1H), 4.00-3.90 (m, 1H), 2.42 (s, 3H), 2.27 (s, 3H), 2.32-2.25 (m, 1H), 2.05-1.90 (m, 4H), 1.75-1.60 (m, 4H), 1.20-1.10 (m, 4H). $^{19}$F NMR (376 MHz, Methanol-d4) δ −77.91.

Example 286

(2-Cyclopropyl-6-(3,5-dimethylisoxazol-4-yl)-1H-benzo[d]imidazol-4-yl)(pyrimidin-2-yl)(tetrahydrofuran-2-yl)methanol (1020-286)

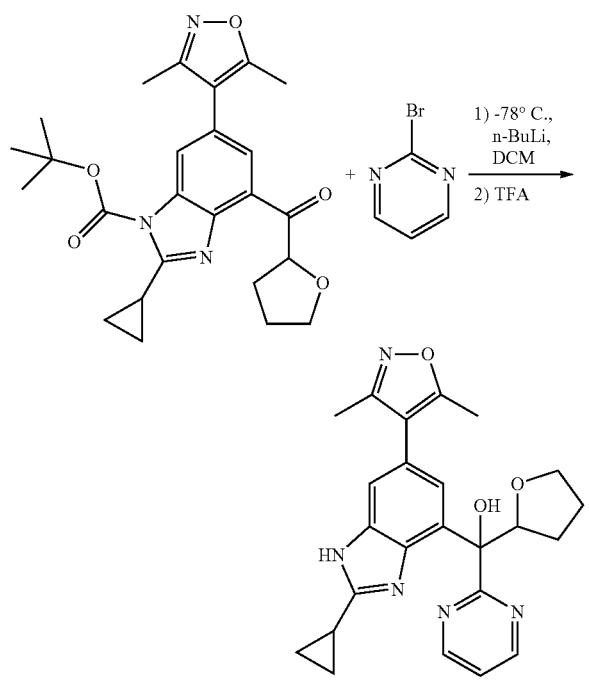

In a flame dried flask containing 2-bromopyrimidine (111 mg, 0.70 mmol) in DCM was added n-BuLi (0.39 mL, 0.62 mmol) at −78° C. The solution was allowed to stir for 30 minutes, followed by the addition of tert-butyl 2-cyclopropyl-6-(3,5-dimethylisoxazol-4-yl)-4-(tetrahydrofuran-2-carbonyl)-1H-benzo[d]imidazole-1-carboxylate (70 mg, 0.16 mmol). The solution was allowed to warm to room temperature. Once complete, the solution was quenched with DI H₂O and extracted three times with EtOAc. The combined organic layers were washed with saturated NaCl, dried over sodium sulfate, filtered and concentrated in vacuo. To the crude product was added 5 mL of TFA and was allowed to stir for 30 minutes. The solution was concentrated in vacuo and was purified via reverse phase HPLC to afford (2-cyclopropyl-6-(3,5-dimethylisoxazol-4-yl)-1H-benzo[d]imidazol-4-yl)(pyrimidin-2-yl)(tetrahydrofuran-2-yl)methanol.

$C_{24}H_{25}N_5O_3$. MS. m/z 432.5 (M+1). $^1$H NMR (400 MHz, cd₃od) δ 8.86 (d, J=4.9 Hz, 2H), 7.94 (d, J=1.4 Hz, 1H), 7.48 (d, J=1.4 Hz, 1H), 7.41 (t, J=4.9 Hz, 1H), 5.24 (t, J=6.8 Hz, 1H), 3.92 (dt, J=13.8, 7.0 Hz, 2H), 3.76 (dd, J=12.4, 7.4 Hz, 2H), 2.43 (s, 3H), 2.26 (s, 3H).

Example 287

6-((2-Cyclopropyl-6-(3,5-dimethylisoxazol-4-yl)-1H-benzo[d]imidazol-4-yl)(hydroxy)(tetrahydrofuran-2-yl)methyl)-1-methylpyridin-2(1H)-one (1020-287)

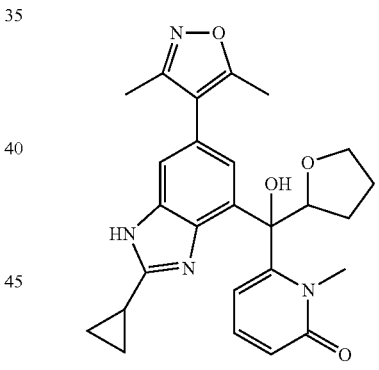

6-((2-cyclopropyl-6-(3,5-dimethylisoxazol-4-yl)-1H-benzo[d]imidazol-4-yl)(hydroxy)(tetrahydrofuran-2-yl)methyl)-1-methylpyridin-2(1H)-one was synthesized in a similar fashion to Example 286, substituting 2-bromopyrimidine for 6-bromo-1-methylpyridin-2(1H)-one (128 mg, 0.68 mmol), and DCM for THF as the solvent.

$C_{26}H_{28}N_4O_4$. MS. m/z 641.5 (M+1). $^1$H NMR (400 MHz, cd₃od) δ 7.61 (dd, J=9.0, 7.4 Hz, 1H), 7.52 (d, J=1.3 Hz, 1H), 7.17 (d, J=6.5 Hz, 1H), 6.80 (d, J=1.1 Hz, 1H), 6.61 (d, J=8.2 Hz, 1H), 3.28 (s, 3H), 2.27 (s, 3H), 2.06 (s, 3H), 1.95-1.79 (m, 3H), 1.59 (td, J=7.8, 5.0 Hz, 2H), 1.49-1.43 (m, 2H), 1.43-1.34 (m, 1H).

Example 288

(2-Cyclopropyl-6-(3,5-dimethylisoxazol-4-yl)-1H-benzo[d]imidazol-4-yl)(pyridin-2-yl)(tetrahydrofuran-2-yl)methanol (1020-288)

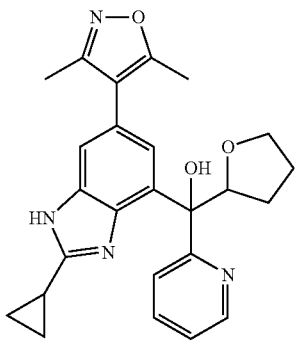 [SMILES: Cc1noc(C)c1-c1cc(C(O)(c2ccccn2)C2CCCO2)c2nc(C3CC3)[nH]c2c1]

(2-cyclopropyl-6-(3,5-dimethylisoxazol-4-yl)-1H-benzo[d]imidazol-4-yl)(pyridin-2-yl)(tetrahydrofuran-2-yl)methanol was synthesized in a similar fashion to Example 286, substituting 6-bromo-1-methylpyridin-2(1H)-one for 2-bromopyridine.

$C_{25}H_{26}N_4O_3$. MS. m/z 431.5 (M+1). $^1$H NMR (400 MHz, cd$_3$od) δ 8.74 (d, J=4.7 Hz, 1H), 8.25 (td, J=7.9, 1.6 Hz, 1H), 8.12 (d, J=8.1 Hz, 1H), 7.73-7.69 (m, 1H), 7.59 (d, J=1.3 Hz, 1H), 7.53 (d, J=1.2 Hz, 1H), 5.19 (t, J=6.8 Hz, 1H), 3.99-3.90 (m, 1H), 3.85 (dd, J=14.2, 6.6 Hz, 1H), 2.67 (ddd, J=13.5, 8.5, 5.0 Hz, 1H), 2.38 (s, 3H), 2.21 (s, 3H), 1.96-1.86 (m, 4H), 1.57-1.51 (m, 2H), 1.45-1.38 (m, 2H).

Example 289 and 290

(2-cyclopropyl-6-(3,5-dimethylisoxazol-4-yl)-1H-benzo[d]imidazol-4-yl)(pyridazin-3-yl)(tetrahydrofuran-2-yl)methanol enantiomer 1 (1020-289) and (2-cyclopropyl-6-(3,5-dimethylisoxazol-4-yl)-1H-benzo[d]imidazol-4-yl)(pyridazin-3-yl)(tetrahydrofuran-2-yl)methanol enantiomer 2 (1020-290)

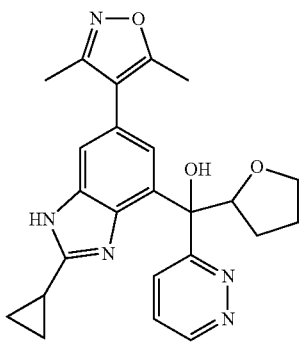 [SMILES: Cc1noc(C)c1-c1cc(C(O)(c2cccnn2)C2CCCO2)c2nc(C3CC3)[nH]c2c1]

Enantiomers were resolved using a Chiralpak AD-H column (Heptane:IPA, 70:30) to afford the two title compounds.

Example 291 tert-butyl 2-cyclopropyl-6-(3,5-dimethylisoxazol-4-yl)-4-(hydroxy(2-(methylthio)phenyl)(tetrahydrofuran-2-yl)methyl)-1H-benzo[d]imidazole-1-carboxylate (1020-291)

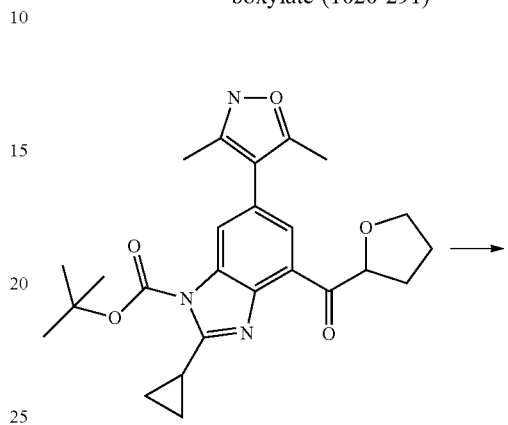

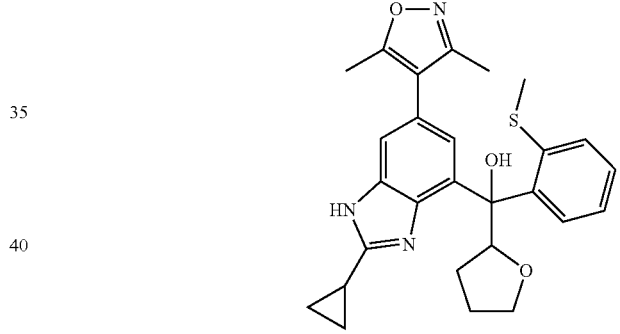

The ketone (0.1 g) was dissolved in 2-Me-THF (4 ml), cooled to −20 C, and the Grignard reagent (0.1 ml, 0.5 M in THF) added drop wise, After stirring for 20 min, MeOH (1 ml) was added, volatiles were removed and the residue purified by reverse phase HPLC (5-95% MeCN in water, 0.1% TFA) to afford tert-butyl 2-cyclopropyl-6-(3,5-dimethylisoxazol-4-yl)-4-(hydroxy(2-(methylthio)phenyl)(tetrahydrofuran-2-yl)methyl) 1H-benzo[d]imidazole-1-carboxylate.

LCMS (m/z+1) 440.1. $^1$H NMR (400 MHz, Acetonitrile-d3) δ 12.05 (s, 1H), 7.81-7.70 (m, 1H), 7.45 (d, J=1.5 Hz, 1H), 7.40 (d, J=1.4 Hz, 0H), 7.27-7.17 (m, 2H), 7.14 (ddd, J=7.7, 6.2, 2.6 Hz, 1H), 7.07 (d, J=1.4 Hz, 0H), 7.00 (d, J=4.4 Hz, 1H), 6.46 (d, J=1.5 Hz, 1H), 4.73 (dd, J=7.6, 6.2 Hz, 1H), 4.34 (d, J=13.0 Hz, 1H), 3.96-3.79 (m, 2H), 3.77-3.58 (m, 1H), 2.52 (tt, J=8.5, 5.1 Hz, 2H), 2.24 (s, 1H), 1.92 (s, 2H), 1.83-1.48 (m, 7H), 1.45-1.33 (m, 2H), 1.34-1.24 (m, 1H), 1.19 (s, 1H).

Example 292

1-(2-cyclopropyl-6-(3,5-dimethylisoxazol-4-yl)-1H-benzo[d]imidazol-4-yl)-2-methyl-1-(tetrahydrofuran-2-yl)propan-1-ol (1020-292)

Example 293

(6-bromo-3-fluoro-2-methylpyridin-4-yl)(2-cyclopropyl-6-(3,5-dimethylisoxazol-4-yl)-1H-benzo[d]imidazol-4-yl)(tetrahydrofuran-2-yl)methanol (1020-293)

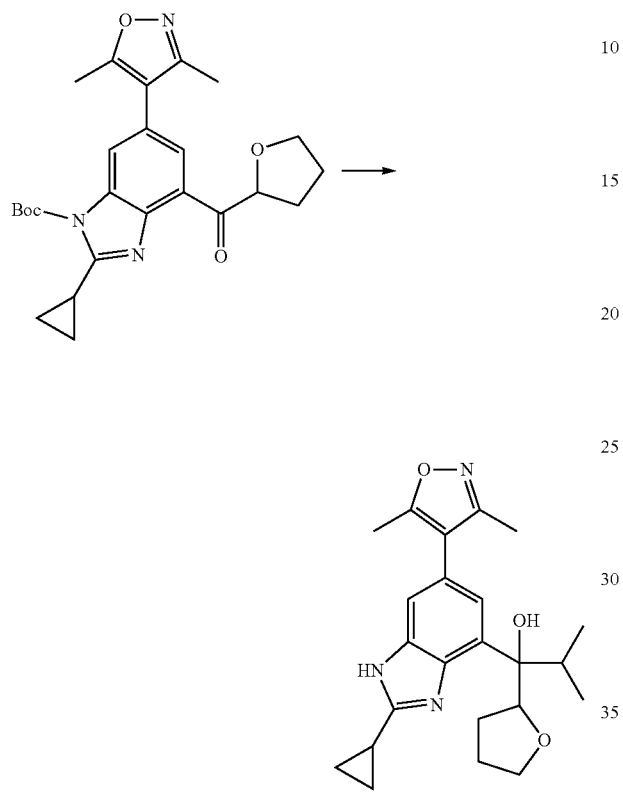

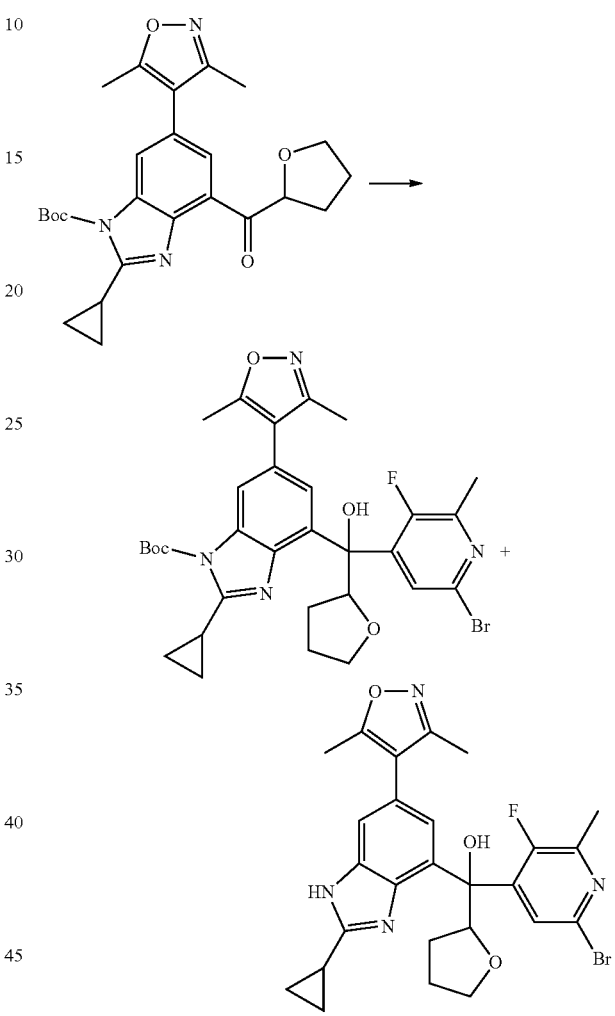

To a solution of tert-butyl 2-cyclopropyl-6-(3,5-dimethylisoxazol-4-yl)-4-(tetrahydrofuran-2-carbonyl)-1H-benzo[d]imidazole-1-carboxylate (100 mg, 0.22 mmol) in toluene (4 mL) was added iPrMgCl (273 mg, 2.66 mmol) and the solution was stirred at room temperature overnight. EtOAc (100 mL) was added and the solution was washed with aq NH₄Cl, brine and dried over Na₂SO₄. Solvent was removed and the residue was purified by silica gel column (0-15% MeOH in CH₂Cl₂), then (0-60% EtOAc in hexane) to give product as N-Boc intermediate which was dissolved in a mixture of MeTHF (2 mL), TFA (2 mL) and H₂O (0.2 mL). The solution was heated at 50° C. for 1 h. The solution was concentrated to dryness and the residue was purified by HPLC to give 1-(2-cyclopropyl-6-(3,5-dimethylisoxazol-4-yl)-1H-benzo[d]imidazol-4-yl)-2-methyl-1-(tetrahydrofuran-2-yl)propan-1-ol.

$C_{23}H_{29}N_3O_3$. MS. m/z 396.2 (M+1). $^1$H NMR (Methanol-$d_4$) δ 7.45 (d, J=1.4 Hz, 1H), 7.19 (d, J=1.5 Hz, 1H), 4.64 (t, J=7.4 Hz, 1H), 3.91-3.76 (m, 2H), 2.66 (tt, J=8.5, 5.1 Hz, 1H), 2.54-2.38 (m, 4H), 2.25 (s, 3H), 1.88-1.73 (m, 2H), 1.70-1.60 (m, 2H), 1.58-1.49 (m, 2H), 1.46-1.33 (m, 2H), 0.94 (dd, J=13.2, 6.8 Hz, 6H).

To a solution of 2-bromo-5-fluoro-6-methyl-2-pyridine (337 mg, 1.77 mmol) in THF (10 mL) was added BuLi (0.113 mg, 1.77 mmol) and the solution was stirred at −78° C. for 1 h. To the solution was added a solution of tert-butyl 2-cyclopropyl-6-(3,5-dimethylisoxazol-4-yl)-4-(tetrahydrofuran-2-carbonyl)-1H-benzo[d]imidazole-1-carboxylate (200 mg, 0.443 mmol) in THF (2 mL) and the solution was stirred at −78° C. for 1 h. Aq NH₄Cl was added and the solution was extracted with EtOAc (200 mL). The organic solution was washed with brine and dried over Na₂OS₄. Solvent was removed and the residue was purified by silica gel column chromatography (0-10% MeOH in CH₂Cl₂) to give tert-butyl 4-((6-bromo-3-fluoro-2-methylpyridin-4-yl)(hydroxy)(tetrahydrofuran-2-yl)methyl)-2-cyclopropyl-6-(3,5-dimethylisoxazol-4-yl)-1H-benzo[d]imidazole-1-carboxylate and (6-bromo-3-fluoro-2-methylpyridin-4-yl)(2-cyclopropyl-6-(3,5-dimethylisoxazol-4-yl)-1H-benzo[d]imidazol-4-yl)(tetrahydrofuran-2-yl)methanol.

tert-Butyl 4-((6-bromo-3-fluoro-2-methylpyridin-4-yl)(hydroxy)(tetrahydrofuran-2-yl)methyl)-2-cyclopropyl-6-(3,5-dimethylisoxazol-4-yl)-1H-benzo[d]imidazole-1-carboxylate: $C_{31}H_{34}BrFN_4O_5$. MS. m/z 640.6 (M+1). $^1$H NMR (Chloroform-d) δ 7.88 (d, J=5.1 Hz, 1H), 7.72 (d, J=1.4 Hz, 1H), 7.32 (dd, J=2.4, 1.5 Hz, 1H), 5.25 (t, J=6.6 Hz, 1H), 4.05-3.95 (m, 1H), 3.88 (td, J=7.5, 5.2 Hz, 1H), 2.91-2.74 (m, 1H), 2.43 (s, 3H), 2.34 (d, J=3.4 Hz, 3H), 2.29 (s, 3H), 2.02-1.76 (m, 4H), 1.68 (s, 9H), 1.18 (ddt, J=10.8, 5.3, 2.6 Hz, 4H).

(6-Bromo-3-fluoro-2-methylpyridin-4-yl)(2-cyclopropyl-6-(3,5-dimethylisoxazol-4-yl)-1H-benzo[d]imidazol-4-yl)(tetrahydrofuran-2-yl)methanol: $C_{26}H_{26}BrFN_4O_3$. MS. m/z 541.5 (M+1). $^1$H NMR (Methanol-d4). $^1$H NMR (Methanol-$d_4$) δ 8.07 (d, J=5.0 Hz, 1H), 7.47 (d, J=1.4 Hz, 1H), 7.31-7.21 (m, 1H), 5.07 (t, J=6.5 Hz, 1H), 4.01 (q, J=7.1 Hz, 1H), 3.95-3.81 (m, 1H), 2.77-2.63 (m, 1H), 2.37-2.29 (m, 6H), 2.17 (s, 3H), 2.01-1.86 (m, 3H), 1.76 (d, J=6.0 Hz, 1H), 1.56 (dd, J=8.5, 2.8 Hz, 2H), 1.47-1.33 (m, 2H).

Example 294

(2-cyclopropyl-6-(3,5-dimethylisoxazol-4-yl)-1H-benzo[d]imidazol-4-yl)(3-fluoro-2-methylpyridin-4-yl)(tetrahydrofuran-2-yl)methanol (1020-294)

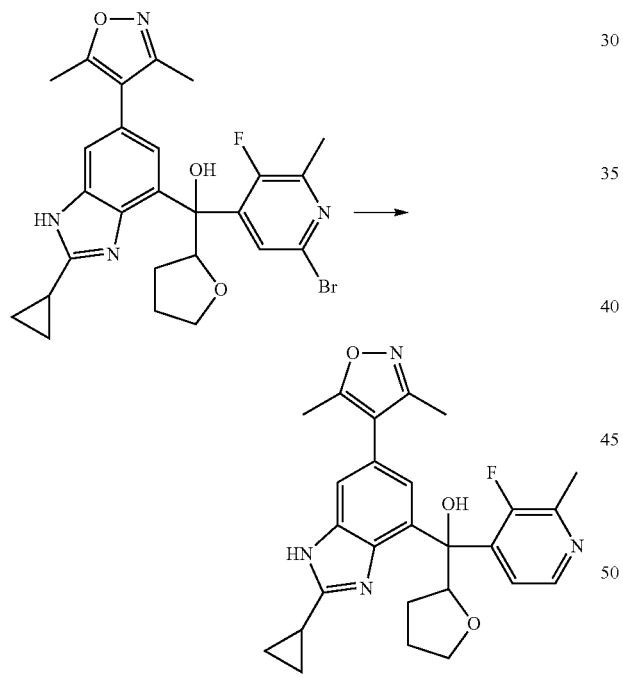

A mixture of (6-bromo-3-fluoro-2-methylpyridin-4-yl)(2-cyclopropyl-6-(3,5-dimethylisoxazol-4-yl)-1H-benzo[d]imidazol-4-yl)(tetrahydrofuran-2-yl)methanol (25 mg, 0.046 mmol) and Pd/C (10% 10 mg) in MeOH (5 mL) was stirred under $H_2$ balloon for 3 h. Reaction mixture was filtered and the filtrate was concentrated to dryness to give (2-cyclopropyl-6-(3,5-dimethylisoxazol-4-yl)-1H-benzo[d]imidazol-4-yl)(3-fluoro-2-methylpyridin-4-yl)(tetrahydrofuran-2-yl)methanol.

$C_{26}H_{27}FN_4O_3$. MS. m/z 463.2 (M+1). $^1$H NMR (Methanol-$d_4$) δ 8.38 (d, J=5.5 Hz, 1H), 8.10 (t, J=5.8 Hz, 1H), 7.50 (d, J=1.4 Hz, 1H), 7.22 (t, J=1.3 Hz, 1H), 5.11 (t, J=7.0 Hz, 1H), 4.09-3.96 (m, 1H), 3.89 (ddd, J=7.9, 6.4, 4.4 Hz, 1H), 2.73 (tt, J=8.4, 5.0 Hz, 1H), 2.44 (d, J=3.2 Hz, 3H), 2.34 (s, 3H), 2.16 (s, 3H), 2.04-1.90 (m, 3H), 1.78 (qd, J=7.1, 4.8 Hz, 1H), 1.62-1.50 (m, 2H), 1.43 (tt, J=5.1, 3.8 Hz, 2H).

Example 295

(2-cyclopropyl-6-(3,5-dimethylisoxazol-4-yl)-1H-benzo[d]imidazol-4-yl)(3-fluoro-2-methyl-6-(methylthio)pyridin-4-yl)(tetrahydrofuran-2-yl)methanol (1020-295)

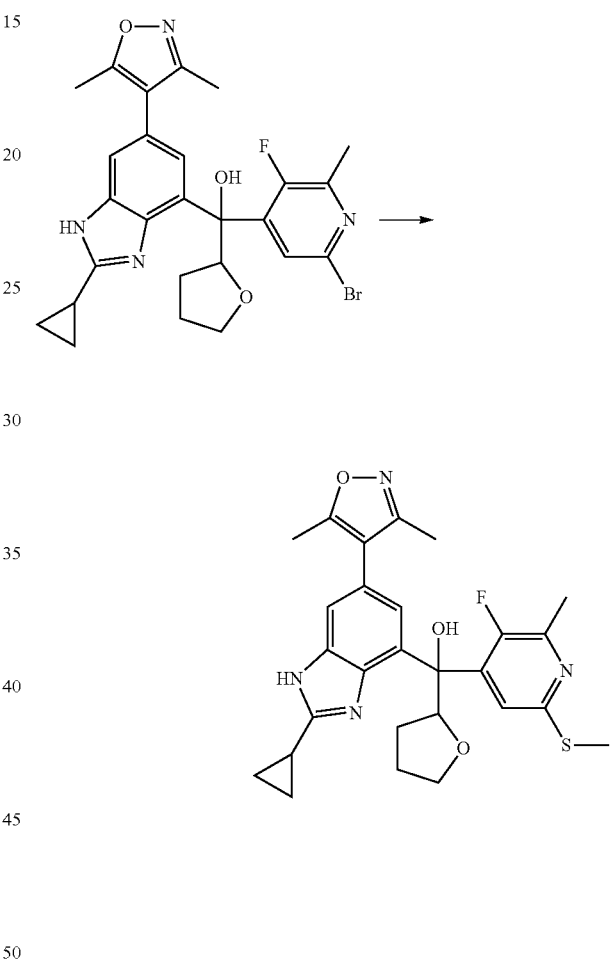

To a solution of (6-bromo-3-fluoro-2-methylpyridin-4-yl)(2-cyclopropyl-6-(3,5-dimethylisoxazol-4-yl)-1H-benzo[d]imidazol-4-yl)(tetrahydrofuran-2-yl)methanol (20 mg, 0.037 mmol) in DMF (5 mL) was added NaSMe (0.1 g, excess) and the mixture was heated a 120° C. for 1 h. Solvent was removed and the residue was purified by HPLC to give (2-cyclopropyl-6-(3,5-dimethylisoxazol-4-yl)-1H-benzo[d]imidazol-4-yl)(3-fluoro-2-methyl-6-(methylthio)pyridin-4-yl)(tetrahydrofuran-2-yl)methanol.

$C_{27}H_{29}FN_4O_3S$. MS m/z 509.3 (M+1). 1H NMR (Methanol-$d_4$) δ 7.74-7.68 (m, 1H), 7.45 (d, J=1.4 Hz, 1H), 7.22 (t, J=1.4 Hz, 1H), 5.06 (d, J=6.8 Hz, 1H), 4.05-3.96 (m, 1H), 3.89 (t, J=6.9 Hz, 1H), 2.68 (dq, J=9.2, 5.3, 4.6 Hz, 1H), 2.54 (s, 3H), 2.37-2.28 (m, 6H), 2.16 (s, 3H), 1.92 (s, 3H), 1.74 (d, J=7.3 Hz, 1H), 1.55 (dd, J=8.5, 2.8 Hz, 2H), 1.45-1.35 (m, 2H).

Example 296

(2-cyclopropyl-6-(3,5-dimethylisoxazol-4-yl)-1H-benzo[d]imidazol-4-yl)(5,5-dimethyltetrahydrofuran-2-yl)(pyridin-2-yl)methanol (1020-296)

Step 1: Tert-butyl 2-cyclopropyl-6-(3,5-dimethylisoxazol-4-yl)-4-((5,5-dimethyltetrahydrofuran-2-yl)(hydroxy)methyl)-1H-benzo[d]imidazole-1-carboxylate

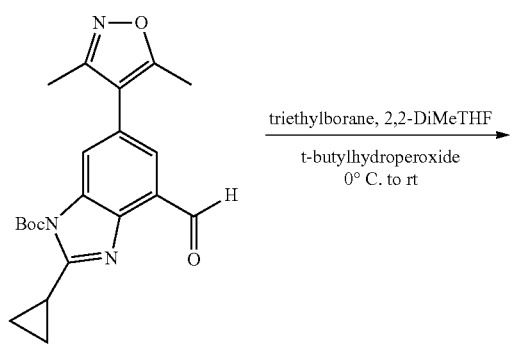

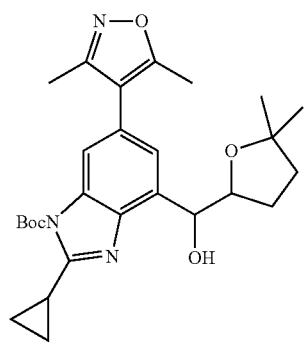

Into a flask containing tert-butyl 2-cyclopropyl-6-(3,5-dimethylisoxazol-4-yl)-4-formyl-1H-benzo[d]imidazole-1-carboxylate (600 mg, 1.57 mmol, 1 equiv.) was added 2,2-dimethyltetrahydrofuran (20 mL) and cooled to 0° C. before adding triethylborane (2.2 mL, 14.16 mmol, 9 equiv.). Tert-butylhydroperoxide (1.7 mL, 9.43 mmol, 6 equiv., 6 M decanes) was added slowly to the reaction mixture and the reaction allowed to warm up slowly to room temperature. After completion, the reaction was quenched with NH$_4$OH solution (5 mL) and extracted with EtOAc and washed with water (spiked with a solution of FeSO$_4$.H$_2$SO$_4$.H$_2$0 (2 mL)) and then with saturated NH$_4$Cl. After drying with MgSO$_4$, it was filtered and concentrated to dryness. Purification was carried out by flash column chromatography to tert-butyl 2-cyclopropyl-6-(3,5-dimethylisoxazol-4-yl)-4-((5,5-dimethyltetrahydrofuran-2-yl)(hydroxy)methyl)-1H-benzo[d]imidazole-1-carboxylate (505 mg, y. 41%, dr 3:2).
LCMS (m/z+1) 481.14

Step 2: tert-butyl-2-cyclopropyl-6-(3,5-dimethylisoxazol-4-yl)-4-(5,5-dimethyltetrahydrofuran-2-carbonyl)-1H-benzo[d]imidazole-1-carboxylate

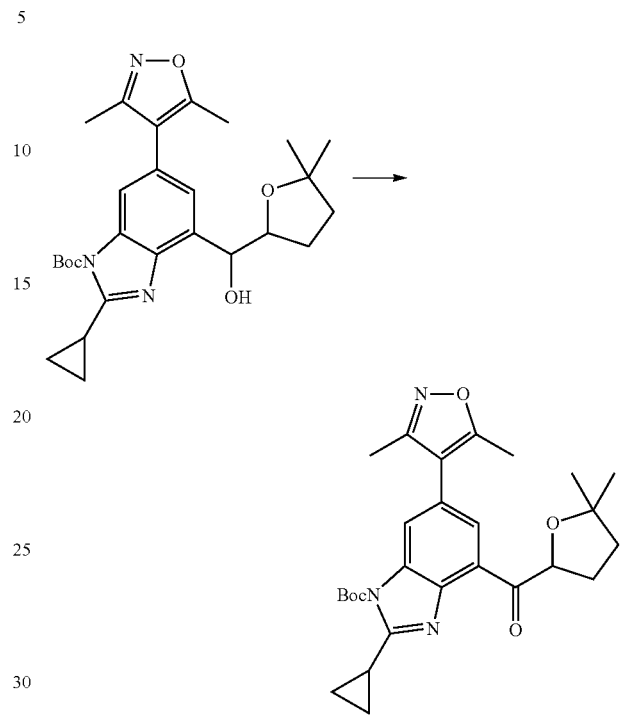

Into a flask containing to tert-butyl 2-cyclopropyl-6-(3,5-dimethylisoxazol-4-yl)-4-((5,5-dimethyltetrahydrofuran-2-yl)(hydroxy)methyl)-1H-benzo[d]imidazole-1-carboxylate (505 mg, 0.73 mmol, 1 equiv.) was added DCM (100 mL) and Dess-Martin periodinane (467 mg, 1.10 mmol, 1.5 equiv.). After completion, the reaction was quenched with sodium thiosulfate solution and allowed to stir for several minutes. It was extracted with DCM and washed with water and saturated NH$_4$Cl. After drying with MgSO$_4$, it was filtered and concentrated to dryness. Purification was carried out by flash column chromatography to furnish tert-butyl 2-cyclopropyl-6-(3,5-dimethylisoxazol-4-yl)-4-(5,5-dimethyltetrahydrofuran-2-carbonyl)-1H-benzo[d]imidazole-1-carboxylate (202 mg, y. 57%).
LCMS (m/z+1) 480.51

Step 3: (2-cyclopropyl-6-(3,5-dimethylisoxazol-4-yl)-1H-benzo[d]imidazol-4-yl)(5,5-dimethyltetrahydrofuran-2-yl)(pyridin-2-yl)methanol

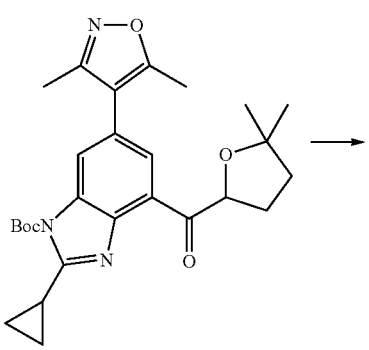

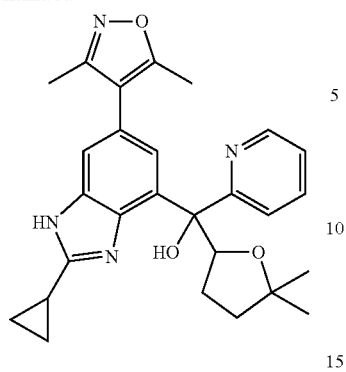

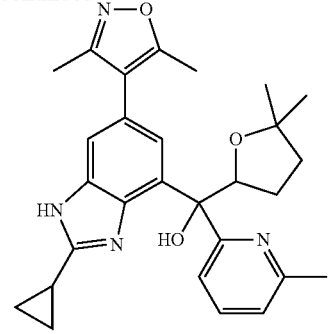

In a flame dried flask containing 2-bromopyrimidine (99 μL, 1.04 mmol, 10 equiv.) in THF was added n-BuLi (0.71 mL, 1.14 mmol, 11 equiv.) at −78° C. The solution was allowed to stir for 30 minutes, followed by the addition furnish tert-butyl 2-cyclopropyl-6-(3,5-dimethylisoxazol-4-yl)-4-(5,5-dimethyltetrahydrofuran-2-carbonyl)-1H-benzo[d]imidazole-1-carboxylate (50 mg, 0.10 mmol, 1 equiv.). The solution was allowed to warm to room temperature. Once complete, the solution was quenched with water and extracted three times with EtOAc. The combined organic layers were washed with saturated NaCl, dried over sodium sulfate, filtered and concentrated in vacuo. To the crude product was added 5 mL of TFA and was allowed to stir for 30 minutes. The solution was concentrated in vacuo and was purified via reverse phase HPLC to afford (2-cyclopropyl-6-(3,5-dimethylisoxazol-4-yl)-1H-benzo[d]imidazol-4-yl)(5,5-dimethyltetrahydrofuran-2-yl)(pyridin-2-yl)methanol.

$^1$H NMR (400 MHz, Methanol-d4) δ 8.76-8.59 (m, 1H), 7.96 (t, J=7.6 Hz, 1H), 7.89-7.80 (m, 1H), 7.71 (d, J=1.5 Hz, 1H), 7.55-7.39 (m, 1H), 5.24 (t, J=7.3 Hz, 1H), 2.61 (ddd, J=8.5, 5.0, 3.5 Hz, 1H), 2.41 (s, 3H), 2.24 (s, 3H), 2.05-1.69 (m, 4H), 1.68-1.44 (m, 2H), 1.44-1.30 (m, 1H), 1.25 (s, 3H), 1.17 (s, 3H), 1.00 (t, J=7.4 Hz, 1H). $^{19}$F NMR (377 MHz, Methanol-d4) δ −77.90.

Example 297

(2-cyclopropyl-6-(3,5-dimethylisoxazol-4-yl)-1H-benzo[d]imidazol-4-yl)(5,5-dimethyltetrahydrofuran-2-yl)(6-methylpyridin-2-yl)methanol (1020-297)

Into a flask containing tert-butyl 2-cyclopropyl-6-(3,5-dimethylisoxazol-4-yl)-4-(5,5-dimethyltetrahydrofuran-2-carbonyl)-1H-benzo[d]imidazole-1-carboxylate (50 mg, 0.10 mmol, 1 equiv.) is added THF (5 mL) and to it is added (6-methylpyridin-2-yl)magnesium bromide (2.5 mL, 0.63 mmol, 6 equiv., 0.25 M THF, Rieke Metals). After completion, the reaction was quenched and extracted with EtOAc and washed with water, saturated NH$_4$Cl. After drying with MgSO$_4$, it was filtered and concentrated to dryness. To the crude material is added TFA (5 mL) and allowed to stir for 30 min. After the reaction was complete, it was concentrated in vacuo. Purification was carried out by reverse phase HPLC to furnish (2-cyclopropyl-6-(3,5-dimethylisoxazol-4-yl)-1H-benzo[d]imidazol-4-yl)(5,5-dimethyltetrahydrofuran-2-yl)(6-methylpyridin-2-yl)methanol (as a racemic single diastereomer).

$^1$H NMR (400 MHz, Methanol-d4) δ 7.99-7.80 (m, 1H), 7.70 (q, J=3.5 Hz, 3H), 7.50-7.46 (m, 1H), 7.37 (s, 1H), 5.21 (t, J=7.3 Hz, 1H), 2.67 (s, 4H), 2.64-2.53 (m, 1H), 2.41 (s, 4H), 2.24 (s, 4H), 2.05-1.81 (m, 2H), 1.83-1.70 (m, 1H), 1.64-1.55 (m, 1H), 1.54-1.47 (m, 2H), 1.36 (dd, J=6.1, 2.6 Hz, 2H), 1.25 (s, 4H), 1.17 (s, 4H). $^{19}$F NMR (377 MHz, Methanol-d4) δ −77.87.

Example 298

(2-cyclopropyl-6-(3,5-dimethylisoxazol-4-yl)-1H-benzo[d]imidazol-4-yl)(5,5-dimethyltetrahydrofuran-2-yl)(pyridazin-3-yl)methanol (1020-298)

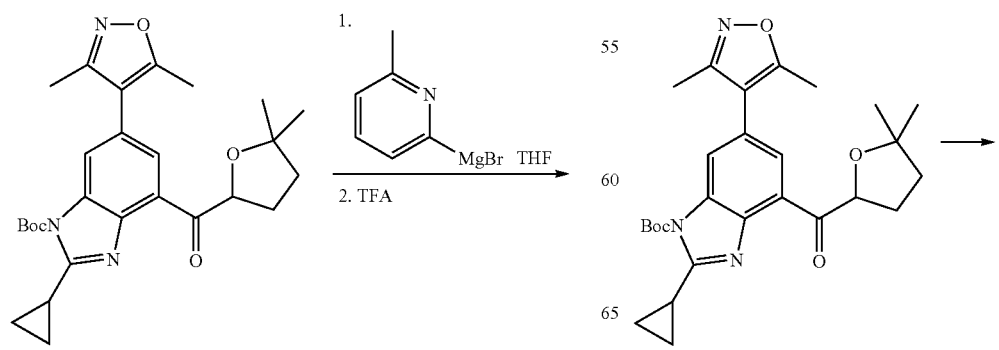

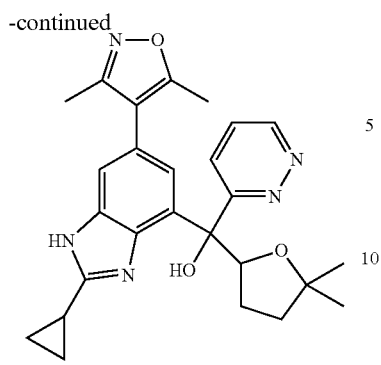
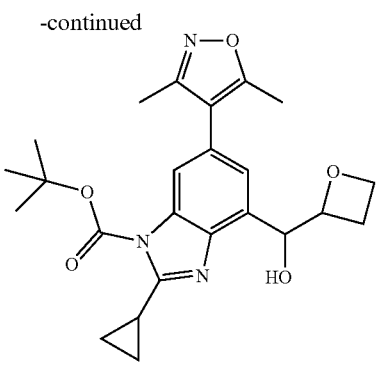

Into a flask containing pyridazine (110 μL, 1.15 mml, 8 equiv.) was added MeTHF (5 mL) and to it slowly added TMP.MgCl.LiCl (1.46 mL, 1.46 mmol, 10 equiv., 1 M) at −78° C. over 10 min. After 45 minutes tert-butyl 2-cyclopropyl-6-(3,5-dimethylisoxazol-4-yl)-4-(5,5-dimethyltetrahydrofuran-2-carbonyl)-1H-benzo[d]imidazole-1-carboxylate (70 mg, 0.14 mmol, 1 equiv.) dissolved in MeTHF (2 ML) is added slowly to the reaction. After completion, the reaction was quenched and extracted with EtOAc and washed with water, saturated $NH_4Cl$. After drying with $MgSO_4$, it was filtered and concentrated to dryness. To the crude material is added TFA (5 mL) and allowed to stir for 30 min. After the reaction was complete, it was concentrated in vacuo. Purification was carried out by reverse phase HPLC (2-cyclopropyl-6-(3,5-dimethylisoxazol-4-yl)-1H-benzo[d]imidazol-4-yl)(5,5-dimethyltetrahydrofuran-2-yl)(pyridazin-3-yl)methanol (as a racemic single diastereomer).

LCMS (m/z+1) 460.23. $^1$H NMR (400 MHz, Methanol-d4) δ 9.33 (dd, J=2.3, 1.2 Hz, 0H), 9.18 (dd, J=5.5, 1.2 Hz, 0H), 9.11 (dd, J=4.9, 1.6 Hz, 1H), 8.12 (dd, J=8.7, 1.6 Hz, 1H), 8.03 (dd, J=5.5, 2.4 Hz, 0H), 7.65 (d, J=1.5 Hz, 1H), 7.53 (d, J=1.5 Hz, 0H), 7.48 (d, J=1.5 Hz, 1H), 5.41 (t, J=7.4 Hz, 1H), 2.65 (s, 3H), 2.43 (d, J=4.8 Hz, 2H), 2.38 (s, 3H), 2.34-2.11 (m, 5H), 2.13-1.86 (m, 3H), 1.86-1.58 (m, 4H), 1.58-1.45 (m, 4H), 1.45-1.34 (m, 4H), 1.34-1.10 (m, 8H), 1.06 (s, 1H). 19F NMR (377 MHz, Methanol-d4) δ −77.96.

Example 299

Preparation of (2-cyclopropyl-6-(3,5-dimethylisoxazol-4-yl)-1H-benzo[d]imidazol-4-yl)(oxetan-2-yl)methanol (1020-299)

Step 1: Preparation of tert-butyl 2-cyclopropyl-6-(3,5-dimethylisoxazol-4-yl)-4-(hydroxy(oxetan-2-yl)methyl)-1H-benzo[d]imidazole-1-carboxylate

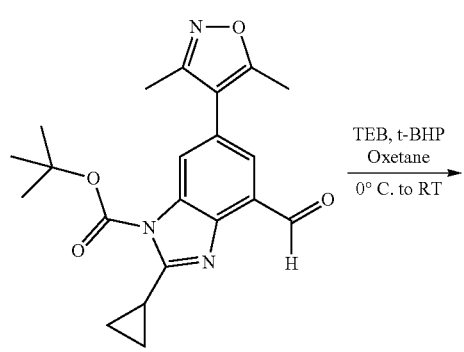

Into a flask containing tert-butyl 2-cyclopropyl-6-(3,5-dimethylisoxazol-4-yl)-4-formyl-1H-benzo[d]imidazole-1-carboxylate (100 mg, 0.73 mmol) is added Oxetane (10 mL) and cooled to 0° C. before adding triethylborane (3.1 mL, 3.14, mmol, 1M in hexanes). Tert-butylhydroperoxide (0.27 mL, 1.6 mmol, 5.5M) is added slowly to the reaction mixture and the reaction was allowed to warm slowly to room temperature. After completion, the reaction was quenched with $NH_4OH$ solution and extracted with EtOAc and washed with water (spiked with a solution of $FeSO_4.H_2SO_4.H_2O$ (2 mL)) and then with saturated $NH_4Cl$. After drying with $MgSO_4$, it was filtered and concentrated to dryness. Purification was carried out by flash column chromatography to afford tert-butyl 2-cyclopropyl-6-(3,5-dimethylisoxazol-4-yl)-4-(hydroxy(oxetan-2-yl)methyl)-1H-benzo[d]imidazole-1-carboxylate.

$C_{24}H_{29}N_3O_5$. MS. m/z 440.5 (M+1).

Step 2: Preparation of tert-butyl 2-cyclopropyl-6-(3,5-dimethylisoxazol-4-yl)-4-(oxetane-2-carbonyl)-1H-benzo[d]imidazole-1-carboxylate

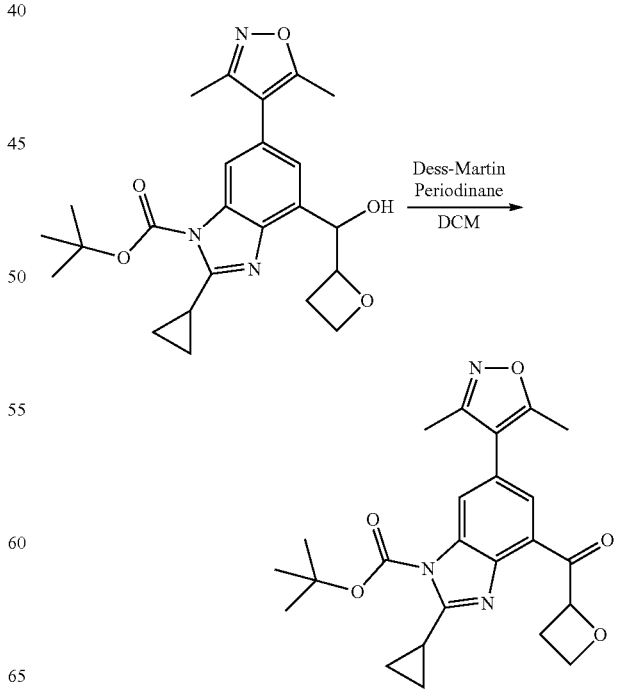

To a flame dried flask containing tert-butyl 2-cyclopropyl-6-(3,5-dimethylisoxazol-4-yl)-4-(hydroxy(oxetan-2-yl)methyl)-1H-benzo[d]imidazole-1-carboxylate (155 mg, 0.35 mmol) was added Dess-Martin Periodinane (0.194 g, 0.46 mmol). The reaction was allowed to stir for 1 hour. Once complete, the solution was quenched with saturated sodium thiosulfate and allowed to stir for 20 minutes. Once complete, the solution was quenched with DI H$_2$O and extracted three times with EtOAc. The combined organic layers were washed with saturated NaCl, dried over sodium sulfate, filtered and concentrated in vacuo and purified via flash column chromatography (97.7 mg, 63% yield).

Step 3: Preparation of (2-cyclopropyl-6-(3,5-dimethylisoxazol-4-yl)-1H-benzo[d]imidazol-4-yl)(oxetan-2-yl)methanol

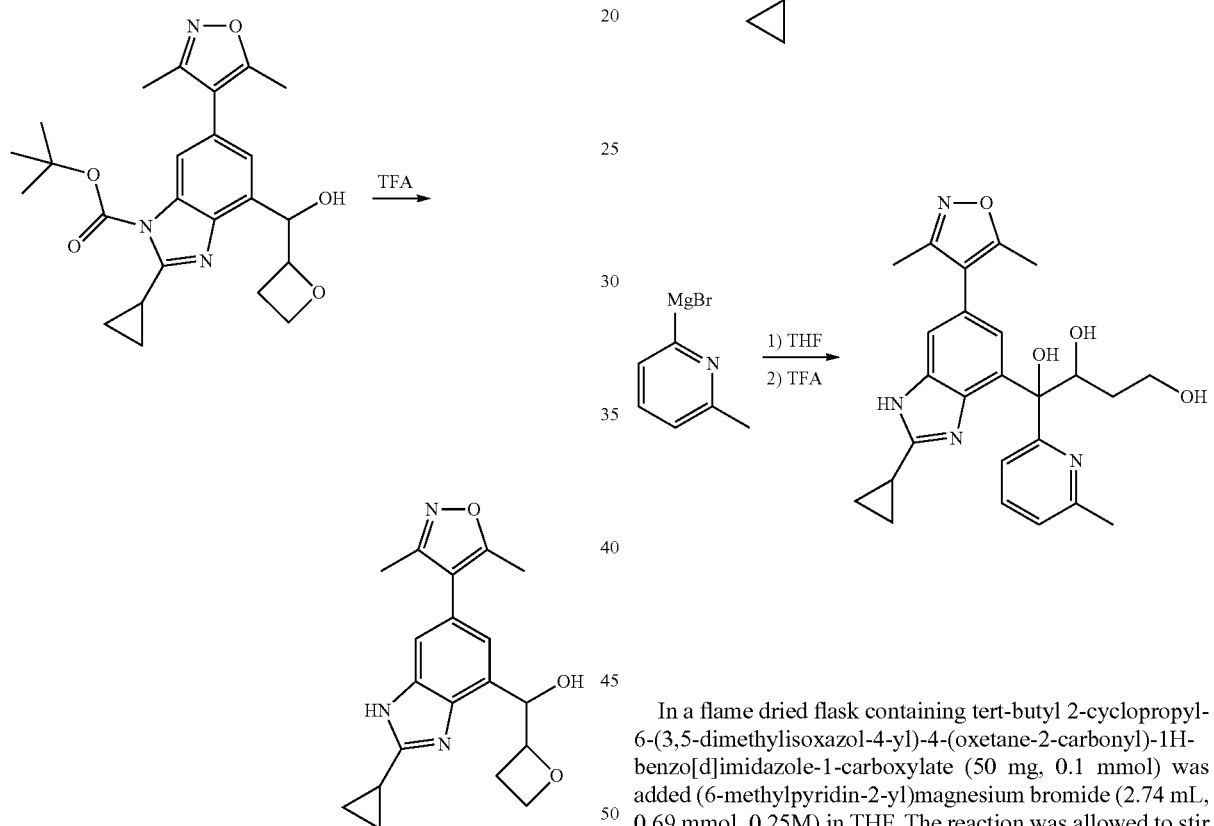

To a flask containing 5 mL of TFS was added tert-butyl 2-cyclopropyl-6-(3,5-dimethylisoxazol-4-yl)-4-(hydroxy(oxetan-2-yl)methyl)-1H-benzo[d]imidazole-1-carboxylate (34 mg, 0.08 mmol). The reaction was allowed to stir for 30 minutes. Once complete, the solution was concentrated in vacuo where is was then purified via reverse phase HPLC to afford (2-cyclopropyl-6-(3,5-dimethylisoxazol-4-yl)-1H-benzo[d]imidazol-4-yl)(oxetan-2-yl)methanol.

$C_{19}H_{21}N_3O_3$. MS. m/z 440.5 (M+1).

Example 300

Preparation of 1-(2-cyclopropyl-6-(3,5-dimethylisoxazol-4-yl)-1H-benzo[d]imidazol-4-yl)-1-(6-methylpyridin-2-yl)butane-1,2,4-triol (1020-300)

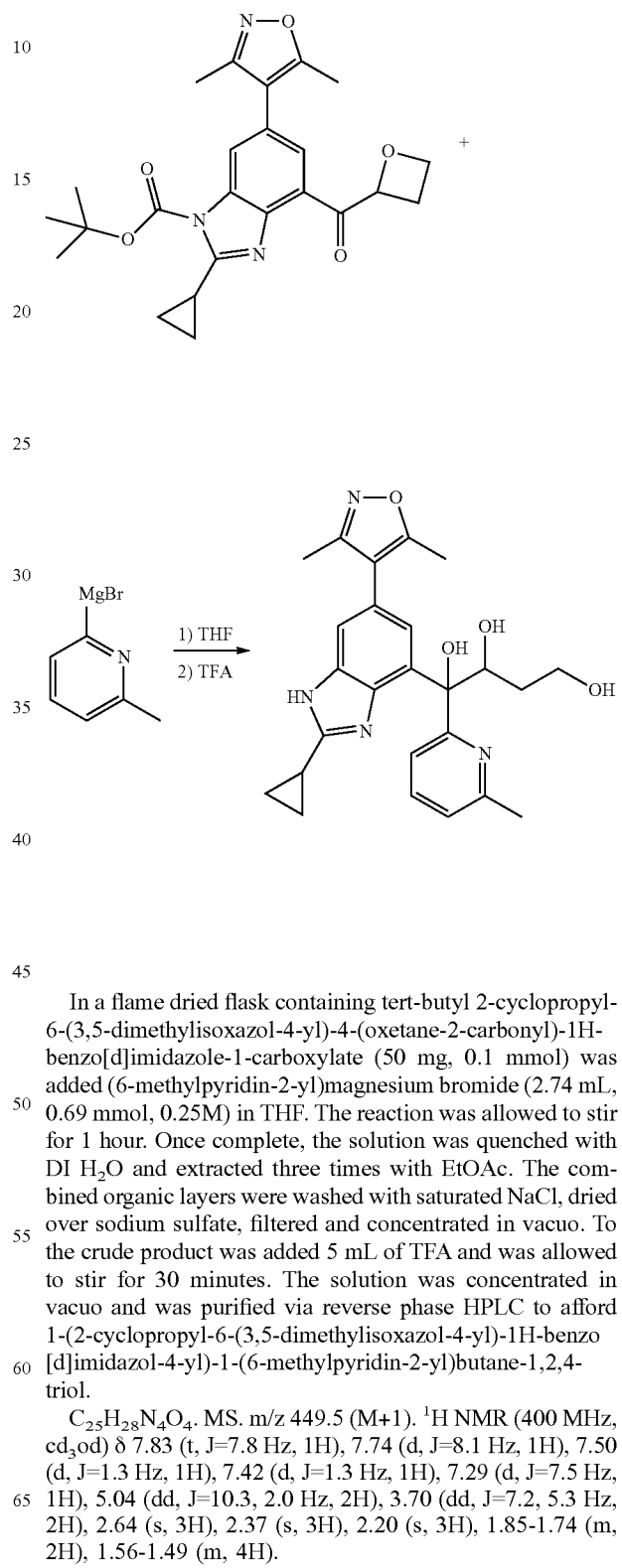

In a flame dried flask containing tert-butyl 2-cyclopropyl-6-(3,5-dimethylisoxazol-4-yl)-4-(oxetane-2-carbonyl)-1H-benzo[d]imidazole-1-carboxylate (50 mg, 0.1 mmol) was added (6-methylpyridin-2-yl)magnesium bromide (2.74 mL, 0.69 mmol, 0.25M) in THF. The reaction was allowed to stir for 1 hour. Once complete, the solution was quenched with DI H$_2$O and extracted three times with EtOAc. The combined organic layers were washed with saturated NaCl, dried over sodium sulfate, filtered and concentrated in vacuo. To the crude product was added 5 mL of TFA and was allowed to stir for 30 minutes. The solution was concentrated in vacuo and was purified via reverse phase HPLC to afford 1-(2-cyclopropyl-6-(3,5-dimethylisoxazol-4-yl)-1H-benzo[d]imidazol-4-yl)-1-(6-methylpyridin-2-yl)butane-1,2,4-triol.

$C_{25}H_{28}N_4O_4$. MS. m/z 449.5 (M+1). $^1$H NMR (400 MHz, cd$_3$od) δ 7.83 (t, J=7.8 Hz, 1H), 7.74 (d, J=8.1 Hz, 1H), 7.50 (d, J=1.3 Hz, 1H), 7.42 (d, J=1.3 Hz, 1H), 7.29 (d, J=7.5 Hz, 1H), 5.04 (dd, J=10.3, 2.0 Hz, 2H), 3.70 (dd, J=7.2, 5.3 Hz, 2H), 2.64 (s, 3H), 2.37 (s, 3H), 2.20 (s, 3H), 1.85-1.74 (m, 2H), 1.56-1.49 (m, 4H).

Example 301

Preparation of (2-cyclopropyl-6-(3,5-dimethylisoxazol-4-yl)-1H-benzo[d]imidazol-4-yl)(pyridin-2-yl)(tetrahydrofuran-3-yl)methanol (1020-301)

Step 1: Preparation of tert-butyl 2-cyclopropyl-6-(3,5-dimethylisoxazol-4-yl)-4-(tetrahydrofuran-3-carbonyl)-1H-benzo[d]imidazole-1-carboxylate

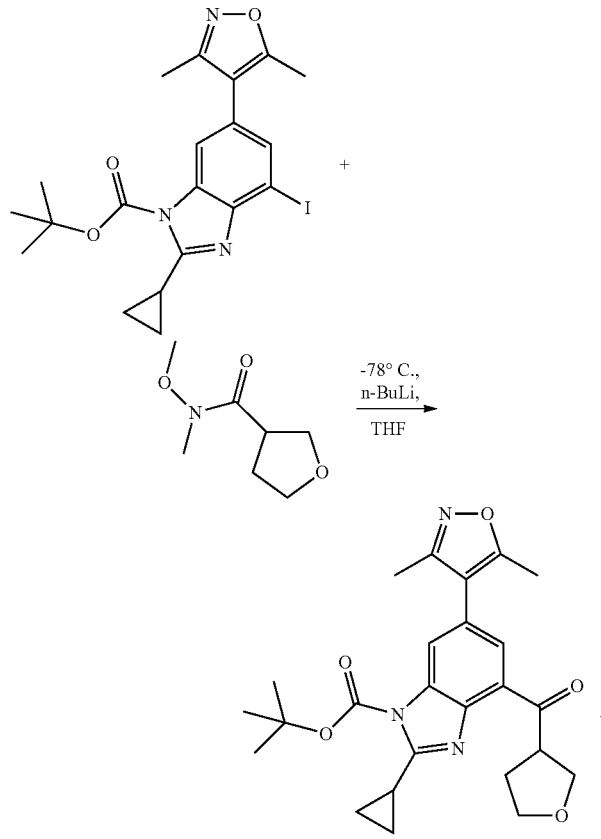

In a flame dried flask containing tert-butyl 2-cyclopropyl-6-(3,5-dimethylisoxazol-4-yl)-4-iodo-1H-benzo[d]imidazole-1-carboxylate (712 mg, 1 mmol) and N-methoxy-N-methyltetrahydrofuran-3-carboxamide (215 mg, 1 mmol) at −78° C. in THF was added n-BuLi (1.1 mL, 2 mmol, 1.6M). The solution was allowed to stir for 10 minutes, then was pulled from the cold bath to warm to room temperature. Once complete, the solution was quenched with DI H₂O and extracted three times with EtOAc. The combined organic layers were washed with saturated NaCl, dried over sodium sulfate, filtered and concentrated in vacuo and purified via flash column chromatography to afford tert-butyl 2-cyclopropyl-6-(3,5-dimethylisoxazol-4-yl)-4-(tetrahydrofuran-3-carbonyl)-1H-benzo[d]imidazole-1-carboxylate (0.56 mg, 46% yield).

$C_{25}H_{29}N_3O_5$. MS. m/z 452.5 (M+1).

Step 2: Preparation of (2-cyclopropyl-6-(3,5-dimethylisoxazol-4-yl)-1H-benzo[d]imidazol-4-yl)(pyridin-2-yl)(tetrahydrofuran-3-yl)methanol

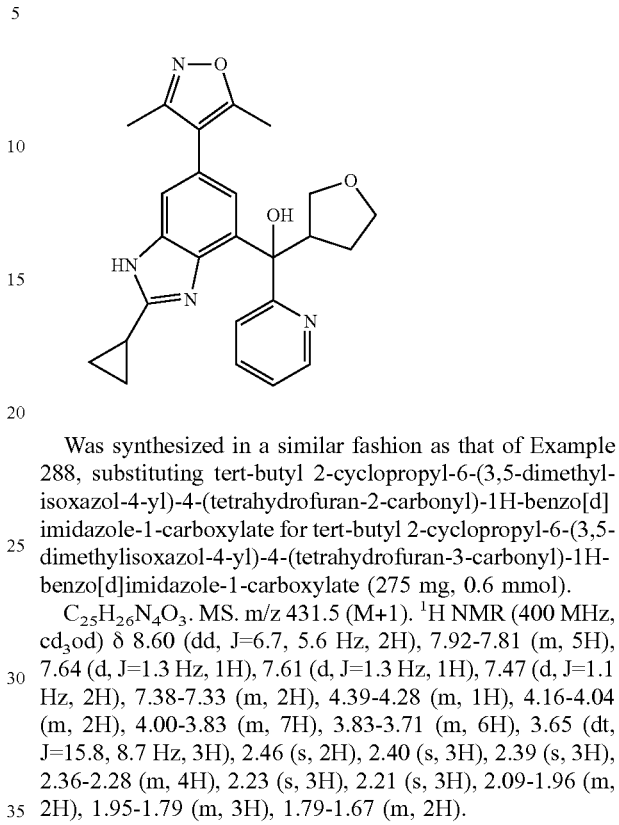

Was synthesized in a similar fashion as that of Example 288, substituting tert-butyl 2-cyclopropyl-6-(3,5-dimethylisoxazol-4-yl)-4-(tetrahydrofuran-2-carbonyl)-1H-benzo[d]imidazole-1-carboxylate for tert-butyl 2-cyclopropyl-6-(3,5-dimethylisoxazol-4-yl)-4-(tetrahydrofuran-3-carbonyl)-1H-benzo[d]imidazole-1-carboxylate (275 mg, 0.6 mmol).

$C_{25}H_{26}N_4O_3$. MS. m/z 431.5 (M+1). ¹H NMR (400 MHz, cd₃od) δ 8.60 (dd, J=6.7, 5.6 Hz, 2H), 7.92-7.81 (m, 5H), 7.64 (d, J=1.3 Hz, 1H), 7.61 (d, J=1.3 Hz, 1H), 7.47 (d, J=1.1 Hz, 2H), 7.38-7.33 (m, 2H), 4.39-4.28 (m, 1H), 4.16-4.04 (m, 2H), 4.00-3.83 (m, 7H), 3.83-3.71 (m, 6H), 3.65 (dt, J=15.8, 8.7 Hz, 3H), 2.46 (s, 2H), 2.40 (s, 3H), 2.39 (s, 3H), 2.36-2.28 (m, 4H), 2.23 (s, 3H), 2.21 (s, 3H), 2.09-1.96 (m, 2H), 1.95-1.79 (m, 3H), 1.79-1.67 (m, 2H).

Example 302

Preparation of (2-cyclopropyl-6-(3,5-dimethylisoxazol-4-yl)-1H-benzo[d]imidazol-4-yl)(6-methylpyridin-2-yl)(tetrahydrofuran-3-yl)methanol (1020-302)

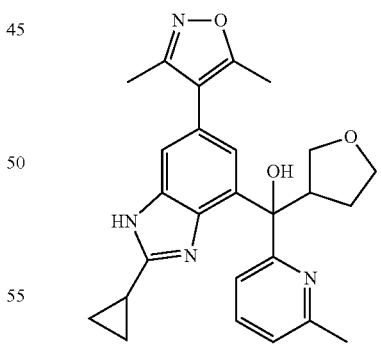

(2-cyclopropyl-6-(3,5-dimethylisoxazol-4-yl)-1H-benzo[d]imidazol-4-yl)(6-methylpyridin-2-yl)(tetrahydrofuran-3-yl)methanol was synthesized in a similar fashion as that of Example 301 step 2, substituting pyridin-2-ylmagnesium bromide for (6-methylpyridin-2-yl)magnesium bromide (2.4 mL, 0.61 mmol, 0.25 M).

$C_{26}H_{28}N_4O_3$. MS. m/z 445.5 (M+1). ¹H NMR (400 MHz, cd₃od) δ 7.89 (ddd, J=13.2, 12.1, 7.8 Hz, 3H), 7.75-7.67 (m, 3H), 7.63 (dd, J=8.3, 1.3 Hz, 2H), 7.49 (dd, J=3.1, 1.3 Hz, 2H), 7.37 (d, J=7.7 Hz, 1H), 7.33 (d, J=7.7 Hz, 1H), 4.16-4.04 (m, 1H), 3.97-3.85 (m, 5H), 3.83-3.72 (m, 5H), 3.70-3.61 (m, 3H), 2.71-2.60 (m, 9H), 2.41 (s, 3H), 2.40 (s, 3H), 2.24 (s, 3H), 2.23 (s, 3H), 2.03 (ddd, J=18.6, 11.8, 5.6 Hz, 2H), 1.97-1.80 (m, 3H), 1.80-1.68 (m, 2H).

Example 303

(2-cyclopropyl-6-(3,5-dimethylisoxazol-4-yl)-1H-benzo[d]imidazol-4-yl)(6-methylpyridin-2-yl)(tetrahydro-2H-pyran-2-yl)methanol (1020-303)

Step 1: Preparation of tert-butyl 2-cyclopropyl-6-(3,5-dimethylisoxazol-4-yl-4-(tetrahydro-2H pyran-2-carbonyl)-1H-benzo[d]imidazole-1-carboxylate

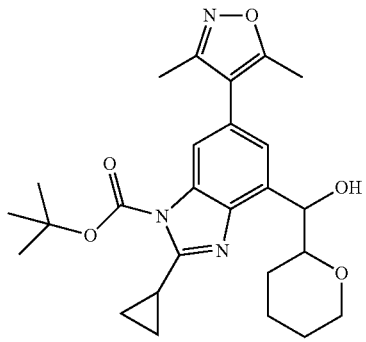 [SMILES: Cc1noc(C)c1-c1cc(C(O)C2CCCCO2)c2nc(C3CC3)n(C(=O)OC(C)(C)C)c2c1]

Tert-butyl 2-cyclopropyl-6-(3,5-dimethylisoxazol-4-yl)-4-(tetrahydro-2H-pyran-2-carbonyl)-1H-benzo[d]imidazole-1-carboxylate was synthesized in a similar fashion as tert-butyl 2-cyclopropyl-6-(3,5-dimethylisoxazol-4-yl)-4-(hydroxy(oxetan-2-yl)methyl)-1H-benzo[d]imidazole-1-carboxylate, substituting the oxetane solvent for tetrahydropyran.
$C_{26}H_{33}N_3O_5$. MS. m/z 468.6 (M+1).

Step 2: Preparation of tert-butyl 2-cyclopropyl-6-(3,5-dimethylisoxazol-4-yl)-(tetrahydro-2H-pyran-2-carbonyl)-1H-benzo[d]imidazole-1-carboxylate

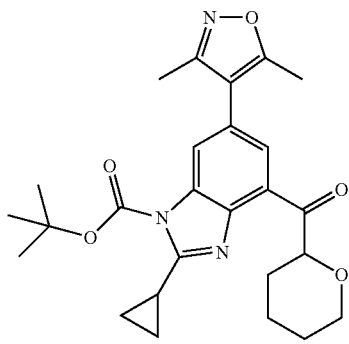 [SMILES: Cc1noc(C)c1-c1cc(C(=O)C2CCCCO2)c2nc(C3CC3)n(C(=O)OC(C)(C)C)c2c1]

Tert-butyl 2-cyclopropyl-6-(3,5-dimethylisoxazol-4-yl)-4-(tetrahydro-2H-pyran-2-carbonyl)-1H-benzo[d]imidazole-1-carboxylate was synthesized in a similar fashion as tert-butyl 2-cyclopropyl-6-(3,5-dimethylisoxazol-4-yl)-4-(oxetane-2-carbonyl)-1H-benzo[d]imidazole-1-carboxylate, substituting tert-butyl 2-cyclopropyl-6-(3,5-dimethylisox-azol-4-yl)-4-(hydroxy(oxetan-2-yl)methyl)-1H-benzo[d]imidazole-1-carboxylate for tert-butyl 2-cyclopropyl-6-(3,5-dimethylisoxazol-4-yl)-4-(hydroxy(tetrahydro-2H-pyran-2-yl)methyl)-1H-benzo[d]imidazole-1-carboxylate (184 mg, 0.39 mmol) (87.5 mg, 48% yield).

Step 3: Preparation of (2-cyclopropyl-6-(3,5-dimethylisoxazol-4-yl)-1H-benzo[d]imidazol-4-yl)(6-methylpyridin-2-yl)(tetrahydro-2H-pyran-2-yl)methanol

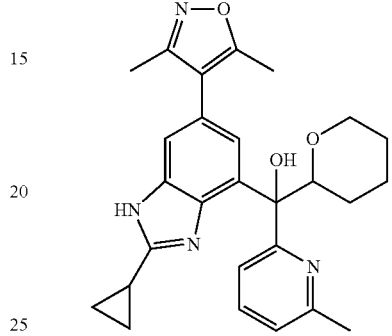

(2-cyclopropyl-6-(3,5-dimethylisoxazol-4-yl)-1H-benzo[d]imidazol-4-yl)(6-methylpyridin-2-yl)(tetrahydro-2H-pyran-2-yl)methanol was synthesized in a similar fashion as that of Example 302, substituting tert-butyl 2-cyclopropyl-6-(3,5-dimethylisoxazol-4-yl)-4-(tetrahydrofuran-3-carbonyl)-1H-benzo[d]imidazole-1-carboxylate for tert-butyl 2-cyclopropyl-6-(3,5-dimethylisoxazol-4-yl)-4-(tetrahydro-2H-pyran-2-carbonyl)-1H-benzo[d]imidazole-1-carboxylate.
$C_{27}H_{30}N_4O_3$. MS. m/z 459.5 (M+1). $^1$H NMR (400 MHz, cd$_3$od) δ 8.03 (t, J=7.9 Hz, 1H), 7.91 (d, J=7.9 Hz, 1H), 7.50 (d, J=1.4 Hz, 1H), 7.46 (dd, J=4.5, 3.1 Hz, 2H), 2.68 (s, 3H), 2.63 (td, J=8.5, 4.2 Hz, 1H), 2.36 (s, 3H), 2.19 (s, 3H), 1.84 (s, 1H), 1.61-1.46 (m, 6H), 1.42-1.18 (m, 6H).

Example 304

Preparation of (2-cyclopropyl-6-(3,5-dimethylisoxazol-4-yl)-1H-benzo[d]imidazol-4-yl)(5,5-dimethyltetrahydrofuran-3-yl)methanol (1020-304)

Step 1: Preparation of tert-butyl 2-cyclopropyl-4-((5,5-dimethyl-2-oxotetrahydrofuran-3-yl)(hydroxy)methyl)-6-(3,5-dimethylisoxazol-4-yl)-1H-benzo[d]imidazole-carboxylate

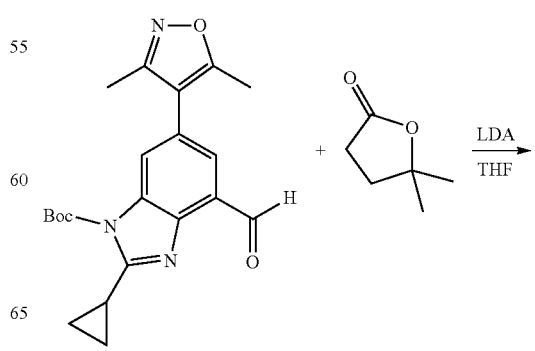

-continued

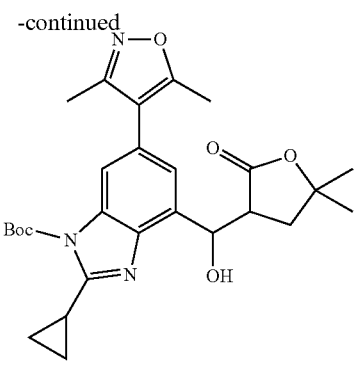

In a flame dried flask containing 5,5-dimethyldihydrofuran-2(3H)-one (90 mg, 0.79 mmol) at −78° C., LDA was added (0.59 mL, 1.18 mmol, 2M). The reaction mixture was allowed to stir for 10 minutes, followed by the addition of tert-butyl 2-cyclopropyl-6-(3,5-dimethylisoxazol-4-yl)-4-formyl-1H-benzo[d]imidazole-1-carboxylate (300 mg, 0.79 mmol). Once complete, the solution was quenched with DI H$_2$O and extracted three times with EtOAc. The combined organic layers were washed with saturated NaCl, dried over sodium sulfate, filtered and concentrated in vacuo. Product was purified via flash column chromatography to afford tert-butyl 2-cyclopropyl-4-((5,5-dimethyl-2-oxotetrahydrofuran-3-yl)(hydroxy)methyl)-6-(3,5-dimethylisoxazol-4-yl)-1H-benzo[d]imidazole-1-carboxylate (40 mg, 10% yield).

$C_{27}H_{33}N_3O_6$. MS m/z 496.6 (M+1).

Step 2: Preparation of tert-butyl 2-cyclopropyl-6-(3,5-dimethylisoxazol-4-yl)-4-hydroxy(2-hydroxy-5,5-dimethyltetrahydrofuran-3-yl)methyl)-1H-benzo[d]imidazole-1-carboxylate

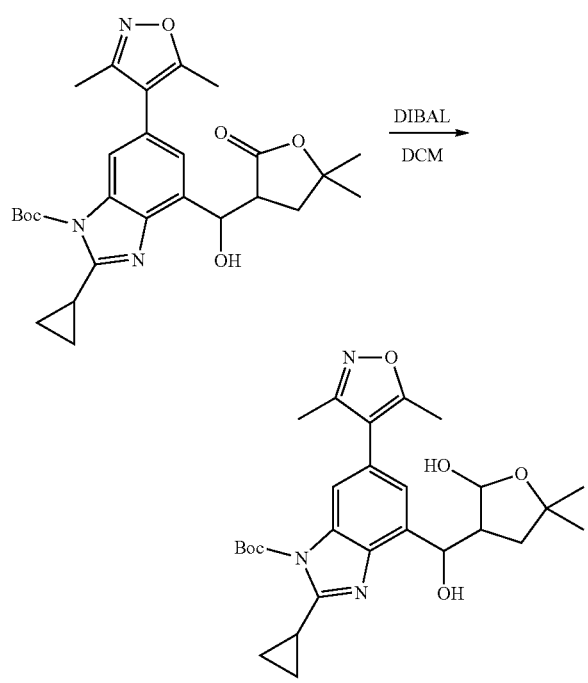

To a flame dried flask containing tert-butyl 2-cyclopropyl-4-((5,5-dimethyl-2-oxotetrahydrofuran-3-yl)(hydroxy)methyl)-6-(3,5-dimethylisoxazol-4-yl)-1H-benzo[d]imidazole-1-carboxylate (30 mg, 0.065 mmol) at −78° C. was added DIBAL (0.21 mL, 1M in hexanes). The reaction was allowed to warm to room temperature. Once complete, the solution was quenched with HCl and extracted three times with EtOAc. The combined organic layers were washed with saturated NaCl, dried over sodium sulfate, filtered and concentrated in vacuo. Product was purified via flash column chromatography to afford tert-butyl 2-cyclopropyl-6-(3,5-dimethylisoxazol-4-yl)-4-(hydroxy(2-hydroxy-5,5-dimethyltetrahydrofuran-3-yl)methyl)-1H-benzo[d]imidazole-1-carboxylate.

$C_{27}H_{35}N_3O_6$. MS m/z 498.6 (M+1).

Step 3: Preparation of (2-cyclopropyl-6-(3,5-dimethylisoxazol-4-yl)-1H-benzo[d]imidazol-4-yl)(5,5-dimethyltetrahydrofuran-3-yl)methanol

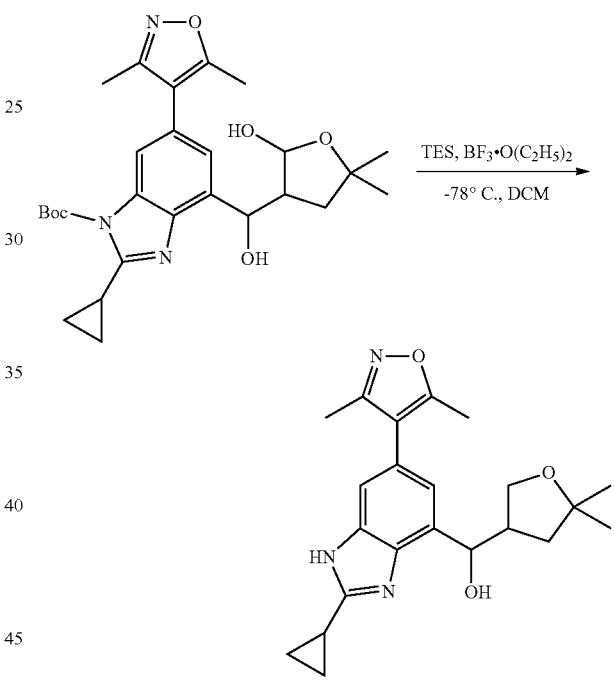

To a flame dried flask containing tert-butyl 2-cyclopropyl-6-(3,5-dimethylisoxazol-4-yl)-4-(hydroxy(2-hydroxy-5,5-dimethyltetrahydrofuran-3-yl)methyl)-1H-benzo[d]imidazole-1-carboxylate (11 mg, 0.02 mmol) at −78° C. was added triethylsilane (0.14 mL, 0.84 mmol), followed by boron trifluoride diethyl etherate (0.06 mL, 0.44 mmol). The reaction was allowed to run overnight. Once complete, the reaction was quenched with sodium bicarbonate and extracted three times with EtOAc. The combined organic layers were washed with saturated NaCl, dried over sodium sulfate, filtered and concentrated in vacuo. Product was purified via prep HPLC to afford (2-cyclopropyl-6-(3,5-dimethylisoxazol-4-yl)-1H-benzo[d]imidazol-4-yl)(5,5-dimethyltetrahydrofuran-3-yl)methanol.

$C_{22}H_{27}N_3O_3$. MS m/z 382.2 (M+1). $^1$H NMR (400 MHz, Methanol-d$_4$) δ 7.47 (d, J=1.4 Hz, 1H), 7.39 (d, J=1.4 Hz, 1H), 4.97 (d, J=7.6 Hz, 1H), 3.67 (d, J=8.0 Hz, 2H), 3.02-2.89 (m, 1H), 2.57 (tt, J=8.5, 5.0 Hz, 1H), 2.43 (s, 3H), 2.26 (s, 3H), 2.03-1.87 (m, 2H), 1.59-1.49 (m, 2H), 1.42 (dt, J=7.9, 4.8 Hz, 2H), 1.33 (s, 3H), 1.20 (s, 3H).

Example 305

Preparation of (4S,5R)-5-(2-cyclopropyl-6-(3,5-dimethylisoxazol-4-yl)-1H-benzo[d]imidazol-4-yl)-1-methyl-4-(phenylsulfonyl)pyrrolidin-2-one (1020-305)

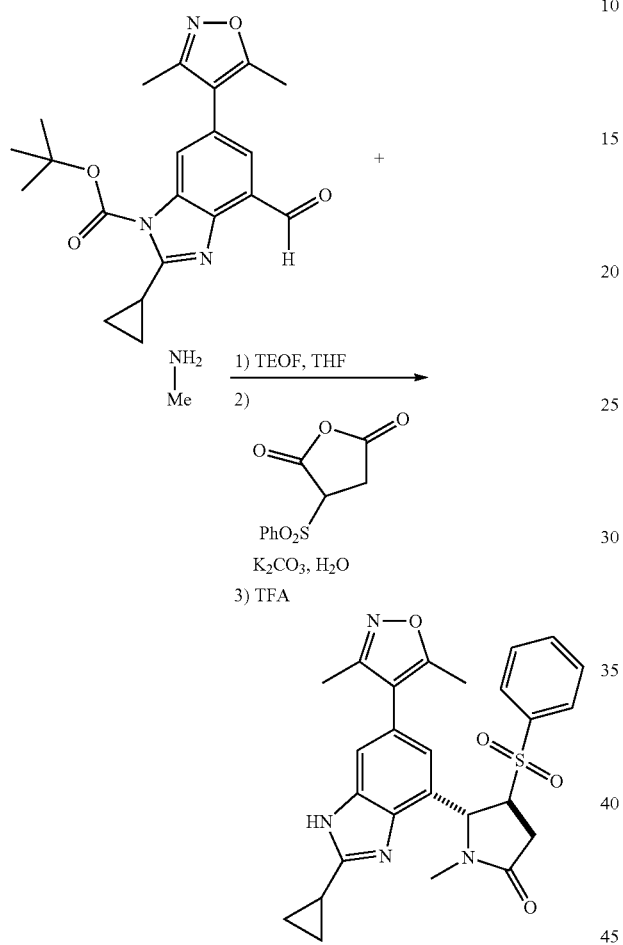

In a flame dried flask containing tert-butyl 2-cyclopropyl-6-(3,5-dimethylisoxazol-4-yl)-4-formyl-1H-benzo[d]imidazole-1-carboxylate (200 mg, 0.52 mmol) was added methylamine (0.262 mL, 0.52 mmol) and triethylorthoformate (0.262 mL, 2 mmol). The solution was allowed to stir for 3 hours, followed by the addition of 3-(phenylsulfonyl)dihydrofuran-2,5-dione (0.13 g, 0.53 mmol). The solution was allowed to stir for 3 more hours, followed by the addition of potassium carbonate (145 mg, 1 mmol) and DI water. Once complete, the solution was quenched with DI H$_2$O and extracted three times with EtOAc. The combined organic layers were washed with saturated NaCl, dried over sodium sulfate, filtered and concentrated in vacuo. To the crude product was added 5 mL of TFA and was allowed to stir for 30 minutes. The solution was concentrated in vacuo and was purified via reverse phase HPLC to afford (4S,5R)-5-(2-cyclopropyl-6-(3,5-dimethylisoxazol-4-yl)-1H-benzo[d]imidazol-4-yl)-1-methyl-4-(phenylsulfonyl)pyrrolidin-2-one.

C$_{26}$H$_{26}$N$_4$O$_4$S. MS. m/z 491.6 (M+1).

Example 306

(2-cyclopropyl-6-(3,5-dimethylisoxazol-4-yl)-1H-benzo[d]imidazol-4-yl)(1,4-dioxan-2-yl)(pyridazin-3-yl)methanol (1020-306)

Step 1: tert-butyl 4-((1,4-dioxan-2-yl)(hydroxy)methyl)-2-cyclopropyl-6-(3,5-dimethylisoxazol-4-yl)-1H-benzo[d]imidazole-1-carboxylate

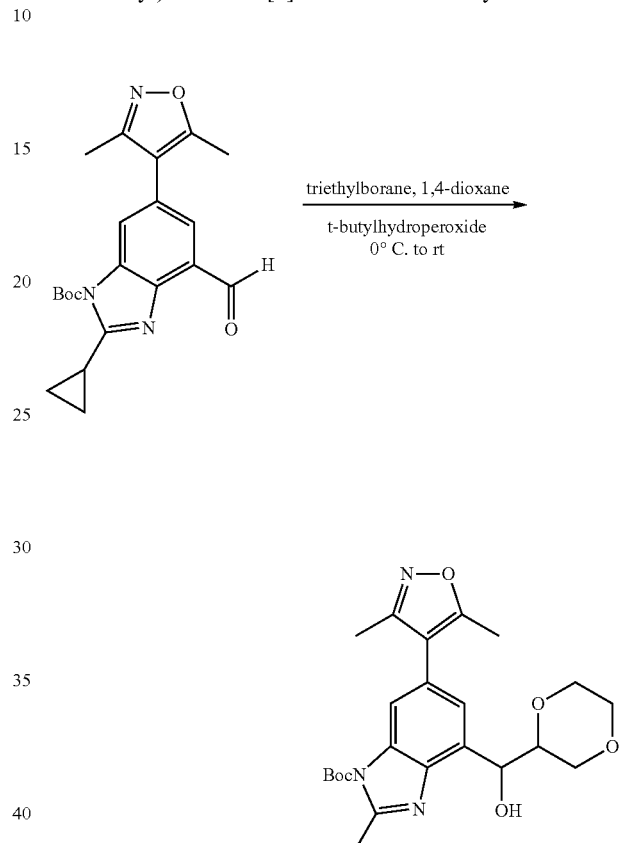

Into a flask containing tert-butyl 2-cyclopropyl-6-(3,5-dimethylisoxazol-4-yl)-4-formyl-1H-benzo[d]imidazole-1-carboxylate (600 mg, 1.57 mmol, 1 equiv.) was added 1,4-dioxane (40 mL) and cooled to 0° C. before adding triethylborane (2.7 mL, 18.88 mmol, 12 equiv.). Tert-butylhydroperoxide (2.86 mL, 15.73 mmol, 10 equiv., 6 M decanes) was added slowly to the reaction mixture and the reaction allowed to warm up slowly to room temperature. After completion, the reaction was quenched with NH$_4$OH solution (5 mL) and extracted with EtOAc and washed with water (spiked with a solution of FeSO$_4$.H$_2$SO$_4$.H$_2$0 (2 mL)) and then with saturated NH$_4$Cl. After drying with MgSO$_4$, it was filtered and concentrated to dryness. Purification was carried out by flash column chromatography to tert-butyl 4-((1,4-dioxan-2-yl)(hydroxy)methyl)-2-cyclopropyl-6-(3,5-dimethylisoxazol-4-yl)-1H-benzo[d]imidazole-1-carboxylate (140 mg, y. 18%, dr 5:3).

LCMS (m/z+1) 470.55

Step 2: tert-butyl 2-cyclopropyl-6-(3,5-dimethyl-isoxazol-4-yl)-4-(1,4-dioxane-2-carbonyl)-1H-benzo[d]imidazole-1-carboxylate

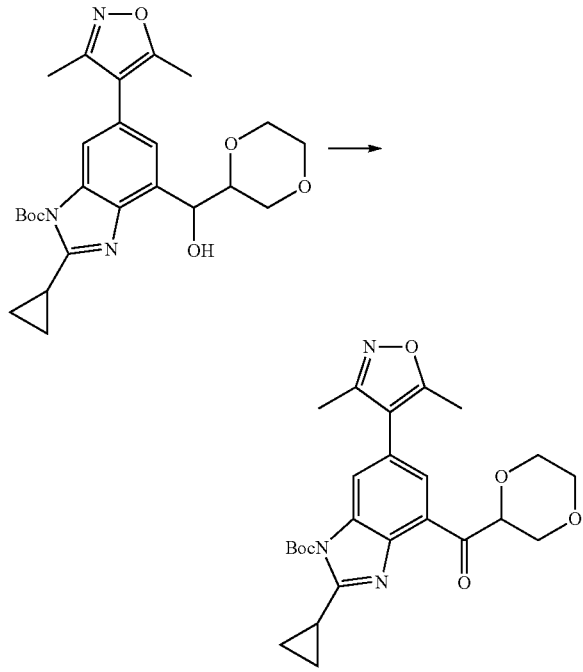

Into a flask containing to tert-butyl 4-((1,4-dioxan-2-yl)(hydroxy)methyl)-2-cyclopropyl-6-(3,5-dimethylisoxazol-4-yl)-1H-benzo[d]imidazole-1-carboxylate (140 mg, 0.29 mmol, 1 equiv.) was added DCM (100 mL) and Dess-Martin periodinane (164 mg, 0.38 mmol, 1.5 equiv.). After completion, the reaction was quenched with sodium thiosulfate solution and allowed to stir for several minutes. It was extracted with DCM and washed with water and saturated NH₄Cl. After drying with MgSO₄, it was filtered and concentrated to dryness. Purification was carried out by flash column chromatography to furnish tert-butyl 2-cyclopropyl-6-(3,5-dimethylisoxazol-4-yl)-4-(1,4-dioxane-2-carbonyl)-1H-benzo[d]imidazole-1-carboxylate (102 mg, y. 75%).

LCMS (m/z+1) 468.55

Step 3: (2-cyclopropyl-6-(3,5-dimethylisoxazol-4-yl)-1H-benzo[d]imidazol-4-yl)(1,4-dioxan-2-yl)(pyridazin-3-yl)methanol

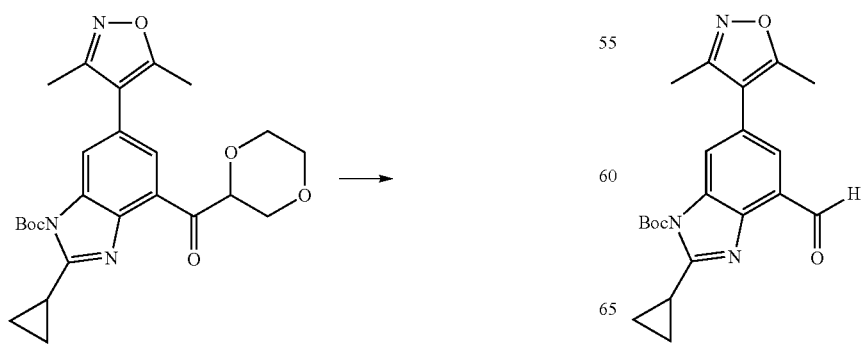

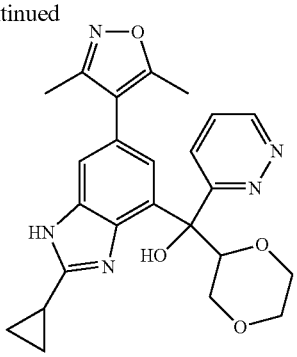

Into a flask containing pyridazine (110 μL, 1.15 mml, 10 equiv.) was added MeTHF (5 mL) and to it slowly added TMP.MgCl.LiCl (1.46 mL, 1.46 mmol, 10 equiv., 1M) at −78° C. over 10 min. After 45 minutes tert-butyl 2-cyclopropyl-6-(3,5-dimethylisoxazol-4-yl)-4-(1,4-dioxane-2-carbonyl)-1H-benzo[d]imidazole-1-carboxylate (70 mg, 0.15 mmol, 1 equiv.) dissolved in MeTHF (2 ML) is added slowly to the reaction. After completion, the reaction was quenched and extracted with EtOAc and washed with water, saturated NH₄Cl. After drying with MgSO₄, it was filtered and concentrated to dryness. To the crude material is added TFA (5 mL) and allowed to stir for 30 min. After the reaction was complete, it was concentrated in vacuo. Purification was carried out by reverse phase HPLC (2-cyclopropyl-6-(3,5-dimethylisoxazol-4-yl)-1H-benzo[d]imidazol-4-yl)(1,4-dioxan-2-yl)(pyridazin-3-yl)methanol (as a racemic single diastereomer).

LCMS (m/z+1) 448.62. ¹H NMR (400 MHz, Methanol-d4) δ 9.45 (dd, J=2.5, 1.2 Hz, 1H), 9.18 (dd, J=5.5, 1.1 Hz, 1H), 8.10-8.01 (m, 1H), 7.48 (dd, J=22.5, 1.3 Hz, 2H), 4.75 (dd, J=9.4, 3.2 Hz, 1H), 3.89 (ddd, J=23.9, 11.5, 2.9 Hz, 2H), 3.79-3.63 (m, 3H), 3.58 (dd, J=11.6, 3.1 Hz, 1H), 2.65 (s, 3H), 2.36 (s, 3H), 2.19 (s, 3H), 1.79-1.46 (m, 2H), 1.40 (ddd, J=7.5, 4.8, 2.7 Hz, 2H). ¹⁹F NMR (377 MHz, Methanol-d4) δ −77.96.

Example 307

(2-cyclopropyl-6-(3,5-dimethylisoxazol-4-yl)-1H-benzo[d]imidazol-4-yl)(2,3-dihydrobenzofuran-2-yl)methanol (1020-307)

Step 1: tert-butyl 2-cyclopropyl-4-((2,3-dihydrobenzofuran-2-yl)(hydroxy)methyl-6-(3,5-dimethylisoxazol-4-yl-1H-benzo[d]imidazole-1-carboxylate

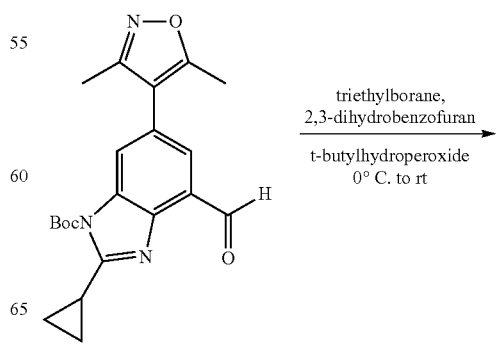

triethylborane, 2,3-dihydrobenzofuran t-butylhydroperoxide
0° C. to rt

-continued

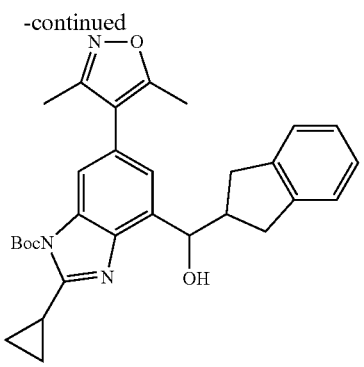

Into a flask containing tert-butyl 2-cyclopropyl-6-(3,5-dimethylisoxazol-4-yl)-4-formyl-1H-benzo[d]imidazole-1-carboxylate (200 mg, 0.52 mmol, 1 equiv.) was added 2,3-dihydrobenzofuran (10 mL) and cooled to 0° C. before adding triethylborane (0.91 mL, 6.29 mmol, 12 equiv.). Tert-butylhydroperoxide (0.57 mL, 3.14 mmol, 6 equiv., 5.5 M decanes) was added slowly to the reaction mixture and the reaction allowed to warm up slowly to room temperature. After completion, the reaction was quenched with NH$_4$OH solution (5 mL) and extracted with EtOAc and washed with water (spiked with a solution of FeSO$_4$.H$_2$SO$_4$.H$_2$0 (2 mL)) and then with saturated NH$_4$Cl. After drying with MgSO$_4$, it was filtered and concentrated to dryness. Purification was carried out by flash column chromatography tert-butyl 2-cyclopropyl-4-((2,3-dihydrobenzofuran-2-yl)(hydroxy)methyl)-6-(3,5-dimethylisoxazol-4-yl)-1H-benzo[d]imidazole-1-carboxylate (dr 3:2).

LCMS (m/z+1) 502.60

Step 2: (2-cyclopropyl-6-(3,5-dimethylisoxazol-4-yl)-1H-benzo[d]imidazol-4-yl(2,3-dihydrobenzofuran-2-yl)methanol

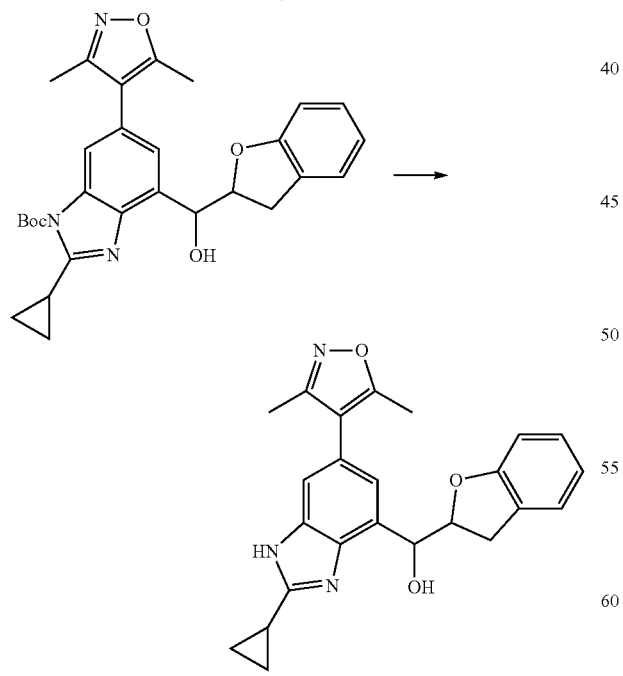

To tert-butyl 2-cyclopropyl-4-((2,3-dihydrobenzofuran-2-yl)(hydroxy)methyl)-6-(3,5-dimethylisoxazol-4-yl)-1H-benzo[d]imidazole-1-carboxylate (50 mg, 0.06 mmol, 1 equiv.) is added TFA (3 mL). After 30 min the reaction is complete and was concentrated in vacuo. Purification was carried out by reverse phase HPLC (2-cyclopropyl-6-(3,5-dimethylisoxazol-4-yl)-1H-benzo[d]imidazol-4-yl)(2,3-dihydrobenzofuran-2-yl)methanol.

LCMS (m/z+1) 402.50. $^1$H NMR (400 MHz, Methanol-d4) δ 7.52 (dd, J=1.6, 0.7 Hz, 1H), 7.45 (d, J=1.4 Hz, 1H), 7.39 (dd, J=3.2, 1.5 Hz, 1H), 7.06 (d, J=8.6 Hz, 1H), 6.94 (t, J=7.7 Hz, 1H), 6.72-6.62 (m, 1H), 6.56-6.43 (m, 1H), 5.39 (d, J=4.6 Hz, 1H), 5.21-5.02 (m, 1H), 3.25 (dt, J=9.0, 4.6 Hz, 2H), 2.57 (t, J=4.9 Hz, 1H), 2.40 (d, J=3.3 Hz, 4H), 2.24 (d, J=3.4 Hz, 4H), 1.56 (ddd, J=8.4, 5.1, 3.3 Hz, 3H), 1.49-1.30 (m, 2H). $^{19}$F NMR (377 MHz, Methanol-d4) δ -77.71

Example 308

(S)-(2-cyclopropyl-6-(3,5-dimethylisoxazol-4-yl)-1H-benzo[d]imidazol-4-yl)(pyridin-2-yl)((R)-4-oxaspiro[2.4]heptan-5-yl)methanol (1020-308)

Step 1: (S)-5-(((tert-butyldiphenylsilyl)oxy)methyl)dihydrofuran-2(3H)-one

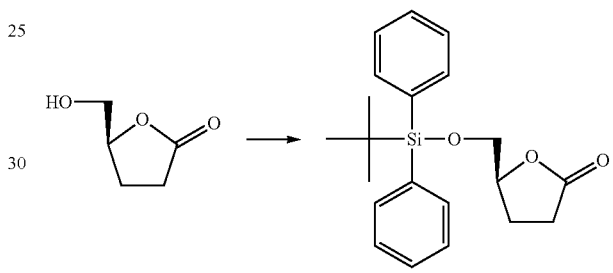

To a solution of (S)-5-(hydroxymethyl)dihydrofuran-2(3H)-one (5 g, 43 mmol) in CH$_2$Cl$_2$ (100 mL) were added imidazole (8.74 g, 129 mmol) and TBDPSCl (14.2 g, 52 mmol), and the solution was stirred at room temperature for 4 h. Solvent was removed and the residue was mixed with EtOAc (300 mL) and the organic solution was washed with water, brine and dried over Na$_2$SO$_4$. Solvent was removed and the residue was purified by silica gel column chromatography (0-60% EtOAc in hexane) to give (S)-5-(((tert-butyldiphenylsilyl)oxy)methyl)dihydrofuran-2(3H)-one.

$^1$H NMR (Chloroform-d) δ 7.71-7.62 (m, 4H), 7.50-7.34 (m, 6H), 4.66-4.55 (m, 1H), 3.88 (dd, J=11.3, 3.4 Hz, 1H), 3.69 (dd, J=11.4, 3.4 Hz, 1H), 2.68 (ddd, J=17.5, 10.1, 7.1 Hz, 1H), 2.51 (ddd, J=17.7, 9.9, 6.6 Hz, 1H), 2.36-2.13 (m, 2H), 1.06 (s, 9H).

Step 2: (S)-1,4-((tert-butyldiphenylsilyl)oxy)-3-hydroxybutyl)cyclopropanol

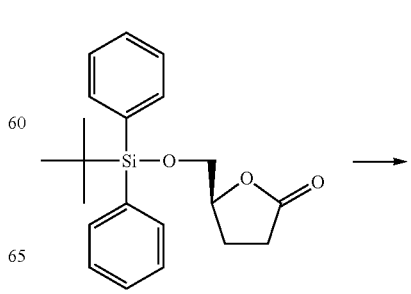

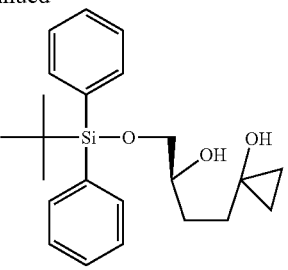

To a solution of (S)-5-(((tert-butyldiphenylsilyl)oxy)methyl)dihydrofuran-2(3H)-one (15.2 g, 42.88 mmol) in THF (200 mL) was added Ti(OiPr)$_4$ (4.87 g, 17.15 mmol) followed by the addition of a solution of EtMgBr (14.29 g, 107 mmol, 3M in Et$_2$O) at 15-20° C. and the solution was stirred at 15° C. for additional 1 h. The reaction was quenched with Aq NH$_4$Cl. Filtered and extracted with EtOAc (200 mL). The combined organic solution was washed with brine and dried over Na$_2$SO$_4$. Solvent was removed and the residue was purified by silica gel column chromatography (0-50% EtOAc in hexane) to give (S)-1-(4-((tert-butyldiphenylsilyl)oxy)-3-hydroxybutyl)cyclopropanol (15.2 g, 92%).

$^1$H NMR (Chloroform-d) δ 7.69-7.63 (m, 4H), 7.50-7.33 (m, 5H), 3.91-3.78 (m, 1H), 3.66 (dd, J=10.1, 3.5 Hz, 1H), 3.52 (dd, J=10.1, 8.1 Hz, 1H), 1.87-1.72 (m, 1H), 1.66-1.51 (m, 3H), 1.07 (s, 9H), 0.84 (td, J=7.5, 3.1 Hz, 1H), 0.78-0.67 (m, 3H).

Step 3: (R)-(4-oxaspiro[2.4]heptan-5-ylmethoxy)tert-butyl)diphenylsilane

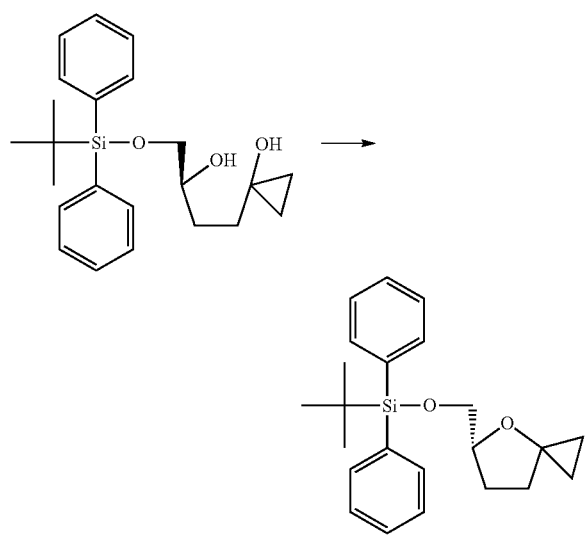

To a solution of (S)-1-(4-((tert-butyldiphenylsilyl)oxy)-3-hydroxybutyl)cyclopropanol (15.2 g, 39.5 mmol) in THF (150 mL) were added Ph$_3$P (15.55 g, 59.3 mmol) then diisopropyl azocarboxylate (11.99 g, 59.28 mmol) at room temperature then the solution was heated at 60° C. for 4 h. The solution was concentrated to dryness and the residue dissolved in CH$_2$Cl$_2$. The solution was filtered through silica gel (2 inches high) to removed most of thiphenyl phosphoxide. The column was washed with CH$_2$Cl$_2$. The combined filtrate was concentrated to dryness and the residue was purified by silica gel column chromatography (0-40% EtOAc in hexane) to give (R)-(4-oxaspiro[2.4]heptan-5-ylmethoxy)(tert-butyl)diphenylsilane (9.5 g, 65.6%).

$^1$H NMR (Chloroform-d) δ 7.71-7.59 (m, 4H), 7.46-7.31 (m, 6H), 4.22-4.11 (m, 1H), 3.72 (dd, J=10.4, 4.9 Hz, 1H), 3.64 (dd, J=10.4, 5.6 Hz, 1H), 2.20-2.09 (m, 1H), 2.07-1.87 (m, 3H), 1.06 (s, 9H), 0.79 (d, J=1.8 Hz, 2H), 0.49-0.40 (m, 2H).

Step 4: (R)-4-oxaspiro[2.4]heptan-5-ylmethanol

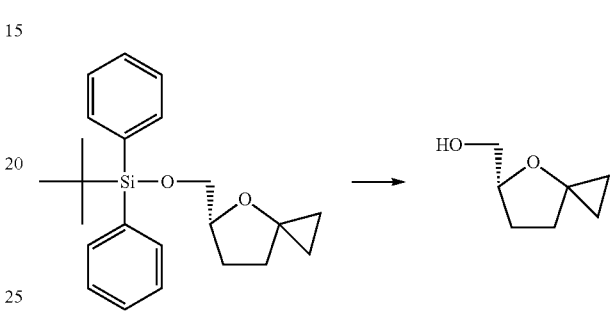

To a solution of (R)-(4-oxaspiro[2.4]heptan-5-ylmethoxy)(tert-butyl)diphenylsilane (9.5 g, 25.9 mmol) in THF (150 mL) was added TBAF (6.8 g, 25.9 mmol, 1 M in THF) and the solution was stirred at room temperature for 3 h. Solvent was removed and the residue was purified by silica gel column chromatography (10-80% EtOAc in hexane) to give (R)-4-oxaspiro[2.4]heptan-5-ylmethanol (3.0 g, 90.4%).

$^1$H NMR (Chloroform-d) δ 4.25-4.08 (m, 1H), 3.68 (dd, J=11.5, 3.3 Hz, 1H), 3.57 (dd, J=11.6, 6.3 Hz, 1H), 2.18-2.03 (m, 1H), 2.00-1.92 (m, 2H), 1.92-1.81 (m, 1H), 0.89-0.80 (m, 2H), 0.61-0.40 (m, 2H).

Step 5: (R)-4-oxaspiro[2.4]heptane-5-carbaldehyde

To a solution of (R)-4-oxaspiro[2.4]heptan-5-ylmethanol (0.2 g, 1.56 mmol) in CH$_2$Cl$_2$ was added Dess-Martin periodinane (0.99 g, 2.34 mmol) in one-portion. To the mixture was added two drops of water and the mixture was stirred at room temperature for 1 h. To the mixture was added Dess-Martin periodinane (0.6 g, 1.4 mmol) and the mixture was stirred at room temperature for additional 1 h. To the mixture was added hexane (10 mL) and the mixture was stirred at room temperature for 10 min. Filtered and solid was washed with 10 mL of solution of CH$_2$Cl$_2$-hexane (1:1). Solvent was removed and the residue was triturated with Et$_2$O (10 mL) and filtered. Solid Filtrate was concentrated to dryness at room temperature and the residue was used for the next reaction without further purification.

Step 6: (R,S)-pyridin-2-yl((R)-4-oxaspiro[2.4]heptan-5-yl)methanol

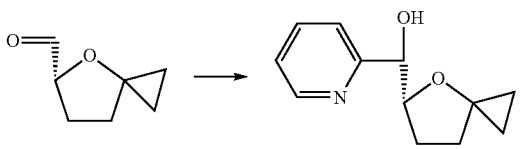 [SMILES: O=C[C@H]1CCC2(CC2)O1 ; OC(c1ccccn1)[C@H]1CCC2(CC2)O1]

To solution of 2-bromopyridine (2.47 g, 15.6 mmol) in THF (20 mL) was added BuLi (1.6 M in hexane, 15.6 mmol) and the solution was stirred at −78° C. for 1 h to form 2-pyridine-litiate.

To the solution was added a solution of the aldehyde prepared on in the step 5 in THF (4 mL) at −78° C. and the solution was stirred at −78° C. for 20 min. To the solution was added aq. NH$_4$Cl and the mixture was extracted with EtOAc (200 mL). The organic solution was washed with brine and dried over Na$_2$SO$_4$. Solvent was removed and the residue was purified by silica gel column chromatography (0-80% EtOAc in hexane) to give (R,S)-pyridin-2-yl((R)-4-oxaspiro[2.4]heptan-5-yl)methanol (45 mg, 14%) as a mixture of diastereomers.

C$_{12}$H$_{15}$NO$_2$. MS m/z 206.2. $^1$H NMR (Chloroform-d) δ 8.54 (ddt, J=6.3, 4.9, 1.3 Hz, 1H), 7.75-7.61 (m, 1H), 7.45-7.35 (m, 1H), 7.20 (dddd, J=7.7, 4.5, 3.0, 1.2 Hz, 1H), 4.76 (dd, J=23.7, 5.6 Hz, 1H), 4.34-4.19 (m, 1H), 2.23-1.74 (m, 4H), 1.05-0.75 (m, 2H), 0.63-0.34 (m, 2H).

Step 7: (R)-pyridin-2-yl(4-oxaspiro[2,4]heptan-5-yl)methanone

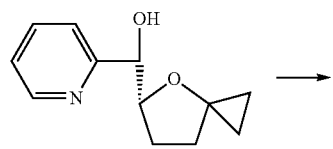

To a solution of (R)-pyridin-2-yl((R)-4-oxaspiro[2.4]heptan-5-yl)methanol (0.19 g, 0.93 mmol) in CH$_2$Cl$_2$ (10 mL) was added Dess-Martin periodinane (0.59 g, 1.39 mmol) in one-portion and the solution was stirred at room temperature for 4 h. Solid was filtered off and the solvent was removed. The residue was purified by silica gel column chromatography (0-70% EtOAc in hexane) to give (R)-pyridin-2-yl(4-oxaspiro[2.4]heptan-5-yl)methanone as solid (85 mmg, 45%).

C$_{12}$H$_{13}$NO$_2$. MS m/z 204.08 (M+1). 1H NMR (400 MHz, Chloroform-d) δ 8.67 (ddd, J=4.9, 1.7, 0.9 Hz, 1H), 8.08 (dt, J=7.9, 1.1 Hz, 1H), 7.84 (td, J=7.7, 1.7 Hz, 1H), 7.46 (ddd, J=7.6, 4.8, 1.3 Hz, 1H), 5.79 (dd, J=8.5, 7.1 Hz, 1H), 2.71 (dtd, J=11.7, 8.2, 5.4 Hz, 1H), 2.21-1.87 (m, 4H), 1.17-1.04 (m, 1H), 1.03-0.90 (m, 1H), 0.65-0.46 (m, 2H).

Step 8: (S)-(2-cyclopropyl-6-(3,5-dimethylisoxazol-4-yl)-1H-benzo[d]imidazol-4-yl)(pyridin-2-yl)((R)-4-oxaspiro[2.4]heptan-5-yl)methanol

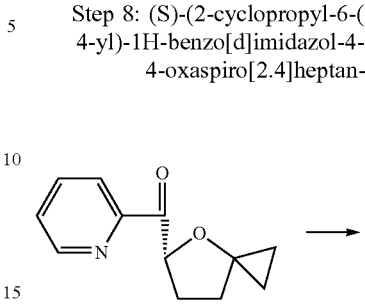

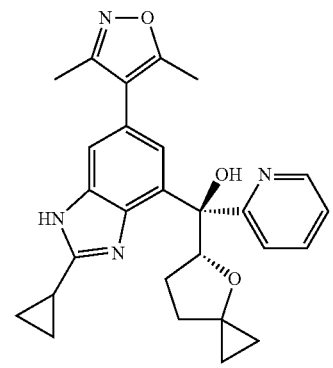

To a solution of tert-butyl 2-cyclopropyl-6-(3,5-dimethylisoxazol-4-yl)-4-iodo-1H-benzo[d]imidazole-1-carboxylate (472 mg, 0.98 mmol) in THF (10 mL) was added BuLi (63 mg, 0.98 mmol, 1.6 M in THF) followed by immediate addition of a solution of (R)-pyridin-2-yl(4-oxaspiro[2.4]heptan-5-yl)methanone (40 mg, 0.2 mmol) in THF (4 mL) and the solution was stirred at −78° C. for 30 min. Aq NH$_4$Cl was added then the mixture was extracted with EtOAc (200 mL). The organic solution was washed with brine and dried over Na$_2$SO$_4$. Solvent was removed and the residue was purified silica gel column chromatography (0-20% MeOH/CH$_2$Cl$_2$) to give tort-butyl 2-cyclopropyl-6-(3,5-dimethylisoxazol-4-yl)-4-((S)-hydroxy(pyridin-2-yl)((R)-4-oxaspiro[2.4]heptan-5-yl)methyl)-1H-benzo[d]imidazole-1-carboxylate which was dissolved in THF (2 mL), TFA (2 mL) and water (0.2 mL). The solution was heated at 50° C. for 1 h. Solvent was removed and the residue was purified by HPLC to give (S)-(2-cyclopropyl-6-(3,5-dimethylisoxazol-4-yl)-1H-benzo[d]imidazol-4-yl)(pyridin-2-yl)((R)-4-oxaspiro[2.4]heptan-5-yl)methanol.

C$_{27}$H$_{28}$N$_4$O$_3$. MS. m/z 457.3 (M+1). $^1$H NMR (Methanol-d$_4$) δ 8.60 (dt, J=5.0, 1.3 Hz, 1H), 8.05-7.96 (m, 2H), 7.61 (d, J=1.5 Hz, 1H), 7.49-7.38 (m, 2H), 5.26 (t, J=7.0 Hz, 1H), 2.64 (ddd, J=8.5, 5.1, 3.5 Hz, 1H), 2.40 (s, 3H), 2.23 (s, 3H), 2.10-1.81 (m, 4H), 1.60-1.47 (m, 2H), 1.47-1.29 (m, 2H), 0.83 (ddd, J=11.3, 6.5, 5.2 Hz, 1H), 0.70 (ddd, J=11.3, 6.3, 4.6 Hz, 1H), 0.59-0.40 (m, 2H).

Example 309

(S)-(2-cyclopropyl-6-(3,5-dimethylisoxazol-4-yl)-1H-benzo[d]imidazol-4-yl)(6-methylpyridin-2-yl)((S)-4-oxaspiro[2.4]heptan-5-yl)methanol (1020-309)

Step 1: (R)-5-(((tert-butyldiphenylsilyl)oxy)methyl)dihydrofuran-2(3H)-one

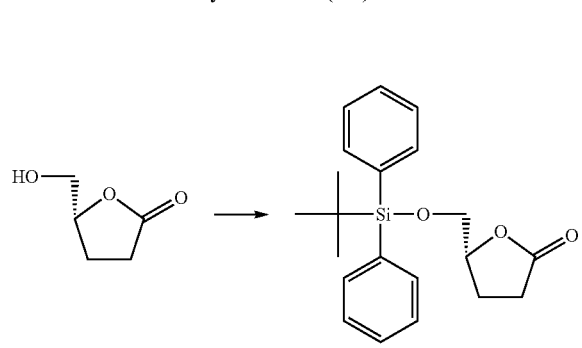

(R)-5-(((tert-butyldiphenylsilyl)oxy)methyl)dihydrofuran-2(3H)-one was synthesized from (R)-5-(hydroxymethyl)dihydrofuran-2(3H)-one in a similar fashion as that of Example 308, step 1.

(R)-5-(((tert-butyldiphenylsilyl)oxy)methyl)dihydrofuran-2(3H)-one: $^1$H NMR (Chloroform-d) δ 7.70-7.61 (m, 4H), 7.49-7.32 (m, 6H), 4.66-4.53 (m, 1H), 3.88 (dd, J=11.3, 3.4 Hz, 1H), 3.69 (dd, J=11.4, 3.4 Hz, 1H), 2.67 (ddd, J=17.4, 10.1, 7.1 Hz, 1H), 2.51 (ddd, J=17.7, 10.0, 6.6 Hz, 1H), 2.36-2.09 (m, 2H), 1.06 (s, 9H).

Step 2: (R)-1-(4-((tert-butyldiphenylsilyl)oxy)-3-hydroxybutyl)cyclopropanol

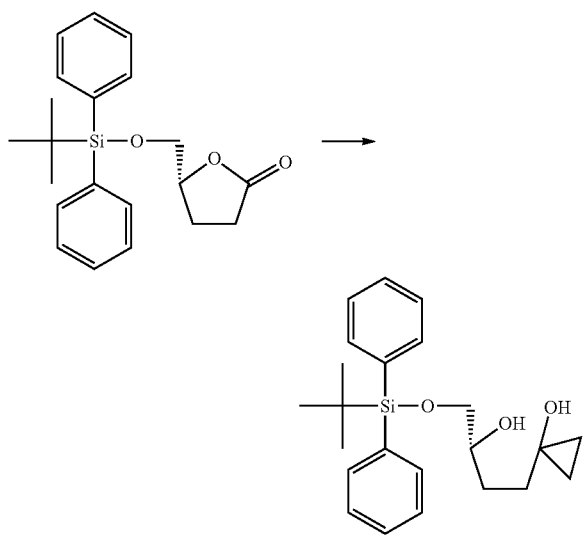

(R)-1-(4-((tert-butyldiphenylsilyl)oxy)-3-hydroxybutyl)cyclopropanol was prepared (R)—S-(((tert-butyldiphenylsilyl)oxy)methyl)dihydrofuran-2(3H)-one in a similar fashion as that of Example 308, step 2.

(R)-1-(4-((tert-butyldiphenylsilyl)oxy)-3-hydroxybutyl)cyclopropanol: $^1$H NMR (Chloroform-d) δ 7.71-7.59 (m, 4H), 7.46-7.33 (m, 6H), 3.85 (dtd, J=11.6, 5.8, 3.5 Hz, 1H), 3.71-3.61 (m, 1H), 3.52 (dd, J=10.1, 8.1 Hz, 1H), 1.88-1.74 (m, 1H), 1.67-1.55 (m, 2H), 1.48-1.40 (m, 1H), 1.07 (d, J=2.6 Hz, 9H), 0.84 (td, J=7.5, 3.1 Hz, 2H), 0.78-0.66 (m, 2H).

Step 3: (S)-(4-oxaspiro[2.4]heptan-5-ylmethoxy)(tert-butyl)diphenylsilane

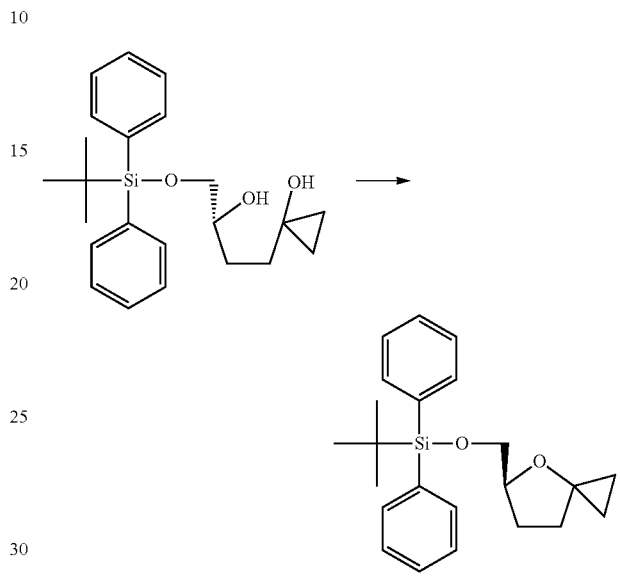

(S)-(4-oxaspiro[2.4]heptan-5-ylmethoxy)(tert-butyl)diphenylsilane was prepared from (R)-1-(4-((tert-butyldiphenylsilyl)oxy)-3-hydroxybutyl)cyclopropanol in a similar fashion as that of Example 308, step 3.

(S)-(4-oxaspiro[2.4]heptan-5-ylmethoxy)(tert-butyl)diphenylsilane: $^1$H NMR (Chloroform-d) δ 7.75-7.61 (m, 4H), 7.48-7.29 (m, 6H), 4.17 (dq, J=7.5, 5.5 Hz, 1H), 3.72 (dd, J=10.4, 5.0 Hz, 1H), 3.64 (dd, J=10.5, 5.6 Hz, 1H), 2.21-2.06 (m, 1H), 2.03-1.84 (m, 3H), 1.06 (s, 9H), 0.79 (q, J=1.6, 1.0 Hz, 2H), 0.51-0.39 (m, 2H).

Step 4: (S)-4-oxaspiro[2.4]heptan-5-ylmethanol

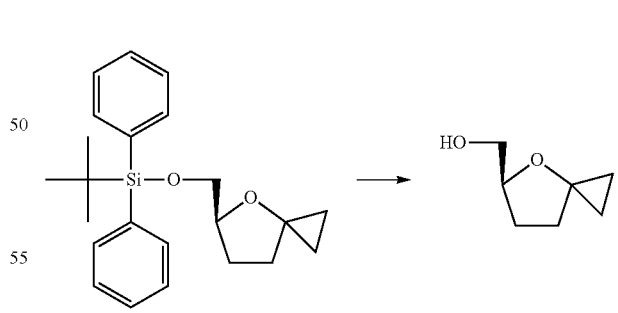

(S)-4-oxaspiro[2.4]heptan-5-ylmethanol was prepared from (S)-(4-oxaspiro[2.4]heptan-5-ylmethoxy)(tert-butyl)diphenylsilane in a similar fashion as that of Example 308, step 4.

(S)-4-oxaspiro[2.4]heptan-5-ylmethanol: $^1$H NMR (Chloroform-d) δ 4.23-4.09 (m, 1H), 3.68 (dd, J=11.5, 3.3 Hz, 1H), 3.57 (dd, J=11.6, 6.2 Hz, 1H), 2.18-2.02 (m, 1H), 2.00-1.92 (m, 2H), 1.92-1.79 (m, 1H), 0.92-0.79 (m, 2H), 0.60-0.40 (m, 2H).

Step 5: (S)-4-oxaspiro[2.4]heptane-5-carbaldehyde

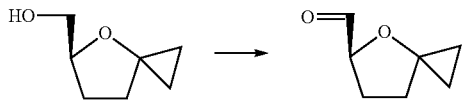 [SMILES: OC[C@@H]1CCC2(CC2)O1 ; O=C[C@@H]1CCC2(CC2)O1]

(S)-4-Oxaspiro[2.4]heptane-5-carbaldehyde was prepared from (S)-4-oxaspiro[2.4]heptan-5-ylmethanol in a similar fashion as that of Example 308, step 5. The prepared crude aldehyde was purified by silica gel column (0-100% Et$_2$O in hexane) to give pure (S)-4-oxaspiro[2.4]heptane-5-carbaldehyde which was used for the next reaction freshly.

$^1$H NMR (Chloroform-d) δ 9.71 (d, J=1.8 Hz, 1H), 4.35 (ddd, J=8.4, 6.2, 1.8 Hz, 1H), 2.33 (dtd, J=12.6, 8.7, 5.6 Hz, 1H), 2.19 (ddt, J=12.8, 8.7, 6.5 Hz, 1H), 2.03 (ddd, J=12.1, 8.5, 6.6 Hz, 1H), 1.88 (ddd, J=12.1, 8.7, 5.6 Hz, 1H), 1.01-0.83 (m, 2H), 0.66-0.43 (m, 2H).

Step 6: tert-butyl 2-cyclopropyl-6-(3,5-dimethylisoxazol-4-yl)-4-(hydroxy((S)-4-oxaspiro[2,4]heptan-5-yl)methyl)-1H-benzo[d]imidazole-1-carboxylate

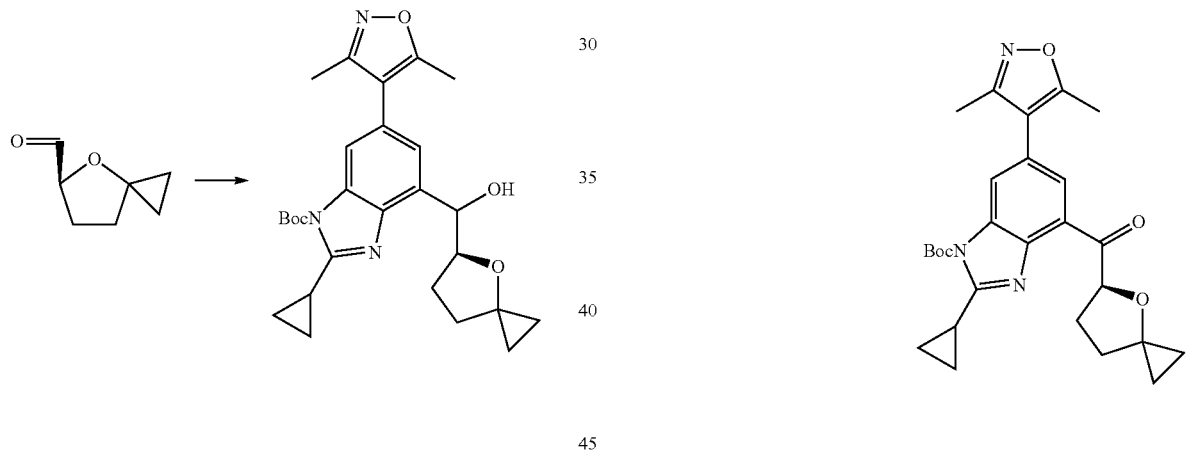

To a solution of tert-butyl 2-cyclopropyl-6-(3,5-dimethylisoxazol-4-yl)-4-iodo-1H-benzo[d]imidazole-1-carboxylate (1.46 g, 3.04 mmol) in THF (40 mL) was added BuLi (2 mL, 1.6 M in hexanes) at −78° C. To the solution was added a solution of freshly prepared in a similar fashion as that of Example 308, step 6 in THF (4 mL) at −78° C. immediately and the solution was stirred at −78° C. for 20 min. To the solution was added aq. NH$_4$Cl and the mixture was extracted with EtOAc (100 mL). The organic solution was washed with brine and dried over Na$_2$SO$_4$. Solvent was removed and the residue was purified by silica gel column chromatography (0-80% EtOAc in hexane) to tert-butyl 2-cyclopropyl-6-(3,5-dimethylisoxazol-4-yl)-4-(hydroxy((S)-4-oxaspiro[2,4]heptan-5-yl)methyl)-1H-benzo[d]imidazole-1-carboxylate (220 mg, 15%) as a mixture of diastereomers.

C$_{27}$H$_{33}$N$_3$O$_5$. MS m/z 479.9 (M+L). $^1$H NMR (Chloroform-d) δ 7.69 (dd, J=7.3, 1.5 Hz, 1H), 7.19-7.09 (m, 1H), 5.09 (br s, 1H), 4.30 (m, 1H), 2.93-2.78 (m, 1H), 2.42 (d, J=2.3 Hz, 3H), 2.28 (t, J=1.4 Hz, 3H), 2.08-1.81 (m, 2H), 1.75-1.62 (m, 11H), 1.31-1.20 (m, 2H), 1.18-1.07 (m, 2H), 0.95-0.72 (m, 2H), 0.49 (ddd, J=28.2, 5.4, 4.1 Hz, 2H).

Step 7: (S)-tert-butyl 2-cyclopropyl-6-(3,5-dimethylisoxazol-4-yl)-4-(4-oxaspiro[2.4]heptane-5-carbonyl)-1H-benzo[d]imidazole-1-carboxylate

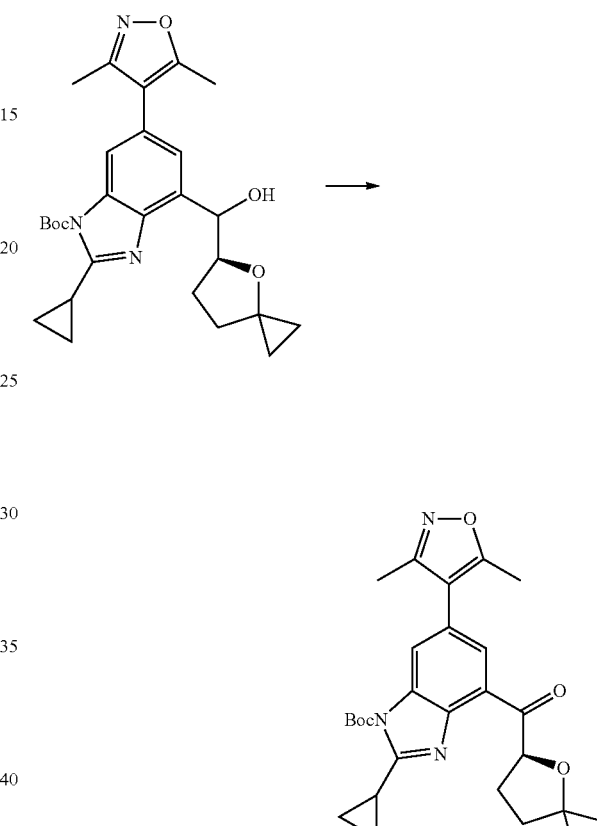

To a solution of tert-butyl 2-cyclopropyl-6-(3,5-dimethylisoxazol-4-yl)-4-(hydroxy((S)-4-oxaspiro[2.4]heptan-5-yl)methyl)-1H-benzo[d]imidazole-1-carboxylate (190 mg, 0.40 mmol) in CH$_2$Cl$_2$ (10 mL) was added Dess-Martin periodinane (252 mg, 0.60 mmol) in one-portion and the mixture was stirred at room temperature for 4 h. Solid was filtered and the solvent was removed. The residue was purified by silica gel column chromatography (0-70% EtOAc in hexane) to give (S)-tert-butyl 2-cyclopropyl-6-(3,5-dimethylisoxazol-4-yl)-4-(4-oxaspiro[2.4]heptane-5-carbonyl)-1H-benzo[d]imidazole-1-carboxylate as solid.

C$_{27}$H$_{31}$N$_3$O$_5$. MS m/z 477.8 (M+1). $^1$H NMR (Chloroform-d) δ 8.01 (d, J=1.7 Hz, 1H), 7.85 (d, J=1.7 Hz, 1H), 6.20 (dd, J=8.7, 5.8 Hz, 1H), 2.97-2.85 (m, 1H), 2.72-2.61 (m, 1H), 2.43 (s, 3H), 2.29 (s, 3H), 2.19-1.91 (m, 3H), 1.72 (s, 9H), 1.43-1.31 (m, 2H), 1.27-1.18 (m, 2H), 1.16-0.93 (m, 2H), 0.62-0.52 (m, 2H).

Step 8: (S)-(2-cyclopropyl-6-(3,5-dimethylisoxazol-4-yl)-1H-benzo[d]imidazol-4-yl)(pyridazin-3-yl)((S)-4-oxaspiro[2.4]heptan-5-yl)methanol

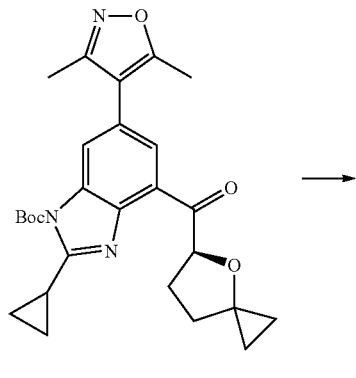

Example 310

(S)-(2-cyclopropyl-6-(3,5-dimethylisoxazol-4-yl)-1H-benzo[d]imidazol-4-yl)(6-methylpyridin-2-yl)((S)-4-oxaspiro[2.4]heptan-5-yl)methanol (1020-310)

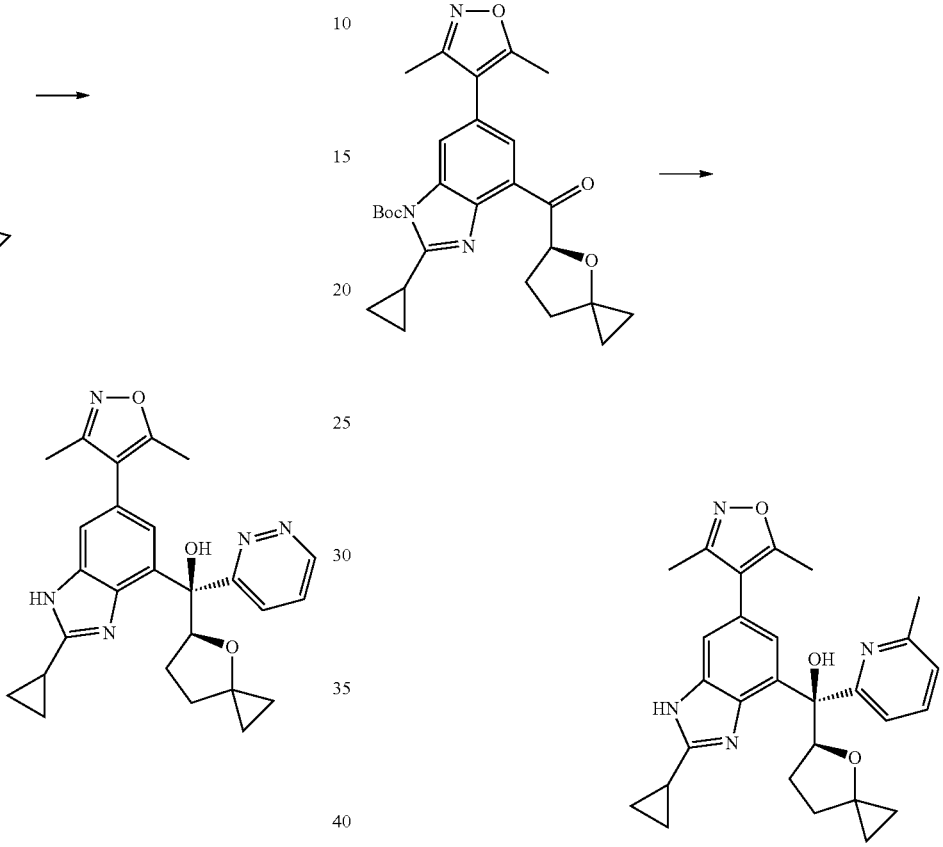

To a solution of pyridazine (84 mg, 1.05 mmol) in THF (4 mL) was added TMP-MgCl—LiCl (1.04 mmol, 1.0 M in Hexane/toluene) at −78° C. and the mixture was stirred at 0° C. for 30 min. A lot of solid precipitated in the reaction mixture. 3 mL of THF was added to rinse solid on wall of flask. To the mixture was added (S)-tert-butyl 2-cyclopropyl-6-(3,5-dimethylisoxazol-4-yl)-4-(4-oxaspiro[2.4]heptan-5-carbonyl) 1H-benzo[d]imidazole-1-carboxylate (50 mg, 0.1 mmol) in THF (4 mL) and the mixture was stirred at 0° C. for 4 h. The reaction was quenched with aq NH$_4$Cl and extracted with EtOAc. Organic solution was washed with brine and dried over Na$_2$SO$_4$. Solvent was evaporated and the residue was purified by silica gel column chromatography (0-20% MeOH/CH$_2$Cl$_2$) to give Boc-protected and de-Boc products. Combined mixture was treated with TFA (2 mL), THF (2 mL) and H$_2$O (0.2 mL). The solution was heated at 50° C. for 1 h. Solvent was removed and the residue was purified by HPLC to give product. HPLC indicated that the product was a mixture of diastereomers with ratio of 92:8.

C$_{26}$H$_{27}$N$_5$O$_3$. MS m/z 558.4 (M+1). $^1$H NMR (Methanol-d4) δ 9.38 (dd, J=2.4, 1.2 Hz, 1H), 9.17 (dd, J=5.5, 1.2 Hz, 1H), 8.03 (dd, J=5.5, 2.4 Hz, 1H), 7.55 (dd, J=18.2, 1.4 Hz, 2H), 5.13 (t, J=7.3 Hz, 1H), 2.65 (td, J=8.4, 4.2 Hz, 1H), 2.39 (s, 3H), 2.22 (s, 3H), 2.17-2.05 (m, 2H), 1.96-1.76 (m, 2H), 1.62-1.48 (m, 2H), 1.47-1.33 (m, 2H), 0.86-0.75 (m, 2H), 0.57-0.42 (m, 2H).

To a solution of (S)-tert-butyl 2-cyclopropyl-6-(3,5-dimethylisoxazol-4-yl)-4-(4-oxaspiro[2.4]heptane-5-carbonyl)-1H-benzo[d]imidazole-1-carboxylate (60 mg, 0.126 mmol) in THF (4 mL) was added a solution of 6-methylpyridinyl-2-magnesium bromide (148 mg, 0.75 mmol) and the solution was stirred at room temperature for 4 h. Aq NH$_4$Cl was added followed by extraction with EtOAc (150 mL). The organic solution was washed with brine and dried over Na$_2$SO$_4$. Solvent was removed and the residue was purified by silica gel column chromatography (0-10% MeOH in CH$_2$Cl$_2$) to give crude N-Boc protected intermediate which was dissolved in THF-TFA-H$_2$O (2 mL-2 mL-0.2 mL). The solution was heated at 50° C. for 1 h. Solvent was removed and the residue was purified by HPLC to give (S)-(2-cyclopropyl-6-(3,5-dimethylisoxazol-4-yl)-1H-benzo[d]imidazol-4-yl)(6-methylpyridin-2-yl)((S)-4-oxaspiro[2.4]heptan-5-yl)methanol containing inseparable impurities (5-8%).

C$_{28}$H$_{30}$N$_4$O$_3$. MS m/z 471.2 (M+1). $^1$H NMR (Methanol-d4) δ 7.87 (t, J=7.8 Hz, 1H), 7.74 (d, J=8.0 Hz, 1H), 7.64 (d, J=1.4 Hz, 1H), 7.46 (d, J=1.4 Hz, 1H), 7.35 (d, J=7.7 Hz, 1H), 5.34 (t, J=7.3 Hz, 1H), 2.68-2.53 (m, 4H), 2.40 (s, 3H), 2.23 (s, 3H), 2.11 (q, J=4.2 Hz, 1H), 2.05-1.83 (m, 3H), 1.53 (dd, J=9.4, 2.5 Hz, 2H), 1.44-1.31 (m, 2H), 0.85 (dt, J=10.4, 5.3 Hz, 1H), 0.79-0.64 (m, 1H), 0.59-0.39 (m, 2H).

Example 311

(2-cyclopropyl-6-(3,5-dimethylisoxazol-4-yl)-1H-benzo[d]imidazol-4-yl)(pyridazin-3-yl)((R)-4-oxaspiro[2.4]heptan-5-yl)methanol (1020-311)

Step 1: tert-butyl 2-cyclopropyl-6-(3,5-dimethylisoxazol-4-yl)-4-(hydroxy (R)-4-oxaspiro[2.4]heptan-5-yl)methyl)-1H-benzo[d]imidazole-1-carboxylate

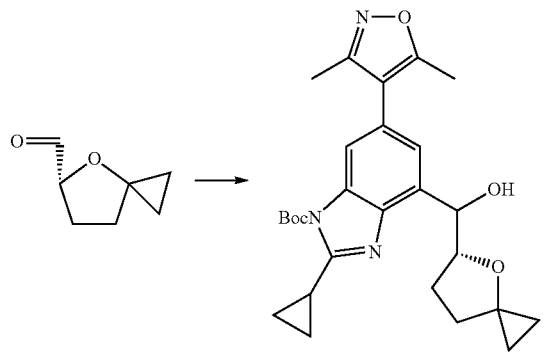 [SMILES: O=C[C@H]1CCC2(CC2)O1 ; Cc1noc(C)c1-c1cc(C(O)[C@H]2CCC3(CC3)O2)c2nc(C3CC3)n(C(=O)OC(C)(C)C)c2c1]

tert-butyl 2-cyclopropyl-6-(3,5-dimethylisoxazol-4-yl)-4-(hydroxy((R)-4-oxaspiro[2.4]heptan-5-yl)methyl)-1H-benzo[d]imidazole-1-carboxylate was prepared from R-aldehyde in a similar fashion as that of Example 309, step 6.

Step 2: (R)-tert-butyl 2-cyclopropyl-6-(3,5-d methylisoxazol-4-yl)-4-(4-oxaspiro[2.4]heptane-5-carbonyl)-1H-benzo[d]imidazolo-1-carboxylate

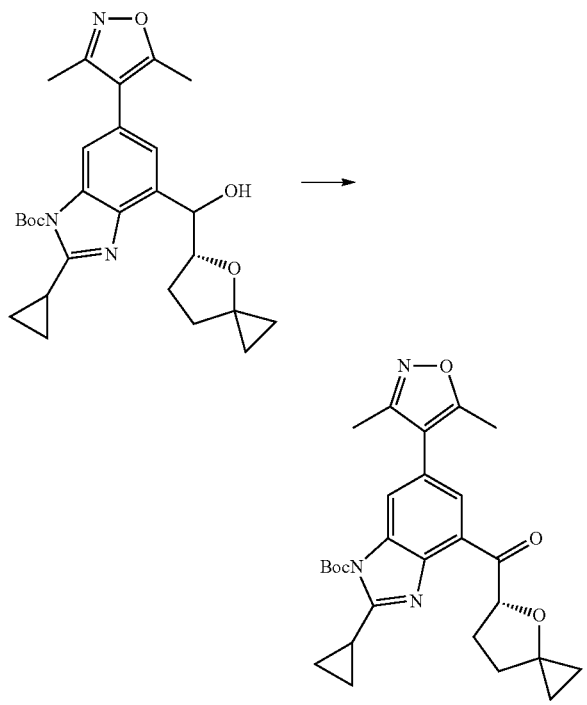

(R)-tert-butyl 2-cyclopropyl-6-(3,5-dimethylisoxazol-4-yl)-4-(4-oxaspiro[2.4]heptane-5-carbonyl)-1H-benzo[d]imidazo-1-carboxylate was prepared from R-alcohol in as similar fashion as that of Example 309, step 7.

$C_{27}H_{31}N_3O_5$. MS m/z 477.7 (M+1). $^1$H NMR (400 MHz. Chloroform-d) δ 8.01 (d, J=1.7 Hz, 1H), 7.85 (d, J=1.7 Hz, 1H), 6.20 (dd, J=8.7, 5.8 Hz, 1H), 2.98-2.82 (m, 1H), 2.75-2.57 (m, 1H), 2.42 (s, 3H), 2.29 (s, 3H), 2.19-1.91 (m, 4H), 1.72 (s, 9H), 1.41-1.29 (m, 2H), 1.20 (dd, J=8.2, 3.5 Hz, 2H), 1.17-0.93 (m, 2H), 0.57 (td, J=2.6, 0.8 Hz, 2H).

Step 3: (2-cyclopropyl-6-(3,5-dimethylisoxazol-4-yl)-1H-benzo[d]imidazol-4-yl)(pyridazin-3-yl)((R)-4-oxaspiro[2.4]heptan-5-yl)methanol

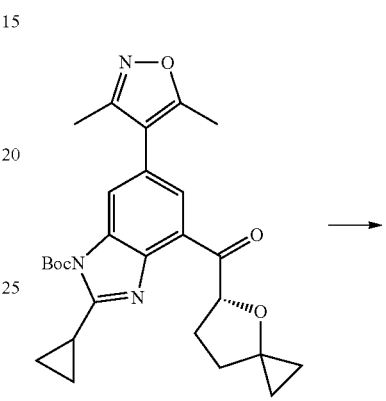

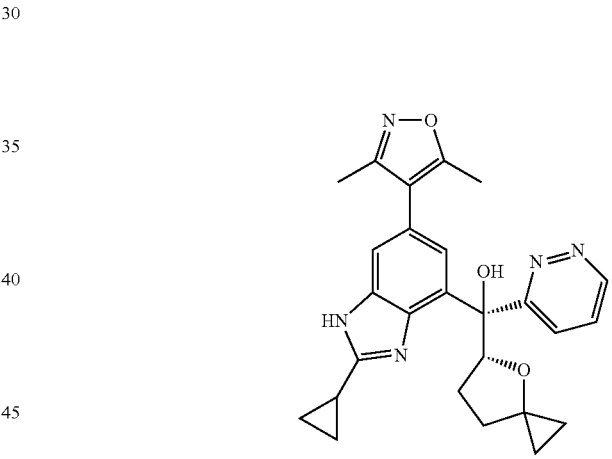

(2-Cyclopropyl-6-(3,5-dimethylisoxazol-4-yl)-1H-benzo[d]imidazol-4-yl)(pyridazin-3-yl)((R)-4-oxaspiro[2.4]heptan-5-yl)methanol was prepared from (R)-tert-butyl 2-cyclopropyl-6-(3,5-dimethylisoxazol-4-yl)-4-(4-oxaspiro[2.4]heptane-5-carbonyl)-1H-benzo[d]imidazole-1-carboxylate in a similar fashion as that of Example 309, step 8. HPLC indicated that the product was a mixture of diastereomers with ratio of 56/39.

$C_{26}H_{27}N_5O_3$. MS m/s 458.15 (M+1). $^1$H NMR (Methanol-$d_4$) δ 9.37 (dd, J=2.4, 1.2 Hz), 9.16 (dd, J=5.5, 1.2 Hz), 9.09 (dd, J=5.0, 1.6 Hz), 8.13 (dd, J=8.7, 1.6 Hz), 8.02 (dd, J=5.5, 2.4 Hz), 7.72 (dd, J=8.7, 5.0 Hz), 7.64 (d, J=1.5 Hz), 7.59-7.43 (m), 5.13 (t, J=7.3 Hz), 2.66 (ddd, J=16.8, 8.4, 4.2 Hz), 2.38 (d, J=4.8 Hz), 2.21 (d, J=6.1 Hz), 2.20-1.72 (m), 1.63-1.28 (m), 0.95-0.35 (m).

Example 312

4-(2-cyclopropyl-7-fluoro-4-(fluorodi(pyridin-2-yl)methyl)-1H-benzo[d]imidazol-6-yl)-3,5-dimethylisoxazole (1020-312)

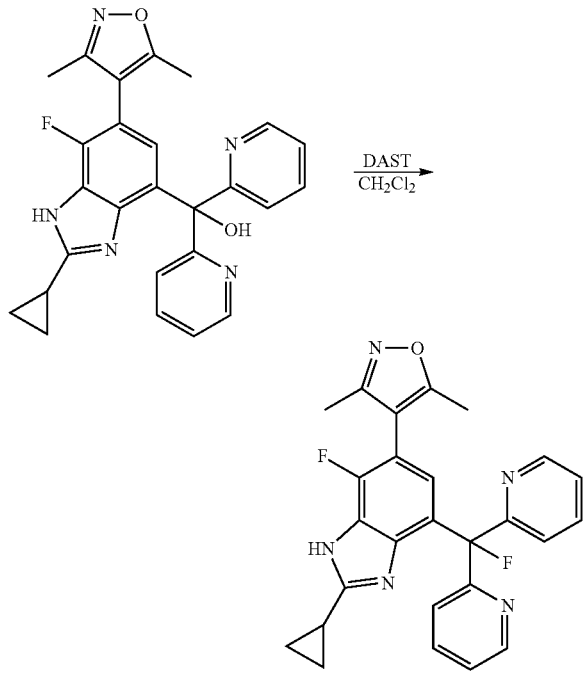

To flask containing (2-cyclopropyl-6-(3,5-dimethylisoxazol-4-yl)-7-fluoro-1H-benzo[d]imidazol-4-yl)di(pyridin-2-yl)methanol (21 mg, 0.046 mmol, 1 equiv.) and DCM (3 mL) is added DAST (31 μL, 0.23 mmol, 5 equiv.). After an hour the reaction is complete and is poured into a solution of sodium bicarbonate and extracted with DCM. The combined organic layers are washed with water and saturated NH₄Cl. After drying with MgSO₄, it was filtered and concentrated to dryness. Purification was carried out by reverse phase HPLC to 4-(2-cyclopropyl-7-fluoro-4-(fluorodi(pyridin-2-yl)methyl)-1H-benzo[d]imidazol-6-yl)-3,5-dimethylisoxazole.

LCMS (m/z+1) 458.48. ¹H NMR (400 MHz, Methanol-d4) δ 8.61-8.49 (m, 1H), 7.97 (td, J=7.8, 1.7 Hz, 1H), 7.74-7.61 (m, 1H), 7.48 (ddt, J=7.0, 5.0, 0.9 Hz, 1H), 7.09-6.84 (m, 0H), 2.50-2.36 (m, 0H), 2.34-2.23 (m, 2H), 2.10 (d, J=0.9 Hz, 1H), 1.47-1.27 (m, 2H). ¹⁹F NMR (376 MHz, Methanol-d4) δ −77.92, −131.68 (d, J=6.1 Hz), −142.09.

Example 313

4-(2-cyclopropyl-4-(fluoro(oxazol-2-yl)(pyridin-3-yl)methyl)-1H-benzo[d]imidazol-6-yl)-3,5-dimethylisoxazole (1020-313)

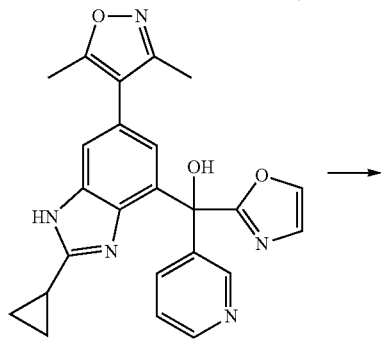

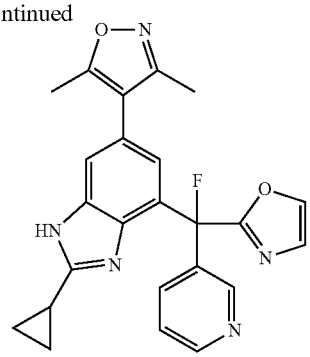

To a solution of (2-cyclopropyl-6-(3,5-dimethylisoxazol-4-yl)-1H-benzo[d]imidazol-4-yl)(oxazol-2-yl)(pyridin-3-yl)methanol (40 mg, 0.094 mmol) in CH₂Cl₂ (5 mL) was added DAST (0.1 mL) and the solution was stirred at room temperature for 2 h. EtOAc (100 mL) was added and the solution was washed with aq NaHCO₃, brine and dried over Na₂SO₄. Solvent was removed and the residue was purified by HPLC to give 4-(2-cyclopropyl-4-(fluoro(oxazol-2-yl)(pyridin-3-yl)methyl)-1H-benzo[d]imidazol-6-yl)-3,5-dimethylisoxazole.

C₂₄H₂₀FN₃O₂. MS m/z 430.2 (M+1). ¹H NMR (Methanol-d₄) δ 8.79-8.65 (m, 2H), 8.19 (dt, J=1.6, 0.8 Hz, 1H), 8.02 (ddd, J=8.3, 2.4, 1.2 Hz, 1H), 7.75-7.62 (m, 2H), 7.43-7.30 (m, 1H), 6.91 (t, J=1.6 Hz, 1H), 2.49 (ddd, J=8.4, 5.0, 3.4 Hz, 1H), 2.34 (d, J=0.8 Hz, 3H), 2.15 (d, J=0.8 Hz, 3H), 1.59-1.48 (m, 2H), 1.40 (dd, J=5.0, 2.6 Hz, 2H). ¹⁹F (Methanol-d4) δ 138.53

Example 314

4-(2-cyclopropyl-4-(fluorodi(pyridin-3-yl)methyl)-1H-benzo[d]imidazol-6-yl)-3,5-dimethylisoxazole (1020-314)

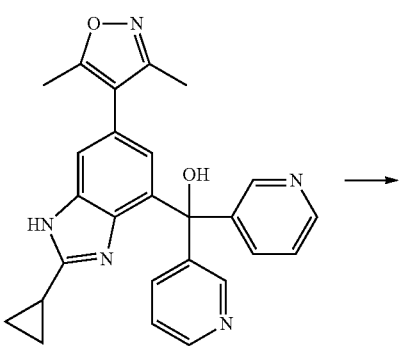

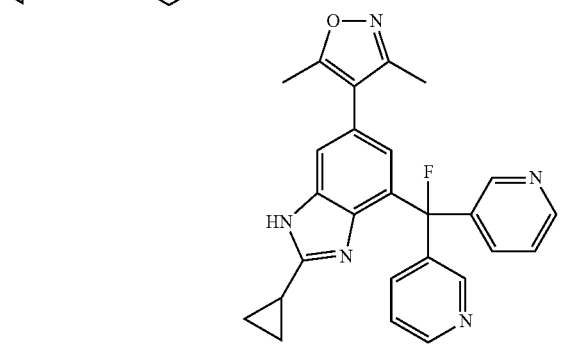

4-(2-Cyclopropyl-4-(fluorodi(pyridin-3-yl)methyl)-1H-benzo[d]imidazol-6-yl)-3,5-dimethylisoxazole was synthesized from (2-cyclopropyl-6-(3,5-dimethylisoxazol-4-yl)-1H-benzo[d]imidazol-4-yl)di(pyridin-3-yl)methanol in a similar fashion as Example 313.

4-(2-cyclopropyl-4-(fluorodi(pyridin-3-yl)methyl)-1H-benzo[d]imidazol-6-yl)-3,5-dimethylisoxazole: $C_{26}H_{22}FN_5O$. MS m/z 440.1. $^1H$ NMR (Methanol-$d_4$) δ 68.75 (d, J=5.0 Hz, 2H), 8.60 (d, J=2.6 Hz, 2H), 7.92 (ddd, J=8.2, 2.6, 1.3 Hz, 2H), 7.74-7.59 (m, 3H), 6.79 (t, J=1.6 Hz, 1H), 2.55-2.38 (m, 1H), 2.30 (d, J=0.9 Hz, 3H), 2.10 (d, J=0.9 Hz, 3H), 1.51 (td, J=7.8, 4.8 Hz, 2H), 1.39 (dt, J=8.1, 5.1 Hz, 2H). $^{19}F$ (Methanol-d4) δ 132.2.

Example 315

4-(2-cyclopropyl-4-(3-fluoro-2,4-dimethylpentan-3-yl)-1H-benzo[d]imidazol-6-yl)-3,5-dimethylisoxazole (1020-315)

Example 316

4-(2-cyclopropyl-4-((S)-fluoro(pyridin-2-yl)((R)-4-oxaspiro[2.4]heptan-5-yl)methyl)-1H-benzo[d]imidazol-6-yl)-3,5-dimethylisoxazole (1020-316)

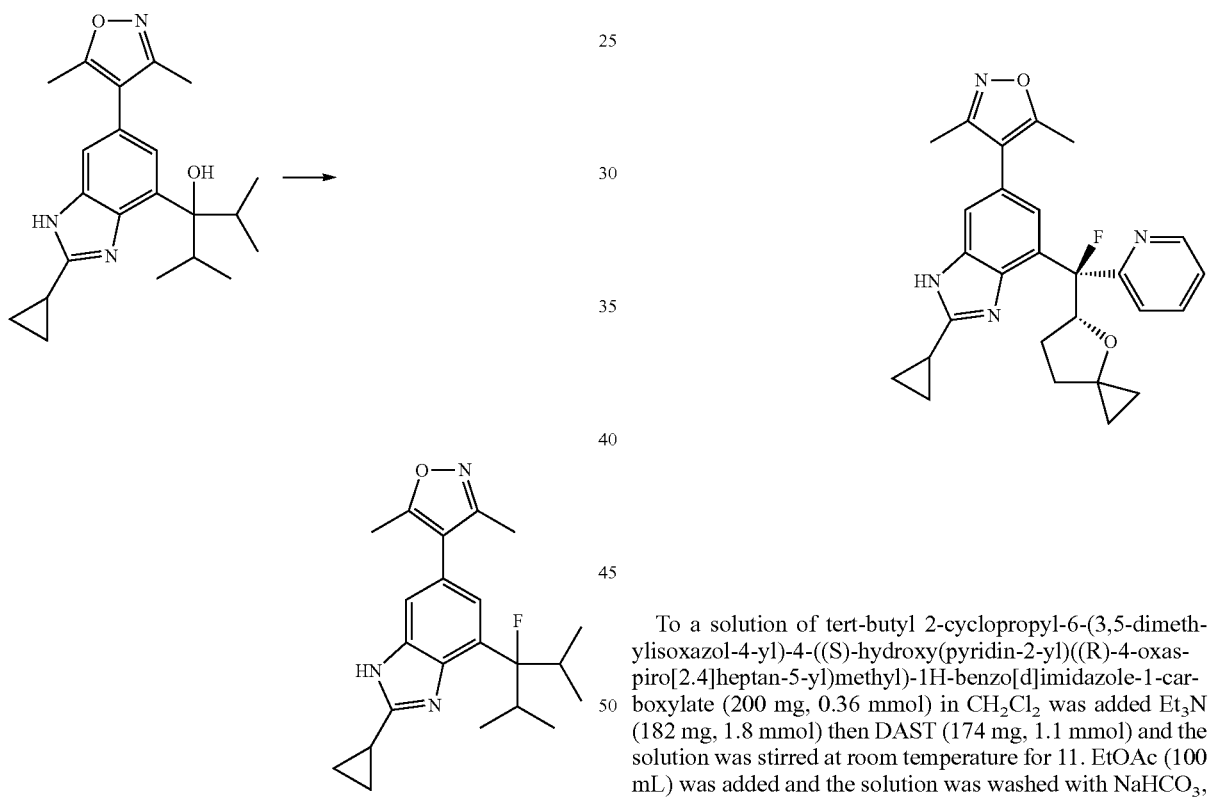

4-(2-cyclopropyl-4-(3-fluoro-2,4-dimethylpentan-3-yl)-1H-benzo[d]imidazol-6-yl)-3,5-dimethylisoxazole was synthesized from 3-(2-cyclopropyl-6-(3,5-dimethylisoxazol-4-yl)-1H-benzo[d]imidazol-4-yl)-2,4-dimethylpentan-3-ol in a similar fashion as Example 313.

4-(2-cyclopropyl-4-(3-fluoro-2,4-dimethylpentan-3-yl)-1H-benzo[d]imidazol-6-yl)-3,5-dimethylisoxazole: $C_{22}H_{28}FN_3O$. MS m/z 370.1. $^1H$ NMR (Methanol-$d_4$) δ 7.53 (d, J=1.4 Hz, 1H), 7.18 (s, 1H), 2.73-2.55 (m, 3H), 2.43 (s, 3H), 2.31, 2.26 (s, 3H), 1.54 (dt, J=7.8, 3.7 Hz, 2H), 1.47-1.38 (m, 2H), 0.96 (dd, J=33.9, 6.8 Hz, 12H). $^{19}F$ (Methanol-d4) δ 172.9.

To a solution of tert-butyl 2-cyclopropyl-6-(3,5-dimethylisoxazol-4-yl)-4-((S)-hydroxy(pyridin-2-yl)((R)-4-oxaspiro[2.4]heptan-5-yl)methyl)-1H-benzo[d]imidazole-1-carboxylate (200 mg, 0.36 mmol) in $CH_2Cl_2$ was added $Et_3N$ (182 mg, 1.8 mmol) then DAST (174 mg, 1.1 mmol) and the solution was stirred at room temperature for 1h. EtOAc (100 mL) was added and the solution was washed with $NaHCO_3$, brine and dried over $Na_2SO_4$. Solvent was removed and the residue was dissolved in THF (5 mL), TFA (5 mL) and water (0.5 mL). The solution was heated at 50° C. for 1 h. Solvent was removed and the residue was purified by PHLC to give 4-(2-cyclopropyl-4-((S)-fluoro(pyridin-2-yl)((R)-4-oxaspiro[2.4]heptan-5-yl)methyl)-1H-benzo[d]imidazol-6-yl)-3,5-dimethylisoxazole.

$C_{27}H_{27}FN_4O_2$. MS. m/z 459.3 (M+1). $^1H$ NMR (Methanol-$d_4$) δ 8.70-8.60 (m, 1H), 7.96-7.82 (m, 2H), 7.64 (t, J=1.4 Hz, 1H), 7.51 (d, J=1.5 Hz, 1H), 7.38 (ddd, J=7.5, 4.8, 1.2 Hz, 1H), 5.51-5.29 (m, 1H), 2.73-2.59 (m, 1H), 2.38 (s, 3H), 2.20 (s, 3H), 2.16-1.87 (m, 2H), 1.72-1.52 (m, 2H), 1.48-1.32 (m, 4H), 0.78-0.35 (m, 4H). $^{19}F$ (Methanol-$d_4$). δ 179.28 (d, J=29 Hz).

Example 317

4-(2-cyclopropyl-4-(fluoro(6-methylpyridin-2-yltetrahydrofuran-2-yl)methyl)-1H-benzo[d]imidazol-6-yl)-3,5-dimethylisoxazole (1020-317)

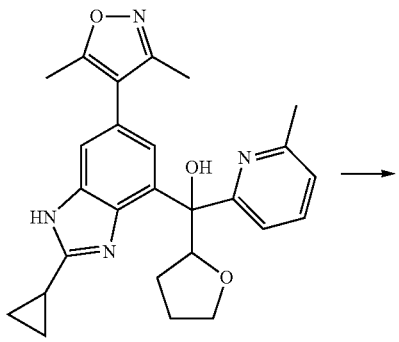

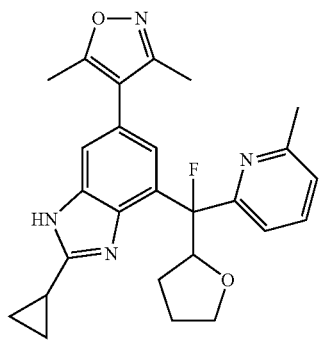

The substrate (0.067 g) was dissolved in DCM (4 ml) and reacted with DAST (0.109 g) at RT for 20 min. Sat. aequ. NaHCO3 (1 ml) was added, stirred for 30 min, the organic layer separated, volatiles removed and the residue purified by reverse phase HPLC (5-95% MeCN in water, 0.1% TFA) to afford 4-(2-cyclopropyl-4-(fluoro(6-methylpyridin-2-yl)(tetrahydrofuran-2-yl)methyl)-1H-benzo[d]imidazol-6-yl)-3,5-dimethylisoxazole.

LCMS (m/z+1) 477.0. $^{19}$F NMR (376 MHz, Methanol-d4) δ −77.70. $^1$H NMR (400 MHz, Methanol-d4) δ 7.66 (t, J=7.8 Hz, 1H), 7.61 (t, J=1.2 Hz, 1H), 7.53 (d, J=7.9 Hz, 1H), 7.42 (d, J=1.4 Hz, 1H), 7.16-7.09 (m, 1H), 5.20 (s, 2H), 3.86-3.61 (m, 3H), 2.53 (s, 1H), 2.47 (s, 2H), 2.33 (s, 2H), 2.16 (s, 2H), 1.85 (dd, J=6.5, 2.8 Hz, 4H), 1.52-1.40 (m, 2H), 1.31 (dd, J=5.6, 3.1 Hz, 2H).

Example 318

4-(2-cyclopropyl-4-(fluorodi(pyridin-2-yl)methyl)-1H-benzo[d]imidazol-6-yl)-3,5-dimethylisoxazole (1020-318)

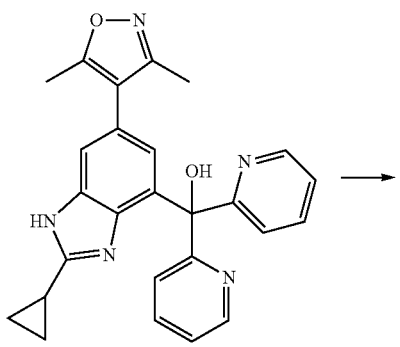

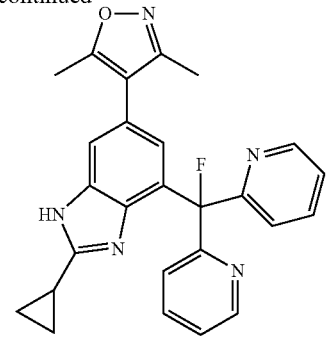

The substrate (0.1 g) was dissolved in DCM (4 ml) and reacted with DAST (0.074 g) at RT for 20 min. Sat. aequ. NaHCO3 (1 ml) was added, stirred for 10 min, the organic layer separated, volatiles removed and the residue purified by reverse phase HPLC (5-95% MeCN in water, 0.1% TFA) to afford 4-(2-cyclopropyl-4-(fluorodi(pyridin-2-yl)methyl)-1H-benzo[d]imidazol-6-yl)-3,5-dimethylisoxazole.

LCMS (m/z+1) 440.1. $^{19}$F NMR (376 MHz, Methanol-d4) δ −142.63. $^1$H NMR (400 MHz, Methanol-d4) δ 8.74-8.59 (m, 1H), 8.12 (t, J=7.4 Hz, 1H), 7.77 (dd, J=8.0, 1.4 Hz, 1H), 7.71-7.66 (m, 0H), 7.62 (d, J=6.9 Hz, 1H), 7.14 (s, 1H), 3.04 (d, J=7.3 Hz, 0H), 2.54 (ddd, J=8.4, 5.0, 3.4 Hz, 1H), 2.33 (s, 1H), 2.14 (s, 1H), 1.64-1.49 (m, 1H), 1.48-1.36 (m, 1H).

Example 319

4-(2-cyclopropyl-7-(fluorodi(pyridin-2-yl)methyl)-1-methyl-1H-benzo[d]imidazol-5-yl)-3,5-dimethylisoxazole (1020-319)

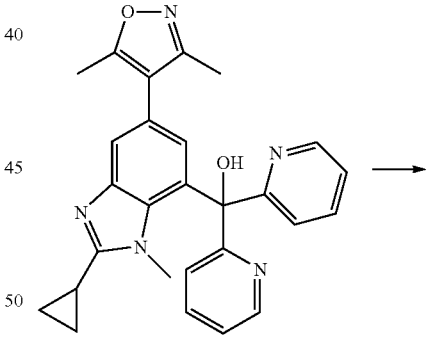

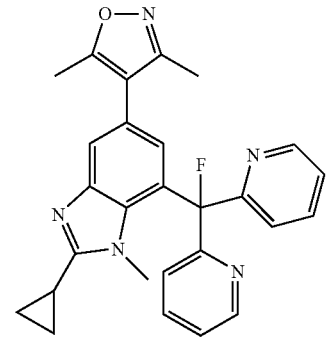

The substrate (0.05 g) was dissolved in DCM (4 ml) and reacted with DAST (0.036 g) at RT for 20 min. Sat. aequ.

NaHCO₃ (1 ml) was added, stirred for 15 min, the organic layer separated, volatiles removed and the residue purified by reverse phase HPLC (5-95% MeCN in water, 0.1% TFA) to afford 4-(2-cyclopropyl-7-(fluorodi(pyridin-2-yl)methyl)-1-methyl-1H-benzo[d]imidazol-5-yl)-3,5-dimethylisoxazole.

LCMS (m/z+1) 454.3. ¹⁹F NMR (376 MHz, Acetonitrile-d3) δ −77.00. ¹H NMR (400 MHz, Acetonitrile-d3) δ 8.62-8.40 (m, 1H), 8.02-7.85 (m, 1H), 7.70-7.55 (m, 1H), 7.53-7.32 (m, 1H), 6.72 (t, J=1.9 Hz, 1H), 3.50 (d, J=2.4 Hz, 2H), 2.24 (s, 2H), 2.07 (s, 1H), 1.42-1.26 (m, 2H).

Example 320

4-(2-cyclopropyl-7-(fluorodi(pyridin-2-yl)methyl)-1-methyl-1H-benzo[d]imidazol-5-yl)-3,5-dimethyl-isoxazole (1020-320)

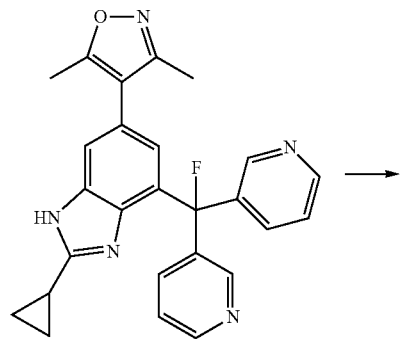

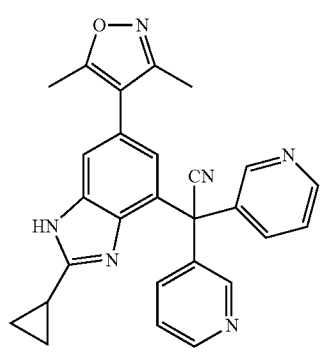

The substrate (0.046 g) was dissolved in water/MeCN (5/1 ml) and NaCN (0.05 g) added at RT. After stirring for 24 h at RT, volatiles were removed and the residue purified by reverse phase HPLC (5-95% MeCN in water, 0.1% TFA) to afford 4-(2-cyclopropyl-7-(fluorodi(pyridin-2-yl)methyl)-1-methyl-1H-benzo[d]imidazol-5-yl)-3,5-dimethylisoxazole.

LCMS (m/z+1) 447.2. ¹H NMR (400 MHz, Methanol-d4) δ 8.61 (dt, J=4.7, 1.5 Hz, 1H), 7.92 (td, J=7.8, 1.8 Hz, 1H), 7.63 (d, J=1.5 Hz, 1H), 7.54-7.37 (m, 2H), 6.72 (d, J=1.4 Hz, 1H), 2.43 (s, 1H), 2.33 (s, 2H), 2.15 (s, 2H), 1.45 (dd, J=8.2, 3.0 Hz, 1H), 1.32 (dd, J=4.9, 2.8 Hz, 1H).

Example 321

(4-(1H-benzo[d]imidazol-6-yl)-5-methylisoxazol-3-yl)methanamine (1020-321)

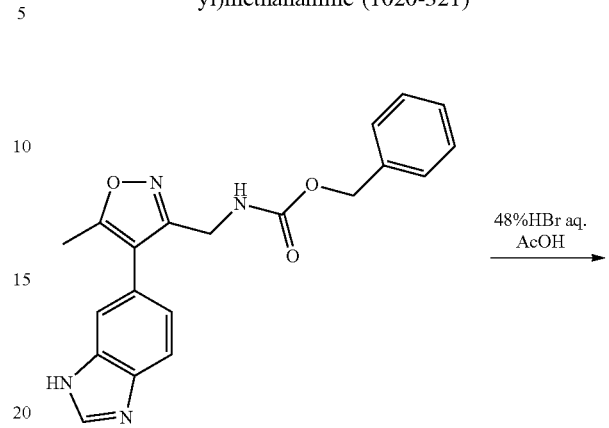

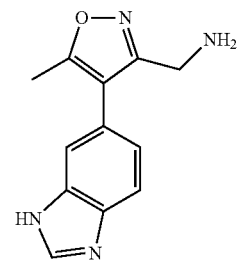

Benzyl ((4-(1H-benzo[d]imidazol-6-yl)-5-methylisoxazol-3-yl)methyl)carbamate was treated with 48% aq. HBr (6.7 mg) in AcOH (1 mL) at room temperature for 30 min. The aqueours AcOH was removed under a reduced pressure to give (4-(1H-benzo[d]imidazol-6-yl)-5-methylisoxazol-3-yl)methanamine.

C₁₂H₁₂N₄O. MS. 229.1 (M+1). ¹H NMR (MeOH-d₄) δ 9.50 (s, 1H), 8.00 (d, J=8.0 Hz, 1H), 7.90 (s, 1H), 7.65 (dd, J=8.0, 1.0 Hz, 1H), 4.32 (s, 2H), 2.52 (s, 3H).

Example 322

N-((4-(1H-benzo[d]imidazol-6-yl)-5-methylisoxazol-3-yl)methyl)acetamide (1020-322)

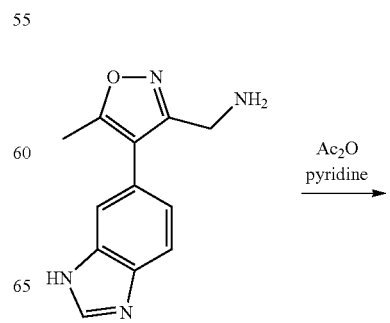

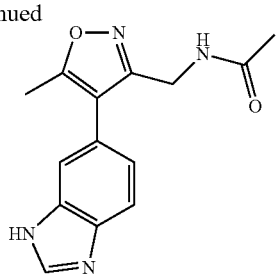

(4-(1H-benzo[d]imidazol-6-yl)-5-methylisoxazol-3-yl)methanamine was treated with Ac$_2$O in pyridine at room temperature for 1 h. The reaction mixture was treated with MeOH (3 mL) at room temperature for 30 min and then 80° C. for 30 min. The mixture was purified by prep-HPLC to give N-((4-(1H-benzo[d]imidazol-6-yl)-5-methylisoxazol-3-yl)methyl)acetamide.

C$_{12}$H$_{12}$N$_4$O. MS. 271.1.1 (M+1). $^1$H NMR (MeOH-d$_4$) δ 9.37 (s, 1H), 7.92 (d, J=9.6 Hz, 1H), 7.81 (s, 1H), 7.59 (dd, J=9.6, 1.0 Hz, 1H), 4.45 (s, 2H), 2.43 (s, 3H), 1.80 (s, 3H).

Example 323

N-((4-(1H-benzo[d]imidazol-6-yl)-3-methylisoxazol-5-yl)methyl)acetamide (1020-323)

Step 1: Preparation of N-((3-methylisoxazol-5-yl)methyl)acetamide

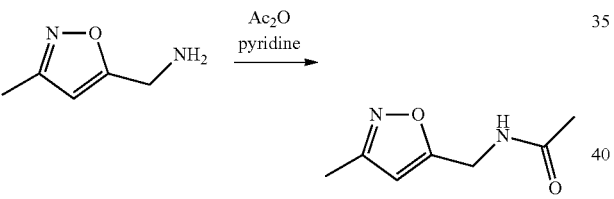

(3-Methylisoxazol-5-yl)methanamine (100.0 mg, 0.892 mmol) was treated with Ac$_2$O and pyridine at room temperature for 7 h. After an aqueours work-up, the crude mixture was purified by a silica-gel column chromatography (20 to 40% EtOAc/hexane) to give N-((3-methylisoxazol-5-yl)methyl)acetamide.

$^1$H NMR (MeOH-d$_4$) δ 6.14 (s, 1H), 4.43 (s, 2H), 2.25 (s, 3H), 1.99 (s, 3H).

Step 2: Preparation of N-((4-bromo-3-methylisoxazol-5-yl)methyl)acetamide

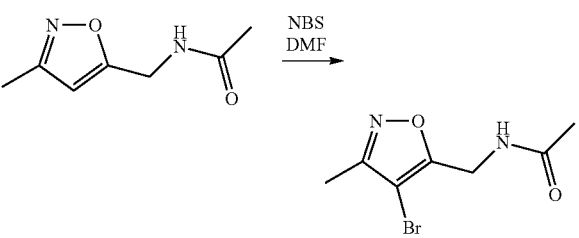

N-((3-methylisoxazol-5-yl)methyl)acetamide. (86.4 mg, 0.56 mmol) was treated with NBS (109.7 mg, 0.616 mmol, 1.1 equiv) in DMF (2 mL) at room temperature for 17 h. The mixture was purified by prep-HPLC to give N-((4-bromo-3-methylisoxazol-5-yl)methyl)acetamide. C$_7$H$_9$BrN$_2$O$_2$. MS. 233.0 (M−1), 235.0 (M+1).

Step 3: Preparation of N-((4-(1H-benzo[d]imidazol-6-yl)-3-methylisoxazol-5-yl)methyl)acetamide

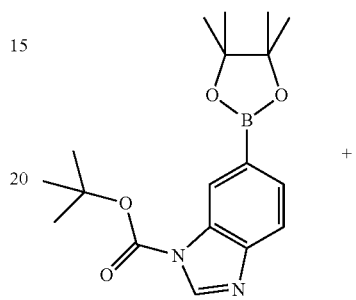

tert-butyl 5- and 6-(4,4,5,5-tetramethyl-1,3,2-dioxaborolan-2-yl)-1H-benzo[d]imidazole-1-carboxylate (116.0 mg, 0.337 mmol, 1.6 equiv) and N-((4-bromo-3-methylisoxazol-5-yl)methyl)acetamide (48.5 mg, 0.208 mmol) were treated with PEPPSIiPr (28.4 mg, 0.042 mmol, 0.2 equiv) and Cs$_2$CO$_3$ (203.4 mg, 0.624 mmol, 3 equiv) in 1,2-dimethoxyethane (2 mL) and water (1 mL) at 140° C. for 30 min using microwave reactor. The mixture was purified by prep-HPLC to give N-((4-(1H-benzo[d]imidazol-6-yl)-3-methylisoxazol-5-yl)methyl)acetamide.

C$_{14}$H$_{14}$N$_4$O$_2$. MS. 271.1 (M+1). $^1$H NMR (MeOH-d$_4$) δ 9.42 (s, 1H), 7.94 (d, J=9.6 Hz, 1H), 7.93 (s, 1H), 7.67 (dd, J=9.6 Hz, 1H), 4.50 (s, 2H), 2.28 (s, 3H), 1.88 (s, 3H).

Example 324

(2-cyclopropyl-6-(3,5-dimethylisoxazol-4-yl)-1H-benzo[d]imidazol-4-yl)(pyridin-3-yl)methanol (1020-324)

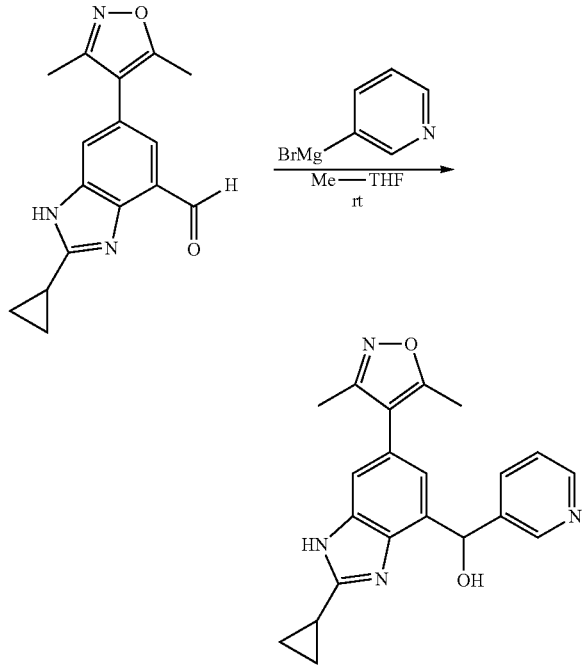

(2-cyclopropyl-6-(3,5-dimethylisoxazol-4-yl)-1H-benzo[d]imidazol-4-yl)(pyridin-3-yl)methanol was obtained from 2-cyclopropyl-6-(3,5-dimethylisoxazol-4-yl)-1H-benzo[d]imidazole-4-carbaldehyde (29.0 mg, 0.103 mmol) by treating with 3-pyridine magnesium bromide (1M in Me-THF, 0.91 mL, 8.8 equiv.) at room temperature for 16 h. After an aqueous work-up, the crude material was purified by an HPLC purification.

$C_{21}H_{20}N_4O_2$. MS. 361.3 (M+1). $^1$H NMR (MeOH-$d_4$) δ 9.00 (br s, 1H), 8.74 (br s, 1H), 8.50 (d, J=8.0 Hz, 1H), 7.91 (br s, 1H), 7.55 (d, J=1.0 Hz, 1H), 7.45 (d, J=1.0 Hz, 1H), 6.47 (s, 1H), 2.62-2.53 (m, 1H), 2.40 (s, 3H), 2.23 (s, 3H), 1.62-1.38 (m, 4H).

Example 325

3-((2-cyclopropyl-6-(3,5-dimethylisoxazol-4-yl)-1H-benzo[d]imidazol-4-yl)(hydroxy)(tetrahydrofuran-2-yl)methyl)pyridine 1-oxide (1020-325)

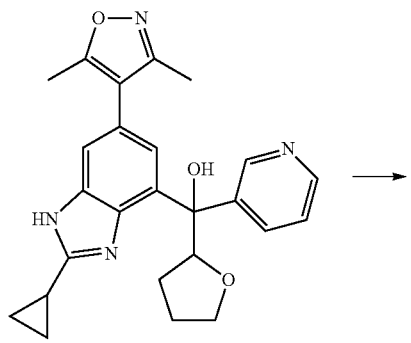

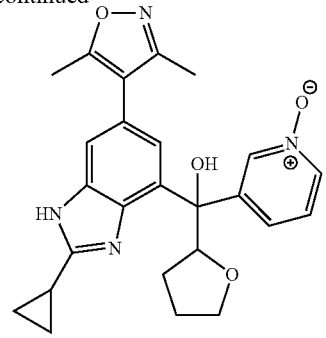

2-Cyclopropyl-6-(3,5-dimethylisoxazol-4-yl)-4-(hydroxy(pyridin-3-yl)(tetrahydrofuran-2-yl)methyl)-1H-benzo[d]imidazole (0.067 g) was subjected to MCPBA (0.175 g) in MeOH/DCM (1/1 ml) and stirred at RT for 24 h. Volatiles were removed and the residue purified by reverse phase HPLC (5-95% MeCN in water, 0.1% TFA) to afford 3-((2-cyclopropyl-6-(3,5-dimethylisoxazol-4-yl)-1H-benzo[d]imidazol-4-yl)(hydroxy)(tetrahydrofuran-2-yl)methyl)pyridine 1-oxide.

LCMS (m/z+1) 461.3. $^1$H NMR (400 MHz, Acetonitrile-d3) δ 7.84-7.78 (m, 1H), 7.59 (d, J=1.5 Hz, 1H), 7.43 (t, J=7.9 Hz, 1H), 7.36 (dd, J=7.8, 1.9 Hz, 1H), 6.69 (s, 1H), 4.70 (s, 2H), 3.82 (q, J=7.2 Hz, 2H), 3.74 (td, J=7.6, 5.3 Hz, 1H), 2.51-2.36 (m, 2H), 2.27 (s, 3H), 2.14 (s, 3H), 2.07-1.97 (m, 1H), 1.96 (s, 3H), 1.75 (dt, J=11.9, 7.7 Hz, 2H), 1.54 (dt, J=7.8, 4.7 Hz, 2H), 1.45-1.28 (m, 4H).

Example 326

2-cyclopropyl-6-(3,5-dimethylisoxazol-4-yl)-4-(hydroxybis(5-methylthiazol-2-yl)methyl)-1H-benzo[d]imidazol-1-yl)(thiophen-2-yl)methanone (1020-326)

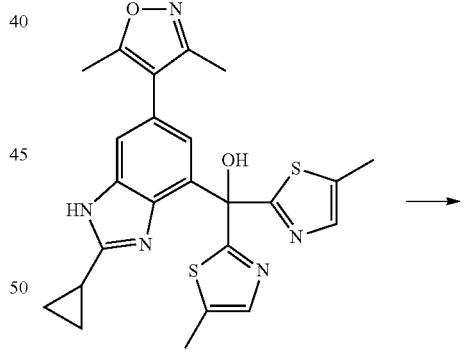

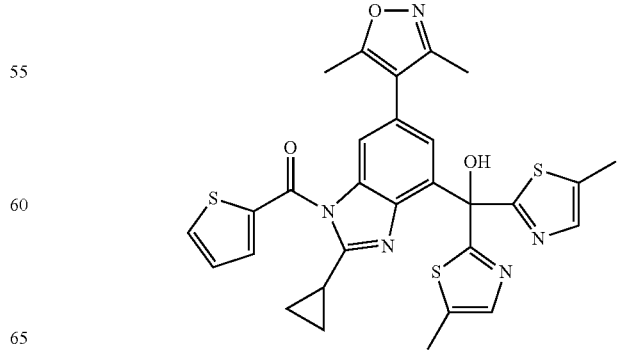

Using the product from Example 219, to a solution of (2-cyclopropyl-6-(3,5-dimethylisoxazol-4-yl)-1H-benzo[d]imidazol-4-yl)bis(5-methylthiazol-2-yl)methanol (60 mg, 0.126 mmol) in CH$_2$Cl$_2$ (5 mL) and pyridine (1 mL) was added thiophenecarbonyl chloride (37 mg, 0.25 mmol) dropwise and the solution was stirred at 0° C. for 1 h. EtOAc (100 mL) was added and the solution was washed with brine and dried over Na$_2$SO$_4$. Solvent was removed and the residue was purified by silica gel column chromatography (0-10% MeOH/CH$_2$Cl$_2$) to give (2-cyclopropyl-6-(3,5-dimethylisoxazol-4-yl)-4-(hydroxybis(5-methylthiazol-2-yl)methyl)-1H-benzo[d]imidazol-1-yl)(thiophen-2-yl)methanone.

C$_{29}$H$_{25}$N$_5$O$_3$S$_3$. MS m/z 587.9 (M+1). $^1$H NMR (Methanol-d$_4$) δ 8.10 (dd, J=5.0, 1.2 Hz, 1H), 7.80 (dd, J=3.9, 1.2 Hz, 1H), 7.39 (q, J=1.1 Hz, 2H), 7.32-7.23 (m, 2H), 7.14 (d, J=1.5 Hz, 1H), 2.45 (d, J=1.2 Hz, 6H), 2.30-2.15 (m, 4H), 2.08 (s, 3H), 1.30-1.16 (m, 2H), 1.16-1.04 (m, 2H).

Example 327 and 328

(S) and (R)-4-(2-cyclopropyl-5-methoxy-4-(2-methylpyridin-3-yl)-1H-benzo[d]imidazol-6-yl)-3,5-dimethylisoxazole (1020-327) and (1020-328)

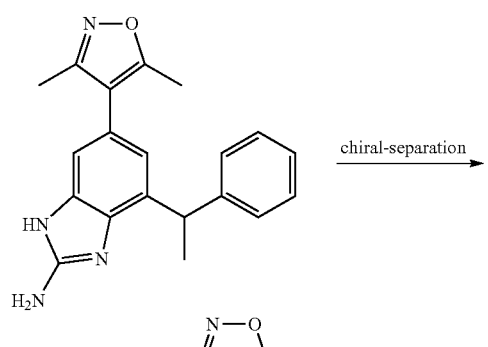

chiral-separation →

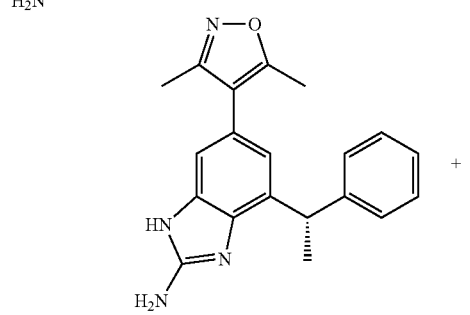

(S)

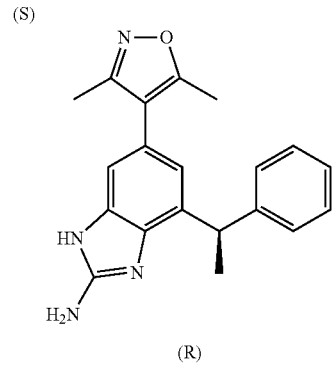

(R)

Racemic 6-(3,5-dimethylisoxazol-4-yl)-4-(1-phenylethyl)-1H-benzo[d]imidazol-2-amine (product from Example 98) was chirally resolved using chiral reverse phase HPLC (Chiralpak AD-H, 150×4.6 mm, 5 micron, 15 ml/min for 15 minutes. 90:10 Heptanes:IPA) to afford both—(R) and (S)-4-(2-cyclopropyl-5-methoxy-4-(2-methylpyridin-3-yl)-1H-benzo[d]imidazol-6-yl)-3,5-dimethylisoxazole.

Compound 1020-327: Retention time—7.808 minutes.

Compound 1020-328: Retention time—11.188 minutes.

Example 329

(2-cyclopropyl-6-(3,5-dimethylisoxazol-4-yl)-1H-benzo[d]imidazol-4-yl)(2,6-dimethylpyridin-3-yl)(pyridin-2-yl)methanol (1020-329)

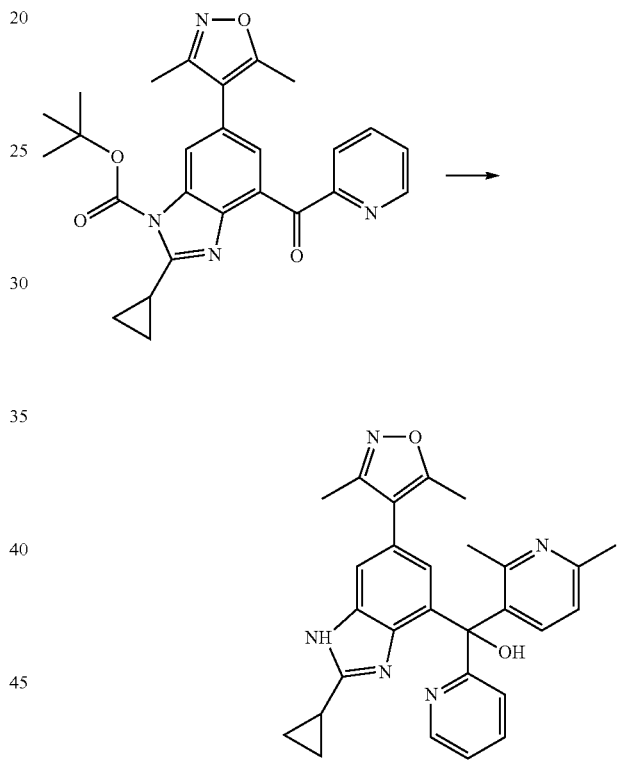

tert-Butyl 2-cyclopropyl-6-(3,5-dimethylisoxazol-4-yl)-4-picolinoyl-1H-benzo[d]imidazole-1-carboxylate (25 mg, 0.05 mmol) was dissolved in 2 ml THF, to the solution was added (2,6-dimethylpyridin-3-yl)magnesium bromide (0.65 mL, 0.5M) at RT. The reaction mixture was stirred at RT overnight. The reaction was quenched with water, to the reaction mixture was added TFA (1 mL) and the reaction mixture was heated at 60° C. for 2 h. Then solvent was evaporated, the residue was purified with Prep HPLC with 0.1% TFA modifier to afford 23 mg product (2-cyclopropyl-6-(3,5-dimethylisoxazol-4-yl)-1H-benzo[d]imidazol-4-yl)(2,6-dimethylpyridin-3-yl)(pyridin-2-yl)methanol.

C$_{28}$H$_{27}$N$_5$O$_2$. 466.2 (M+1). $^1$H NMR (400 MHz, CD$_3$OD) δ 8.63-8.62 (m, 1H), 7.99-7.95 (m, 1H), 7.81-7.78 (m, 2H), 7.60-7.46 (m, 2H), 7.45-7.42 (m, 1H), 6.86 (d, J=1.2 Hz, 1H), 2.74 (s, 3H), 2.57-2.54 (m, 1H), 2.52 (s, 3H), 2.31 (s, 3H), 2.12 (s, 3H), 1.52-1.49 (m, 2H), 1.40-1.38 (m, 2H).

Example 330

(6-aminopyridin-3-yl)(2-cyclopropyl-6-(3,5-dimethylisoxazol-4-yl)-1H-benzo[d]imidazol-4-yl)(pyridin-2-yl)methanol (1020-330)

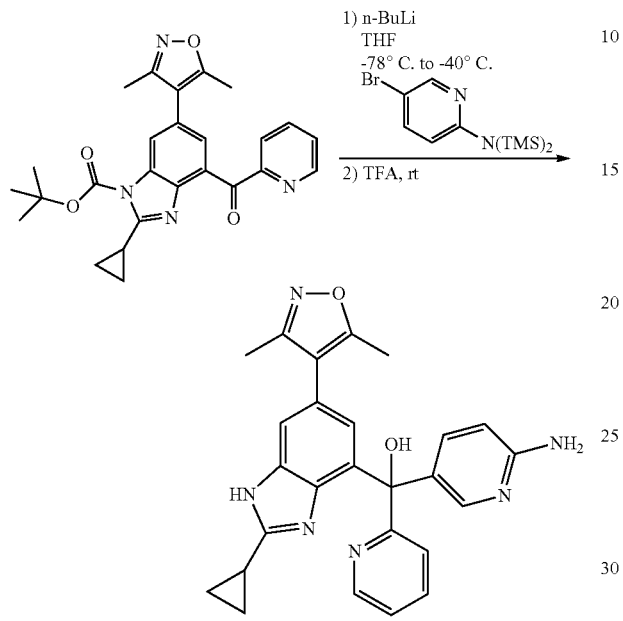

In a 2-neck, 25-mL round bottom flask, 2-amino-5-bromopyridine (38.4 mg, 0.222 mmol) was dissolved in tetrahydrofuran (1.1 mL), followed by chlorotrimethylsilane (58 µL, 0.46 mmol). The reaction mixture was stirred under nitrogen at room temperature for 30 min and subsequently cooled to −78° C. in a dry ice/acetone bath. A 1.6 M solution of n-butyllithium in hexanes (0.43 mL, 0.69 mmol) was added dropwise and the reaction mixture was warmed to −40° C. in a dry ice/acetonitrile bath and allowed to stir for 1 hour. The reaction mixture was cooled back to −78° C., before a solution of tert-butyl 2-cyclopropyl-6-(3,5-dimethylisoxazol-4-yl)-4-picolinoyl-1H-benzo[d]imidazole-1-carboxylate (25.9 mg, 0.0565 mmol) in tetrahydrofuran (0.5 mL) was added slowly to the reaction mixture. The reaction was stirred at −78° C. for thirty minutes before it was quenched with brine, followed by aqueous sodium bicarbonate to neutralize the reaction mixture. The aqueous layer was extracted with ethyl acetate (three times). The combined organic layers were dried over magnesium sulfate, filtered and concentrated. The crude reaction mixture was dissolved in trifluoroacetic acid (for complete boc deprotection) and stirred for 30 minutes at room temperature. The reaction mixture was concentrated and the title compound was isolated by preparatory HPLC to yield (6-aminopyridin-3-yl)(2-cyclopropyl-6-(3,5-dimethylisoxazol-4-yl)-1H-benzo[d]imidazol-4-yl)(pyridin-2-yl)methanol.

$C_{26}H_{23}N_5O_3$. 453.1 (M+1). $^1$H NMR (400 MHz, Methanol-$d_4$) δ 8.66 (dt, J=4.9, 1.3 Hz, 1H), 8.03-7.92 (m, 2H), 7.88 (dt, J=8.0, 1.1 Hz, 1H), 7.68 (d, J=2.2 Hz, 1H), 7.60 (d, J=1.5 Hz, 1H), 7.47 (ddd, J=7.6, 4.9, 1.2 Hz, 1H), 7.12 (d, J=1.5 Hz, 1H), 7.05 (d, J=9.4 Hz, 1H), 2.66 (tt, J=8.5, 5.0 Hz, 1H), 2.37 (s, 3H), 2.18 (s, 3H), 1.56 (dt, J=9.4, 3.8 Hz, 2H), 1.44 (dt, J=7.7, 4.9 Hz, 2H).

Example 331

(2-cyclopropyl-6-(5-(hydroxymethyl)-3-methylisoxazol-4-yl)-1H-benzo[d]imidazol-4-yl)di(pyridin-2-yl)methanol (1020-331)

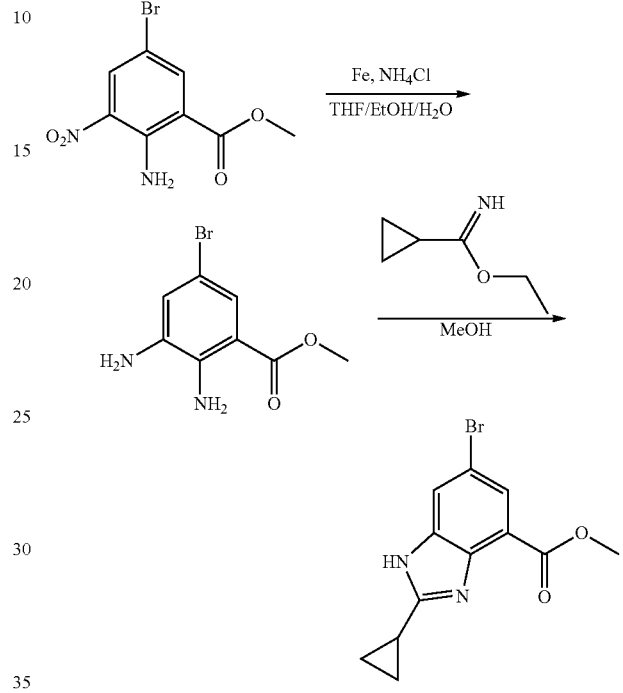

Step 1: methyl 2,3-diamino-5-bromobenzoate

Methyl 2-amino-5-bromo-3-nitrobenzoate (0.67 g, 2.44 mmol), iron (0.68 g, 12.0 mmol), and ammonium chloride (1.96 g, 37.0 mmol) were dissolved in a 1:1:0.4 mixture of THF/ethanol/water (29 mL) and heated at 95° C. with vigorous stirring for 1 hour. The reaction mixture was cooled to room temperature and filtered through a plug of Celite to remove solids. The plug was rinsed repeatedly with methanol and tetrahydrofuran. The filterate was concentrated and the residue partitioned between ethyl acetate and water. The organic later was washed once with brine and concentrated to give methyl 2,3-diamino-5-bromobenzoate (0.59 g, 99%) as a yellow powder which was used without further purification.

Step 2: methyl 6-bromo-2-cyclopropyl-1H-benzo[d]imidazole-4-carboxylate

Methyl 2,3-diamino-5-bromobenzoate (0.59 g, 2.0 mmol) and ethyl cyclopropanecarbimidate (0.43 g, 3.0 mmol) was dissolved in methanol (20 mL) and heated to 50° C. for 5 hours. Reaction was then cooled to rt and solvent was removed in vacuo. Crude material was dissolved in EtOAc and washed 3 times with sodium bicarbonate, once with water and concentrated to give methyl 6-bromo-2-cyclopropyl-1H-benzo[d]imidazole-4-carboxylate (0.7 g, 98%) which was used without further purification.

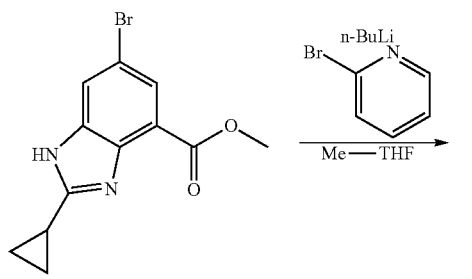

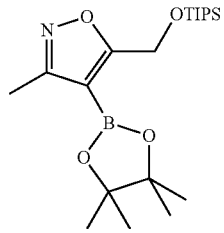

Step 4: 4-bromo-3-methyl-5-(((triisopropylsilyl)oxy)methyl)isoxazole

To a solution of (4-bromo-3-methylisoxazol-5-yl)methanol (0.58, 2.6 mmol) in DMF (2.6 mL) at 0° C. under Ar, was added TIPS-Cl (0.72 mL, 0.65 g, 3.0 mmol) and imidazole (0.27 g, 4.0 mmol) and the reaction was allowed to come to rt and stir for 5 hours. The mixture was then diluted with water and DCM and washed three times with water and once with brine. The organic layer was concentrated in vacuo and purified by silica gel flash chromatography (0-10% EtOAc/hex, Rf: 0.6 10% EtOAc/hex) to give 4-bromo-3-methyl-5-(((triisopropylsilyl)oxy)methyl)isoxazole (0.65 g, 71%) as a clear, colorless oil.

Step 5: 3-methyl-4-(4,4,5,5-tetramethyl-1,3,2-dioxaborolan-2-yl)-5-(((triisopropylsilyloxy)methyl)isoxazole 4-bromo-3-methyl-5-(((triisopropylsilyl)oxy)methyl)isoxazole (0.32 g, 0.93 mmol), bis(acetonitrile)palladium(II) chloride (9.6 mg, 0.037 mmol), and 2-dicyclohexylphosphino-2'-6'-dimethoxybiphenyl (61 mg, 0.15 mmol) were dissolved in 1,4-dioxane (1 mL) under Ar. 4,4,5,5-tetramethyl-1,3,2-dioxaborolane (0.20 mL, 0.18 g, 1.0 mmol) and triethylamine (0.4 mL, 0.28 g, 3.0 mmol) were added via syringe and the reaction was heated to 80° C. for 1.5 hours. The reaction was then cooled to rt, diluted with EtOAc, filtered through celite, and concentrated in vacuo to give 3-methyl-4-(4,4,5,5-tetramethyl-1,3,2-dioxaborolan-2-yl)-5-(((triisopropylsilyl)oxy)methyl)isoxazole which was used without further purification.

Step 3: (6-bromo-2-cyclopropyl-1H-benzo[d]imidazol-4-yl)di(pyridin-2-yl)methanol 2-bromopyridine (1.3 mL, 2.2 g, 14.0 mmol) was dissolved in Me-THF under Ar and cooled to −78° C. n-BuLi (9.0 mL, 0.92 g, 14.0 mmol) was added dropwise over 15 minutes and the reaction was allowed to stir for an additional 5 minutes at −78° C. Methyl 6-bromo-2-cyclopropyl-1H-benzo[d]imidazole-4-carboxylate (0.7 g, 2.4 mmol), dissolved in a minimal amount of Me-THF, was added to the reaction and allowed to stir for 3 minutes at −78° C. before being quenched with water. The reaction was extracted three times with EtOAc and combined organic layers were washed once with water then concentrated. Crude material was purified by silica gel flash chromatography (80-100% EtOAc/hex, Rf 0.42 in 100% EtOAc) to give (6-bromo-2-cyclopropyl-1H-benzo[d]imidazol-4-yl)di(pyridin-2-yl)methanol (0.62 g, 62%) as a pale yellow powder.

$C_{21}H_{17}BrN_4O$ 422.4 (M+1). $^1$H NMR (400 MHz, DMSO-d6) δ 12.45 (s, 1H), 11.78 (s, 1H), 8.55-8.49 (m, 2H), 7.82 (dt, J=8.3, 4.3 Hz, 2H), 7.58 (d, J=8.0 Hz, 2H), 7.53 (d, J=1.9 Hz, 1H), 7.32 (dt, J=7.4, 3.1 Hz, 2H), 7.08 (s, 1H), 6.85 (s, 1H), 2.27 (q, J=6.5, 6.0 Hz, 1H), 0.99 (ddt, J=13.1, 7.7, 4.4 Hz, 4H).

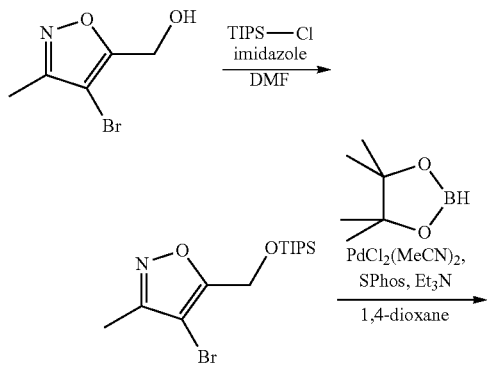

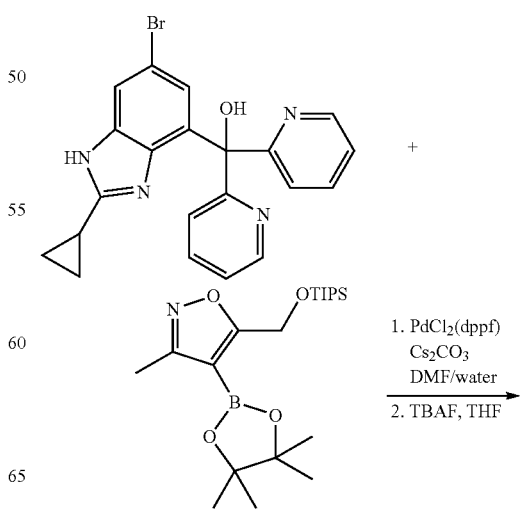

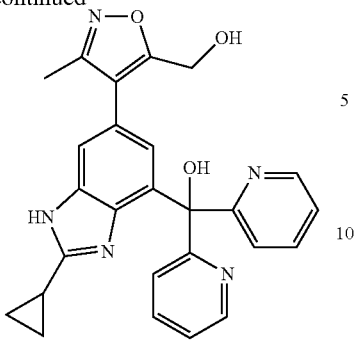

Step 6: (2-cyclopropyl-6-(5-(hydroxymethyl)-3-methylisoxazol-4-yl)-1H-benzo[d]imidazol-4-yl)di(pyridin-2-yl)methanol (6-Bromo-2-cyclopropyl-1H-benzo[d]imidazol-4-yl)di(pyridin-2-yl)methanol (40 mg, 0.095 mmol) and 3-methyl-4-(4,4,5,5-tetramethyl-1,3,2-dioxaborolan-2-yl)-5-(((triisopropylsilyl)oxy)methyl)isoxazole (150 mg, 0.38 mmol) was dissolved in DMF (2 mL) and water (1 mL). Dichloro 1,1-bis(diphenylphosphino)ferrocene palladium(II) dichloromethane (6.9 mg, 0.009 mmol) and cesium carbonate (123 mg, 0.38 mmol) were added, the reaction vessel was sealed and heated to 85° C. for 1.5 hours. The reaction was cooled to rt, diluted with EtOAc, washed three times with water, and concentrated in vacuo. The crude material was taken up in THF (2 mL) and a few drops of TBAF solution (1.0M in THF) was added and the reaction was allowed to stir for 6 hours. The reaction was concentrated and purified by silica gel flash chromatography (0-15% MeOH/DCM) to give (2-cyclopropyl-6-(5-(hydroxymethyl)-3-methylisoxazol-4-yl)-1H-benzo[d]imidazol-4-yl)di(pyridin-2-yl)methanol.

$C_{26}H_{23}N_5O_3$ 454.1 (M+1). $^1$H NMR (400 MHz, Methanol-d4) δ 8.53 (ddd, J=4.9, 1.8, 0.9 Hz, 2H), 7.80 (td, J=7.8, 1.8 Hz, 2H), 7.59 (dt, J=8.1, 1.0 Hz, 2H), 7.47 (d, J=1.5 Hz, 1H), 7.32 (ddd, J=7.6, 4.8, 1.1 Hz, 2H), 6.77 (d, J=1.5 Hz, 1H), 4.54 (s, 2H), 2.25-2.08 (m, 4H), 1.10 (d, J=6.2 Hz, 4H).

Example 332

(2-cyclopropyl-6-(3-(hydroxymethyl)-5-methylisoxazol-4-yl)-1H-benzo[d]imidazol-4-yl)di(pyridin-2-yl)methanol (1020-332)

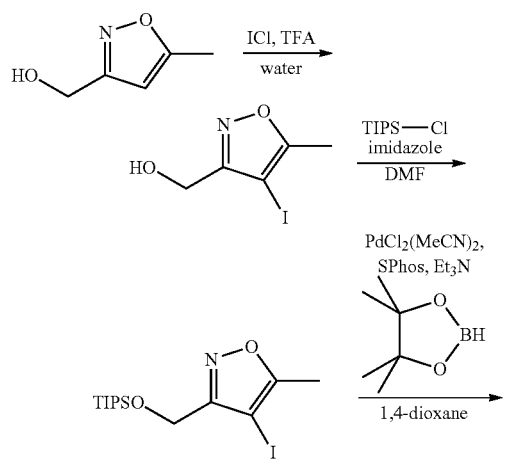

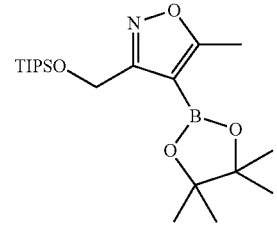

Step 1: (4-iodo-5-methylisoxazol-3-yl)methanol (5-Methylisoxazol-3-yl)methanol (200 mg, 1.77 mmol) was added to a suspension of ICl (0.115 mL, 0.37 g, 2.0 mmol) in water (4.5 mL) followed by TFA (0.135 mL, 0.2 g, 2.0 mmol) and the reaction was heated to 65° C. under argon for 2 hours. The reaction was allowed to cool to rt, diluted with water, and treated with 10% $Na_2S_2O_5$ (5 mL). The mixture was made basic by addition of solid $Na_2CO_3$ and then extracted three times with DCM. Combined organic layers were washed once with water, then brine, dried over sodium sulfate, filtered, and concentrated to dryness to give (4-iodo-5-methylisoxazol-3-yl)methanol (0.24 g, 56%) as a white powder.

Step 2: 4-iodo-5-methyl-3-(((triisopropylsilyl)oxymethyl)isoxazole

TIPS-Cl (0.52 mL, 0.46 g, 2.0 mmol) and imidazole (0.19 g, 3.0 mmol) was added to a solution of (4-iodo-5-methylisoxazol-3-yl)methanol (0.24 g, 1.86 mmol) in DMF (1.9 mL) under Ar and the reaction was allowed to stir at rt for 4 hours. The mixture was then diluted with water and DCM and washed three times with water and once with brine. The organic layer was concentrated in vacuo and purified by silica gel flash chromatography (0-10% EtOAc/hex, Rf: 0.36 10% EtOAc/hex) to give 4-iodo-5-methyl-3-(((triisopropylsilyl)oxy)methyl)isoxazole (0.31 g, 42%) as a clear, colorless oil.

Step 3: 5-methyl-4-(4,4,5,5-tetramethyl-1,3,2-dioxaborolan-2-yl)-3-(((triisopropylsilyl)oxy)methyl)isoxazol 4-Iodo-5-methyl-3-(((triisopropylsilyl)oxy)methyl)isoxazole (0.31 g, 0.79 mmol), bis(acetonitrile)palladium(II) chloride (8.0 mg, 0.031 mmol), and 2-dicyclohexylphosphino-2'-6'-dimethoxybiphenyl (52 mg, 0.13 mmol) were dissolved in 1,4-dioxane (1 mL) under Ar. 4,4,5,5-tetramethyl-1,3,2-dioxaborolane (0.17 mL, 0.11 g, 1.0 mmol) and triethylamine (0.33 mL, 0.24 g, 2.0 mmol) were added via syringe and the reaction was heated to 80° C. for 1.5 hours. The reaction was then cooled to rt, diluted with EtOAc, filtered through celite, and concentrated in vacuo to give 5-methyl-4-(4,4,5,5-tetramethyl-1,3,2-dioxaborolan-2-yl)-3-(((triisopropylsilyl)oxy)methyl)isoxazole which was used without further purification.

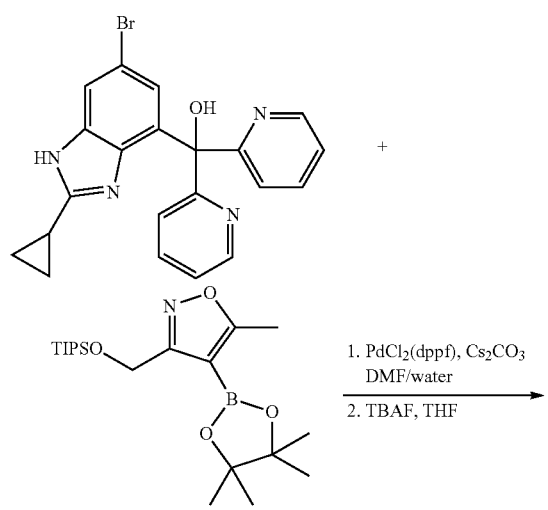

Step 4: (2-cyclopropyl-6-(3-(hydroxymethyl)-5-methylisoxazol-4-yl)-1H-benzo[d]imidazol-4-yl)di(pyridin-2-yl)methanol (6-Bromo-2-cyclopropyl-1H-benzo[d]imidazol-4-yl)di(pyridin-2-yl)methanol (40 mg, 0.095 mmol) and 5-methyl-4-(4,4,5,5-tetramethyl-1,3,2-dioxaborolan-2-yl)-3-(((triisopropylsilyl)oxy)methyl)isoxazole (225 mg, 0.57 mmol) was dissolved in DMF (2 mL) and water (1 mL). Dichloro 1,1-bis(diphenylphosphino)ferrocene palladium(II) dichloromethane (7.0 mg, 0.0095 mmol) and cesium carbonate (186 mg, 0.57 mmol) were added, the reaction vessel was sealed and heated to 85° C. for 1.5 hours. The reaction was cooled to rt, diluted with EtOAc, washed three times with water, and concentrated in vacuo. The crude material was taken up in THF (2 mL) and a few drops of TBAF solution (1.0M in THF) was added and the reaction was allowed to stir for 6 hours. The reaction was concentrated and purified by silica gel flash chromatography (0-15% MeOH/DCM) to give (2-cyclopropyl-6-(3-(hydroxymethyl)-5-methylisoxazol-4-yl)-1H-benzo[d]imidazol-4-yl)di(pyridin-2-yl)methanol.

$C_{26}H_{23}N_5O_3$ 454.3 (M+1). $^1$H NMR (400 MHz, Methanol-d4) δ 8.52 (ddd, J=4.9, 1.8, 0.9 Hz, 2H), 7.78 (td, J=7.8, 1.8 Hz, 2H), 7.59 (dt, J=8.0, 1.0 Hz, 2H), 7.54 (d, J=1.5 Hz, 1H), 7.30 (ddd, J=7.6, 4.9, 1.2 Hz, 2H), 6.79 (d, J=1.5 Hz, 1H), 4.53 (s, 2H), 2.30 (s, 3H), 2.21-2.11 (m, 1H), 1.12-1.04 (m, 4H).

Example 333

(6-(3,5-dimethylisoxazol-4-yl)-2-ethoxy-1H-benzo[d]imidazol-4-yl)di(pyridin-2-yl)methanol (1020-333)

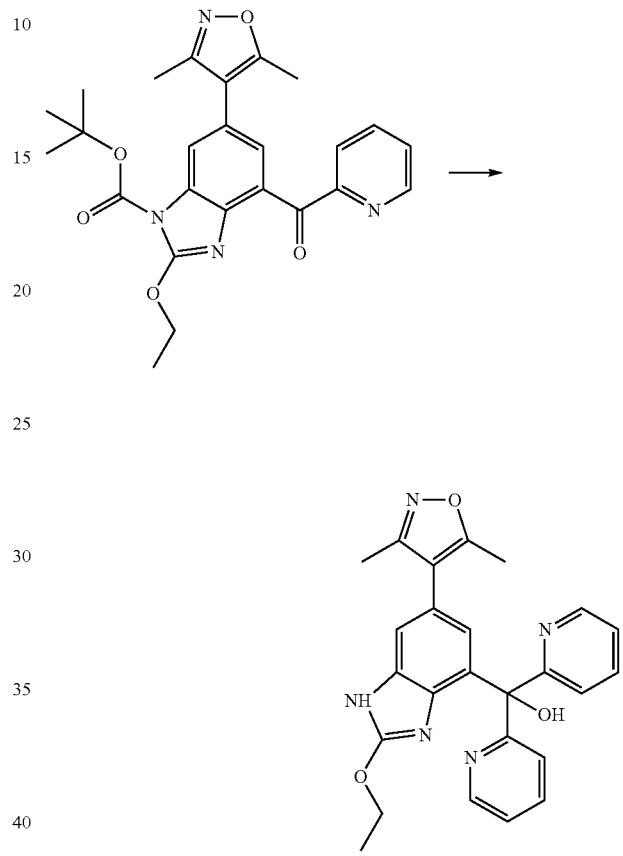

2-Bromopyridine (85 mg, 0.54 mmol) was dissolved in 2 ml THF, to the solution was added N-butyllithium (0.34 mL, 1.6M) at −78° C. and stirred at −78° C. for 15 mins, then to above solution was added tert-butyl 6-(3,5-dimethylisoxazol-4-yl)-2-ethoxy-4-picolinoyl-1H-benzo[d]imidazole-1-carboxylate (50 mg, 0.11 mmol). The reaction temperature was slowly raised to RT and stirred overnight. The reaction was then quenched with water. Then solvent was evaporated, the residue was purified with Prep HPLC with 0.1% TFA modifier to afford 13 (6-(3,5-dimethylisoxazol-4-yl)-2-ethoxy-1H-benzo[d]imidazol-4-yl)di(pyridin-2-yl)methanol.

$C_{23}H_{23}N_5O_3$. 442.2 (M+1). 1H NMR (400 MHz, CD$_3$OD) δ 8.65 (ddd, J=5.3, 1.7, 0.8 Hz, 2H), 8.19 (ddd, J=8.2, 7.6, 1.7 Hz, 2H), 8.06 (dt, J=8.1, 1.1 Hz, 2H), 7.67 (ddd, J=7.6, 5.3, 1.2 Hz, 2H), 7.30 (d, J=1.5 Hz, 1H), 6.72 (d, J=1.5 Hz, 1H), 4.37 (q, J=7.1 Hz, 2H), 2.31 (s, 3H), 2.13 (s, 3H), 1.35 (t, J=7.1 Hz, 3H).

Example 334

4-(2-cyclopropyl-4-(2-cyclopropylpyridin-3-yl)-1H-benzo[d]imidazol-6-yl)-3,5-dimethylisoxazole (1020-334)

Step 1

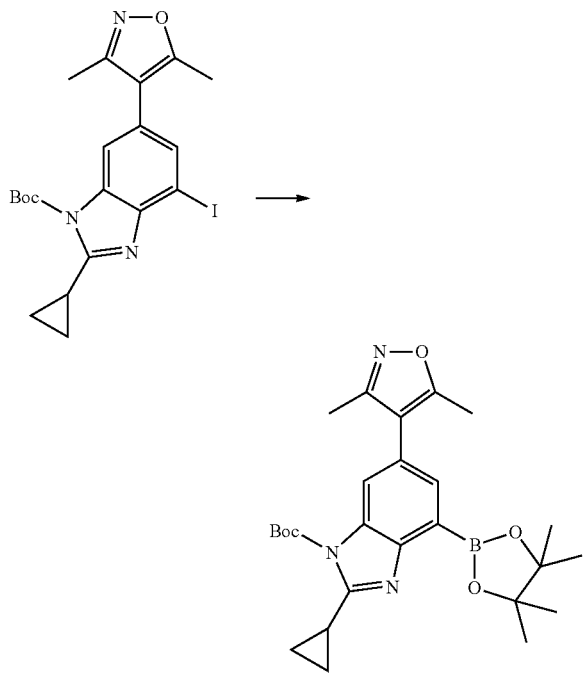

tert-Butyl 2-cyclopropyl-6-(3,5-dimethylisoxazol-4-yl)-4-iodo-1H-benzo[d]imidazole-1-carboxylate (400 mg, 0.83 mmol) and Bis(pinacolato)diboron (848 mg, 3 mmol) was added to 1,4-dioxane (5 ml). To the above mixture were added Pd(dppf)Cl$_2$ (61 mg, 0.084 mmol) and potassium acetate (491 mg, 5 mmol). The reaction mixture was heated at 80° C. for 1 h. The reaction mixture was then diluted with EtOAc (100 ml), washed with bring (50 ml×2). The organic solvent was evaporated and the residue was dissolved in DCM and purified with combi-flash column chromatography to afford 300 mg tert-butyl 2-cyclopropyl-6-(3,5-dimethylisoxazol-4-yl)-4-(4,4,5,5-tetramethyl-1,3,2-dioxaborolan-2-yl)-1H-benzo[d]imidazole-1-carboxylate.

$C_{26}H_{34}BN_3O_5$. 480.3 (M+1).

Step 2

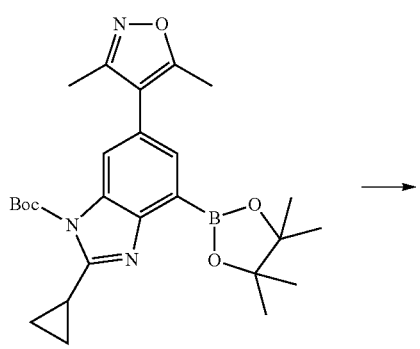

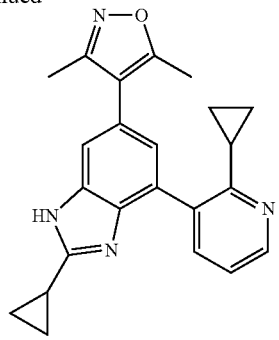

tert-Butyl 2-cyclopropyl-6-(3,5-dimethylisoxazol-4-yl)-4-(4,4,5,5-tetramethyl-1,3,2-dioxaborolan-2-yl)-1H-benzo[d]imidazole-1-carboxylate (200 mg, 0.53 mmol) and 3-bromo-2-cyclopropylpyridine (209 mg, 1 mmol) were added to a solvent mixture of 1,2-dimethoxyethane (2 ml) and water (1 ml). To the above mixture were added PEPPSI-Ipr (36 mg, 0.053 mmol) and Cs$_2$CO$_3$ (687 mg, 2 mmol). The reaction mixture was heated at 150° C. in microwave reactor for 30 mins. The reaction mixture was then filtered and organic solvent was evaporated and the residue was purified with Prep HPLC (0-100% CH$_3$CN/H$_2$O) to afford 8 mg 4-(2-cyclopropyl-4-(2-cyclopropylpyridin-3-yl)-1H-benzo[d]imidazol-6-yl)-3,5-dimethylisoxazole.

$C_{23}H_{22}N_4O$. 371.4 (M+1). 1H NMR (400 MHz, CD$_3$OD) δ 8.67-8.58 (m, 1H), 8.09 (dt, J=7.7, 1.3 Hz, 1H), 7.69 (d, J=1.4 Hz, 1H), 7.61 (dt, J=7.7, 5.0 Hz, 1H), 7.48 (d, J=1.4 Hz, 1H), 2.46 (s, 3H), 2.45-2.38 (m, 1H), 2.30 (s, 3H), 1.98-1.85 (m, 1H), 1.59-1.44 (m, 2H), 1.44-1.32 (m, 2H), 1.23-1.16 (m, 2H), 1.01 (dt, J=8.3, 3.3 Hz, 2H).

Example 335

HTRF Assay:

Binding of the two tandem bromodomains, BRD4-1 and BRD4-2, to an acetylated histone H4 peptide was measured using a homogeneous time resolved fluorescence resonance energy transfer (TR-FRET) assay. The synthetic peptide containing amino acids 1-18 of histone H4 was acetylated at lysine 5, 8, 12, 16 and conjugated to biotin (SGRGACKG-GACKGLGACKGGAACKRH-GSGSK-biotin[SEQ ID NO:1]) was purchased from Millipore. BRD4-1 and BRD4-2 were expressed and purified from *Escherichia coli* as N-terminal His$_6$-tagged proteins. An XL665 labeled anti-His antibody (Cisbio) was used to specifically bind BRD4 and a cryptate labeled streptavidin protein was used because it specifically recognized the biotinylated H4 peptide. Binding of BRD4 to the peptide resulted in an increase in FRET signal whereas disruption of this protein-peptide interaction with a small molecule inhibitor resulted in a decrease in FRET signal. Assays were performed in 50 mM Hepes (pH 7.5), 150 mM NaCl, 0.1 mg/ml BSA, 0.01% (v/v) Brij, 0.5% (v/v) DMSO and 200 nM H4 peptide at the following concentrations for each BRD4 isoform: 60 nM BRD4-1 and 120 nM BRD4-2. After an assay reaction time of 60 minutes at 25° C., binding was measured with 2 nM crytptate labeled streptavidin and 10 nM anti-His-XL665 antibody. TR-FRET signal was detected on an Envision plate reader (Ex: 320 nm; Em: 615/665 nm; 100 As delay and 200 µs read window). Data were normalized based on a positive (2 µM I-BET) and negative (DMSO) controls and IC$_{50}$ values were calculated from the fit of the dose-response curves to a four-parameter equation. All IC$_{50}$ values represent geometric mean values of a minimum of four determinations. These assays generally produced results within 3-fold of the reported mean.

Alpha Assay:

Binding of the bromodomain BRD4-I to an acetylated histone H4 peptide was measured using a bead-based Amplified Luminescent Proximity Homogeneous Assay (AL-PHA). The synthetic peptide containing amino acids 1-18 of histone H4 was acetylated at lysine 5, 8, 12, 16 and conjugated to biotin (SGRGACKGGACKGLGACKG-GAACKRH-GSGSK-biotin[SEQ ID NO:1]) was purchased from Millipore. BRD4-I was expressed and purified from *Escherichia coli* as an N-terminal $His_6$-tagged protein. Nickel-Chelate ALPHA acceptor beads (Perkin Elmer) were used to specifically bind BRD4-1 and ALPHA streptavidin donor beads (Perkin Elmer) were used because they specifically recognized the biotinylated H4 peptide. Binding of BRD4-1 to the peptide resulted in proximity of the donor and acceptor beads which leads to an increase in ALPHA signal whereas disruption of this protein-peptide interaction with a small molecule inhibitor resulted in a decrease in ALPHA signal. Assays were performed in 50 mM Hepes (pH 7.5), 150 mM NaCl, 0.1 mg/ml BSA, 0.01% (v/v) Brij, 0.5% (v/v) DMSO, 200 nM H4 peptide and 15 nM of BRD4-1 protein. After an assay reaction time of 60 minutes at 25° C., binding was measured with 20 μg/ml streptavidin donor beads and 20 μg/ml nickle-chelate acceptor beads. ALPHA signal was detected on an Envision plate reader (Ex: 320 nm; Em: 570 nm; Ex time: 180 ms). Data were normalized based on a positive (2 μM I-BET) and negative (DMSO) controls and $IC_{50}$ values were calculated from the fit of the dose-response curves to a four-parameter equation. All $IC_{50}$ values represent geometric mean values of a minimum of four determinations. These assays generally produced results within 3-fold of the reported mean. Results are reported in Table 1.

MT-4 Proliferation Assay:

Compounds were tested in a standardized high-throughput 384-well assay format. Each compound was serially diluted 3-fold in 100% DMSO in polypropylene 384-well plates using a Biomek FX Workstation, and 0.4 μL compound added to an assay plate containing 40 μL RPMI media. Compounds were arranged in a horizontal pattern, with 10 concentrations per compound, and 8 compounds added per plate. Due to low DMSO tolerability, the final DMSO concentration never exceeded 0.5% (v/v). Each assay plate contained 10 μM Puromycin and 0.5% DMSO in RPMI-1640 as positive and negative controls respectively. MT-4 cells (HTLV-1 transformed, human T lymphoblastoid cells, NIH Aids Reagent program) were added in volumes of 35 μL per well and 2,000 cells per well using a Biotek uFlow Workstation (Biotek, Winooski, Vt.), and the plates subsequently incubated for 5 days at 37° C. in an incubator set at 5% $CO_2$ and 90% humidity.

After 5 days, 22 μL Cell Titer Glo (Promega) was added to the assay plates with a Biotek uFlow Workstation. Plates were subsequently placed on a Perkin Elmer Envision Plate Reader for 5 minutes before the luminescence signal was read. $EC_{50}$ values were calculated from the compound concentration that caused a 50% decrease in luminescence signal, a measure of toxicity, and calculated by non-linear regression using Pipeline Pilot software (Accelrys, San Diego, Calif.). Results are reported in Table 1.

TABLE 1

| Comp. No. | Structure | HTRF BRD4-1 ($IC_{50}$, nM) | HTRF BRD4-2 ($IC_{50}$, nM) | Alpha Assay ($IC_{50}$, nM) | MT4 Assay, ($IC_{50}$, nM) |
| --- | --- | --- | --- | --- | --- |
| 1020-1 | 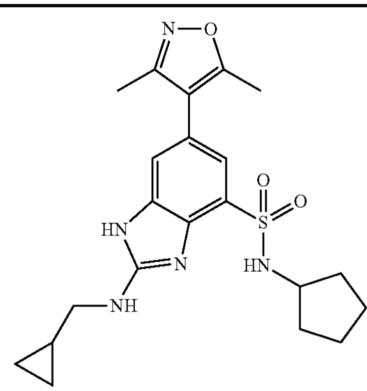 | 200.6 | 97.6 | n/a | 193.0 |
| 1020-4 | 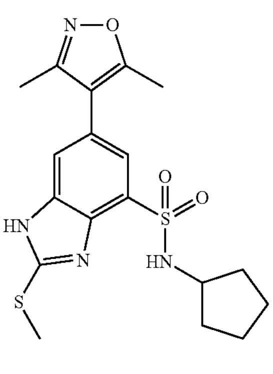 [SMILES: CSc1nc2c(S(=O)(=O)NC3CCCC3)cc(-c3c(C)noc3C)cc2[nH]1] | 336.6 | 229.9 | n/a | 192.1 |

TABLE 1-continued

| Comp. No. | Structure | HTRF BRD4-1 (IC$_{50}$, nM) | HTRF BRD4-2 (IC$_{50}$, nM) | Alpha Assay (IC$_{50}$, nM) | MT4 Assay, (IC$_{50}$, nM) |
|---|---|---|---|---|---|
| 1020-5 | 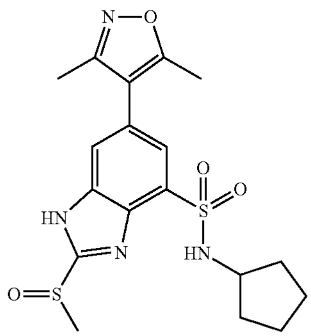 [SMILES: Cc1noc(C)c1-c1cc(S(=O)(=O)NC2CCCC2)c2nc(S(C)=O)[nH]c2c1] | 616.3 | 357.1 | n/a | 329.2 |
| 1020-12 | 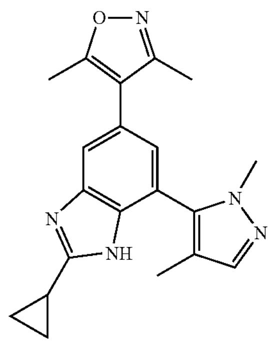 [SMILES: Cc1cnn(C)c1-c1cc(-c2c(C)noc2C)cc2nc(C3CC3)[nH]c12] | 137.9 | 69.2 | 46.2 | 21.3 |
| 1020-18 | 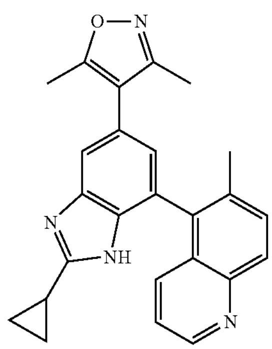 [SMILES: Cc1ccc2ncccc2c1-c1cc(-c2c(C)noc2C)cc2nc(C3CC3)[nH]c12] | 87.1 | 78.6 | 14.4 | 7.5 |
| 1020-19 | 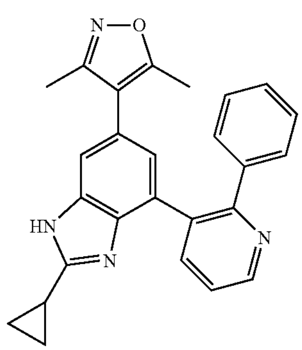 [SMILES: Cc1noc(C)c1-c1cc(-c2cccnc2-c2ccccc2)c2nc(C3CC3)[nH]c2c1] | 134.3 | 171.6 | 28.0 | 24.4 |

TABLE 1-continued

| Comp. No. | Structure | HTRF BRD4-1 (IC$_{50}$, nM) | HTRF BRD4-2 (IC$_{50}$, nM) | Alpha Assay (IC$_{50}$, nM) | MT4 Assay, (IC$_{50}$, nM) |
|---|---|---|---|---|---|
| 1020-28 | 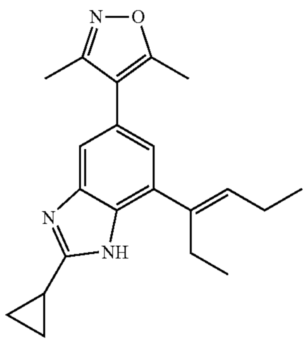 [SMILES: CC/C=C(\CC)c1cc(-c2c(C)noc2C)cc2nc(C3CC3)[nH]c12] | 71.8 | 65.5 | 18.1 | 51.6 |
| 1020-37 | 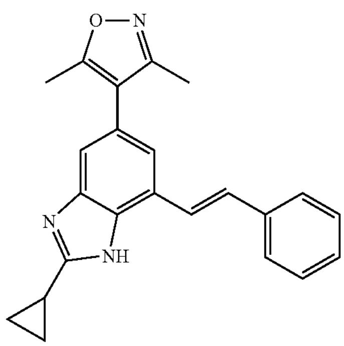 [SMILES: Cc1noc(C)c1-c1cc(/C=C/c2ccccc2)c2[nH]c(C3CC3)nc2c1] | 2089.3 | 2509.7 | 3170.1 | 518.0 |
| 1020-44 | 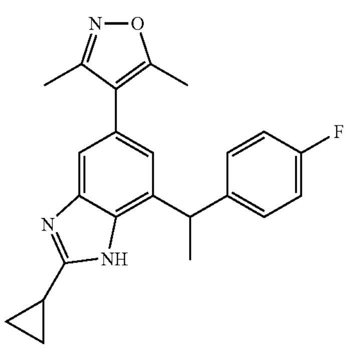 [SMILES: Cc1noc(C)c1-c1cc(C(C)c2ccc(F)cc2)c2[nH]c(C3CC3)nc2c1] | 139.1 | 110.9 | 22.0 | 86.1 |
| 1020-50 | 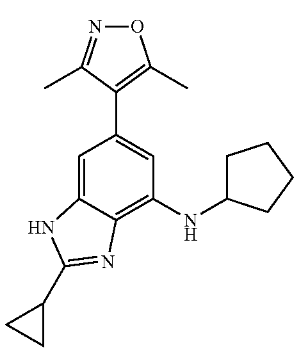 [SMILES: Cc1noc(C)c1-c1cc(NC2CCCC2)c2nc(C3CC3)[nH]c2c1] | 299.0 | 317.6 | 125.1 | 353.0 |

TABLE 1-continued
| Comp. No. | Structure | HTRF BRD4-1 (IC$_{50}$, nM) | HTRF BRD4-2 (IC$_{50}$, nM) | Alpha Assay (IC$_{50}$, nM) | MT4 Assay, (IC$_{50}$, nM) |
|---|---|---|---|---|---|
| 1020-57 | 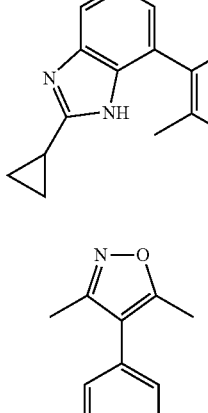 | 109.2 | 54.4 | 22.6 | 13.6 |
| 1020-72 | 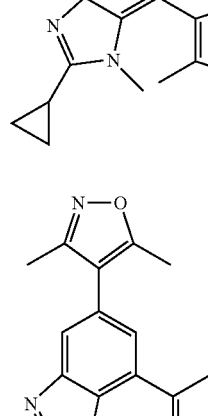 | 100.7 | 69.1 | 12.3 | 6.5 |
| 1020-74 | 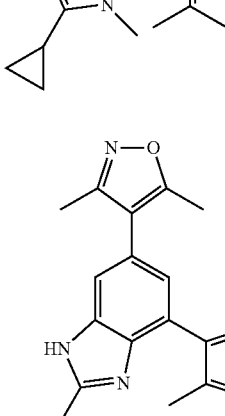 | 97.1 | 111.8 | 18.9 | 15.3 |
| 1020-75 | 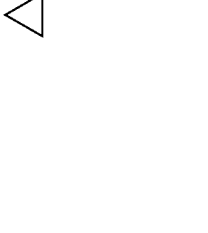 | 120.9 | 78.2 | 33.5 | 18.4 |

TABLE 1-continued

| Comp. No. | Structure | HTRF BRD4-1 (IC$_{50}$, nM) | HTRF BRD4-2 (IC$_{50}$, nM) | Alpha Assay (IC$_{50}$, nM) | MT4 Assay, (IC$_{50}$, nM) |
|---|---|---|---|---|---|
| 1020-77 | 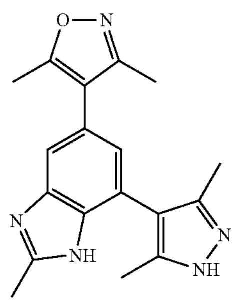 [SMILES: Cc1nc2cc(-c3c(C)noc3C)cc(-c3c(C)n[nH]c3C)c2[nH]1] | 244.5 | 64.8 | 42.7 | 39.4 |
| 1020-78 | 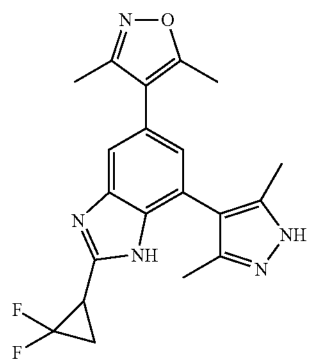 [SMILES: Cc1n[nH]c(C)c1-c1cc(-c2c(C)noc2C)cc2nc(C3CC3(F)F)[nH]c12] | 160.5 | 94.1 | 25.1 | 25.7 |
| 1020-79 | 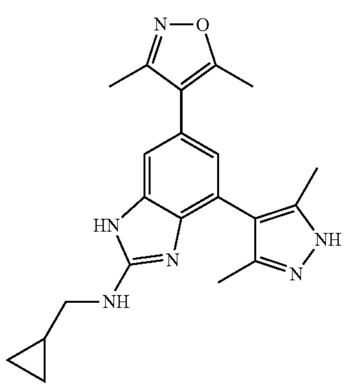 [SMILES: Cc1n[nH]c(C)c1-c1cc(-c2c(C)noc2C)cc2[nH]c(NCC3CC3)nc12] | 161.0 | 87.2 | 33.6 | 33.8 |
| 1020-81 | 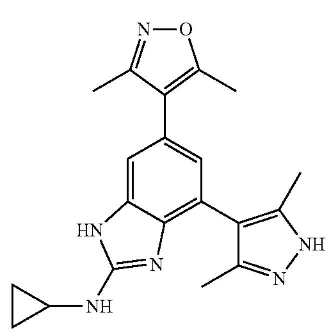 [SMILES: Cc1n[nH]c(C)c1-c1cc(-c2c(C)noc2C)cc2[nH]c(NC3CC3)nc12] | 168.8 | 118.8 | 50.7 | 7.6 |

TABLE 1-continued
| Comp. No. | Structure | HTRF BRD4-1 (IC$_{50}$, nM) | HTRF BRD4-2 (IC$_{50}$, nM) | Alpha Assay (IC$_{50}$, nM) | MT4 Assay, (IC$_{50}$, nM) |
|---|---|---|---|---|---|
| 1020-84 | 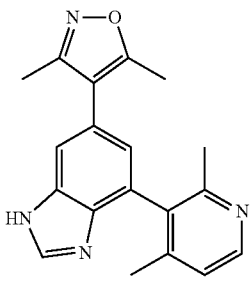 [SMILES: Cc1ccnc(C)c1-c1cc(-c2c(C)noc2C)cc2[nH]cnc12] | 481.0 | 234.0 | 277.3 | 236.0 |
| 1020-88 | 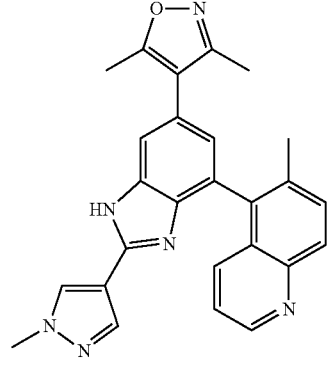 [SMILES: Cc1ccc2ncccc2c1-c1cc(-c2c(C)noc2C)cc2[nH]c(-c3cnn(C)c3)nc12] | 104.0 | 131.0 | 15.9 | 45.2 |
| 1020-89 | 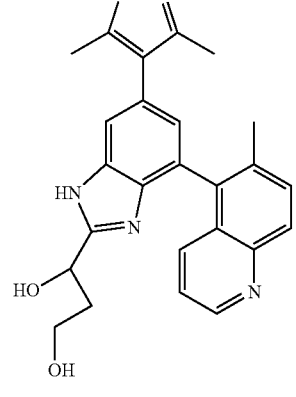 | 379.0 | 151.0 | 130.3 | 104.3 |
| 1020-90 | 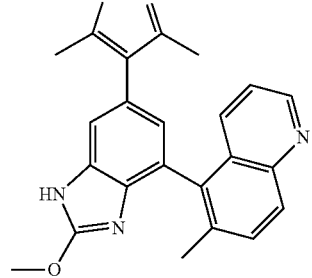 | 110.0 | 121.0 | 29.9 | 25.0 |

TABLE 1-continued

| Comp. No. | Structure | HTRF BRD4-1 (IC$_{50}$, nM) | HTRF BRD4-2 (IC$_{50}$, nM) | Alpha Assay (IC$_{50}$, nM) | MT4 Assay, (IC$_{50}$, nM) |
|---|---|---|---|---|---|
| 1020-92 | 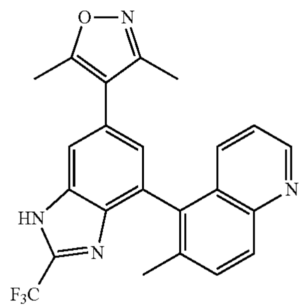 [SMILES: Cc1ccc2ncccc2c1-c1cc(-c2c(C)noc2C)cc2[nH]c(C(F)(F)F)nc12] | 133.0 | 102.0 | 37.7 | 73.1 |
| 1020-96 | 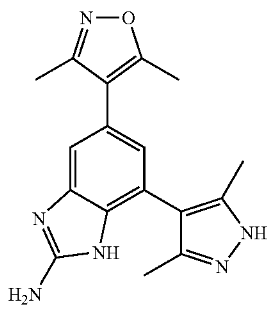 [SMILES: Cc1n[nH]c(C)c1-c1cc(-c2c(C)noc2C)cc2nc(N)[nH]c12] | 276.4 | 96.9 | 53.7 | 318.4 |
| 1020-102 | 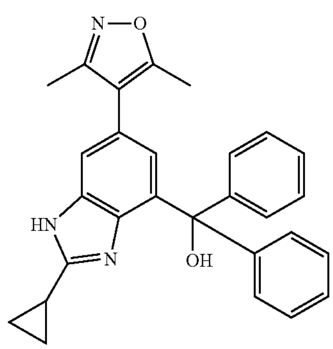 [SMILES: Cc1noc(C)c1-c1cc(C(O)(c2ccccc2)c2ccccc2)c2nc(C3CC3)[nH]c2c1] | 101.2 | 75.7 | 14.3 | 49.7 |
| 1020-120 | 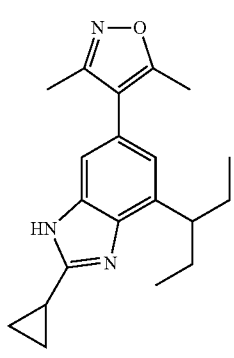 [SMILES: CCC(CC)c1cc(-c2c(C)noc2C)cc2[nH]c(C3CC3)nc12] | 88.5 | 76.1 | 39.7 | 48.8 |

TABLE 1-continued
| Comp. No. | Structure | HTRF BRD4-1 (IC$_{50}$, nM) | HTRF BRD4-2 (IC$_{50}$, nM) | Alpha Assay (IC$_{50}$, nM) | MT4 Assay, (IC$_{50}$, nM) |
|---|---|---|---|---|---|
| 1020-121 | 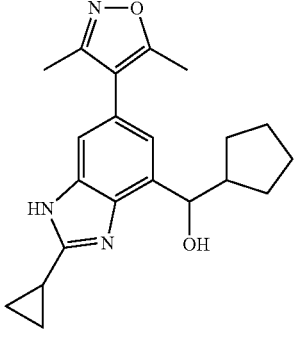 [SMILES: Cc1noc(C)c1-c1cc(C(O)C2CCCC2)c2nc(C3CC3)[nH]c2c1] | 95.2 | 80.8 | 24.7 | 42.8 |
| 1020-132 | 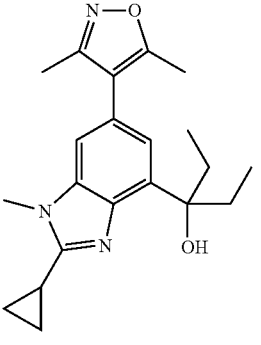 [SMILES: CCC(O)(CC)c1cc(-c2c(C)noc2C)cc2c1nc(C1CC1)n2C] | 609.8 | 882.9 | 572.7 | 543.6 |
| 1020-136 | 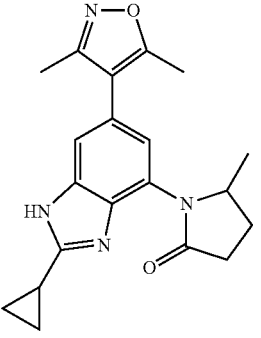 [SMILES: Cc1noc(C)c1-c1cc(N2C(=O)CCC2C)c2nc(C3CC3)[nH]c2c1] | 823.2 | 727.1 | 512.9 | 335.2 |

TABLE 1-continued
| Comp. No. | Structure | HTRF BRD4-1 (IC$_{50}$, nM) | HTRF BRD4-2 (IC$_{50}$, nM) | Alpha Assay (IC$_{50}$, nM) | MT4 Assay, (IC$_{50}$, nM) |
|---|---|---|---|---|---|
| 1020-137 | 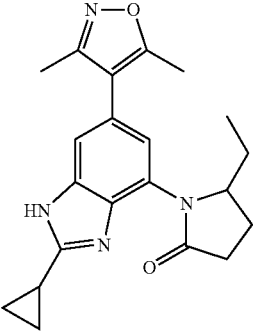 [SMILES: CCC1CCC(=O)N1c1cc(-c2c(C)noc2C)cc2[nH]c(C3CC3)nc12] | 186.6 | 399.0 | 52.8 | 112.7 |
| 1020-141 | 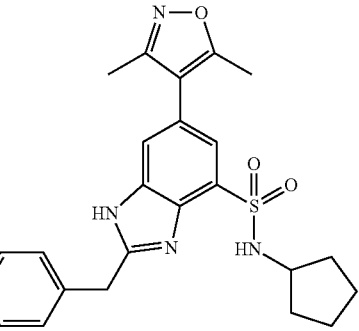 | 704.4 | 111.0 | n/a | 887.2 |
| 1020-148 | 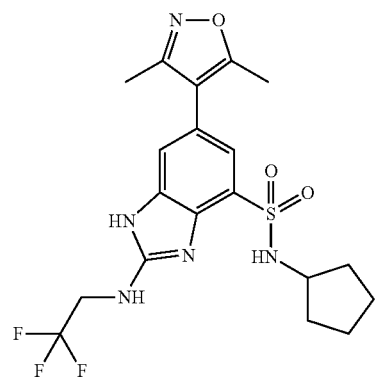 [SMILES: Cc1noc(C)c1-c1cc(S(=O)(=O)NC2CCCC2)c2nc(NCC(F)(F)F)[nH]c2c1] | 185.618 | 180.0 | n/a | 494.7 |
n/a: data not available (assay not performed)

Example 336

BRD4-1 Ligand KI and BRD4-2 Ligand KI Assays

Binding of the two tandem bromodomains, BRD4-I and BRD4-2, to a Cy5 labeled probe/ligand (Compound 1020-501) were measured using a homogeneous time resolved fluorescence resonance energy transfer (TR-FRET) assay.

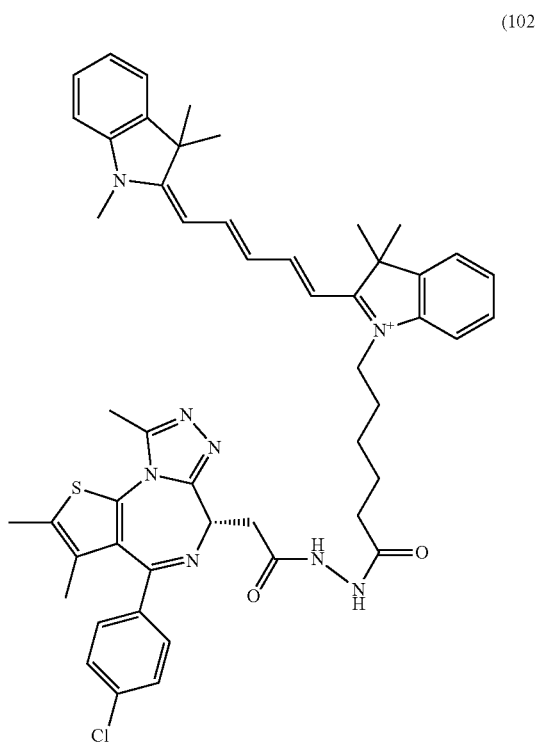

(1020-501)

The labeled ligand specifically binds BRD4-1 and BRD4-2 and can be displaced by a small molecule inhibitor that shares a similar or overlapping binding site. BRD4-I and BRD4-2 were expressed and purified from *Escherichia coli* as N-terminal $His_6$ tagged proteins. A Eu-cryptate labeled anti-His antibody (Perkin Elmer) was used to specifically bind BRD4. Binding of BRD4 to the labeled probe/ligand resulted in an increase in FRET signal whereas displacement of this labeled ligand from BRD4 with a small molecule inhibitor resulted in a decrease in FRET signal. Assays were performed in 50 mM Hepes (pH 7.5), 150 mM NaCl, 0.1 mg/ml BSA, 0.01% (v/v) Brij, 0.5% (v/v) DMSO and 10 nM labeled ligand at the following concentrations for each BRD4 isoform: 2 nM BRD4-1 and 0.5 nM BRD4-2. After an assay reaction time of 60 minutes at 25° C., binding was measured with 2 nM Eu-cryptate labeled anti-His antibody. TR-FRET signal was detected on an Envision plate reader (Ex: 320 nm; Em: 615/665 nm; 100 µs delay and 200 µs read window). Data were normalized based on a positive (2 µM I-BET) and negative (DMSO) controls and IC50 values were calculated from the fit of the dose-response curves to a four-parameter equation. All IC50 values represent geometric mean values of a minimum of four determinations. The IC50 values were converted to Ki values (dissociation constant for BRD4-inhibitor complex) using the Cheng and Prusoff equation for a competitive inhibitor mode of action. These assays generally produced results within 3-fold of the reported mean.

MT-4 Proliferation Assay:

As described above.

c-Myc Down Regulation and MM.1S Viability Assays:

An enzyme linked immunosorbent assay using the Meso Scale Diagnostic (MSD) technology was used to detect levels of c-Myc produced in MM.1S cells (ATCC). MM.1S cells were cultured in RPMI-1640 media (Corning), supplemented with 10% FBS (Hyclone), 1% penicillin-streptomycin (Cellgro), 2-mercaptoethanol (Gibco) and seeded onto 384-tissue culture treated filter binding plates (Millipore) at a density of 40K cells/well containing titrations of small molecule inhibitors or DMSO (0.4%) in a volume of 100 µl of media. After an incubation time of 24 hrs, cells were lysed (1× lysis buffer (Thermo) supplemented with protease and phosphatase inhibitor cocktail (Thermo)) and the plates centrifuged (1000 rpm, 1 min) to capture c-Myc on MSD plates coated with a monoclonal c-Myc antibody (Origene). Assay wells were washed (3× Invitrogen wash buffer) and probed with a polyclonal c-Myc antibody (Abcam) and MSD detection antibody solution in order to detect levels of c-Myc on the MSD platform. c-Myc capture was reported in pg/ml based on a standard curve using recombinant c-Myc protein (Prosci). EC50 values were calculated from the fit of the dose-response curves to a four-parameter equation. All EC50 values represent geometric mean values of a minimum of four determinations. These assays generally produced results within 3-fold of the reported mean.

For cell viability in the MM.1S cell line, cells were seeded onto 384-tissue culture treated plates (Greiner) at a density of 60K cells/well containing titrations of small molecule inhibitors or DMSO (0.2%). After 72 hr incubation cells were analyzed for cell viability by addition of CellTiter Glo (Promega) to the assay plates. After 15 min incubation at room temperature the signal from the viable cells was analyzed on an Envision plate reader (Perkin Elmer). EC50 values were calculated from the fit of the dose-response curves to a four-parameter equation. All EC50 values represent geometric mean values of a minimum of four determinations. These assays generally produced results within 3-fold of the reported mean.

Results are reported in Table 2.

TABLE 2

| Comp. No. | Structure | BRD4-1 Ligand KI (IC$_{50}$, nM) | BRD4-2 Ligand KI (IC$_{50}$, uM) | MT4 Assay (EC50, nM) | c-Myc (EC50, nM) | MM.1S Cell viability (EC50, nM) |
| --- | --- | --- | --- | --- | --- | --- |
| 1020-103 | 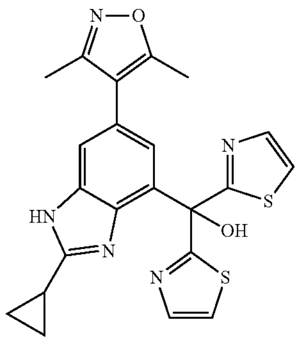 [SMILES: Cc1noc(C)c1-c1cc(C(O)(c2nccs2)c2nccs2)c2nc(C3CC3)[nH]c2c1] | 4.0 | 12.4 | 10.0 | 37.3 | 72.8 |
| 1020-104 | 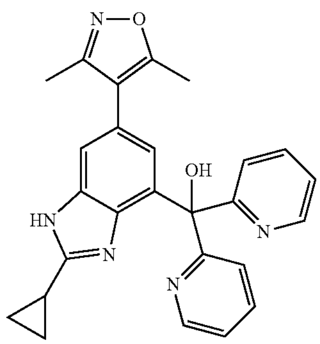 [SMILES: Cc1noc(C)c1-c1cc(C(O)(c2ccccn2)c2ccccn2)c2nc(C3CC3)[nH]c2c1] | 7.2 | 11.7 | 12.6 | 51.5 | 55.5 |
| 1020-112 | racemate | 10.4 | 13.5 | 18.2 | 56.7 | 145.3 |
| 1020-113 | racemate | 10.7 | 12.8 | 19.9 | 63.1 | 168.8 |

TABLE 2-continued

| Comp. No. | Structure | BRD4-1 Ligand KI (IC$_{50}$, nM) | BRD4-2 Ligand KI (IC$_{50}$, uM) | MT4 Assay (EC50, nM) | c-Myc (EC50, nM) | MM.1S Cell viability (EC50, nM) |
|---|---|---|---|---|---|---|
| 1020-114 | pure single diastereomer | 3.8 | 2.7 | 2.5 | 4.8 | 21.2 |
| 1020-224 | 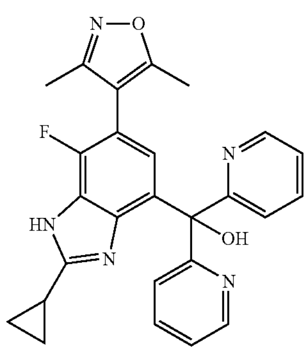 [SMILES: Cc1noc(C)c1-c1cc(C(O)(c2ccccn2)c2ccccn2)c2nc(C3CC3)[nH]c2c1F] | 10.8 | 20.2 | 20.5 | 103.6 | 84.0 |
| 1020-239 | pure enantiomer the second eluting compound | 5.9 | 6.0 | 14.0 | 33.1 | 47.5 |

TABLE 2-continued

| Comp. No. | Structure | BRD4-1 Ligand KI (IC$_{50}$, nM) | BRD4-2 Ligand KI (IC$_{50}$, uM) | MT4 Assay (EC50, nM) | c-Mye (EC50, nM) | MM.1S Cell viability (EC50, nM) |
|---|---|---|---|---|---|---|
| 1020-257 | 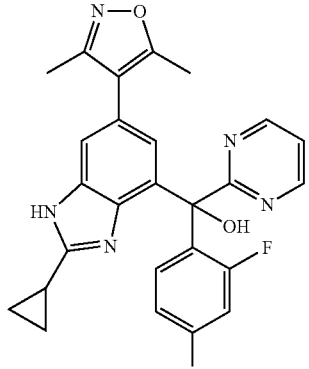 racemate | 4.7 | 5.6 | 14.2 | 55.7 | 28.4 |
| 1020-289 | 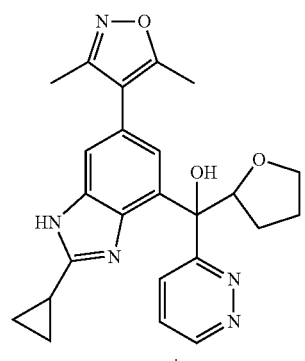 pure enantiomer | 2.0 | 2.0 | 4.2 | 5.7 | 17.8 |
| 1020-298 | 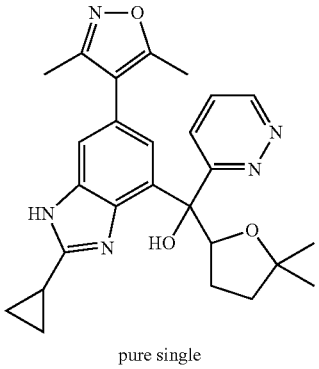 pure single diastereomer | 5.4 | 3.6 | 5.6 | 15.3 | 16.9 |

Example 337

Compound 1020-18 reduced the viability of 17 Diffuse Large B Cell Lymphoma (DLBCL), three Multiple Myeloma (MM), and two Follicular Lymphoma (FL) cell lines as shown in Table 3. EC$_{50}$ values across all cell lines ranged from 9 to 2300 nM with a median of 53 nM.

Cell Titer Glo Viability Assay:

All procedures were performed at Gilead Sciences, Inc. in Seattle, Wash. and Branford, Conn. Compound 1020-18 was dissolved in DMSO to prepare a 10 mM stock solution then serially diluted three-fold in DMSO in a 96 well plate format to achieve a final dose range of 10 μM to 0.17 nM in 0.1% DMSO in the test medium. Cells were plated at 10,000-30,000 cells per well in duplicate or triplicate plates and incubated at 37° C. with 5% CO$_2$ for four days in RPMI supplemented with 10-20% FBS and 100 U/L penicillin-streptomycin. Cell viability was assessed using Cell Titer Glo (Promega, Madison, Wis.) following the manufacturer's protocol. EC$_{50}$ values were determined using a four parameter variable slope model (GraphPad Prism 6). All EC$_{50}$ values represent mean values of three to five determinations. These assays generally produced results within three-fold of the reported mean. Results are reported in Table 3.

TABLE 3

| Cell line | Disease | Inhibition of Viability, EC$_{50}$ (nM) |
| --- | --- | --- |
| DB | DLBCL | 153 |
| SU-DHL-2 | DLBCL | 11 |
| SU-DHL-4 | DLBCL | 351 |
| SU-DHL-5 | DLBCL | 67 |
| SU-DHL-6 | DLBCL | 29 |
| SU-DHL-8 | DLBCL | 18 |
| SU-DHL-10 | DLBCL | 31 |
| HT | DLBCL | 147 |
| Karpas 422 | DLBCL | 9 |
| OCI-LY3 | DLBCL | 162 |
| OCI-LY4 | DLBCL | 135 |
| OCI-LY7 | DLBCL | 2300 |
| OCI-LY10 | DLBCL | 410 |
| OCI-LY19 | DLBCL | 29 |
| Pfeiffer | DLBCL | 16 |
| Toledo | DLBCL | 59 |
| U-2932 | DLBCL | 56 |
| KMS-11 | MM | 13 |
| NCI-H929 | MM | 7 |
| OPM-2 | MM | 20 |
| RPMI-8226 | MM | 70 |
| WSU-FSCCL | FL | 19 |
| WSU-NHL | FL | 34 |

Example 338

Compound 1020-18 inhibited the viability of 240 cancer cell lines in the Onco240 cell line panel (Eurofins, Bothell, Wash.) across 15 different broad cancer types (FIG. 1). Relative IC50 values across all cell lines ranged from 0.012 to >10 µM with a median value of 0.22 µM and a mean value of 0.575 µM.

Onco240 Ricerca Panel:

All procedures were performed at Eurofins PanLabs. Bothell, Wash. Cells were seeded into 384 well plates at a single cell density in standard media in duplicate. Test compounds were added 24 hrs later, and the time zero plate was fixed, stained and analyzed for doubling calculations. Compound was diluted in DMSO starting at 10 µM and then serially diluted in DMSO by 3.16-fold to complete the concentration curves. Compounds were added directly from these dilutions to cell plates using Echo 550 acoustic energy based transfer. The control compound Staurosporine was included on each test plate. Test compound plates were incubated for 72 hrs. Relative cell count IC$_{50}$ values were calculated as the concentration on the dose curve where 50% growth inhibition is achieved relative to the DMSO control (100% growth). Relative cell count IC$_{50}$ values are reported in FIG. 1. Medians for each cancer type are indicated by horizontal lines.

Example 339

Compound 1020-18 inhibited c-MYC protein expression in 17 Diffuse Large B Cell Lymphoma (DLBCL), four Multiple Myeloma (MM), and two Follicular Lymphoma (FL) cell lines (Table 4). EC$_{50}$ values across all cell lines ranged from 19 to 853 nM with a median of 103 nM and maximum percent c-MYC inhibition ranged from 31 to 108%.

c-MYC Protein Assay:

All procedures were performed at Gilead Sciences, Inc. in Branford, Conn. c-MYC cellular protein levels were measured with a MesoScale (Rockville, Md.) assay. Cells were seeded into a 96-well plate at 2.5×10$^5$ cells per well in 270 µl of growth media appropriate to the cell line. OCI-Ly3, OCI-Ly4 and OCI-Ly7 were grown in Iscove's+20% FBS, OCI-Ly10 was grown in RPMI+20% FBS, OCI-Ly19 was grown in alphaMEM+20% FBS, and all other cell lines were grown in RPMI+10% FBS. To each well, 30 µl of 100× compound in serum-free media was added and cells were incubated at 37° C. in 5% CO$_2$ for 4 hours. Compound final concentrations in 3-fold serial dilutions ranged from 10 to 0.0005 µM with a final DMSO concentration of 0.1% (v/v). Assay plates were centrifuged at 300×g at room temperature for 5 minutes and cell pellets were washed once with DPBS and centrifuged at 300×g. Drained pellets were vortexed briefly to loosen and lysed in 30 µl 1×RIPA buffer (Cell Signaling Technology, Danvers Mass.) containing protease (Roche, Palo Alto Calif.) and phosphatase inhibitors (Sigma, Saint Louis Mo.; Santa Cruz Technologies, Dallas Tex.). Assay plates were incubated on ice for 10 minutes, and either used directly or frozen at −80° C. for use in a MesoScale assay.

MesoScale assay standard-bind 96-well plates were coated with mouse anti-c-MYC antibody at 1 µg/mL (Origene, Rockville Md.) overnight at 4° C., washed 3 times in Wash Buffer (TBS-Tween 0.05%, v/v) and blocked in 3% Blocker A (w/v; MesoScale) in PBS. Sample lysate was added at 30 µl per well and incubated 1 hour with oscillation at room temperature. A standard 9-point, 3-fold serial dilution curve of c-MYC purified recombinant protein (ProSci, Poway Calif.) starting at 60 ng/mL diluted in PBMC lysate was included on every assay plate. Lysates from unstimulated human B cells (AllCells Ltd, Alemeda Calif.; 2.5×10$^5$ cells/well) as a negative control and human B cells stimulated with 20 µg/mL anti-CD40 (R&D Systems) and 40 µg/mL anti-IgG/anti-IgM (Jackson ImmunoResearch, West Grove Pa.) as a positive control were included on every assay plate. Assay plates were washed 3 times in Wash Buffer, secondary antibody rabbit anti-c-MYC (Abcam, Cambridge Mass.) was added at 0.1 µg/mL in Assay Buffer (1% Blocker A (w/v) in PBS/0.05% Tween, MesoScale), plates were incubated for 1 hour and washed 3 times in Wash Buffer. Detection antibody anti-rabbit Sulfo-TAG (MesoScale) was added at 0.5 µg/mL in Assay Buffer and incubated for 1 hour, plates were washed 3 times in Wash Buffer, and Read Buffer (MesoScale) was added for 5 minutes. Signal was immediately detected on a Meso Scale Sector 2400 Imager (MesoScale). Sample signal was normalized to c-MYC signal in DMSO-treated cells (100% c-MYC) and unstimulated B cells (0% c-MYC). The c-MYC protein concentration was interpolated from the standard curve. EC$_{50}$ values were calculated from the fit of the dose response curves to a four-parameter logistical fit equation. All EC$_{50}$ values represent means of two-four determinations. These assays generally produced results within 3-fold of the reported mean. Results are reported in Table 4.

TABLE 4

| Cell line | Disease | Compound 1020-18 c-MYC Inhibition, EC$_{50}$ (nM) | Compound 1020-18 Maximum % c-MYC Inhibition |
| --- | --- | --- | --- |
| DB | DLBCL | 122 | 73 |
| SU-DHL-2 | DLBCL | 20 | 99 |
| SU-DHL-4 | DLBCL | 93 | 86 |
| SU-DHL-5 | DLBCL | 82 | 40 |
| SU-DHL-6 | DLBCL | 46 | 70 |
| SU-DHL-8 | DLBCL | 150 | 48 |
| SU-DHL-10 | DLBCL | 33 | 90 |
| HT | DLBCL | 84 | 108 |
| Karpas 422 | DLBCL | 369 | 49 |
| OCI-LY3 | DLBCL | 78 | 84 |
| OCI-LY4 | DLBCL | 177 | 82 |
| CCI-LY7 | DLBCL | 853 | 31 |
| OCI-LY10 | DLBCL | 662 | 44 |
| OCI-LY19 | DLBCL | 103 | 59 |
| Pfeiffer | DLBCL | 124 | 68 |
| Toledo | DLBCL | 182 | 46 |

TABLE 4-continued

| Cell line | Disease | Compound 1020-18 c-MYC Inhibition, $EC_{50}$ (nM) | Compound 1020-18 Maximum % c-MYC Inhibition |
|---|---|---|---|
| U-2932 | DLBCL | 330 | 35 |
| KMS-11 | MM | 74 | 99 |
| MM.1S | MM | 53 | 106 |
| NCI-H929 | MM | 62 | 41 |
| OPM-2 | MM | 19 | 92 |
| WSU-FSCCL | FL | 143 | 66 |
| WSU-NHL | FL | 166 | 55 |

Example 340

Compound 1020-18 significantly inhibited tumor growth in MM.1S (FIG. 2) and DHL-10 (FIG. 3) xenograft models.

MM.1S Xenograft Model:

All procedures were performed at Molecular Imaging, Inc. (Ann Arbor, Mich.). Male Charles River SCID Beige Mice (CB17.Cg-PrkdcscidLystbg-J/Crl) at 7-8 weeks old were used in this experiment. MM.1S-luc cells were obtained from DFCI. Cells were grown in RPMI 1640 Media supplemented with 10% FBS and 1% PSG. Test animals were implanted subcutaneously on Day 0 with 200 µL of MM.1S-luc cells ($5 \times 10^6$ cells/mouse) using a 27-gauge needle. The mean estimated tumor burden for all groups on Day 10 was 167 mg and all of the groups were matched (range of group means, 158 mg-175 mg). Groups of 12 animals were dosed PO twice a day (see Table 5) according to individual body weight on the day of treatment (0.1 mL/20 g) beginning on Day 11. All animals were observed for clinical signs at least daily. Animals with tumors in excess of 2 g or with ulcerated and weeping tumors for longer than 48 hours were euthanized, as were those found in obvious distress or in a moribund condition.

Vehicle and compound solutions were supplied by Gilead Sciences, Inc. and prepared weekly. Solutol HS-15, EtOH, PEG400, and water (HCL adjusted) [10/10/40/40 v/v] vehicle was stored at 4° C. Compound 1020-18, at concentrations of 8 mg/mL, 4 mg/mL, and 2 mg/mL in vehicle were stored at 4° C. The pH of solutions ranged from 7.3-7.68 for vehicle and 3.25-4.54 for Compound 1020-18.

Figure 2:
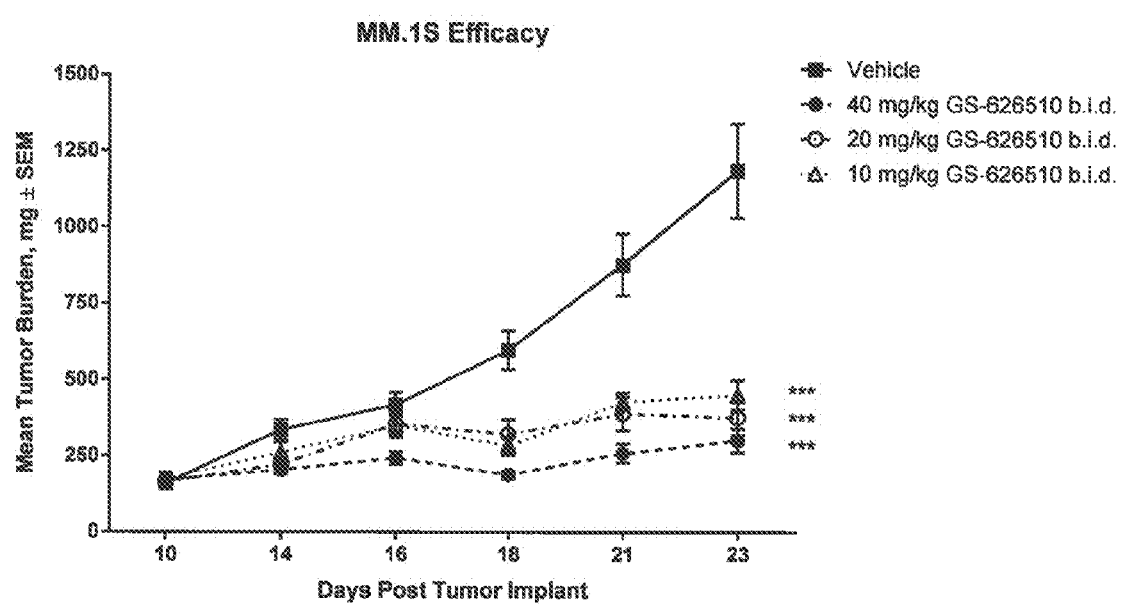
FIG. 2 shows inhibition of tumor growth in an MM.1S xenograft model by compound 1020-18.
Figure 3:
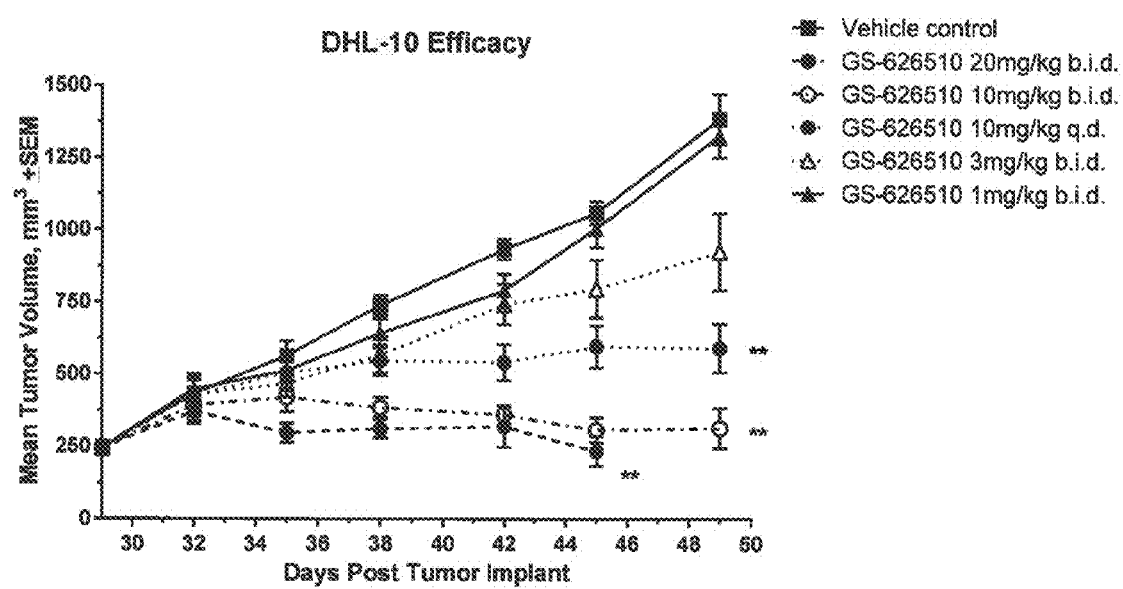
FIG. 3 shows inhibition of tumor growth in a DHL-10 xenograft model by compound 1020-18.

Body weights and tumor measurements were recorded three times a week. Tumor burden (mg) was estimated from caliper measurements by the formula for the volume of a prolate ellipsoid assuming unit density as: Tumor burden (mg)=(L×W2)/2, where L and W are the respective orthogonal tumor length and width measurements (mm). Tumor weights per day between groups were analyzed by the application of a two-way analysis of variance (ANOVA) and P values for each treatment group were highly significant compared to vehicle (***<0.0001) on the last day of dosing. Results of tumor burden as means±SEM per group are shown in FIG. 2.

TABLE 5

| Group # | Treatment | Dose (mg/kg/inj) | Schedule |
|---|---|---|---|
| 1 | Vehicle Control | 0.1 mL/20 g | b.i.d. |
| 2 | Compound 1020-18 | 40 | b.i.d. |
| 3 | Compound 1020-18 | 20 | b.i.d. |
| 4 | Compound 1020-18 | 10 | b.i.d. |

DHL-10 Xenograft Model:

All procedures were carried out at Omcros Animal Facility (Seattle, Wash.). Female Scid beige mice (CB17.Cg-PrkdcscidLystbg-J/Crl) from Charles River were used in this study. Animals were 6-7 weeks old on Day 1 of the experiment (the day of tumor cell inoculation). SU-DHL-10 cells were obtained from ATCC and grown in RPMI 1640 Media supplemented with 10% FBS. Cells were grown and resuspended using scrum-free media and 50% Matrigel® to generate a concentration of $25 \times 10^6$ cells/mL in 0.2 mL. Test animals were implanted subcutaneously in the right axilla (just under arm) on Day 1 with 0.2 mL ($5 \times 10^6$ cells/mouse) using a 27-gauge needle. All animals were observed for clinical signs at least daily. Body weights and tumor volume were monitored with a laser scan system, Biopticon Tumorimager (Biopticon), and recorded two times per week. Clinical signs were monitored daily during the dosing phase of the study. All animals were sacrificed by carbon dioxide exposure at designated time points.

The day of tumor cell inoculation was marked as day 1 with treatment beginning on day 29. The mean tumor volume for all experimental animals on day 29 was 246.3 $mm^3$ and all of the groups in the experiment were well matched (range of group means, 244.5-248.9 $mm^3$). All mice weighed from 16.9 to 23.1 grams on day 29.

Vehicle contained Solutol HS-15/EtOH/PEG400/pH2.5 water [10/10/40/40 v/v]. Compound 1020-18 was formulated as solutions at concentrations of 4 mg/mL, 2 mg/mL, 0.6 mg/mL, and 0.2 mg/mL in vehicle. All vehicle and pre-formulated compound in the vehicle were stored at 4° C. and prepared weekly.

The mice in Groups 1, 2, 3, 5, and 6 were orally dosed twice a day with vehicle, Compound 1020-18 at 20 mg/kg, 10 mg/kg, 3 mg/kg, and 1 mg/kg, respectively. The mice in Group 4 were dosed once daily with Compound 1020-18 at 10 mg/kg (Table 6). All mice were dosed according to individual body weight on the day of treatment (5 mL/kg). After 21 days of treatment, 5 mice from all groups were euthanized via exposure to carbon dioxide between 2 hours and 12 hours post-last dose.

Daily inter-group tumor weights were analyzed by the application of a two-way analysis of variance (ANOVA) and P values on the last day of dosing for the 20 mg/kg b.i.d., 10 mg/kg b.i.d. and 10 mg/kg q.d. and treatment groups were significant compared to vehicle (**<0.005). The 3 mg/kg b.i.d. and 1 mg/kg b.i.d. groups were not significantly different from the vehicle group on the last day of dosing. Results of tumor burden as means±SEM per group are reported in FIG. 3.

TABLE 6

| Group # | Treatment | Dose (mg/kg/inj) | Schedule |
|---|---|---|---|
| 1 | Vehicle Control | 0.1 mL/20 g | b.i.d. |
| 2 | Compound 1020-18 | 20 | b.i.d. |
| 3 | Compound 1020-18 | 10 | b.i.d. |
| 4 | Compound 1020-18 | 10 | q.d. |
| 5 | Compound 1020-18 | 3 | b.i.d. |
| 6 | Compound 1020-18 | 1 | b.i.d. |

Example 341

Figure 4:
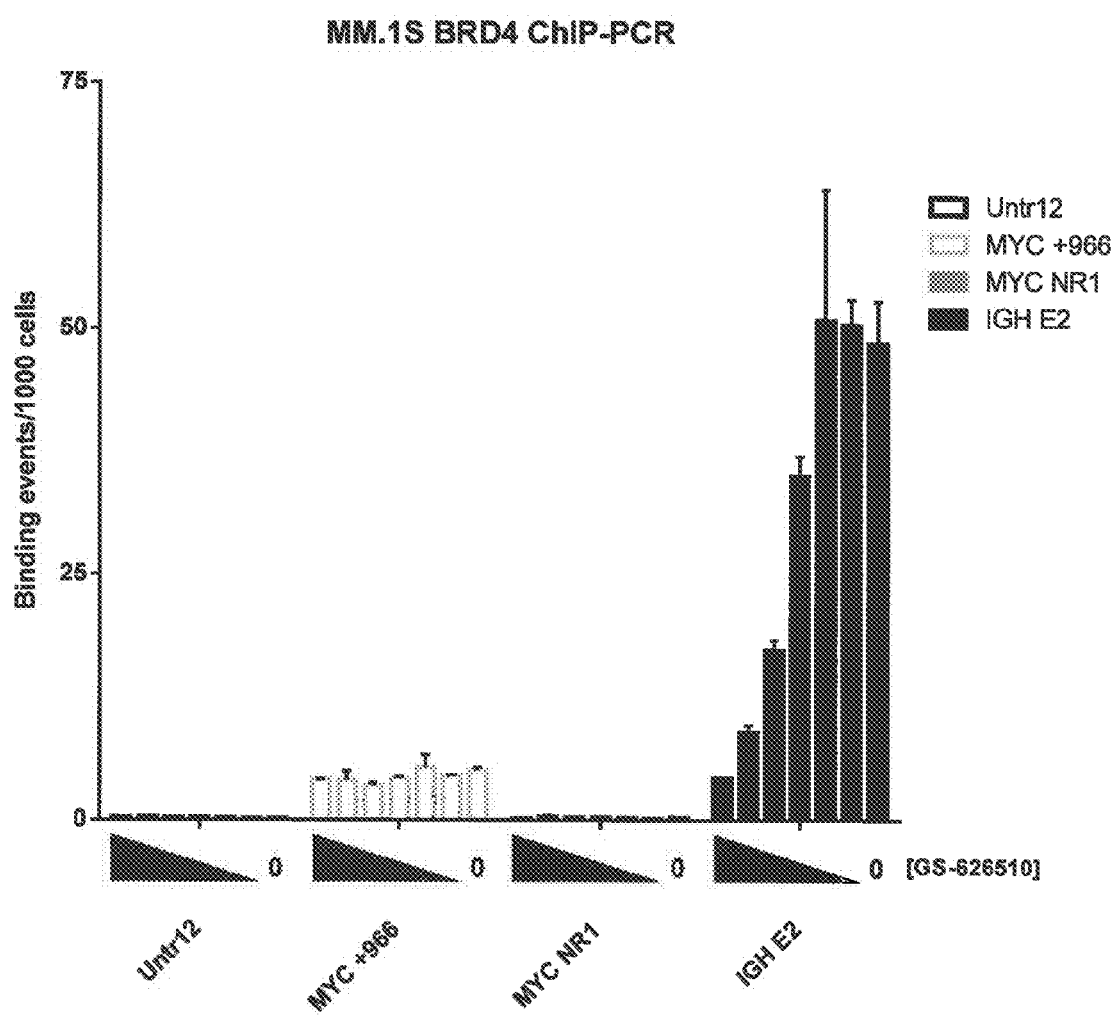
FIG. 4 shows inhibition by compound 1020-18 of BRD4 binding at the IgH superenhancer.

MM.1S cells contain an IgH insertion at breakpoint of der3t(3:8) which hyperactivates the transcription of MYC. BRD4 was shown previously to bind to this IgH superenhancer and to the MYC promoter in MM.1S cells (Delmore et al., BET Bromodomain Inhibition as a Therapeutic Strategy to Target c-Myc, Cell (2011), doi:10.1016/j.cell.2011.08.017). BRD4 binding at the IgH superenhancer was >420-fold over the control Utr12 locus and was inhibited by Compound 1020-18, as determined by dose responsive inhibition of BRD4 binding by chromatin immunoprecipitation followed by PCR (ChIP-PCR) shown in FIG. 4. Results in FIG. 4 are reported as mean of duplicates±SEM as binding events per 1000 cells. Concentrations of Compound 1020-18 ranged from 1.0 µM to 0.0015 nM and the 0 points were treated with DMSO alone. By contrast, BRD4 only bound weakly at the promoter of the MYC gene (MYC-+966), and not at all to a non-control region of the MYC gene (MYC-NR1), or to a control locus in a gene desert on chromosome 12 (Utr12).

ChIP-PCR Assay:

MM.1S cells (1×10⁷ cells per dose) were treated in duplicate with Compound 1020-18 in a three-fold serial dilution series ranging from 1111 nM to 1.5 nM for 4 hours in a final concentration of 0.1% DMSO. Cells were fixed with 1/10 volume of freshly-prepared Formaldehyde Solution (final concentration of 11% v/v formaldehyde, 0.1 M NaCl, 1 mM EDTA, pH 8 in 50 mM HEPES buffer) added directly to the existing media in each flask of cells and agitated for 15 minutes at room temperature. Fixation was stopped by addition of 1/20 volume Glycine Solution (final concentration of 0.125 M Glycine, M.W. 75) to the existing media and cells were incubated at room temperature for 5 minutes. Cells were centrifuged at 800×g in a refrigerated centrifuge for 10 minutes in 50 mL conical tubes and pellets were re-suspended in 10 mL of chilled PBS-Igepal (0.5% Nonidet P-40 in PBS). Cells were centrifuged again at 800×g for 10 minutes and pellets were re-suspended in 10 mL of chilled PBS-Igepal with 1 mM PMSF. Cells were centrifuged a third time at 800×g for 10 minutes and pellets were snap-frozen on dry ice, stored at 80° C., and shipped to Active Motif (Carlsbad, Calif.) for ChIP-PCR analysis.

Chromatin was isolated by adding lysis buffer, followed by disruption with a Dounce homogenizer. Lysates were sonicated and the DNA sheared to an average length of 300-500 bp. Genomic DNA (Input) was prepared by treating aliquots of chromatin with RNase, proteinase K, and heated for de-crosslinking, followed by ethanol precipitation. Pellets were resuspended and the resulting DNA was quantified on a NanoDrop spectrophotometer. Extrapolation to the original chromatin volume allowed quantitation of the total chromatin yield. An aliquot of chromatin (30 g) was pre-cleared with protein A agarose beads (Invitrogen). Genomic DNA regions were isolated using an antibody against BRD4 (Bethyl Laboratories, A301-985A100, 4 μg per IP). After incubation at 4° C. overnight, protein-A agarose beads were used to isolate the immune complexes. Complexes were washed, eluted from the beads with SDS buffer, and subjected to RNase and proteinase K treatment. Crosslinks were reversed by incubation overnight at 65° C., and ChIP DNA was purified by phenol-chloroform extraction and ethanol precipitation. Quantitative PCR (QPCR) reactions were carried out in triplicate on specific genomic regions shown in Table 7 using SYBR Green Supermix (Bio-Rad). The resulting signals were normalized for primer efficiency by carrying out QPCR for each primer pair using input DNA. The primer efficiency ratio was determined with internal controls by Active Motif. Data was normalized to binding events per 1000 cells with the following formula:

(Average qPCR value×(resuspension volume/5)× (1000/cell equivalents in ChIP))/primer efficiency ratio=binding events per 1000 cells

TABLE 7

| Genomic Locus | Primer Set[1] | Chromosomal Location |
|---|---|---|
| Untr12 | Please refer to Active Motif human negative control primer set 1, catalog number 71001 | Gene desert on chromosome 12 |
| MYC_+966 | CGGACATTCCTGCTTTATTG (SEQ ID NO: 2) GCGATATGCGGTCCCTACTC (SEQ ID NO: 3) | chr8: 128,749,029- 128,749,395 |
| MYC_NR1 | GCAGCTAGATCGTTGGGAAG (SEQ ID NO: 4) GCTGGTGATTTCAGTGCAGA (SEQ ID NO: 5) | chr8: 127,714,271- 127,788,621 |
| IGH_E2 | TGGGGTACAAGAGGCTTCAG (SEQ ID NO: 6) CAGTACAGGAGTGGGGACAG (SEQ ID NO: 7) | chr14: 106,047,824- 106,049,452 |

Example 342

Meningioma Growth Inhibition

Sixteen 8- to 10-week-old nude mice are used for subarachnoidal tumor inoculation with IOMM-Lee cells. The animals are anesthetized i.p. (Rompun/Ketamin) and stabilized in a stereotactic head frame. Two holes are drilled 2 mm anterior of the bregma and 1.5 mm left and right from the sagittal suture, just deep enough to penetrate bone and underlying meninges with minimal alteration of the neocortex. Approximately 2.5×10⁵ cells in 5 mL PBS are slowly (1 minute) injected per hole to a depth of 1 mm with a Hamilton syringe. After 2 days, 8 mice receive a daily dose of a compound of Formula (I), for example compound 1020-18, at 20 mg/kg i.p., and the remaining 8 receive only the diluent PBS (control group). Meningioma growth is monitored my magnetic resonance imaging at 2 days and 9 days after inoculation.

While the foregoing description describes specific embodiments and aspects, those with ordinary skill in the art will appreciate that various modifications and alternatives can be developed. Accordingly, the particular embodiments and aspects described above are meant to be illustrative only, and not to limit the scope of the invention, which is to be given the full breadth of the appended claims, and any and all equivalents thereof.

We claim:
1. A compound of Formula (Ie)

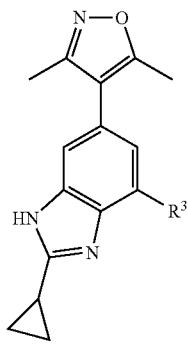

wherein
R³ is
—C(O)OR$^a$, —NHC(O)OR$^a$, —NHS(O)₂R$^a$, or —S(O)₂NR$^a$R$^b$; or
selected from the group consisting of C$_{1-10}$ alkyl, C$_{1-10}$ alkoxy, amino, C$_{5-10}$ aryl, C$_{6-20}$ arylalkyl, C$_{1-10}$ heteroalkyl, C$_{5-10}$ heteroaryl, and C$_{6-20}$ heteroarylalkyl, each of which is optionally substituted with from 1 to 5 R²⁰ groups;
each R$^a$ and R$^b$ is independently selected from the group consisting of H, C$_{1-10}$ alkyl, C$_{5-10}$ aryl, C$_{6-20}$ arylalkyl, C$_{1-10}$ heteroalkyl, C$_{5-10}$ heteroaryl, and C$_{6-20}$ heteroarylalkyl, each of which is optionally substituted with from 1 to 5 R²⁰ groups; and
each R²⁰ is independently selected from the group consisting of acyl, C$_{1-10}$ alkyl, C$_{1-10}$ alkoxy, amino, amido, amidino, C$_{5-10}$ aryl, C$_{6-20}$ arylalkyl, azido, carbamoyl, carboxyl, carboxyl ester, cyano, guanidino, halo, C$_{1-10}$ haloalkyl, C$_{1-10}$ heteroalkyl, C$_{5-10}$ heteroaryl, C$_{6-20}$ heteroarylalkyl, hydroxy, hydrazino, hydroxyl, imino, oxo, nitro, sulfinyl, sulfonic acid, sulfonyl, thiocyanate, thiol, and thione;
wherein the C$_{1-10}$ alkyl, C$_{5-10}$ aryl, C$_{6-20}$ arylalkyl, C$_{1-10}$ heteroalkyl, C$_{5-10}$ heteroaryl, and C$_{6-20}$ heteroarylalkyl groups are optionally substituted with from 1 to 3 substituents independently selected from C$_{1-6}$ alkyl, C$_{5-10}$ aryl, halo, C$_{1-6}$ haloalkyl, cyano, hydroxyl, and C$_{1-6}$ alkoxy;
or a pharmaceutically acceptable salt thereof.

2. A compound of claim 1, wherein R³ is C$_{1-10}$ alkyl, C$_{1-10}$ alkoxy, or C$_{1-10}$ heteroalkyl, each of which may be optionally substituted with from 1 to 5 R²⁰ groups, or a pharmaceutically acceptable salt thereof.

3. A compound of claim 1, wherein R³ is an, C$_{5-10}$ aryl, C$_{6-20}$ arylalkyl, C$_{5-10}$ heteroaryl, or C$_{6-20}$ heteroarylalkyl, each of which may be optionally substituted with from 1 to 5 R²⁰ groups, or a pharmaceutically acceptable salt thereof.

4. A compound of claim 1 selected from the group consisting of

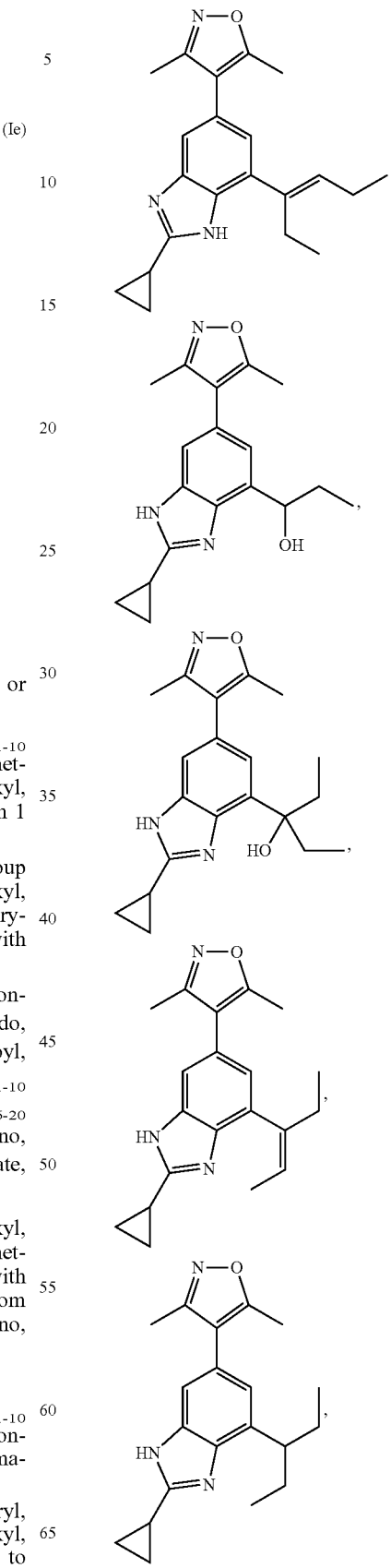

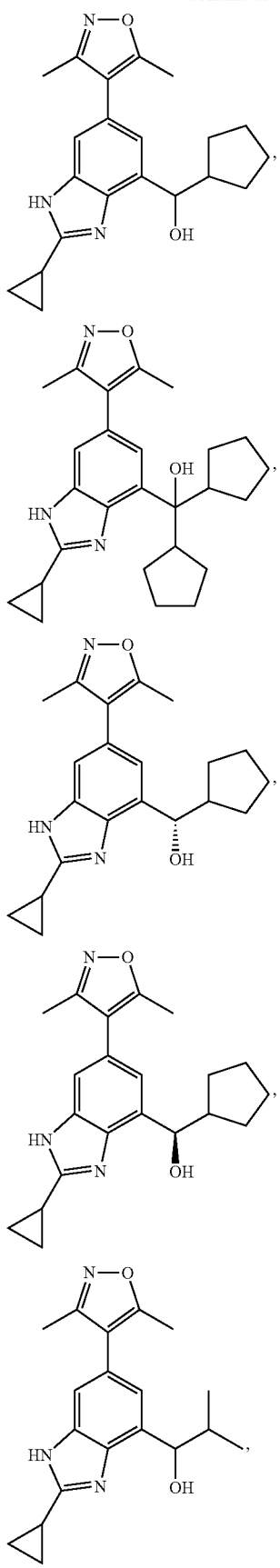
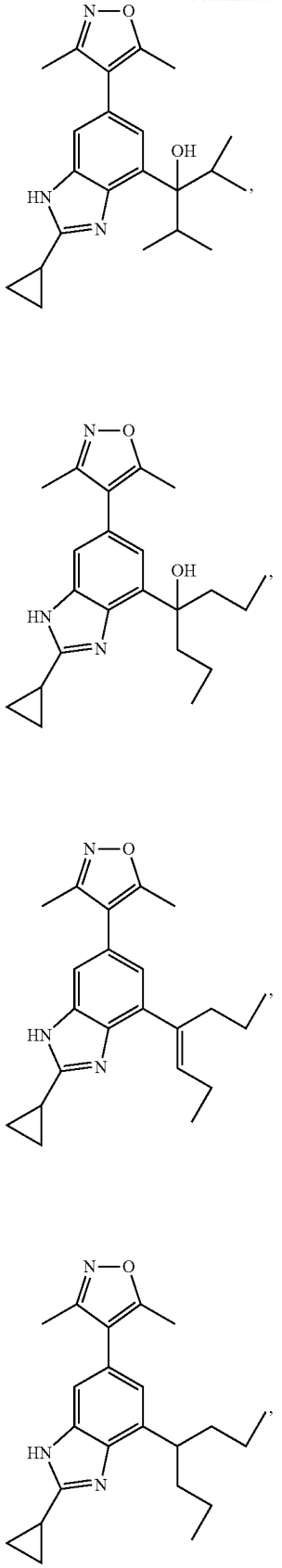
or a pharmaceutically acceptable salt thereof.

5. A compound of claim 1 selected from the group consisting of
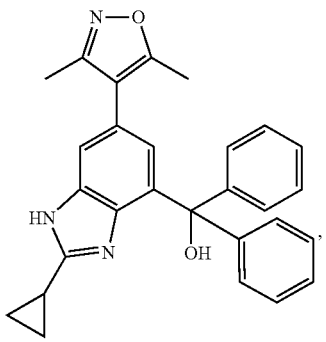
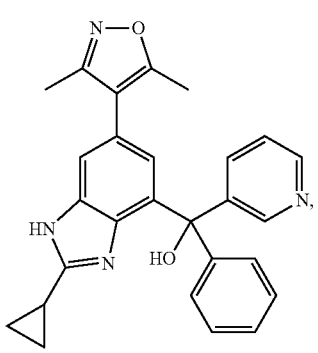
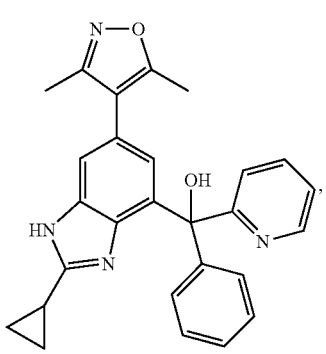
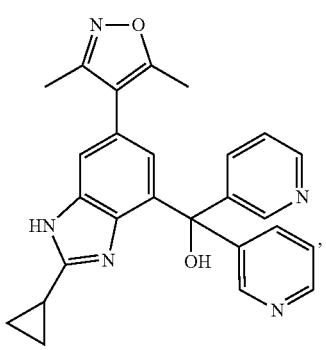
-continued
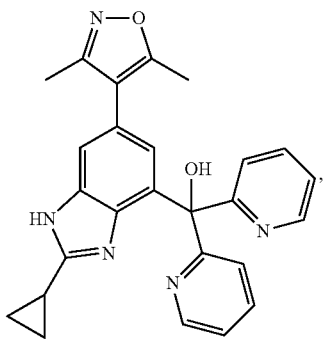
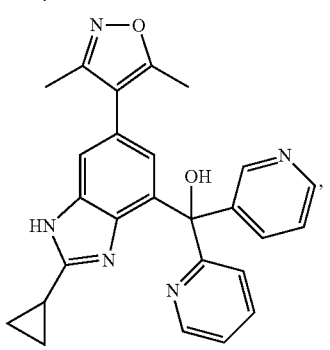
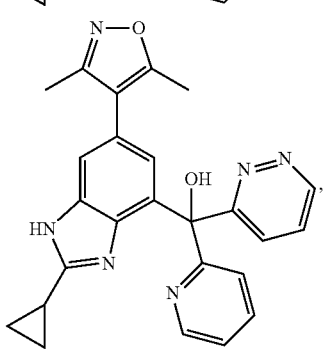
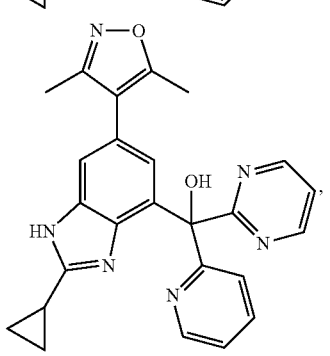
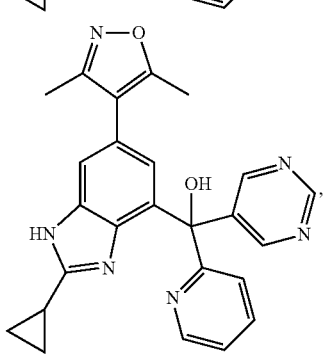

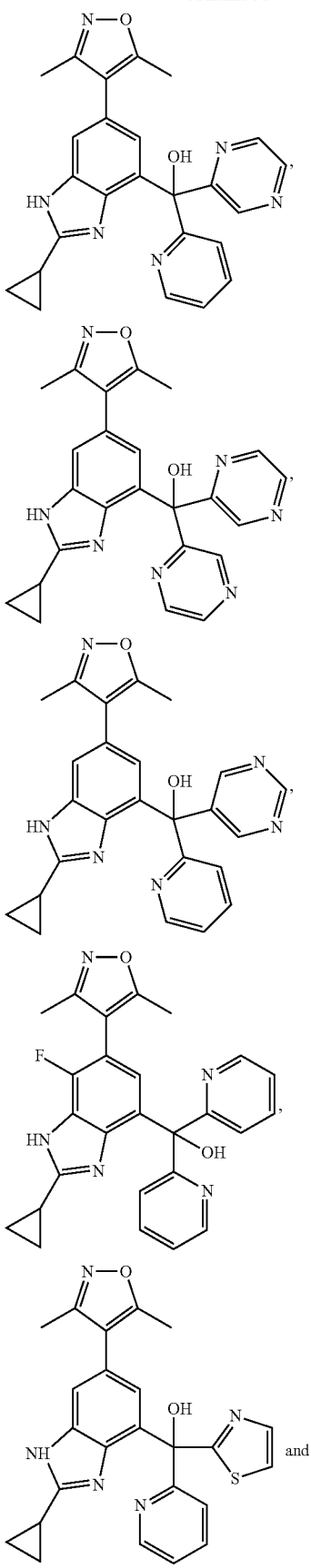
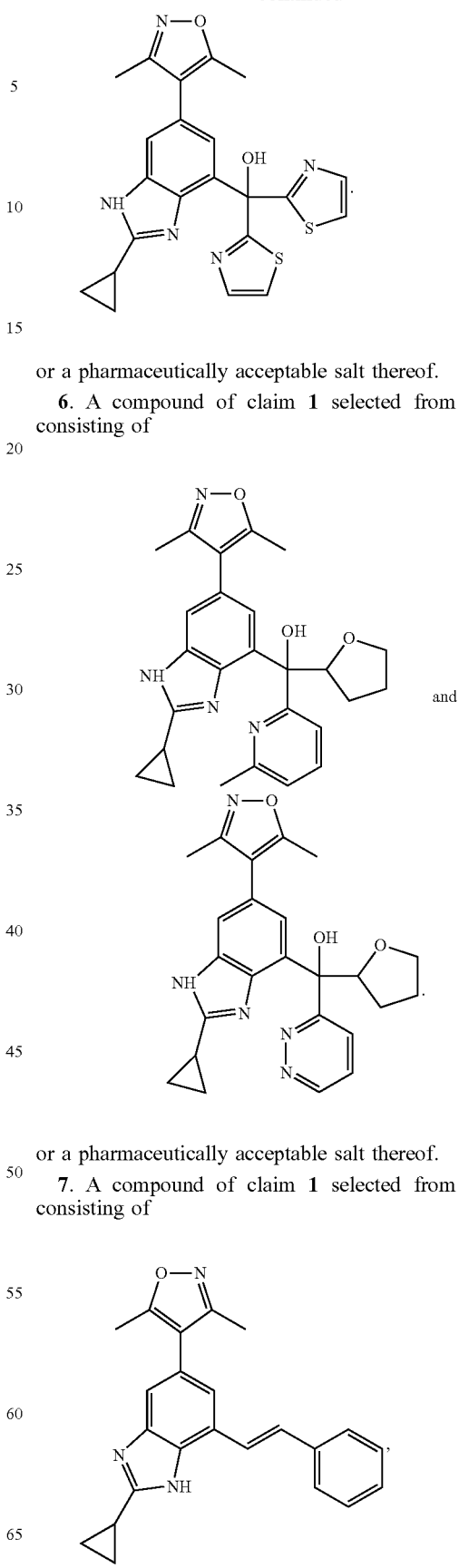
or a pharmaceutically acceptable salt thereof.
6. A compound of claim 1 selected from the group consisting of
or a pharmaceutically acceptable salt thereof.
7. A compound of claim 1 selected from the group consisting of 461
-continued
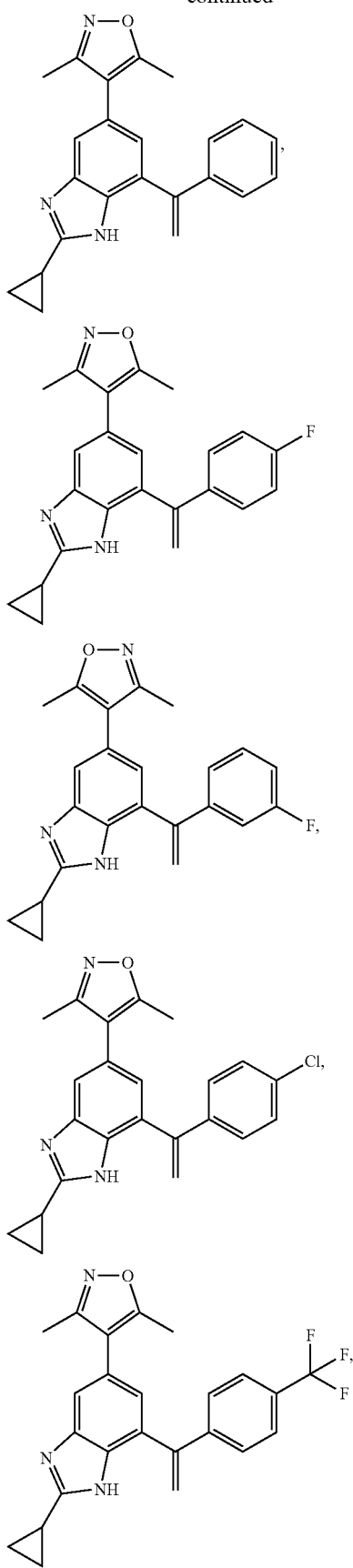
462
-continued
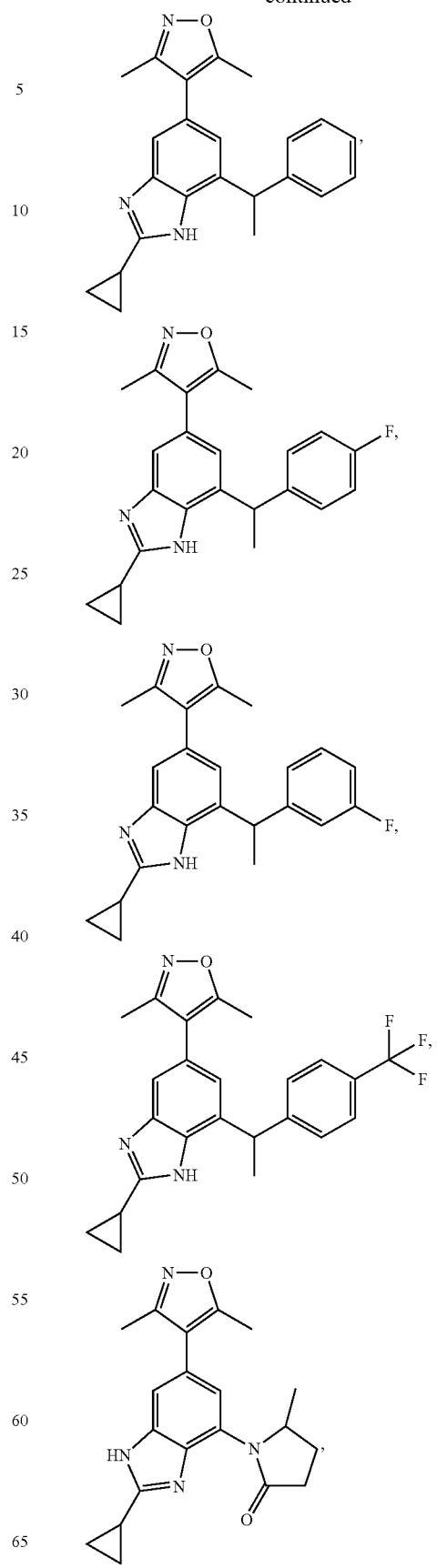

-continued
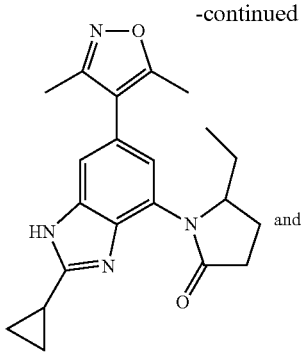
and
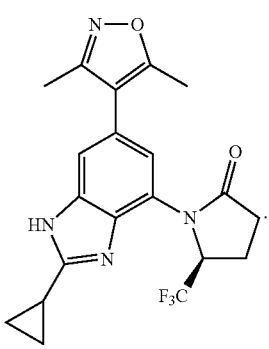
or a pharmaceutically acceptable salt thereof.
8. A compound of claim 1 selected from the group consisting of
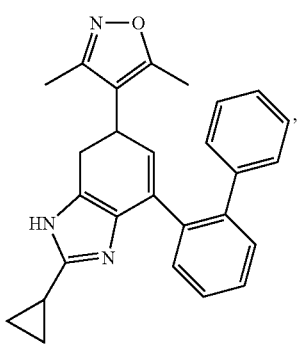
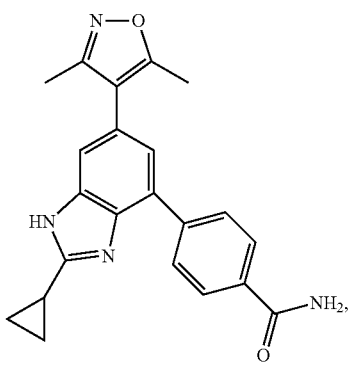
-continued
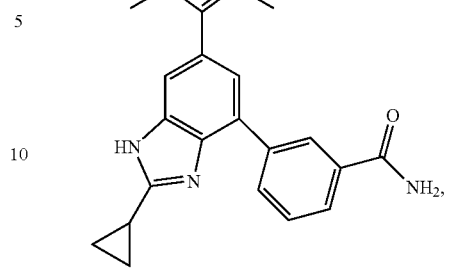
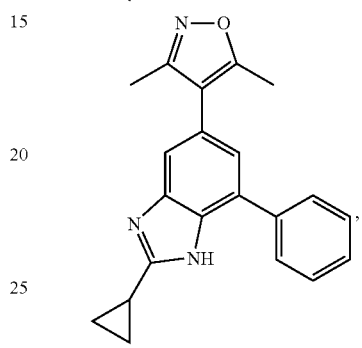
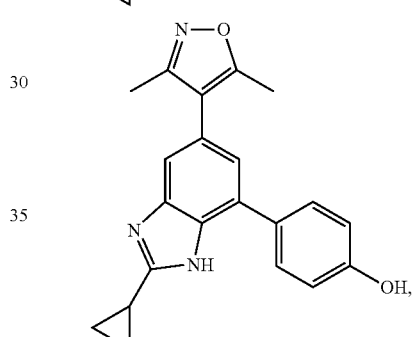
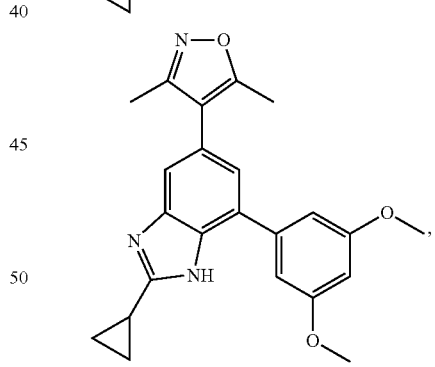
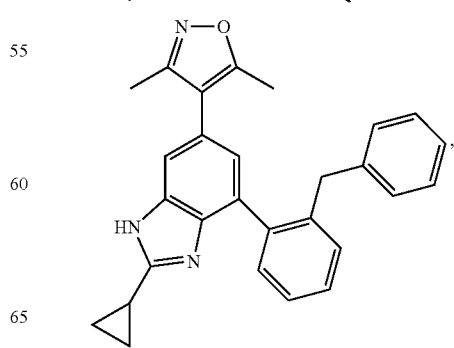

465
-continued
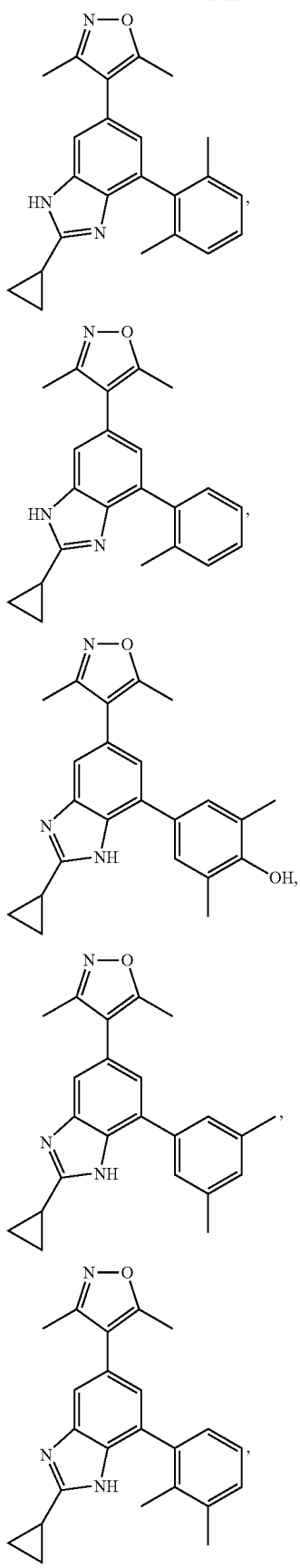
466
-continued
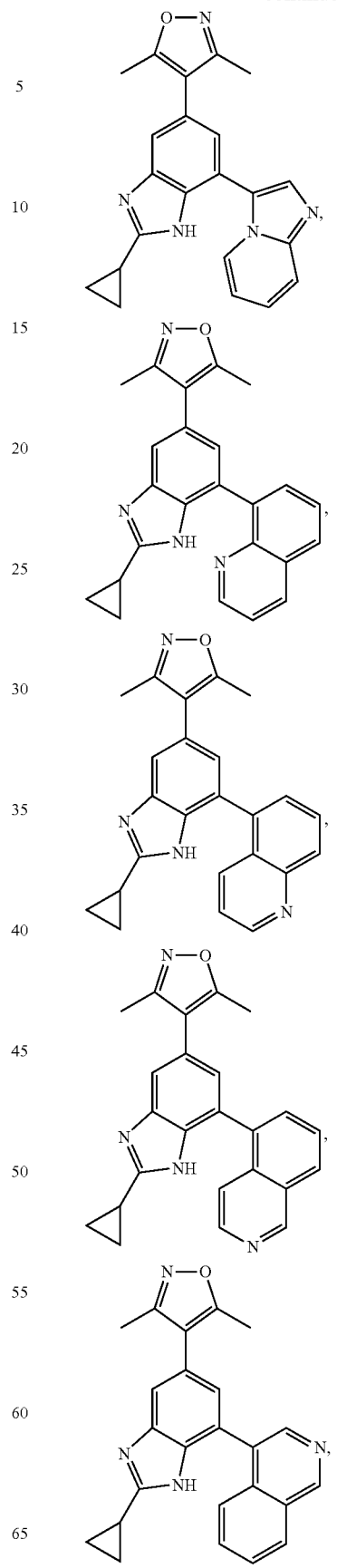

467
-continued
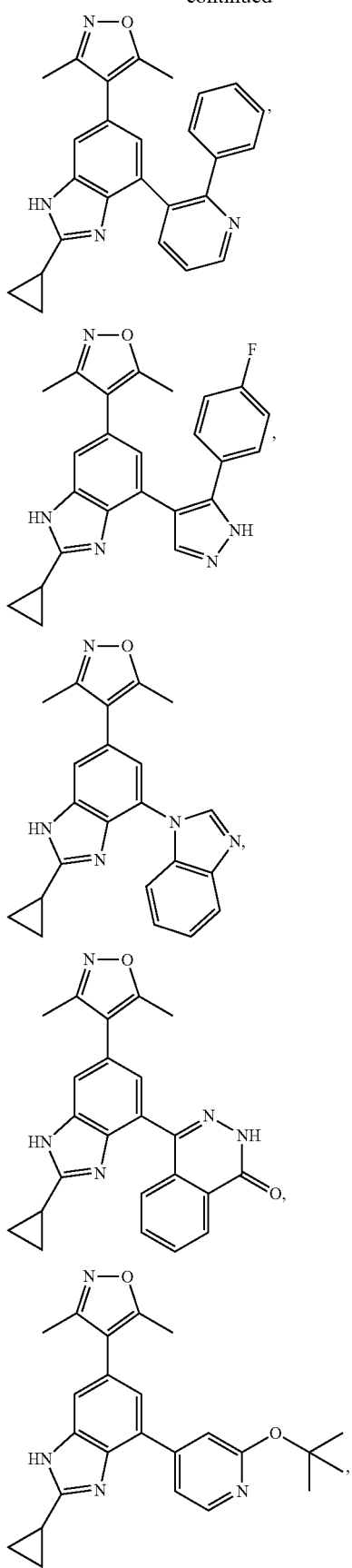
468
-continued
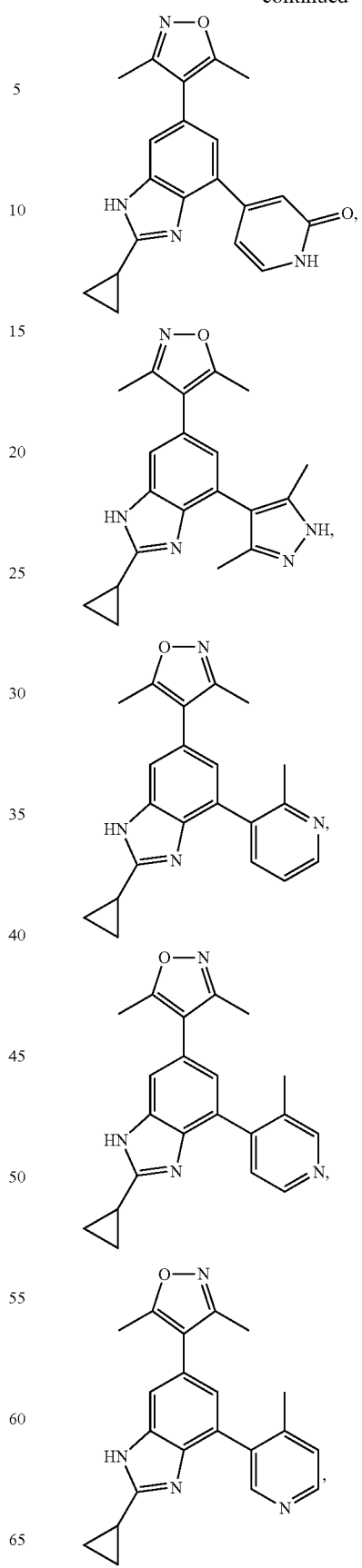

469
-continued
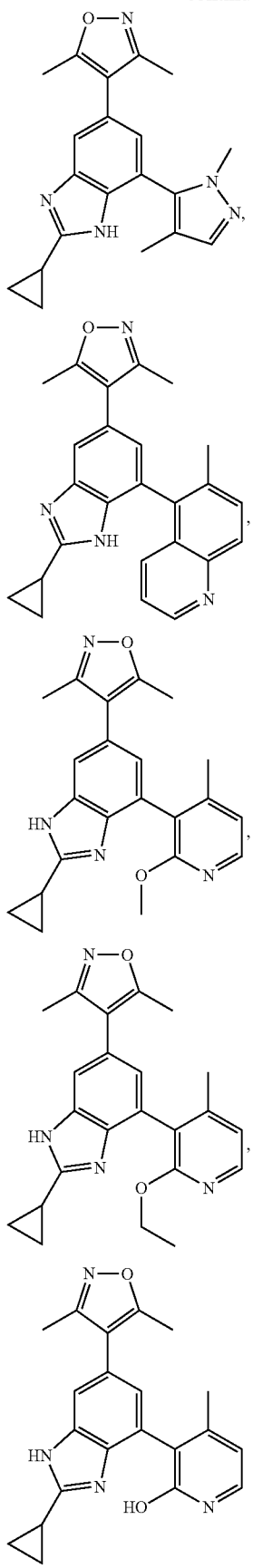
470
-continued
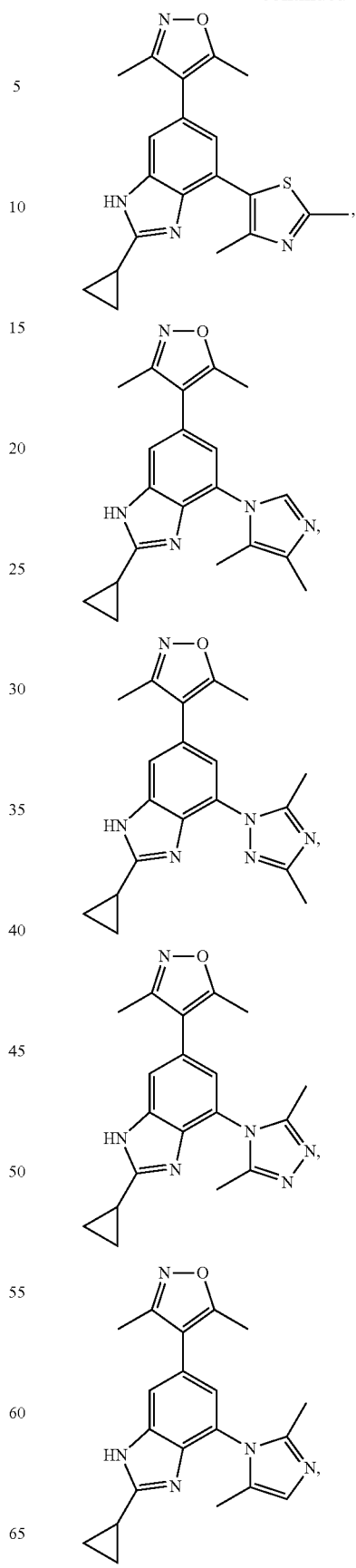

471
-continued
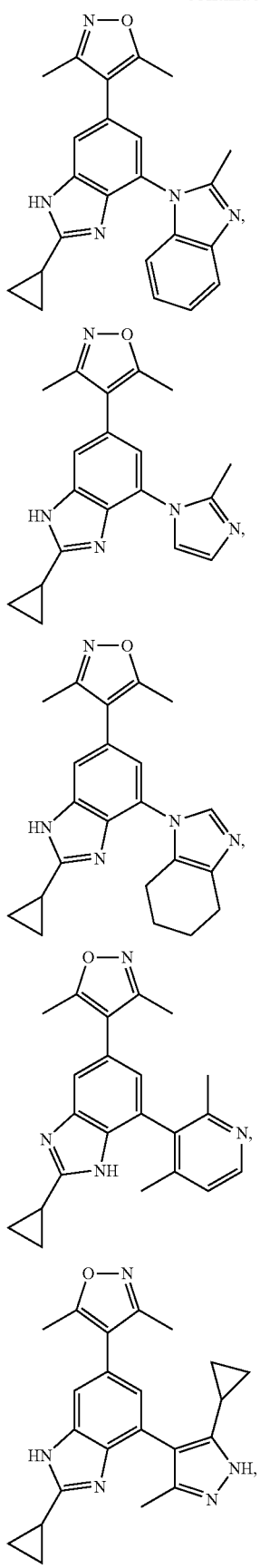
472
-continued
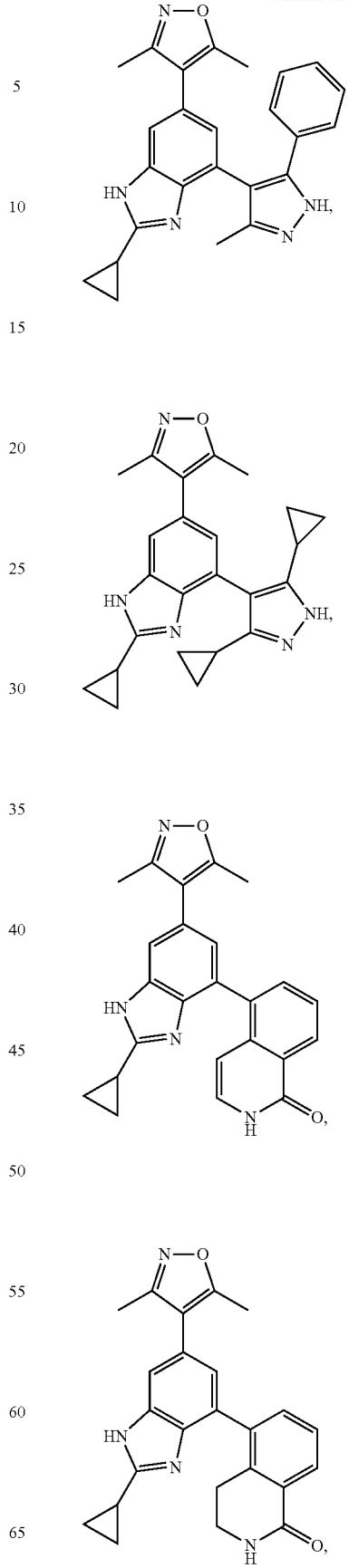

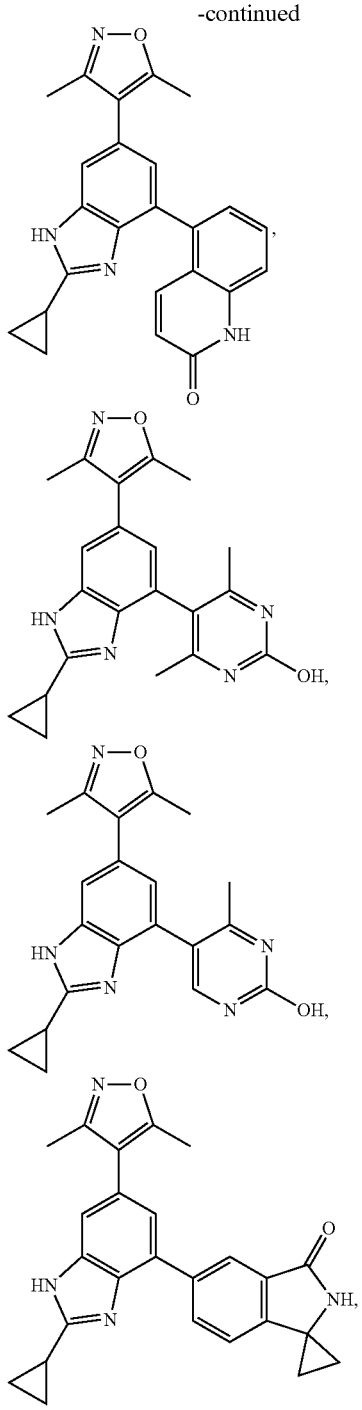
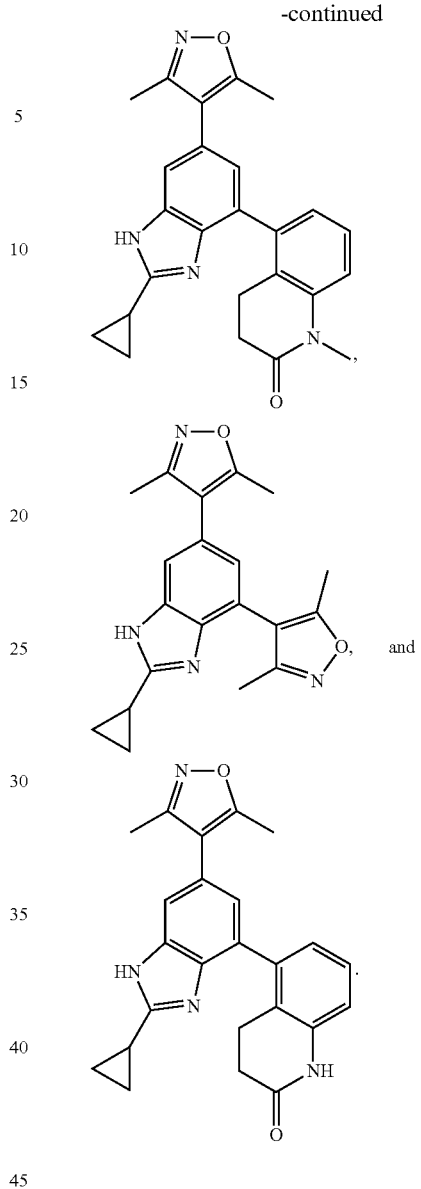
or a pharmaceutically acceptable salt thereof.
9. A pharmaceutical composition comprising a compound of claim 1, or a pharmaceutically acceptable salt thereof, and a pharmaceutically acceptable carrier.
* * * * *

SEQUENCE LISTING

<160> NUMBER OF SEQ ID NOS: 7

<210> SEQ ID NO 1
<211> LENGTH: 23
<212> TYPE: PRT
<213> ORGANISM: Artificial Sequence
<220> FEATURE:
<223> OTHER INFORMATION: Synthetic peptide containing amino acids 1-18 or histone H4

<400> SEQUENCE: 1

Ser Gly Arg Gly Lys Gly Gly Lys Gly Leu Gly Lys Gly Gly Ala Lys
1               5                   10                  15

Arg His Gly Ser Gly Ser Lys
            20

<210> SEQ ID NO 2
<211> LENGTH: 20
<212> TYPE: DNA
<213> ORGANISM: Homo sapiens

<400> SEQUENCE: 2
cggacattcc tgctttattg                                          20

<210> SEQ ID NO 3
<211> LENGTH: 20
<212> TYPE: DNA
<213> ORGANISM: Homo sapiens

<400> SEQUENCE: 3
gcgatatgcg gtccctactc                                          20

<210> SEQ ID NO 4
<211> LENGTH: 20
<212> TYPE: DNA
<213> ORGANISM: Homo sapiens

<400> SEQUENCE: 4
gcagctagat cgttgggaag                                          20

<210> SEQ ID NO 5
<211> LENGTH: 20
<212> TYPE: DNA
<213> ORGANISM: Homo sapiens

<400> SEQUENCE: 5
gctggtgatt tcagtgcaga                                          20

<210> SEQ ID NO 6
<211> LENGTH: 20
<212> TYPE: DNA
<213> ORGANISM: Homo sapiens

<400> SEQUENCE: 6
tggggtacaa gaggcttcag                                          20

<210> SEQ ID NO 7
<211> LENGTH: 20
<212> TYPE: DNA
<213> ORGANISM: Homo sapiens

<400> SEQUENCE: 7
cagtacagga gtggggacag                                          20